US009169260B2

(12) United States Patent
McElroy et al.

(10) Patent No.: US 9,169,260 B2
(45) Date of Patent: Oct. 27, 2015

(54) AMIDOPYRAZOLE INHIBITORS OF INTERLEUKIN RECEPTOR-ASSOCIATED KINASES

(75) Inventors: William T. McElroy, Plainfield, NJ (US); Guoqing Li, Belle Mead, NJ (US); Ginny Dai Ho, Murray Hill, NJ (US); Zheng Tan, Westfield, NJ (US); Sunil Paliwal, Monroe Township, NJ (US); William Michael Seganish, Scotch Plains, NJ (US); Deen Tulshian, Lebanon, NJ (US); John Lampe, Norfolk, MA (US); Joey L. Methot, Westwood, MA (US); Hua Zhou, Acton, MA (US); Michael D. Altman, Needham, MA (US); Liang Zhu, Waltham, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 97 days.

(21) Appl. No.: 14/006,565

(22) PCT Filed: Mar. 21, 2012

(86) PCT No.: PCT/US2012/029870
§ 371 (c)(1),
(2), (4) Date: Mar. 18, 2014

(87) PCT Pub. No.: WO2012/129258
PCT Pub. Date: Sep. 27, 2012

(65) Prior Publication Data
US 2014/0194404 A1 Jul. 10, 2014

Related U.S. Application Data

(60) Provisional application No. 61/460,751, filed on Mar. 22, 2011.

(51) Int. Cl.
*C07D 487/04* (2006.01)
*A61K 31/519* (2006.01)
*A61K 31/4162* (2006.01)

(52) U.S. Cl.
CPC .......... *C07D 487/04* (2013.01); *A61K 31/4162* (2013.01)

(58) Field of Classification Search
CPC ........................... C07D 487/04; A61K 31/519
See application file for complete search history.

(56) References Cited

U.S. PATENT DOCUMENTS

| 7,608,635 | B2 | 10/2009 | Ying et al. |
| 2009/0264412 | A1 | 10/2009 | Kampen et al. |
| 2010/0021420 | A1 | 1/2010 | Lyons et al. |

FOREIGN PATENT DOCUMENTS

| WO | WO03/030902 | 4/2003 |
| WO | WO2010051549 | 5/2010 |
| WO | WO2011/003065 | 1/2011 |
| WO | WO2012/007375 | 1/2012 |

OTHER PUBLICATIONS

Buckley, George M. et al, IRAK-4 Inhibitors. Part 1: A Series of Amides, Bioorganic & Medicinal Chemistry Letters, 2008, 3211-3214, 18.

*Primary Examiner* — Susanna Moore
(74) *Attorney, Agent, or Firm* — Matthew A. Leff; John C. Todaro

(57) ABSTRACT

This invention relates to amidopyrazole compounds that are inhibitors of Interleukin receptor-associated kinases, in particular IRAK-4, and are useful in the treatment of cellular proliferative diseases, for example, cancer, hyperplasia, restenosis, cardiac hypertrophy, immune disorders and inflammation.

7 Claims, No Drawings

AMIDOPYRAZOLE INHIBITORS OF INTERLEUKIN RECEPTOR-ASSOCIATED KINASES

BACKGROUND OF THE INVENTION

This invention relates to amidopyrazole compounds that are inhibitors of Interleukin receptor-associated kinases, in particular IRAK-4, and are useful in the treatment of cellular proliferative diseases, for example, cancer, hyperplasia, restenosis, cardiac hypertrophy, immune disorders and inflammation.

Interleukin-1 receptor-associated kinases (IRAKs) are key components in the signal transduction pathways utilized by interleukin-1 receptor (IL-1R), interleukin-18 receptor (IL-18R), and Toll-like receptors (TLRs). Since TLRs initiate the first-wave of inflammatory signals and innate immune responses, they play a key role in many disease processes, including response to infections and auto-inflammatory disorders.

IRAK-4 belongs to a family of mammalian IRAKs that include IRAK-1, IRAK-2 and IRAK-M (also known as IRAK-3). IRAK-4 shares the domain structure of the other IRAKs and it is able to activate similar signal transduction pathways, namely NF-κB and MAPK pathways. It rapidly and transiently associates with IRAK-1 and TRAF6 in an IL-1-dependent manner but it is not functionally redundant with IRAK-1. Most strikingly, IRAK-4 is an active protein kinase and requires its kinase activity to activate NF-κB. Additionally, IRAK-4 might act upstream of IRAK-1 as an IRAK-1 activator. See Li, S. et al., "IRAK-4: a novel member of the IRAK family with the properties of an IRAK-kinase," Proc Natl Acad Sci USA. 2002 Apr. 16; 99(8):5567-72.

All four IRAK family members appear to play a role in Toll and IL-1R signaling. However, out of four members in the mammalian IRAK family, IRAK-4 is considered to be the "master IRAK", the only family member indispensable for IL-1R/TLR signaling. Mouse knock-out studies have demonstrated the essential role for IRAK-4 in IL-1R, IL-18R and most TLR signaling (see, Suzuki, N, et al, "Severe impairment of interleukin-1 and Toll-like receptor signaling in mice lacking IRAK-4," Nature, 2002, 416, 750-756). Furthermore, knock-in experiments by several groups have clearly demonstrated that IRAK-4 requires its kinase activity for its function.

In humans, mutations resulting in IRAK-4 deficiency have been linked to susceptibility to bacterial infections, especially recurrent pyogenic bacterial infections (see, Picard, C., et al. "Pyogenic bacterial infections in humans with IRAK-4 deficiency." Science, 2003, 299, 2076-2079). While IRAK-4 deficient children are susceptible to certain pyogenic infections, adults are not prone to chronic infections. It is possible that protective immunity remains sufficiently preserved to protect against infection while modulation of IRAK-4 function through kinase inhibition may tone down inflammatory response.

Given the critical role of IRAK-4 in inflammatory processes, modulation of IRAK-4 kinase activity presents an attractive therapeutic approach for the treatment of immune and inflammatory diseases. The recent success in the determination of the 3-dimensional structure of the IRAK-4 kinase domain in complex with inhibitors has facilitated the understanding of the mechanistic role of IRAK-4 in immunity and inflammation as well as the development of specific IRAK-4 kinase inhibitors. See, Wang, et al, "IRAK-4 Inhibitors for Inflammation," Current Topics in Medicinal Chemistry, 2009, 9, 724-737.

It would be useful to develop potent IRAK-4 inhibitors with desired properties as new anti-inflammatory and anti-neoplastic therapeutic agents.

A number of studies have established the relationship between activation of the NF-κB and the progression of cancer. Since TLRs are prominent activators of the NF-κB pathway, it has been hypothesized that stimulation of TLRs is a factor in the development of human cancers. See, Chen, et al, "Inflammation, Cancer, and Chemoresistance: Taking Advantage of the Toll-Like Receptor Signaling Pathway," American Journal of Reproductive Immunology, 2007, 57 (2), 93-107. Given the central role of IRAK-4 in the TLR driven inflammation pathway, it has been proposed that inhibition of IRAK-4 may lead to a new class of anticancer agents. See, Shaw, et al, "Characterization of Novel Diaryl Oxazole-Based Compounds as Potential Agents to Treat Pancreatic Cancer," Journal of Pharmacology and Experimental Therapeutics, 2009, 331 (2), 636-647.

There exists a need in the art for small molecule compounds having desirable physiochemical properties that are useful for treating cancer and other proliferative disorders. Specifically, it would be useful to develop potent IRAK-4 inhibitors with desired properties as new anticancer therapeutic agents.

SUMMARY OF THE INVENTION

The present invention relates to novel amidopyrazole compounds that are inhibitors of Interleukin receptor-associated kinases, in particular IRAK-4, and are useful in the treatment of cellular proliferative diseases, for example, cancer. The compounds of the invention may be illustrated by the Formula I:

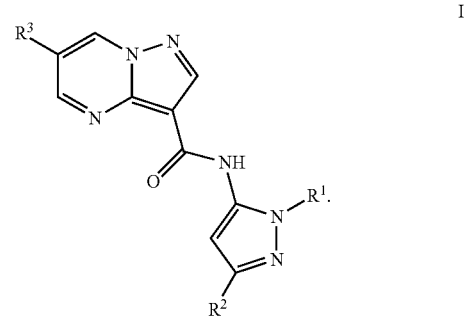

DETAILED DESCRIPTION OF THE INVENTION

The compounds of this invention are useful in the inhibition of Interleukin receptor-associated kinases, in particular IRAK-4, and are illustrated by a compound of the formula:

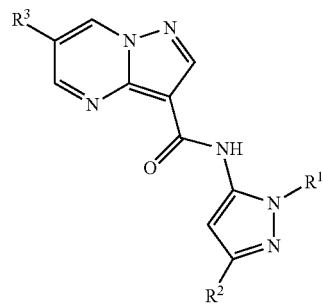

wherein $R^1$ is aryl, heteroaryl, heterocyclyl or $(C_{1-6}$ alkyl$)R^6$, wherein said aryl, heteroaryl, and heterocyclyl groups are optionally substituted with one or two substituents selected from the group consisting of halo, cyano, $R^4$, $C_{1-3}$ aminoalkyl, $C_{1-3}$ hydroxyalkyl, $C_{3-4}$ cycloalkyl, $OR^4$, $NR^4R^5$, $NR^4COR^6$, $NR^4SO_2R^6$, $SO_2NR^4R^5$, $CONR^4R^5$;

$R^2$ is aryl, heteroaryl, $C_{3-8}$ cycloalkyl, heterocyclyl or $(C_{1-6}$ alkyl)$R^6$, wherein said aryl, heteroaryl, cycloalkyl and heterocyclyl groups are optionally substituted with one or two substituents selected from the group consisting of halo, cyano, oxo, hydroxyl, imino, hydroxyimino, $R^4$, $OR^4$, $O(C_{3-8}$ cycloalkyl), $(C=O)OR^4$, $SO_mR^6$, $SO_mR^4$, $NR^4R^5$, $SO_2NR^4R^5$ and $NR^4SO_2R^6$;

$R^3$ is halo, cyano, oxo, hydroxyl, imino, hydroxyimino, $R^4$, $OR^4$, $C_{3-8}$ cycloalkyl, $SO_mR^6$, $SO_mR^4NR^4R^5$, or $(C=O)NR^4R^5$, $NR^4(CO)R^6$, $SO_mNR^4R^5$ and $NR^4SO_2R^6$;

$R^4$ is hydrogen or $C_{1-6}$ alkyl, wherein said alkyl is optionally substituted with one to three halo or hydroxyl;

$R^5$ is hydrogen or $C_{1-6}$ alkyl, wherein said alkyl is optionally substituted with halo or hydroxyl;

$R^6$ is aryl, heteroaryl, $C_{3-8}$ cycloalkyl or heterocyclyl;

m is an integer from zero to two;

or a pharmaceutically acceptable salt thereof.

In a class of the invention, $R^1$ is aryl, wherein said aryl group is optionally substituted with one or two substituents selected from the group consisting of halo, cyano, $R^4$, $C_{3-8}$ cycloalkyl, $C_{1-3}$ aminoalkyl, $C_{1-3}$ hydroxyalkyl, $OR^4$, $NR^4R^5$, $NR^4COR^6$, $NR^4SO_2R^6$, $SO_2NR^4R^5$, $CONR^4R^5$ and $CONR^4R^5$. In a subclass of the invention, $R^1$ is aryl, wherein said aryl group is optionally substituted with $R^4$ or $OR^4$. In a further subclass of the invention, $R^1$ is phenyl, wherein said phenyl group is optionally substituted with $R^4$ or $OR^4$.

In a class of the invention, $R^2$ is heteroaryl, wherein said heteroaryl group is optionally substituted with one or two substituents selected from the group consisting of halo, cyano, oxo, hydroxyl, imino, hydroxyimino, $R^4$, $OR^4$, $O(C_{3-8}$ cycloalkyl), $(C=O)OR^4$, $SO_mR^6$, $SO_mR^4$, $NR^4R^5$, $SO_2NR^4R^5$ and $NR^4SO_2R^6$. In a subclass of the invention, $R^2$ is heteroaryl, wherein said heteroaryl group is optionally substituted with one or two substituents selected from the group consisting of halo, cyano, oxo, hydroxyl, imino, hydroxyimino, $R^4$, $OR^4$, $O(C_{3-8}$ cycloalkyl), $(C=O)OR^4$, $SO_mR^6$, $SO_mR^4$, $NR^4R^5$, $SO_2NR^4R^5$ and $NR^4SO_2R^6$.

Specific examples of the compounds of the instant invention include, but are not limited to:

N-(3-(4-oxocyclohexyl)-1-(p-tolyl)-1H-pyrazol-5-yl)pyrazolo[1,5-a]pyrimidine-3-carboxamide (Example 1);

N-(3-(4-(hydroxyimino)cyclohexyl)-1-(p-tolyl)-1H-pyrazol-5-yl)pyrazolo[1,5-a]pyrimidine-3-carboxamide (2);

N-(3-(4-(methoxyimino)cyclohexyl)-1-(p-tolyl)-1H-pyrazol-5-yl)pyrazolo[1,5-a]pyrimidine-3-carboxamide (3);

N-(3-(7-oxoazepan-4-yl)-1-(p-tolyl)-1H-pyrazol-5-yl)pyrazolo[1,5-a]pyrimidine-3-carboxamide (4);

N-(3-(4-(dimethylamino)cyclohexyl)-1-(p-tolyl)-1,4-pyrazol-5-yl)pyrazolo[1,5-a]pyrimidine-3-carboxamide (5);

N-(3-(4-hydroxycyclohexyl)-1-(p-tolyl)-1H-pyrazol-5-yl)pyrazolo[1,5-a]pyrimidine-3-carboxamide (6);

N-(3-(piperidin-4-yl)-1-(p-tolyl)-1H-pyrazol-5-yl)pyrazolo[1,5-a]pyrimidine-3-carboxamide (7);

N-(1-(4-methoxyphenyl)-3-(piperidin-4-yl)-1H-pyrazol-5-yl)pyrazolo[1,5-a]pyrimidine-3-carboxamide (8);

N-(1-(4-chlorophenyl)-3-(piperidin-4-yl)-1H-pyrazol-5-yl)pyrazolo[1,5-a]pyrimidine-3-carboxamide (9);

N-(1-(4-fluorophenyl)-3-(piperidin-4-yl)-1H-pyrazol-5-yl)pyrazolo[1,5-a]pyrimidine-3-carboxamide (10);

N-(3-(piperidin-4-yl)-1-(4-(trifluoromethyl)phenyl)-1H-pyrazol-5-yl)pyrazolo[1,5-a]pyrimidine-3-carboxamide (11);

N-(1-(4-cyanophenyl)-3-(piperidin-4-yl)-1H-pyrazol-5-yl)pyrazolo[1,5-a]pyrimidine-3-carboxamide (12);

N-(3-(piperidin-4-yl)-1-(4-(trifluoromethoxy)phenyl)-1H-pyrazol-5-yl)pyrazolo[1,5-a]pyrimidine-3-carboxamide (13);

N-(3-(piperidin-4-yl)-1-(o-tolyl)-1H-pyrazol-5-yl)pyrazolo[1,5-a]pyrimidine-3-carboxamide (14);

N-(3-(piperidin-4-yl)-1-(m-tolyl)-1H-pyrazol-5-yl)pyrazolo[1,5-a]pyrimidine-3-carboxamide (15);

N-(1-(4-methoxyphenyl)-3-(1-(methylsulfonyl)piperidin-4-yl)-1H-pyrazol-5-yl)pyrazolo[1,5-a]pyrimidine-3-carboxamide (16);

N-(3-(1-(methylsulfonyl)piperidin-4-yl)-1-(m-tolyl)-1H-pyrazol-5-yl)pyrazolo[1,5-a]pyrimidine-3-carboxamide (17);

N-(3-(1-(methylsulfonyl)piperidin-4-yl)-1-(p-tolyl)-1H-pyrazol-5-yl)pyrazolo[1,5-a]pyrimidine-3-carboxamide (18);

N-(3-(1-(cyclopropylsulfonyl)piperidin-4-yl)-1-(4-(trifluoromethoxy)phenyl)-1H-pyrazol-5-yl)pyrazolo[1,5-a]pyrimidine-3-carboxamide (19);

N-(3-(1-(methylsulfonyl)piperidin-4-yl)-1-phenyl-1H-pyrazol-5-yl)pyrazolo[1,5-a]pyrimidine-3-carboxamide (20);

N-(3-(1-(cyclopropylsulfonyl)piperidin-4-yl)-1-(m-tolyl)-1H-pyrazol-5-yl)pyrazolo[1,5-a]pyrimidine-3-carboxamide (21);

N-(3-(1-(cyclopropylsulfonyl)piperidin-4-yl)-1-(4-fluorophenyl)-1H-pyrazol-5-yl)pyrazolo[1,5-a]pyrimidine-3-carboxamide (22);

N-(3-(1-(isopropylsulfonyl)piperidin-4-yl)-1-(4-methoxyphenyl)-1H-pyrazol-5-yl)pyrazolo[1,5-a]pyrimidine-3-carboxamide (23);

N-(3-(1-(cyclopropylsulfonyl)piperidin-4-yl)-1-(4-methoxyphenyl)-1H-pyrazol-5-yl)pyrazolo[1,5-a]pyrimidine-3-carboxamide (24);

N-(3-(1-(cyclopentylsulfonyl)piperidin-4-yl)-1-(p-tolyl)-1H-pyrazol-5-yl)pyrazolo[1,5-a]pyrimidine-3-carboxamide (25);

N-(3-(1-(cyclopropylsulfonyl)piperidin-4-yl)-1-(p-tolyl)-1H-pyrazol-5-yl)pyrazolo[1,5-a]pyrimidine-3-carboxamide (26);

N-(3-(1-(cyclopropylsulfonyl)piperidin-4-yl)-1-(4-(trifluoromethoxy)phenyl)-1H-pyrazol-5-yl)pyrazolo[1,5-a]pyrimidine-3-carboxamide (27);

N-(1-(2,4-difluorophenyl)-3-(4-(N-methylsulfamoyl)phenyl)-1H-pyrazol-5-yl)pyrazolo[1,5-a]pyrimidine-3-carboxamide (28);

N-(1-(4-chloro-2-fluorophenyl)-3-(1-(methylsulfonyl)piperidin-4-yl)-1H-pyrazol-5-yl)pyrazolo[1,5-a]pyrimidine-3-carboxamide (29);

N-(1-(4-methoxyphenyl)-3-(1-((trifluoromethyl)sulfonyl)piperidin-4-yl)-1H-pyrazol-5-yl)pyrazolo[1,5-a]pyrimidine-3-carboxamide (30);

N-(3-(1-acetylpiperidin-4-yl)-1-(p-tolyl)-1H-pyrazol-5-yl)pyrazolo[1,5-a]pyrimidine-3-carboxamide (31);

methyl 4-(1-(4-methoxyphenyl)-5-(pyrazolo[1,5-a]pyrimidine-3-carboxamido)-1H-pyrazol-3-yl)piperidine-1-carboxylate (32);

N-(3-(1-(cyclopropanecarbonyl)piperidin-4-yl)-1-(4-methoxyphenyl)-1H-pyrazol-5-yl)pyrazolo[1,5-a]pyrimidine-3-carboxamide (33);

N-(1-(2,4-difluorophenyl)-3-(4-(N-methylsulfamoyl)phenyl)-1H-pyrazol-5-yl)pyrazolo[1,5-a]pyrimidine-3-carboxamide (34);

N-(3-(1-carbamoylpiperidin-4-yl)-1-(p-tolyl)-1H-pyrazol-5-yl)pyrazolo[1,5-a]pyrimidine-3-carboxamide (35);

N-(3-(1-methylpiperidin-4-yl)-1-(p-tolyl)-1H-pyrazol-5-yl) pyrazolo[1,5-a]pyrimidine-3-carboxamide (36);
N-(3-(1-isopropylpiperidin-4-yl)-1-(p-tolyl)-1H-pyrazol-5-yl)pyrazolo[1,5-a]pyrimidine-3-carboxamide (37);
N-(3-(1-cyclobutylpiperidin-4-yl)-1-(p-tolyl)-1H-pyrazol-5-yl)pyrazolo[1,5-a]pyrimidine-3-carboxamide (38);
N-(3-(1-cyclopentylpiperidin-4-yl)-1-(p-tolyl)-1H-pyrazol-5-yl)pyrazolo[1,5-a]pyrimidine-3-carboxamide (39);
N-(3-(1-cyclopropylpiperidin-4-yl)-1-(p-tolyl)-1H-pyrazol-5-yl)pyrazolo[1,5-a]pyrimidine-3-carboxamide (40);
N-(1-(p-tolyl)-3-(1-(2,2,2-trifluoroethyl)piperidin-4-yl)-1H-pyrazol-5-yl)pyrazolo[1,5-a]pyrimidine-3-carboxamide (41);
N-(3-(piperidin-3-yl)-1-(p-tolyl)-1H-pyrazol-5-yl)pyrazolo[1,5-a]pyrimidine-3-carboxamide (42);
N-(3-(1-(methylsulfonyl)piperidin-3-yl)-1-(p-tolyl)-1H-pyrazol-5-yl)pyrazolo[1,5-a]pyrimidine-3-carboxamide (43);
N-(3-(1-(cyclopropylsulfonyl)piperidin-3-yl)-1-(p-tolyl)-1H-pyrazol-5-yl)pyrazolo[1,5-a]pyrimidine-3-carboxamide (44);
N-(3-((tetrahydro-2H-pyran-4-yl)methyl)-1-(p-tolyl)-1H-pyrazol-5-yl)pyrazolo[1,5-a]pyrimidine-3-carboxamide (45);
N-(3-(tetrahydro-2H-pyran-4-yl)-1-(p-tolyl)-1H-pyrazol-5-yl)pyrazolo[1,5-a]pyrimidine-3-carboxamide (46);
N-(3-(1-isopropylpiperidin-4-yl)-1-(4-methoxyphenyl)-1H-pyrazol-5-yl)pyrazolo[1,5-a]pyrimidine-3-carboxamide (47);
N-(1-(2,4-difluorophenyl)-3-(1-methylpiperidin-4-yl)-1H-pyrazol-5-yl)pyrazolo[1,5-a]pyrimidine-3-carboxamide (48);
N-(3-(1-cyclobutylpiperidin-4-yl)-1-(2,4-difluorophenyl)-1H-pyrazol-5-yl)pyrazolo[1,5-a]pyrimidine-3-carboxamide (49);
N-(1-(4-chloro-2-fluorophenyl)-3-(1-methylpiperidin-4-yl)-1H-pyrazol-5-yl)pyrazolo[1,5-a]pyrimidine-3-carboxamide (50);
N-(1-(4-chloro-2-fluorophenyl)-3-(1-cyclobutylpiperidin-4-yl)-1H-pyrazol-5-yl)pyrazolo[1,5-a]pyrimidine-3-carboxamide (51);
N-(1-(4-cyclopropylphenyl)-3-(piperidin-4-yl)-1H-pyrazol-5-yl)pyrazolo[1,5-a]pyrimidine-3-carboxamide (52);
N-(1-(4-cyclopropylphenyl)-3-(1-(methylsulfonyl)piperidin-4-yl)-1H-pyrazol-5-yl)pyrazolo[1,5-a]pyrimidine-3-carboxamide (53);
N-(1-(4-cyclopropylphenyl)-3-(1-(cyclopropylsulfonyl)piperidin-4-yl)-1H-pyrazol-5-yl)pyrazolo[1,5-a]pyrimidine-3-carboxamide (54);
N-(1-(4-cyclopropylphenyl)-3-(1-isopropylpiperidin-4-yl)-1H-pyrazol-5-yl)pyrazolo[1,5-a]pyrimidine-3-carboxamide (55);
N-(1-(2-fluoro-4-methylphenyl)-3-(piperidin-4-yl)-1H-pyrazol-5-yl)pyrazolo[1,5-a]pyrimidine-3-carboxamide (56);
N-(1-(2-fluoro-4-methylphenyl)-3-(1-(methylsulfonyl)piperidin-4-yl)-1H-pyrazol-5-yl)pyrazolo[1,5-a]pyrimidine-3-carboxamide (57);
N-(1-(2-fluoro-4-methylphenyl)-3-(1-isopropylpiperidin-4-yl)-1H-pyrazol-5-yl)pyrazolo[1,5-a]pyrimidine-3-carboxamide (58);
N-(3-(1-cyclobutylpiperidin-4-yl)-1-(2-fluoro-4-methylphenyl)-1H-pyrazol-5-yl)pyrazolo[1,5-a]pyrimidine-3-carboxamide (59);
N-(1-(2-fluoro-4-methylphenyl)-3-(1-methylpiperidin-4-yl)-1H-pyrazol-5-yl)pyrazolo[1,5-a]pyrimidine-3-carboxamide (60;
N-(1-(2-fluoro-4-methoxyphenyl)-3-(piperidin-4-yl)-1H-pyrazol-5-yl)pyrazolo[1,5-a]pyrimidine-3-carboxamide (61);
N-(1-(2-fluoro-4-methoxyphenyl)-3-(1-isopropylpiperidin-4-yl)-1H-pyrazol-5-yl)pyrazolo[1,5-a]pyrimidine-3-carboxamide (62);
N-(3-(1-(cyclopropylsulfonyl)piperidin-4-yl)-1-(2-fluoro-4-methoxyphenyl)-1H-pyrazol-5-yl)pyrazolo[1,5-a]pyrimidine-3-carboxamide (63);
N-(1-(2-fluoro-4-methoxyphenyl)-3-(1-(methylsulfonyl)piperidin-4-yl)-1H-pyrazol-5-yl)pyrazolo[1,5-a]pyrimidine-3-carboxamide (64);
N-(1-(2-chloro-4-methylphenyl)-3-(piperidin-4-yl)-1H-pyrazol-5-yl)pyrazolo[1,5-a]pyrimidine-3-carboxamide (65);
N-(1-(2-chloro-4-methylphenyl)-3-(1-isopropylpiperidin-4-yl)-1H-pyrazol-5-yl)pyrazolo[1,5-a]pyrimidine-3-carboxamide (66);
N-(1-(3,5-difluorophenyl)-3-(piperidin-4-yl)-1H-pyrazol-5-yl)pyrazolo[1,5-a]pyrimidine-3-carboxamide (67);
N-(1-(4-fluoro-2-methylphenyl)-3-(piperidin-4-yl)-1H-pyrazol-5-yl)pyrazolo[1,5-a]pyrimidine-3-carboxamide (68);
N-(1-(4-fluoro-2-methylphenyl)-3-(1-isopropylpiperidin-4-yl)-1H-pyrazol-5-yl)pyrazolo[1,5-a]pyrimidine-3-carboxamide (69);
N-(1-(4-bromo-2-fluorophenyl)-3-(piperidin-4-yl)-1H-pyrazol-5-yl)pyrazolo[1,5-a]pyrimidine-3-carboxamide (70);
N-(1-(4-bromo-2-fluorophenyl)-3-(1-(methylsulfonyl)piperidin-4-yl)-1H-pyrazol-5-yl)pyrazolo[1,5-a]pyrimidine-3-carboxamide (71);
N-(1-(4-cyclopropyl-2-fluorophenyl)-3-(piperidin-4-yl)-1H-pyrazol-5-yl)pyrazolo[1,5-a]pyrimidine-3-carboxamide (72);
N-(1-(4-cyclopropyl-2-fluorophenyl)-3-(1-(methylsulfonyl)piperidin-4-yl)-1H-pyrazol-5-yl)pyrazolo[1,5-a]pyrimidine-3-carboxamide (73);
N-(1-(4-cyclopropyl-2-fluorophenyl)-3-(1-isopropylpiperidin-4-yl)-1H-pyrazol-5-yl)pyrazolo[1,5-a]pyrimidine-3-carboxamide (74);
N-(3-(1-cyclobutylpiperidin-4-yl)-1-(4-cyclopropyl-2-fluorophenyl)-1H-pyrazol-5-yl)pyrazolo[1,5-a]pyrimidine-3-carboxamide (75);
N-(1-(4-cyclopropyl-2-fluorophenyl)-3-(1-(2,2,2-trifluoroethyl)piperidin-4-yl)-1H-pyrazol-5-yl)pyrazolo[1,5-a]pyrimidine-3-carboxamide (76);
N-(1-(4-cyclopropyl-2,6-difluorophenyl)-3-(piperidin-4-yl)-1H-pyrazol-5-yl)pyrazolo[1,5-a]pyrimidine-3-carboxamide (77);
N-(3-(piperidin-4-yl)-1-(tetrahydro-2H-pyran-4-yl)-11'-pyrazol-5-yl)pyrazolo[1,5-a]pyrimidine-3-carboxamide (78);
N-(3-(morpholin-3-yl)-1-(p-tolyl)-1H-pyrazol-5-yl)pyrazolo[1,5-a]pyrimidine-3-carboxamide (79);
N-(3-(pyrrolidin-3-yl)-1-(p-tolyl)-1H-pyrazol-5-yl)pyrazolo[1,5-a]pyrimidine-3-carboxamide (80);
N-(3-(1-(methylsulfonyl)pyrrolidin-3-yl)-1-(p-tolyl)-1H-pyrazol-5-yl)pyrazolo[1,5-a]pyrimidine-3-carboxamide (81);
N-(3-(azetidin-3-yl)-1-(p-tolyl)-1H-pyrazol-5-yl)pyrazolo[1,5-a]pyrimidine-3-carboxamide (82);
N-(3-(1-(methylsulfonyl)azetidin-3-yl)-1-(p-tolyl)-1H-pyrazol-5-yl)pyrazolo[1,5-a]pyrimidine-3-carboxamide (83);

N-(3-(1-(cyclopropylsulfonyl)azetidin-3-yl)-1-(p-tolyl)-1H-pyrazol-5-yl)pyrazolo[1,5-a]pyrimidine-3-carboxamide (84);

N-(3-(1-(cyclopentylsulfonyl)azetidin-3-yl)-1-(p-tolyl)-1H-pyrazol-5-yl)pyrazolo[1,5-a]pyrimidine-3-carboxamide (85);

N-(3-(1-((2-methoxyethyl)sulfonyl)azetidin-3-yl)-1-(p-tolyl)-1H-pyrazol-5-yl)pyrazolo[1,5-a]pyrimidine-3-carboxamide (86);

N-(3-(azetidin-3-yl)-1-(4-cyclopropyl-2-fluorophenyl)-1H-pyrazol-5-yl)pyrazolo[1,5-a]pyrimidine-3-carboxamide (87);

N-(1-(4-cyclopropyl-2-fluorophenyl)-3-(1-isopropylazetidin-3-yl)-1H-pyrazol-5-yl)pyrazolo[1,5-a]pyrimidine-3-carboxamide (88);

N-(3-(1-cyclobutylazetidin-3-yl)-1-(4-cyclopropyl-2-fluorophenyl)-1H-pyrazol-5-yl)pyrazolo[1,5-a]pyrimidine-3-carboxamide (89);

N-(1-(4-acetylphenyl)-3-(1-(methylsulfonyl)piperidin-4-yl)-1H-pyrazol-5-yl)pyrazolo[1,5-a]pyrimidine-3-carboxamide (90);

N-(3-(4-methylpiperidin-4-yl)-1-(p-tolyl)-1H-pyrazol-5-yl)pyrazolo[1,5-a]pyrimidine-3-carboxamide (91);

N-(3-(4-methyl-1-(methylsulfonyl)piperidin-4-yl)-1-(p-tolyl)-1H-pyrazol-5-yl)pyrazolo[1,5-a]pyrimidine-3-carboxamide (92);

methyl 4-(5-(pyrazolo[1,5-a]pyrimidine-3-carboxamido)-1-(p-tolyl)-1H-pyrazol-3-yl)cyclohexanecarboxylate (93);

4-(5-(pyrazolo[1,5-]pyrimidine-3-carboxamido)-1-(p-tolyl)-1H-pyrazol-3-yl)cyclohexanecarboxylic acid (94);

N-(3-(4-carbamoylcyclohexyl)-1-(p-tolyl)-1H-pyrazol-5-yl)pyrazolo[1,5-a]pyrimidine-3-carboxamide (95);

N-(3-(4-(dimethylcarbamoyl)cyclohexyl)-1-(p-tolyl)-1H-pyrazol-5-yl)pyrazolo[1,5-a]pyrimidine-3-carboxamide (96);

N-(1-(p-tolyl)-3-(4-(trifluoromethyl)cyclohexyl)-1H-pyrazol-5-yl)pyrazolo[1,5-a]pyrimidine-3-carboxamide (97);

N-(3-(1,1-dioxidotetrahydro-2H-thiopyran-4-yl)-1-(p-tolyl)-1H-pyrazol-5-yl)pyrazolo[1,5-a]pyrimidine-3-carboxamide (98);

N-(3-(4-sulfamoylphenyl)-1-(p-tolyl)-1H-pyrazol-5-yl)pyrazolo[1,5-a]pyrimidine-3-carboxamide (99);

N-(1-(2-fluoro-4-methylphenyl)-3-(4-(N-methylsulfamoyl)phenyl)-1H-pyrazol-5-yl)pyrazolo[1,5-a]pyrimidine-3-carboxamide (100);

N-(1-(4-cyclopropyl-2-fluorophenyl)-3-(4-(N-methylsulfamoyl)phenyl)-1H-pyrazol-5-yl)pyrazolo[1,5-a]pyrimidine-3-carboxamide (101);

N-(3-(4-aminophenyl)-1-(p-tolyl)-1H-pyrazol-5-yl)pyrazolo[1,5-a]pyrimidine-3-carboxamide (102);

N-(3-(4-(methylsulfonamido)phenyl)-1-(p-tolyl)-1H-pyrazol-5-yl)pyrazolo[1,5-a]pyrimidine-3-carboxamide (103);

6-bromo-N-(1-(4-methoxyphenyl)-3-(piperidin-4-yl)-1H-pyrazol-5-yl)pyrazolo[1,5-a]pyrimidine-3-carboxamide (104);

N3-(1-(4-methoxyphenyl)-3-(piperidin-4-yl)-1H-pyrazol-5-yl)pyrazolo[1,5-a]pyrimidine-3,6-dicarboxamide (105);

6-cyclopropyl-N-(1-(4-methoxyphenyl)-3-(piperidin-4-yl)-1H-pyrazol-5-yl)pyrazolo[1,5-a]pyrimidine-3-carboxamide (106);

6-bromo-N-(3-(piperidin-4-yl)-1-(p-tolyl)-1H-pyrazol-5-yl)pyrazolo[1,5-a]pyrimidine-3-carboxamide (107);

6-bromo-N-(3-(1-isopropylpiperidin-4-yl)-1-(p-tolyl)-1H-pyrazol-5-yl)pyrazolo[1,5-a]pyrimidine-3-carboxamide (108);

6-bromo-N-(3-(1-(tetrahydro-2H-pyran-3-yl)piperidin-4-yl)-1-(p-tolyl)-1H-pyrazol-5-yl)pyrazolo[1,5-a]pyrimidine-3-carboxamide (109);

6-bromo-N-(3-(1-(tetrahydro-2H-pyran-4-yl)piperidin-4-yl)-1-(p-tolyl)-1H-pyrazol-5-yl)pyrazolo[1,5-a]pyrimidine-3-carboxamide (110);

6-bromo-N-(3-(1-methylpiperidin-4-yl)-1-(p-tolyl)-1H-pyrazol-5-yl)pyrazolo[1,5-a]pyrimidine-3-carboxamide (111);

6-bromo-N-(3-(1-(2-hydroxyacetyl)piperidin-4-yl)-1-(p-tolyl)-1H-pyrazol-5-yl)pyrazolo[1,5-a]pyrimidine-3-carboxamide (112);

6-bromo-N-(3-(1-(3-(dimethylamino)propanoyl)piperidin-4-yl)-1-(p-tolyl)-1H-pyrazol-5-yl)pyrazolo[1,5-a]pyrimidine-3-carboxamide (113);

6-bromo-N-(3-(1-(3-(diethylamino)propanoyl)piperidin-4-yl)-1-(p-tolyl)-1H-pyrazol-5-yl)pyrazolo[1,5-a]pyrimidine-3-carboxamide (114);

N-(3-(1-(2-amino-2-oxoethyl)piperidin-4-yl)-1-(p-tolyl)-1H-pyrazol-5-yl)-6-bromopyrazolo[1,5-a]pyrimidine-3-carboxamide (115);

6-bromo-N-(3-(1-(1-hydroxycyclobutanecarbonyl)piperidin-4-yl)-1-(p-tolyl)-1H-pyrazol-5-yl)pyrazolo[1,5-a]pyrimidine-3-carboxamide (116);

6-bromo-N-(3-(1-(4-methylmorpholine-2-carbonyl)piperidin-4-yl)-1-(p-tolyl)-1H-pyrazol-5-yl)pyrazolo[1,5-a]pyrimidine-3-carboxamide (117);

methyl 4-(5-(6-bromopyrazolo[1,5-a]pyrimidine-3-carboxamido)-1-(p-tolyl)-1H-pyrazol-3-yl)piperidine-1-carboxylate (118);

6-bromo-N-(3-(1-(methylsulfonyl)piperidin-4-yl)-1-(p-tolyl)-1H-pyrazol-5-yl)pyrazolo[1,5-a]pyrimidine-3-carboxamide (119);

N3-(3-(1-(methylsulfonyl)piperidin-4-yl)-1-(p-tolyl)-1H-pyrazol-5-yl)pyrazolo[1,5-a]pyrimidine-3,6-dicarboxamide (120);

6-cyano-N-(3-(1-(methylsulfonyl)piperidin-4-yl)-1-(p-tolyl)-1H-pyrazol-5-yl)pyrazolo[1,5-a]pyrimidine-3-carboxamide (121);

6-methyl-N-(3-(1-(methylsulfonyl)piperidin-4-yl)-1-(p-tolyl)-1H-pyrazol-5-yl)pyrazolo[1,5-a]pyrimidine-3-carboxamide (122);

N-(3-(pyridin-3-yl)-1-(p-tolyl)-1H-pyrazol-5-yl)pyrazolo[1,5-a]pyrimidine-3-carboxamide (123);

N-(3-(6-methoxypyridin-3-yl)-1-(p-tolyl)-1H-pyrazol-5-yl)pyrazolo[1,5-a]pyrimidine-3-carboxamide (124);

N-(3-(pyridin-4-yl)-1-(p-tolyl)-1H-pyrazol-5-yl)pyrazolo[1,5-a]pyrimidine-3-carboxamide (125);

N-(1-(4-fluorophenyl)-3-(pyridin-4-yl)-1H-pyrazol-5-yl)pyrazolo[1,5-a]pyrimidine-3-carboxamide (126);

N-(1-(4-methoxyphenyl)-3-(pyridin-4-yl)-1H-pyrazol-5-yl)pyrazolo[1,5-a]pyrimidine-3-carboxamide (127);

N-(1-(3-fluoro-4-methylphenyl)-3-(pyridin-4-yl)-1H-pyrazol-5-yl)pyrazolo[1,5-a]pyrimidine-3-carboxamide (128);

N-(3-(2-methoxypyridin-4-yl)-1-(p-tolyl)-1H-pyrazol-5-yl)pyrazolo[1,5-a]pyrimidine-3-carboxamide (129);

N-(3-cyclopropyl-1-(p-tolyl)-1H-pyrazol-5-yl)pyrazolo[1,5-a]pyrimidine-3-carboxamide (130);

N-(3-(4-methoxyphenyl)-1-(p-tolyl)-1H-pyrazol-5-yl)pyrazolo[1,5-a]pyrimidine-3-carboxamide (131);

N-(1-(3-fluorophenyl)-3-(4-methoxyphenyl)-1H-pyrazol-5-yl)pyrazolo[1,5-a]pyrimidine-3-carboxamide (132);

N-(3-(3,4-dimethoxyphenyl)-1-(p-tolyl)-1H-pyrazol-5-yl)pyrazolo[1,5-a]pyrimidine-3-carboxamide (133);

N-(3-(4-(methylsulfonyl)phenyl)-1-(p-tolyl)-1H-pyrazol-5-yl)pyrazolo[1,5-a]pyrimidine-3-carboxamide (134);

N-(3-(4-fluorophenyl)-1-(p-tolyl)-1H-pyrazol-5-yl)pyrazolo[1,5-a]pyrimidine-3-carboxamide (135);

N-(3-(5-fluoropyridin-3-yl)-1-(p-tolyl)-1H-pyrazol-5-yl)pyrazolo[1,5-a]pyrimidine-3-carboxamide (136);

N-(3-(pyrimidin-5-yl)-1-(p-tolyl)-1H-pyrazol-5-yl)pyrazolo[1,5-a]pyrimidine-3-carboxamide (137);

N-(3-(1,2,3,6-tetrahydropyridin-4-yl)-1-(p-tolyl)-1H-pyrazol-5-yl)pyrazolo[1,5-a]pyrimidine-3-carboxamide (138);

N-(3-(1-(methylsulfonyl)-1,2,3,6-tetrahydropyridin-4-yl)-1-(p-tolyl)-1H-pyrazol-5-yl)pyrazolo[1,5-a]pyrimidine-3-carboxamide (139);

N-(3-(1-methyl-1,2,3,6-tetrahydropyridin-4-yl)-1-(p-tolyl)-1H-pyrazol-5-yl)pyrazolo[1,5-a]pyrimidine-3-carboxamide (140);

N-(3-(4-(morpholinosulfonyl)phenyl)-1-(p-tolyl)-1H-pyrazol-5-yl)pyrazolo[1,5-a]pyrimidine-3-carboxamide (141);

N-(3-(pyrrolidin-1-ylmethyl)-1-(p-tolyl)-1,4-pyrazol-5-yl)pyrazolo[1,5-a]pyrimidine-3-carboxamide (142);

N-(3-(4-(pyrrolidin-1-ylmethyl)phenyl)-1-(p-tolyl)-1H-pyrazol-5-yl)pyrazolo[1,5-a]pyrimidine-3-carboxamide (143);

N-(3-(4-((4-methylpiperazin-1-yl)methylphenyl)-1-(p-tolyl)-1H-pyrazol-5-yl)pyrazolo[1,5-a]pyrimidine-3-carboxamide (144);

N-(3-(4-(morpholinomethyl)phenyl)-1-(p-tolyl)-1H-pyrazol-5-yl)pyrazolo[1,5-a]pyrimidine-3-carboxamide (145);

N-(1-(4-cyclopropylphenyl)-3-(piperidin-4-yl)-1H-pyrazol-5-yl)pyrazolo[1,5-a]pyrimidine-3-carboxamide (146);

N-(1-(5-cyclopropylpyridin-2-yl)-3-(1-methylpiperidin-4-yl)-1H-pyrazol-5-yl)pyrazolo[1,5-a]pyrimidine-3-carboxamide (147);

N-(3-(1-cyclobutylpiperidin-4-yl)-1-(5-cyclopropylpyridin-2-yl)-1H-pyrazol-5-yl)pyrazolo[1,5-a]pyrimidine-3-carboxamide (148);

N-(1-(5-cyclopropylpyridin-2-yl)-3-(1-(methylsulfonyl)piperidin-4-yl)-1H-pyrazol-5-yl)pyrazolo[1,5-a]pyrimidine-3-carboxamide (149);

N-(1-(5-cyclopropylpyridin-2-yl)-3-(1-(cyclopropylsulfonyl)piperidin-4-yl)-1H-pyrazol-5-yl)pyrazolo[1,5-a]pyrimidine-3-carboxamide (150);

N-(1-(5-cyclopropylpyridin-2-yl)-3-(4-(N-methylsulfamoyl)phenyl)-1H-pyrazol-5-yl)pyrazolo[1,5-a]pyrimidine-3-carboxamide (151);

N-(1-(5-methylpyridin-2-yl)-3-(piperidin-4-yl)-1H-pyrazol-5-yl)pyrazolo[1,5-a]pyrimidine-3-carboxamide (152);

N-(1-(5-methylpyridin-2-yl)-3-(1-(methylsulfonyl)piperidin-4-yl)-1H-pyrazol-5-yl)pyrazolo[1,5-a]pyrimidine-3-carboxamide (153);

N-(3-(1-(cyclopropylsulfonyl)piperidin-4-yl)-1-(5-methylpyridin-2-yl)-1H-pyrazol-5-yl)pyrazolo[1,5-a]pyrimidine-3-carboxamide (154);

N-(1-(5-trideuteromethylpyridin-2-yl)-3-(1-(methylsulfonyl)piperidin-4-yl)-1H-pyrazol-5-yl)pyrazolo[1,5-a]pyrimidine-3-carboxamide (155);

N-(1-(5-methoxypyridin-2-yl)-3-(1-(methylsulfonyl)piperidin-4-yl)-1H-pyrazol-5-yl)pyrazolo[1,5-a]pyrimidine-3-carboxamide (156);

N-(1-(5-(aminomethyl)pyridin-2-yl)-3-(1-(methylsulfonyl)piperidin-4-yl)-1H-pyrazol-5-yl)pyrazolo[1,5-a]pyrimidine-3-carboxamide (157);

N-(1-(5-(1-amino-2-methylpropan-2-yl)pyridin-2-yl)-3-(1-(methylsulfonyl)piperidin-4-yl)-1H-pyrazol-5-yl)pyrazolo[1,5-a]pyrimidine-3-carboxamide (158);

N-(1-(5-(2-aminopropan-2-yl)pyridin-2-yl)-3-(1-(methylsulfonyl)piperidin-4-yl)-1H-pyrazol-5-yl)pyrazolo[1,5-a]pyrimidine-3-carboxamide (159);

N-(1-(5-carbamoylpyridin-2-yl)-3-(piperidin-4-yl)-1H-pyrazol-5-yl)pyrazolo[1,5-a]pyrimidine-3-carboxamide (160);

N-(1-(5-(1-(methylamino)ethyl)pyridin-2-yl)-3-(1-(methylsulfonyl)piperidin-4-yl)-1H-pyrazol-5-yl)pyrazolo[1,5-a]pyrimidine-3-carboxamide (161);

N-(1-(5-(hydroxymethyl)pyridin-2-yl)-3-(1-(methylsulfonyl)piperidin-4-yl)-1H-pyrazol-5-yl)pyrazolo[1,5-a]pyrimidine-3-carboxamide (162);

(R)—N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide (163);

(S)—N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide (164);

N-(1-(5-formylpyridine-2-yl)-3-(1-(methylsulfonyl)piperidin-4-yl)-1H-pyrazol-5-yl)pyrazolo[1,5-a]pyrimidine-3-carboxamide (165);

N-(1-(5-methylpyridin-2-yl)-3-(morpholin-3-yl)-1H-pyrazol-5-yl)pyrazolo[1,5-a]pyrimidine-3-carboxamide (166);

N-(1-(6-methylpyridin-3-yl)-3-(piperidin-4-yl)-1H-pyrazol-5-yl)pyrazolo[1,5-a]pyrimidine-3-carboxamide (167);

N-(1-(6-methylpyridin-3-yl)-3-(1-(methylsulfonyl)piperidin-4-yl)-1H-pyrazol-5-yl)pyrazolo[1,5-a]pyrimidine-3-carboxamide (168);

N-(1-(5-methylpyrimidin-2-yl)-3-(piperidin-4-yl)-1H-pyrazol-5-yl)pyrazolo[1,5-a]pyrimidine-3-carboxamide (169);

N-(1-(5-methylpyrimidin-2-yl)-3-(1-(methylsulfonyl)piperidin-4-yl)-1H-pyrazol-5-yl)pyrazolo[1,5-a]pyrimidine-3-carboxamide (170);

N-(3-(1-(cyclopropylsulfonyl)piperidin-4-yl)-1-(5-methylpyrimidin-2-yl)-1H-pyrazol-5-yl)pyrazolo[1,5-a]pyrimidine-3-carboxamide (171);

N-(1-(5-methylpyrazin-2-yl)-3-(1-(methylsulfonyl)piperidin-4-yl)-1H-pyrazol-5-yl)pyrazolo[1,5-a]pyrimidine-3-carboxamide (172);

N-(3-(1-(methylsulfonyl)piperidin-4-yl)-1-(pyridin-2-yl)-1H-pyrazol-5-yl)pyrazolo[1,5-a]pyrimidine-3-carboxamide (173);

N-(1-(5,6-dimethylpyridin-2-yl)-3-(1-(methylsulfonyl)piperidin-4-yl)-1H-pyrazol-5-yl)pyrazolo[1,5-a]pyrimidine-3-carboxamide (174);

N-(1-(1,3-dimethyl-1H-pyrazolo[3,4-b]pyridin-6-yl)-3-(1-(methylsulfonyl)piperidin-4-yl)-1H-pyrazol-5-yl)pyrazolo[1,5-a]pyrimidine-3-carboxamide (175);

N-(1-(5-(aminomethyl)pyridin-2-yl)-3-(1-methylcyclopropyl)-1H-pyrazol-5-yl)pyrazolo[1,5-a]pyrimidine-3-carboxamide (176);

N-(1-(5-methylpyridin-2-yl)-3-(4-(morpholinosulfonyl)phenyl)-1H-pyrazol-5-yl)pyrazolo[1,5-a]pyrimidine-3-carboxamide (177);

N-(3-(4-((4-methylpiperazin-1-yl)sulfonyl)phenyl)-1-(5-methylpyridin-2-yl)-1H-pyrazol-5-yl)pyrazolo[1,5-a]pyrimidine-3-carboxamide (178);

N-(1-(5-methylpyridin-2-yl)-3-(4-(methylsulfonyl)phenyl)-1H-pyrazol-5-yl)pyrazolo[1,5-a]pyrimidine-3-carboxamide (179);

N-(3-cyclopropyl-1-(5-methylpyridin-2-yl)-1H-pyrazol-5-yl)pyrazolo[1,5-a]pyrimidine-3-carboxamide (180);

N-(3-(1-methylcyclopropyl)-1-(5-methylpyridin-2-yl)-1H-pyrazol-5-yl)pyrazolo[1,5-a]pyrimidine-3-carboxamide (181);

N-(3-methoxy-1-(5-methylpyridin-2-yl)-1H-pyrazol-5-yl)pyrazolo[1,5-a]pyrimidine-3-carboxamide (182);

methyl((4-(5-(pyrazolo[1,5-a]pyrimidine-3-carboxamido)-1-(p-tolyl)-1H-pyrazol-3-yl)cyclohexyl)methyl)carbamate (183);

N-(3-(4-(aminomethyl)cyclohexyl)-1-(p-tolyl)-1H-pyrazol-5-yl)pyrazolo[1,5-a]pyrimidine-3-carboxamide (184);

N-(3-(4-aminocyclohexyl)-1-(5-methylpyridin-2-yl)-1H-pyrazol-5-yl)pyrazolo[1,5-a]pyrimidine-3-carboxamide (185);

N-(1-(2-aminoethyl)-3-(1-(methylsulfonyl)piperidin-4-yl)-1H-pyrazol-5-yl)pyrazolo[1,5-a]pyrimidine-3-carboxamide (186);

N-(1-(1H-imidazol-2-yl)-3-(1-isopropylpiperidin-4-yl)-1H-pyrazol-5-yl)pyrazolo[1,5-a]pyrimidine-3-carboxamide (187);

N-(1-(1-(methylsulfonyl)-1H-imidazol-2-yl)-3-(1-(methylsulfonyl)piperidin-4-yl)-1H-pyrazol-5-yl)pyrazolo[1,5-a]pyrimidine-3-carboxamide (188);

N-(3-(piperidin-4-yl)-1-(thiazol-2-yl)-1H-pyrazol-5-yl)pyrazolo[1,5-a]pyrimidine-3-carboxamide (189);

6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (190);

6-cyano-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (191);

N3-(3-(1-(methylsulfonyl)piperidin-4-yl)-1-(p-tolyl)-1H-pyrazol-5-yl)pyrazolo[1,5-a]pyrimidine-3,6-dicarboxamide (192);

6-ethynyl-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (193);

6-bromo-N-(1-(5-methylpyridin-2-yl)-3-(4-(N-methylsulfamoyl)phenyl)-1H-pyrazol-5-yl)pyrazolo[1,5-a]pyrimidine-3-carboxamide (194);

6-cyclopropyl-N-(1-(5-methylpyridin-2-yl)-3-(4-(N-methylsulfamoyl)phenyl)-1H-pyrazol-5-yl)pyrazolo[1,5-a]pyrimidine-3-carboxamide (195);

6-chloro-N-(1-(5-methylpyridin-2-yl)-3-(4-(N-methylsulfamoyl)phenyl)-1H-pyrazol-5-yl)pyrazolo[1,5-a]pyrimidine-3-carboxamide (196);

N-(3-(4-methylpiperazin-1-yl)-1-(5-methylpyridin-2-yl)-1H-pyrazol-5-yl)pyrazolo[1,5-a]pyrimidine-3-carboxamide (197);

N-(3-(4-methylpiperazin-1-yl)-1-(5-trideuteromethylpyridin-2-yl)-1H-pyrazol-5-yl)pyrazolo[1,5-a]pyrimidine-3-carboxamide (198);

N-(1-(5-methylpyridin-2-yl)-3-(4-(methylsulfonyl)piperazin-1-yl)-1H-pyrazol-5-yl)pyrazolo[1,5-a]pyrimidine-3-carboxamide (199);

N-(1-(5-trideuteromethylpyridin-2-yl)-3-(4-(methylsulfonyl)piperazin-1-yl)-1H-pyrazol-5-yl)pyrazolo[1,5-a]pyrimidine-3-carboxamide (200);

N-(1-(5-cyclopropylpyridin-2-yl)-3-(4-methylpiperazin-1-yl)-1H-pyrazol-5-yl)pyrazolo[1,5-a]pyrimidine-3-carboxamide (201);

N-(1-(5-methylpyridin-2-yl)-3-morpholino-1H-pyrazol-5-yl)pyrazolo[1,5-a]pyrimidine-3-carboxamide (202);

N-[3-(1'-acetyl-1,4'-bipiperidin-4-yl)-1-(4-methylphenyl)-1H-pyrazol-5-yl]pyrazolo[1,5-a]pyrimidine-3-carboxamide (203);

N-[3-(1-cyclohexylpiperidin-4-yl)-1-(4-methylphenyl)-1H-pyrazol-5-yl]pyrazolo[1,5-a]pyrimidine-3-carboxamide (204);

N-[3-(1-cyclobutylpiperidin-4-yl)-1-(4-methylphenyl)-1H-pyrazol-5-yl]pyrazolo[1,5-a]pyrimidine-3-carboxamide (205);

N-[3-(1'-methyl-1,4'-bipiperidin-4-yl)-1-(4-methylphenyl)-1H-pyrazol-5-yl]pyrazolo[1,5-a]pyrimidine-3-carboxamide (206);

N-{1-(4-methylphenyl)-3-[1-(tetrahydro-2H-pyran-4-yl)piperidin-4-yl]-1H-pyrazol-5-yl}pyrazolo[1,5-a]pyrimidine-3-carboxamide (207);

ethyl 4-{1-(4-methylphenyl)-5-[(pyrazolo[1,5-a]pyrimidin-3-ylcarbonyl)amino]-1H-pyrazol-3-yl}-1,4'-bipiperidine-1'-carboxylate (208);

N-(3-(1-(3-methylbutan-2-yl)piperidin-4-yl)-1-(p-tolyl)-1H-pyrazol-5-yl)pyrazolo[1,5-a]pyrimidine-3-carboxamide (209);

N-(3-(1-(sec-butyl)piperidin-4-yl)-1-(p-tolyl)-1H-pyrazol-5-yl)pyrazolo[1,5-a]pyrimidine-3-carboxamide (210);

N-(3-(1-(1-methoxypropan-2-yl)piperidin-4-yl)-1-(p-tolyl)-1H-pyrazol-5-yl)pyrazolo[1,5-a]pyrimidine-3-carboxamide (211):

N-(3-(1-(1-(3-fluoropyridin-2-yl)ethyl)piperidin-4-yl)-1-(p-tolyl)-1H-pyrazol-5-yl)pyrazolo[1,5-a]pyrimidine-3-carboxamide (212);

N-(3-(1-(1-oxo-1-(piperidin-1-yl)propan-2-yl)piperidin-4-yl)-1-(p-tolyl)-1H-pyrazol-5-yl)pyrazolo[1,5-a]pyrimidine-3-carboxamide (213);

N-(3-(1-(1-oxo-1-(pyrrolidin-1-yl)propan-2-yl)piperidin-4-yl)-1-(p-tolyl)-1H-pyrazol-5-yl)pyrazolo[1,5-a]pyrimidine-3-carboxamide (214);

N-(3-(1-(1-(6-fluoropyridin-2-yl)ethyl)piperidin-4-yl)-1-(p-tolyl)-1H-pyrazol-5-yl)pyrazolo[1,5-a]pyrimidine-3-carboxamide (215);

N-[3-(1'-cyclopropyl-1,4'-bipiperidin-4-yl)-1-(4-methylphenyl)-1H-pyrazol-5-yl]pyrazolo[1,5-a]pyrimidine-3-carboxamide (216);

N-[1-(4-methylphenyl)-3-{1-[1-(1,3-thiazol-2-yl)ethyl]piperidin-4-yl}-1H-pyrazol-5-yl]pyrazolo[1,5-a]pyrimidine-3-carboxamide (217);

N-[3-(1-benzylpiperidin-4-yl)-1-(4-methylphenyl)-1H-pyrazol-5-yl]pyrazolo[1,5-a]pyrimidine-3-carboxamide (218);

N-{1-(4-methylphenyl)-3-[1-(2-methylpropyl)piperidin-4-yl]-1H-pyrazol-5-yl}pyrazolo[1,5-a]pyrimidine-3-carboxamide (219);

N-[1-(4-methylphenyl)-3-(1-propylpiperidin-4-yl)-1H-pyrazol-5-yl]pyrazolo[1,5-a]pyrimidine-3-carboxamide (220);

N-{3-[1-(cyclopropylmethyl)piperidin-4-yl]-1-(4-methylphenyl)-1H-pyrazol-5-yl}pyrazolo[1,5-a]pyrimidine-3-carboxamide (221);

N-{1-(4-methylphenyl)-3-[1-(1,3-thiazol-2-ylmethyl)piperidin-4-yl]-1H-pyrazol-5-yl}pyrazolo[1,5-a]pyrimidine-3-carboxamide (222);

N-{1-(4-methylphenyl)-3-[1-(thiophen-3-ylmethyl)piperidin-4-yl]-1H-pyrazol-5-yl}pyrazolo[1,5-a]pyrimidine-3-carboxamide (223);

N-(3-(1-(pyridin-4-ylmethyl)piperidin-4-yl)-1-(p-tolyl)-1H-pyrazol-5-yl)pyrazolo[1,5-a]pyrimidine-3-carboxamide (224);

N-{1-(4-methylphenyl)-3-[1-(pyridin-3-ylmethyl)piperidin-4-yl]-1H-pyrazol-5-yl}pyrazolo[1,5-a]pyrimidine-3-carboxamide (225);

N-{1-(4-methylphenyl)-3-[1-(pyridin-2-ylmethyl)piperidin-4-yl]-1H-pyrazol-5-yl}pyrazolo[1,5-a]pyrimidine-3-carboxamide (226);

N-[3-{1-[(6-methoxypyridin-3-yl)methyl]piperidin-4-yl}-1-(4-methylphenyl)-1H-pyrazol-5-yl]pyrazolo[1,5-a]pyrimidine-3-carboxamide (227);

N-{1-(4-methylphenyl)-3-[1-(tetrahydrofuran-3-ylmethyl)piperidin-4-yl]-1H-pyrazol-5-yl}pyrazolo[1,5-a]pyrimidine-3-carboxamide (228);

N-{1-(4-methylphenyl)-3-[1-(1,3-thiazol-5-ylmethyl)piperidin-4-yl]-1H-pyrazol-5-yl}pyrazolo[1,5-a]pyrimidine-3-carboxamide (229);
N-{1-(4-methylphenyl)-3-[1-(1H-pyrazol-5-ylmethyl)piperidin-4-yl]-1H-pyrazol-5-yl}pyrazolo[1,5-a]pyrimidine-3-carboxamide (230);
N-{1-(4-methylphenyl)-3-[1-(1,3-thiazol-4-ylmethyl)piperidin-4-yl]-1H-pyrazol-5-yl}pyrazolo[1,5-a]pyrimidine-3-carboxamide (231);
N-{1-(4-methylphenyl)-3-[1-(1,3-oxazol-2-ylmethyl)piperidin-4-yl]-1H-pyrazol-5-yl}pyrazolo[1,5-a]pyrimidine-3-carboxamide (232);
N-{1-(4-methylphenyl)-3-[1-(1H-pyrazol-4-ylmethyl)piperidin-4-yl]-1H-pyrazol-5-yl}pyrazolo[1,5-a]pyrimidine-3-carboxamide (233);
N-[3-(1-azetidin-3-ylpiperidin-4-yl)-1-(4-m ethylphenyl)-1H-pyrazol-5-yl]pyrazolo[1,5-a]pyrimidine-3-carboxamide (234);
N-[3-(1-{1-[(1-methylethyl)carbamoyl]azetidin-3-yl}piperidin-4-yl)-1-(4-methylphenyl)-1H-pyrazol-5-yl]pyrazolo[1,5-a]pyrimidine-3-carboxamide (235);
N-[3-{1-[1-(tert-butylcarbamoyl)azetidin-3-yl]piperidin-4-yl}-1-(4-methylphenyl)-1H-pyrazol-5-yl]pyrazolo[1,5-a]pyrimidine-3-carboxamide (236);
N-[3-{1-[1-(ethylcarbamoyl)azetidin-3-yl]piperidin-4-yl}-1-(4-methylphenyl)-1H-pyrazol-5-yl]pyrazolo[1,5-a]pyrimidine-3-carboxamide (237);
methyl 3-(4-{1'-(4-methylphenyl)-5-[(pyrazolo[1,5-a]pyrimidin-3-ylcarbonyl)amino]-1H-pyrazol-3-yl}piperidin-1-yl)azetidine-1-carboxylate (238);
ethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (239);
1-methylethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (240);
2-fluoroethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (241);
2-methoxyethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (242);
N-[3-{1-[1-(ethylsulfonyl)azetidin-3-yl]piperidin-4-yl}-1-(4-methylphenyl)-1H-pyrazol-5-yl]pyrazolo[1,5-a]pyrimidine-3-carboxamide (243);
N-[1-(4-methylphenyl)-3-{1-[1-(methylsulfonyl)azetidin-3-yl]piperidin-4-yl}-1H-pyrazol-5-yl]pyrazolo[1,5-a]pyrimidine-3-carboxamide (244);
N-[3-{1-[1-(cyclopropylsulfonyl)azetidin-3-yl]piperidin-4-yl}-1-(4-methylphenyl)-1H-pyrazol-5-yl]pyrazolo[1,5-a]pyrimidine-3-carboxamide (245);
N-[3-(1-{1-[(1-methylethyl)sulfonyl]azetidin-3-yl}piperidin-4-yl)-1-(4-methylphenyl)-1H-pyrazol-5-yl]pyrazolo[1,5-a]pyrimidine-3-carboxamide (246);
N-[3-(1-{1-[(fluoromethyl)sulfonyl]azetidin-3-yl}piperidin-4-yl)-1-(4-methylphenyl)-1H-pyrazol-5-yl]pyrazolo[1,5-a]pyrimidine-3-carboxamide (247);
N-{3-[1-(1-acetylazetidin-3-yl)piperidin-4-yl]-1-(4-methylphenyl)-1H-pyrazol-5-yl}pyrazolo pyrimidine-3-carboxamide (248);
N-{1-(4-methylphenyl)-3-[1-(1-propanoylazetidin-3-yl)piperidin-4-yl]-1H-pyrazol-5-yl}pyrazolo[1,5-a]pyrimidine-3-carboxamide (249);
N-[1-(4-methylphenyl)-3-{1-[4-(trifluoromethyl)cyclohexyl]piperidin-4-yl}-1H-pyrazol-5-yl]pyrazolo[1,5-a]pyrimidine-3-carboxamide (250);
N-[3-(1-{4-[methyl(methylsulfonyl)amino]cyclohexyl}piperidin-4-yl)-1-(4-methylphenyl)-1H-pyrazol-5-yl]pyrazolo[1,5-a]pyrimidine-3-carboxamide (251);
N-[1-(4-methylphenyl)-3-(1-{4-[(methylsulfonyl)amino]cyclohexyl}piperidin-4-yl)-1H-pyrazol-5-yl]pyrazolo[1,5-a]pyrimidine-3-carboxamide (252);
N-{3-[1-(4-cyanocyclohexyl)piperidin-4-yl]-1-(4-methylphenyl)-1H-pyrazol-5-yl}pyrazolo[1,5-a]pyrimidine-3-carboxamide (253);
N-[3-(1-bicyclo[3.1.0]hex-2-ylpiperidin-4-yl)-1-(4-methylphenyl)-1H-pyrazol-5-yl]pyrazolo[1,5-a]pyrimidine-3-carboxamide (254);
N-{1-(4-methylphenyl)-3-[1-(2-oxo-1-azaspiro[4.5]dec-8-yl)piperidin-4-yl]-1H-pyrazol-5-yl}pyrazolo[1,5-a]pyrimidine-3-carboxamide (255);
N-{3-[1-(3-tert-butylcyclobutyl)piperidin-4-yl]-1-(4-methylphenyl)-1H-pyrazol-5-yl}pyrazolo[1,5-a]pyrimidine-3-carboxamide (256);
N-[1-(4-methylphenyl)-3-(1-spiro[3.4]oct-2-ylpiperidin-4-yl)-1H-pyrazol-5-yl]pyrazolo[1,5-a]pyrimidine-3-carboxamide (257);
N-{3-[1-(3-cyanocyclobutyl)piperidin-4-yl]-1-(4-methylphenyl)-1H-pyrazol-5-yl}pyrazolo[1,5-a]pyrimidine-3-carboxamide (258);
N-{3-[1-(4,4-difluorocyclohexyl)piperidin-4-yl]-1-(4-methylphenyl)-1H-pyrazol-5-yl}pyrazolo[1,5-a]pyrimidine-3-carboxamide (259);
N-{1-(4-methylphenyl)-3-[1-(3,3,3-trifluoro-1-methylpropyl)piperidin-4-yl]-1H-pyrazol-5-yl}pyrazolo[1,5-a]pyrimidine-3-carboxamide (260);
tert-butyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate (261);
N-[3-(1-{4-[methyl(methylsulfonyl)amino]cyclohexyl}piperidin-4-yl)-1-(5-methylpyridin-2-yl)-1H-pyrazol-5-yl]pyrazolo[1,5-a]pyrimidine-3-carboxamide (262);
N-[1-(5-methylpyridin-2-yl)-3-(1-{4-[(methylsulfonyl)amino]cyclohexyl}piperidin-4-yl)-1H-pyrazol-5-yl}pyrazolo[1,5-a]pyrimidine-3-carboxamide (263);
N-{1-(5-methylpyridin-2-yl)-3-[1-(tetrahydro-2H-pyran-3-yl)piperidin-4-yl]-1H-pyrazol-5-yl}pyrazolo[1,5-a]pyrimidine-3-carboxamide (264);
N-{3-[1-(4-cyanocyclohexyl)piperidin-4-yl]-1-(5-methylpyridin-2-yl)-1H-pyrazol-5-yl}pyrazolo[1,5-a]pyrimidine-3-carboxamide (265);
N-[3-{1-[1-(4-fluorophenyl)pyrrolidin-3-yl]piperidin-4-yl]-1-(5-methylpyridin-2-yl)-1H-pyrazol-5-yl}pyrazolo-[1,5-a]pyrimidine-3-carboxamide (266);
N-[3-(1'-cyclopropyl-1,4'-bipiperidin-4-yl)-1-(5-methylpyridin-2-yl)-1H-pyrazol-5-yl]pyrazolo[1,5-a]pyrimidine-3-carboxamide (267);
N-{1-(5-methylpyridin-2-yl)-3-[1-(5,6,7,8-tetrahydroisoquinolin-7-yl)piperidin-4-yl]-1H-pyrazol-5-yl}pyrazolo[1,5-a]pyrimidine-3-carboxamide (268);
N-[3-{1-[3-(dimethylamino)cyclobutyl]piperidin-4-yl}-1-(5-methylpyridin-2-yl)-1H-pyrazol-5-yl]pyrazolo[1,5-a]pyrimidine-3-carboxamide (269);
N-{3-[1-(1-methylethyl)piperidin-4-yl]-1-(5-methylpyridin-2-yl)-1H-pyrazol-5-yl}pyrazolo[1,5-a]pyrimidine-3-carboxamide (270);
N-[1-(5-methylpyridin-2-yl)-3-{1-[4-(trifluoromethyl)cyclohexyl]piperidin-4-yl}-1H-pyrazol-5-yl]pyrazolo[1,5-a]pyrimidine-3-carboxamide (271);
N-{3-[1-(3-methylcyclopentyl)piperidin-4-yl]-1-(5-methylpyridin-2-yl)-1H-pyrazol-5-yl}pyrazolo[1,5-a]pyrimidine-3-carboxamide (272);

N-[3-{1-[(3R)-3-methylcyclopentyl]piperidin-4-yl}-1-(5-methylpyridin-2-yl)-1H-pyrazol-5-yl]pyrazolo[1,5-a]pyrimidine-3-carboxamide (273);

N-[3-(1-cyclobutylpiperidin-4-yl)-1-(5-methylpyridin-2-yl)-1H-pyrazol-5-yl]pyrazolo[1,5-a]pyrimidine-3-carboxamide (274);

N-[3-(1'-methyl-1,4'-bipiperidin-4-yl)-1-(5-methylpyridin-2-yl)-1H-pyrazol-5-yl]pyrazolo[1,5-a]pyrimidine-3-carboxamide (275);

ethyl 4-{1-(5-methylpyridin-2-yl)-5-[(pyrazolo[1,5-a]pyrimidin-3-ylcarbonyl)amino]-1H-pyrazol-3-yl}-1,4'-bipiperidine-1'-carboxylate (276);

N-{3-[1-(3-methylcyclohexyl)piperidin-4-yl]-1-(5-methylpyridin-2-yl)-1H-pyrazol-5-yl}pyrazolo[1,5-a]pyrimidine-3-carboxamide (277);

N-{3-[1-(2-methylpropyl)piperidin-4-yl]-1-(5-methylpyridin-2-yl)-1H-pyrazol-5-yl}pyrazolo[1,5-a]pyrimidine-3-carboxamide (278);

N-[3-(1'-ethyl-1,4'-bipiperidin-4-yl)-1-(5-methylpyridin-2-yl)-1H-pyrazol-5-yl]pyrazolo[1,5-a]pyrimidine-3-carboxamide (279);

N-[1-(5-methylpyridin-2-yl)-3-(1-propylpiperidin-4-yl)-1H-pyrazol-5-yl]pyrazolo[1,5-a]pyrimidine-3-carboxamide (280);

N-{3-[1-(cyclopropylmethyl)piperidin-4-yl]-1-(5-methylpyridin-2-yl)-1H-pyrazol-5-yl}pyrazolo[1,5-a]pyrimidine-3-carboxamide (281);

N-{3-[1-(2,3-dihydro-1H-inden-2-yl)piperidin-4-yl]-1-(5-methylpyridin-2-yl)-1H-pyrazol-5-yl}pyrazolo[1,5-a]pyrimidine-3-carboxamide (282);

N-{1-(4-methylphenyl)-3-[1-(tetrahydrofuran-3-ylmethyl)piperidin-3-yl]-1H-pyrazol-5-yl}pyrazolo[1,5-a]pyrimidine-3-carboxamide (283);

N-{1-(4-methylphenyl)-3-[1-(1,3-thiazol-5-ylmethyl)piperidin-3-yl]-1H-pyrazol-5-yl}pyrazolo[1,5-a]pyrimidine-3-carboxamide (284);

N-[1-(4-methylphenyl)-3-{1-[(3-oxo-2,3-dihydro-1H-isoindol-5-yl)methyl]piperidin-3-yl}-1H-pyrazol-5-yl]pyrazolo[1,5-a]pyrimidine-3-carboxamide (285);

N-[3-(1-{[2-(dimethylamino)-1,3-thiazol-5-yl]methyl}piperidin-3-yl)-1-(4-methylphenyl)-1H-pyrazol-5-yl]pyrazolo[1,5-a]pyrimidine-3-carboxamide (286);

N-{1-(4-methylphenyl)-3-[1-(1H-pyrazol-5-ylmethyl)piperidin-3-yl]-1H-pyrazol-5-yl}pyrazolo[1,5-a]pyrimidine-3-carboxamide (287);

N-{1-(4-methylphenyl)-3-[1-(1,3-thiazol-4-ylmethyl)piperidin-3-yl]-1H-pyrazol-5-yl}pyrazolo[1,5-a]pyrimidine-3-carboxamide (288);

N-{1-(4-methylphenyl)-3-[1-(1,3-oxazol-2-ylmethyl)piperidin-3-yl]-1H-pyrazol-5-yl}pyrazolo[1,5-a]pyrimidine-3-carboxamide (289);

N-[3-{1-[(2-fluoropyridin-3-yl)methyl]piperidin-3-yl}-1-(4-methylphenyl)-1H-pyrazol-5-yl]pyrazolo[1,5-a]pyrimidine-3-carboxamide (290);

N-[3-{1-[(2-methoxypyrimidin-5-yl)methyl]piperidin-3-yl}-1-(4-methylphenyl)-1H-pyrazol-5-yl]pyrazolo[1,5-a]pyrimidine-3-carboxamide (291);

N-[3-{1-[(5-fluoropyridin-2-yl)methyl]piperidin-3-yl}-1-(4-methylphenyl)-1H-pyrazol-5-yl]pyrazolo[1,5-a]pyrimidine-3-carboxamide (292);

N-[3-{1-[4-(3-cyanooxetan-3-3/1)benzyl]piperidin-3-yl}-1-(4-methylphenyl)-1H-pyrazol-5-yl]pyrazolo[1,5-a]pyrimidine-3-carboxamide (293);

N-{1-(4-methylphenyl)-3-[1-(1H-pyrazol-4-ylmethyl)piperidin-3-yl]-1H-pyrazol-5-yl}pyrazolo[1,5-a]pyrimidine-3-carboxamide (294);

N-[1-(4-methylphenyl)-3-{1-[(1-oxo-2,3-dihydro-1H-isoindol-4-yl)methyl]piperidin-3-yl}-1H-pyrazol-5-yl]pyrazolo[1,5-a]pyrimidine-3-carboxamide (295);

N-[1-(4-methylphenyl)-3-{1-[4-(methylsulfonyl)benzyl]piperidin-3-yl}-1H-pyrazol-5-yl]pyrazolo[1,5-a]pyrimidine-3-carboxamide (296);

N-{3-[1-(cyclopropylmethyl)piperidin-3-yl]-1-(4-methylphenyl)-1H-pyrazol-5-yl}pyrazolo[1,5-a]pyrimidine-3-carboxamide (297);

N-{1-(4-methylphenyl)-3-[1-(1,3-thiazol-2-ylmethyl)piperidin-3-yl]-1H-pyrazol-5-yl}pyrazolo[1,5-a]pyrimidine-3-carboxamide (298);

N-{1-(4-methylphenyl)-3-[1-(pyridin-4-ylmethyl)piperidin-3-yl]-1H-pyrazol-5-yl}pyrazolo[1,5-a]pyrimidine-3-carboxamide (299);

N-{1-(4-methylphenyl)-3-[1-(pyridin-3-ylmethyl)piperidin-3-yl]-1H-pyrazol-5-yl}pyrazolo[1,5-a]pyrimidine-3-carboxamide (300);

N-{1-(4-methylphenyl)-3-[1-(pyridin-2-ylmethyl)piperidin-3-yl]-1H-pyrazol-5-yl}pyrazolo[1,5-a]pyrimidine-3-carboxamide (301);

N-[3-{1-[(6-methoxypyridin-3-yl)methyl]piperidin-3-yl}-1-(4-methylphenyl)-1H-pyrazol-5-yl]pyrazolo[1,5-a]pyrimidine-3-carboxamide (302);

N-[3-{1-[(1-ethyl-1H-pyrazol-5-yl)methyl]piperidin-3-yl}-1-(4-methylphenyl)-1H-pyrazol-5-yl]pyrazolo[1,5-a]pyrimidine-3-carboxamide (303);

N-{1-(4-methylphenyl)-3-[1-(pyrazin-2-ylmethyl)azetidin-3-yl]-1H-pyrazol-5-yl}pyrazolo[1,5-a]pyrimidine-3-carboxamide (304);

N-{1-(4-methylphenyl)-3-[1-(1H-pyrazol-4-ylmethyl)azetidin-3-yl]-1H-pyrazol-5-yl}pyrazolo[1,5-a]pyrimidine-3-carboxamide (305);

N-{1-(4-methylphenyl)-3-[1-(1H-pyrazol-5-ylmethyl)azetidin-3-yl]-1H-pyrazol-5-yl}pyrazolo[1,5-a]pyrimidine-3-carboxamide (306);

N-{1-(4-methylphenyl)-3-[1-(1,3-thiazol-2-ylmethyl)azetidin-3-yl]-1H-pyrazol-5-yl}pyrazolo[1,5-a]pyrimidine-3-carboxamide (307);

N-{1-(4-methylphenyl)-3-[1-(pyridin-2-ylmethyl)azetidin-3-yl]-1H-pyrazol-5-yl}pyrazolo[1,5-a]pyrimidine-3-carboxamide (308);

N-{1-(4-methylphenyl)-3-[1-(pyridin-4-ylmethyl)azetidin-3-yl]-1H-pyrazol-5-yl}pyrazolo[1,5-a]pyrimidine-3-carboxamide (309);

N-{1-(4-methylphenyl)-3-[1-(pyrimidin-5-ylmethyl)azetidin-3-yl]-1H-pyrazol-5-yl}pyrazolo[1,5-a]pyrimidine-3-carboxamide (310);

N-[3-{1-[(5-methylisoxazol-3-yl)methyl]azetidin-3-yl]-1-(4-methylphenyl)-1H-pyrazol-5-yl}pyrazolo[1,5-a]pyrimidine-3-carboxamide (311);

N-{1-(4-methylphenyl)-3-[1-(1,3-thiazol-5-ylmethyl)azetidin-3-yl]-1H-pyrazol-5-yl}pyrazolo[1,5-a]pyrimidine-3-carboxamide (312);

N-[3-{1-[(2-methoxypyridin-3-yl)methyl]azetidin-3-yl}-1-(4-methylphenyl)-1H-pyrazol-5-yl]pyrazolo[1,5-a]pyrimidine-3-carboxamide (313);

N-{1-(4-methylphenyl)-3-[1-(pyridin-3-ylmethyl)azetidin-3-yl]-1H-pyrazol-5-yl}pyrazolo[1,5-a]pyrimidine-3-carboxamide (314);

N-[3-{1-[(6-methoxypyridin-2-yl)methyl]azetidin-3-yl}-1-(4-methylphenyl)-1H-pyrazol-5-yl]pyrazolo pyrimidine-3-carboxamide (315);

N-{1-(4-methylphenyl)-3-[1-(1,3-oxazol-2-ylmethyl)azetidin-3-yl]-1H-pyrazol-5-yl}pyrazolo[1,5-a]pyrimidine-3-carboxamide (316);

N-[3-{1-[(2-methoxypyrimidin-5-yl)methyl]azetidin-3-yl}-1-(4-methylphenyl)-1H-pyrazol-5-yl]pyrazolo[1,5-a]pyrimidine-3-carboxamide (317);

N-{1-(4-methylphenyl)-3-[1-(1,3-oxazol-4-ylmethyl)azetidin-3-yl]-1H-pyrazol-5-yl}pyrazolo[1,5-a]pyrimidine-3-carboxamide (318);

N-[3-(4-cyclohexylpiperazin-1-yl)-1-(5-methylpyridin-2-yl)-1H-pyrazol-5-yl]pyrazolo[1,5-a]pyrimidine-3-carboxamide (319);

N-[3-(4-cyclobutylpiperazin-1-yl)-1-(5-methylpyridin-2-yl)-1H-pyrazol-5-yl]pyrazolo[1,5-a]pyrimidine-3-carboxamide (320);

N-{1-(5-methylpyridin-2-yl)-3-[4-(tetrahydro-2H-pyran-4-yl)piperazin-1-yl]-1H-pyrazol-5-yl}pyrazolo[1,5-a]pyrimidine-3-carboxamide (321);

N-[3-(4-cycloheptylpiperazin-1-yl)-1-(5-methylpyridin-2-yl)-1H-pyrazol-5-yl]pyrazolo[1,5-a]pyrimidine-3-carboxamide (322)

N-[3-(4-cyclopentylpiperazin-1-yl)-1-(5-methylpyridin-2-yl)-1H-pyrazol-5-yl]pyrazolo[1,5-a]pyrimidine-3-carboxamide (323);

N-{3-[4-(2-methylpropyl)piperazin-1-yl]-1-(5-methylpyridin-2-yl)-1H-pyrazol-5-yl}pyrazolo[1,5-a]pyrimidine-3-carboxamide (324);

N-(3-(1-cyclopentylpiperidin-4-yl)-1-(p-tolyl)-1H-pyrazol-5-yl)pyrazolo[1,5-a]pyrimidine-3-carboxamide (325);

N-[1'-methyl-1-(4-methylphenyl)-1H,1'H-3,4'-bipyrazol-5-]pyrazolo[1,5-a]pyrimidine-3-carboxamide (326);

N-{1-(4-methylphenyl)-3-[5-(4-methylpiperazin-1-yl)pyridin-3-yl]-1H-pyrazol-5-yl}pyrazolo[1,5-a]pyrimidine-3-carboxamide (327);

N-{1-(4-methylphenyl)-3-[2-(piperidin-1-ylmethyl)pyridin-4-yl]-1H-pyrazol-5-yl}pyrazolo[1,5-a]pyrimidine-3-carboxamide (328);

N-{3-[2-(hydroxymethyl)pyridin-4-yl]-1-(4-methylphenyl)-1H-pyrazol-5-yl}pyrazolo[1,5-a]pyrimidine-3-carboxamide (329);

N-{3-[6-(hydroxymethyl)pyridin-3-yl]-1-(4-methylphenyl)-1H-pyrazol-5-yl}pyrazolo[1,5-a]pyrimidine-3-carboxamide (330);

N-[2'-methyl-1-(4-methylphenyl)-1H,2'H-3,3'-bipyrazol-5-yl]pyrazolo[1,5-a]pyrimidine-3-carboxamide (331);

N-{3-[5-(hydroxymethyl)pyridin-3-yl]-1-(4-methylphenyl)-1H-pyrazol-5-yl}pyrazolo[1,5-a]pyrimidine-3-carboxamide (332);

N-{1-(4-methylphenyl)-1'-[2-(methylsulfonyl)ethyl]-1H,1'H-3,4'-bipyrazol-5-yl}pyrazolo[1,5-a]pyrimidine-3-carboxamide (333);

N-[3-(3-methylisoxazol-4-yl)-1-(4-methylphenyl)-1H-pyrazol-5-yl]pyrazolo[1,5-a]pyrimidine-3-carboxamide (334);

N-[1-(4-methylphenyl)-3-(2-morpholin-4-yl-1,3-thiazol-4-yl)-1H-pyrazol-5-yl]pyrazolo[1,5-a]pyrimidine-3-carboxamide (335);

N-{3-[4-(cyclopropylsulfonyl)phenyl]-1-(4-methylphenyl)-1H-pyrazol-5-yl}pyrazolo[1,5-a]pyrimidine-3-carboxamide (336);

N-[3-(1-methyl-6-oxo-1,6-dihydropyridin-3-yl)-1-(4-methylphenyl)-1H-pyrazol-5-yl]pyrazolo[1,5-a]pyrimidine-3-carboxamide (337);

N-{1-(4-methylphenyl)-3-[4-(methylsulfonyl)-2-(trifluoromethyl)phenyl]-1H-pyrazol-5-yl}pyrazolo[1,5-a]pyrimidine-3-carboxamide (338);

N-{3-[2-(benzyloxy)-6-fluorophenyl]-1-(4-methylphenyl)-1H-pyrazol-5-yl}pyrazolo[1,5-a]pyrimidine-3-carboxamide (339);

N-{3-[4-(diethylsulfamoyl)-2-methylphenyl]-1-(4-methylphenyl)-1H-pyrazol-5-yl}pyrazolo[1,5-a]pyrimidine-3-carboxamide (340);

N-[3-{4-[(1-methylethyl)sulfonyl]phenyl}-1-(4-methylphenyl)-1H-pyrazol-5-yl]pyrazolo[1,5-a]pyrimidine-3-carboxamide (341);

N-[1-(4-methylphenyl)-3-{4-[(4-methylpiperazin-1-yl)sulfonyl]phenyl}-1H-pyrazol-5-yl]pyrazolo[1,5-a]pyrimidine-3-carboxamide (342);

N-{3-[4-(diethylsulfamoyl)phenyl]-1-(4-methylphenyl)-1H-pyrazol-5-yl}pyrazolo[1,5-a]pyrimidine-3-carboxamide (343);

N-{3-[4-(azetidin-1-ylsulfonyl)phenyl]-1-(4-methylphenyl)-1H-pyrazol-5-yl}pyrazolo[1,5-a]pyrimidine-3-carboxamide (344);

N-{3-[4-(dimethylsulfamoyl)-2-methylphenyl]-1-(4-methylphenyl)-1H-pyrazol-5-yl}pyrazolo[1,5-a]pyrimidine-3-carboxamide (345);

N-[1-(4-methylphenyl)-3-{3-[(methylsulfonyl)amino]phenyl}-1H-pyrazol-5-yl]pyrazolo[1,5-a]pyrimidine-3-carboxamide (346);

N-{1-(4-methylphenyl)-3-[4-(methylsulfamoyl)phenyl]-1H-pyrazol-5-yl}pyrazolo[1,5-a]pyrimidine-3-carboxamide (347);

N-{3-[4-(methylcarbamoyl)phenyl]-1-(4-methylphenyl)-1H-pyrazol-5-yl}pyrazolo[1,5-a]pyrimidine-3-carboxamide (348);

N-{3-[4-(dimethylcarbamoyl)phenyl]-1-(4-methylphenyl)-1H-pyrazol-5-yl}pyrazolo[1,5-a]pyrimidine-3-carboxamide (349);

N-{3-[3-(methylcarbamoyl)phenyl]-1-(4-methylphenyl)-1H-pyrazol-5-yl}pyrazolo[1,5-a]pyrimidine-3-carboxamide (350);

N-{1-(4-methylphenyl)-3-[6-(methylsulfonyl)pyridin-3-yl]-1H-pyrazol-5-yl}pyrazolo[1,5-a]pyrimidine-3-carboxamide (351);

N-{3-[4-(ethylsulfonyl)phenyl]-1-(4-methylphenyl)-1H-pyrazol-5-yl}pyrazolo[1,5-a]pyrimidine-3-carboxamide (352);

N-{3-[4-(dimethylsulfamoyl)phenyl]-1-(4-methylphenyl)-1H-pyrazol-5-yl}pyrazolo[1,5-a]pyrimidine-3-carboxamide (353);

N-[3-(1-methyl-6-oxo-1,2,3,6-tetrahydropyridin-4-yl)-1-(4-methylphenyl)-1H-pyrazol-5-yl]pyrazolo[1,5-a]pyrimidine-3-carboxamide (354);

N-[3-(2-aminopyridin-4-yl)-1-(4-methylphenyl)-1H-pyrazol-5-yl]pyrazolo[1,5-a]pyrimidine-3-carboxamide (355);

N-[3-{1-[(1,2-benzisoxazol-3-ylmethyl)sulfonyl]piperidin-4-yl}-1-(4-methylphenyl)-1H-pyrazol-5-yl]pyrazolo[1,5-a]pyrimidine-3-carboxamide (356);

N-{1-(4-methylphenyl)-3-[1-(naphthalen-1-ylsulfonyl)piperidin-4-yl]-1H-pyrazol-5-yl}pyrazolo[1,5-a]pyrimidine-3-carboxamide (357);

N-[1-(4-methylphenyl)-3-{1-[(pyridin-4-ylmethyl)sulfonyl]piperidin-4-yl}-1H-pyrazol-5-yl]pyrazolo[1,5-a]pyrimidine-3-carboxamide (358);

N-[3-{1-[(3,4-dimethoxyphenyl)sulfonyl]piperidin-4-yl}-1-(4-methylphenyl)-1H-pyrazol-5-yl]pyrazolo[1,5-a]pyrimidine-3-carboxamide (359);

N-[3-{1-[(3,5-difluorophenyl)sulfonyl]piperidin-4-yl}-1-(4-methylphenyl)-1H-pyrazol-5-yl]pyrazolo[1,5-a]pyrimidine-3-carboxamide (360);

N-{1-(4-methylphenyl)-3-[1-(propylsulfonyl)piperidin-4-yl]-1H-pyrazol-5-yl}pyrazolo[1,5-a]pyrimidine-3-carboxamide (361);

N-[3-{1-[(2-cyanophenyl)sulfonyl]piperidin-4-yl}-1-(4-methylphenyl)-1H-pyrazol-5-yl]pyrazolo[1,5-a]pyrimidine-3-carboxamide (362);

N-[1-(4-methylphenyl)-3-{1-[(3,3,3-trifluoropropyl)sulfonyl]piperidin-4-yl}-1H-pyrazol-5-yl]pyrazolo[1,5-a]pyrimidine-3-carboxamide (363);

N-[3-{1-[(2,4-dimethyl-1,3-thiazol-5-yl)sulfonyl]piperidin-4-yl}-1-(4-methylphenyl)-1H-pyrazol-5-yl]pyrazolo[1,5-a]pyrimidine-3-carboxamide (364);

N-3-{1-[(3,4-difluorophenyl)sulfonyl]piperidin-4-yl}-1-(4-methylphenyl)-1H-pyrazol-5-yl]pyrazolo[1,5-a]pyrimidine-3-carboxamide (365);

N-[3-{1[(4-fluorophenyl)sulfonyl]piperidin-4-yl}-1-(4-methylphenyl)-1H-pyrazol-5-yl]pyrazolo[1,5-a]pyrimidine-3-carboxamide (366);

N-[3-{1-[(4-methoxyphenyl)sulfonyl]piperidin-4-yl}-1-(4-methylphenyl)-1H-pyrazol-5-yl]pyrazolo[1,5-a]pyrimidine-3-carboxamide (367);

N-[3-{1-[(1-methylethyl)sulfonyl]piperidin-4-yl}-1-(4-methylphenyl)-1H-pyrazol-5-yl]pyrazolo[1,5-a]pyrimidine-3-carboxamide (368);

N-{3-[1-(butylsulfonyl)piperidin-4-yl]-1-(4-methylphenyl)-1H-pyrazol-5-yl}pyrazolo[1,5-a]pyrimidine-3-carboxamide (369);

N-[3-{1-[(2,4-difluorophenyl)sulfonyl]piperidin-4-yl}-1-(4-methylphenyl)-1H-pyrazol-5-yl]pyrazolo[1,5-a]pyrimidine-3-carboxamide (370);

N-[1-(4-methylphenyl)-3-(1-{[3-(trifluoromethyl)phenyl]sulfonyl}piperidin-4-yl)-1H-pyrazol-5-yl]pyrazolo[1,5-a]pyrimidine-3-carboxamide (371);

N-[3-{1-[(2,4-dimethoxyphenyl)sulfonyl]piperidin-4-yl}-1-(4-methylphenyl)-1H-pyrazol-5-yl]pyrazolo[1,5-a]pyrimidine-3-carboxamide (372);

N-{3-[1-(cyclohexylsulfonyl)piperidin-4-yl]-1-(4-methylphenyl)-1H-pyrazol-5-yl}pyrazolo[1,5-a]pyrimidine-3-carboxamide (373);

N-[3-{1-[(3-cyanophenyl)sulfonyl]piperidin-4-yl}-1-(4-methylphenyl)-1H-pyrazol-5-yl]pyrazolo[1,5-a]pyrimidine-3-carboxamide (374);

N-[1-(4-methylphenyl)-3-{1-[(1-methyl-1H-pyrazol-4-yl)sulfonyl]piperidin-4-yl}-1H-pyrazol-5-yl]pyrazolo[1,5-a]pyrimidine-3-carboxamide (375);

N-[3-{1-[(1-methyl-1H-imidazol-4-yl)sulfonyl]piperidin-4-yl}-1-(4-methylphenyl)-1H-pyrazol-5-yl]pyrazolo[1,5-a]pyrimidine-3-carboxamide (376);

N-{1-(4-methylphenyl)-3-[1-(naphthalen-2-ylsulfonyl)piperidin-4-yl]-1H-pyrazol-5-yl}pyrazolo[1,5-a]pyrimidine-3-carboxamide (377);

N-[3-{1-[(2-fluorophenyl)sulfonyl]piperidin-4-yl}-1-(4-methylphenyl)-1H-pyrazol-5-yl]pyrazolo[1,5-a]pyrimidine-3-carboxamide (378);

N-[3-{1-[(3-fluorophenyl)sulfonyl]piperidin-4-yl}-1-(4-methylphenyl)-1H-pyrazol-5-yl]pyrazolo[1,5-a]pyrimidine-3-carboxamide (379);

N-[3-{1-[(4-cyanophenyl)sulfonyl]piperidin-4-yl}-1-(4-methylphenyl)-1H-pyrazol-5-yl]pyrazolo[1,5-a]pyrimidine-3-carboxamide (380);

N-[1-(4-methylphenyl)-3-(1-{[4-(trifluoromethyl)phenyl]sulfonyl}piperidin-4-yl)-1H-pyrazol-5-yl]pyrazolo[1,5-a]pyrimidine-3-carboxamide (381);

N-[3-{1-[(4-chloropyridin-3-yl)sulfonyl]piperidin-4-yl}-1-(4-methylphenyl)-1H-pyrazol-5-yl]pyrazolo[1,5-a]pyrimidine-3-carboxamide (382);

N-[1-(4-methylphenyl)-3-{1-[(6-morpholin-4-ylpyridin-3-yl)sulfonyl]piperidin-4-yl}-1H-pyrazol-5-yl]pyrazolo[1,5-a]pyrimidine-3-carboxamide (383);

N-{3-[1-(1,3-benzothiazol-6-ylsulfonyl)piperidin-4-yl]-1-(4-methylphenyl)-1H-pyrazol-5-yl}pyrazolo[1,5-a]pyrimidine-3-carboxamide (384);

N-[3-{1-[(3-methoxyphenyl)sulfonyl]piperidin-4-yl}-1-(4-methylphenyl)-1H-pyrazol-5-yl]pyrazolo[1,5-a]pyrimidine-3-carboxamide (385);

N-[3-{1-[(1,2-dimethyl-1H-imidazol-4-yl)sulfonyl]piperidin-4-yl}-1-(4-methylphenyl)-1H-pyrazol-5-yl]pyrazolo[1,5-a]pyrimidine-3-carboxamide (386);

N-{3-[1-(benzylsulfonyl)piperidin-4-yl]-1-(4-methylphenyl)-1H-pyrazol-5-yl}pyrazolo[1,5-a]pyrimidine-3-carboxamide (387);

N-[3-{1-[(2-chloropyridin-3-yl)sulfonyl]piperidin-4-yl}-1-(4-methylphenyl)-1H-pyrazol-5-yl]pyrazolo[1,5-a]pyrimidine-3-carboxamide (388);

N-[3-{1-[(6-methoxypyridin-3-yl)sulfonyl]piperidin-4-yl}-1-(4-methylphenyl)-1H-pyrazol-5-yl]pyrazolo[1,5-a]pyrimidine-3-carboxamide (389);

N-[3-{1-[(2,6-dichlorophenyl)sulfonyl]piperidin-4-yl}-1-(4-methylphenyl)-1H-pyrazol-5-yl]pyrazolo[1,5-a]pyrimidine-3-carboxamide (390);

N-[3-{1[(2,4-dichlorophenyl)sulfonyl]piperidin-4-yl}-1-(4-methylphenyl)-1H-pyrazol-5-yl]pyrazolo[1,5-a]pyrimidine-3-carboxamide (391);

N-[1-(4-methylphenyl)-3-{1-[(pyridin-3-ylmethyl)sulfonyl]piperidin-4-yl}-1H-pyrazol-5-yl]pyrazolo[1,5-a]pyrimidine-3-carboxamide (392);

N-[3-{1-[(5-chlorothiophen-2-yl)sulfonyl]piperidin-4-yl}-1-(4-methylphenyl)-1H-pyrazol-5-yl]pyrazolo[1,5-a]pyrimidine-3-carboxamide (393);

N-[1-(4-methylphenyl)-3-(1-{[6-(trifluoromethyl)pyridin-2-yl]sulfonyl}piperidin-4-yl)-1H-pyrazol-5-yl]pyrazolo[1,5-a]pyrimidine-3-carboxamide (394);

N-[1-(4-methylphenyl)-3-{1-[(2-phenylethyl)sulfonyl]piperidin-4-yl}-1H-pyrazol-5-yl]pyrazolo[1,5-a]pyrimidine-3-carboxamide (395);

N-{1-(4-methylphenyl)-3-[1-(quinolin-8-ylsulfonyl)piperidin-4-yl]-1H-pyrazol-5-yl}pyrazolo[1,5-a]pyrimidine-3-carboxamide (396);

N-[1-(4-methylphenyl)-3-{1-[(pyridin-2-ylmethyl)sulfonyl]piperidin-4-yl}-1H-pyrazol-5-yl]pyrazolo[1,5-a]pyrimidine-3-carboxamide (397);

N-(1-(4-cyclopropyl-2-fluorophenyl)-3-(1-methylpiperidin-4-yl)-1H-pyrazol-5-yl)pyrazolo[1,5-a]pyrimidine-3-carboxamide (398); and N-(3-(1-methylpiperidin-4-yl)-1-(5-methylpyridin-2-yl)-1H-pyrazol-5-yl)pyrazolo[1,5-a]pyrimidine-3-carboxamide (399);

or a pharmaceutically acceptable salt or stereoisomer thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When any variable (e.g. $R^4$) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases another embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, n-propyl, i-propyl, n-butyl, t-butyl, 1-butyl, pentyl, hexyl, heptyl, octyl, nonyl, decyl, and so on. The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethyl-cyclobutyl, 2-ethyl-cyclopentyl, cyclohexyl, cyclopentenyl, cyclobutenyl and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, benzimidazolonyl, benzoxazolonyl, quinolinyl, isoquinolinyl, dihydroisoindolonyl, imidazopyridinyl, isoindolonyl, indazolyl, oxazolyl, oxadiazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. For the purposes of this invention, the term "heterocyclic" is also considered to be synonymous with the terms "heterocycle" and "heterocyclyl" and is understood as also having the definitions set forth herein. "Heterocyclyl" therefore includes the above mentioned heteroaryls, as well as dihydro and tetrahydro analogs thereof. Further examples of "heterocyclyl" include, but are not limited to the following: azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxooxazolidinyl, oxazolyl, oxazoline, oxopiperazinyl, oxopyrrolidinyl, oxomorpholinyl, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrofuranyl, tetrahydrothiopyranyl, tetrahydroisoquinolinyl, tetrazolyl, tetrazolopyridyl, thiadiazolyl, thiazolyl, thienyl, triazolyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dioxidothiomorpholinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro, fluoro, bromo and iodo.

The alkyl, cycloalkyl, aryl, heteroaryl and heterocyclyl substituents may be substituted or unsubstituted, unless specifically defined otherwise. For example, a ($C_1$-$C_6$)alkyl may be substituted with one, two or three substituents selected from OH, oxo, halogen, alkoxy, dialkylamino, or heterocyclyl, such as morpholinyl, piperidinyl, and so on. In this case, if one substituent is oxo and the other is OH, the following are included in the definition: —C(=O)$CH_2$CH(OH)$CH_3$, —(C=O)OH, —$CH_2$(OH)$CH_2$CH(O), and so on.

Included in the instant invention is the free form of compounds of the instant invention, as well as the pharmaceutically acceptable salts and stereoisomers thereof. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,$N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. When the compound of the present invention is acidic, the term "free form" refers to the compound in its non-salt form, such that the acidic functionality is still protonated.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention may potentially be internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom. An isolated compound having internally balanced charges, and thus not associated with an intermolecular counterion, may also be considered the "free form" of a compound.

Utilities

The compounds of the invention are useful to bind to and/or modulate the activity of IRAK-4. In this context, modulate means either increasing or decreasing kinase activity of IRAK-4. In an embodiment, the compounds of the instant invention inhibit the kinase activity of IRAK-4.

The compounds of the invention find use in a variety of applications. As will be appreciated by those skilled in the art, the kinase activity of IRAK-4 may be modulated in a variety of ways; that is, one can affect the phosphorylationlactivation of IRAK-4 either by modulating the initial phosphorylation of the protein or by modulating the autophosphorylation of the other active sites of the protein. Alternatively, the kinase activity of IRAK-4 may be modulated by affecting the binding of a substrate of IRAK-4 phosphorylation.

The compounds of the invention are used to treat or prevent cellular proliferation diseases. Disease states which can be treated by the methods and compositions provided herein include, but are not limited to, cancer (further discussed below), autoimmune disease, viral disease, fungal disease, eurological/neurodegenerative disorders, arthritis, inflammation, anti-proliferative (e.g. ocular retinopathy), neuronal, alopecia, cardiovascular disease, graft rejection, inflammatory bowel disease, proliferation induced after medical procedures, including, but not limited to, surgery, angioplasty, and the like. It is appreciated that in some cases the cells may not be in a hyper- or hypoproliferation state (abnormal state) and still require treatment. Thus, in one embodiment, the invention herein includes application to cells or individuals which are afflicted or may eventually become afflicted with any one of these disorders or states.

The compounds, compositions and methods provided herein are particularly deemed useful for the treatment and prevention of cancer including solid tumors such as skin, breast, brain, cervical carcinomas, testicular carcinomas, etc. In an embodiment, the instant compounds are useful for treating cancer. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia,), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord (neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions. In an embodiment of the invention, cancers that may be treated by the compounds, compositions and methods of the invention include, in addition to the cancers listed above: Lung: bronchogenic carcinoma (non-small cell lung); Gastrointestinal: rectal, colorectal and colon; Genitourinary tract: kidney (papillary renal cell carcinoma); and Skin: head and neck squamous cell carcinoma.

In another embodiment, the compounds of the instant invention are useful for treating or preventing cancer selected from: head and neck squamous cell carcinomas, histiocytic lymphoma, lung adenocarcinoma, small cell lung cancer, non-small cell lung cancer, pancreatic cancer, papillary renal cell carcinoma, liver cancer, gastric cancer, colon cancer, multiple myeloma, glioblastomas and breast carcinoma. In yet another embodiment, the compounds of the instant invention are useful for treating or preventing cancer selected from: histiocytic lymphoma, lung adenocarcinoma, small cell lung cancer, pancreatic cancer, liver cancer, gastric cancer, colon cancer, multiple myeloma, glioblastomas and breast carcinoma. In still another embodiment, the compounds of the instant invention are useful for treating cancer selected from: histiocytic lymphoma, lung adenocarcinoma, small cell lung cancers, pancreatic cancer, liver cancer, gastric cancer, colon cancer, multiple myeloma, glioblastomas and breast carcinoma.

In another embodiment, the compounds of the instant invention are useful for the prevention or modulation of the metastases of cancer cells and cancer. In particular, the compounds of the instant invention are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

The compounds of this invention may be administered to mammals, preferably humans, either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and anti-oxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the instant invention can be selected in accordance with a variety of factors including type, species, age, weight, sex and the type of cancer being treated; the severity (i.e., stage) of the cancer to be treated; the route of administration; the renal and hepatic function of the patient; and the particular compound or salt thereof employed. An ordinarily skilled physician or veterinarian can readily determine and prescribe the effective amount of the drug required to treat, for example, to prevent, inhibit (fully or partially) or arrest the progress of the disease.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

In a further example, compounds of the instant invention can be administered in a total daily dose of up to 1000 mg. Compounds of the instant invention can be administered once daily (QD), or divided into multiple daily doses such as twice daily (BID), and three times daily (TID). Compounds of the instant invention can be administered at a total daily dosage of up to 1000 mg, e.g., 200 mg, 300 mg, 400 mg, 600 mg, 800 mg or 1000 mg, which can be administered in one daily dose or can be divided into multiple daily doses as described above.

In addition, the administration can be continuous, i.e., every day, or intermittently. The terms "intermittent" or "intermittently" as used herein means stopping and starting at either regular or irregular intervals. For example, intermittent administration of a compound of the instant invention may be administration one to six days per week or it may mean administration in cycles (e.g. daily administration for two to eight consecutive weeks, then a rest period with no administration for up to one week) or it may mean administration on alternate days.

In addition, the compounds of the instant invention may be administered according to any of the schedules described above, consecutively for a few weeks, followed by a rest period. For example, the compounds of the instant invention may be administered according to any one of the schedules described above from two to eight weeks, followed by a rest period of one week, or twice daily at a dose of 100-500 mg for three to five days a week. In another particular embodiment, the compounds of the instant invention may be administered three times daily for two consecutive weeks, followed by one week of rest.

The instant compounds are also useful in combination with known therapeutic agents and anti-cancer agents. For example, instant compounds are useful in combination with known anti-cancer agents. Combinations of the presently disclosed compounds with other anti-cancer or chemotherapeutic agents are within the scope of the invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of histone deacetylase, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunorubicin (see WO 00/50032).

An example of a hypoxia activatable compound is tirapazamine.

Examples of proteasome inhibitors include but are not limited to lactacystin and bortezomib.

Examples of microtubule inhibitors/microtubule-stabilising agents include paclitaxel, vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H- pyrido[4,3-b]carbazole-1-carboxamide, asulacrine, (5a,5aB, 8aa,9b)-9-[2-[N-[2-(dimethylamino)ethyl]-N-methylamino] ethyl]-5-[4-hydroxy-3,5-dimethoxyphenyl]-5,5a,6,8,8a,9-hexohydrofuro(3',4': 6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2-(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 03/050,064, WO 03/050,122, WO 03/049,527, WO 03/049,679, WO 03/049,678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

Examples of "histone deacetylase inhibitors" include, but are not limited to, SAHA, TSA, oxamflatin, PXD 101, MG98, valproic acid and scriptaid. Further reference to other histone deacetylase inhibitors may be found in the following manuscript; Miller, T. A. et al. J. Med. Chem. 46(24):5097-5116 (2003).

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabin furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZO-COR®, see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-1), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat Rec., Vol. 238, p. 68 (1994); FEBS Letters, Vol. 372, p. 83 (1995); Clin. Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol, 93, p. 705 (1998); Intl. J. Mol. Med., Vol. 2, p. 715 (1998); J. Biol. Chem., Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetylcarbonyl)-fumagillol, thalidomide, angiostatin, troponin-1, angiotensin II antagonists (see Fernandez et al., J. Lab. Clin. Med. 105:141-145 (1985)), and antibodies to VEGF (see, Nature Biotechnology, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in Clin. Chem. La. Med. 3 8:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR, inhibitors of cytokine receptors, inhibitors of MET, inhibitors of PI3K (for example LY294002), serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344), inhibitors of Raf kinase (for example BAY-43-9006), inhibitors of MEK (for example CI-1040 and PD-098059) and inhibitors of mTOR (for example Wyeth CCI-779). Such agents include small molecule inhibitor compounds and antibody antagonists.

Specific anti-IGF-1R antibodies include, but are not limited to, dalotuzumab, figitumumab, cixutumumab, SHC 717454, Roche R1507, EM164 or Amgen AMG479. The mTOR inhibitors in current clinical development are structural analogs of rapamycin and include ridaforolimus, temsirolimus, everolimus, a rapamycin-analog and combinations thereof.

Ridaforolimus, also known as AP 23573, MK-8669 and deforolimus, is a unique, non-prodrug analog of rapmycin that has antiproliferative activity in a broad range of human tumor cell lines in vitro and in murine tumor xenograft models utilizing human tumor cell lines. Ridaforolimus has been administered to patients with advanced cancer and is currently in clinical development for various advanced malignancies, including studies in patients with advanced soft tissue or bone sarcomas. Thus far, these trials have demonstrated that ridaforolimus is generally well-tolerated with a predictable and manageable adverse event profile, and possess anti-tumor activity in a broad range of cancers. A description and preparation of ridaforolimus is described in U.S. Pat. No. 7,091,213 to Ariad Gene Therapeutics, Inc., which is hereby incorporated by reference in its entirety.

Temsirolimus, also known as Torisel®, is currently marketed for the treatment of renal cell carcinoma. A description and preparation of temsirolimus is described in U.S. Pat. No. 5,362,718 to American Home Products Corporation, which is hereby incorporated by reference in its entirety.

Everolimus, also known as Certican® or RAD001, marketed by Novartis, has greater stability and enhanced solubility in organic solvents, as well as more favorable pharmokinetics with fewer side effects than rapamycin (sirolimus). Everolimus has been used in conjunction with microemulsion cyclosporin (Neoral®, Novartis) to increase the efficacy of the immunosuppressive regime.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633,272, and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)-phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_2\beta_1$, $\alpha_2\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$, and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl]methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]-benzodiazocin-1-one, SH268, genistein, imatinib (STI571), CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, ST1571A, N4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol. Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, 513219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am J Hum Genet.* 61:785-789, 1997) and Kufe et al (*Cancer Medicine,* 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy,* August 1998; 5(8):1105-13), and interferon gamma (*J Immunol* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be administered with an agent useful in the treatment of anemia. Such an anemia treatment agent is, for example, a continuous erythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); ehlorambucil (Leukeran®); cisplatin (Platinol®); cladribine (Leustatin®, 2-CdA®); clofarabine (Clolar); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®); didemnin B; 17-DMAG; docetaxel (Taxotere®); doxorubicin (Adriamycin PFS®); doxorubicin (Adriamycin®, Rubex); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludar®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin); idarubicin (Idamycin®); ifosfamide (IFEX®); imatinib mesylate (Gleevec®); interferon alfa 2a (Roferon A®); Interferon alfa-2b (Intron A®); iobenguane I 123 injection (Adre View®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®);

pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek); raloxifene hydrochloride (Evista®); Rituximab (Rituxan®); romidepsin (Istodax); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstare); vinblastine (Velban®); vincristine (Oncovin®); vinorelbine (Navelbine®); vorinostat (Zolinza); wortmannin; and zoledronate (Zometa®).

Thus, the scope of the instant invention encompasses the use of the instantly claimed compounds in combination with a second compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic γ-secretase inhibitors, agents that interfere with receptor tyrosine kinases (RTKs), an agent that interferes with a cell cycle checkpoint and any of the therapeutic agents listed above.

Any one or more of the specific dosages and dosage schedules of the compounds of the instant invention, may also be applicable to any one or more of the therapeutic agents to be used in the combination treatment (hereinafter referred to as the "second therapeutic agent").

Moreover, the specific dosage and dosage schedule of this second therapeutic agent can further vary, and the optimal dose, dosing schedule and route of administration will be determined based upon the specific second therapeutic agent that is being used.

Of course, the route of administration of the compounds of the instant invention is independent of the route of administration of the second therapeutic agent. In an embodiment, the administration for a compound of the instant invention is oral administration. In another embodiment, the administration for a compound of the instant invention is intravenous administration. Thus, in accordance with these embodiments, a compound of the instant invention is administered orally or intravenously, and the second therapeutic agent can be administered orally, parenterally, intraperitoneally, intravenously, intraarterially, transdermally, sublingually, intramuscularly, rectally, transbuecally, intranasally, liposomally, via inhalation, vaginally, intraoccularly, via local delivery by catheter or stent, subcutaneously, intraadiposally, intraarticularly, intrathecally, or in a slow release dosage form.

In addition, a compound of the instant invention and second therapeutic agent may be administered by the same mode of administration, i.e. both agents administered e.g. orally, by IV. However, it is also within the scope of the present invention to administer a compound of the instant invention by one mode of administration, e.g. oral, and to administer the second therapeutic agent by another mode of administration, e.g. IV or any other ones of the administration modes described hereinabove.

The first treatment procedure, administration of a compound of the instant invention, can take place prior to the second treatment procedure, i.e., the second therapeutic agent, after the treatment with the second therapeutic agent, at the same time as the treatment with the second therapeutic agent, or a combination thereof. For example, a total treatment period can be decided for a compound of the instant invention. The second therapeutic agent can be administered prior to onset of treatment with a compound of the instant invention or following treatment with a compound of the instant invention. In addition, anti-cancer treatment can be administered during the period of administration of a compound of the instant invention but does not need to occur over the entire treatment period of a compound of the instant invention.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an apoptosis inducing agent, a bisphosphonate, an aromatase inhibitor, an siRNA therapeutic and an agent that interferes with a cell cycle checkpoint.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPARδ agonist; an inhibitor of cell proliferation and survival signaling, a bisphosphonate, an aromatase inhibitor, an siRNA therapeutic and an agent that interferes with a cell cycle checkpoint.

Further included within the scope of the invention is a method of treating or preventing a disease in which angiogenesis is implicated, which is comprised of administering to a mammal in need of such treatment a therapeutically effective amount of a compound of the present invention. Other inhibitors of MET may also be administered for this method of treatment. Ocular neovascular diseases, which may result in certain forms of blindness, are examples of conditions where much of the resulting tissue damage can be attributed to aberrant infiltration of blood vessels in the eye. The undesirable infiltration can be triggered by ischemic retinopathy, such as that resulting from diabetic retinopathy, retinopathy of prematurity, retinal vein occlusions, etc., or by degenerative diseases, such as the choroidal neovascularization observed in age-related macular degeneration. Inhibiting the growth of blood vessels by administration of the present compounds would therefore prevent the infiltration of blood vessels and prevent or treat diseases where angiogenesis is implicated, such as ocular diseases like retinal vascularization, diabetic retinopathy, age-related macular degeneration, and the like.

Routes of systemic administration of the compounds of the present invention described above may be utilized in the treatment of such ocular neovascular diseases. Other routes of ocular administration may also be employed, such as topical, periocular, intravitreal and the like. Intravitreal implants coated with a drug:polymer matrix may also be employed.

Ophthalmic pharmaceutical compositions that are adapted for topical administration to the eye may be in the form of solutions, suspensions, ointments, creams or as a solid insert. Ophthalmic formulations of this compound may contain from 0.01 ppm to 1% and especially 0.1 ppm to 1% of medicament. For a single dose, from between 0.01 to 5000 ng, preferably 0.1 to 500 ng, and especially 1 to 100 ng of the compound can be applied to the human eye. Formulations useful for intravitreal administration are similar to saline solutions described previously for intravenous administration.

These and other aspects of the invention will be apparent from the teachings contained herein.

SCHEMES AND EXAMPLES

The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention hereinabove.

Examples provided are intended to assist in a further understanding of the invention. Particular materials employed, species and conditions are intended to be illustrative of the invention and not limiting of the reasonable scope thereof.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| DCE = | Dichloroethylene |
| DIPEA = | N-Ethyldiisopropylamine |
| DMSO = | Dimethyl sulfoxide |
| EtOH = | ethanol |
| $Et_2O$ = | diethyl ether |
| EtOAc = | ethyl acetate |
| HCl = | hydrochloric acid |
| HPLC = | high performance liquid chromatography |
| hr = | hour |
| $K_2CO_3$ = | potassium carbonate |
| KOt-Bu = | potassium t-butoxide |
| MeOH = | methanol |
| $MgSO_4$ = | Magnesium sulfate |
| LRMS = | low resolution mass spectrometry |
| $NaHCO_3$ = | sodium bicarbonate |
| NaOH = | sodium hydroxide |
| n-BuLi = | n-butyl lithium |
| NSAID = | non-steroidal anti-inflammatory drug |
| Ph = | phenyl |
| i-PrOH = | isopropanol |
| $SOCl_2$ = | Thionyl chloride |
| rt = | room temperature |
| rac- = | racemic |
| THF = | tetrahydrofuran |
| TLC = | thin layer chromatography |

Alkyl Group Abbreviations

| | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

Scheme 1

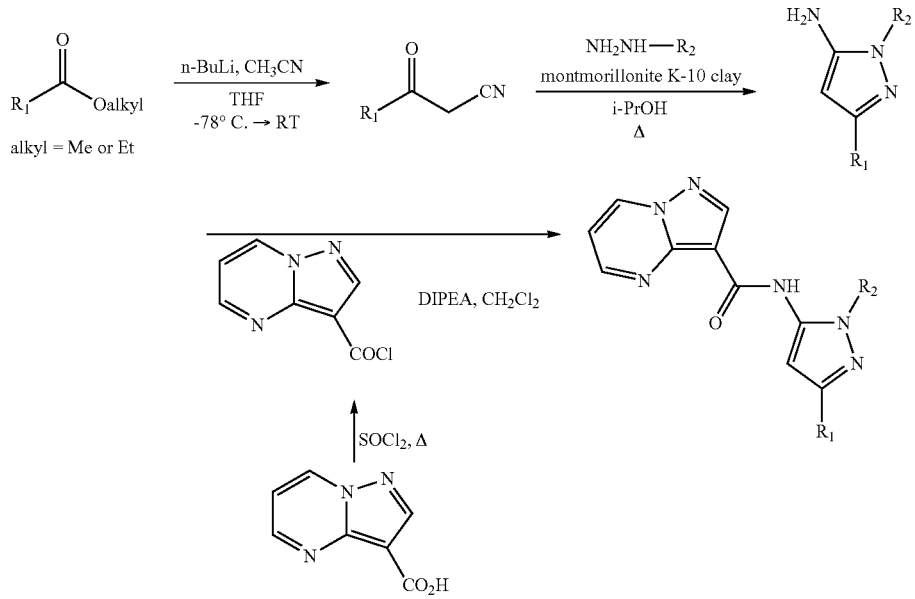

Example 1

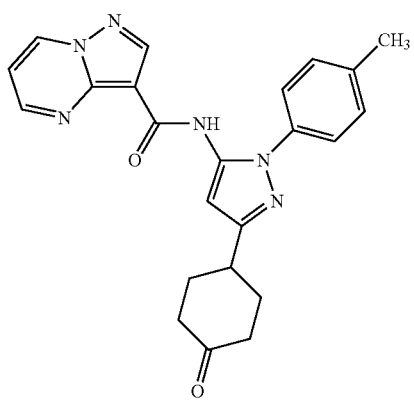

N-(3-(4-oxocyclohexyl)-1-p-tolyl-1H-pyrazol-5-yl)pyrazolo[1,5-a]pyrimidine-3-carboxamide General methods for preparation of the synthetic intermediates follow below.

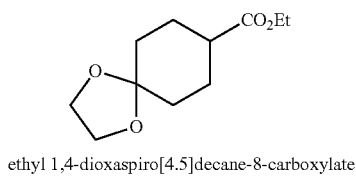 [SMILES: CCOC(=O)C1CCC2(CC1)OCCO2]

ethyl 1,4-dioxaspiro[4.5]decane-8-carboxylate

A solution of ethyl 4-oxocyclohexanecarboxylate (20.0 mL, 126 mmol), ethylene glycol (9.0 mL, 160 mmol), p-toluenesulfonic acid monohydrate (2.37 g, 12.5 mmol) and toluene (500 mL) were combined and heated at reflux for 18 h during which time water was removed azeotropically. The solution was cooled to rt and concentrated in vacuo. Sat NaHCO$_3$ (200 mL) was added and the mixture was extracted with Et$_2$O (3×200 mL). The combined organic extracts were dried (MgSO$_4$) and concentrated in vacuo. The residue was purified by vacuum distillation (bp=164° C. at 10 mm Hg) to give the title compound as a colorless oil. Spectral data matched that of the reported compound.[1]

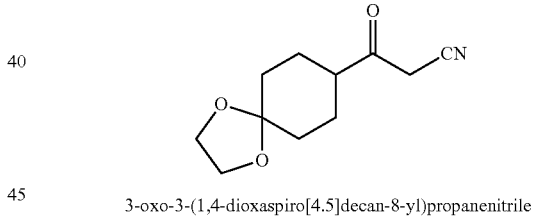

3-oxo-3-(1,4-dioxaspiro[4.5]decan-8-yl)propanenitrile

THF (200 mL) was cooled to −78° C. n-BuLi (22.0 mL of 1.6 M solution in hexanes, 35.2 mmol) was added. The solution was stirred at −78° C. for 5 min. CH$_3$CN (1.80 mL, 34.5 mmol) was added. The resulting mixture was stirred at −78° C. for 1 h, whereupon a solution of ethyl 1,4-dioxaspiro[4.5]decane-8-carboxylate (3.54 g, 16.5 mmol) in THF (50 mL) was added dropwise over 15 min. The mixture was stirred at −78° C. for 2 h, then allowed to slowly warm to rt over 1 h. The mixture was stirred at rt. for 16 h, whereupon 1 M HCl (30 mL) was added. The phases were separated and the organic layer washed with brine (300 mL). The combined aqueous washings were back-extracted with EtOAc (300 mL). The combined organic extracts were dried (MgSO$_4$) and concentrated in vacuo. The residue was purified by silica gel chromatography, eluting with a solvent gradient of 0 to 100% EtOAc in hexanes to give the title compound as a pale yellow oil. $^1$H NMR (400 MHz, CDCl$_3$) δ 3.91 (m, 4H), 3.51 (s, 2H), 2.54 (tt, J=11.2, 3.6 Hz, 1H), 1.92-1.86 (m, 2H), 1.81-1.65 (m, 4H), 1.55 (dt, J=12.0, 4.4 Hz, 2H).

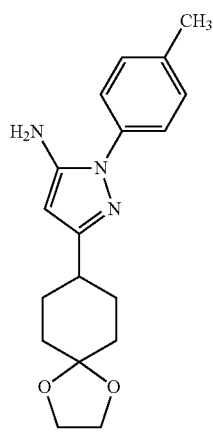

3-(1,4-dioxaspiro[4.5]decan-8-yl)-1-p-tolyl-1H-pyrazol-5-amine

A mixture of 3-oxo-3-(1,4-dioxaspiro[4.5]decan-8-yl)propanenitrile (1.00 g, 4.78 mmol), 4-methylphenyl hydrazine hydrochloride (1.17 g, 7.36 mmol), montmorillonite K-10 clay (260 mg), and i-PrOH (15 mL) was heated at 55° C. for 50 min. The mixture was cooled to rt. and filtered. The solid was washed with EtOH and the filtrate concentrated in vacuo. The residue was dissolved in EtOAc (60 mL) and washed with 1 M NaOH (2×60 mL) and brine (60 mL). The combined aqueous washings were back-extracted with EtOAc (60 mL). The combined organic extracts were dried (MgSO$_4$) and concentrated in vacuo. The residue was purified by silica gel chromatography, eluting with a solvent gradient of 0 to 100% EtOAc in hexanes to give the title compound as a pale yellow oil. $^1$H NMR (400 MHz, CDCl$_3$) δ 7.38 (m, 2H), 7.22 (m, 2H), 5.46 (s, 1H), 3.95 (s, 4H), 3.71 (br s, 2H), 2.64 (tt, J=11.2, 3.6 Hz, 1H), 2.36 (s, 3H), 1.96 (m, 2H), 1.84-1.60 (m, 6H).

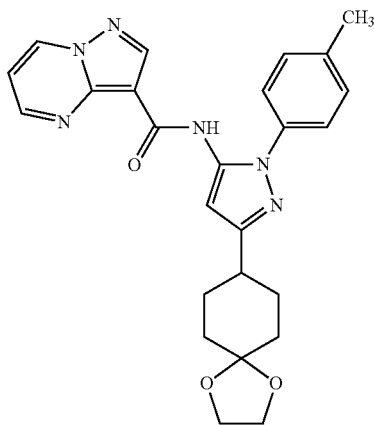

N-(3-(1,4-dioxaspiro[4.5]decan-8-yl)-1-p-tolyl-1H-pyrazol-5-yl)pyrazolo[1,5-a]pyrimidine-3-carboxamide A mixture of pyrazolo[1,5-a]pyrimidine-3-carboxylic acid (640 mg, 3.93 mmol) and SOCl$_2$ (7 mL) was heated at 80° C. for 90 min, whereupon the mixture was cooled to rt. and concentrated in vacuo. 3-(1,4-Dioxaspiro[4.5]decan-8-yl)-1-p-tolyl-1H-pyrazol-5-amine (953 mg, 3.04 mmol), DIPEA (700 μL, 4.03 mmol), and CH$_2$Cl$_2$ (20 mL) were added. The resulting mixture was stirred at it for 18 h and concentrated in vacuo. The residue was purified by silica gel chromatography, eluting with a solvent gradient of 0 to 100% EtOAc in hexanes to give the title compound as a white solid. $^1$H NMR (400 MHz, CDCl$_3$) δ 10.25 (br s, 1H), 8.76 (dd, J=7.0, 1.6 Hz, 1H), 8.71 (s, 1H), 8.30 (dd, J=4.2, 1.6 Hz, 1H), 7.45 (m, 2H), 7.29 (m, 2H), 6.97 (dd, J=7.0, 4.2 Hz, 1H), 6.76 (s, 1H), 3.96 (s, 4H), 2.76 (tt, J=11.6, 3.2 Hz, 1H), 2.44 (s, 3H), 2.07-2.03 (m, 2H), 1.93-1.84 (m, 4H), 1.67 (dt, J=5.2, 13.6 Hz, 2H).

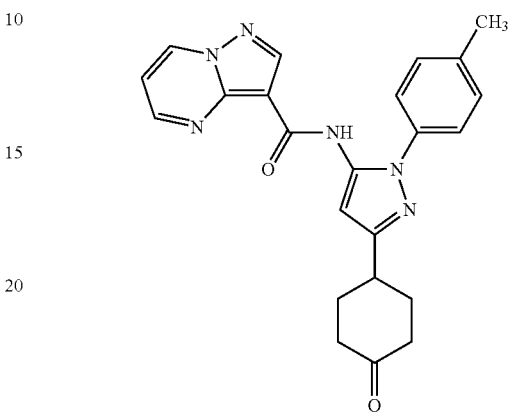

A mixture of N-(3-(1,4-dioxaspiro[4.5]decan-8-yl)-1-p-tolyl-1H-pyrazol-5-yl)pyrazolo[1,5-a]pyrimidine-3-carboxamide (1.07 g, 2.33 mmol), 1 M HCl (20 mL), and THF (100 mL) was stirred at it for 3 d. 1 M NaOH (100 mL) was added and the mixture was extracted with EtOAc (2×100 mL). The combined organic extracts were dried (MgSO$_4$) and concentrated in vacuo. The residue was recrystallized from EtOH to give the title compound as a white, crystalline solid. $^1$H NMR (400 MHz, CDCl$_3$) δ 10.30 (br s, 1H), 8.77 (dd, J=7.0, 1.6 Hz, 1H), 8.71 (s, 1H), 8.30 (dd, J=4.4, 2.0 Hz, 1H), 7.46 (m, 2H), 7.32 (m, 2H), 6.99 (dd, J=7.0, 4.4 Hz, 1H), 6.78 (s, 1H), 3.20 (tt, J=10.8, 3.2 Hz, 1H), 2.57-2.35 (m, 9H), 2.14-2.04 (m, 2H).

Example 2

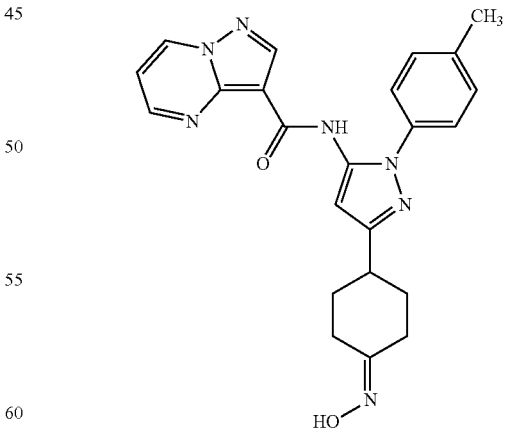

N-(3-(4-(hydroxyimino)cyclohexyl)-1-p-tolyl-1H-pyrazol-5-yl)pyrazolo[1,5-a]pyrimidine-3-carboxamide A mixture of N-(3-(4-oxocyclohexyl)-1-p-tolyl-1H-pyrazol-5-yl)pyrazolo[1,5-c]pyrimidine-3-carboxamide (43 mg, 0.10 mmol), hydroxylamine hydrochloride (41 mg, 0.59 mmol) and pyridine (5 mL) was heated at 45° C. for 2 h. The solution was cooled to rt. and CH$_2$Cl$_2$ (30 mL) was added. The mixture was washed with 1 M HCl (3×30 mL) and brine (30 mL). The organic phase was dried (MgSO$_4$) and concentrated in vacuo. The residue was triturated from hexanes/EtOH to give the title compound as a white solid, $^1$H NMR (400 MHz, CDCl$_3$) δ 10.29 (br s, 1H), 8.78-8.73 (m, 2H), 8.32 (app br s, 1H), 7.47-7.33 (m, 4H), 7.00 (app br s, 1H), 6.67 (app br s, 1H), 3.00-1.25 (m, 12H).

Example 3

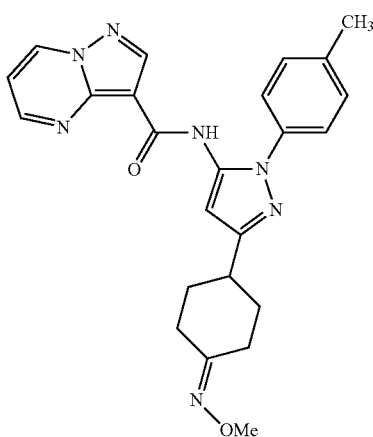

N-(3-(4-(methoxyimino)cyclohexyl)-1-(p-tolyl)-1H-pyrazol-5-yl)pyrazolo[1,5-a]pyrimidine-3-carboxamide This compound was prepared according to the general method described for Example 2 using methoxyamine hydrochloride in place of hydroxylamine hydrochloride. $^1$H NMR (400 MHz, CDCl$_3$) δ 10.27 (br s, 1H), 8.76 (dd, J=6.8, 1.6 Hz, 1H), 8.70 (s, 1H), 8.29 (dd, J=4.0, 1.6 Hz, 1H), 7.46 (m, 2H), 7.31 (m, 2H), 6.98 (dd, J=6.8, 4.0 Hz, 1H), 6.73 (s, 1H), 3.82 (s, 3H), 3.25 (m, 1H), 2.95 (m, 1H), 2.51 (com, 1H), 2.44 (s, 3H), 2.26-2.16 (m, 3H), 1.96 (m, 1H), 1.85-1.64 (m, 2H).

Example 4

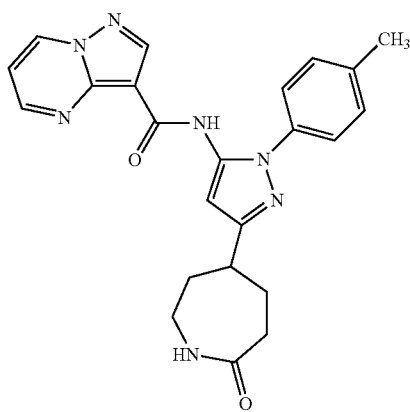

N-(3-(7-oxoazepan-4-yl)-1-p-tolyl-1H-pyrazol-5-yl)pyrazol[1,5-a]pyrimidine-3-carboxamide A solution of N-(3-(4-oxocyclohexyl)-1-p-tolyl-1H-pyrazol-5-yl)pyrazolo[1,5-a]pyrimidine-3-carboxamide (68 mg, 0.16 mmol) and CHCl$_3$ (4 mL) was cooled to 0° C. H$_2$SO$_4$ (100 μL, 1.8 mmol) and NaN$_3$ (54 mg, 0.83 mmol) were added. The resulting mixture was stirred at 0° C. for 30 min, then warmed to rt. and stirred 20 h. H$_2$O (25 mL) was added and the solution brought to pH=3 with 1M HCl. The mixture was extracted with CH$_2$Cl$_2$ (2×20 mL). The combined organic extracts were dried (MgSO$_4$) and concentrated in vacuo. The residue was triturated with hexanes/CH$_2$Cl$_2$ to give the title compound as a white solid. $^1$H NMR (400 MHz, CDCl$_3$) δ 10.28 (br s, 1H), 8.78 (dd, J=7.2, 2.0 Hz, 1H), 8.71 (s, 1H), 8.30 (dd, J=4.2, 2.0 Hz, 1H), 7.45 (m, 2H), 7.31 (m, 2H), 6.98 (dd, J=7.2, 4.2, 1H), 6.73 (s, 1H), 5.81 (br s, 1H), 3.38-3.33 (m, 2H), 3.02 (m, 1H), 2.67-2.54 (m, 2H), 2.45 (s, 3H), 2.30-2.19 (m, 2H), 1.96-1.85 (m, 2H).

Example 5

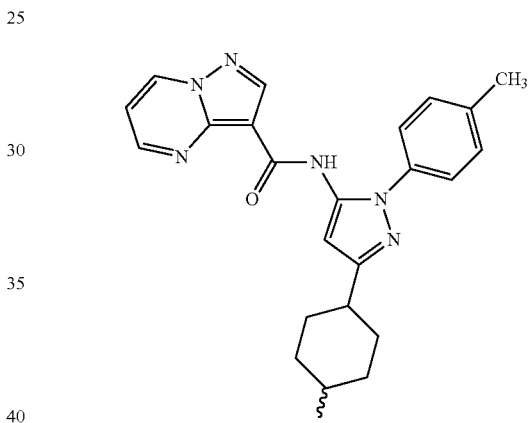

N-(3-(4-(dimethylamino)cyclohexyl)-1-p-tolyl-1H-pyrazol-5-yl)pyrazolo[1,5-a]pyrimidine-3-carboxamide Acetic acid (1 drop) and Me$_2$NH (90 μL, 2.0 M in THF, 0.18 mmol) were added to a solution of N-(3-(4-oxocyclohexyl)-1-p-tolyl-1H-pyrazol-5-yl)pyrazolo[1,5-a]pyrimidine-3-carboxamide (58 mg, 0.14 mmol) and CH$_2$Cl$_2$ (3 mL). The resulting solution was cooled to 0° C., whereupon NaBH(OAc)$_3$ (46 mg, 0.22 mmol) was added. The mixture was stirred at 0° C. for 1 h, then warmed to rt. Sat NaHCO$_3$ (20 mL) was added and the mixture was extracted with CH$_2$Cl$_2$ (2×20 mL). The combined organic extracts were dried (MgSO$_4$) and concentrated in vacuo. The residue was purified by silica gel chromatography, eluting with a solvent gradient of 0 to 10% 7M NH$_3$/MeOH in CH$_2$Cl$_2$ to give the title compound as a gummy white solid. $^1$H NMR (400 MHz, CDCl$_3$) δ 9.08 (dd, J=7.2, 1.2 Hz, 1H), 8.62 (s, 1H), 8.42 (dd, J=4.2, 1.2 Hz, 1H), 7.45 (m, 4H), 7.19 (dd, J=7.2, 4.2 Hz, 1H), 6.77 (s, 1H), 2.99 (m, 1H), 2.49 (s, 3H), 2.33-2.22 (m, 9H), 1.82-1.71 (m, 6H).

Example 6

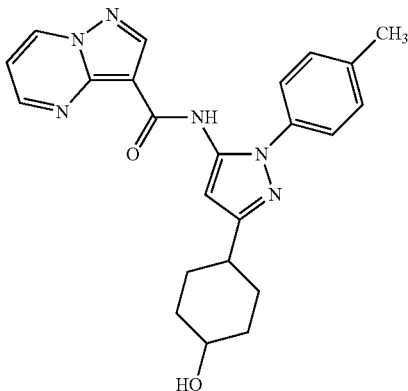

N-(3-(4-hydroxycyclohexyl)-1-(p-tolyl)-
1H-pyrazol-5-yl)
pyrazolo[1,5-a]pyrimidine-3-carboxamide BH$_3$THF (80 µL, 0.80 mmol) was added to a mixture of N-(3-(4-oxocyclohexyl)-1-p-tolyl-1H-pyrazol-5-yl)pyrazolo[1,5-a]pyrimidine-3-carboxamide (105 mg, 0.254 mmol) and THF (5 mL). The resulting mixture was stirred for 1 h. 1M HCl (30 mL) was added and the mixture was extracted with CH$_2$Cl$_2$ (2×30 mL). The combined organic extracts were dried (MgSO$_4$) and concentrated in vacuo. The residue was purified by silica gel chromatography, eluting with a solvent gradient of 0 to 100% EtOAc in hexanes to give the title compound as a white solid. $^1$H NMR (400 MHz, CDCl$_3$) δ 10.3 (br s, 1H), 8.77 (dd, J=6.8, 1.6 Hz, 1H), 8.70 (s, 1H), 8.29 (dd, J=4.0, 1.6 Hz, 1H), 7.45 (m, 2H), 7.31 (m, 2H), 6.98 (dd, J=6.8, 4.0 Hz, 1H), 6.72 (s, 1H), 6.68 (m, 1H), 2.69 (m, 1H), 2.44 (s, 3H), 2.14-2.02 (m, 4H), 1.70-1.36 (m, 4H).

Example 7

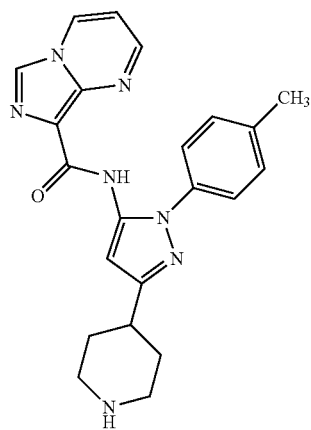

N-(3-(piperidin-4-yl)-1-(p-tolyl)-
1H-pyrazol-5-yl)
pyrazolo[1,5-a]pyrimidine-3-carboxamide General methods for preparation of the synthetic intermediates follow below.

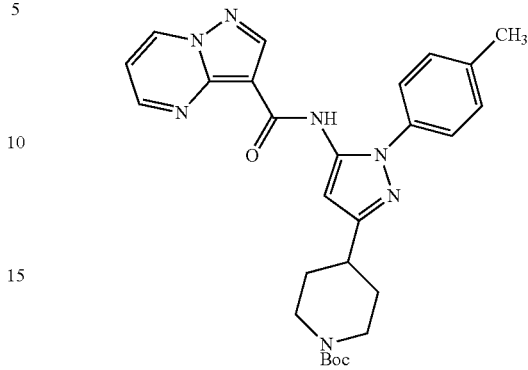

tert-butyl 4-(5-(pyrazolo[1,5-a]pyrimidine-
3-carboxamido)-1-(p-tolyl)-
1H-pyrazol-3-yl)piperidine-1-carboxylate This compound was prepared according to the general methods described in Example 1, using 1-tert-butyl 4-ethyl piperidine-1,4-dicarboxylate in place of ethyl 1,4-dioxaspiro [4.5]decane-8-carboxylate. $^1$H NMR (400 MHz, CDCl$_3$) δ 10.27 (br s, 1H), 8.77 (dd, J=7.0, 1.6 Hz, 1H), 8.71 (s, 1H), 8.30 (dd, J=4.0, 1.6 Hz, 1H), 7.46 (m, 2H), 7.31 (m 2H), 6.98 (dd, J=7.0, 4.0 Hz, 1H), 6.73 (s, 1H), 4.16 (app br s, 2H), 2.88-2.82 (m, 2H), 2.45 (s, 3H), 2.01 (m, 2H), 1.72 (m, 2H), 1.46 (s, 9H).

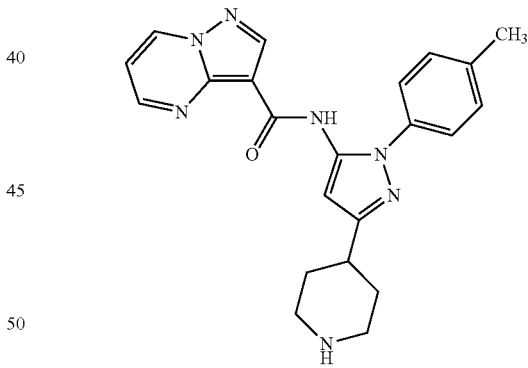

A solution of tert-butyl 4-(5-(pyrazolo[1,5-a]pyrimidine-3-carboxamido)-1-(p-tolyl)-1H-pyrazol-3-yl)piperidine-1-carboxylate (5.43 g, 10.8 mmol), TFA (12 mL), and CH$_2$Cl$_2$ (200 mL) was stirred at rt for 30 min. The solution was concentrated in vacuo and the residue so obtained was recrystallized with hexanes/EtOH to give the title piperidine TFA salt as a white, crystalline solid. $^1$H NMR (CD$_3$OD, 400 MHz) δ 9.09 (dd, J=7.2, 1.6 Hz, 1H), 8.62 (s, 1H), 8.41 (dd, J=4.0, 1.6 Hz, 1H), 7.45 (app s, 4H), 7.19 (dd, J=7.2, 4.0 Hz, 1H), 6.74 (s, 1H), 3.46 (m, 2H), 3.15 (m, 2H), 3.06 (tt, J=11.6, 4.4 Hz, 1H), 2.49 (s, 3H), 2.25 (m, 2H), 1.98 (m, 2H).

Example 8

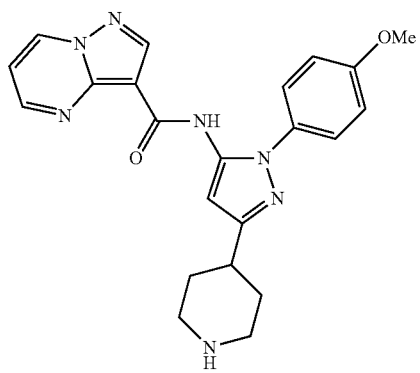

N-(1-(4-methoxyphenyl)-3-(piperidin-4-yl)-
1H-pyrazol-5-yl)
pyrazolo[1,5-a]pyrimidine-3-carboxamide This compound was prepared according to the general methods described in Example 7, using 4-methoxyphenylhydrazine hydrochloride in place of 4-methylphenylhydrazine hydrochloride. $^1$H NMR (400 MHz, CDCl$_3$) δ 10.24 (s, 1H), 9.55 (br s, 1H), 9.18 (br s, 1H), 8.76 (dd, J=6.8, 1.6 Hz, 1H), 8.71 (s, 1H), 8.30 (dd, J=3.8, 1.6 Hz, 1H), 7.48 (m, 2H), 7.04 (m, 2H), 6.98 (dd, J=6.8, 3.8 Hz, 1H), 6.74 (s, 1H), 3.88 (s, 3H), 3.48-3.46 (m, 2H), 3.09-3.03 (m, 3H), 2.31-2.26 (m, 2H), 2.22-2.13 (m, 2H).

Example 9

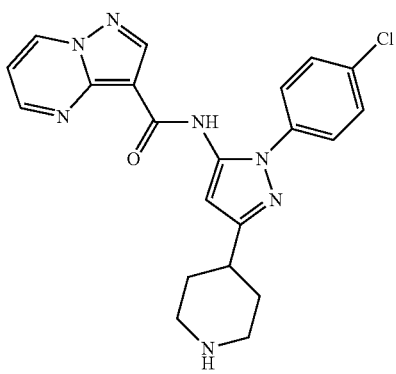

N-(1-(4-chlorophenyl)-3-(piperidin-4-yl)-
1H-pyrazol-5-yl)
pyrazolo[1,5-a]pyrimidine-3-carboxamide This compound was prepared according to the general methods described in Example 7, using 4-chlorophenylhydrazine hydrochloride in place of 4-methylphenylhydrazine hydrochloride. $^1$H NMR (400 MHz, CD$_3$OD) δ 9.12 (dd, J=7.0, 1.6 Hz, 1H), 8.65 (s, 1H), 8.50 (dd, J=4.2, 1.6 Hz, 1H), 7.70-7.61 (m, 4H), 7.23 (dd, J=7.0, 4.2 Hz, 1H), 3.49 (m, 2H), 3.20-3.05 (m, 3H), 2.27 (m, 2H), 2.00 (m, 2H).

Example 10

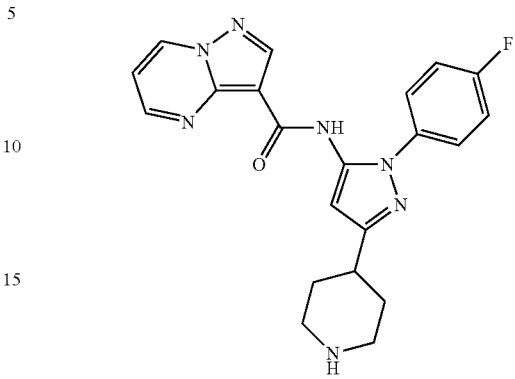

N-(1-(4-fluorophenyl)-3-(piperidin-4-yl)-
1H-pyrazol-5-yl)
pyrazolo[1,5-a]pyrimidine-3-carboxamide This compound was prepared according to the general methods described in Example 7, using 4-fluorophenylhydrazine hydrochloride in place of 4-methylphenylhydrazine hydrochloride. $^1$H NMR (400 MHz, CDCl$_3$) δ 10.21 (br s, 1H), 9.85 (br s, 1H), 9.22 (br s, 1H), 8.78 (dd, J=7.0, 1.8 Hz, 1H), 8.72 (s, 1H), 8.35 (dd, J=4.0, 1.8 Hz, 1H), 7.56 (m, 2H), 7.25 (m, 2H), 7.01 (dd, J=7.0, 4.0 Hz, 1H), 6.75 (s, 1H), 3.46 (m, 2H), 3.13-3.03 (m, 3H), 2.29 (m, 2H), 2.18 (m, 2H).

Example 11

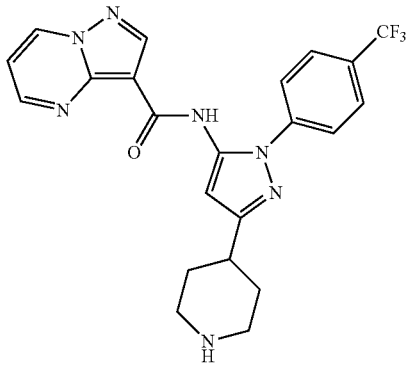 [SMILES: Cc1ccc(-n2nc(C3CCNCC3)cc2NC(=O)c2cnn3cccnc23)cc1]

N-(3-(piperidin-4-yl)-1-(4-(trifluoromethyl)
phenyl)-1H-pyrazol-
5-yl)pyrazolo[1,5-a]pyrimidine-3-carboxamide This compound was prepared according to the general methods described in Example 7, using 4-trifluoromethylphenylhydrazine hydrochloride in place of 4-methylphenylhydrazine hydrochloride. $^1$H NMR (400 MHz, CD$_3$OD) δ 9.13 (dd, J=7.2, 1.6 Hz, 1H), 8.65 (s, 1H), 8.49 (dd, J=4.4, 1.6 Hz, 1H), 7.95 (m, 2H), 7.87 (m, 2H), 7.23 (dd, J=7.2, 4.4 Hz, 1H), 6.78 (s, 1H), 3.48 (m, 214), 3.21-3.07 (m, 3H), 2.28 (m, 2H), 2.01 (m 2H).

Example 12

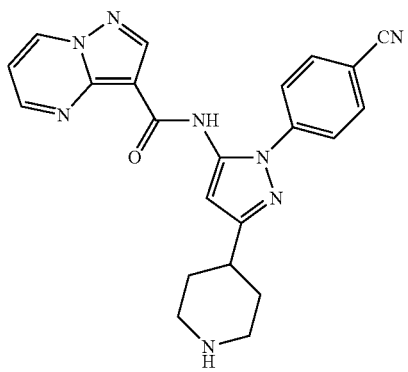

N-(1-(4-cyanophenyl)-3-(piperidin-4-yl)-
1H-pyrazol-5-yl)
pyrazolo[1,5-a]pyrimidine-3-carboxamide This compound was prepared according to the general methods described in Example 7, using 4-cyanophenylhydrazine hydrochloride in place of 4-methylphenylhydrazine hydrochloride. $^1$H NMR (400 MHz, CD$_3$OD) δ 9.14 (dd, J=7.0, 1.6 Hz, 1H), 8.65 (s, 1H), 8.62 (dd, J=4.0, 1.6 Hz, 1H), 7.97 (m, 2H), 7.89 (m, 2H), 7.25 (dd, J=7.0, 4.0 Hz, 1H), 6.77 (s, 1H), 3.47 (m, 2H)m 3.21-3.07 (m, 3H), 2.28 (m, 2H), 2.02 (m, 2H).

Example 13

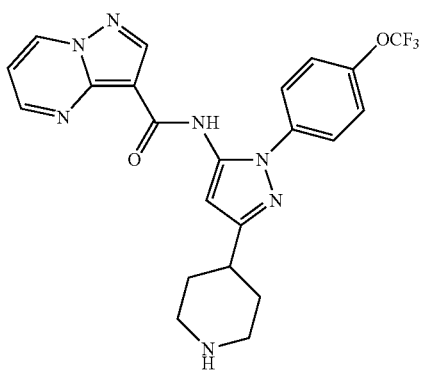

N-(3-(piperidin-4-yl)-1-(4-(trifluoromethoxy)
phenyl)-1H-pyrazol-5-yl)pyrazolo
[1,5-a]pyrimidine-3-carboxamide This compound was prepared according to the general methods described in Example 7, using 4-trifluoromethoxyphenylhydrazine hydrochloride in place of 4-methylphenylhydrazine hydrochloride. $^1$H NMR (400 MHz, CD$_3$OD) δ 9.12 (dd, J=7.2, 1.8 Hz, 1H), 8.65 (s, 1H), 8.46 (dd, J=4.4, 1.8 Hz, 1H), 7.76 (m, 2H), 7.58 (m, 2H), 7.23 (dd, J=7.2, 4.4 Hz, 1H), 6.77 (s, 1H), 3.48 (m, 2H), 3.20-3.05 (m, 3H), 2.27 (m, 2H), 2.01 (m, 2H).

Example 14

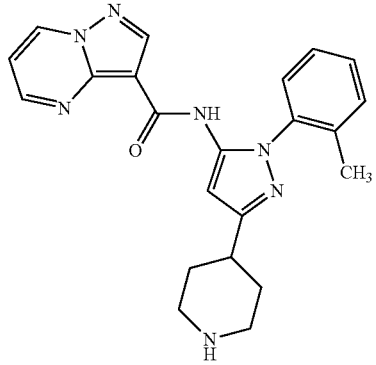

N-(3-(piperidin-4-yl)-1-(o-tolyl)-1H-
pyrazol-5-yl)pyrazolo[1,5-a]
pyrimidine-3-carboxamide This compound was prepared following the general procedure outlined for Example 7, using 2-methylphenylhydrazine hydrochloride in place of 4-methylphenylhydrazine hydrochloride.

Example 15

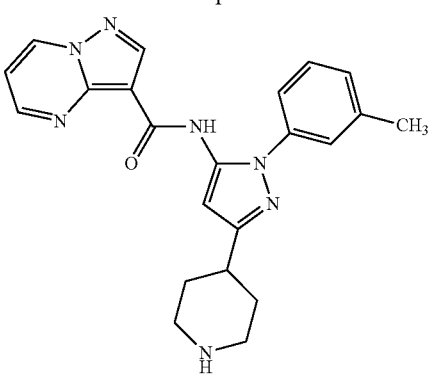

N-(3-(piperidin-4-yl)-1-(m-tolyl)-1H-
pyrazol-5-yl)pyrazolo[1,5-a]pyrimidine-3-carboxamide This compound was prepared following the general procedure outlined for Example 7, using 3-methylphenylhydrazine hydrochloride in place of 4-methylphenylhydrazine hydrochloride.

Example 16

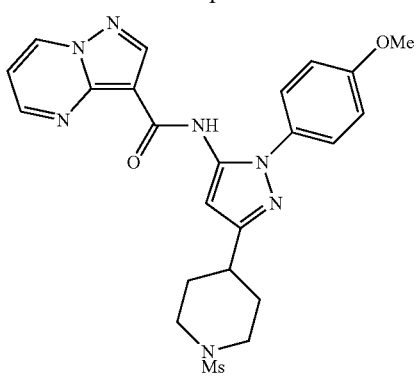

N-(1-(4-methoxyphenyl)-3-
(1-methylsulfonyl)piperidin-4-yl)-1H-pyrazol-
5-yl)pyrazolo[1,5-a]pyrimidine-3-carboxamide MsCl (20 µL, 0.26 mmol) and TEA (40 µL, 0.39 mmol) were added to a solution of N-(1-(4-methoxyphenyl)-3-(piperidin-4-yl)-1H-pyrazol-5-yl)pyrazolo[1,5-a]pyrimidine-2-carboxamide (126 mg, 0.302 mmol) and CH$_2$Cl$_2$ (15 mL). The resulting mixture was stirred at rt for 2 d. CH$_2$Cl$_2$ (50 mL) was added and the mixture washed with water (50 mL), 1 M HCl (50 mL), and brine (50 mL). The organic layer was dried (MgSO$_4$) and concentrated in vacuo. The residue was purified by silica gel chromatography, eluting with a solvent gradient of 0 to 100% EtOAc in hexanes to give the title compound as a white solid. $^1$H NMR (400 MHz, CDCl$_3$) δ 10.23 (br s, 1H), 8.76 (dd, J=7.0, 1.6 Hz, 1H), 8.71 (s, 1H), 8.30 (dd, J=4.2, 1.6 Hz, 1H), 7.48 (m, 2H), 7.03 (m 2H), 6.97 (dd, J=7.0, 4.2 Hz, 1H), 6.73 (s, 1H), 3.88 (s, 3H), 3.84 (m, 1H), 2.88-2.83 (m, 2H), 2.82 (s, 3H), 2.17-2.13 (m, 2H), 1.98-1.88 (m, 2H).

Example 17

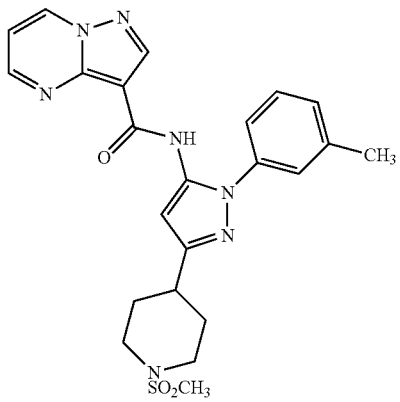

N-(3-(1-(methylsulfonyl)piperidin-4-yl)-1-(m-tolyl)-1H-pyrazol-5yl)-pyrazolo[1,5-a]pyrimidine-3-carboxamide This compound was prepared following the general procedure outlined for Example 16, using N-(3-(piperidin-4-yl)-1-(m-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.32 (br s, 1H), 8.79 (dd, J=6.8, 1.6 Hz, 1H), 8.71 (s, 1H), 8.31 (dd, J=4.4, 1.6 Hz, 1H), 7.38 (m, 3H), 7.27 (m, 1H), 6.99 (m, 1H), 6.77 (s, 1H), 3.86 (m, 2H), 2.84 (m, 6H), 2.42 (s, 31-1), 2.17 (m, 2H), 1.95 (m, 2H).

Example 18

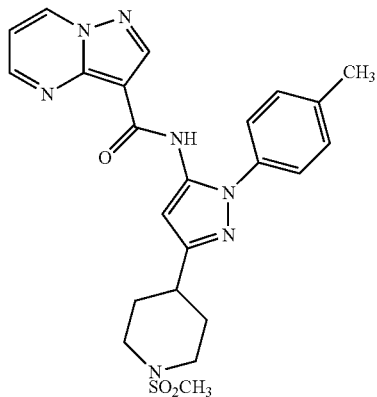

N-(3-(1-(methylsulfonyl)piperidin-4-yl)-1-(p-tolyl)-1H-pyrazol-5yl)-pyrazolo[1,5-a]pyrimidine-3-carboxamide This compound was prepared according to the general methods described in Example 16, using N-(3-(piperidin-4-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.29 (br s, 1H), 8.77 (dd, J=6.8, 1.6 Hz, 1H), 8.71 (s, 3H), 8.30 (dd, J=4.0, 1.6 Hz, 1H), 7.45 (m, 2H), 7.32 (m, 2H), 6.99 (dd, J=6.8, 4.0 Hz, 1H), 6.75 (s, 1H), 3.85 (m, 2H), 2.88-2.81 (m, 3H), 2.80 (s, 3H), 2.45 (s, 3H), 2.15 (m, 2H), 1.93 (m 2H).

Example 19

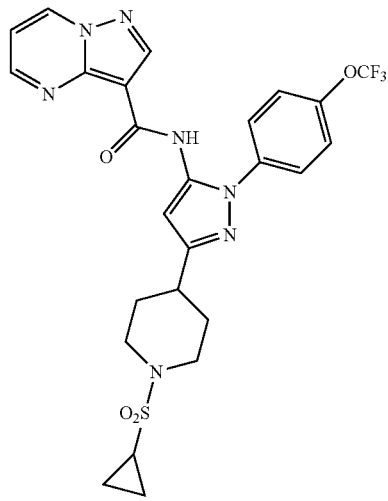

N-(3-(1-(cyclopropylsulfonyl)piperidin-4-yl)-1-(4-trifluoromethoxy)-phenyl)-1H-pyrazol-5yl)-pyrazolo[1,5-a]pyrimidine-3-carboxamide This compound was prepared according to the general methods described in Example 16, using N-(3-(piperidin-4-yl)-1-(4-(trifluoromethoxy)phenyl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. $^1$H NMR (400 MHz, CDCl$_3$) δ 10.28 (br s, 1H), 8.77 (dd, J=7.2, 1.6 Hz, 1H), 8.71 (s, 1H), 8.30 (dd, J=4.0, 1.6 Hz, 1H), 7.46 (m, 2H), 7.31 (m 2H), 6.89 (dd, J=7.2, 4.0 Hz, 1H), 6.75 (s, 1H), 3.88 (m, 2H), 2.97 (dt, J=12.0, 2.8 Hz, 2H), 8.85 (tt, J=7.6, 4.0 Hz, 1H), 2.45 (s, 3H), 2.28 (m, 1H), 2.14 (m, 2H), 1.93 (m, 2H), 1.18 (m, 2H), 1.00 (m, 2H).

Example 20

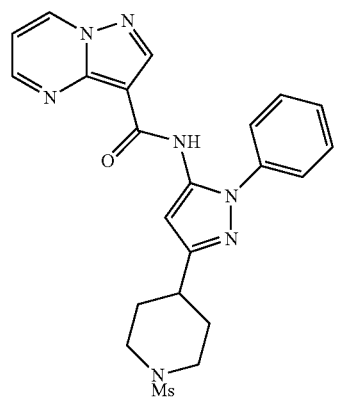

N-(3-(1-(methylsulfonyl)piperidin-4-yl)-1-phenyl-1H-pyrazol-5yl)-pyrazolo[1,5-a]pyrimidine-3-carboxamide This compound was prepared according to the general method described in Example 16, using N-(1-phenyl-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazolo[1,5-a]pyrimidine-3-carboxamide. ¹H NMR (400 MHz, CDCl₃) δ 10.35 (br s, 1H), 8.78 (dd, J=6.8, 2.0 Hz, 1H), 8.72 (s, 1H), 8.31 (dd, J=4.0, 1.6 Hz, 1H), 7.61-7.45 (m, 5H), 6.99 (m, 1H), 6.79 (s, 1H), 3.86 (m, 2H), 2.90-2.80 (m, 6H), 2.18 (m, 2H), 2.00-1.93 (m, 2H).

Example 21

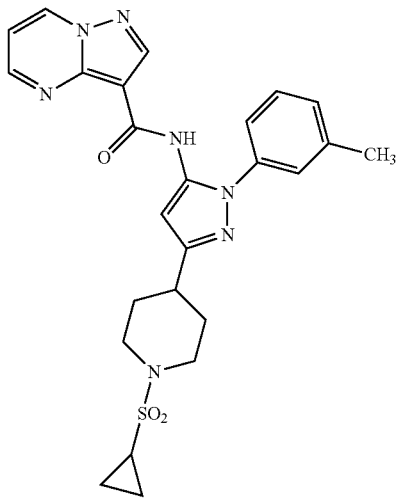

N-(3-(1-(cyclopropylsulfonyl)piperidin-4-yl)-1-(m-tolyl)-1H-pyrazol-5yl)-pyrazolo[1,5-a]pyrimidine-3-carboxamide This compound was prepared according to the general method described in Example 16, using N-(3-(piperidin-4-yl)-1-(m-tolyl)-1H-pyrazol-5-yl)pyrazolo[1,5-a]pyrimidine-3-carboxamide and cyclopropyl sulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. ¹H NMR (400 MHz, CDCl₃) δ 10.32 (br s, 1H), 8.78 (dd, J=7.2, 1.6 Hz, 1H), 8.70 (s, 1H), 8.32 (dd, J=4.0, 1.6 Hz, 1H), 7.43-7.36 (m, 4H), 7.27 (m, 1H), 6.99 (m, 1H), 6.77 (s, 1H), 3.87 (m, 2H), 2.97 (m, 2H), 2.85 (m, 1H), 2.42, (s, 3H), 2.28 (m, 1H), 2.14 (m, 2H), 1.93 (m, 2H), 1.17 (m, 2H), 0.98 (m, 2H).

Example 22

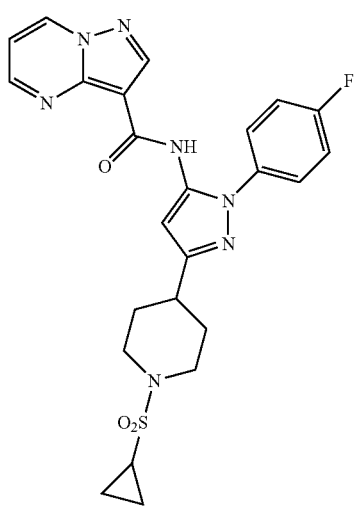

N-(3-(1-(cyclopropylsulfonyl)piperidin-4-yl)-1-(4-fluorophenyl)-1H-pyrazol-5yl)-pyrazolo[1,5-a]pyrimidine-3-carboxamide This compound was prepared according to the general methods outline in Example 16, using N-(1-(4-fluorophenyl)-3-(piperidin-4-yl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-α]pyrimidine-2-carboxamide and methanesulfonyl chloride, respectively. ¹H NMR (400 MHz, CDCl₃) δ 10.20 (br s 1H), 8.78 (dd, J=6.8, 1.6 Hz, 1H), 8.71 (s, 1H), 8.34 (dd, J=4.0, 1.6 Hz, 1H), 7.56 (m, 2H), 7.21 (m, 2H), 7.01 (dd, J=7.2, 4.0 Hz, 1H), 6.74 (s, 1H), 3.87 (m, 2H), 2.97 (dt, J=11.8, 1.6 Hz, 2H), 2.83 (tt, J=11.8, 4.4 Hz, 1H), 2.28 (m, 1H), 2.15 (m, 1H), 1.89 (m, 2H), 1.19 (m, 2H), 0.99 (m, 2H).

Example 23

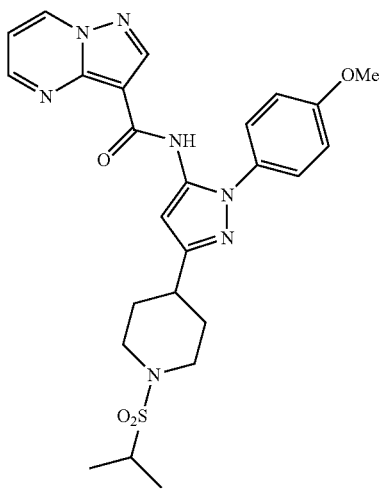

N-(3-(1-(isopropylsulfonyl)piperidin-4-yl)-1-(4-methoxyphenyl)-1H-pyrazol-5yl)-pyrazolo[1,5-a]pyrimidine-3-carboxamide This compound was prepared according to the general methods outlined in Example 16, using iso-propylsulfonyl chloride in place of methanesulfonylchloride. ¹H NMR (400 MHz, CDCl₃) δ 10.23 (br s, 114), 8.76 (dd, J=7.0, 1.6 Hz, 1H), 8.71 (s, 1H), 8.30 (dd, J=4.0, 1.6 Hz, 1H), 7.48 (m, 2H), 7.03 (m, 2H), 6.98 (dd, J=7.0, 4.0 Hz, 1H), 6.73 (s, 1H), 3.88-3.86 (m, 5H), 3.19 (m, 1H), 3.03 (dt, J=12.4, 2.4 Hz, 2H), 2.84 (m, 1H), 2.09 (m, 2H), 1.87 (m, 2H), 1.34 (d, J=6.8 Hz).

Example 24

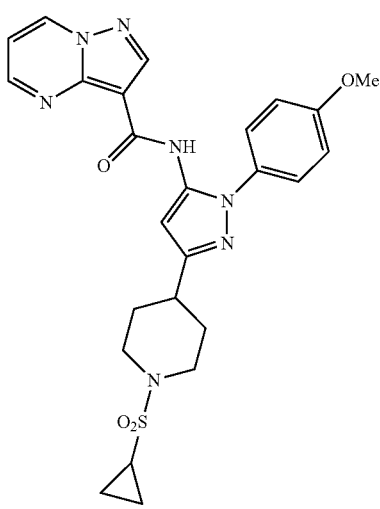

N-(3-(1-(cyclopropylsulfonyl)piperidin-4-yl)-1-(4-methoxyphenyl)-1H-pyrazol-5yl)-pyrazolo[1,5-a]pyrimidine-3-carboxamide This compound was prepared according to the general methods outlined in Example 16, using cyclopropylsulfonyl chloride in place of methanesulfonylchloride. $^1$H NMR (400 MHz, CDCl$_3$) δ 10.23 (br s, 1H), 8.76 (dd, J=7.2, 1.6 Hz, 1H), 8.71 (s, 1H), 8.30 (dd, J=4.2, 1.6 Hz, 1H), 7.48 (m, 2H), 7.02 (m, 2H), 6.98 (dd, J=7.2, 4.4 Hz, 1H), 6.73 (s, 1H), 3.89-3.86 (m, 5H), 2.97 (dt, J=12.0, 2.4 Hz, 2H), 2.83 (tt, J=12.0, 4.0 Hz, 1H), 2.28 (m, 1H), 2.13 (m, 2H), 1.92 (m, 2H), 1.18 (m, 2H), 0.97 (m, 2H).

Example 25

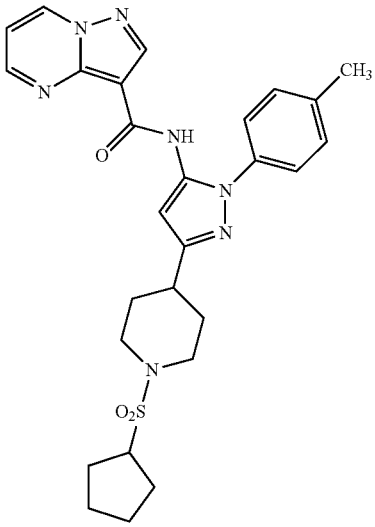

N-(3-(1-(cyclopentylsulfonyl)piperidin-4-yl)-1-p-tolyl)-1H-pyrazol-5yl)-pyrazolo[1,5-a]pyrimidine-3-carboxamide This compound was prepared according to the general methods outline in Example 16, using N-(3-(piperidin-4-yl)-1-(p-tolyl)-1H-pyrazol-5-yl)pyrazolo[1,5-a]pyrimidine-3-carboxamide and cyclopentylsulfonyl chloride in place of N-(1-(4-methoxyphenyl)-3-(piperidin-4-yl)-1H-pyrazol-5-yl)pyrazolo[1,5-c]pyrimidine-2-carboxamide and methanesulfonyl chloride, respectively. $^1$H NMR (400 MHz, CDCl$_3$) δ 10.28 (br s, 1H), 8.77 (dd, J=7.2, 1.6 Hz, 1H), 8.71 (s, 1H), 8.30 (dd, J=4.4, 1.6 Hz, 1H), 7.46 (m, 2H), 7.31 (m, 2H), 6.98 (dd, J=7.2, 4.4 Hz, 1H), 6.74 (s, 1H), 3.87 (m, 2H), 3.45 (m, 1H), 2.97 (dt, J=12.0, 2.4 Hz, 2H), 2.83 (m, 2H), 2.45 (s, 3H), 2.10 (m, 2H), 2.04-1.97 (m, 4H), 1.91-1.74 (m, 4H), 1.65-1.57 (m, 3H).

Example 26

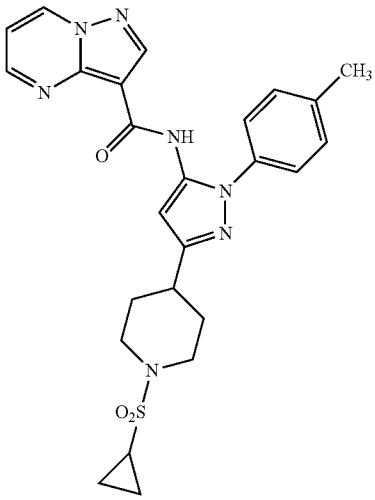

N-(3-(1-(cyclopropylsulfonyl)piperidin-4-yl)-1-(p-tolyl)-1H-pyrazol-5yl)-pyrazolo[1,5-a]pyrimidine-3-carboxamide This compound was prepared according to the general method outlined for Example 16, using N-(3-(piperidin-4-yl)-1-(p-tolyl)-1H-pyrazol-5-yl)pyrazolo[1,5-a]pyrimidine-3-carboxamide and cyclopropylsulfonyl chloride in place of N-(3-(1-(cyclopropylsulfonyl)piperidin-4-yl)-1-(4-methoxyphenyl)-1H-pyrazol-5-yl)pyrazolo[1,5-a]pyrimidine-3-carboxamide and methanesulfonyl chloride, respectively. $^1$H NMR (400 MHz, CDCl$_3$ δ 10.28 (br s, 1H), 8.77 (dd, J=7.2, 1.6 Hz, 1H), 8.71 (s, 1H), 8.30 (dd, J=4.0, 1.6 Hz, 1H), 7.46 (m, 2H), 7.31 (m, 2H), 6.89 (dd, J=7.2, 4.0 Hz, 1H), 6.75 (s, 1H), 3.88 (m, 2H), 2.97 (dt, J=12.0, 2.8 Hz, 2H), 8.85 (tt, J=7.6, 4.0 Hz, 1H), 2.45 (s, 3H), 2.28 (m, 1H), 2.14 (m, 2H), 1.93 (m, 2H), 1.18 (m, 2H), 1.00 (m, 2H).

Example 27

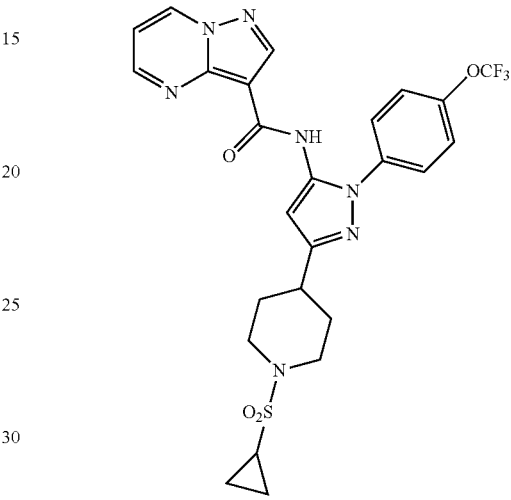

N-(3-(1-(cyclopropylsulfonyl)piperidin-4-yl)-1-(4-trifluoromethoxy)phenyl)-1H-pyrazol-5yl)-pyrazolo[1,5-a]pyrimidine-3-carboxamide This compound was prepared according to the general method outlined for Example 16, using N-(3-(piperidin-4-yl)-1-(4-(trifluoromethoxy)phenyl)-1H-pyrazol-5-yl)pyrazolo[1,5-a]pyrimidine-3-carboxamide and cyclopropyl sulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. $^1$H NMR (400 MHz, CDCl$_3$) δ 10.24 (br s), 8.97 (dd, J=7.0, 1.6 Hz, 1H), 8.72 (s, 1H), 8.29 (dd, J=4.0, 1.6 Hz, 1H), 7.64 (m, 2H), 7.38 (m, 2H), 7.01 (dd, J=7.0, 4.0 Hz, 1H), 6.76 (s, 1H), 3.88 (m, 2H), 2.97 (dt, J=12.0, 2.8 Hz, 2H), 2.82 (dt, J=11.2, 4.0 Hz, 1H), 2.28 m, 1H), 2.11 (m, 2H), 1.92 (m, 2H), 1.19 (m, 2H), 0.99 (m, 2H).

Example 28

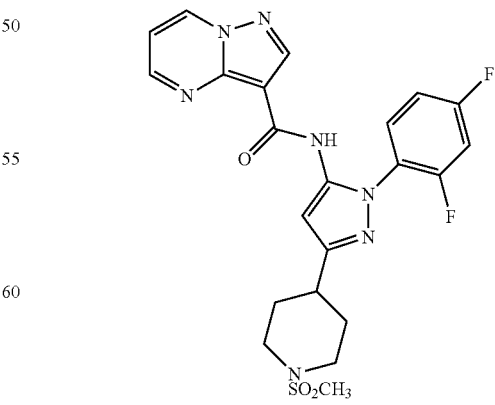

N-(1-(2,4-difluorophenyl)-3-(1-(methylsulfonyl)piperidin-4-yl)-1H-pyrazol-5-yl)pyrazolo[1,5-a]pyrimidine-3-carboxamide This compound was prepared according to the general method outlined for Example 16, using N-(1-(2,4-difluorophenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (400 MHz, CDCl₃) δ 1.92-2.02 (m, 2H), 2.18-2.22 (m, 2H), 2.84 (s, 3H), 2.85-2.93 (m, 3H), 3.87-3.90 (m, 2H), 6.75 (s, 1H), 7.02-7.27 (m, 3H), 7.54-7.64 (m, 1H), 8.36 (dd, J=3.3, 1.2 Hz, 1H), 8.74 (s, 1H), 8.82 (dd, J=5.1, 1.2 Hz, 1H), 10.09 (s, 1H).

Example 29

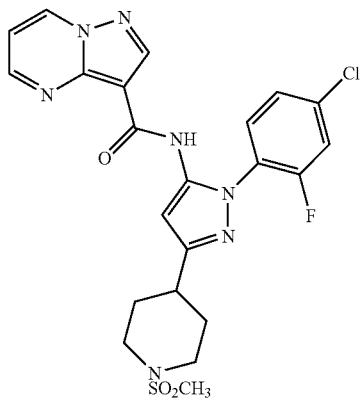

N-(1-(4-chloro-2-fluorophenyl)-3-(1-(methylsulfonyl)piperidin-4-yl)-1H-pyrazol-5-yl)pyrazolo[1,5-a]pyrimidine-3-carboxamide This compound was prepared according to the general method outlined for Example 16, using N-(1-(4-chloro-2-fluorophenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (300 MHz, CDCl3) δ 1.90 (m, 2H), 2.17 (d, 2H), 2.84 (s, 3H), 2.86 (m, 3H), 3.87 (d, J=12.3 Hz, 2H), 6.75 (s, 1H), 7.06 (dd, J=6.9, 4.2 Hz, 1H), 7.37 (d, J=8.1 Hz, 2H), 7.53-7.56 (m, 1H), 8.36 (dd, J=4.2, 1.8 Hz, 1H), 8.74 (s, 1H), 8.82 (dd, J=6.9, 1.5 Hz, 1H), 10.10 (s, 1H).

Example 30

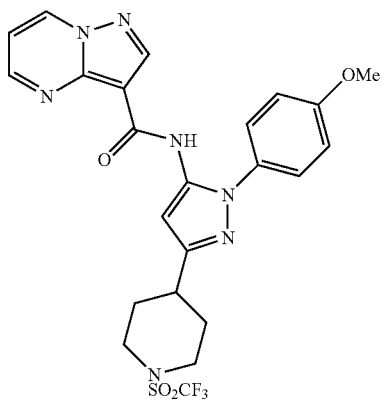

N-(1-(4-methoxyphenyl)-3-(1-(trifluoromethyl)sulfonyl)piperidin-4-yl)-1H-pyrazol-5-yl)pyrazolo[1,5-a]pyrimidine-3-carboxamide This compound was prepared according to the general method outlined for Example 16, using trifluoromethanesulfonic anhydride in place of cyclopropylsulfonyl chloride. ¹H NMR (400 MHz, CDCl₃) δ 10.25 (br s, 1H), 8.78 (dd, J=7.2, 1.6 Hz, 1H), 8.71 (s, 1H), 8.29 (dd, J=4.0, 1.6 Hz, 1H), 7.47 (m, 2H), 7.03 (m, 2H), 6.98 (dd, J=7.2, 4.0 Hz, 1H), 6.73 (s, 1H), 4.02 (m, 2H), 3.88 (s, 3H), 3.24 (m, 2H), 2.92 (tt, J=10.8, 4.0 Hz, 1H), 2.16 (m, 2H), 1.91 (m, 2H).

Example 31

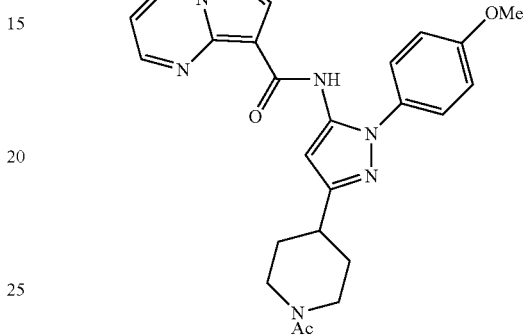

N-(3-(1-acetylpiperidin-4-yl)-1-p-tolyl-)1H-pyrazol-5-yl)pyrazolo[1,5-a]pyrimidine-3-carboxamide AcCl (20 μL, 0.28 mmol) and TEA (40 μL, 0.29 mmol) were added to a mixture of N-(1-(4-methylphenyl)-3-(piperidin-4-yl)-1H-pyrazol-5-yl)pyrazolo[1,5-α]pyrimidine-2-carboxamide (104 mg, 0.259 mmol) and CH₂Cl₂ (15 mL). The resulting mixture was stirred at rt. for 24 h, whereupon CH₂Cl₂ (50 mL) was added. The mixture was washed with water (50 mL), 1 M HCl (50 mL), and brine (50 mL). The organic layer was dried (MgSO₄) and concentrated in vacuo. The residue was purified by silica gel chromatography, eluting with a solvent gradient of 0 to 10% MeOH in CH₂Cl₂ to give the title compound as a white solid. ¹H NMR (400 MHz, CDCl₃) δ 10.28 (br s, 1H), 8.76 (dd, J=7.0, 2.0 Hz, 1H), 8.70 (s, 1H), 8.29 (dd, J=4.2, 2.0 Hz, 1H), 7.44 (m, 2H), 7.31 (m, 2H), 6.98 (dd, J=7.0, 4.2 Hz, 1H), 6.73 (s, 1H), 4.63 (m, 1H), 3.89 (m, 1H), 3.18 (dt, J=2.6, 11.8 Hz, 1H), 2.94 (tt, J=11.8, 4.4 Hz, 1H), 2.75 (dt, J=2.6, 12.8 Hz, 1H), 2.45 (s, 3H), 2.11-2.03 (m, 5H), 1.83-1.66 (m, 2H).

Example 32

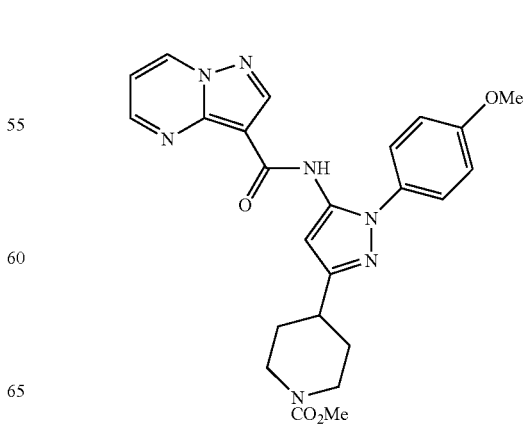

This compound was prepared according to the general method outlined for Example 31, using N-(1-(4-methoxyphenyl)-3-(piperidin-4-yl)-1H-pyrazol-5-yl)pyrazolo[1,5-a]pyrimidine-3-carboxamide and methylchloroformate in place N-(3-(piperidin-4-yl)-1-(p-tolyl)-1H-pyrazol-5-yl)pyrazolo[1,5-a]pyrimidine-3-carboxamide and acetyl chloride, respectively. $^1$H NMR (400 MHz, CDCl$_3$) δ 10.22 (br s, 1H), 8.64 (dd, J=7.2, 1.6 Hz, 1H), 8.70 (s, 1H), 8.29 (dd, J=4.0, 1.6 Hz, 1H), 7.47 (m, 2H, 7.02 (m, 2H), 6.97 (dd, J=7.2, 4.0 Hz, 1H), 6.71 (s, 1H), 7.20 (app br s, 2H), 3.87 (s, 3H), 3.69 (s, 3H), 2.94-2.82 (m, 3H), 2.02 (m, 2H), 1.73 (m, 2H).

This compound was prepared according to the general method outlined for Example 1, using ethyl 4-(N-methylsulfamoyl)benzoate and 2,4-difluoroaniline in place of ethyl 1,4-dioxaspiro[4.5]decane-8-carboxylate and 4-methylphenylhydrazine hydrochloride, respectively. $^1$H NMR (300 MHz, CDCl$_3$) δ 2.72 (d, T=5.4 Hz, 3H), 4.32 (q, 3=5.4 Hz, 1H), 7.04-7.23 (m, 3H), 7.36 (s, 1H), 7.63-7.74 (m, 1H), 7.93 (d, J=8.4 Hz, 2H), 8.08 (d, J=8.4 Hz, 2H), 8.36-8.39 (m, 1H), 8.77 (s, 1H), 8.84 (dd, J=7.2, 1.8 Hz, 1H), 10.32 (s, 1H).

Example 33

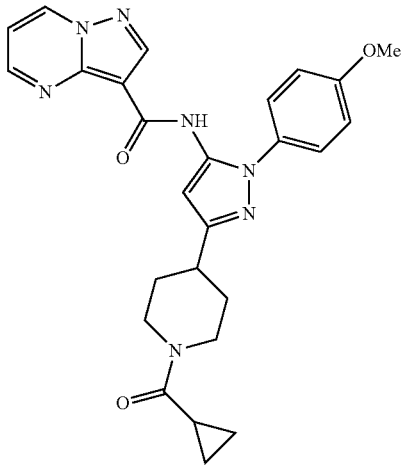

N-(3-(1-(cyclopropanecarbonyl)piperidin-4-yl)-1-(4-methoxyphenyl)-1H-pyrazol-5-yl)pyrazolo[1,5-a]pyrimidine-3-carboxamide This compound was prepared according to the general method outlined for Example 31, using cyclopropanecarbonyl chloride and N-(1-(4-methoxyphenyl)-3-(piperidin-4-yl)-1H-pyrazol-5-yl)pyrazolo[1,5-a]pyrimidine-3-carboxamide in place of acetyl chloride and N-(3-(piperidin-4-yl)-1-(p-tolyl)-1H-pyrazol-5-yl)pyrazolo[1,5-a]pyrimidine-3-carboxamide, respectively. $^1$H NMR (400 MHz, CDCl$_3$) δ 10.22 (br s, 1H), 8.77 (dd, J=7.0, 1.6 Hz, 1H), 8.70 (s, 1H), 8.29 (dd, J=4.0, 1.6 Hz, 1H), 7.48 (m, 2H), 7.02 (m, 2H), 6.97 (dd, J=7.0, 4.0 Hz, 1H), 6.71 (s, 1H), 4.63 (m, 1H), 4.28 (m, 1H), 3.87 (s, 3H), 3.24 (m, 1H), 2.96 (tt, J=11.6, 4.0 Hz, 1H), 2.80 (m, 1H), 2.10 (m, 1H), 1.83-1.71 (m, 4H), 0.97 (m, 2H), 0.74 (m, 2H).

Example 34

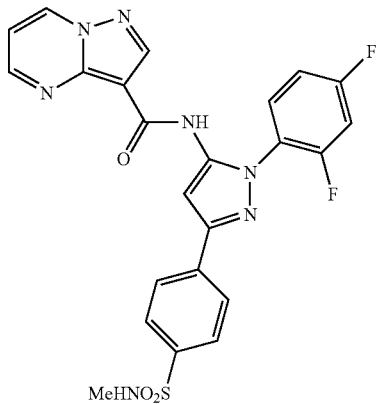

N-(1-(2,4-difluorophenyl)-3-(4-(N-methylsulfamoyl)phenyl)-1H-pyrazol-5-yl)pyrazolo[1,5-a]pyrimidine-3-carboxamide Example 35

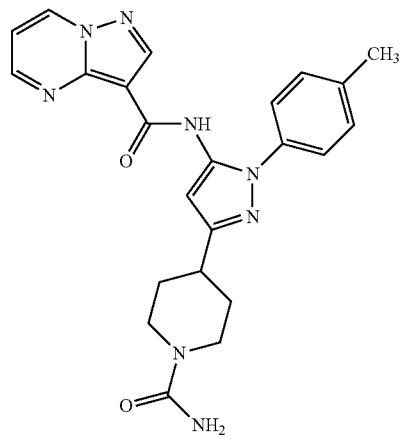

N-(3-(1-carbamoylpiperidin-4-yl)-1-(p-tolyl)-1H-pyrazol-5-yl)pyrazolo[1,5-a]pyrimidine-3-carboxamide Trimethylsilyl isocyanate (70 μL, 0.52 mmol) was added to a mixture of the piperidine TFA salt (70 mg, 0.14 mmol), TEA, (40 μL, 0.29 mmol), and THF (5 mL). The mixture was stirred at rt for 22 h. Sat NH$_4$Cl (30 mL) was added and the mixture was extracted with EtOAc (3×30 mL). The combined organic extracts were dried (MgSO$_4$) and concentrated in vacuo. The residue was triturated with hexanes/EtOH to give the expected product as a white solid. $^1$H NMR (400 MHz, CDCl$_3$) δ 9.08 (dd, J=7.2, 1.6 Hz, 1H), 8.62 (s, 1H), 8.42 (dd, J=4.2, 1.6 Hz, 1H), 7.48-7.43 (m, 4H), 7.19 (dd, J=7.2, 4.2 Hz, 1H), 6.69 (s, 1H), 4.22-4.019 (m, 2H), 3.07-2.86 (m, 3H), 2.50 (s, 3H), 2.06-2.00 (m, 2H), 1.76-1.66 (m, 2H).

Example 36

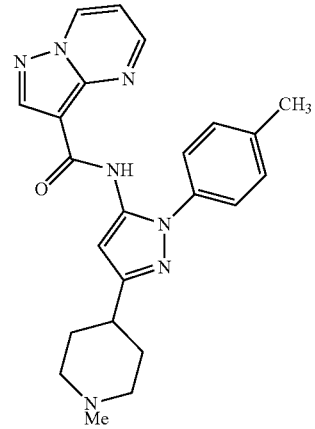 [SMILES: Cc1ccc(-n2nc(C3CCN(C)CC3)cc2NC(=O)c2cnn3cccnc23)cc1]

Formaldehyde (50 µl, 37% soln in water, 0.67 mmol) and DIPEA (120 µL, 0.687 mmol) were added to a mixture of N-(1-(4-methoxyphenyl)-3-(piperidin-4-yl)-1H-pyrazol-5-yl)pyrazolo[1,5-α]pyrimidine-2-carboxamide (120 mg, 0.233 mmol) and CH$_2$Cl$_2$ (5 mL). The resulting mixture was stirred at rt for 15 min. NaBH(OAc)$_3$ (151, 0.712 mmol) was added and the mixture was stirred at RT for 20 h. Sat NaHCO$_3$ (30 mL) was added and the mixture was extracted with DCM (3×30 mL). The combined organic extracts were dried (MgSO$_4$) and concentrated in vacuo. A small amount of hexanes and CH$_2$Cl$_2$ was added and the solution was concentrated in vauo to give the title compound as a foamy white solid that was used without further purification. $^1$H NMR (400 MHz, CDCl$_3$) δ 10.25 (br s, 1H), 8.76 (dd, J=6.8, 1.6 Hz, 1H), 8.71 (s, 1H), 8.30 (dd, J=4.0, 1.6 Hz, 1H), 7.46 (m, 2H), 7.30 (m, 2H), 6.80 (dd, J=6.8, 4.0 Hz, 1H), 6.75 (s, 1H), 2.95 (m, 2H), 2.68 (m, 2H), 2.44 (s, 3H), 2.30 (s, 3H), 2.09-2.02 (m, 3H), 1.86 (m, 2H).

Example 37

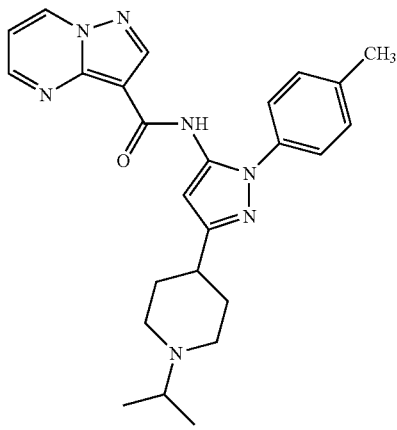

N-(3-(1-isopropylpiperidin-4-yl)-1-(p-tolyl)-1H-pyrazol-5-yl)pyrazolo[1,5-a]pyrimidine-3-carboxamide This compound was prepared according to the general method outline for Example 36, using acetone in place of formaldehyde. $^1$H NMR (400 MHz, CD$_3$OD) δ 9.10 (dd, J=7.2, 1.6 Hz, 1H), 8.64 (s, 1H), 8.42 (dd, J=4.4, 1.6 Hz, 1H), 7.47 (app s, 4H), 7.20 (dd, J=7.2, 4.4 Hz), 6.76 (s, 1H), 3.63-3.48 (m, 3H), 3.22 (m, 2H), 3.07 (m, 1H), 2.51 (s, 3H), 2.33 (m, 2H), 2.04 (m, 2H), 1.40 (d, J=6.8 Hz, 6H).

Example 38

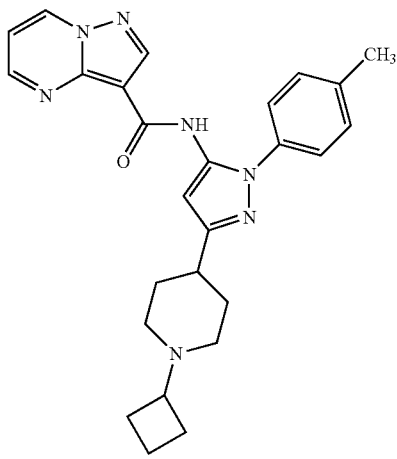

N-(3-(1-cyclobutylpiperidine-4-yl)-1-(p-tolyl)-1H-pyrazol-5-yl)pyrazolo[1,5-a]pyrimidine-3-carboxamide This compound was prepared according to the general method outlined for Example 36, using cyclobutanone in place of formaldehyde. $^1$H NMR (400 MHz, CD$_3$OD) δ 9.09 (dd, J=7.2, 1.6 Hz, 1H), 8.63 (s, 1H), 8.42 (dd, J=4.4, 1.6 Hz, 1H), 7.48-7.43 (m, 4H), 7.19 (dd, J=7.2, 4.4 Hz, 1H), 6.71 (s, 1H), 3.09 (m, 2H), 2.85 (m, 1H), 2.72 (m 1H), 2.50 (s, 3H), 2.13-1.72 (m, 12H).

Example 39

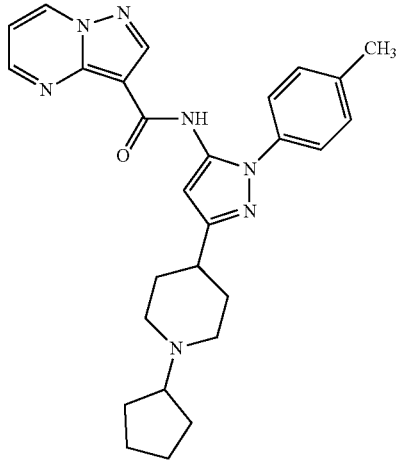

N-(3-(1-cyclopentylpiperidin-4-yl)-1-(p-tolyl)-1H-pyrazol-5-yl)pyrazolo[1,5-a]pyrimidine-3-carboxamide This compound was prepared according to the general method outlined for Example 36, using cyclopentanone in place of formaldehyde. (400 MHz, CD$_3$OD) δ 9.08 (dd, J=7.2, 1.6 Hz, 1H), 8.62 (s, 1H), 8.41-8.40 (m, 2H), 7.45 (app br s, 4H), 7.18 (dd, J=7.2, 4.0 Hz), 6.74 (s, 1H), 3.66-3.53 (m, 3H), 3.16-3.05 (m, 3H), 2.49 (s, 3H), 2.30 (m, 2H), 2.18 (m, 2H), 2.06 (m, 2H), 1.84-1.70 (m, 6H).

Example 40

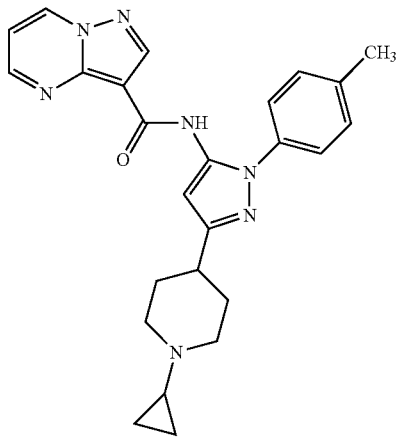

N-(3-(1-cyclopentylpiperidin-4-yl)-1-(p-tolyl)-1H-pyrazol-5-yl)pyrazolo[1,5-a]pyrimidine-3-carboxamide Acetic acid (200 µL, 3.49 mmol), 4 Å molecular sieves (500 mg), (1-ethoxycyclopropoxy)trimethylsilane (400 µL, 2.00 mmol), and NaBH(CN)$_3$ (94 mg, 1.50 mmol) were added to a mixture of N-(1-(4-methoxyphenyl)-3-(piperidin-4-yl)-1H-pyrazol-5-yl)pyrazolo[1,5-α]pyrimidine-2-carboxamide (172 mg, 0.334 mmol) and MeOH (5 mL). The resulting solution was heated to reflux for 5 h. CH$_2$Cl$_2$ (50 mL) was added and the mixture was washed with water (50 mL), 1M NaOH (50 mL), and brine (50 mL). The organic layer was dried (MgSO$_4$) and concentrated in vacuo. The residue was trituraed with Et$_2$O. The solid was purified by reverse phase HPLC to give the title compound as a colorless oil. $^1$H NMR (400 MHz, CD$_3$OD) δ 9.08 (dd, J=7.2, 1.6 Hz, 1H), 8.63 (s, 1H), 8.41 (dd, J=4.4, 1.6 Hz, 1H), 7.45 (m, 4H), 7.19 (dd, J=7.2, 4.4 Hz, 1H), 6.70 (s, 1H), 3.26 (m, 2H), 2.80 (m, 1H), 2.57 (m, 2H), 2.56 (s, 3H), 2.07 (m, 2H), 1.93-1.79 (m, 3H), 0.62-0.57 (m, 4H).

Example 41

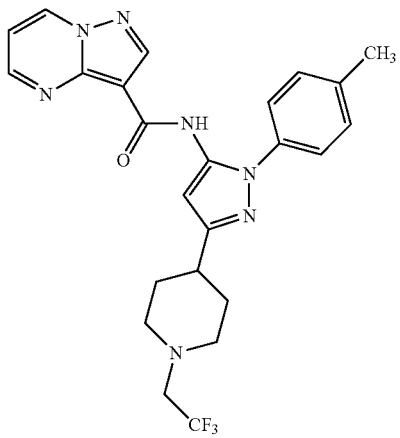

N-(1-(p-tolyl)-3-(1-(2,2,2-trifluoroethyl)piperidin-4-yl)-1H-pyrazol-5-yl)pyrazolo[1,5-a]pyrimidine-3-carboxamide A mixture of N-(3-(piperidin-4-yl)-1-(p-tolyl)-1H-pyrazol-5-yl)pyrazolo[1,5-a]pyrimidine-3-carboxamide TFA salt (112 mg) and sat NaHCO$_3$ (30 mL) was extracted with CH$_2$Cl$_2$ (3×30 mL). The combined organic extracts were dried (MgSO$_4$) and concentrated in vacuo. THF (10 mL) and 2,2,2-trifluoroethyl trifluoromethanesulfonate (40 µL, 0.28 mmol) were added. DIPEA (50 µL, 0.286 mmol) was added and the solution was stirred at 50° C. for 17 h. The solution was concentrated in vacuo. Sat NaHCO$_3$ (30 mL) was added and the mixture was extracted with CH$_2$Cl$_2$ (3×30 mL). The combined organic extracts were dried (MgSO$_4$) and concentrated in vacuo. The residue was washed with a small amount of warm hexanes/CH$_2$Cl$_2$ to give the title compound as a white solid. $^1$H NMR (400 MHz, CDCl$_3$) δ 10.26 (br s, 1H), 8.76 (dd, J=7.0, 1.6 Hz, 1H), 8.71 (s, 1H), 8.30 (dd, J=4.0, 1.6 Hz, 1H), 7.46 (m, 2H), 7.31 (m, 2H), 6.78 (dd, J=7.0, 4.0 Hz, 1H), 6.75 (s, 1H), 3.07-2.96 (m, 4H), 2.70 (m, 1H), 2.51-2.44 (m, 5H), 2.00 (m, 2H) 1.90 (m, 2H).

Example 42

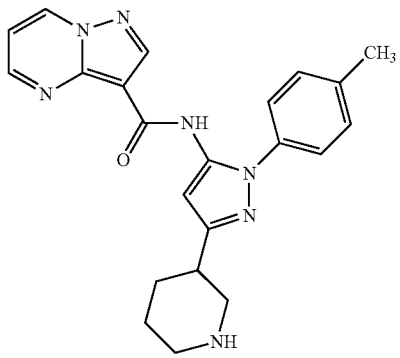

N-(3-(piperidin-3-yl)-1-(p-tolyl)-1H-pyrazol-5-yl)pyrazolo[1,5-a]pyrimidine-3-carboxamide This compound was prepared according to the general method outlined for Example 7, using 1-tert-butyl 3-ethyl piperidine-1,3-dicarboxylate in place of 1-tert-butyl 4-ethyl piperidine-1,4-dicarboxylate. $^1$H NMR (400 MHz, CD$_3$OD) δ 9.10 (m, 1H), 8.61 (s, 1H), 8.40 (m, 1H), 7.45 (m, 4H), 7.20 (m, 1H), 6.80 (m, 1H), 3.75-3.55 (m, 2H), 3.40-3.05 (m, 4H), 2.45 (s, 3H), 2.25-1.84 (m, 3H).

Example 43

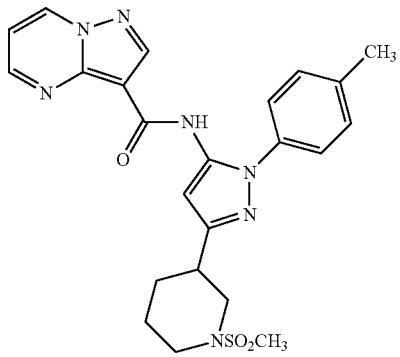

N-(3-(1-(methylsulfonyl)piperidin-3-yl)-1-(p-tolyl)-1H-pyrazol-5-yl)pyrazolo[1,5-a]pyrimidine-3-carboxamide This compound was prepared following the general method outlined for Example 16, using N-(3-(piperidin-3-yl)-1-(p-tolyl)-1H-pyrazol-5-yl)pyrazolo pyrimidine-3-carboxamide in place of N-(3-(piperidin-4-yl)-1-(p-tolyl)-1H-pyrazol-5-yl)pyrazolo[1,5-a]pyrimidine-3-carboxamide. $^1$H NMR (400 MHz, CDCl$_3$) δ 10.30 (br s, 1H), 8.78 (dd, J=7.2, 2.0 Hz, 1H), 8.70 (s, 1H), 8.30 (dd, J=4.0, 1.6 Hz, 1H), 7.45 (m, 2H), 7.33 (m, 2H), 7.00 (dd, J=6.8, 4.0 Hz, 1H), 6.77 (s, 1H), 4.10 (m, 1H), 3.88 (m, 1H), 3.05 (m, 1H), 2.89 (m, 1H), 2.79 (s, 3H), 2.69 (m, 1H), 2.46 (s, 3H), 2.24-2.20 (m, 1H), 1.92-1.63 (m, 3H).

Example 44

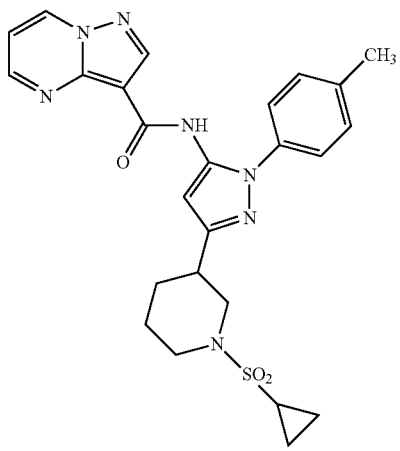

N-(3-(1-(cyclopropylsulfonyl)piperidin-3-yl)-1-(p-tolyl)-1H-pyrazol-5-yl)pyrazolo[1,5-a]pyrimidline-3-carboxamide This compound was prepared following the general method outlined for Example 16, using cyclopropylsulfonyl chloride and N-(3-(piperidin-3-yl)-1-(p-tolyl)-1H-pyrazol-5-yl)pyrazolo[1,5-a]pyrimidine-3-carboxamide in place of methanesulfonyl chloride and N-(3-(piperidin-4-yl)-1-(p-tolyl)-1H-pyrazol-5-yl)pyrazolo[1,5-a]pyrimidine-3-carboxamide, respectively. ¹H NMR (400 MHz, CDCl₃) δ 10.30 (br s, 1H), 8.79 (dd, J=6.8, 2.0 Hz, 1H), 8.70 (s, 1H), 8.30 (dd, J=4.4, 1.6 Hz, 1H), 7.45 (m, 2H), 7.32 (m, 2H), 7.01 (dd, J=7.2, 4.4 Hz, 1H), 6.76 (s, 1H), 4.10 (m, 2H), 3.83 (m, 1H), 3.09-2.95 (m, 2H), 2.83 (m, 1H), 2.45 (s, 3H), 2.30 (m, 1H), 2.20 (m, 1H), 2.03 (s, 1H), 1.88 (m, 1H), 1.80-1.64 (m, 2H), 1.17 (m, 2H), 0.96 (m, 2H).

Example 45

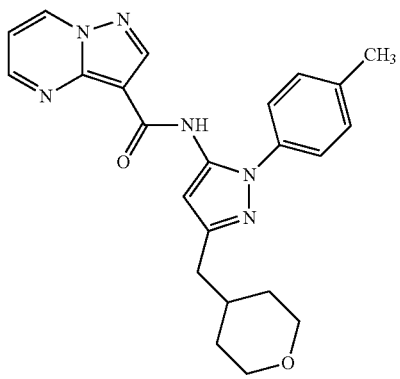

N-(3-((tetrahydro-2H-pyran-4-yl)methyl)-1-(p-tolyl)-1H-pyrazol-5-yl)pyrazolo[1,5-a]pyrimidine-3-carboxamide This compound was prepared using the general methods described for Example 1, using ethyl 2-(tetrahydro-2H-pyran-4-yl)acetate in place of ethyl 1,4-dioxaspiro[4.5]decane-8-carboxylate. ¹H NMR (400 MHz, CD₃OD) δ 10.29 (br s, 1H), 8.77 (dd, J=7.2, 1.6 Hz, 1H), 8.71 (s, 1H), 8.30 (4.0, 1.6 Hz, 1H), 7.46 (m, 2H), 7.32 (m, 2H), 6.98 (dd, J=4.4, 1.6 Hz, 1H), 6.72 (s, 1H), 3.94 (m, 2H), 3.38 (dt, J=11.8, 2.0 Hz, 2H), 2.61 (d, J=11.8 Hz, 1H), 2.45 (s, 3H), 1.91 (m, 1H), 1.71 (m, 2H), 1.42 (m, 2H).

Example 46

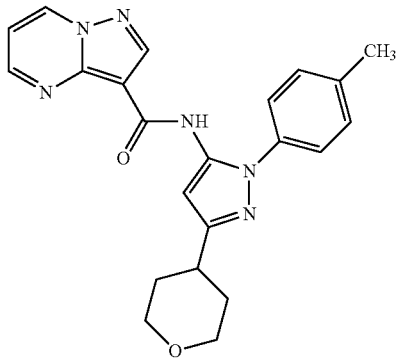

N-(3-(tetrahydro-2H-pyran-4-yl)-1-(p-tolyl)-1H-pyrazol-5-yl)pyrazolo[1,5-a]pyrimidine-3-carboxamide This compound was prepared using the general methods described for Example 1, using ethyl tetrahydro-2H-pyran-4-carboxylate in place of ethyl 1,4-dioxaspiro[4.5]decane-8-carboxylate. ¹H NMR (400 MHz, CDCl₃) δ 10.28 (br s, 1H), 8.77 (dd, J=7.0, 1.6 Hz, 1H), 8.71 (s, 1H), 8.30 (dd, J=4.2, 1.6 Hz, 1H), 7.46 (m, 2H), 7.31 (m, 2H), 6.98 (dd, J=7.0, 4.2 Hz, 1H), 6.76 (s, 1H), 4.06 (m, 2H), 3.54 (dt, J=2.8, 10.8 Hz, 2H), 2.53 (m, 1H), 2.45 (s, 3H), 1.97-1.84 (m, 4H).

Example 47

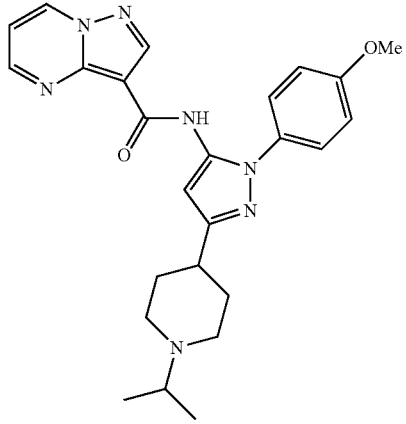

N-(3-(1-isopropylpiperidin-4-yl)-1-(4-methoxyphenyl)-1H-pyrazol-5-yl)pyrazolo[1,5-a]pyrimidine-3-carboxamide This compound was prepared according to the general method outlined for Example 36, using N-(1-(4-methoxyphenyl)-3-(piperidin-4-yl)-1H-pyrazol-5-yl)pyrazolo[1,5-a]pyrimidine-3-carboxamide and acetone in place of N-(3-(piperidin-4-yl)-1-(p-tolyl)-1H-pyrazol-5-yl)pyrazolo[1,5-a]pyrimidine-3-carboxamide and formaldehyde, respectively. ¹H NMR (400 MHz, CD₃OD) δ 9.10 (dd, J=7.2, 1.6 Hz, 1H), 8.63 (s, 1H), 8.41 (dd, J=4.4, 1.6 Hz, 1H), 7.50 (m, 2H), 7.21-7.17 (m, 3H), 6.74 (s, 1H), 3.93 (s, 3H), 3.55-3.49 (m, 3H), 3.19 (m, 2H), 3.04 (m, 1H), 2.32 (m, 2H), 1.39 (d, 6H).

Example 48

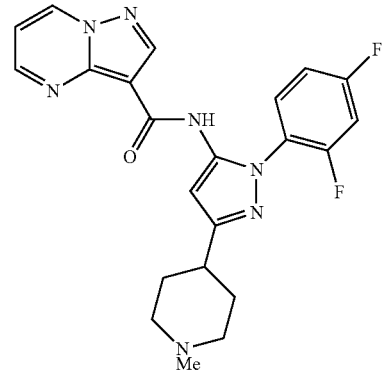

N-(1-(2,4-difluorophenyl)-3-(1-methylpiperidin-4-yl)-1H-pyrazol-5-yl)pyrazolo[1,5-a]pyrimidine-3-carboxamide This compound was prepared according to the general method outlined for Example 36, using N-(1-(2,4-difluorophenyl)-3-(piperidin-4-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. ¹H NMR (400 MHz, CDCl₃) δ 2.22-2.46 (m, 4H), 2.80-3.00 (m, 4H), 3.16-3.23 (m, 2H), 3.50 (d, J=11.6 Hz, 1H), 3.81 (d, J=11.6 Hz, 1H), 6.77 (d, J=7.6 Hz, 1H), 7.02-7.25 (m, 3H), 7.54-7.63 (m, 1H), 8.35 (d, J=3.6 Hz, 1H), 8.73 (d, J=3.2 Hz, 1H), 8.82-8.85 (m, 1H), 10.09 (s, 0.5H), 10.14 (s, 0.5H), 11.67 (s, 0.5H), 12.14 (s, 0.5H).

Example 49

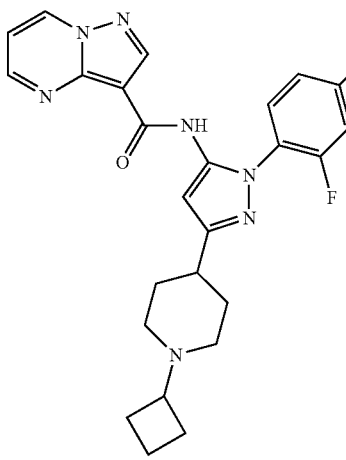

N-(3-(1-cyclobutylpiperidin-4-yl)-1-(2,4-difluorophenyl)-1H-pyrazol-5-yl) pyrazolo[1,5-a]pyrimidine-3-carboxamide This compound was prepared according to the general method outlined for Example 36, using N-(1-(2,4-difluorophenyl)-3-(piperidin-4-yl)-1H-pyrazol-5-yl)pyrazolo[1,5-a]pyrimidine-3-carboxamide and cyclobutanone in place of N-(3-(piperidin-4-yl)-1-(p-tolyl)-1H-pyrazol-5-yl)pyrazolo[1,5-a]pyrimidine-3-carboxamide and formaldehyde, respectively. $^1$H NMR (400 MHz, CDCl$_3$) δ1.72-1.80 (m, 1H), 1.83-1.97 (m, 1H), 2.21-2.34 (m, 6H), 2.41-2.63 (m, 3H), 2.90-3.05 (m, 1H), 3.25-3.45 (m, 2H), 3.75-3.78 (m, 1H), 6.77 (s, 1H), 7.04-7.16 (m, 3H), 7.56-7.63 (m 1H), 8.36 (d, J=3.2 Hz, 1H), 8.73 (d, J=4.8 Hz, 1H), 8.83-8.86 (m, 1H), 9.59 (s broad, 1H), 10.11 (s, 0.5H), 10.15 (s, 0.5H), 10.80 (s broad, 0.5H), 11.20 (s broad, 0.5H).

Example 50

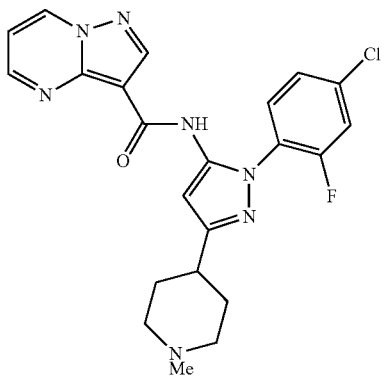

N-(1-(4-chloro-2-fluorophenyl)-3-(1-methylpiperidin-4-yl)-1H-pyrazol-5-yl)pyrazolo[1,5-a]pyrimidine-3-carboxamide This compound was prepared according to the general method outlined for Example 36, using N-(1-(4-chloro-2-fluorophenyl)-3-(piperidin-4-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. $^1$H NMR (300 MHz, CDCl$_3$) δ 2.19-2.57 (m, 4H), 2.80-3.00 (m, 5H), 3.18-3.30 (m, 1H), 4.47-3.51 (m, 1H), 3.79-3.82 (m, 1H), 6.75 (d, J=4.8 Hz, 1H), 6.09-7.12 (m, 1H), 7.35-7.41 (m, 2H), 7.52-7.62 (m, 1H), 8.35 (d, J=3.9 Hz, 1H), 8.68-8.75 (m, 1H), 8.81-8.45 (m, 1H), 9.59 (s broad, 1H), 10.10 (s, 0.5H), 10.15 (0.5H), 11.36 (s, 0.5H), 11.82 (s, 0.5H).

Example 51

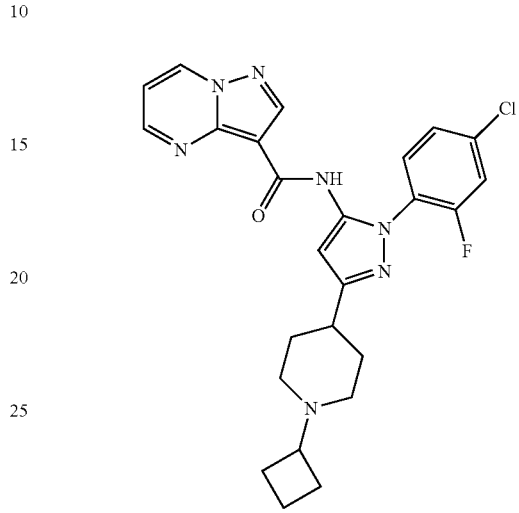

N-(1-(4-chloro-2-fluorophenyl)-3-(1-cyclobutylpiperidin-4-yl)-1H-pyrazol-5-yl)pyrazolo[1,5-a]pyrimidine-3-carboxamide This compound was prepared according to the general method outlined for Example 36, using N-(1-(4-chloro-2-fluorophenyl)-3-(piperidin-4-yl)-1H-pyrazol-5-yl)pyrazolo[1,5-a]pyrimidine-3-carboxamide and cyclobutanone in place of N-(3-(piperidin-4-yl)-1-(p-tolyl)-1H-pyrazol-5-yl)pyrazolo[1,5-a]pyrimidine-3-carboxamide and formaldehyde, respectively. $^1$H NMR (400 MHz, CDCl$_3$) δ 1.69-1.93 (m, 2H), 2.18-2.65 (m, 8H), 2.91-2.96 (m, 2H), 3.29-3.44 (m, 3H), 3.71-3.74 (m, 1H), 6.71-6.75 (m, 1H), 7.04-7.09 (m, 1H), 7.34-7.41 (m, 2H), 7.52-7.57 (m, 1H), 8.36-8.38 (m, 1H), 8.73 (d, J=4.8 Hz, 1H), 8.81 (t, J=7.2 Hz, 1H), 10.05 (s, 0.5; H), 10.13 (s, 0.5; H).

Example 52

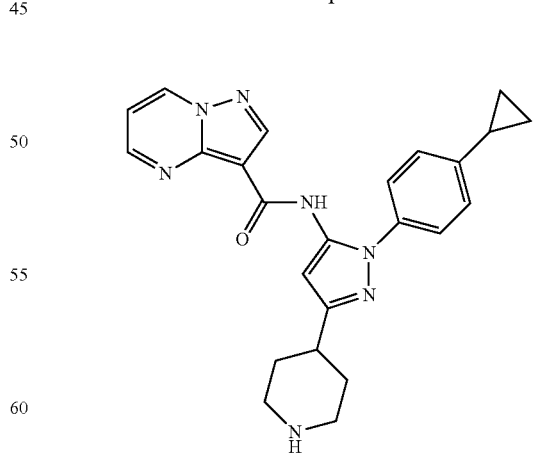

N-(1-(4-cyclopropylphenyl)-3-(piperidin-4-yl)-1H-pyrazol-5-yl) pyrazolo[1,5-a]pyrimidine-3-carboxamide General methods for preparation of the synthetic intermediates follow below.

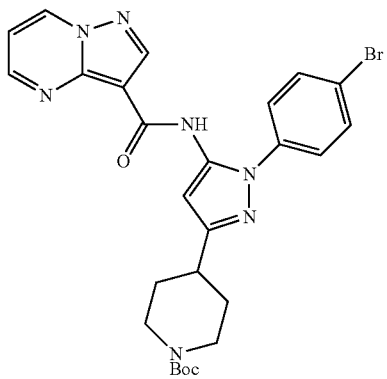

tert-butyl 4-(1-(4-bromophenyl)-5-(pyrazolo[1,5-a]pyrimidine-3-carboxamido)-1H-pyrazol-3-yl)piperidine-1-carboxylate Tert-butyl 4-(1-(4-bromophenyl)-5-(pyrazolo[1,5-a]pyrimidine-3-carboxamido)-1H-pyrazol-3-yl)piperidine-1-carboxylate was prepared according to the general methods described for the synthesis of Example 7, using 4-bromophenylhydrine hydrochloride in place of 4-methylphenyl hydrazine hydrochloride.

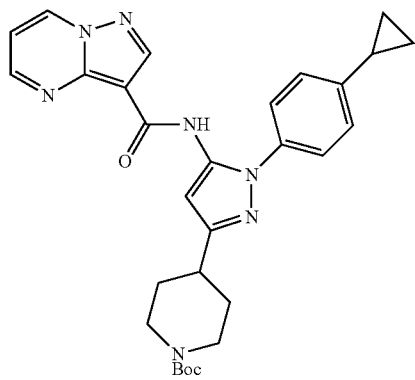 [SMILES: O=C(Nc1cc(C2CCNCC2)nn1-c1ccc(C2CC2)cc1)c1cnn2cccnc12]

tert-butyl 4-(1-(4-cyclopropylphenyl)-5-(pyrazolo[1,5-a]pyrimidine-3-carboxamido)-1H-pyrazol-3-yl)piperidine-1-carboxylate A mixture of tert-butyl 4-(1-(4-bromophenyl)-5-pyrazolo[1,5a]pyrimidine-3-carboxamide)-1H-pyrazol-3-yl)piperidine-1-carboxylate (111 mg, 0.196 mmol), potassium cyclopropyltrifluoroborate (52 mg, 0.351 mmol), Pd(OAc)$_2$ (7 mg, 0.031 mmol), butyl diadamantylphosphine (29 mg, 0.081 mmol), cesium carbonate (190, 0.583 mmol), toluene (5 mL), and water (1 mL) was purges with N$_2$ for 30 min. The mixture was heated to 100° C. in a sealed tube for 15 h. The mixture was cooled to rt. and water (30 mL) was added. The mixture was extracted with EtOAc (3×30 mL). The combined organic extracts were dried (MgSO$_4$) and concentrated in vacuo. The residue was purified by silica gel chromatography, eluting with a solvent gradient of 0 to 100% EtOAc in hexanes to give the product as a colorless oil.

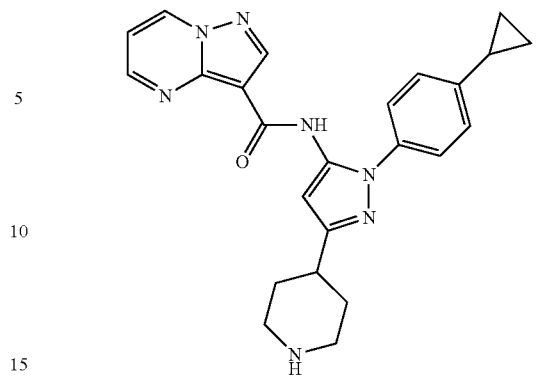

This compound was prepared according to the general methods outlined for Example 7 using tert-butyl 4-(1-(4-cyclopropylphenyl)-5-(pyrazolo pyrimidine-3-carboxamido)-1H-pyrazol-3-yl)piperidine-1-carboxylate in place of tert-butyl 4-(5-(pyrazolo[1,5-a]pyrimidine-3-carboxamido)-1-(p-tolyl)-1H-pyrazol-3-yl)piperidine-1-carboxylate. $^1$H NMR (400 MHz, CDCl$_3$) δ 10.24 (br s, 1H), 8.76 (dd, J=7.0, 1.8 Hz, 1H), 8.70 (s, 1H), 8.28 (dd, J=4.0 1.8 Hz, 1H), 7.43 (m, 2H), 7.18 (m, 2H), 6.98 (dd, J=7.0, 4.0 Hz, 1H), 6.71 (s, 1H), 4.15 (app br s, 2H), 2.88-2.80 (m, 3H), 2.02-1.94 (m, 3H), 1.73-1.61 (m, 2H), 1.45 (s, 9H), 1.05 (m, 2H), 0.73 (m, 2H).

Example 53

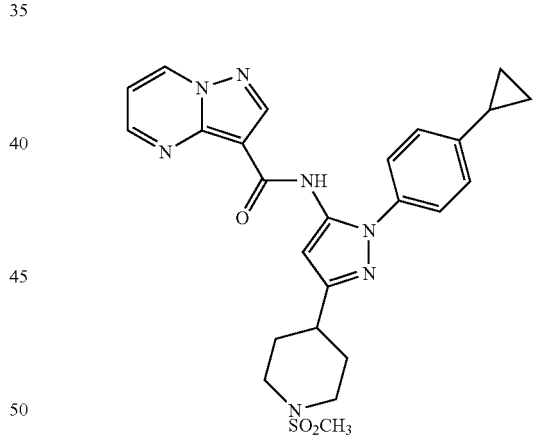

N-(1-(4-cyclopropylphenyl)-3-(1-(methylsulfonyl)piperidin-4-yl)-1H-pyrazol-5-yl)pyrazolo[1,5-a]pyrimidine-3-carboxamide This compound was prepared according to the general method outlined for Example 16, using N-(1-(4-cyclopropylphenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.26 (br s, 1H), 8.76 (dd, J=6.8, 1.6 Hz, 1H), 8.71 (s, 1H), 8.30 (dd, J=4.0, 1.6 Hz, 1H), 7.44 (m, 2H), 7.19 (m, 2H), 6.99 (dd, J=6.8, 4.0 Hz, 1H), 6.74 (s, 1H), 3.84 (m, 2H), 2.88-2.79 (m, 6H), 2.15 (m, 2H), 2.02-1.88 (m, 3H), 1.06 (m, 2H), 0.73 (m, 2H).

Example 54

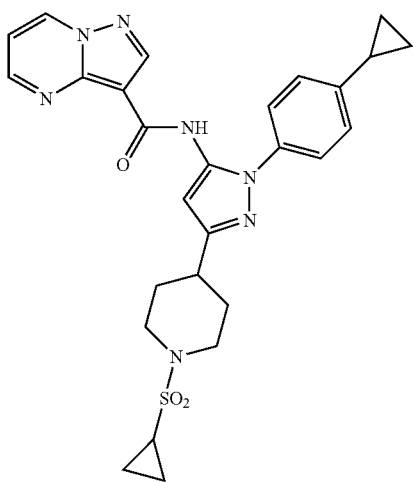

N-(1-(4-cyclopropylphenyl)-3-(1-(cyclopropylsulfonyl)piperidin-4-yl)-1H-pyrazol-5-yl)pyrazolo[1,5-a]pyrimidne-3-carboxamide This compound was prepared according to the general method outlined for Example 16, using N-(1-(4-cyclopropylphenyl)-3-(piperidin-4-yl)-1H-pyrazol-5-yl)pyrazolo[1,5-a]pyrimidine-3-carboxamide and cyclopropysulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. $^1$H NMR (400 MHz, CDCl$_3$) δ 10.26 (br s, 1H), 8.78 (dd, J=6.8, 1.6 Hz, 1H), 8.70 (s, 1H), 8.28 (dd, J=4.0, 1.6 Hz, 1H), 7.44 (m, 2H), 7.19 (m, 2H), 6.99 (dd, J=6.8, 4.0 Hz, 1H), 6.74 (s, 1H), 3.88 (m, 2H), 2.97 (dt, J=11.8, 2.4 Hz, 1H), 2.82 (tt, J=11.8, 4.0 Hz, 1H), 2.27 (m, 1H), 2.13 (m, 2H), 2.01-1.86 (m, 3H), 1.18 (m, 2H), 1.06 (m, 2H), 0.99 (m, 2H), 0.74 (m, 2H).

Example 55

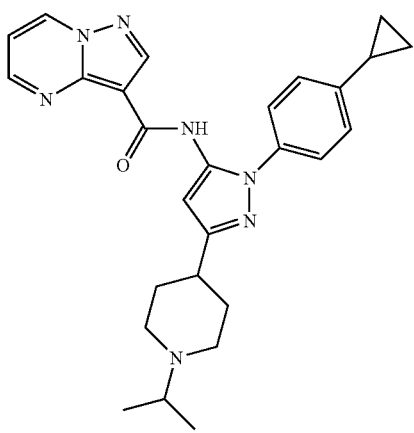

N-(1-(4-cyclopropylphenyl)-3-(1-isopropylpiperidin-4-yl)-1H-pyrazol-5-yl)pyrazolo[1,5-a]pyrimidine-3-carboxamide This compound was prepared according to the method outlined for Example 36 using N-(1-(4-cyclopropylphenyl)-3-(piperidin-4-yl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD$_3$OD) δ 9.11 (dd, J=7.2, 1.4 Hz, 1H), 8.64 (s, 1H), 8.40 (dd, J=4.0, 1.4 Hz, 1H), 7.45 (m, 2H), 7.34 (m, 2H), 7.22, J=7.2, 4.0 Hz, 1H), 6.75 (s, 1H), 3.55 (m, 2H), 3.29-3.02 (m, 3H), 2.37 (m, 2H), 2.12-2.05 (m, 4H), 1.39 (d, J=6.8 Hz, 6H), 1.11 (m, 2H), 0.81 (m, 2H).

Example 56

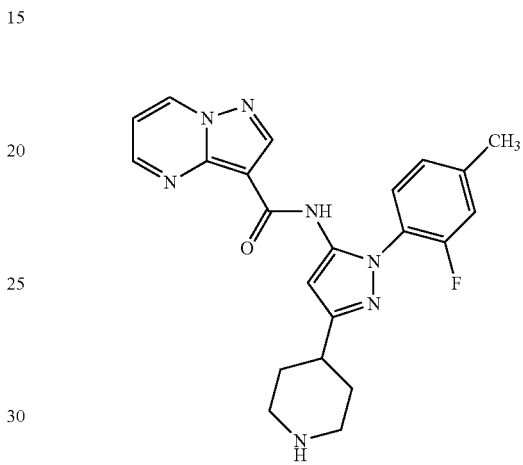

N-(1-(2-fluoro-4-methylphenyl)-3-(piperidin-4-yl)-1H-pyrazol-5-yl)pyrazolo[1,5-a]pyrimidine-3-carboxamide General methods for preparation of the synthetic intermediates follow below.

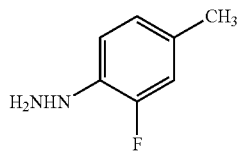

(2-fluoro-4-methylphenyl)hydrazine

A mixture of 2-fluoro-5-methyl aniline (997 mg, 7.97 mmol) and conc HCl (10 mL) was cooled to 0° C., whereupon a solution of NaNO$_2$ (660 mg, 9.56 mmol) and water (2 mL) was added dropwise over 2 min. The resulting mixture was stirred at 0° C. for 1 h. A solution of tin (II) chloride dehydrate (7.19 g, 31.9 mmol) and conc HCl (10 mL0 was added dropwise over 3 min. The resulting mixture was stirred at rt for 3 h. Water (40 mL) was added and the mixture was washed with Et$_2$O (3×30 mL). The aqueous layer was brought to pH=13 using 20% NaOH. The mixture was extracted with Et$_2$O (3×50 mL). The combined organic extracts were dried (MgSO$_4$) and concentrated in vacuo to give the title compound as a pale yellow solid. $^1$H NMR (400 MHz, DMSO-d$_6$) δ 9.95 (br s, 2H), 7.65 (br s, 1H), 7.05-7.01 (m, 2H), 6.87 (m, 1H), 2.17 (s, 3H).

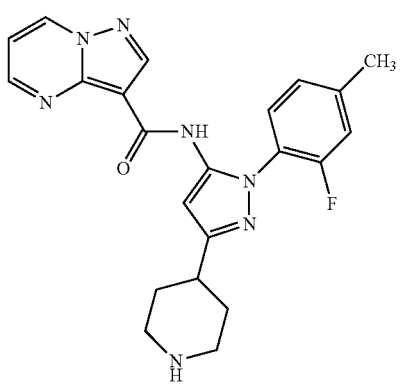 [SMILES: Cc1ccc(-n2nc(C3CCNCC3)cc2NC(=O)c2cnn3cccnc23)c(F)c1]

This compound was prepared according to the general methods outlined for Example 7, using (2-fluoro-4-methylphenyl)hydrazine in place of 4-methylphenylhydrazine hydrochloride. $^1$H NMR (400 MHz, CD$_3$OD) δ 9.11 (dd, J=7.0, 1.6 Hz, 1H), 8.64 (s, 1H), 8.36 (dd, J=4.4, 1.6 Hz, 1H), 7.48 (t, J=8.0 Hz, 1H), 7.35-7.28 (m, 2H), 7.20 (dd, J=7.0, 4.4 Hz, 1H), 6.74 (s, 1H), 3.49 (m, 2H), 3.15 (dt, J=15.6, 3.2 Hz, 1H), 3.08 (m, 1H), 2.54 (s, 3H), 2.26 (m, 2H), 2.00 (m, 2H).

Example 57

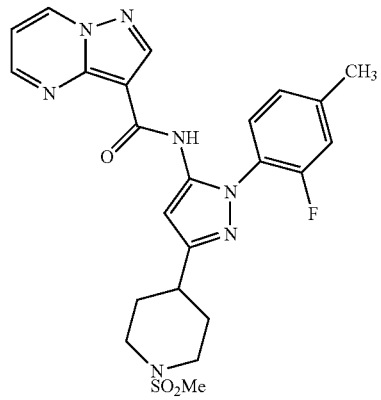

N-(1-(2-fluoro-4-methylphenyl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(2-fluoro-4-methylphenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.11 (br s, 1H), 8.77 (dd, J=7.2, 1.6 Hz, 1H), 8.69 (s, 1H), 8.26 (dd, J=4.0, 1.6 Hz, 1H), 7.42 (t, J=8.0 Hz, 1H), 7.12-7.09 (m, 2H), 6.98 (dd, J=7.2, 4.0 Hz, 1H), 6.71 (s, 1H), 3.84 (m, 2H), 2.88-2.79 (m, 6H), 2.47 (s, 3H), 2.15 (m, 2H), 1.95 (m, 2H).

Example 58

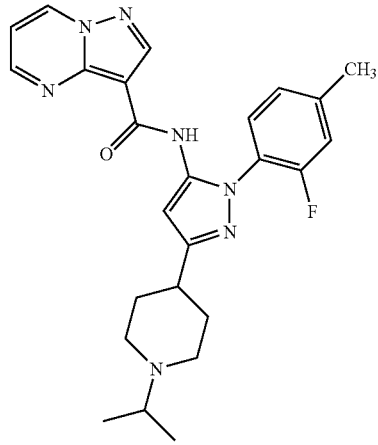

N-(1-(2-fluoro-4-methylphenyl)-3-(1-isopropylpiperidin-4-yl)-1H-pyrazol-5-yl)pyrazolo[1,5-a]pyrimidine-3-carboxamide This compound was prepared according to the method outlined for Example 36 using N-(1-(2-fluoro-4-methylphenyl)-3-(piperidin-4-yl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD$_3$OD) δ 10.42 (br s, 1H), 9.11 (dd, J=7.0, 1.8 Hz, 1H), 8.64 (s, 1H), 8.36 (dd, J=4.0, 1.8 Hz, 1H), 7.47 (t, J=8.0 Hz, 1H), 7.35-7.29 (m, 2H), 7.20 (dd, J=7.0, 4.0 Hz, 1H), 6.74 (s, 1H), 3.56 (m, 2H), 3.25-3.02 (m, 4H), 2.54 (s, 3H), 2.37 (m, 2H), 2.03 (m, 2H).

Example 59

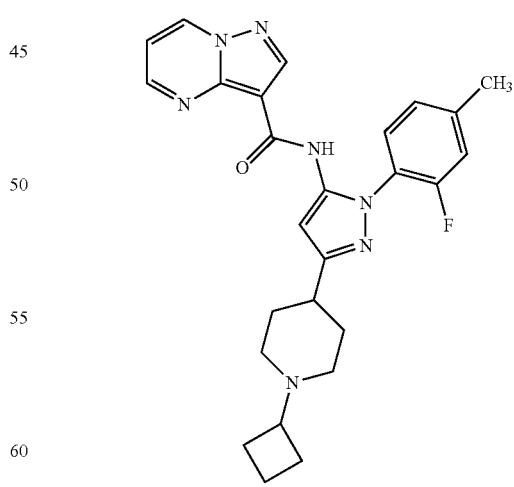

N-(3-(1-cyclobutylpiperidin-4-yl)-1-(2-fluoro-4-methylphenyl)-1H-pyrazol-5-yl)pyrazolo[1,5-a]pyrimidine-3-carboxamide This compound was prepared according to the method outlined for Example 36 using N-(1-(2-fluoro-4-methylphenyl)-3-(piperidin-4-yl)-1H-pyrazol-5-yl)pyrazolo[1,5-a]pyrimidine-3-carboxamide and cyclobutanone in place of N-(1-(4-methoxyphenyl)-3-(piperidin-4-yl)-1H-pyrazol-5-yl)pyrazolo[1,5-a]pyrimidine-3-carboxamide and formaldehyde, respectively. (400 MHz, CDCl$_3$) δ 10.06 (br s, 1H), 8.76 (dd, J=7.0, 1.8 Hz, 1H), 8.69 (s, 1H), 8.26 (dd, J=4.4, 1.8 Hz, 1H), 7.42 (t, J=7.6 Hz, 1H), 7.11-7.07 (m, 2H), 6.96 (dd, J=7.0, 4.4 Hz, 1H), 6.71 (s, 1H), 2.96 (m, 2H), 2.70 (m, 2H), 2.45 (s, 3H), 2.05-2.02 (m, 214), 1.94-1.84 (m, 6H), 1.71-1.64 (m, 2H).

Example 60

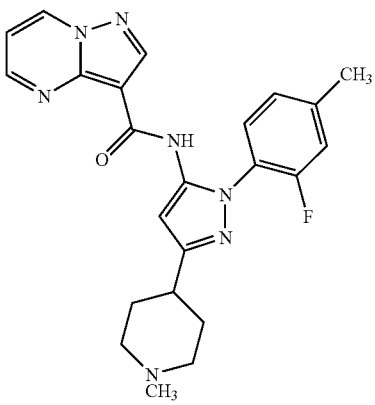

N-(1-(2-fluoro-4-methylphenyl)-3-(1-methylpiperidin-4-yl)-1H-pyrazol-5-yl)pyrazolo[1,5-a]pyrimidine-3-carboxamide This compound was prepared according to the method outlined for Example 36 using N-(1-(2-fluoro-4-methylphenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CD$_3$OD) δ 1.97-2.37 (m, 4H), 2.56 (s, 3H), 2.91-3.29 (m, 6H), 3.45-3.67 (m, 2H), 6.76 (s, 1H), 7.20-7.22 (m, 1H), 7.30-7.36 (m, 2H), 7.47-7.53 (m, 1H), 8.37-8.41 (m, 1H), 8.65 (s, 1H), 9.10-9.12 (m, 1H).

Example 61

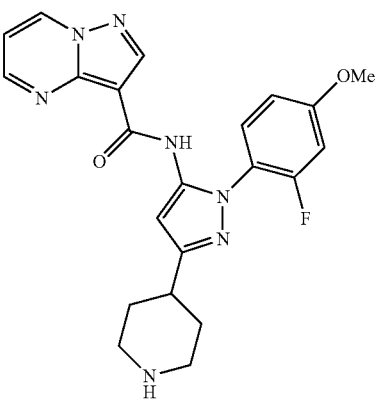

N-(1-(2-fluoro-4-methoxyphenyl)-3-(piperidin-4-yl)-1H-pyrazol-5-yl)pyrazolo[1,5-a]pyrimidine-3-carboxamide General methods for preparation of the synthetic intermediates follow below.

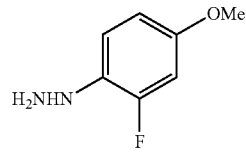

(2-fluoro-4-methoxyphenyl)hydrazine

A mixture of 2-fluoro-4-methoxyaniline hydrochloride (2.04 g, 11.5 mmol) and conc HCl (20 mL) was cooled to 0° C., whereupon a solution of sodium nitrite (825 mg, 12.0 mmol) and water (5 mL) was added dropwise over 5 min. The mixture was stirred at 0° C. for 90 min. A mixture of SnCl$_2$ dihydrate (10.75 g, 47.6 mmol) and conc HCl (15 mL) was added over 15 min. The mixture was stirred at rt for 2.5 h. The mixture was filtered and the solid was washed with a small amount of conc HCl to give the desired product as a marron solid. $^1$H NMR (400 MHz, DMSO-d$_6$) δ 9.92 (br s, 2H), 7.80 (br s, 1H), 7.28 (s, 1H), 7.12 (t, J=9.4 Hz, 1H), 7.02 (s, 1H), 6.90 (dd, J=13.2, 2.8 Hz, 1H), 6.78 (dd, J=9.4, 2.8 Hz, 1H), 3.71 (s, 3H).

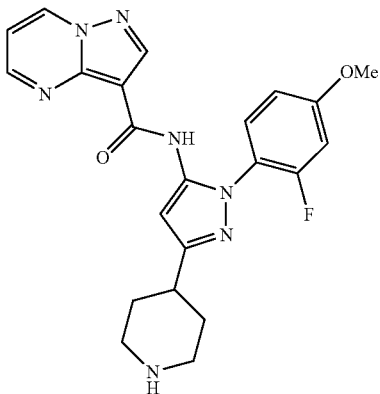

N-(1-(2-fluoro-4-methoxyphenyl)-3-(piperidin-4-yl)-1H-pyrazol-5-yl)pyrazolo[1,5-a]pyrimidine-3-carboxamide N-(1-(2-fluoro-4-methoxyphenyl)-3-(piperidin-4-yl)-1H-pyrazol-5-yl)pyrazolo[1,5-a]pyrimidine-3-carboxamide was prepared according to the general methods outlined for Example 7, using (2-fluoro-4-methoxyphenyl)hydrazine in place of 4-methylphenylhydrazine hydrochloride. $^1$H NMR (400 MHz, CD$_3$OD) δ 10.40 (br s, 1H), 9.11 (dd, J=7.0, 1.8 Hz, 1H), 8.64 (s, 1H), 8.38 (dd, J=4.0, 1,8 Hz, 1H), 7.51 (t, J=8.8 Hz, 1H), 7.20 (dd, J=7.0, 4.0 Hz, 1H), 7.09 (dd, J=12.0, 2.6 Hz, 1H), 7.02 (ddd, J=8.8, 2.6, 1.2, 1H), 6.73 (s, 3H), 3.95 (s, 3H), 3.47 (m, 2H), 3.20-3.04 (m, 5H), 2.27 (m, 2H), 2.00 (m, 2H).

Example 62

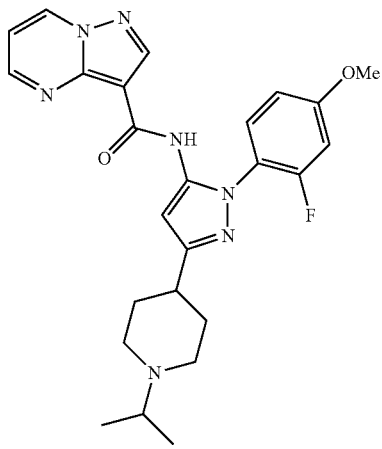

N-(1-(2-fluoro-4-methoxyphenyl)-3-(isopropylpiperidin-4-yl)-1H-pyrazol-5-yl)pyrazolo[1,5-a]pyrimidine-3-carboxamide This compound was prepared according to the method outlined for Example 36 using tert-butyl 4-(1-(2-fluoro-4-methoxyphenyl)-5-(pyrazolo[1,5-a]pyrimidine-3-carboxamido)-1H-pyrazol-3-yl)piperidine-1-carboxylate and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD$_3$OD) δ 9.10 (dd, J=7.0, 1.8 Hz, 1H), 8.64 (s, 1H), 8.38 (dd, J=4.4, 1.8 Hz, 1H), 7.51 (t, J=8.8 Hz, 1H), 7.20 (dd, J=7.0, 4.4 Hz, 1H), 7.09 (dd, J=12.4, 2.8 Hz, 1H), 7.03 (ddd, J=8.8, 2.8, 1.2 Hz, 1H), 6.73 (s, 1H), 3.94 (s, 3H), 3.50-3.46 (m, 3H), 3.19-3.12 (m, 3H), 2.33 (m, 2H), 2.06 (m, 2H), 1.36 (d, J=6.4 Hz, 6H).

Example 63

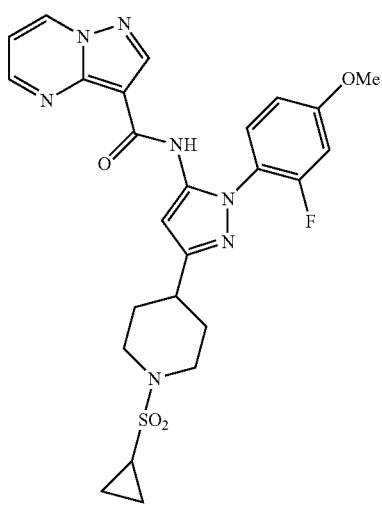

N-(3-(1-(cyclopropylsulfonyl)piperidin-4-yl)-1-(2-fluoro-4-methoxyphenyl)-1H-pyrazol-5-yl)pyrazolo[1,5-a]pyrimidine-3-carboxammide This compound was prepared according to the general methods outlined for Example 16, using N-(1-(2-fluoro-4-methoxyphenyl)-3-(piperidin-4-yl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. $^1$H NMR (400 MHz, CDCl$_3$) δ 10.09 (br s, 1H), 8.77 (dd, J=7.2, 1.8 Hz, 1H), 8.69 (s, 1H), 8.27 (dd, J=4.0, 1.8 Hz, 1H), 7.45 (t, J=8.4 Hz, 1H), 6.98 (dd, J=7.2, 4.0 Hz, 1H), 6.86-6.80 (m, 2H), 6.70 (s, 1H), 3.88-3.84 (m, 5H), 2.97 (dt, J=12.0, 2.8 Hz, 2H), 2.82 (m, 1H), 2.13 (m, 2H), 1.90 (m, 2H), 1.17 (m, 2H), 0.97 (m, 2H).

Example 64

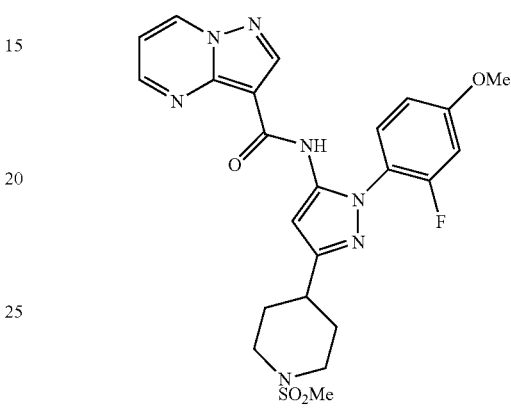

N-(1-(2-fluoro-4-methoxyphenyl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(2-fluoro-4-methoxyphenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR 10.09 (br s, 1H), 8.77 (dd, J=7.2, 1.8 Hz, 1H), 8.70 (s, 1H), 8.27 (dd, J=4.0, 1.8 Hz, 1H), 7.45 (t, J=9.2 Hz, 1H), 6.97 (dd, J=7.2, 4.0 Hz, 1H), 6.84 (m, 2H), 6.71 (s, 1H), 3.88 (s, 3H), 3.82 (m, 2H), 2.88-2.82 (m, 3H), 2.79 (s, 3H), 2.16 (m, 2H), 1.95 (m, 2H).

Example 65

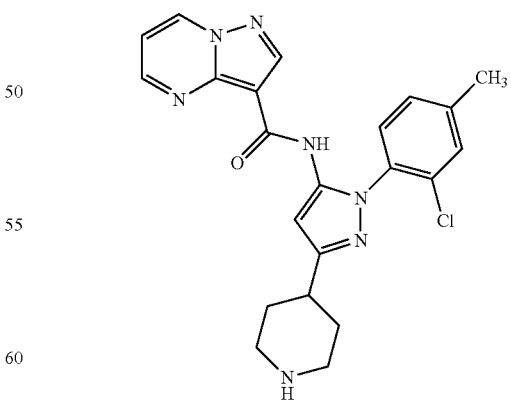

N-(1-(2-chloro-4-methylphenyl)-3-(piperidin-4-yl)-1H-pyrazol-5-yl)pyrazolo[1,5-a]pyrimidine-3-carboxamide This compound was prepared according to the method outlined for Example 61 using 2-chloro-5-methyl aniline in place of 2-fluoro-5-methyl aniline.

Example 66

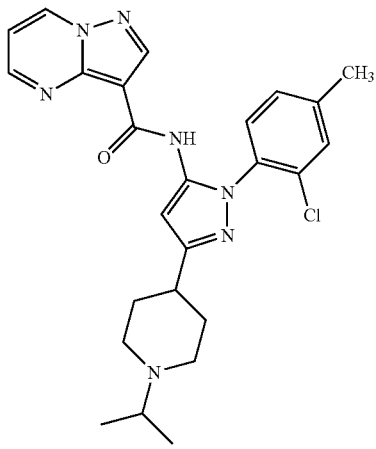

N-(1-(2-fluoro-4-methylphenyl)-3-(isopropylpiperidin-4-yl)-1H-pyrazol-5-yl)pyrazolo[1,5-a]pyrimidine-3-carboxamide This compound was prepared according to the method outlined for Example 36 using N-(1-(2-chloro-4-methylphenyl)-3-(piperidin-4-yl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CDCl$_3$) δ 9.97 (br s, 1H), 8.74 (dd, J=7.0, 1.8 Hz, 1H), 8.68 (s, 1H), 8.15 (dd, J=4.0, 1.8 Hz, 1H), 7.43-7.39 (m, 2H), 6.95 (dd, J=7.0, 4.0 Hz, 1H), 6.70 (s, 1H), 2.98 (m, 2H), 2.70 (m, 2H), 2.45 (s, 3H), 2.24 (m, 2H), 2.05 (m, 2H), 1.83 (m, 2H), 1.06 (app br s, 6H).

Example 67

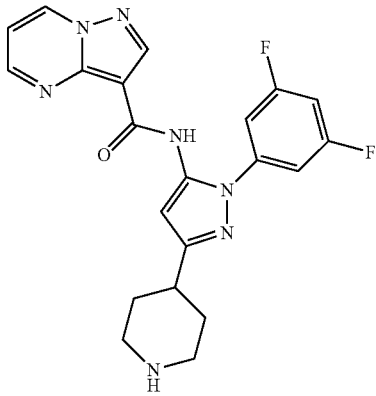

N-(1-(3,5-difluorophenyl)-3-(piperidin-4-yl)-1H-pyrazol-5-yl)pyrazolo[1,5-a]pyrimidine-3-carboxamide This compound was prepared according to the method outlined for Example 61 using 3,5-difluoro aniline in place of 2-fluoro-4-methoxy aniline. $^1$H NMR (400 MHz, CDCl$_3$) δ 10.39 (br s, 1H), 9.63 (app br s, 9.63, 1H), 9.25 (app, br s, 1H), 8.26 (dd, J=7.0, 1.8 Hz, 1H), 8.74 (s, 1H), 8.56 (dd, J=4.2, 1.8 Hz, 1H), 7.29-7.24 (m, 2H), 7.06 (dd, J=7.0, 4.2 Hz, 1H), 6.82 (s, 1H), 3.46 (m, 2H), 3.11-3.03 (m, 3H), 2.30 (m, 2H), 2.18 (m, 1H).

Example 68

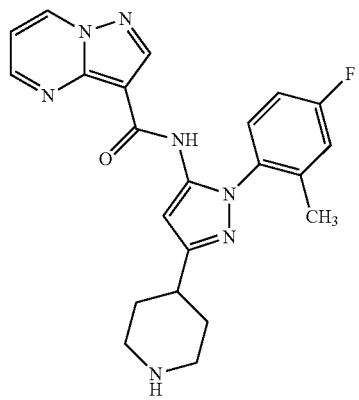

N-(1-(4-fluoro-2-methylphenyl)-3-(piperidin-4-yl)-1H-pyrazol-5-yl)pyrazolo[1,5-a]pyrimidine-3-carboxamide This compound was prepared according to the method outlined for Example 61 using 2-methyl-4-fluoro aniline in place of 2-fluoro-4-methoxy aniline. $^1$H NMR (400 MHz, CD$_3$OD) δ 10.26 (br s, 1H), 9.10 (dd, J=7.0, 1.8 Hz, 1H), 8.63 (s, 1H), 8.31 (dd, J=4.0, 1.8 Hz, 1H), 7.50 (dd, J=8.6, 5.6 Hz, 1H), 7.32 (dd, J=9.6, 3.0 Hz, 1H), 7.27 (dt, J=8.6, 3.0, 1H), 7.18 (dd, J=7.0, 4.0 Hz, 1H), 6.74 (s, 1H), 3.48 (m, 2H), 3.20-3.05 (m, 3H), 2.27 (m, 2H), 2.04 (s, 3H), 1.98 (m, 2H).

Example 69

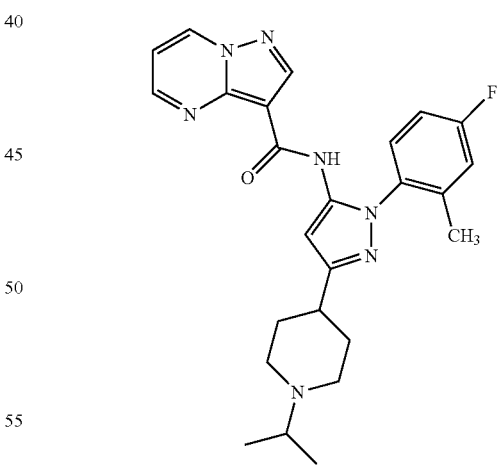

N-(1-(4-fluoro-2-methylphenyl)-3-(isopropylpiperidin-4-yl)-1H-pyrazol-5-yl)pyrazolo[1,5-a]pyrimidine-3-carboxamide This compound was prepared according to the method outlined for Example 36 using N-(1-(4-fluoro-2-methylphenyl)-3-(piperidin-4-yl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD$_3$OD) δ

9.09 (dd, J=7.0, 1.8 Hz, 1H), 8.63 (s, 1H), 8.54 (br s, 1H), 8.31 (dd, J=4.4, 1.8 Hz, 1H), 7.50 (dd, J=5.2, 4.2 Hz, 1H), 7.31 (dd, J=9.2, 2.4 Hz, 1H), 7.25 (dt, J=8.4, 2.4 Hz, 1H), 7.17 (dd, J=7.0, 4.2 Hz, 1H), 6.74 (s, 1H), 3.51-3.43 (m, 1H-1), 3.16-3.02 (m, 3H), 2.30 (m, 2H), 2.09-2.03 (m, 5H), 1.37 (d, J=6.4 Hz, 1H).

Example 70

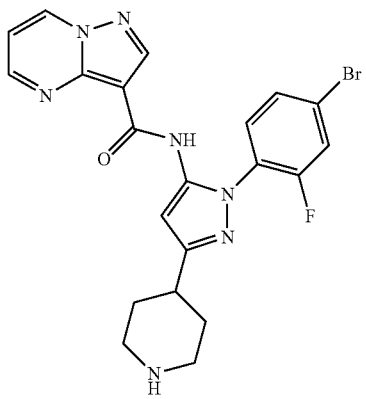

N-(1-(4-bromo-4-fluorophenyl)-3-(piperidin-4-yl)-1H-pyrazol-5-yl)pyrazolo[1,5-a]pyrimidine-3-carboxamide This compound was prepared according to the method outlined for Example 61 using 2-fluoro-4-bromo aniline in place of 2-fluoro-4-methoxy aniline. $^1$H NMR (400 MHz, CD$_3$OD) δ 9.12 (dd, J=6.8, 2.0 Hz, 1H), 8.64 (s, 1H), 8.43 (dd, J=4.2, 2.0 Hz, 1H), 7.80 (dd, J=5.6, 2.0 Hz, 1H), 7.68 (m, 1H), 7.57 (t, J=8.0 Hz, 1H), 7.23 (dd, J=6.8, 4.2 Hz, 1H), 6.74 (s, 1H), 3.49 (m, 2H), 3.17 (dt, J=12.8, 4.8 Hz, 2H), 3.09 (m, 1H), 2.26 (m, 2H), 2.00 (m, 2H).

Example 71

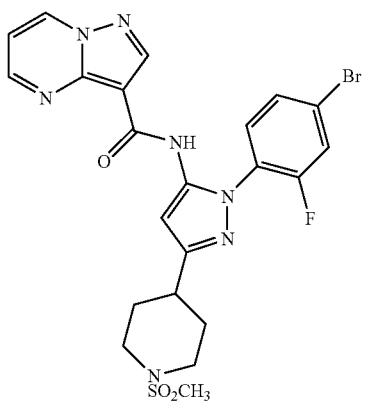

N-(1-(4-bromo-4-fluorophenyl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(4-bromo-2-fluorophenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.06 (br s, 1H), 8.79 (dd, J=7.2, 1.8 Hz, 1H), 8.70 (s, 1H), 8.33 (dd, J=4.4, 1.8 Hz, 1H), 7.50-7.45 (m, 3H), 7.02 (dd, J=72, 4.4 Hz, 1H), 6.71 (s, 1H), 3.85 (m, 2H), 2.82-2.80 (m, 6H), 2.17 (m, 1H), 1.94 (m, 2H).

Example 72

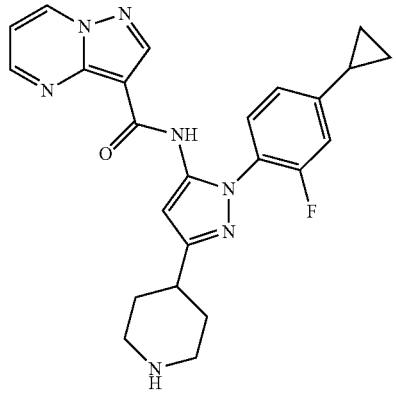

N-(1-(4-cyclopropyl-2-fluorophenyl)-3-(piperidin-4-yl)-1H-pyrazol-5-yl)pyrazolo[1,5-a]pyrimidine-3-carboxamide This compound was prepared according to the general methods outlined for Example 52, using 2-fluoro-4-bromo-hydrazine hydrochloride in place of 4-bromophenylhydrine. $^1$H (400 MHz, CD$_3$OD) δ 9.11 (dd, J=7.2, 1.8 Hz, 1H), 8.64 (s, 1H), 8.35 (dd, J=4.0, 1.8 Hz, 1H), 7.45 (t, J=8.0 Hz, 1H), 7.22-7.18 (m, 3H), 6.73 (s, 1H), 3.47 (m, 2H), 3.19-3.04 (m, 3H), 2.25 (m, 2H), 2.12 (m, 1H), 2.00 (m, 2H), 1.17 (m, 2H), 0.87 (m, 2H).

Example 73

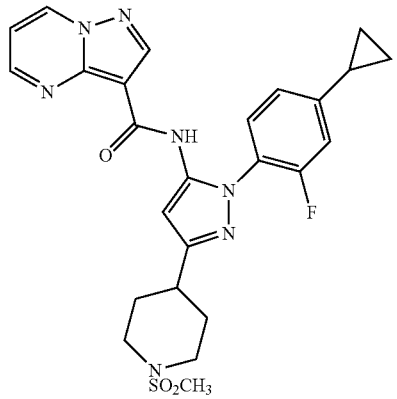

N-(1-(4-cyclopropyl-2-fluorophenyl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(4-cyclopropyl-2-fluorophenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3 carboxamide. $^1$H NMR (400 MHz, CDCl$_3$) δ 10.10 (br s, 1H), 8.77 (dd, J=7.2, 2.0 Hz, 1H), 8.69 (s, 1H), 8.25 (dd, J=4.0, 2.0 Hz, 1H), 7.40 (t, J=8.0 Hz, 1H), 7.02-6.93, m, 3H), 6.71 (s, 1H), 3.84 (m, 2H), 2.89-2.79 (m, 6H), 2.17 (m, 2H), 2.01-1.88 (m, 3H), 1.11 (m, 2H), 0.75 (m, 2H).

Example 74

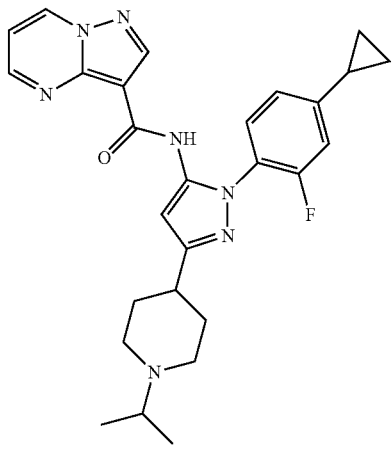

N-(1-(4-cyclopropyl-2-fluorophenyl)-3-(1-(isopropylpiperidin-4-yl)-1H-pyrazol-5-yl)pyrazolo[1,5-a]pyrimidine-3-carboxamide This compound was prepared according to the method outlined for Example 36 using N-(1-(4-cyclopropyl-2-fluorophenyl)-3-(piperidin-4-yl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD$_3$OD) δ 9.10 (dd, J=6.8, 1.8 Hz, 1H), 8.63 (s, 1H), 8.54 (br s, 1H), 8.35 (dd, J=4.0, 1.8 Hz, 1H), 7.45 (t, J=8.0 Hz, 1H), 7.22-7.17 (m, 3H), 6.71 (s, 1H), 3.23 (app br s, 1H0, 2.90-2.81 (m, 4H), 2.19 (m, 2H), 2.10 (m, 1H), 1.97 (m, 2H), 1.27 (d, J=6.8 Hz, 1H), 1.15 (m, 2H), 0.85 (m, 2H).

Example 75

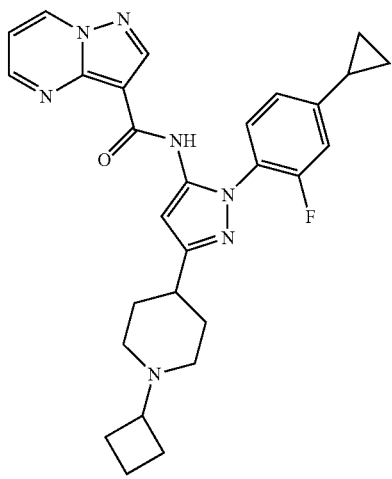

N-(3-(1-cyclobutylpiperidin-4-yl)-1-(4-cyclopropyl-2-fluorophenyl)-1H-pyrazol-5-yl)pyrazolo[1,5-a]pyrimidine-3-carboxamide This compound was prepared according to the method outlined for Example 36 using N-(1-(4-cyclopropyl-2-fluorophenyl)-3-(piperidin-4-yl)-1H-pyrazol-5-yl)pyrazolo[1,5-a]pyrimidine-3-carboxamide and cyclobutanone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CDCl$_3$) δ 10.05 (br s, 1H), 8.76 (dd, J=6.8, 1.8 Hz, 1H), 8.69 (s, 1H), 8.25 (dd, J=4.0, 1.8 Hz, 1H), 7.41 (t, J=7.6 Hz, 1H), 7.00-6.91 (m, 3H), 6.70 (s, 1H), 2.96 (app br s, 2H), 2.71 (app br s, 2H), 2.05-1.64 (m, 12H), 1.10 (m, 2H), 0.74 (m, 2H).

Example 76

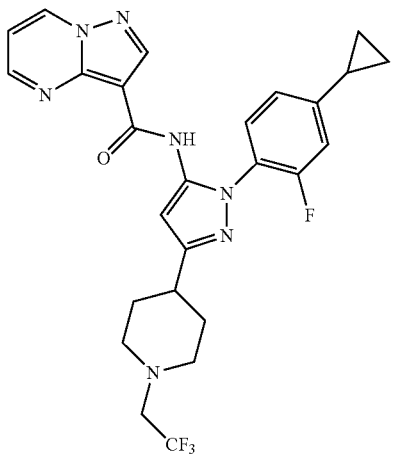

N-(1-(4-cyclopropyl-2-fluorophenyl)-3-(1-(2,2,2-trifluoroethyl)piperidin-4-yl)-1H-pyrazol-5-yl)pyrazolo[1,5-a]pyrimidine-3-carboxamide This compound was prepared according to the method outlined for Example 41 using N-(1-(4-cyclopropyl-2-fluorophenyl)-3-(piperidin-4-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. $^1$H NMR (400 MHz, CDCl$_3$) δ 10.06 (br s, 1H), 8.76 (dd, J=7.2, 1.8 Hz, 1H), 8.69 (s, 1H), 8.25 (dd, J=4.4, 1.8 Hz, 1H), 7.41 (t, J=8.4 Hz, 1H), 7.01-6.92, m, 3H), 6.70 (s, 1H), 3.06-2.96 (m, 4H), 231 (m, 1H), 2.49 (m, 2H), 2.03-1.84 (m, 5H), 1.10 (m, 2H), 0.76 (m, 2H).

Example 77

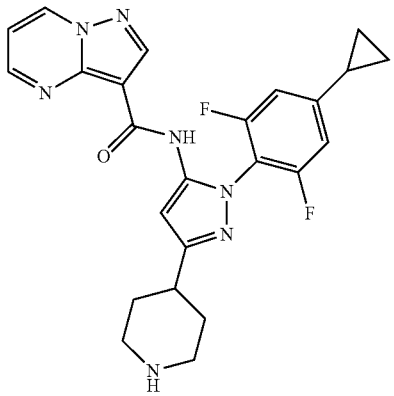

N-(1-(4-cyclopropyl-2,6-difluorophenyl)-3-(piperidin-4-yl)-1H-pyrazol-5-yl)pyrazolo[1,5-a]pyrimidine-3-carboxamide This compound was prepared according to the general methods outlined for Example 52, using 2,6-difluoro-4-bromohydrazine hydrochloride in place of 4-bromophenylhydrine. ¹H NMR (400 MHz, CDCl₃) δ 10.10 (br s, 1H), 9.22 (br s, 2H), 8.79 (dd, J=7.0, 1.8 Hz, 1H), 8.70-8.62 (m, 2H), 8.22 (dd, J=4.0, 1.8 Hz, 1H), 6.99 (dd, J=7.0, 4.0 Hz, 1H), 6.81 (m, 2H), 6.73 (s, 1H), 3.99 (m, 2H), 3.49 (m, 2H), 3.11 (m, 1H), 2.29 (m, 2H), 2.20 (m, 2H), 2.01 (m, 1H), 1.17 (m, 2H), 0.79 (m, 2H).

Example 78

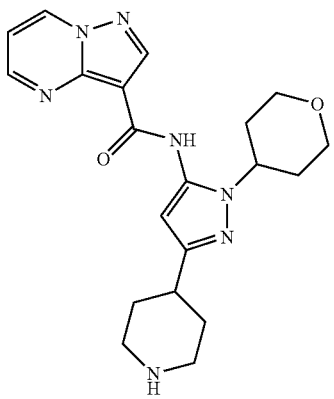

N-(3-(piperidin-4-yl)-1-(tetrahydro-2H-pyran-4-yl)-1H-pyrazol-5-yl)pyrazolo[1,5-a]pyrimidine-3-carboxamide This compound was prepared according to the general method outlined for Example 7, using (tetrahydro-2H-pyran-4-yl)hydrazine in place of 4-methylphenylhydrazine hydrochloride. ¹H NMR (400 MHz, CDCl₃) δ 9.85 (br s, 1H), 8.87 (dd, J=6.8, 1.6 Hz, 1H), 8.70 (dd, J=4.0, 1.6 Hz, 1H), 7.11 (m, 1H), 6.29 (s, 1H), 4.30 (m, 1H), 4.09 (m, 2H), 3.78 (m, 2H), 3.48 (m, 2H), 2.82-2.71 (m, 6H), 2.33 (m, 2H), 2.07 (m, 2H), 1.94 (m, 2H), 1.80 (m, 2H).

Example 79

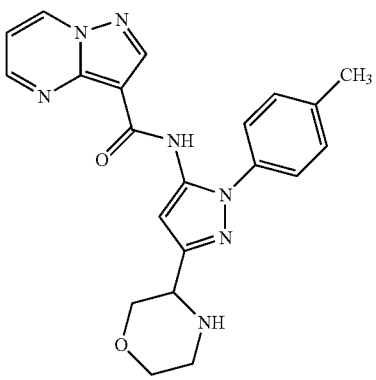

N-(3-(morpholin-3-yl)-1-(p-tolyl)-1H-pyrazol-5-yl)pyrazolo[1,5-a]pyrimidine-3-carboxamide This compound was prepared according to the general method outlined for Example 7, using 4-tert-butyl 3-ethyl morpholine-3,4-dicarboxylate in place of 1-tert-butyl 4-ethyl piperidine-1,4-dicarboxylate.

Example 80

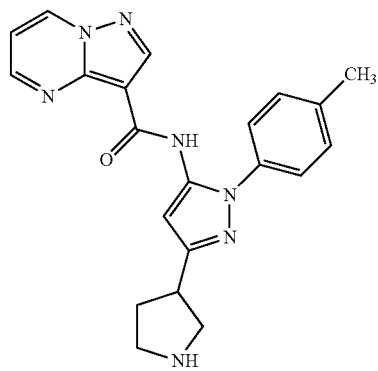

N-(3-(pyrrolidin-3-yl)-1-(p-tolyl)-1H-pyrazol-5-yl)pyrazolo[1,5-a]pyrimidine-3-carboxamide This compound was prepared following the general procedure outlined for Example 7, using 1-tert-butyl 3-ethyl pyrrolidine-1,3-dicarboxylate in place of 1-tert-butyl 4-ethyl piperidine-1,4-dicarboxylate. (400 MHz, CD3OD) δ 9.08 (dd, J=6.8, 1.6 Hz, 1H), 8.62 (s, 1H), 8.41 (dd, J=6.8, 1.6 Hz, 1H), 7.45 (m, 4H), 7.190 (m, 1H), 6.73 (s, 1H), 3.44-3.35 (m, 2H), 3.22-3.05 (m, 3H), 2.50 (s, 3H), 2.37-2.27 (m, 1H), 2.09-2.03 (m, 1H).

Example 81

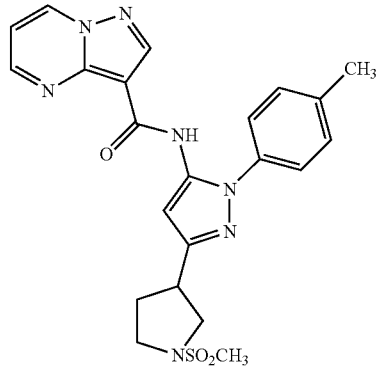

N-(3-(1-(methylsulfonyl)pyrrolidin-3-yl)-1-(p-tolyl)-1H-pyrazol-5-yl)pyrazolo[1,5-a]pyrimidine-3-carboxamide This compound was prepared according to the general methods outlined for Example 16, using N-(3-(pyrrolidin-3-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (400 MHz, CDCl₃) δ 10.33 (br s, 1H), 8.79 (dd, J=6.8, 1.6 Hz, 1H), 8.71 (s, 1H), 8.31 (dd, J=4.4, 1.6

Hz, 1H), 7.44 (m, 2H), 7.34 (m, 2H), 7.01 (m, 1H), 6.80 (s, 1H), 3.81 (m, 1H), 3.54 (m, 4H), 2.84 (s, 3H), 2.47 (s, 3H), 2.39 (m, 1H), 2.29 (m, 1H).

Example 82

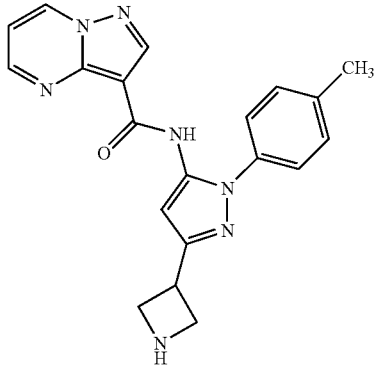

N-(3-(azetidin-3-yl)-1-(p-tolyl)-1H-pyrazol-5-yl)pyrazolo[1,5-a]pyrimidine-3-carboxamide This compound was prepared following the general procedure outlined for Example 7, using 1-tert-butyl 3-ethyl azetidine-1,3-dicarboxylate in place of 1-tert-butyl 4-ethyl piperidine-1,4-dicarboxylate. $^1$H NMR (400 MHz, CDCl$_3$) δ 9.10 (m, 1H), 8.64 (s, 1H), 8.42 (m, 1H), 7.88 (s, 1H), 7.46 (m, 3H), 7.47 (m, 1H), 7.20 (m, 1H), 6.88 (s, 1H), 4.07-4.01 (m, 4H), 3.31 (m, 1H).

Example 83

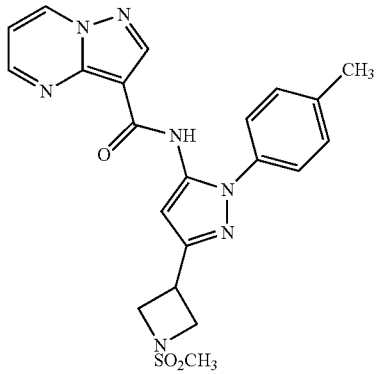

N-(3-(1-(methylsulfonyl)azetidin-3-yl)-1-(p-tolyl)-1H-pyrazol-5-yl)pyrazolo[1,5-a]pyrimidine-3-carboxamide This compound was prepared according to the general methods outlined for Example 16, using N-(3-(azetidin-3-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.34 (br s, 1H), 8.81 (dd, J=7.2, 1.6 Hz, 1H), 8.69 (s, 1H), 8.28 (dd, J=4.4, 1.6 Hz, 1H), 7.43 (m, 2H), 7.33 (m, 2H), 7.01 (m, 1H), 6.87 (s, 1H), 4.28 (m, 2H), 4.16 (m, 2H), 3.85 (m, 1H), 2.93 (s, 3H), 2.45 (s, 3H).

Example 84

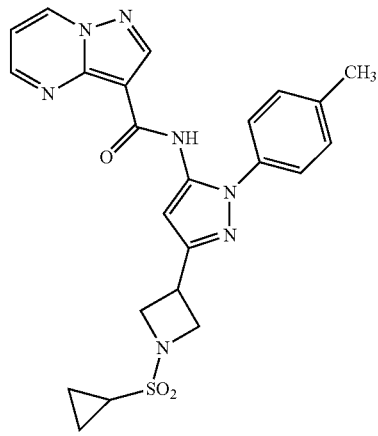

N-(3-(1-(cyclopropylsulfonyl)azetidin-3-yl)-1-(p-tolyl)-1H-pyrazol-5-yl)pyrazolo[1,5-a]pyrimidine-3-carboxamide This compound was prepared according to the general methods outlined for Example 16, using N-(3-(azetidin-3-yl)-1-(p-tolyl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. $^1$H NMR (400 MHz, CDCl$_3$) δ 10.34 (br s, 1H), 8.79 (dd, J=7.2, 1.6 Hz, 1H), 8.69 (s, 1H), 8.30 (dd, J=4.4, 1.6 Hz, 1H), 7.44 (m, 2H), 7.33 (m, 2H), 7.02 (m, 1H), 6.93 (s, 1H), 4.28 (m, 4H), 3.93 (m, 1H), 2.46 (m, 4H), 1.19 (m, 2H), 1.04 (m, 2H).

Example 85

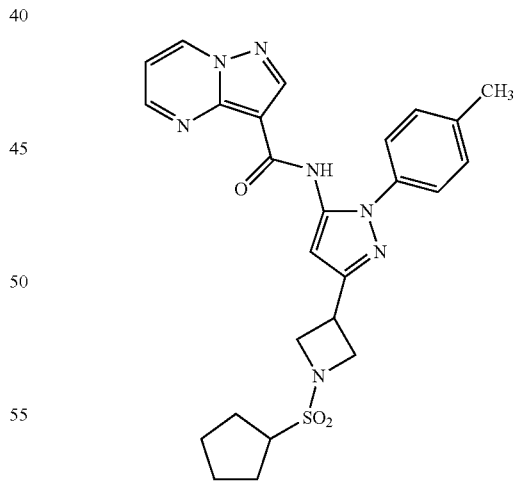

N-(3-(1-(cyclopentylsulfonyl)azetidin-3-yl)-1-(p-tolyl)-1H-pyrazol-5-yl)pyrazolo[1,5-a]pyrimidine-3-carboxamide This compound was prepared according to the general methods outlined for Example 16, using N-(3-(azetidin-3-yl)-1-(p-tolyl)-1H-pyrazol-5-yl)pyrazolo pyrimidine-3-carboxamide and cyclopentylsulfonyl chloride in place of N-(1-(4-methoxyphenyl)-3-(piperidin-4-yl)-1H-pyrazol-5-yl) pyrazolo[1,5-a]pyrimidine-3-carboxamide and methanesulfonyl chloride, respectively. (400 MHz, CDCl₃) δ 10.33 (br, s, 1H), 8.81-8.76 (m, 1H), 8.71 (m, 1H), 8.30 (m, 1H), 7.45 (m, 2H), 7.33 (m, 2H), 7.05-7.00 (m, 1H), 6.94 (s, 1H), 4.31 (t, J=8 Hz, 2H), 4.21 (t, J=6.8 Hz, 2H), 3.96 (s, 1H), 3.45 (t, J=8.4 Hz, 1H), 2.46 (s, 3H), 2.03 (m, 4H), 1.79 (m, 2H), 1.61 (m, 2H).

Example 86

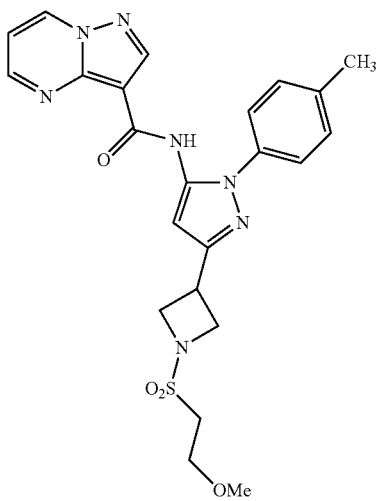

N-(3-(1-((2-methoxyethyl)sulfonyl)azetidin-3-yl)-1-(p-tolyl)-1H-pyrazol-5-yl)pyrazolo[1,5-a]pyrimidine-3-carboxamide This compound was prepared according to the general methods outlined for Example 16, using N-(3-(azetidin-3-yl)-1-(p-tolyl)-1H-pyrazol-5-yl)pyrazolo[1,5-a]pyrimidine-3-carboxamide and 2-methoxyethanesulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. ¹H NMR (400 MHz, CDCl₃) δ 10.33 (br s, 1H), 8.79 (dd, J=7.2, 1.6 Hz, 1H), 8.71 (s, 1H), 8.31 (dd, J=4.0, 1.6 Hz, 1H), 7.45 (m, 2H), 7.33 (m, 2H), 7.01 (m, 1H), 6.94 (s, 1H), 4.33-4.23 (m, 4H), 3.96-3.88 (m, 1H), 3.81 (t, J=6.4 Hz, 2H), 3.41 (s, 3H), 3.33 (t, J=6.4 Hz, 2H), 2.47 (s, 3H).

Example 87

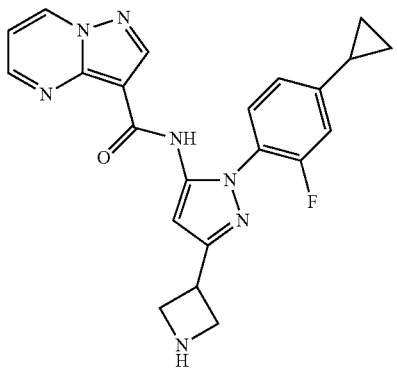

N-(3-(azetidin-3-yl)-1-(4-cyclopropyl-2-fluorophenyl)-1H-pyrazol-5-yl)pyrazolo[1,5-a]pyrimidine-3-carboxamide This compound was prepared according to the general methods outlined for Example 52, using 2-fluoro-4-bromophenylhydrazine hydrochloride and 1-tert-butyl 3-ethyl azetidine-1,3-dicarboxylate in place of 4-bromophenylhydrine and 1-tert-butyl 4-ethyl piperidine-1,4-dicarboxylate, respectively. ¹H NMR (400 MHz, CD₃OD) δ 10.42 (br s, 1H), 9.11 (dd, J=7.2, 1.8 Hz, 1H), 8.64 (s, 1H), 8.36 (ddd, J=8.4, 1.8, 0.9 Hz, 1H), 7.47 (t, J=6.4 Ha, 1H), 7.23-7.18 (m, 3H), 6.86 (s, 1H), 4.45-4.33 (m, 4H), 4.25 (m, 1H), 2.12 (m, 1H), 1.17 (m, 2H), 0.88 (m, 2H).

Example 88

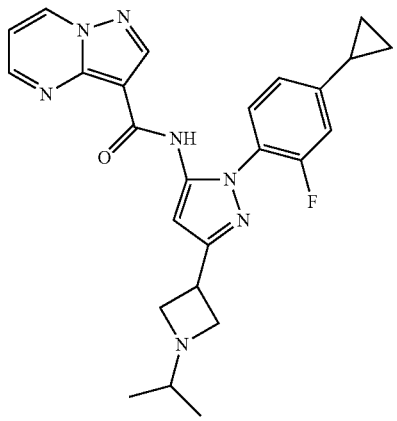

N-(1-(4-cyclopropyl-2-fluorophenyl)-3-(1-isopropylazetidin-3-yl)-1H-pyrazol-5-yl)pyrazolo[1,5-a]pyrimidine-3-carboxamide This compound was prepared according to the method outlined for Example 36 using N-(3-(azetidin-3-yl)-1-(p-tolyl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. ¹H NMR (400 MHz, CD₃OD) δ 10.42 (br s, 1H), 9.12 (dd, J=7.2, 1.8, 1H), 8.64 (s, 1H), 8.53 (m, 1H), 7.47 (m, 1H), 7.22-7.19 (m, 3H), 6.86 (s, 1H), 4.53-4.50 (m, 2H), 4.44 (m, 1H), 4.34 (t, J=10.4 Hz, 1H), 4.15 (m, 1H), 3.55 (m, 1H), 2.15 (m, 1H), 1.26 (d, J=6.8 Hz, 6H), 1.15 (m, 2H), 0.87 (m, 2H).

Example 89

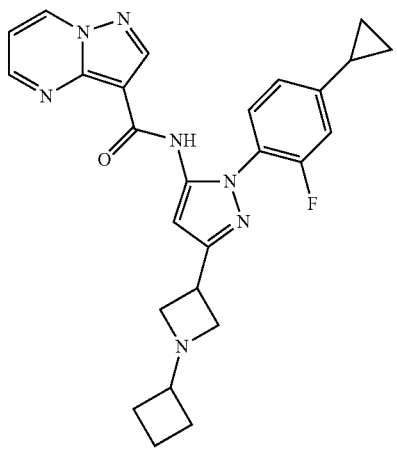

N-(3-(1-cyclobutylazetidin-3-yl)-1-(4-cyclopropyl-2-fluorophenyl)-1H-pyrazol-5-yl)pyrazolo[1,5-a]pyrimidine-3-carboxamide This compound was prepared according to the method outlined for Example 36 using N-(3-(azetidin-3-yl)-1-(p-tolyl)-1H-pyrazol-5-yl)pyrazolo[1,5-a]pyrimidine-3-carboxamide and cyclobutanone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD$_3$OD) δ 10.18 (br s, 1H), 9.35 (dd, J=7.2, 1.8 Hz, 1H), 8.68 (s, 1H), 8.38 (dd, J=4.4, 1.8 Hz, 1H), 7.47 (t, J=8.8 Hz, 1H), 7.32-7.29 (m, 2H), 7.16 (dd, J=8.4, 2.0 Hz, 1H), 6.68 (s, 1H), 3.55-3.53 (m, 3H), 3.25-3.15 (m, 3H), 2.09 (m, 1H), 1.87 (m, 2H), 1.81-1.60 (m, 4H), 1.08 (m, 2H), 0.84 (m, 2H).

Example 90

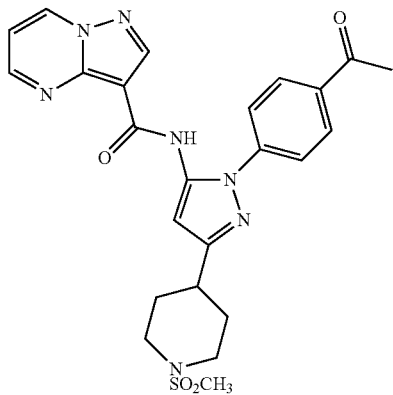

N-(1-(4-acetylphenyl)-3-(1-(methylsulfonyl)piperidin-4-yl)-1H-pyrazol-5-yl)pyrazolo[1,5-a]pyrimidine-3-carboxamide Synthesis of the intermediates follows below.

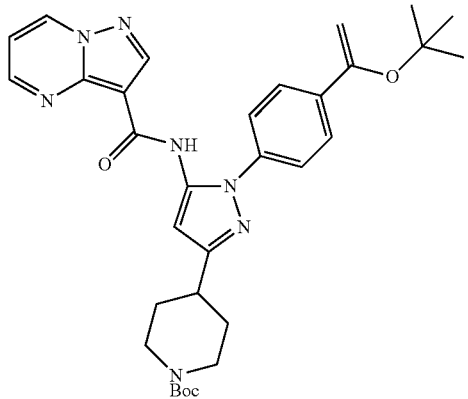

tert-butyl 4-(1-(4-(1-(tert-butoxy)vinyl)phenyl)-5-(pyrazolo[1,5-a]pyrimidine-3-carboxamido)-1H-pyrazol-3-yl)piperidine-1-carboxylate tert-Butyl 4-(1-(4-bromophenyl)-5-(pyrazolo[1,5-a]pyrimidine-3-carboxamido)-1H-pyrazol-3-yl)piperidine-1-carboxylate (600 mg, 1.059 mmol) was dissolved in 10 ml of 2-methyl-2-butanol. To it, added tert-butyl vinyl ether (0.21 ml, 1.589 mmol), tris(dibenzylideneacetone)dipalladium (0) (25 mg, 0.026 mmol), tri-o-tolylphosphine (33 mg, 0.106 mmol), and DIEA (0.36 ml, 2.118 mmol), the combined mixture was degassed for 3 min, then heated to 90° C. for 12 h. The mixture was cooled to rt. and water (50 mL) was added. The mixture was extracted with EtOAc (3×50 mL). The combined organic extracts were dried (MgSO$_4$) and concentrated in vacuo. The residue was purified by silica gel chromatography, eluting with a solvent gradient of 0 to 50% EtOAc in hexanes to give the product as a white solid. $^1$H NMR (400 MHz, CDCl$_3$) δ 10.26 (s, 1H), 8.75 (m, 1H), 8.67 (m, 1H), 8.27 (m, 1H), 7.70 (m, 1H), 7.50 (m, 1H), 7.41 (m, 1H), 7.33 (m, 1H), 7.11 (m, 1H), 6.95 (m, 1H), 6.72 (m, 1H), 6.02 (dd, J=12, 1.6 Hz, 1H) 4.16 (m, 2H), 2.82 (m, 3H), 1.97 (m, 2H), 1.71 (m, 2H), 1.45 (s, 9H), 1.36 (s, 9H).

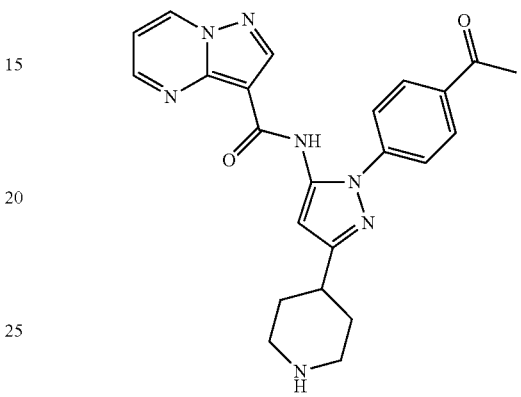

N-(1-(4-acetylphenyl)-3-(piperidin-4-yl)-1H-pyrazol-5-yl)pyrazolo[1,5-a]pyrimidine-3-carboxamide This compound was prepared following the general methods outlined for Example 146, using tert-butyl 4-(1-(4-(1-(tert-butoxy)vinyl)phenyl)-5-(pyrazolo[1,5-a]pyrimidine-3-carboxamido)-1H-pyrazol-3-yl)piperidine-1-carboxylate in place of tert-butyl 4-(1-(5-cyclopropylpyridin-2-yl)-5-(pyrazolo[1,5-a]pyrimidine-3-carboxamido)-1H-pyrazol-3-yl)piperidine-1-carboxylate.

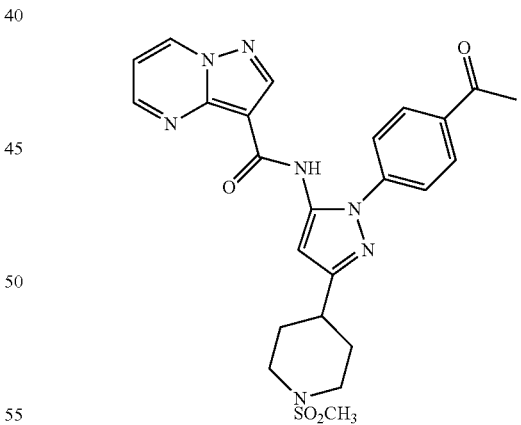

This compound was prepared following the general methods outline for Example 16, using N-(1-(4-acetylphenyl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.35 (br s, 1H), 8.82 (dd, J=6.8, 1.6 Hz, 1H), 8.74 (s, 1H), 8.39 (dd, J=4.0, 1.6 Hz, 1H), 8.11 (m, 2H), 7.76 (m, 2H), 7.04 (m, 1H), 6.81 (s, 1H), 3.88 (m, 2H), 2.88 (m, 3H), 2.82 (s, 3H), 2.67 (s, 3H), 2.17 (m, 2H), 1.95 (m, 2H).

Example 91

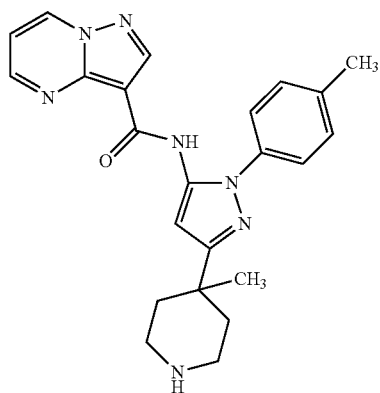

N-(3-(4-methylpiperidin-4-yl)-1-(p-toly))-1H-pyrazol-5-yl)pyrazolo[1,5-a]pyrimidine-3-carboxamide General methods for preparation of the synthetic intermediates follow below.

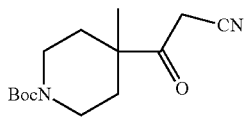

tert-butyl 4-(2-cyanoacetyl)-4-methylpiperidine-1-carboxylate

To a mixture of 1-tert-butyl 4-ethyl 4-methylpiperidine-1,4-dicarboxylate (1.14 g, 4.2 mmol), acetonitrile (1.1 mL, 21 mmol) in THF (20 mL) was added 60% NaH in mineral oil (0.84 g, 21 mmol). The reaction mixture was heated at 70° C. in a sealed tube overnight. Cooled to rt, poured into ice water and acidified with 1N HCl. Extracted with EtOAc (2×100 mL). Organic layer dried (Na$_2$SO$_4$), filtered and concentrated. Purified on silica using 20-100% EtOAc/hexane to give a residue that was used without further purification.

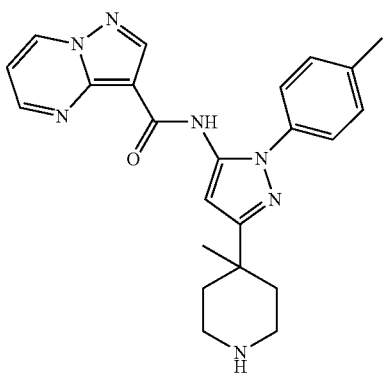

N-(3-(4-methylpiperidin-4-yl)-1-(p-toly))-1H-pyrazol-5-yl)pyrazolo[1,5-a]pyrimidine-3-carboxamide The compound was prepared following the general methods outlined for Example 7, using tert-butyl 4-(2-cyanoacetyl)-4-methylpiperidine-1,4-dicarboxylate in place of tert-butyl 4-(2-cyanoacetyl)piperidine-1-carboxylate. $^1$H NMR (500 MHz, CD$_3$OD) δ 9.12 (dd, J=7, 1.5 Hz, 1H), 8.66 (s, 1H), 8.47 (dd, J=4, 1.5 Hz, 1H), 7.52-7.46 (m, 4H), 7.23 (dd, J=7, 4 Hz, 1H), 6.79 (s, 1H), 3.34-3.2 (m, 4H), 2.52-2.43 (m, 5H), 1.92-1.86 (m, 2H), 1.42 (s, 3H).

Example 92

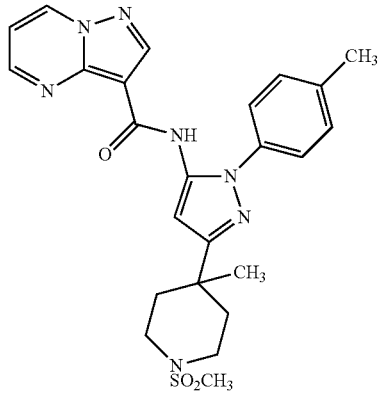

N-(3-(4-methyl-1-(methylsulfonyl)piperidin-4-yl)-1-(p-tolyl)-1H-pyrazol-5-yl)pyrazolo[1,5-a]pyrimidine-3-carboxamide This compound was prepared according to the general methods outline for Example 16, using N-(3-(4-methylpiperidin-4-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (500 MHz, CD$_3$OD) δ 9.12 (dd, J=7, 1.5 Hz, 1H), 8.67 (s, 1H), 8.47 (dd, J=4, 1.5 Hz, 1H), 7.52-7.47 (m, 4H), 7.23 (dd, J=7, 4 Hz, 1H), 6.76 (s, 1H), 3.58-3.12 (m, 4H), 2.82 (s, 3H), 2.53 (s, 3H), 2.4-2.36 (m, 2H), 1.84-1.79 (m, 2H), 1.38 (s, 3H).

Example 93

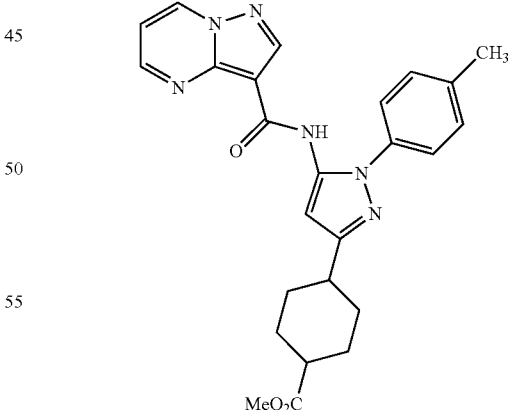

methyl 4-(5-(pyrazolo[1,5-a]pyrimidine-3-carboxamido)-1-(p-tolyl)-1H-pyrazol-3-yl)cyclohexanecarboxylate This compound was prepared following the general methods outlined for Example 1, using dimethyl cyclohexane-1,4-dicarboxylate in place of ethyl 1,4-dioxaspiro[4.5]decane-8-carboxylate.

Example 94

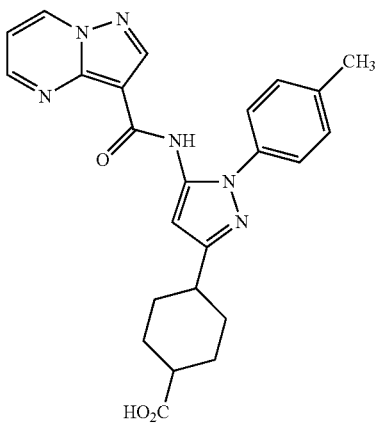

4-(5-(pyrazolo[1,5-a]pyrimidine-3-carboxamido)-1-(p-tolyl)-1H-pyrazol-3-yl)cyclohexanecarboxylic acid A mixture of methyl 4-(5-(pyrazolo[1,5-a]pyrimidine-3-carboxamido)-1-(p-tolyl)-1H-pyrazol-3-yl)cyclohexanecarboxylate (0.16 g, 0.349 mmol), 1N NaOH (0.9 mL, 0.9 mmol) and methanol (5 mL), THF (3 mL) was stirred at rt for 72 hr. Concentrated and purified on silica using 1-50% MeOH/CH$_2$Cl$_2$ to give the title compound. $^1$H NMR (400 MHz, CDCl$_3$) δ 10.23 (br s, 1H), 8.76 (dd, J=7.0, 1.6 Hz, 1H), 8.71 (s, 1H), 8.30 (dd, J=4.2, 1.6 Hz, 1H), 7.48 (m, 2H), 7.03 (m 2H), 6.97 (dd, J=7.0, 4.2 Hz, 1H), 6.73 (s, 1H), 3.88 (s, 3H), 3.84 (m, 1H), 2.88-2.83 (m, 2H), 2.82 (s, 3H), 2.17-2.13 (m, 2H), 1.98-1.88 (m, 2H).

Example 95

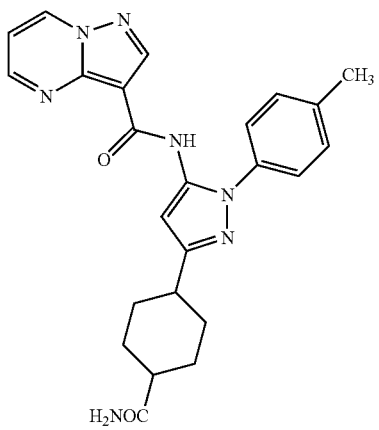

N-(3-(4-carbamoylcyclohexyl)-1-(p-tolyl)-1H-pyrazol-5-yl)pyrazolo[1,5-a]pyrimidine-3-carboxamide A mixture of methyl 4-(5-(pyrazolo[1,5-a]pyrimidine-3-carboxamido)-1-(p-tolyl)-1H-pyrazol-3-yl)cyclohexanecarboxylate (0.06 g, 0.131 mmol) and 7N ammonia in methanol (5 mL) was heated in a sealed tube at 70° C. overnight. Concentrated and purified on silica using 5-50% CH$_2$Cl$_2$/MeOH to the title compound. $^1$H NMR (500 MHz, CD$_3$OD) δ 9.08 (dd, J=7, 1.5 Hz, 1H), 8.62 (s, 1H), 8.41 (dd, J=4, 1.5 Hz, 1H), 7.45-7.44 (m, 4H), 7.19 (dd, J=7, 4.5 Hz, 1H), 6.67 (s, 1H), 2.73-2.67 (m, 1H), 2.51 (s, 3H), 2.36-2.3 (m, 1H), 2.15-2.13 (m, 2H), 2.02-2 (m, 2H), 1.69-1.57 (m, 4H).

Example 96

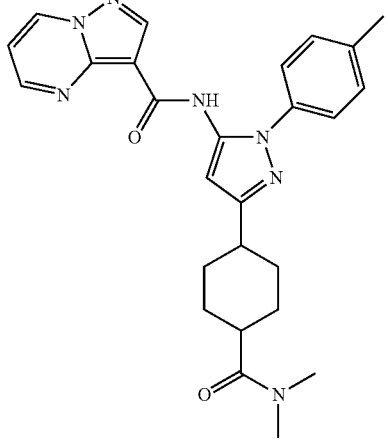

N-(3-(4-(dimethylcarbamoyl)cyclohexyl)-1-(p-tolyl)-1H-pyrazol-5-yl)pyrazolo[1,5-a]pyrimidine-3-carboxamide A mixture of 4-(5-(pyrazolo[1,5-a]pyrimidine-3-carboxamido)-1-(p-tolyl)-1H-pyrazol-3-yl)cyclohexanecarboxylic acid (100 mg, 0.225 mmol), dimethylamine hydrochloride (55 mg, 0.675 mmol), DIEA (0.153 mL, 0.9 mmol), HATU (171 mg, 0.45 mmol) in DMF (5 mL) was stirred at rt for overnight. Poured into EtOAc (100 mL) and washed with sat, NaHCO$_3$. Organic layer dried (Na$_2$SO$_4$), filtered and concentrated. Purified on column using 1-30% MeOH/CH$_2$Cl$_2$ to give the title compound.

Example 97

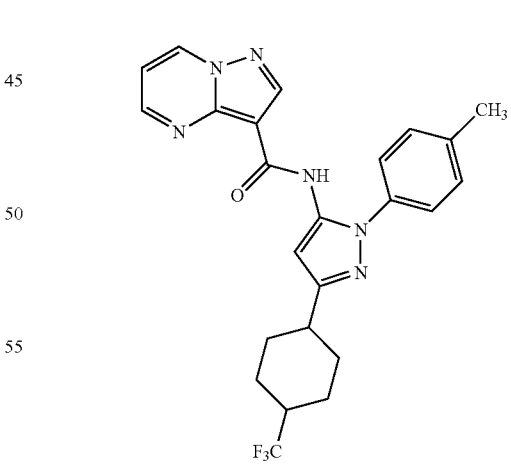

N-(1-(p-tolyl)-3-(4-(trifluoromethyl)cyclohexyl)-1H-pyrazol-5-yl)pyrazolo[1,5-a]pyrimidine-3-carboxamide This compound was prepared following the general methods outline in Example 1, using methyl 4-(trifluoromethyl)cyclohexanecarboxylate in place of methyl 1,4-dioxaspiro[4.5]decane-8-carboxylate.

Example 98

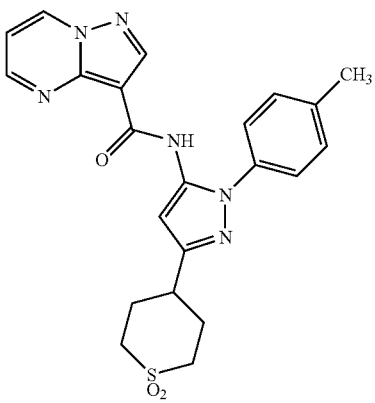

N-(3-(1,1-dioxidotetrahydro-2H-thiopyran-4-yl)-1-(p-tolyl)-1H-pyrazol-5-yl)pyrazolo[1,5-a]pyrimidine-3-carboxamide This compound was prepared following the general methods outline in Example 1, using methyl tetrahydro-2H-thiopyran-4-carboxylate 1,1-dioxide in place of methyl 1,4-dioxaspiro[4.5]decane-8-carboxylate.

Example 99

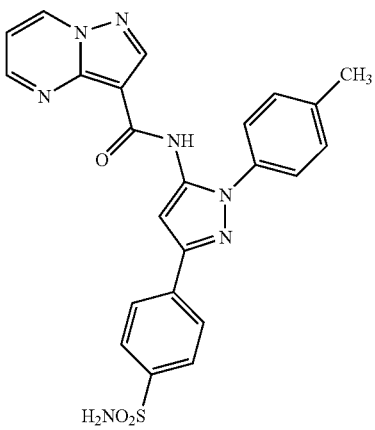

N-(3-(4-sulfamoylphenyl)-1-(p-tolyl)-1H-pyrazol-5-yl)pyrazolo[1,5-a]pyrimidine-3-carboxamide Synthesis of the intermediates is described below.

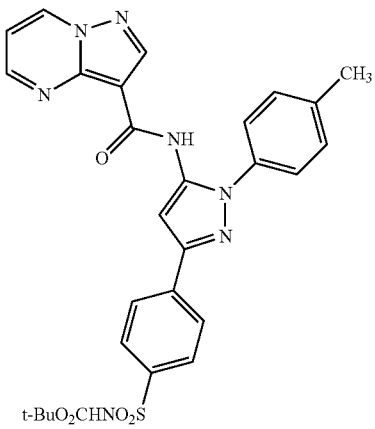

tert-butyl (4-(5-(pyrazolo[1,5-a]pyrimidine-3-carboxamido)-1-(p-tolyl)-1H-pyrazol-3-yl)phenyl)sulfonylcarbamate tert-butyl (4-(5-(pyrazolo[1,5-a]pyrimidine-3-carboxamido)-1-(p-tolyl)-1H-pyrazol-3-yl)phenyl)sulfonylcarbamate was prepared using the general methods described for Example 1, using ethyl 4-(N-(tert-butoxycarbonyl)sulfamoyl)benzoate in place of ethyl 1,4-dioxaspiro[4.5]decane-8-carboxylate.

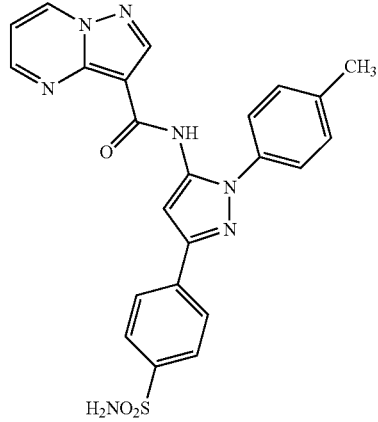

N-(3-(4-sulfamoylphenyl)-1-(p-tolyl)-1H-pyrazol-5-yl)pyrazolo[1,5-a]pyrimidine-3-carboxamide A solution of tert-butyl (4-(5-(pyrazolo[1,5-a]pyrimidine-3-carboxamido)-1-(p-tolyl)-1H-pyrazol-3-yl)phenyl)sulfonylcarbamate (19 mg, 0.33 mmol) and TFA (100 µL) was stirred at rt for 75 min. The solution was concentrated in vacuo. The residue was triturated with MeOH to give the title compound as a white solid. $^1$H NMR (400 MHz, DMSO-$d_6$) δ 10.47 (br s, 1H), 9.37 (dd, J=7.2, 1.8 Hz, 1H), 8.73 (s, 1H), 8.57 (dd, J=4.4, 1.8 Hz, 1H), 8.05 (m, 2H), 7.87 (m, 2H), 7.61 (m, 2H), 7.46 (m, 2H), 7.38 (br s, 2H), 7.30 (dd, J=7.2, 4.4 Hz, 1H), 7.26 (s, 1H).

Example 100

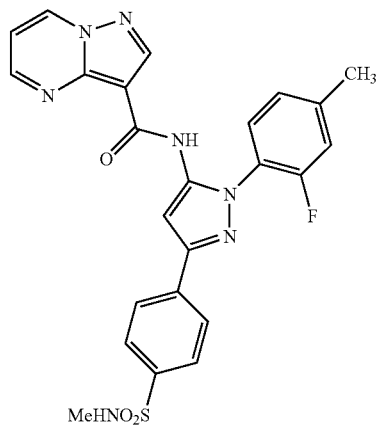

N-(1-(2-fluoro-4-methylphenyl)-3-(4-(N-methylsulfamoyl)phenyl)-1H-pyrazol-5-yl)pyrazolo[1,5-a]pyrimidine-3-carboxamide This compound was prepared following the general methods outlined for Example 56, using ethyl 4-(N-methylsulfamoyl)benzoate in place of 1-tert-butyl 4-ethyl piperidine-1,4-dicarboxylate. $^1$H NMR (400 MHz, DMSO-$d_6$) δ 2.44 (d, J=5.2 Hz, 3H), 2.60 (s, 3H), 7.08-7.34 (m, 3H), 7.45-7.57 (m, 2H), 7.57-7.68 (m, 1H), 7.85 (d, J=8.4 Hz, 2H), 8.08-8.13 (m, 2H), 8.40 (s, 1H), 8.74 (s, 1H), 9.38 (d, J=6.8 Hz, 1H), 10.36 (s, 1H).

Example 101

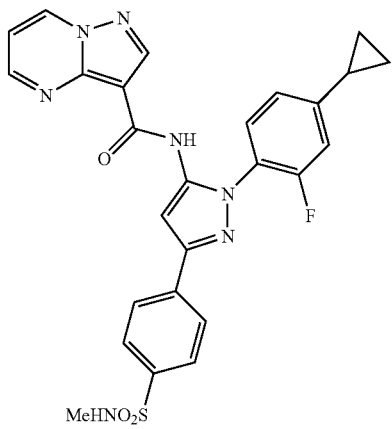

N-(1-(4-cyclopropyl-2-fluorophenyl)-3-(4-(N-methylsulfamoyl)phenyl)-1H-pyrazol-5-yl)pyrazolo[1,5-a]pyrimidine-3-carboxamide This compound was prepared according to the general methods outlined for Example 52, using 2-fluoro-4-bromohydrazine hydrochloride and ethyl 4-(N-methylsulfamoyl)benzoate in place of 4-bromophenylhydrine and 1-tert-butyl 4-ethyl piperidine-1,4-dicarboxylate, respectively. $^1$H NMR (300 MHz, DMSO-$d_6$): δ 0.84-0.87 (m, 2H), 1.05-1.11 (m, 2H), 2.03-2.15 (m, 1H), 2.39-2.41 (m, 3H), 7.18-7.22 (m, 2H), 7.28-7.33 (m, 2H), 7.41-7.45 (m, 1H), 7.58 (t, J=8.1 Hz, 1H), 7.80 (d, J=8.4 Hz, 2H), 8.06 (d, J=8.4 Hz, 2H), 8.38-8.39 (m, 1H), 8.70 (s, 1H), 9.34 (d, J=5.7 Hz, 1H), 10.28 (s, 1H).

Example 102

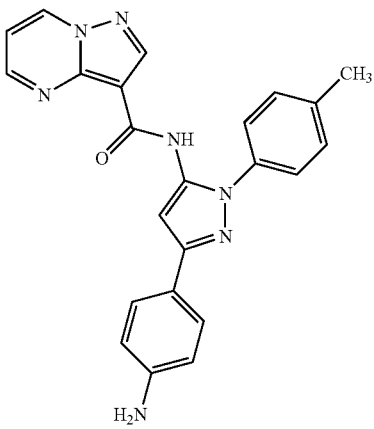

N-(3-(4-aminophenyl)-1-(p-tolyl)-1H-pyrazol-5-yl)pyrazolo[1,5-a]pyrimidine-3-carboxamide General methods for the preparation of synthetic intermediates follow below.

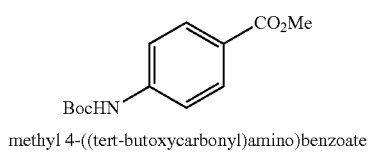 [SMILES: COC(=O)c1ccc(NC(=O)OC(C)(C)C)cc1]

methyl 4-((tert-butoxycarbonyl)amino)benzoate

A mixture of methyl 4-aminobenzoate (3.94 g, 26.1 mmol), di-tert-butyl dicarbonate (6.84 g, 31.3 mmol), DIPEA (5.5 mL, 31.5 mmol), and acetonitrile (50 mL) was heated to 70° C. for 3 d. The solution was concentrated in vacuo to a volume of 30 mL. The mixture was filtered to give the title compound as a white solid. $^1$H NMR (400 MHz, CDCl$_3$) δ 7.95 (m, 2H), 7.41 (m, 2H), 6.63 (br s, 1H), 3.87 (s, 3H), 1.51 (s, 9H).

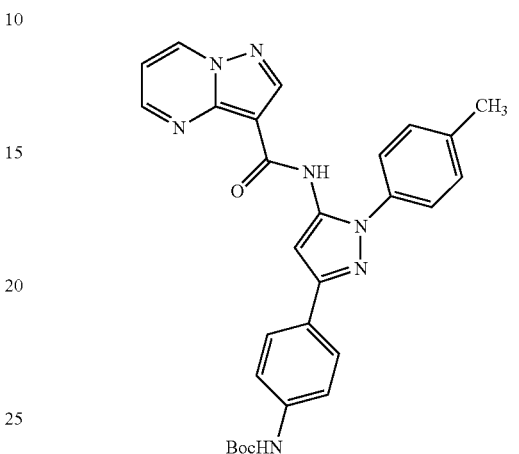

tert-butyl (4-(5-(pyrazolo[1,5-a]pyrimidine-3-carboxamido)-1-(p-tolyl)-1H-pyrazol-3-yl)phenyl)carbamate This compound was prepared following the general methods outlined for Example 7, using methyl 4-((tert-butoxycarbonyl)amino)benzoate in place of 1-tert-butyl 4-ethyl piperidine-1,4-dicarboxylate. $^1$H NMR (400 MHz, CDCl$_3$) δ 10.33 (br s, 1H), 8.78 (dd, J=7.0, 1.8 Hz, 1H), 8.73 (s, 1H), 8.30 (dd, J=4.0, 1.8 Hz, 1H), 7.85 (m, 2H), 7.55 (m, 2H), 7.40 (m, 2H), 7.34 (m, 2H), 7.20 (s, 1H), 6.99 (dd, J=7.0, 4.0 Hz, 1H), 6.50 (br s, 6.50), 2.47 (s, 3H), 1.51 (s, 9H).

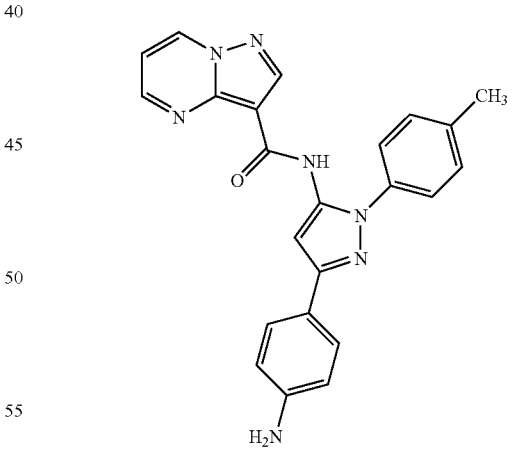

This compound was prepared following the general methods outlined for Example 7, using tert-butyl (4-(5-(pyrazolo[1,5-a]pyrimidine-3-carboxamido)-1-(p-tolyl)-1H-pyrazol-3-yl)phenyl)carbamate in place of tert-butyl 4-(5-(pyrazolo[1,5-a]pyrimidine-3-carboxamido)-1-(p-tolyl)-1H-pyrazol-3-yl)piperidine-1-carboxylate. $^1$H NMR (400 MHz, CD$_3$OD) δ 9.11 (dd, J=7.2, 1.8 Hz, 1H), 8.66 (s, 1H), 8.44 (dd, J=4.4, 1.8 Hz, 1H), 7.97 (m, 2H), 7.57 (m, 2H), 7.49 (m, 2H), 7.33 (m, 2H), 7.23-7.20 (m, 2H), 2.53 (s, 3H).

Example 103

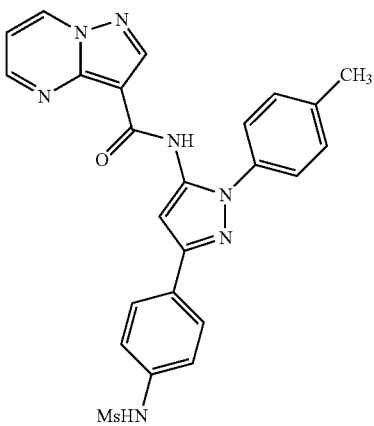

N-(3-(4-(methylsulfonamido)phenyl)-1-(p-tolyl)-1H-pyrazol-5-yl)pyrazolo[1,5-a]pyrimidine-3-carboxamide This compound was prepared following the general method outlined in Example 36, using N-(3-(4-aminophenyl)-1-(p-tolyl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. NMR (400 MHz, CDCl$_3$) δ 10.37 (br s, 1H), 8.78 (dd, J=7.2, 1.8 Hz, 1H), 8.75 (s, 1H), 8.30 (dd, J=4.4, 1.8 Hz, 1H), 7.91 (m, 2H), 7.53 (m, 2H), 7.36 (m, 2H), 7.26 (m, 2H), 7.00 (dd, J=7.2, 4.4 Hz, 1H0, 6.33 (s, 1H), 3.02 (s, 3H), 2.48 (s, 3H).

Example 104

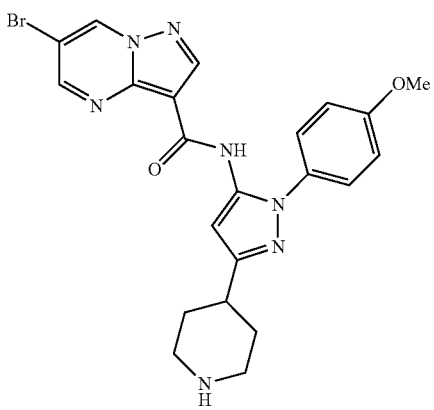

6-bromo-N-(1-(4-methoxyphenyl)-3-(piperidin-4-yl)-1H-pyrazol-5-yl)pyrazolo[1,5-a]pyrimidine-3-carboxamide This compound was prepared according to the general methods outlined for Example 7, using 6-bromopyrazolo[1,5-a]-pyrimidine-3-carboxylic acid and tert-butyl 4-(5-amino-1-(p-tolyl)-1H-pyrazol-3-yl)piperidine-1-carboxylate in place of pyrazolo[1,5-a]pyrimidine-3-carboxylic acid and tert-butyl 4-(5-amino-1-(4-methoxyphenyl)-1H-pyrazol-3-yl)piperidine-1-carboxylate, respectively. $^1$H NMR (400 MHz, CDCl$_3$) δ 9.95 (br s, 1H), 8.91 (d, J=2.0 Hz, 1H), 8.68 (s, 1H), 8.29 (d, J=2.0 Hz, 1H), 7.46 (m, 2H), 7.04 (m, 2H), 6.73 (s, 1H), 3.90 (s, 3H), 3.47 (m, 2H), 3.08-3.04 (m, 3H), 2.28 (m, 2H), 2.18 (m, 2H).

Example 105

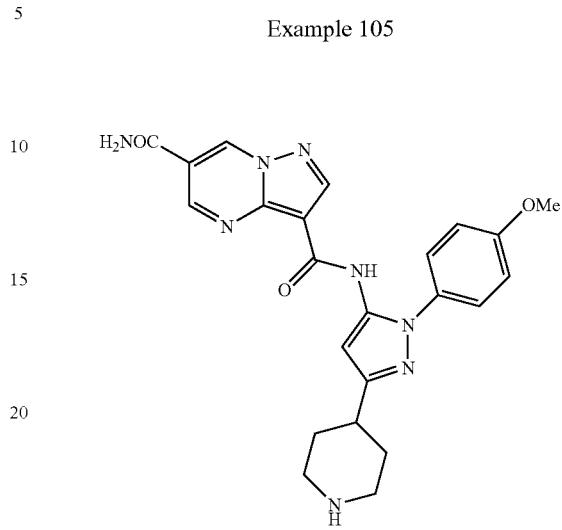

N$^3$-(1-(4-methoxyphenyl)-3-(piperidin-4-yl)-1H-pyrazol-5-yl)pyrazolo[1,5-a]pyrimidine-3,6-dicarboxamide Synthesis of the intermediate follows below.

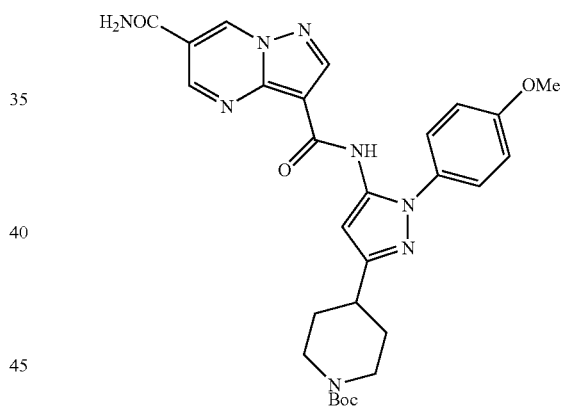

tert-butyl 4-(5-(6-carbamoylpyrazolo[1,5-a]pyrimidine-3-carboxamido)-1-(4-methoxyphenyl)-1H-pyrazol-3-yl)piperidine-1-carboxylate A mixture of 6-bromo-N-(1-(4-methoxyphenyl)-3-(piperidin-4-yl)-1H-pyrazolo[1,5-a]pyrimidine-3-carboxamide (183 mg, 0.307 mmol), Pd(PPh$_3$)$_4$ (137 mg, 0.119 mmol), Zn(CN)$_2$ (91 mg, 0.775 mmol), and DMF (10 mL) was purged with N$_2$ for 10 min. The mixture was heated for 3 d at 110° C. The mixture was cooled to rt. and EtOAc (40 mL) was added. The mixture was washed with H$_2$O (3×40 mL). The organic layer was dried (MgSO$_4$) and concentrated in vacuo. The residue was purified by silica gel chromatography, eluting with a solvent gradient of 0 to 100% EtOAc in hexanes to give the title compound as a yellow solid. $^1$H NMR (400 MHz, CDCl$_3$) δ 10.33 (br s, 1H), 9.92 (s, 1H), 9.20 (br s, 1H), 8.61 (s, 1H), 8.24 (s, 1H), 7.75 (m, 2H), 7.20 (br s, 1H), 7.03 (m, 2H), 6.69 (s, 1H), 4.17 (app br s, 2H), 3.88 (s, 3H), 2.87-2.80 (m, 3H), 2.00-1.97 (m, 2H), 1.76-1.65 (m, 2H), 1.46 (s, 9H).

107

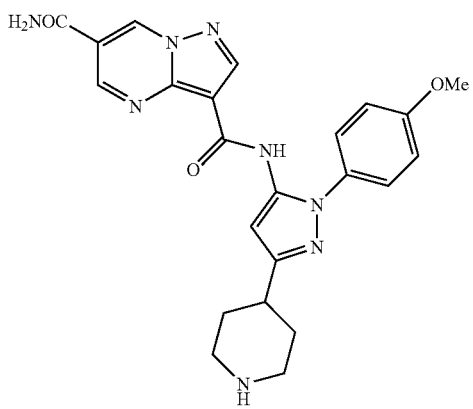 [SMILES: COc1ccc(-n2nc(C3CCNCC3)cc2NC(=O)c2cnn3cc(C(N)=O)cnc23)cc1]

This compound was prepared following the general method outline in Example 7, using tert-butyl 4-(5-(6-carbamoylpyrazolo[1,5-a]pyrimidine-3-carboxamido)-1-(4-methoxyphenyl)-1H-pyrazol-3-yl)piperidine-1-carboxylate in place of tert-butyl 4-(5-(pyrazolo[1,5-a]pyrimidine-3-carboxamido)-1-(p-tolyl)-1H-pyrazol-3-yl)piperidine-1-carboxylate. (400 MHz, CD$_3$OD) δ 9.91 (s, 1H), 8.54 (s, 1H), 8.33 (s, 1H), 7.48 (m, 2H), 7.19 (m, 2H), 6.72 (s, 1H), 3.93 (s, 3H), 3.48 (m, 2H), 3.16 (dt, J=12.8, 3.2 Hz, 2H), 3.06 (m, 1H), 2.24 (m, 2H), 1.99 (m, 2H).

Example 106

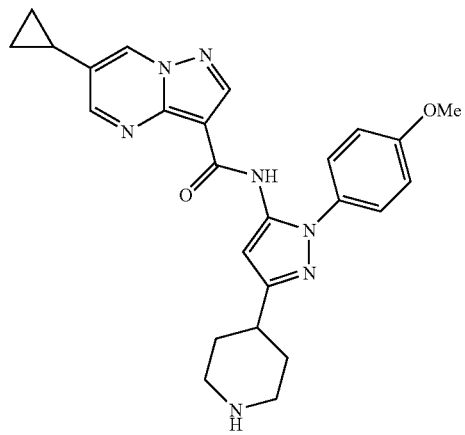

6-cyclopropyl-N-(1-(4-methoxyphenyl)-3-(piperidin-4-yl)-1H-pyrazol-5-yl)pyrazolo-1,5-a]pyrimidine-3-carboxamide Synthesis of the intermediates follows below.

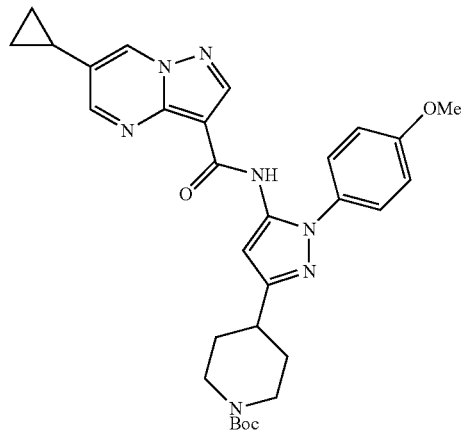 [SMILES: COc1ccc(-n2nc(C3CCNCC3)cc2NC(=O)c2cnn3cc(C4CC4)cnc23)cc1]

tert-butyl 4-(5-(6-cyclopropylpyrazolo[1,5-a]pyrimidine-3-carboxamido)-1-(4-methoxyphenyl)-1H-pyrazol-3-yl)piperidine-1-carboxylate

108

A mixture of tert-butyl 4-(5-(6-bromopyrazolo[1,5-a]pyrimidine-3-carboxamido)-1-(4-methoxyphenyl)-1H-pyrazol-3-yl)piperidine-1-carboxylate (25 mg, 0.042 mmol), Pd(OAc)$_2$ (10 mg, 0.045 mmol), butyl diadamantylphosphine (37 mg, 0.103 mmol), Cs$_2$CO$_3$ (223, 0.684 mmol), potassium cyclopropyltrifluoroborate (48, 0.324 mmol), toluene (2.5 mL), and water (0.5 mL) was purged with N$_2$ for 5 min. The mixture was heated to 100° C. for 24 h. Water (15 mL) was added and the mixture was extracted with EtOAc (3×15 mL). The combined organic extracts were dried (MgSO$_4$) and concentrated in vacuo. The residue was purified by silica gel chromatography, eluting with a solvent gradient of 0 to 100% EtOAc to give the title compound as a white solid. $^1$H NMR (400 MHz, CDCl$_3$) δ 10.15 (br s, 1H), 8.62 (s, 1H), 8.43 (d, J=2.0 Hz, 1H), 8.17 (d, J=2.0 Hz, 1H), 7.47 (m, 2H), 7.03 (m, 2H), 6.70 (s, 1H), 4.16 (app br s, 2H), 3.89 (s, 3H), 2.00-1.93 (m, 3H), 1.73 (m, 2H), 1.46 (s, 9H), 1.13 (m, 2H), 0.76 (m, 2H).

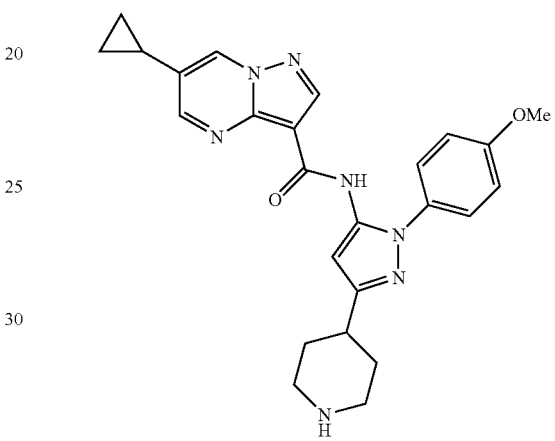

This compound was prepared following the general methods outlined for Example 7, using tert-butyl 4-(5-(6-cyclopropylpyrazolo[1,5-a]pyrimidine-3-carboxamido)-1-(4-methoxyphenyl)-1H-pyrazol-3-yl)piperidine-1-carboxylate in place of tert-butyl 4-(5-(pyrazolo[1,5-a]pyrimidine-3-carboxamido)-1-(p-tolyl)-1H-pyrazol-3-yl)piperidine-1-carboxylate. $^1$H NMR (400 MHz, CD$_3$OD) δ 8.83 (d, J=2.2 Hz, 1H), 8.55 (s, 1H), 8.27 (d, J=2.2 Hz, 1H), 7.48 (m, 2H), 7.19 (m, 2H), 6.71 (s, 1H), 3.94 (s, 3H), 3.48 (m, 2H), 3.16 (dt, J=12.0, 3.2 Hz, 2H), 3.06 (tt, J=11.0, 4.4 Hz, 1H), 2.28 (m, 2H), 2.10-1.93 (m, 3H), 1.12 (m, 2H), 0.84 (m, 2H).

Example 107

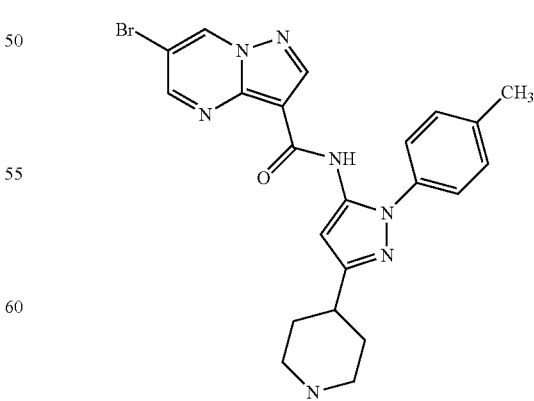

6-bromo-N-(3-(piperidin-4-yl)-1-(p-tolyl)-1H-pyrazol-5-yl)pyrazolo[1,5-a]pyrimidine-3-carboxamide This compound was prepared according to the general methods outlined for Example 7, using 6-bromopyrazolo[1,5-a]-pyrimidine-3-carboxylic acid in place of pyrazolo[1,5-a]pyrimidine-3-carboxylic acid. $^1$H NMR (400 MHz, CD$_3$OD) δ 9.48 (d, J=2.2 Hz, 1H), 8.60 (s, 1H), 8.45 (dd, J=2.2 Hz, 1H), 7.46 (app s, 4H), 6.73 (s, 1H), 3.48 (dt, J=12.8, 3.6 Hz, 2H), 3.16 (dt, J=12.4, 2.8 Hz, 2H), 3.07 (tt, J=7.2, 3.6 Hz, 1H), 2.27 (m, 2H), 1.99 (m, 2H).

Example 108

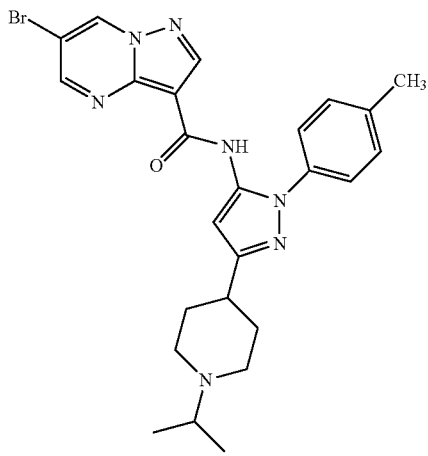

6-bromo-N-(3-(1-isopropylpiperidin-4-yl)-1-(p-tolyl)-1H-pyrazol-5-yl)pyrazolo[1,5-a]pyrimidine-3-carboxamide This compound was prepared according to the method outlined for Example 36 using 6-bromo-N-(3-(piperidin-4-yl)-1-(p-tolyl)-1H-pyrazol-5-yl)pyrazolo[1,5-a]pyrimidine-3-carboxamide and acetone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (600 MHz, DMSO) δ 10.09 (s, 1H), 9.83 (d, J=2.1, 1H), 8.91 (s, 1H), 8.75-8.56 (m, 2H), 7.45 (d, J=8.4, 2H), 7.41 (d, J=8.3, 2H), 6.59 (s, 1H), 3.52-3.43 (m, 3H), 3.08 (dd, J=22.9, 10.4, 2H), 3.00-2.92 (m, 1H), 2.39 (s, 3H), 2.18 (d, J=14.5, 2H), 1.97-1.79 (m, 2H), 1.24 (d, J=6.7, 6H).

Example 109

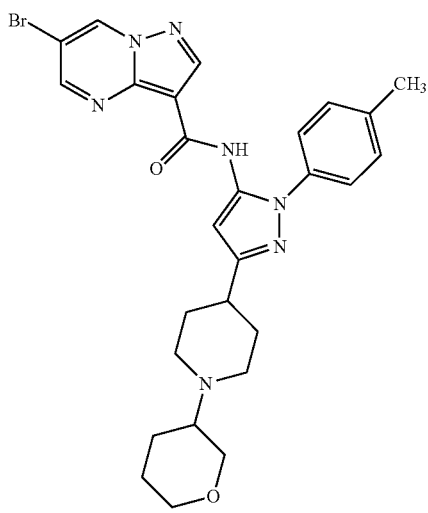

6-bromo-N-(3-(1-(tetrahydro-2H-pyran-3-yl)piperidin-4-yl)-1-(p-tolyl)-1H-pyrazol-5-yl)pyrazolo[1,5-a]pyrimidine-3-carboxamide This compound was prepared according to the method outlined for Example 36 using 6-bromo-N-(3-(piperidin-4-yl)-1-(p-tolyl)-1H-pyrazol-5-yl)pyrazolo[1,5-a]pyrimidine-3-carboxamide and dihydro-2H-pyran-3(4H)-one in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (600 MHz, dmso) δ 10.09 (s, 1H), 9.83 (d, J=2.1, 1H), 9.21 (s, 1H), 8.72-8.57 (m, 2H), 7.45 (d, J=8.3, 2H), 7.40 (d, J=8.4, 2H), 6.59 (s, 1H), 4.03 (d, J=12.4, 1H), 3.72 (d, J=11.2, 1H), 3.60-3.50 (m, 3H), 3.44-3.20 (m, 2H), 3.18-3.08 (m, 1H), 2.92 (t, J=12.2, 1H), 2.38 (s, 3H), 2.20-2.00 (m, 4H), 1.90 (dd, J=26.7, 13.3, 2H), 1.77 (dd, J=18.7, 10.6, 2H), 1.61-1.47 (m, 1H).

Example 110

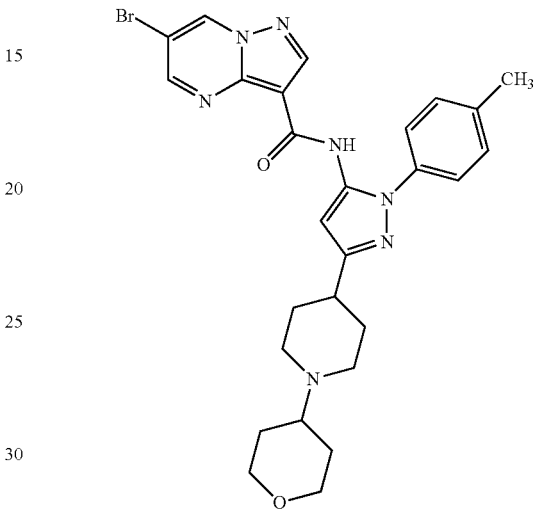

6-bromo-N-(3-(1-(tetrahydro-2H-pyran-4-yl)piperidin-4-yl)-1-(p-tolyl)-1H-pyrazol-5-yl)pyrazolo[1,5-a]pyrimidine-3-carboxamide This compound was prepared according to the method outlined for Example 36 using 6-bromo-N-(3-(piperidin-4-yl)-1-(p-tolyl)-1H-pyrazol-5-yl)pyrazolo[1,5-a]pyrimidine-3-carboxamide and dihydro-2H-pyran-4(3H)-one in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (600 MHz, DMSO) δ 10.09 (s, 1H), 9.83 (d, J=2.1, 1H), 9.19 (s, 1H), 8.74-8.56 (m, 2H), 7.45 (d, J=8.3, 2H), 7.40 (d, J=8.4, 2H), 6.59 (s, 1H), 3.96 (dd, J=11.0, 3.9, 2H), 3.56 (d, J=11.6, 2H), 3.48-3.36 (m, 1H), 3.29 (dd, J=25.7, 14.3, 2H), 3.08 (dd, J=22.7, 10.5, 2H), 3.00-2.90 (m, 1H), 2.39 (s, 3H), 2.20 (d, J=13.7, 2H), 2.02-1.80 (m, 4H), 1.70-1.60 (m, 2H).

Example 111

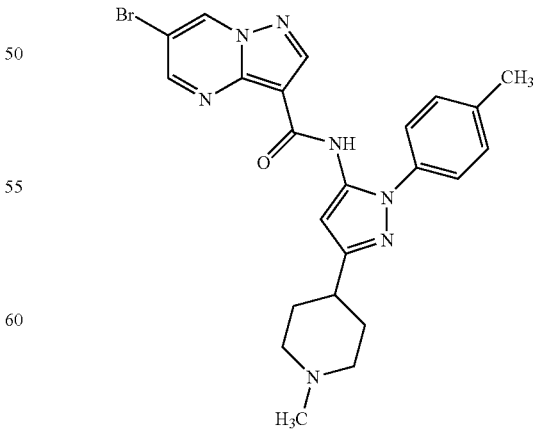

6-bromo-N-(3-(1-(methylpiperidin-4-yl)-1-(p-tolyl)-1H-pyrazol-5-yl)pyrazolo[1,5-a]pyrimidine-3-carboxamide This compound was prepared according to the method outlined for Example 36 using 6-bromo-N-(3-(piperidin-4-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (600 MHz, DMSO) δ 10.08 (s, 1H), 9.83 (d, J=2.1, 1H), 9.33 (s, 1H), 8.70-8.60 (m, 2H), 7.45 (d, J=8.3, 2H), 7.40 (d, J=8.4, 2H), 6.58 (s, 1H), 3.48 (d, J=11.3, 2H), 3.05 (dd, J=22.8, 10.2, 2H), 2.90-2.82 (m, 1H), 2.78 (s, 3H), 2.38 (s, 3H), 2.17 (d, J=14.2, 2H), 1.86-1.73 (m, 2H).

Example 112

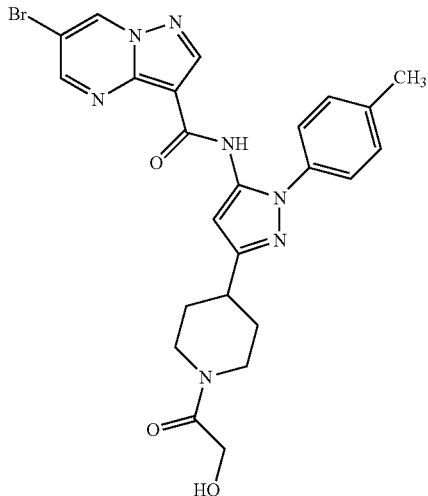

6-bromo-N-(3-(1-(2-hydroxyacetyl)piperidin-4-yl)-1-(p-tolyl)-1H-pyrazol-5-yl)pyrazolo[1,5-a]pyrimidine-3-carboxamide This compound was prepared according to the general method outlined for Example 31, using 2-hydroxyacetic acid and 6-bromo-N-(3-(piperidin-4-yl)-1-(p-tolyl)-1H-pyrazol-5-yl)pyrazolo[1,5-a]pyrimidine-3-carboxamide in place of acetyl chloride and N-(3-(piperidin-4-yl)-1-(p-tolyl)-1H-pyrazol-5-yl)pyrazolo[1,5-a]pyrimidine-3-carboxamide, respectively. ¹H NMR (600 MHz, DMSO) δ 10.05 (s, 1H), 9.82 (d, J=1.8, 1H), 8.73-8.58 (m, 2H), 7.45 (d, J=8.3, 2H), 7.38 (d, J=8.3, 2H), 6.55 (s, 1H), 4.35 (d, J=12.5, 1H), 4.08 (q, J=14.9, 2H), 3.70 (d, J=13.2, 1H), 3.06 (t, 12.1, 1H), 2.92-2.82 (m, 1H), 2.76 (t, J=11.7, 1H), 2.37 (s, 3H), 1.92 (d, J=13.1, 2H), 1.60 (dd, J=21.1, 11.5, 1H), 1.47 (dd, J=20.8, 11.7, 1H).

Example 113

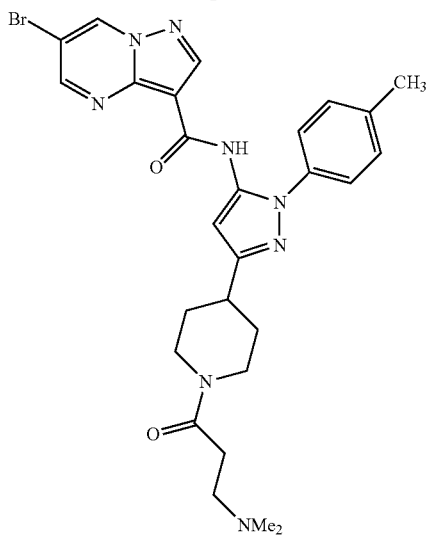

6-bromo-N-(3-(1-(3-(dimethylamino)propanoyl)piperidin-4-yl)-1-(p-tolyl)-1H-pyrazol-5-yl)pyrazolo[1,5-a]pyrimidine-3-carboxamide This compound was prepared according to the general method outlined for Example 31, using 3-(dimethylamino)propanoic acid and 6-bromo-N-(3-(piperidin-4-yl)-1-(p-tolyl)-1H-pyrazol-5-yl)pyrazolo[1,5-a]pyrimidine-3-carboxamide in place of acetyl chloride and N-(3-(piperidin-4-yl)-1-(p-tolyl)-1H-pyrazol-5-yl)pyrazolo[1,5-a]pyrimidine-3-carboxamide, respectively. ¹H NMR (600 MHz, DMSO) δ 10.06 (s, 1H), 9.83 (d, J=3.0, 1H), 8.66-8.65 (m, 2H), 7.44 (d, J=8.3, 2H), 7.39 (d, J=8.3, 2H), 6.57 (s, 1H), 4.40 (d, J=13.2, 1H), 3.88 (d, J=13.7, 1H), 3.25 (q, J=14.7, 2H), 3.16 (t, J=12.1, 1H), 2.93-2.82 (m, 10H), 2.38 (s, 3H), 1.96 (t, J=15.0, 2H), 1.65 (m, 1H), 1.46 (m, 1H).

Example 114

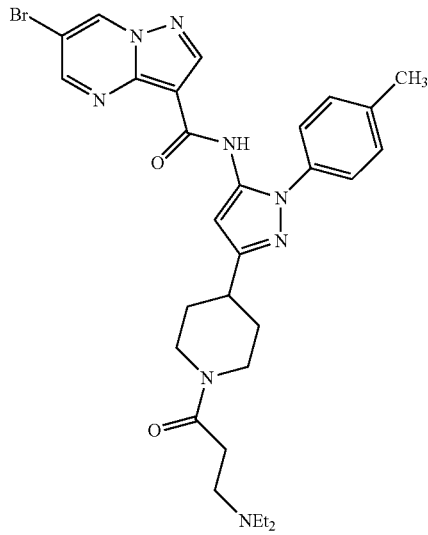

6-bromo-N-(3-(1-(3-(diethylamino)propanoyl)piperidin-4-yl)-1-(p-tolyl)-1H-pyrazol-5-yl)pyrazolo[1,5-a]pyrimidine-3-carboxamide This compound was prepared according to the general method outlined for Example 31, using 3-(diethylamino)propanoic acid and 6-bromo-N-(3-(piperidin-4-yl)-1-(p-tolyl)-1H-pyrazol-5-yl)pyrazolo[1,5-a]pyrimidine-3-carboxamide in place of acetyl chloride and N-(3-(piperidin-4-yl)-1-(p-tolyl)-1H-pyrazol-5-yl)pyrazolo[1,5-a]pyrimidine-3-carboxamide, respectively. ¹H NMR (600 MHz, DMSO) δ 10.06 (s, 1H), 9.83 (d, J=3.0, 1H), 8.66-8.65 (m, 2H), 7.44 (d, J=8.3, 2H), 7.39 (d, J=8.3, 2H), 6.57 (s, 1H), 4.40 (d, J=13.2, 1H), 3.88 (d, J=13.7, 1H), 3.25 (q, J=14.7, 2H), 3.16 (t, J=12.1, 1H), 2.93-2.82 (m, 10H), 2.38 (s, 3H), 1.96 (t, J=15.0, 2H), 1.65 (m, 1H), 1.46 (m, 1H).

Example 115

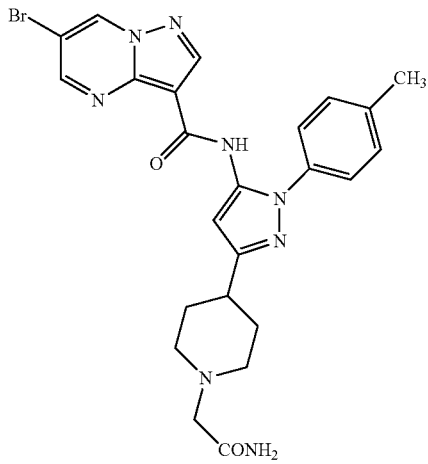

N-(3-(1-(2-amino-2-oxoethyl)piperidin-4-yl)-1-(p-tolyl)-1H-pyrazol-5-yl)-6-bromopyrazolo[1,5-a]pyrimidine-3-carboxamide This compound was prepared according to the general method outlined for Example 16, using 3-2-oxoacetamide and 6-bromo-N-(3-(piperidin-4-yl)-1-(p-tolyl)-1H-pyrazol-5-yl)pyrazolo[1,5-a]pyrimidine-3-carboxamide in place of formaldehyde and N-(3-(piperidin-4-yl)-1-(p-tolyl)-1'-1-pyrazol-5-yl)pyrazolo[1,5-a]pyrimidine-3-carboxamide, respectively.

Example 116

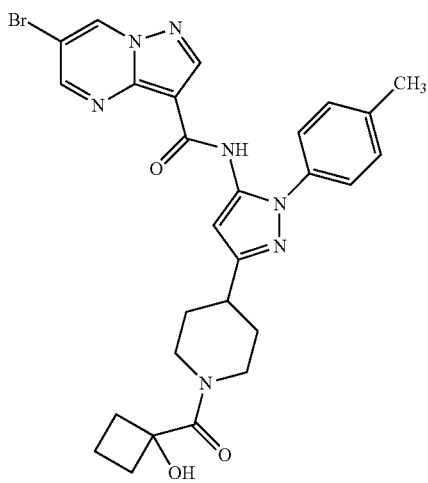

6-bromo-N-(3-(1-(1-hydroxycyclobutanecarbonyl)piperidin-4-yl)-1-(p-tolyl)-1H-pyrazol-5-yl)pyrazolo[1,5-a]pyrimidine-3-carboxamide This compound was prepared according to the general method outlined for Example 31, using 3-1-hydroxycyclobutanecarboxylic acid and 6-bromo-N-(3-(piperidin-4-yl)-1-(p-tolyl)-1H-pyrazol-5-yl)pyrazolo[1,5-a]pyrimidine-3-carboxamide in place of acetyl chloride and N-(3-(piperidin-4-yl)-1-(p-tolyl)-1H-pyrazol-5-yl)pyrazolo[1,5-a]pyrimidine-3-carboxamide, respectively.

Example 117

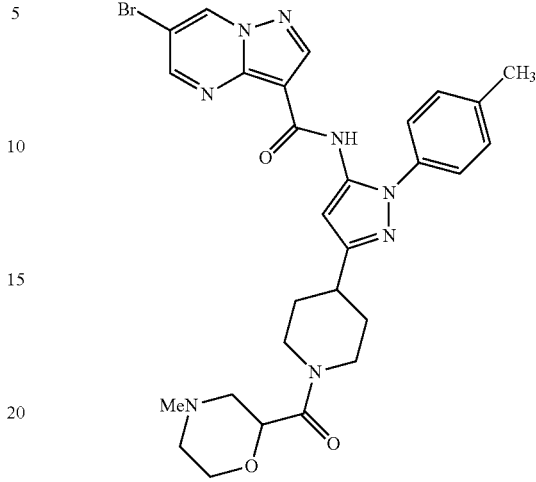

6-bromo-N-(3-(1-(4-methylmorpholine-2-carbonyl)piperidin-4-yl)-1-(p-tolyl)-1H-pyrazol-5-yl)pyrazolo[1,5-a]pyrimidine-3-carboxamide This compound was prepared according to the general method outlined for Example 31, using 3-4-methylmorpholine-2-carboxylic acid and 6-bromo-N-(3-(piperidin-4-yl)-1-(p-tolyl)-1H-pyrazol-5-yl)pyrazolo[1,5-a]pyrimidine-3-carboxamide in place of acetyl chloride and N-(3-(piperidin-4-yl)-1-(p-tolyl)-1H-pyrazol-5-yl)pyrazolo[1,5-a]pyrimidine-3-carboxamide, respectively.

Example 118

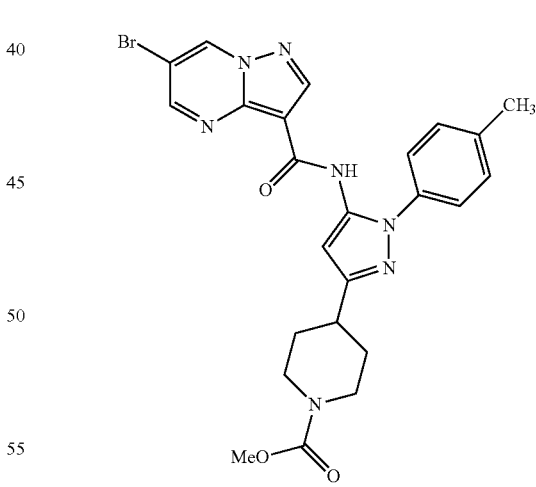

methyl 4-(5-(6-bromopyrazolo(1,5-a]pyrimidine-3-carboxamido)-1-(p-tolyl)-1H-pyrazol-3-yl)piperidine-1-carboxylate This compound was prepared according to the general method outlined for Example 31, using 6-bromo-N-(3-(piperidin-4-yl)-1-(p-tolyl)-1H-pyrazol-5-yl)pyrazolo[1,5-a]pyrimidine-3-carboxamide and methylchloroformate in place N-(3-(piperidin-4-yl)-1-(p-tolyl)-1H-pyrazol-5-yl)pyrazolo[1,5-a]pyrimidine-3-carboxamide and acetyl chloride, respectively.

Example 119

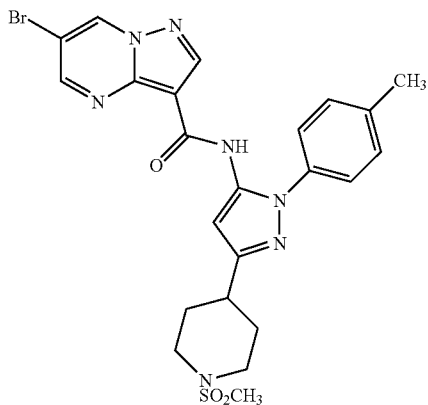

6-bromo-N-(3-(1-(1-methylsulfonyl)piperidin-4-yl)-1-(p-tolyl)-1H-pyrazol-5-yl)pyrazolo[1,5-a]pyrimidine-3-carboxamide This compound was prepared according to the general methods outlined in Example 16, using 6-bromo-N-(3-(piperidin-4-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide $^1$H NMR (400 MHz, CDCl$_3$) δ 9.99 (br s, 1H), 8.91 (d, J=2.2 Hz, 1H), 8.68 (s, 1H), 227 (dd, J=2.2 Hz, 1H), 7.43 (m, 2H), 7.32 (m, 2H), 6.74 (s, 1H), 3.84 (m, 2H), 2.88-279 (m, 6H), 2.47 (s, 3H), 2.15 (m, 2H), 1.91 (m, 2H).

Example 120

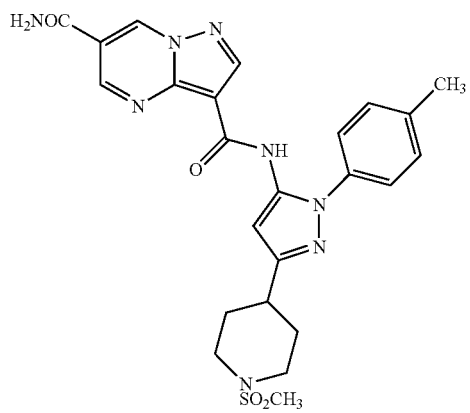

N$^3$-(3-(1-(methylsulfonyl)piperidin-4-yl)-1-(p-tolyl)-1H-pyrazol-5-yl)pyrazolo[1,5-a]pyrimidine-3,6-dicarboxamide A mixture of 6-bromo-N-(3-(1-(methylsulfonyl)piperidin-4-yl)-1-(p-tolyl)-1H-pyrazol-5-yl)pyrazolo[1,5-a]pyrimidine-3-carboxamide (90 mg, 0.16 mmol), zinc cyanide (46 mg, 0.39 mmol), Pd(PPh$_3$)$_4$ (86 mg, 0.074 mmol), and DMF (5 mL) was purged with N$_2$ for 5 min. The mixture was heated to 100° C. for 4 d. EtOAc (30 mL) was added and the mixture was washed with water (3×30 mL), dried (MgSO$_4$) and concentrated in vacuo. The residue was purified by silica gel chromatography, eluting with a solvent gradient of 0 to 100% EtOAc in hexanes. The solid so obtained was triturated with EtOH to give the title compound as a white solid. $^1$H NMR (400 MHz, CDCl$_3$) δ 10.39 (br s, 1H), 9.40 (s, 1H), 9.21 (br s, 1H), 8.63 (s, 1H), 8.24 (s, 1H), 7.46 (m, 2H), 7.33 (m, 2H), 7.17 (br s, 1H), 6.73 (s, 1H), 3.86 (m, 2H), 2.88-2.79 (m, 6H), 2.46 (s, 3H), 2.14 (m, 2H), 1.94 (m, 2H).

Example 121

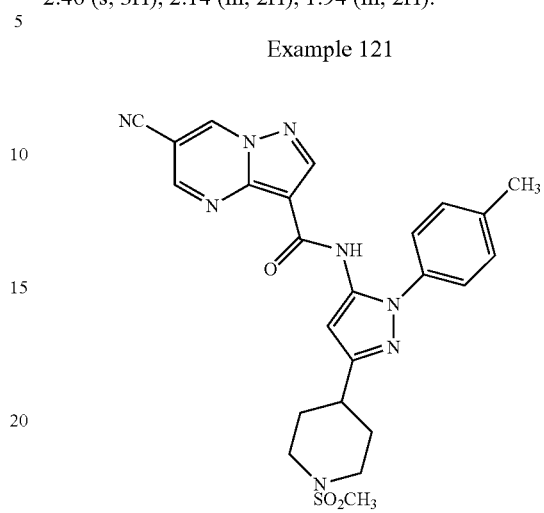

6-cyano-N-(3-(1-(methylsulfonyl)piperidin-4-yl)-1-(p-tolyl)-1H-pyrazol-5-yl)pyrazolo[1,5-a]pyrimidine-3-carboxamide A mixture of 6-bromo-N-(3-(1-(methylsulfonyl)piperidin-4-yl)-1-(p-tolyl)-1H-pyrazol-5-yl)pyrazolo[1,5-a]pyrimidine-3-carboxamide (17 mg, 0.030 mmol), zinc cyanide (19 mg, 0.16 mmol), Pd(PPh$_3$)$_4$ (15 mg, 0.013 mmol) and DMF (2 mL) was heated to 120° C. for 30 min, under microwave irradiation. EtOAc (20 mL) was added and the mixture was washed with water (3×20 mL), dried (MgSO$_4$), and concentrated in vacuo. The residue was purified by silica gel chromatography to give the title compound as a pale yellow solid. $^1$H NMR (400 MHz, CDCl$_3$) 9.91 (br s, 1H), 9.14 (dd, J=2.2 Hz, 1H), 8.87 (s, 1H), 8.39 (dd, J=2.2 Hz, 1H), 7.42 (m, 214), 7.34 (m, 2H), 6.74 (s, 1H), 3.86 (m, 2H), 2.87-2.79 (m, 3H), 2.48 (s, 3H), 2.15 (m, 2H), 1.91 (m, 2H).

Example 122

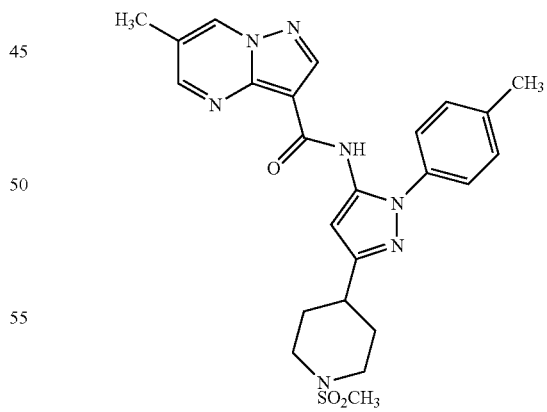

6-methyl-N-(3-(1-(methylsulfonyl)piperidin-4-yl)-1-(p-tolyl)-1H-pyrazol-5-yl)pyrazolo[1,5-a]pyrimidine-3-carboxamide This compound was prepared following the general methods for Example 16, using 6-methylpyrazolo[1,5-a]pyrimidine-3-carboxylic acid in place of pyrazolo[1,5-a]pyrimidine-3-carboxylic acid. $^1$H NMR (400 MHz, CD$_3$OD) δ 8.93 (s, 1H), 8.56 (s, 1H), 8.34 (s, 1H), 6.74 (s, 1H), 3.51 (m, 2H), 3.20-3.04 (m, 3H), 2.27 (m, 2H), 2.00 (m, 2H).

Scheme 2

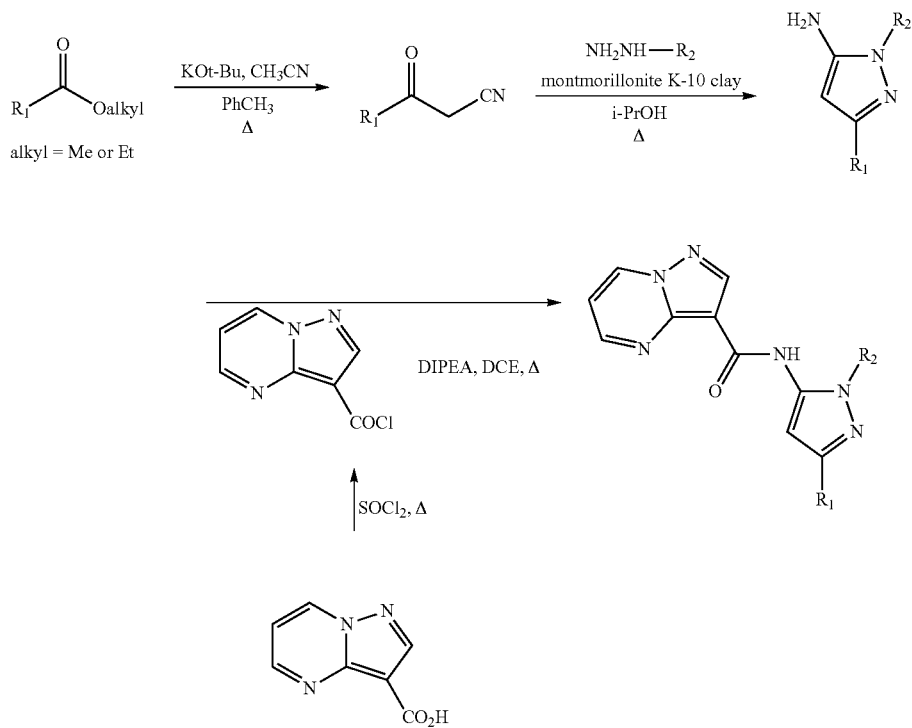

Example 123

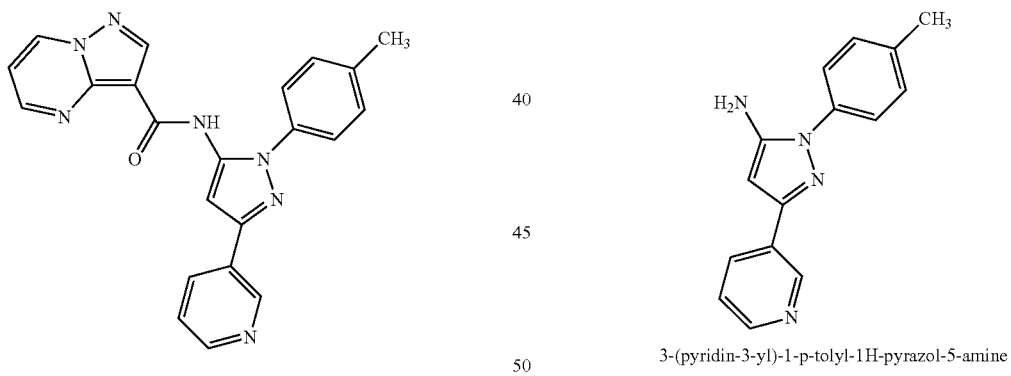

General methods for preparation of the synthetic intermediates follow below.

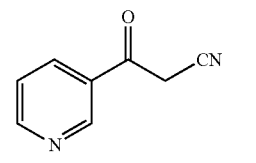

3-oxo-3-(pyridin-3-yl)propanenitrile

CH₃CN (1.2 mL, 23 mmol) was added to a mixture of KOt-Bu (4.35 g, 38.8 mmol) and toluene (100 mL). The resulting mixture was stirred at rt for 10 min, whereupon methyl nicotinate (2.49 g, 18.2 mmol) was added. The mixture was heated to reflux for 20 h. The mixture was cooled to rt, and filtered. The solid was washed with toluene to give the crude product that was used without further purification.

3-(pyridin-3-yl)-1-p-tolyl-1H-pyrazol-5-amine

A mixture of 3-oxo-3-(pyridine-3-yl)propanenitrile (1.81 g from the above reaction), 4-methylphenyl hydrazine hydrochloride (1.01 g, 6.35 mmol), montmorillonite K-10 clay (290 mg), and i-PrOH (25 mL) was heated to 85° C. for 1 h. The mixture was cooled to rt. and filtered. The filtrate was concentrated in vacuo. CH₂Cl₂ (80 mL) was added to the residue and the mixture was washed with 1M NaOH (2×80 mL) and brine (80 mL). The combined aqueous washings were back-extracted with CH₂Cl₂ (80 mL). The combined organic extracts were dried (MgSO₄) and concentrated in vacuo. The residue was purified by silica gel chromatography, eluting with a solvent gradient of 0 to 10% MeOH in CH₂Cl₂ to give the title compound as a pale yellow oil. $^1$H NMR (400 MHz CDCl₃) δ 8.97 (dd, J=2.4, 1.4 Hz, 1H), 8.51 (dd, J=4.8, 2.0 Hz, 1H), 8.11 (ddd, J=7.6, 2.0, 1.4 Hz, 1H), 7.47 (m, 2H), 7.29 (m, 2H), 7.27 (m, 3H), 5.96 (s, 1H), 3.87 (br s, 2H), 2.40 (s, 3H).

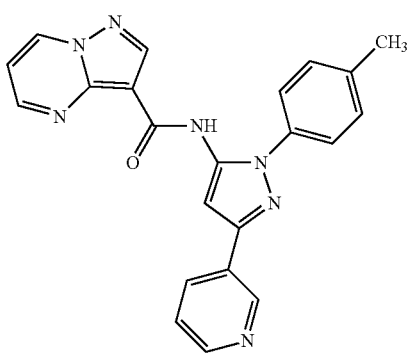

N-(3-(pyridin-3-yl)-1-p-tolyl-1H-pyrazol-5-yl)pyrazolo[1,5-a]pyrimidine-3-carboxamide A mixture of pyrazolo[1,5-a]yrimidine-3-carboxylic acid (140 mg) and SOCl₂ (3 mL) was heated for at 80° C. for 90 min, whereupon the mixture was cooled to rt. and concentrated in vacuo. 3-(yridine-3-yl)-1-p-tolyl-1H-pyrazol-5-amine (113 mg, 0.45 mmol), DIPEA (120 μL, 0.69 mmol), and DCE (10 mL) were added. The resulting mixture was heated to 50° C. for 3.5 h, whereupon the mixture was concentrated in vacuo. The residue was purified by silica gel chromatography, eluting with a solvent gradient of 0 to 10% MeOH in CH₂Cl₂. The product so obtained was further purified by triturating with DMSO. The solid was washed with MeOH to give the title compound as a white solid. ¹H NMR (400 MHz, CDCl₃) δ 10.38 (br s, 1H), 9.14 (dd, J=2.2, 0.8 Hz, 1H), 8.78 (dd, J=7.0, 2.0 Hz, 1H), 8.74 (s, 1H), 8.55 (dd, J=4.8, 1.8 Hz, 1H), 8.31 (dd, J=4.4, 2.0 Hz, 1H), 8.19 (ddd, J=8.0, 2.2, 1.8 Hz, 1H), 7.54 (m, 2H), 7.36 (m, 2H), 7.33 (ddd, J=8.0, 4.8, 0.8 Hz), 7.29, (s, 1H), 7.01 (dd, J=7.0, 4.4 Hz, 1H), 2.49 (s, 3H).

Example 124

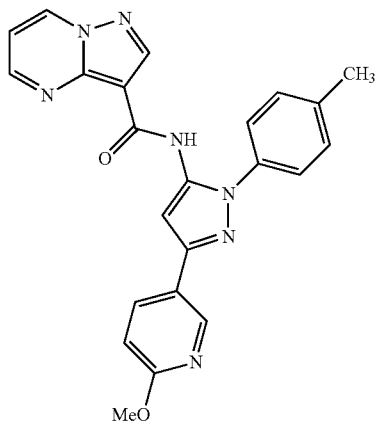

N-(3-(6-methoxypyridin-3-yl)-1-(p-tolyl)-1H-pyrazol-5-yl)pyrazolo[1,5-a]pyrimidine-3-carboxamide This compound was prepared following the general methods outlined for Example 123, using methyl 6-methoxynicotinate in place of methyl nicotinate. ¹H NMR (400 MHz, CDCl₃) δ 10.35 (br s, 1H), 8.78 (dd, J=7.2, 1.8 Hz, 1H), 8.73 (s, 1H), 8.65 (dd, J=2.4, 0.6 Hz, 1H), 8.31 (dd, J=4.0, 1.8 Hz, 1H), 8.12 (dd, J=8.6, 2.4 Hz, 1H), 7.53 (m, 2H), 7.35 (m, 2H), 7.19 (s, 1H), 7.00 (dd, J=7.2, 4.0 Hz, 1H), 6.78 (dd, J=8.6, 0.6 Hz, 1H), 3.97 (s, 3H), 2.47 (s, 3H).

Example 125

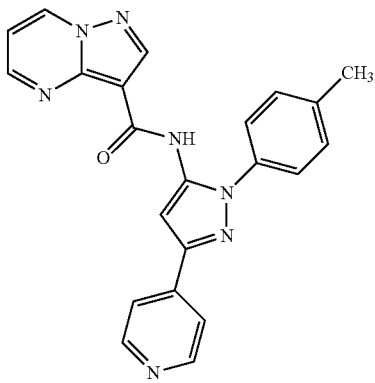

N-(3-(pyridin-4-yl)-1-(p-tolyl)-1H-pyrazol-5-yl)pyrazolo[1,5-a]pyrimidine-3-carboxamide This compound was prepared following the general methods outlined for Example 123, using methyl isonicotinate in place of methyl nicotinate. ¹H NMR (400 MHz, CDCl₃) δ 8.60 (dd, J=4.4, 1.6 Hz, 2H), 8.58 (dd, J=7.0, 2.0 Hz, 1H), 8.46 (dd, J=4.2, 2.0 Hz, 1H), 7.71 (s, 1H), 7.64 (dd, J=4.4, 1.6 Hz, 2H), 7.28 (m, 2H), 7.10 (m, 2H), 6.85 (dd, J=7.0, 4.2 Hz, 1H), 6.62 (s, 1H), 3.36 (s, 3H), 2.30 (s, 3H).

Example 126

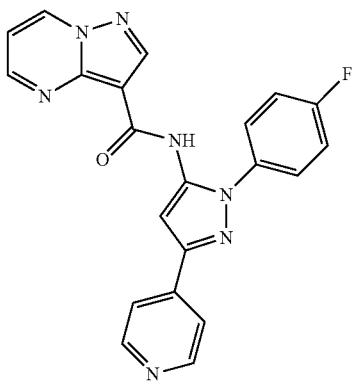

N-(1-(4-fluorophenyl)-3-(pyridin-4-yl)-1H-pyrazol-5-yl)pyrazolo[1,5-a]pyrimidine-3-carboxamide This compound was prepared following the general methods outlined for Example 123, using methyl isonicotinate and 4-fluorophenylhydrazine hydrochloride in place of methyl nicotinate and 4-methylphenylhydrazine hydrochloride, respectively. ¹H NMR (400 MHz, CDCl₃) δ 10.32 (br s, 1H), 8.81 (dd, J=7.2, 1.8 Hz, 1H), 8.74 (s, 1H), 8.63 (dd, J=4.4, 0.8 Hz, 1H), 8.34 (dd, J=4.2, 1.8 Hz, 1H), 7.77 (dd, J=4.4, 1.8 Hz, 1H), 7.66-7.64 (m, 2H), 7.29-7.24 (m, 2H), 7.02 (dd, J=4.2, 7.2 Hz, 1H).

Example 127

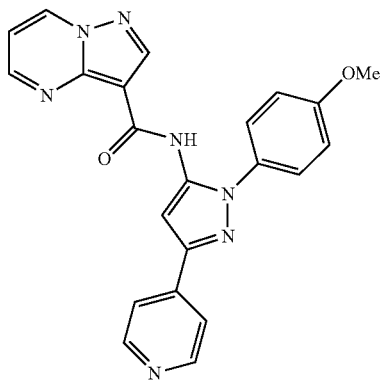

N-(1-(4-methoxyphenyl)-3-(pyridin-4-yl)-1H-pyrazol-5-yl)pyrazolo[1,5-a]pyrimidine-3-carboxamide This compound was prepared following the general methods outlined for Example 123, using methyl isonicotinate and 4-methoxyphenylhydrazine hydrochloride in place of methyl nicotinate and 4-methylphenylhydrazine hydrochloride, respectively. $^1$H NMR (400 MHz, CDCl$_3$) δ 10.35 (br s, 1H), 8.79 (dd, J=7.2, 1.8 Hz, 1H), 8.63 (m, 2H), 8.30 (dd, J=4.4, 1.8 Hz, 1H), 7.78 (m, 2H), 7.55 (m, 2H), 7.32 (s, 1H), 7.08 (m, 2H), 7.00 (dd, J=7.2, 4.4 Hz, 1H), 3.91 (s, 3H).

Example 128

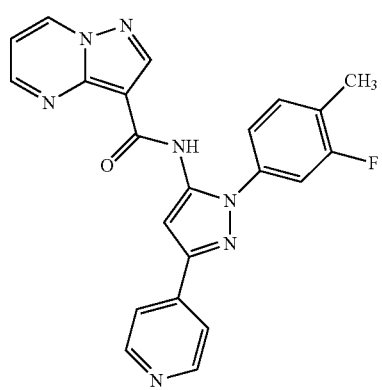

N-(1-(3-fluoro-4-methylphenyl)-3-(pyridin-4-yl)-1H-pyrazol-5-yl)pyrazolo[1,5-a]pyrimidine-3-carboxamide This compound was prepared following the general methods outlined for Example 123, using methyl isonicotinate and 3-fluoro-4-methylphenylhydrazine hydrochloride in place of methyl nicotinate and 4-methylphenylhydrazine hydrochloride, respectively. $^1$H NMR (400 MHz, CDCl$_3$) δ 10.45 (br s, 1H), 8.82 (dd, J=7.2, 4.0 Hz, 1H), 8.75 (s, 1H), 8.64 (m, 2H), 8.45 (dd, J=3.2, 1.8 Hz, 1H), 7.80 (m, 2H), 7.45-7.36 (m, 3H), 7.05 (dd, J=7.2, 3.2 Hz, 1H), 2.40 (s, 3H).

Example 129

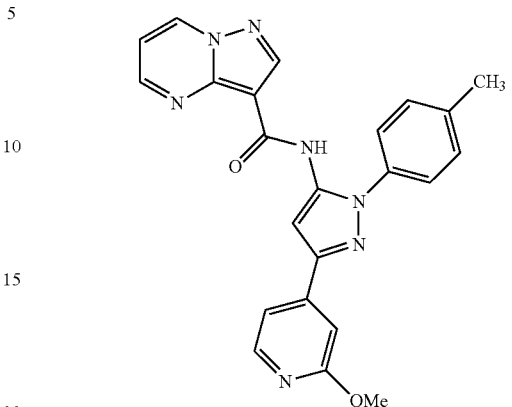

N-(3-(2-methoxypyridin-4-yl)-1-(p-tolyl)-1H-pyrazol-5-yl)pyrazolo[1,5-a]pyrimidine-3-carboxamide This compound was prepared following the general methods outlined for Example 123, using methyl 2-methoxyisonicotinate in place of methyl nicotinate. $^1$H NMR (CDCl$_3$, 400 MHz) δ 10.37 (br s, 1H), 8.78 (dd, J=6.8, 1.6 Hz, 1H), 8.74 (s, 1H), 8.30 (dd, J=4.0, 1.6 Hz, 1H), 8.18 (dd, J=5.2, 0.8 Hz, 1H), 7.53 (m, 2H), 7.41 (dd, J=5.6, 1.6 Hz, 1H), 7.37 (m, 2H), 7.29 (s, 1H), 7.23 (dd, J=1.6, 0.8 Hz, 1H), 7.00 (dd, J=6.8, 4.0 Hz, 1H).

Example 130

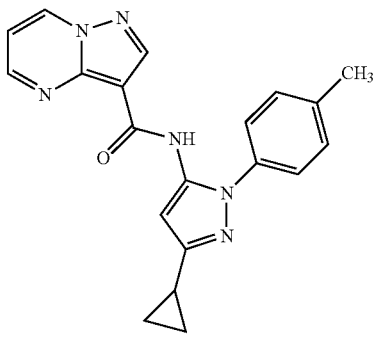

N-(3-cyclopropyl-1-(p-tolyl)-1H-pyrazol-5-yl)pyrazolo[1,5-a]pyrimidine-3-carboxamide This compound was prepared following the general methods outlined for Example 123, using ethyl cyclopropanecarboxylate in place of methyl nicotinate. $^1$H NMR (400 MHz, CDCl$_3$) δ 10.24 (br s, 1H), 8.76 (dd, J=7.2, 1.6 Hz, 1H), 8.69 (s, 3H), 8.29 (dd, J=4.2, 1.6 Hz, 1H), 7.45 (m, 2H), 7.30 (m, 2H), 6.97 (dd, J=6.8, 4.2 Hz, 1H), 6.54 (s, 3H), 2.44 (s, 3H), 1.99 (m, 1H), 0.93 (m 2H), 0.83 (m, 2H).

Example 131

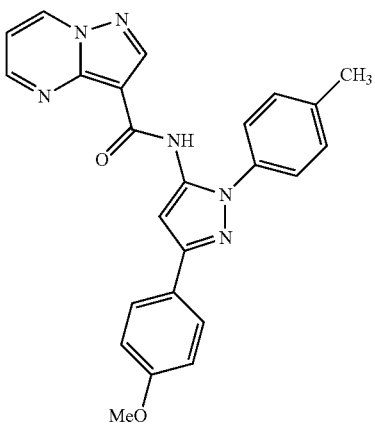

N-(3-(4-methoxyphenyl)-1-(p-tolyl)-1H-pyrazol-5-yl)pyrazolo[1,5-a]pyrimidine-3-carboxamide This compound was prepared following the general methods outlined for Example 123, using methyl 4-methoxybenzoate in place of methyl nicotinate. $^1$H NMR (400 MHz, CDCl$_3$) δ 10.33 (br s, 1H), 8.78 (dd, J=7.2, 2.0 Hz, 1H), 8.74 (s, 1H), 8.71 (dd, J=4.0, 2.0 Hz, 1H), 7.85 (m, 2H), 7.54 (m, 2H), 7.35 (m, 2H), 7.19 (s, 1H), 6.99 (dd, J=7.2, 4.0 Hz, 1H), 6.94 (m, 2H), 3.83 (s, 3H), 2.47 (s, 3H).

Example 132

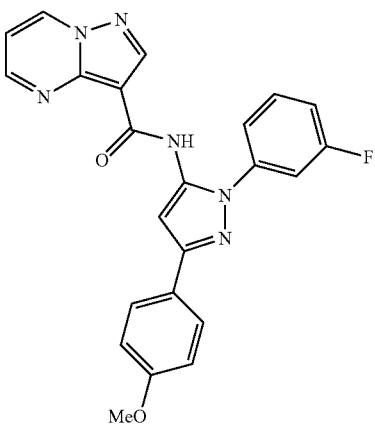

N-(1-(3-fluorophenyl)-3-(4-methoxyphenyl)-1H-pyrazol-5-yl)pyrazolo[1,5-a]pyrimidine-3-carboxamide This compound was prepared following the general methods outlined for Example 123, using methyl 4-methoxybenzoate and 4-fluorophenylhydrazine hydrochloride in place of methyl nicotinate and 4-methylphenylhydrazine hydrochloride, respectively. $^1$H NMR (400 MHz, CDCl$_3$) δ 10.42 (br s, 1H), 8.81 (dd, J=6.8, 1.8 Hz, 1H), 8.75 (s, 1H), 8.47 (dd, J=4.4, 1.8 Hz, 1H), 7.84 (m, 2H), 7.54-7.48 (m, 3H), 7.23 (s, 1H), 7.17 (m, 1H), 7.03 (dd, J=6.8, 4.4 Hz, 1H), 6.95 (m, 2H), 3.82 (s, 3H).

Example 133

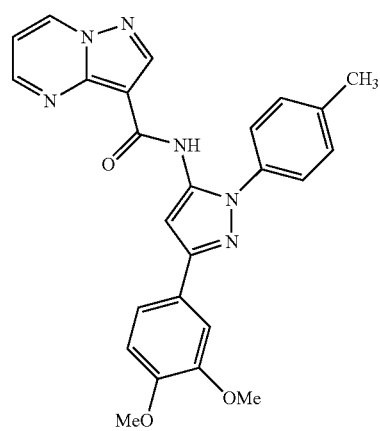

N-(3-(3,4-dimethoxyphenyl)-1-(p-tolyl)-1H-pyrazol-5-yl)pyrazolo[1,5-a]pyrimidine-3-carboxamide This compound was prepared following the general methods outlined for Example 123, using methyl 3,4-dimethoxybenzoate in place of methyl nicotinate. $^1$H NMR (400 MHz, CDCl$_3$) δ 10.35 (br s, 1H), 8.79 (dd, J=7.0, 1.6 Hz, 1H), 8.73 (s, 1H), 8.31 (dd, J=4.0, 1.6 Hz, 1H), 7.55 (m, 2H), 7.47 (d, J=2.0 Hz, 1H), 7.45 (dd, J=8.0, 2.0 Hz, 1H), 7.36 (m, 2H), 7.21 (s, 1H), 7.00 (dd, J=7.0, 4.0 Hz, 1H), 6.92 (d, J=8.0 Hz, 1H), 3.95 (s, 3H), 3.91 (s, 3H), 2.48 (s, 3H).

Scheme 3

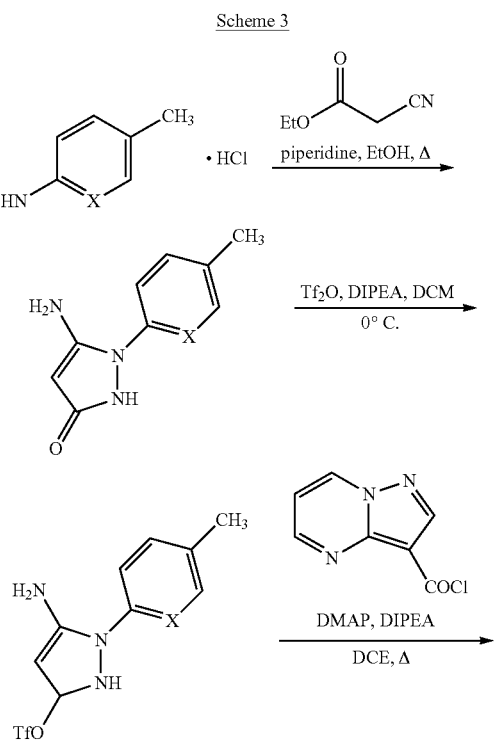

-continued

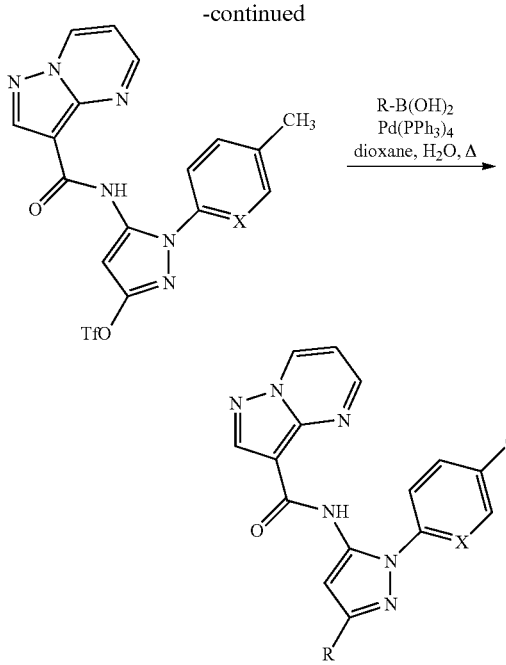

General methods for the preparation of synthetic intermediates follow below.

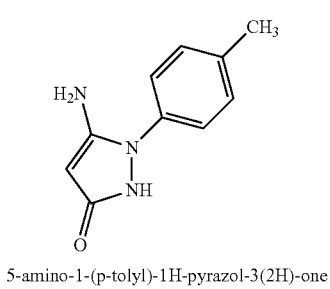

5-amino-1-(p-tolyl)-1H-pyrazol-3(2H)-one

A mixture of 4-methylphenylhydrazine hydrochloride (2.79 g, 17.6 mmol), ethyl cyanoacetate (1.9 mL, 18 mmol), piperidine (1.8 mL, 18 mmol) and ethanol (50 mL) was heated to 90° C. for 3 d. The mixture was concentrated in vacuo. The residue was purified by silica gel chromatography, eluting with a solvent gradient of 0 to 30% MeOH in $CH_2Cl_2$ to give 3.61 g of a red solid, that was used without further purification.

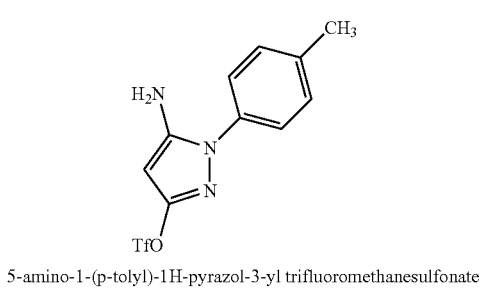 [SMILES: Cc1ccc(-n2nc(OS(=O)(=O)C(F)(F)F)cc2N)cc1]

5-amino-1-(p-tolyl)-1H-pyrazol-3-yl trifluoromethanesulfonate

A mixture of 5-amino-1-(p-tolyl)-1H-pyrazol-3(2H)-one (3.33 g, prepared as described above) and $CH_2Cl_2$ (200 mL) was cooled to 0° C. Triflic anhydride (3.6 mL, 21 mmol) and pyridine (3.2 mL, 40 mmol) were added. The resulting solution was stirred at 0° C. for 4 h, Sat $NaHCO_3$ (200 mL) was added and the phases were separated. The aqueous layer was extracted with $CH_2Cl_2$ (2×200 mL). The combined organic extracts were dried ($MgSO_4$) and concentrated in vacuo. The residue was purified by silica gel chromatography, eluting with a solvent gradient of 0 to 50% EtOAc in hexanes to give the title compound as a tan solid, $^1$H NMR (400 MHz, $CDCl_3$) δ 7.35 (m, 2H), 7.28 (m, 2H), 5.50 (s, 1H), 3.91 (br s, 1H), 2.38 (s, 3H).

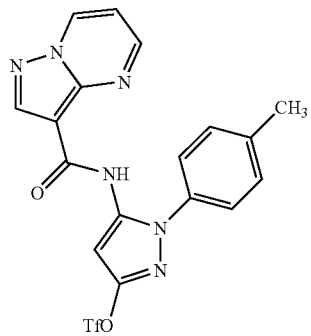

5-(pyrazolo[1,5-a]pyrimidine-3-carboxamido)-1-(p-tolyl)-1H-pyrazol-3-yl trifluoromethanesulfonate A mixture of pyrazolo[1,5-a]pyrimidine-3-carboxylic acid (1.04, 6.34 mmol) and thionyl chloride (5 mL) was heated to 80° C. for 75 min. The mixture was concentrated in vacuo. 5-amino-1-(p-tolyl)-1H-pyrazol-3-yl trifluoromethanesulfonate (1.64 g, 5.10 mmol), DIPEA (1.2 mL, 6.9 mmol), and $CH_2Cl_2$ (100 mL) were added and the resulting mixture was stirred at rt for 20 h. Sat $NaHCO_3$ (100 mL) was added and the phases were separated. The aqueous layer was extracted with $CH_2Cl_2$ (2×200 mL) and the combined organic extracts were dried ($MgSO_4$) and concentrated in vacuo. The residue was purified by silica gel chromatography, eluting with a solvent gradient of 0 to 100% EtOAc to give the title compound as a white solid. $^1$H NMR ($CDCl_3$) δ 10.45 (br s, 1H), 8.79 (dd, J=7.0, 1.8 Hz, 1H), 8.71 (s, 1H), 8.28 (dd, J=4.4, 1.8 Hz, 1H), 7.46 (m, 2H), 7.35 (m, 2H), 7.01 (dd, J=7.0, 4.0 Hz, 1H), 6.84 (s, 1H), 2.48 (s, 3H).

Example 134

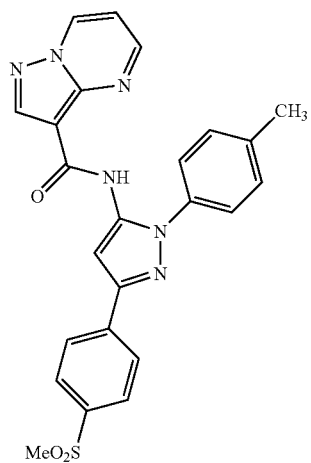

N-(3-(4-methylsulfonyl)phenyl)-1-(p-tolyl)-1H-pyrazol-5-yl)pyrazolo[1,5-a]pyrimidine-3-carboxamide A mixture of 5-(pyrazolo[1,5-a]pyrimidine-3-carboxamido)-1-(p-tolyl)-1H-pyrazol-3-yl trifluoromethanesulfonate (1.07 g, 2.29 mmol), 4-(methylsulfonyl)phenyl boronic acid (730 mg, 3.65 mmol), Pd(PPh₃)₄ (285 mg, 0.247 mmol), K₂CO₃ (990 mg, 7.16 mmol), dioxane (16 mL) and water (4 mL) was purged with N₂ for 15 min. The reaction vessel was immersed in an oil bath, that had been preheated to 100° C., and heated for 2 h. Water (100 mL) was added and the mixture was extracted with EtOAc (3×100 mL). The combined organic extracts were dried (MgSO₄) and concentrated in vacuo. The residue was purified by silica gel chromatography, eluting with a solvent gradient of 0 to 100% EtOAc in hexanes to give the title compound as a white solid. $^1$H NMR (400 MHz, CDCl₃) δ 10.39 (br s, 1H), 8.79 (dd, J=7.0, 1.6 Hz, 1H), 8.74 (s, 1H), 8.30 (dd, J=4.2, 1.6 Hz, 1H), 8.11 (m, 2H), 7.97 (m, 2H), 7.55 (m, 2H), 7.38 (m, 2H), 7.34 (s, 1H), 7.01 (dd, J=7.0, 4.2 Hz, 1H).

Example 135

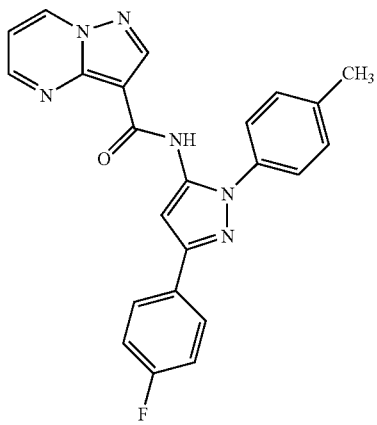

N-(3-(4-fluorophenyl)-1-(p-tolyl)-1H-pyrazol-5-yl)pyrazolo[1,5-a]pyrimidine-3-carboxamide This compound was prepared following the general methods outline for Example 134, using (4-fluorophenyl)boronic acid in place of 4-(methylsulfonyl)phenyl boronic acid. $^1$H NMR (400 MHz, CDCl₃) δ 10.35 (br s, 1H), 8.88 (dd, J=7.0, 1.8 Hz 1H), 8.74 (s, 1H), 8.30 (dd, J=4.0, 1.8 Hz, 1H), 7.88 (m, 2H), 7.53 (d, J=8.4 Hz, 2H), 7.37 (m, 2H), 7.09 (m, 2H), 7.00 (dd, J=7.0, 4.0 Hz, 1H), 2.48 (s, 3H).

Example 136

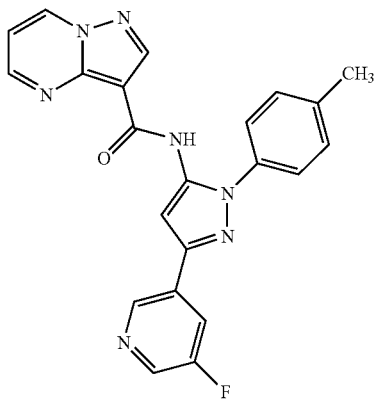

N-(3-(5-fluoropyridin-3-yl)-1-(p-tolyl)-1H-pyrazol-5-yl)pyrazolo[1,5-a]pyrimidine-3-carboxamide This compound was prepared following the general methods outline for Example 134, using (5-fluoropyridin-3-yl) boronic acid in place of 4-(methylsulfonyl)phenyl boronic acid. $^1$H NMR (400 MHz, CDCl₃) δ 10.40 (br s, 1H), 8.94 (t, J=1.8 Hz, 1H), 8.80 (dd, J=7.0, 1.8 Hz, 1H), 8.74 (s, 1H), 8.41 (d, J=2.8 Hz, 1H), 8.30 (dd, J=4.0, 1.8 Hz, 1H), 7.94 (ddd, J=9.6, 2.8, 1.8 Hz, 1H), 7.54 (m, 2H), 7.53 (m, 2H), 7.30 (s, 1H), 7.02 (dd, J=7.0, 4.0 Hz, 1H), 2.49 (s, 3H).

Example 137

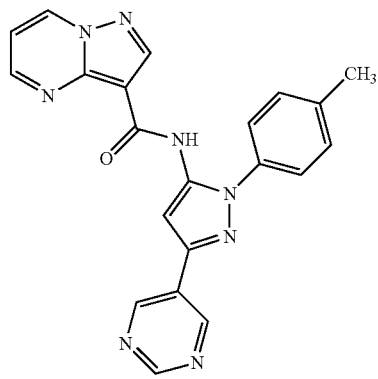

N-(3-(pyrimidin-5-yl)-1-(p-tolyl)-1H-pyrazol-5-yl)pyrazolo[1,5-a]pyrimidine-3-carboxamide This compound was prepared following the general methods outline for Example 134, using pyrimidin-5-ylboronic acid in place of 4-(methylsulfonyl)phenyl boronic acid. $^1$H NMR (400 MHz, CDCl₃) δ 10.43 (br s, 1H), 9.22 (s, 1H), 9.16 (s, 1H), 8.80 (dd, J=7.2, 2.0 Hz, 1H), 8.74 (s, 1H), 8.30 (dd, J=4.4, 2.0 Hz, 1H), 7.53 (m, 2H), 7.39 (m, 2H), 7.01 (dd, J=7.2, 4.4 Hz, 1H), 2.50 (s, 3H).

Example 138

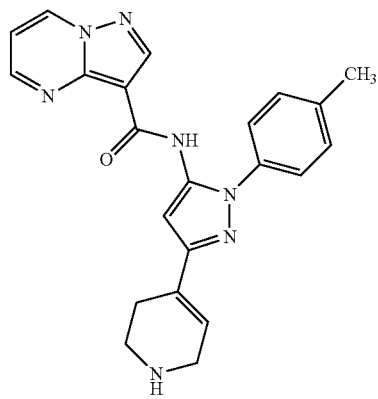 [SMILES: Cc1ccc(-n2nc(C3=CCNCC3)cc2NC(=O)c2cnn3cccnc23)cc1]

N-(3-(1,2,3,6-tetrahydropyridin-4-yl)-1-(p-tolyl)-1H-pyrazol-5-yl)pyrazolo[1,5-a]pyrimidine-3-carboxamide Synthesis of the intermediate is described below.

129

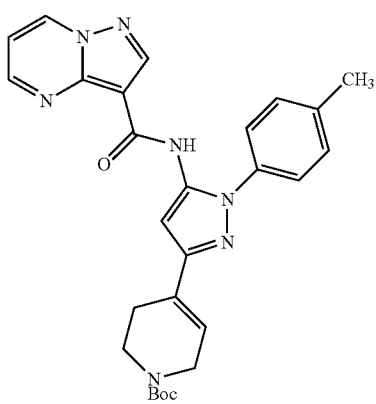

tert-butyl 4-(5-(pyrazolo[1,5-a]pyrimidine-3-carboxamido)-
1-(p-tolyl)-1H-pyrazol-3-yl)-5,6-dihydropyridine-1(2H)-carboxylate This compound was prepared following the general methods outline for Example 134, using tert-butyl 4-(4,4,5,5-tetramethyl-1,3,2-dioxaborolan-2-yl)-5,6-dihydropyridine-1(2H)-carboxylate in place of 4-(methylsulfonyl)phenyl boronic acid.

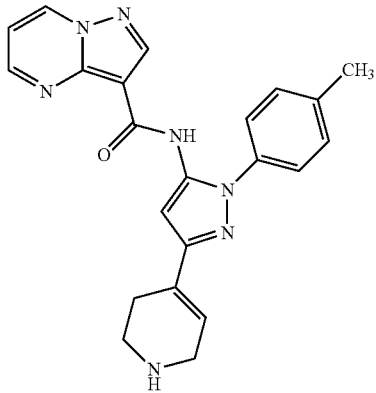

This compound was prepared following the general methods for Example 7, using tert-butyl 4-(5-(pyrazolo[1,5-a]pyrimidine-3-carboxamido)-1-(p-tolyl)-1H-pyrazol-3-yl)-5,6-dihydropyridine-1(2H)-carboxylate in place of tert-butyl 4-(5-(pyrazolo[1,5-a]pyrimidine-3-carboxamido)-1-(p-tolyl)-1H-pyrazol-3-yl)piperidine-1-carboxylate. $^1$H NMR (400 MHz, CD$_3$OD) δ 10.53 (br s, 1H), 9.09 (dd, J=7.0, 1.8 Hz, 1H), 8.64 (s, 1H), 8.42 (dd, J=4.2, 1.8 Hz, 1H), 7.51-7.45 (m, 4H), 7.20 (dd, J=7.0, 4.2, Hz, 1H), 7.01 (s, 1H), 6.38 (m, 1H), 3.88 (m, 2H), 3.46 (t, J=2.4 Hz, 2H), 2.88 (m, 2H), 2.51 (s, 3H).

Example 139

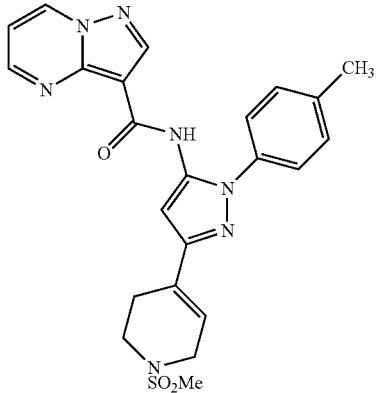

N-(3-(1-(methylsulfonyl)-1,2,3,6-
tetrahydropyridin-4-yl)-1-(p-tolyl)-
1H-pyrazol-5-yl)pyrazolo[1,5-a]
pyrimidine-3-carboxamide

130

This compound was prepared following the general methods for Example 16, using N-(3-(1,2,3,6-tetrahydropyridin-4-yl)-1-(p-tolyl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. $^1$H NMR (400 MHz, CDCl$_3$) δ 10.28 (br s, 1H), 8.77 (dd, J=7.2, 1.6 Hz, 1H), 8.71 (s, 1H), 8.28 (dd, J=4.0, 1.6 Hz, 1H), 7.47 (m, 2H), 7.33 (m, 2H), 7.00-6.97 (m, 2H), 6.32 (m, 1H), 3.99 (m, 2H), 3.51 (t, J=6.0 Hz, 2H), 2.84 (s, 3H), 2.77 (m, 2H0, 2.46 (t, 3H).

Example 140

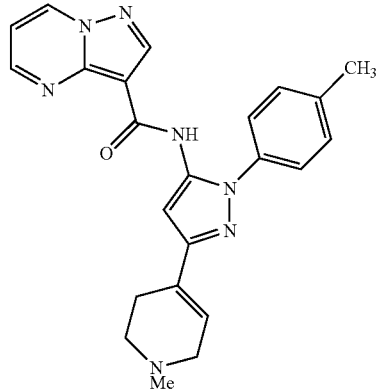

N-(3-(1-(methyl-1,2,3,6-tetrahydropyridin-4-yl)-
1-(p-tolyl)-1H-pyrazol-5-yl)pyrazolo[1,5-a]
pyrimidine-3-carboxamide This compound was prepared according to the method outlined for Example 36 using N-(3-(1,2,3,6-tetrahydropyridin-4-yl)-1-(p-tolyl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 10.29 (br s, 1H), 8.78 (dd, J=7.2, 1.8 Hz, 1H), 8.28 (dd, J=4.0, 1.8 Hz, 1H), 7.47 (m, 2H), 7.35 (m, 2H), 7.00-6.98 (m, 2H), 6.25 (m, 1H), 3.68 (app br s, 2H), 3.19 (app br s, 2H), 2.96 (app br s, 2H), 2.78 (app br s, 3H), 2.46 (s, 3H).

Example 141

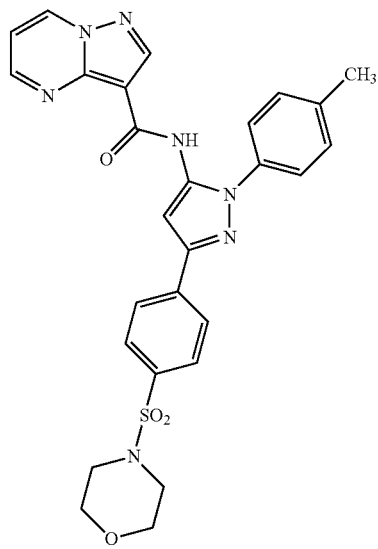

N-(3-(4-(morpholinosulfonyl)phenyl)-1-
(p-tolyl)-1H-pyrazol-5-yl)pyrazolo[1,5-a]
pyrimidine-3-carboxamide This compound was prepared following the general methods for Example 134, using 4-((4-(4,4,5,5-tetramethyl-1,3,2-dioxaborolan-2-yl)phenyl)sulfonyl)morpholine in place of 4-(methylsulfonyl)phenyl boronic acid. $^1$H NMR (400 MHz, CDCl$_3$) δ 10.33 (br s, 1H), 8.77 (dd, J=7.2, 1.6 Hz, 1H), 8.73 (s, 1H), 8.31 (dd, J=4.4, 1.6 Hz, 1H), 7.82 (m, 2H), 7.53 (m, 2H), 7.35 (m, 2H), 7.19 (s, 1H), 6.99 (dd, J=7.2, 4.4 Hz, 1H), 6.94 (m, 2H), 3.88 (m, 4H), 3.20 (m, 4H), 2.47 (s, 3H).

Example 142

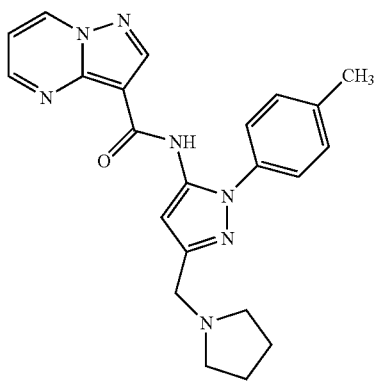

N-(3-(pyrrolidin-1-ylmethyl)-1-(p-tolyl)-1H-pyrazol-5-yl)pyrazolo[1,5-a]pyrimidine-3-carboxamide General methods for the preparation of the intermediates follow below.

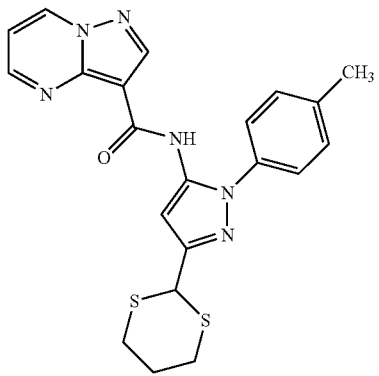

N-(3-(1,3-dithian-2-yl)-1-(p-tolyl)-1H-pyrazol-5-yl)pyrazolo[1,5-a]pyrimidine-3-carboxamide This compound was prepared according to the general methods outlined for Example 1, using methyl 1,3-dithiane-2-carboxylate in place of ethyl 1,4-dioxaspiro[4.5]decane-8-carboxylate. $^1$H NMR (400 MHz, CDCl$_3$) δ 10.27 (br s, 1H), 8.77 (dd, J=7.0, 1.8 Hz, 1H), 8.71 (s, 1H), 8.28 (dd, J=4.4, 1.8 Hz, 1H), 7.47 (m, 2H), 7.29 (m, 2H), 7.01 (s, 1H), 6.97 (dd, J=7.0, 4.4 Hz, 1H), 5.36 (s, 1H), 3.07-2.94 (m, 4H), 2.45 (s, 3H), 2.16 (m, 1H), 2.06-1.96 (m, 2H).

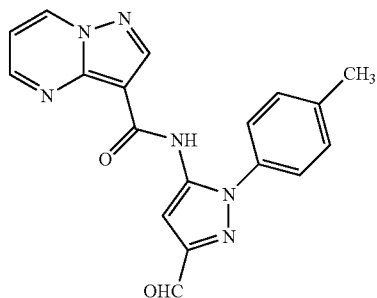

N-(3-formyl-1-(p-tolyl)-1H-pyrazol-5-yl)pyrazolo[1,5-a]pyrimidine-3-carboxamide

NaHCO$_3$ (202 mg, 2.41 mmol) and the [bis(trifluoroacetoxy)iodo]benzene (386 mg, 0.898 mmol) were added to a mixture of N-(3-(1,3-dithian-2-yl)-1-(p-tolyl)-1H-pyrazol-5-yl)pyrazolo[1,5-a]pyrimidine-3-carboxamide (199 mg, 0.456 mmol), acetonitrile (10 mL) and water (2 mL). The mixture was stirred at rt for 4 h, at which point bis(trifluoroacetoxy)iodo]benzene (400 mg) was added. The mixture was stirred at rt for an additional 2 h. Sat NaHCO$_3$ (50 mL) was added and the mixture was extracted with EtOAc (2×50 mL). The combined organic extracts were washed with brine (2×50 mL), dried (MgSO$_4$) and concentrated in vacuo. The residue was purified by silica gel chromatography, eluting with a solvent gradient of 0 to 100% EtOAc in hexanes to give the title compound as a white solid. $^1$H NMR (400 MHz, CDCl$_3$) δ 10.33 (br s, 1H), 9.99 (s, 1H), 8.79 (m, 1H), 8.72 (s, 1H), 8.28 (m, 1H), 7.52 (m, 2H), 7.38 (m, 2H), 7.35 (s, 1H), 7.00 (m, 1H), 2.50 (s, 3H).

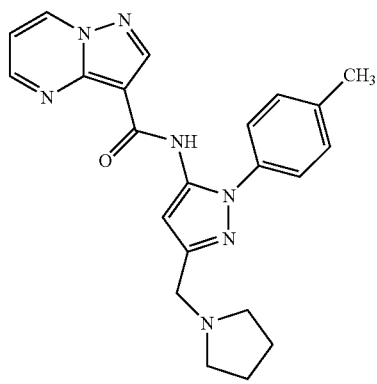 [SMILES: Cc1ccc(-n2nc(CN3CCCC3)cc2NC(=O)c2cnn3cccnc23)cc1]

A mixture of N-(3-formyl-1-(p-tolyl)-1H-pyrazol-5-yl)pyrazolo[1,5-a]pyrimidine-3-carboxamide (24 mg, 0.069 mmol), pyrrolidine (20 µL, 0.24 mmol), sodium triacetoxyborohydride (44 mg, 0.21 mmol), and DCE (5 mL) was stirred at rt for 3 d. Sat NaHCO$_3$ (50 mL) was added and the mixture was extracted with CH$_2$Cl$_2$ (3×50 mL). The combined organic extracts were dried (MgSO$_4$) and concentrated in vacuo. The residue was washed with a small amount of Et$_2$O/EtOH to give the title compound as white solid. $^1$H NMR (400 MHz, CDCl$_3$) δ 10.25 (br s, 1H), 8.77 (dd, J=6.8, 1.6 Hz, 1H), 8.71 (s, 1H), 8.29 (dd, J=4.4, 1.6 Hz, 1H), 7.46 (m, 2H), 7.29 (m, 2H), 6.98 (dd, J=6.8, 4.4 Hz, 1H), 6.88 (s, 1H), 3.74 (s, 2H), 2.67 (app br s, 4H), 2.44 (s, 3H), 1.80 (m, 4H).

Example 143

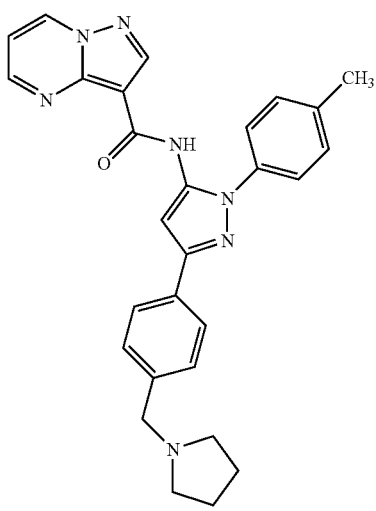 [SMILES: Cc1ccc(-n2nc(-c3ccc(CN4CCCC4)cc3)cc2NC(=O)c2cnn3cccnc23)cc1]

N-(3-(4-(pyrrolidin-1-ylmethyl)
phenyl)-1-(p-tolyl)-
1H-pyrazol-5-yl)pyrazolo[1,5-a]
pyrimidine-3-
carboxamide General methods for the synthesis of intermediates follow below.

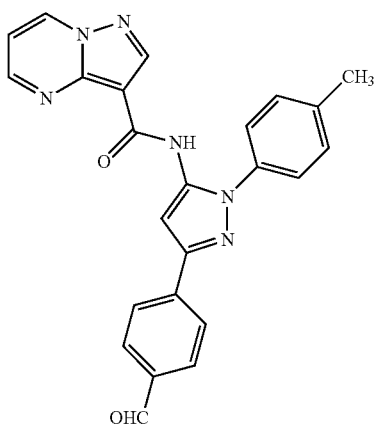

N-(3-(4-formylphenyl)-1-(p-tolyl)-
1H-pyrazol-5-yl)pyrazolo[1,5-a]
pyrimidine-3-carboxamide A mixture of 5-(pyrazolo pyrimidine-3-carboxamido)-1-(p-tolyl)-1H-pyrazol-3-yl trifluoromethanesulfonate (275 mg, 0.590 mmol), (4-(1,3-dioxolan-2-yl)phenyl)boronic acid (352 mg, 1.82 mmol), potassium carbonate (286 mg, 2.07 mmol), Pd(PPh$_3$)$_4$ (59, 0.051 mmol), dioxane (10 mL), and water (2 mL) was purged with N$_2$ for 10 min. The mixture was heated to 100° C. for 18 h. Water (50 mL) was added and the mixture was extracted with EtOAc (3×50 mL). The combined organic extracts were dried (MgSO$_4$) and concentrated in vacuo. The residue was purified by silica gel chromatography, eluting with a solvent gradient of 0 to 100% EtOAc in hexnaes to give the title compound as a white solid. $^1$H NMR (400 MHz, CDCl$_3$) δ 10.38 (br s, 1H), 10.02 (s, 1H), 8.79 (dd, J=6.8, 1.8 Hz, 1H), 8.30 (dd, J=4.0, 1.8 Hz, 1H), 8.09 (m, 2H), 7.92 (m, 2H), 7.55 (m, 2H), 7.38 (m, 2H), 7.35 (s, 1H), 7.00 (dd, J=6.8, 4.0, Hz, 1H), 2.49 (s, 3H).

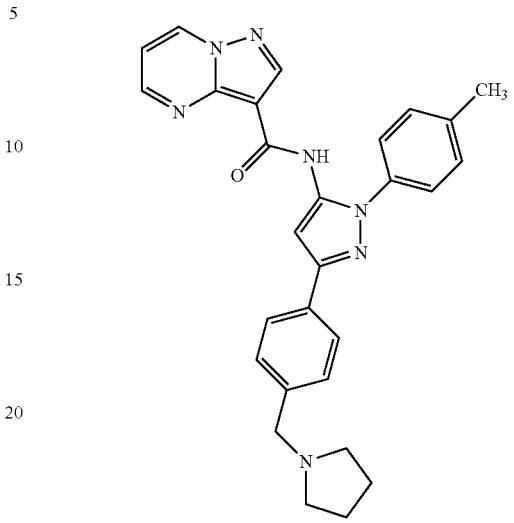

A mixture of N-(3-(4-formylphenyl)-1-(p-tolyl)-1H-pyrazol-5-yl)pyrazolo[1,5-a]pyrimidine-3-carboxamide (12 mg, 0.028 mmol), NaBH(OAc)$_3$ (18 mg, 0.085 mmol), pyrrolidine (20 μL, 0.24 mmol), and DCE (5 mL) was heated to 45° C. for 3 h. Sat NaHCO$_3$ (20 mL) was added and the mixture was extracted with CH$_2$Cl$_2$ (3×20 mL). The combined organic extracts were dried (MgSO$_4$) and concentrated in vacuo. The residue was triturated with hexanes/Et$_2$O to give the title compound as an orange solid. $^1$H NMR (400 MHz, CDCl$_3$) δ 10.25 (br s, 1H), 8.77 (dd, J=6.8, 1.8 Hz, 1H), 8.71 (s, 1H), 8.29 (dd, J=4.4, 1.8 Hz, 1H), 7.46 (m, 2H), 7.29 (m, 2H), 6.98 (dd, J=6.8, 4.4 Hz, 1H), 6.88 (s, 1H), 3.74 (app br s, 2H), 2.67 (app br s, 4H), 2.44 (s, 3H), 1.80 m, 4H).

Example 144

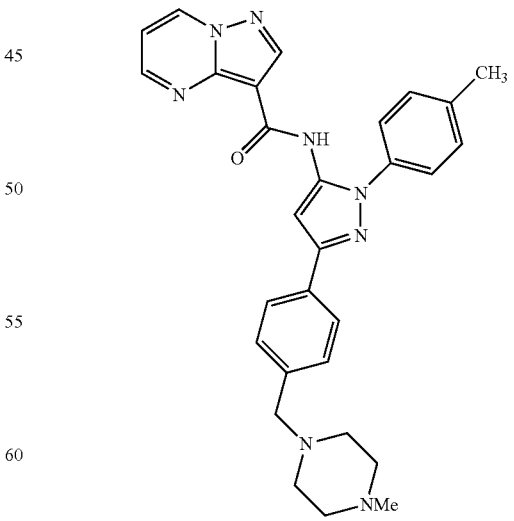

N-(3-(4-((4-methylpiperazin-1-yl)
methyl)phenyl)-1-(p-tolyl)-
1H-pyrazol-5-yl)pyrazolo[1,5-a]
pyrimidine-3-carboxamide This compound was prepared following the general methods outlined for Example 143, using 1-methylpiperazine in place of pyrollidine. ¹H NMR (400 MHz, CDCl₃) δ 10.33 (br s, 1H), 8.78 (dd, J=7.2, 2.0 Hz, 1H), 8.74 (s, 1H), 8.30 (dd, J=4.0, 2.0 Hz, 1H), 7.86 (m, 2H), 7.55 (m, 2H), 7.36-7.34 (m, 4H), 6.99 (dd, J=7.2, 4.0 Hz, 1H), 4.19 (t, J=6.0 Hz, 2H), 3.57 (br s, 3H), 2.65-2.36 (m, 11H).

Example 145

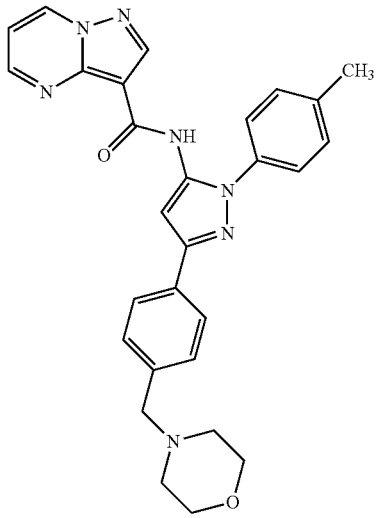

N-(3-(4-(morpholinomethyl)phenyl)-1-(p-tolyl)-1H-pyrazol-5-yl)pyrazolo[1,5-a]pyrimidine-3-carboxamide This compound was prepared following the general methods outlined for Example 143, using morpholine in place of pyrollidine. ¹H NMR (400 MHz, CDCl₃) δ 10.35 (br s, 1H), 8.79 (dd, J=7.2, 1.8 Hz, 1H), 8.74 (s, 1H), 8.30 (dd, J=4.0, 1.8 Hz, 1H), 7.89 (m, 2H), 7.54 (m, 2H), 7.40-7.35 (m, 3H), 6.99 (dd, J=7.2, 4.0 Hz, 1H), 3.76-3.47 (m, 6H), 2.63-2.48 (m, 7H).

Scheme 4

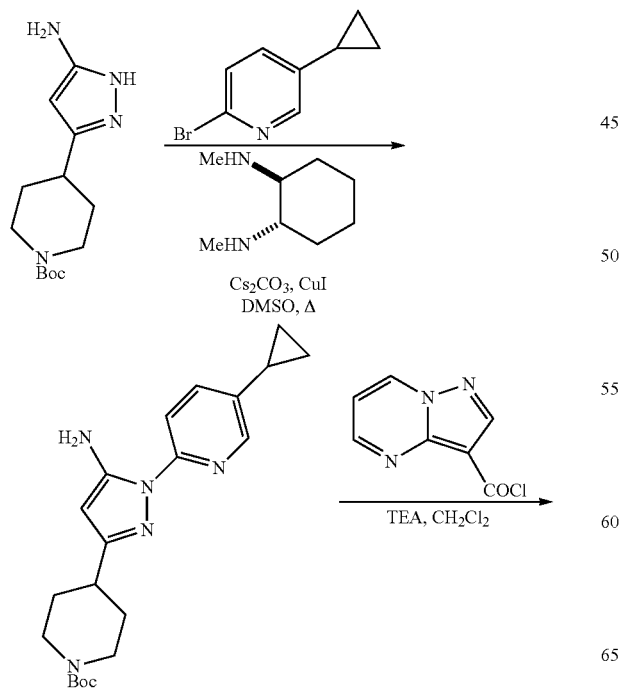

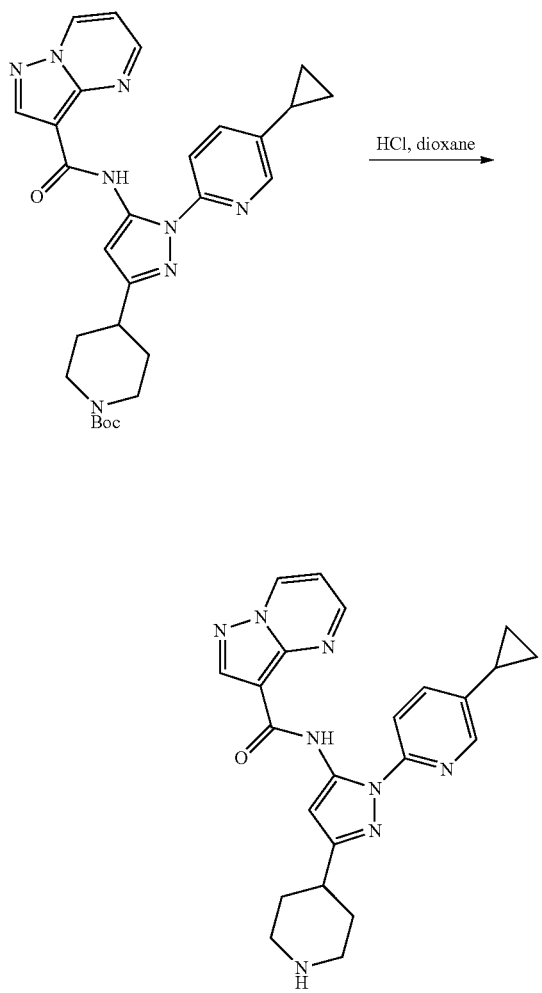

Example 146

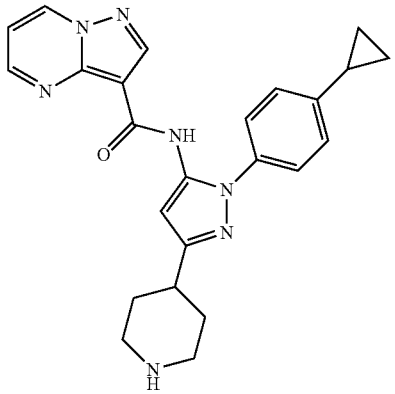

N-(1-(4-cyclopropylphenyl)-3-(piperidin-4-yl)-1H-pyrazol-5-yl)pyrazolo[1,5-a]pyrimidine-3-carboxamide Synthesis of the intermediates follows below.

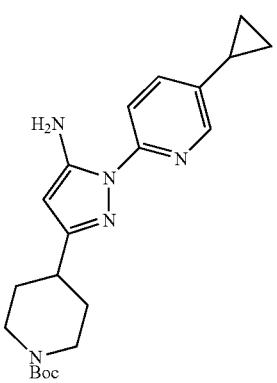

tert-butyl 4-(5-amino-1-(5-cyclopropylpyridin-2-yl)-1H-pyrazol-3-yl)piperidine-1-carboxylate A mixture of tert-butyl 4-(5-amino-1H-pyrazol-3-yl)piperidine-1-carboxylate (300 mg, 1.126 mmol), 2-bromo-5-cyclopropylpyridine (234 mg, 1.183 mmol), copper(I) iodide (21.45 mg, 0.113 mmol), (1S,2S)—$N^1,N^2$-dimethylcyclohexane-1,2-diamine (16.02 mg, 0.113 mmol), and cesium carbonate (734 mg, 2.253 mmol), DMSO (3 mL), was purged with $N_2$ for 30 min. The mixture was heated to 130° C. in a sealed tube for 15 h. The mixture was cooled to rt. and water (30 mL) was added. The mixture was extracted with EtOAc (3×30 mL). The combined organic extracts were dried ($MgSO_4$) and concentrated in vacuo. The residue was purified by silica gel chromatography, eluting with a solvent gradient of 0 to 40% EtOAc in hexanes to give the product as a white solid. $^1$H NMR (400 MHz, $CDCl_3$) δ 8.03 (m, 1H), 7.74 (m, 1H), 7.32 (m, 1H), 5.88 (bs, 2H), 5.26 (s, 1H), 4.10 (m, 2H), 2.79 (m, 2H), 2.67 (m, 1H), 1.88-1.79 (m, 3H), 1.61-1.54 (m, 2H), 1.42 (s, 9H), 1.20 (t, J=7.2 Hz, 1H), 0.94 (m, 2H), 0.63 (m, 2H).

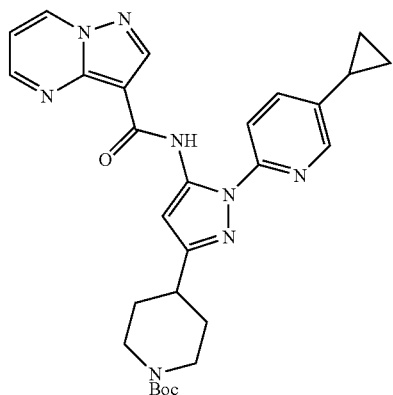

tert-butyl 4-(1-(5-cyclopropylpyridin-2-yl)-5-(pyrazolo[1,5-a]pyrimidine-3-carboxamido)-1H-pyrazol-3-yl)piperidine-1-carboxylate This compound was prepared according to the general methods outlined for Example 7, using tert-butyl 4-(5-amino-1-(5-cyclopropylpyridin-2-yl)-1H-pyrazol-3-yl)piperidine-1-carboxylate in place of tert-butyl 4-(5-amino-1-(p-tolyl)-1H-pyrazol-3-yl)piperidine-1-carboxylate. $^1$H NMR (400 MHz, $CDCl_3$) δ 8.65 (m, 3H), 8.14 (m, 1H), 7.75 (m, 1H), 7.35 (m, 1H), 6.93 (m, 2H), 4.27-4.02 (br s, 2H), 2.94-2.77 (m, 3H), 1.90 (m, 2H), 1.87 (m, 1H), 1.71 (m, 2H), 1.44 (s, 9H), 1.00 (m, 2H), 0.67 (m, 2H).

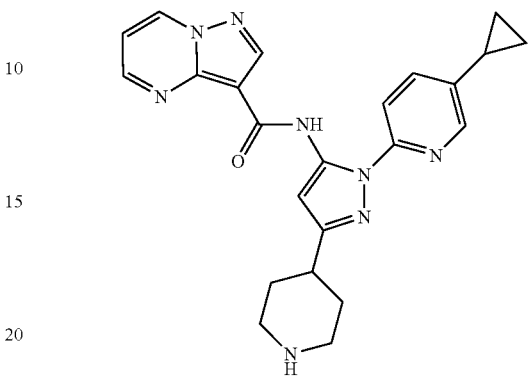

N-(1-(5-cyclopropylpyridin-2-yl)-3-(piperidin-4-yl)-1H-pyrazol-5-yl)pyrazolo[1,5-a]pyrimidine-3-carboxamide tert-Butyl 4-(1-(5-cyclopropyridin-2-yl)-5-(pyrazolo pyrimidine-3-carboxamido)-1H-pyrazol-3-yl)piperidine-1-carboxylate (219 mg, 0.414 mmol), 1.0 mL of hydrogen chloride solution (4M in dioxane), DCM (10 ml), MeOH (3 ml) were combined and stirred at room temperature overnight. The mixture was concentrated to give the desired product as a white solid.

Example 147

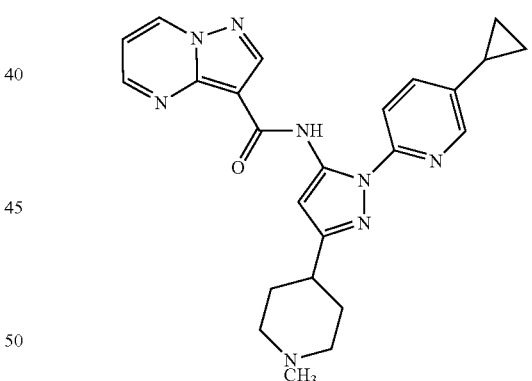

N-(1-(5-cyclopropylpyridin-2-yl)-3-(1-methylpiperidin-4-yl)-1H-pyrazol-5-yl)pyrazolo[1,5-a]pyrimidine-3-carboxamide This compound was prepared according to the method outlined for Example 36 using N-(1-(5-cyclopropylpyridin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. NMR (300 MHz, $CDCl_3$) δ 0.76-0.80 (m, 2H), 1.08-1.14 (m, 2H), 1.95-2.01 (m, 1H), 2.34-2.43 (m, 4H), 2.78-2.89 (m, 6H), 3.30-3.83 (m, 2H), 7.16-7.02 (m, 2H), 7.50-7.53 (m, 1H), 7.85-7.89 (m, 1H), 8.34 (d, J=2.1 Hz, 1H), 8.89-8.83 (m, 3H), 11.80 (s broad, 0.5H), 12.15 (s broad, 0.5H), 13.17 (s, 0.5H), 13.22 (s, 0.5H).

Example 148

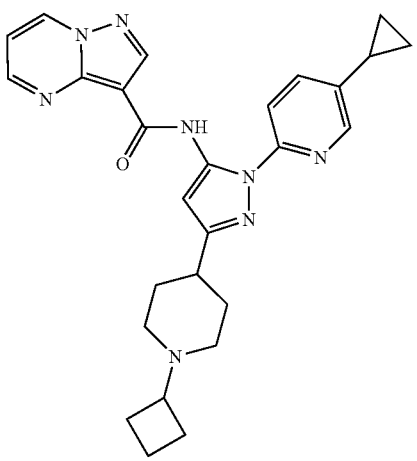

N-(3-(1-cyclobutylpiperidin-4-yl)-1-(5-cyclopropylpyridin-2-yl)-1H-pyrazol-5-yl)pyrazolo[1,5-a]pyrimidine-3-carboxamide This compound was prepared according to the method outlined for Example 36 using N-(1-(5-cyclopropylpyridin-2-yl)-3-(piperidin-4-yl)-1H-pyrazol-5-yl)pyrazolo[1,5-a]pyrimidine-3-carboxamide and cyclobutanone in place of N-(1-(4-methoxyphenyl)-3-(piperidin-4-yl)-1H-pyrazol-5-yl)pyrazolo[1,5-a]pyrimidine-3-carboxamide and formaldehyde, respectively. $^1$H NMR (400 MHz, CD3OD) δ 0.81-0.86 (m, 2H), 1.11-1.16 (m, 2H), 1.92-2.45 (m, 10H), 3.32-3.34 (m, 3H), 3.62-3.74 (m, 3H), 6.98 (s, 1H), 7.29 (d, J=4.0 Hz, 1H), 7.60 (d, J=8.4 Hz, 1H), 7.83 (d, J=8.8 Hz, 1H), 8.46 (s, 1H), 8.69 (s, 1H), 8.99 (s, 1H), 9.13 (d, J=6.8 Hz, 1H).

Example 149

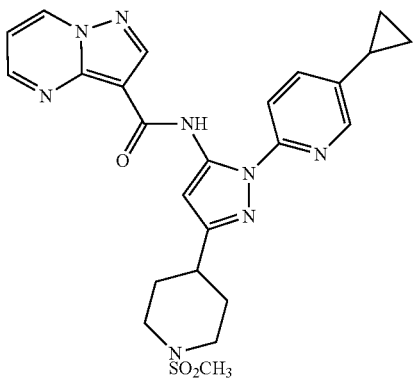

N-(1-(5-cyclopropylpyridin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-cyclopropylpyridin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 8.80 (m, 2H), 8.64 (m, 1H), 8.21 (m, 1H), 7.72 (m, 1H), 7.38 (m, 1H), 7.06 (m, 1H), 6.87 (s, 1H), 3.73 (m, 3H), 2.80 (m, 5H), 2.05 (m, 2H), 1.86 (m, 3H), 0.98 (m, 2H), 0.65 (m, 2H).

Example 150

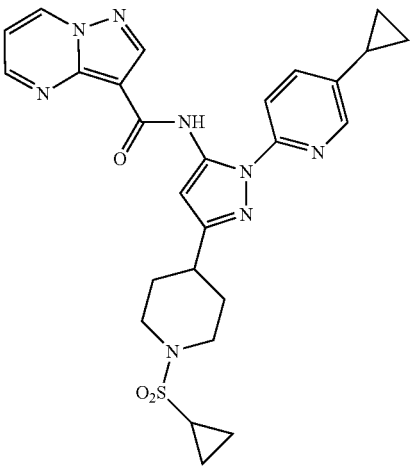

N-(1-(5-cyclopropylpyridin-2-yl)-3-(1-(cyclopropylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-cyclopropylpyridin-2-yl)-3-(piperidin-4-yl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. $^1$H NMR (400 MHz, CDCl$_3$) δ 8.81 (m, 2H), 8.74 (m, 1H), 8.27 (m, 1H), 7.83 (m, 1H), 7.44 (m, 1H), 7.08 (m, 1H), 6.97 (s, 1H), 3.84 (m, 2H), 2.99 (m, 2H), 2.82 (m, 1H), 2.28 (m, 1H), 2.13 (m, 2H), 1.95 (m, 3H), 1.16 (m, 2H), 1.05 (m, 2H), 1.03 (m, 2H), 0.73 (m, 2H).

Example 151

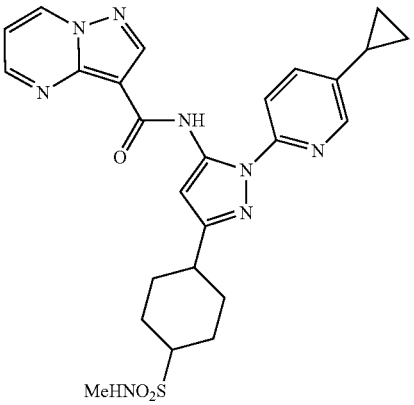

N-(1-(5-cyclopropylpyridin-2-yl)-3-(4-(N-methylsulfamoyl)phenyl)-1H-pyrazol-5-yl)pyrazolo[1,5-a]pyrimidine-3-carboxamide This compound was prepared following the general methods outlined for Example 146 using N-(4-(5-amino-1H-pyrazol-3-yl)phenyl)methanesulfonamide in place of tert-butyl 4-(5-amino-1H-pyrazol-3-yl)piperidine-1-carboxylate. ¹H NMR (400 MHz, DMSO-d6) δ 0.85-1.28 (m, 4H), 2.07-2.17 (m, 1H), 2.45-2.55 (m, 6H), 7.52 (s, 2H), 7.69-8.14 (m, 6H), 8.47-8.66 (m, 2H), 8.80-9.10 (m, 2H), 13.13 (s, 1H).

Example 152

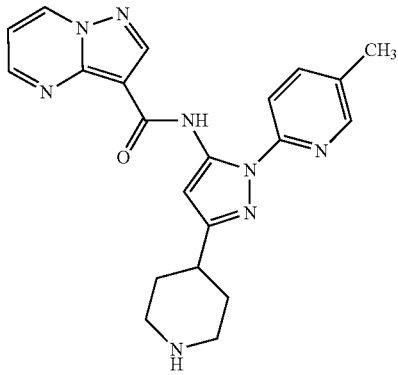

N-(1-(5-methylpyridin-2-yl)-3-(piperidin-4-yl)-1H-pyrazol-5-yl)pyrazolo[1,5-a]pyrimidine-3-carboxamide This yridine was prepared according to the genial methods outlined for Example 146, using 2-bromo-5-methylpyridine in place of 2-bromo-5-cyclopropylpyridine. ¹H NMR (400 MHz, CD₃OD) δ 9.13 (dd, J=7.2, 1.6 Hz, 1H), 9.03 (dd, J=4.4, 2.0 Hz, 1H), 8.70 (s, 1H), 8.50 (m, 1H), 7.88-7.86 (m, 3H), 7.32-7.29 (m, 1H), 6.99 (s, 1H), 3.75-3.72 (m, 4H), 3.68-3.65 (m, 4), 3.57-3.56 (m, 4H).

Example 153

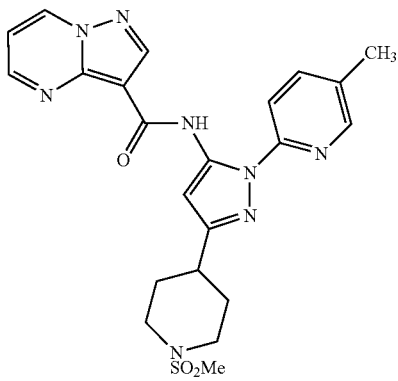

N-(1-(5-methylpyridin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-methylpyridin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (400 MHz, CDCl₃) δ 8.83 (s, 1H), 8.79 (dd, J=2.8, 1.6 Hz, 1H), 8.77 (s, 1H), 8.30 (dd, J=1.6, 0.8 Hz, 1H), 7.91 (m, 1H), 7.66 (m, 1H), 7.09 (m, 1H), 7.03 (s, 1H), 3.86-3.82 (m, 2H), 2.93-2.81 (m, 3H), 2.81 (s, 3H), 2.40 (s, 3H), 2.22-2.11 (m, 2H), 2.02-1.95 (m, 2H).

Example 154

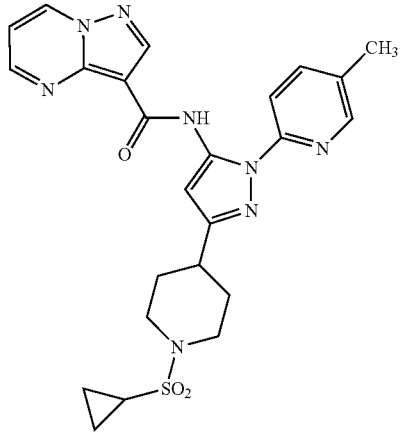

N-(3-(1-(cyclopropylsulfonyl)piperidin-4-yl)-1-(5-methylpyridin-2-yl)-1H-pyrazol-5-yl)pyrazolo[1,5-a]pyrimidine-3-carboxamide This compound was prepared according to the general methods outlined for Example 16, using N-(1-(5-methylpyridin-2-yl)-3-(piperidin-4-yl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-a]pyrimidine-3-carboxamide and methanesulfonyl chloride, respectively. ¹H NMR (400 MHz, CDCl₃) δ 8.80 (d, J=5.6 Hz, 2H), 8.73 (s, 1H), 8.26 (m, 1H), 7.88 (m, 1H), 7.64 (dd, J=8.4, 2 Hz, 1H), 7.06 (m, 1H), 7.00 (s, 1H), 7.03 (s, 1H), 3.86 (m, 2H), 3.01 (td, J=11.6, 2.4 Hz, 2H), 2.90-2.84 (m, 1H), 2.37 (s, 3H), 2.29 (m, 1H), 2.16-2.12 (m, 2H), 1.99-1.88 (m, 2H), 1.18 (m, 2H), 0.98 (m, 2H).

Example 155

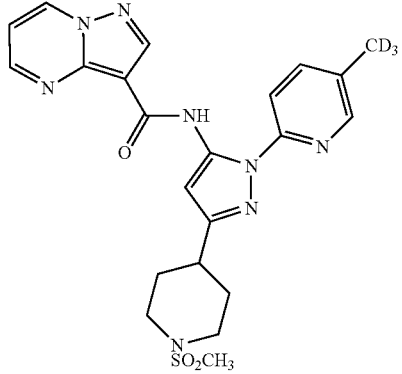

N-(1-(5-trideuteromethylpyridin-2-yl)-3-(1-methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-trideuteromethylpyridin-2-yl)-3-(piperidin-4-yl)-1H-pyrazol-5-yl)pyrazolo[1,5-a]pyrimidine-3-carboxamide in place of N-(1-

(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 8.81 (m, 2H), 8.76 (s, 1H), 8.28 (m, 1H), 8.27 (m, 1H), 7.87 (m, 1H), 7.65 (m, 1H), 7.07 (m, 1H), 7.00 (s, 1H), 3.83 (m, 2H), 2.93-2.83 (m, 3H), 2.81 (s, 3H), 2.16 (m, 2H), 2.02-1.92 (m, 2H).

Example 156

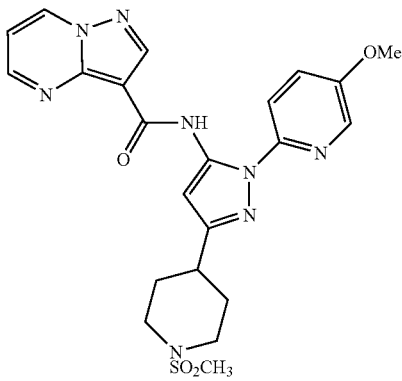

N-(1-(5-methoxypyridin-2-yl)-3-(1-(methylsulfonyl)piperidin-4-yl)-1H-pyrazol-5-yl)pyrazolo[1,5-a]pyrazolo[1,5-a]pyrimidine-3-carboxamide This compound was prepared according to the general methods outlined for Example 16, using N-(1-(5-methoxypyridin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 8.80 (dd, J=6.8, 1.6 Hz, 1H), 8.75 (dd, J=4.0, 1.6 Hz, 1H), 8.67 (s, 1H), 8.09 (m, 1H), 7.80 (m, 1H), 7.36 (m, 1H), 7.06 (m, 1H), 6.88 (s, 1H), 3.85 (s, 3H), 3.76 (m, 2H), 3.51 (s, 1H), 2.82 (m, 2H), 2.75 (s, 3H), 2.07 (m, 2H), 1.92-1.82 (m, 2H).

Example 157

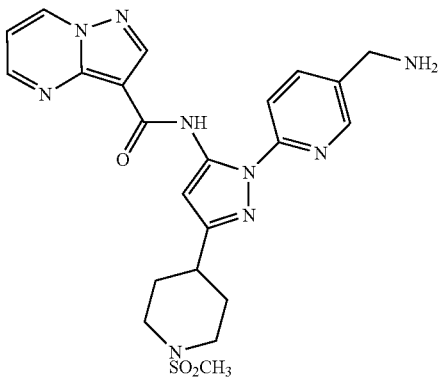

N-(1-(5-(aminomethyl)pyridin-2-yl)-3-(1-(methylsulfonyl)piperidin-4-yl)-1H-pyrazol-5-yl)pyrazolo[1,5-a]pyrimidine-3-carboxamide Synthesis of the intermediates follows below.

This compound was prepared following the general methods outlined for Example 146, using (6-bromopyridin-3-yl)methanamine in place of 2-bromo-5-cyclopropylpyridine.

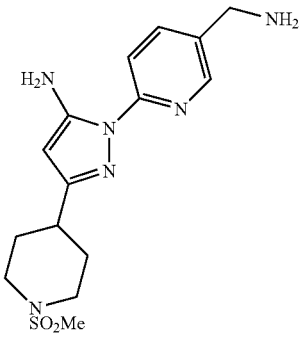

1-(5-(aminomethyl)pyridin-2-yl)-3-(1-(methylsulfonyl)piperidin-4-yl)-1H-pyrazol-5-amine

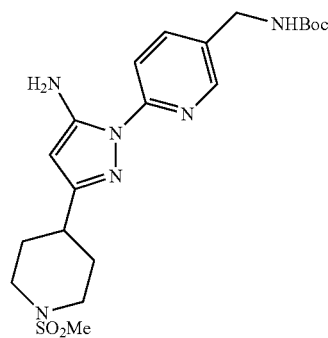

tert-butyl((6-(5-amino-3-(1-(methylsulfonyl)piperidin-4-yl)-1H-pyrazol-1-yl)pyridin-3-yl)methyl)carbamate 1-(5-(Aminomethyl)yridine-2-yl-3-(1-(methylsulfonyl)piperidin-4-yl)-1H-pyrazol-5-amine (45.7 mg, 0.130 mmol), di-tert-butyl dicarbonate (28.5 mg, 0.130 mmol) and DCM (5 ml) were combined and stirred at room temperature overnight. Water (20 mL) was added. The mixture was extracted with DCM (3×20 mL). The combined organic extracts were dried (MgSO$_4$) and concentrated in vacuo. The residue was used without further purification.

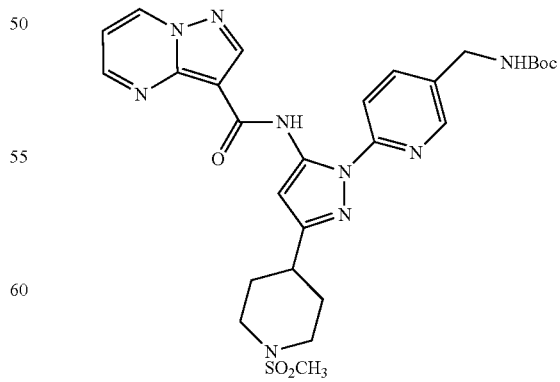

tert-butyl((6-(3-(1-(methyisulfonyl)piperidin-4-yl)-5-(pyrazolo[1,5-a]pyrimidine-3-carboxamido)-1H-pyrazol-1-yl)pyridin-3-yl)methyl)carbamate This compound was prepared following the general methods outlined in Example 7, using tert-butyl ((6-(5-amino-3-(1-(methylsulfonyl)piperidin-4-yl)-1H-pyrazol-1-yl)yridine-3-yl)methyl)carbamate in place of tert-butyl 4-(5-amino-1-(p-tolyl)-1H-pyrazol-3-yl)piperidine-1-carboxylate.

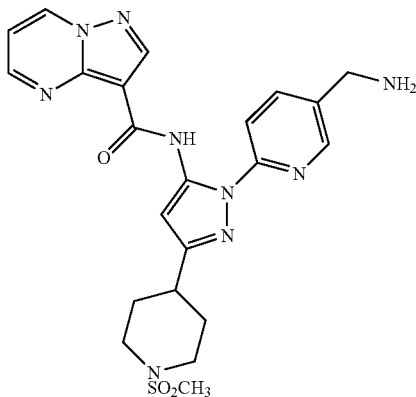

tert-Butyl((6-(3-(1-(methylsulfonyl)piperidin-4-yl)-5-(pyrazolo[1,5-a]pyrimidine-3-carboxamido)-1H-pyrazol-1-yl)yridine-3-yl)methyl)carbamate 0.1 ml of hydrogen chloride solution (4M in dioxane) and DCM (2 ml), MeOH (3 ml) were combined and stirred at room temperature overnight. The mixture was concentrated to give the desired product as white solid.

Example 158

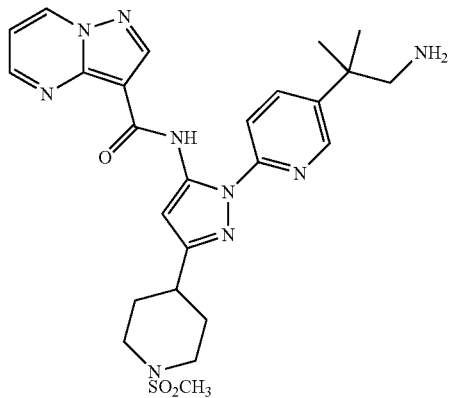

N-(1-(5-(1-amino-2-methylpropan-2-yl)pyridin-2-yl)-3-(1-(methylsulfonyl)piperidin-4-yl)-1H-pyrazol-5-yl)pyrazolo[1,5-a]pyrimidine-3-carboxamide This compound was prepared following the general methods outlined for the synthesis of Example 146, using tert-butyl (2-methyl-2-(6-(3-(1-(methylsulfonyl)piperidin-4-yl)-5-(pyrazolo[1,5-a]pyrimidine-3-carboxamido)-1H-pyrazol-1-yl)yridine-3-yl)propyl)carbamate in place of tert-butyl (2-(6-(3-(1-(methylsulfonyl)piperidin-4-yl)-5-(pyrazolo[1,5-a]pyrimidine-3-carboxamido)-1H-pyrazol-1-yl)yridine-3-yl)ethyl)carbamate.

Example 159

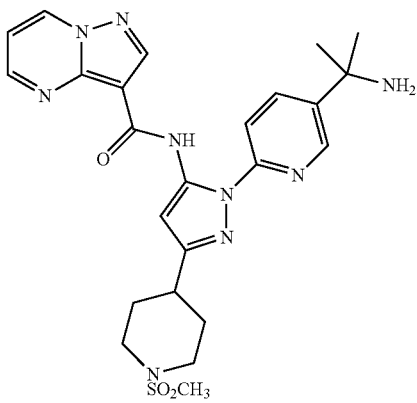

N-(1-(5-(2-aminopropan-2-yl)pyridin-2-yl)-3-(1-(methylsulfonyl)piperidin-4-yl)-1H-pyrazol-5-yl)pyrazolo[1,5-a]pyrimidine-3-carboxamide This compound was prepared following the general methods outlined for the synthesis of Example 146, using tert-butyl (2-(6-(3-(1-(methylsulfonyl)piperidin-4-yl)-5-(pyrazolo[1,5-a]pyrimidine-3-carboxamido)-1H-pyrazol-1-yl)yridine-3-yl)propan-2-yl)carbamate in place of tert-butyl (2-(6-(3-(1-(methylsulfonyl)piperidin-4-yl)-5-(pyrazolo[1,5-a]pyrimidine-3-carboxamido)-1H-pyrazol-1-yl)yridine-3-yl)ethyl)carbamate.

Example 160

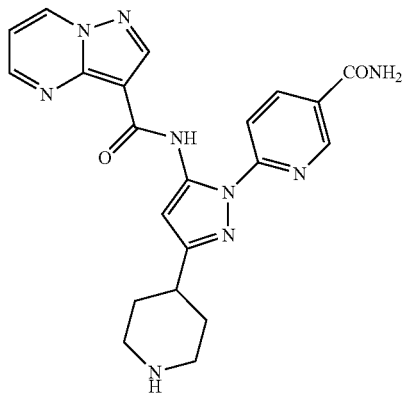

N-(1-(5-carbamoylpyridin-2-yl)-3-(piperidin-4-yl)-1H-pyrazol-5-yl)pyrazolo[1,5-a]pyrimidine-3-carboxamide This compound was prepared according to the general methods outlined for Example 146, using 6-bromonicotinamide in place of 2-bromo-5-cyclopropylpyridine.

Example 161

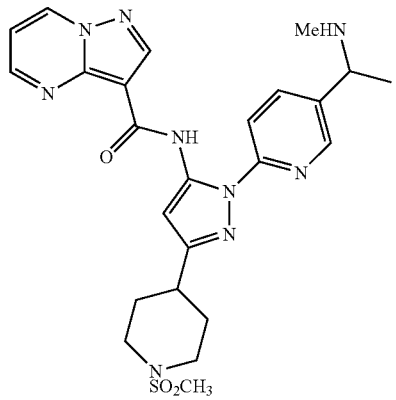

N-(1-(5-(1-(methylamino)ethyl)pyridin-2-yl)-3-(1-(methylsulfonyl)piperidin-4-yl)-1H-pyrazol-5-yl)pyrazolo[1,5-a]pyrimidine-3-carboxamide This compound was prepared following the general methods outlined in Example 36, using N-(1-(4-acetylphenyl)-3-(1-(methylsulfonyl)piperidin-4-yl)-1H-pyrazol-5-yl)pyrazolo[1,5-a]pyrimidine-3-carboxamide and methylamine in place of formaldehyde and N-(3-(piperidin-4-yl)-1-(p-tolyl)-1H-pyrazol-5-yl)pyrazolo[1,5-a]pyrimidine-3-carboxamide, respectively. $^1$H NMR (400 MHz, CDCl$_3$) δ 10.33 (br s, 1H), 8.79 (dd, J=7.2, 1.6 Hz, 1H), 8.73 (s, 1H), 8.32 (dd, J=4.0, 1.6 Hz, 1H), 7.55 (m, 2H), 7.49 (m, 2H), 6.99 (m, 1H), 6.79 (s, 1H), 3.86 (m, 2H), 3.76 (m, 1H), 2.90-2.81, 2.90-2.81 (m, 6H), 2.35 (s, 3H), 2.17 (m, 2H), 2.00-1.90 (m, 2H), 1.41 (d, J=6.4 Hz, 3H).

Example 162

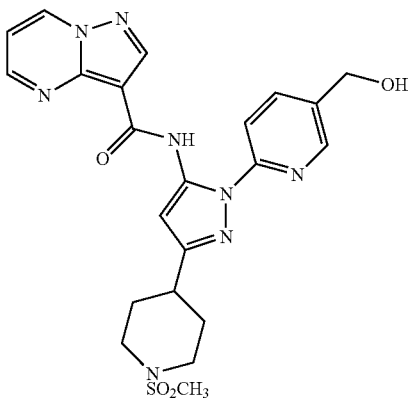

N-(1-(5-(hydroxymethyl)pyridin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-(hydroxymethyl)yridine-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR 400 MHz, (CDCl$_3$) δ 8.78 (m, 2H), 8.72 (s, 1H), 8.43 (m, 1H), 8.90 (m, 1H), 7.80 (m, 1H), 7.05 (m, 1H), 7.03 (s, 1H), 5.38 (m, 1H), 4.77 (s, 2H), 3.85 (m, 2H), 2.87 (m, 2H), 2.83 (s, 3H), 2.23-2.15 (m, 3H), 2.04-1.93 (m, 2H).

Example 163

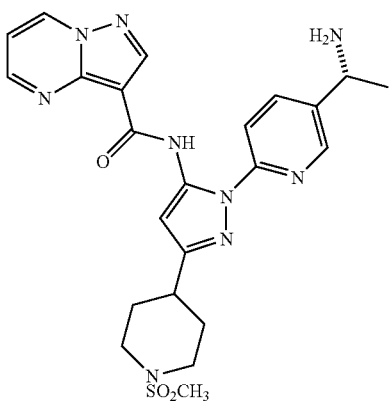

(R)-N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide This compound was prepared following the general methods outlined for Example 146, using R-1-(6-bromopyridin-3-yl)ethanamine in place of 2-bromo-5-cyclopropylpyridine.

Example 164

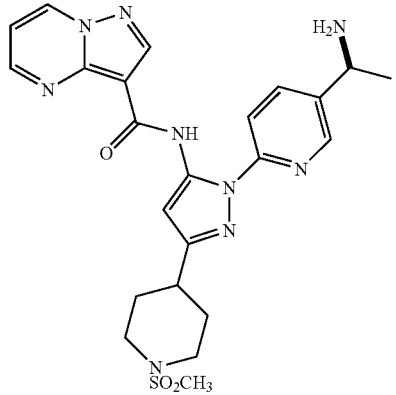

(S)-N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide This compound was prepared following the general methods outlined for Example 146, using S-1-(6-bromopyridin-3-yl)ethanamine in place of 2-bromo-5-cyclopropylpyridine.

Example 165

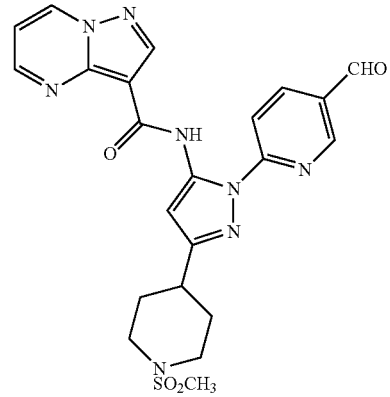

N-(1-(5-formylpyridin-2-yl)-3-(1-(methylsulfonyl)piperidin-4-yl)-1H-pyrazol-5-yl)pyrazolo[1,5-a]pyrimidine-3-carboxamide Synthesis of the intermediate follows below.

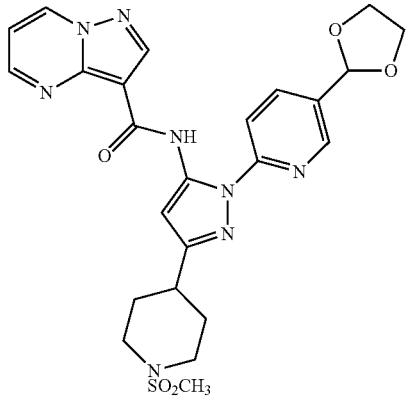

N-(1-(5-(1,3-dioxolan-2-yl)pyridin-2-yl)-3-(1-(methylsulfonyl)piperidin-4-yl)-1H-pyrazol-5-yl)pyrazolo[1,5-a]pyrimidine-3-carboxamide

149

This compound was prepared following the general methods outlined for Example 146, using 2-bromo-5-(1,3-dioxolan-2-yl)pyridine in place of 2-bromo-5-cyclopropylpyridine.

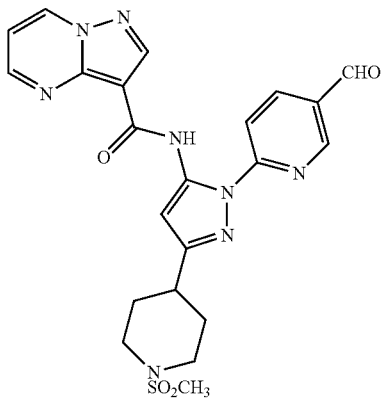

This compound was prepared following the general methods outline for Example 146, using N-(1-(5-(1,3-dioxolan-2-yl)yridine-2-yl)-3-(1-(methylsulfonyl)piperidin-4-yl)-1H-pyrazol-5-yl)pyrazolo[1,5-a]pyrimidine-3-carboxamide in place of tert-butyl 4-(1-(4-(1-(tert-butoxy)vinyl)phenyl)-5-(pyrazolo[1,5-a]pyrimidine-3-carboxamido)-1H-pyrazol-3-yl)piperidine-1-carboxylate. ¹H NMR (400 MHz, CDCl₃) δ 10.11 (s, 1H), 8.98 (m, 1H), 8.88 (m, 2H), 8.01 (s, 1H), 8.30 (m, 1H), 8.18 (m, 1H), 7.14 (m, 1H), 7.10 (s, 1H), 3.86 (m, 2H), 2.90 (m, 3H), 2.83 (s, 3H), 2.16 (m, 2H), 2.00 (m, 2H).

Example 166

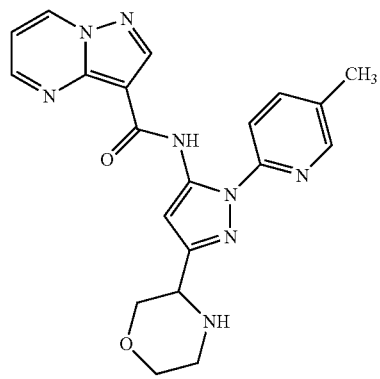

N-(1-(5-methylpyridin-2-yl)-3-(morpholin-3-yl)-1H-pyrazol-5-yl)pyrazolo[1,5-a]pyrimidine-3-carboxamide This compound was prepared following the general methods outline for Example 146 using tert-butyl 3-(5-amino-1H-pyrazol-4-yl)morpholine-4-carboxylate in place of tert-butyl 4-(5-amino-1H-pyrazol-4-yl)piperidine-1-carboxylate.

150

Example 167

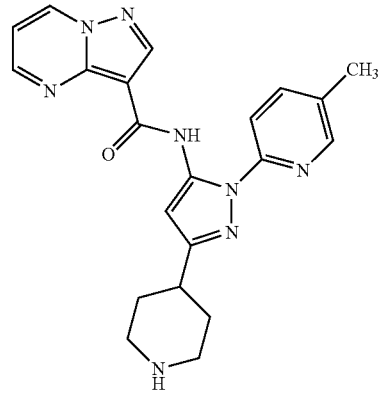

N-(1-(6-methylpyridin-3-yl)-3-(piperidin-4-yl)-1H-pyrazol-5-yl)pyrazolo[1,5-a]pyrimidine-3-carboxamide This compound was prepared according to the general methods outlined for Example 146, using 3-bromo-6-methylpyridine in place of 2-bromo-5-cyclopropylpyridine. ¹H NMR (400 MHz, CDCl₃) δ 9.25 (dd, J=7.2, 1.6 Hz, 1H), 9.15 (s, 1H), 8.99 (dd, J=4.4, 2.0 Hz, 1H), 8.44 (m, 1H), 7.80 (m, 1H), 7.30 (m, 1H), 7.18 (m, 1H), 6.71 (s, 1H), 3.76-3.70 (m, 2H), 3.66-3.58 (m, 3H), 3.42-3.37 (m, 1H), 2.61 (s, 3H), 1.39-1.34 (m, 1H), 0.86-0.77 (m, 2H).

Example 168

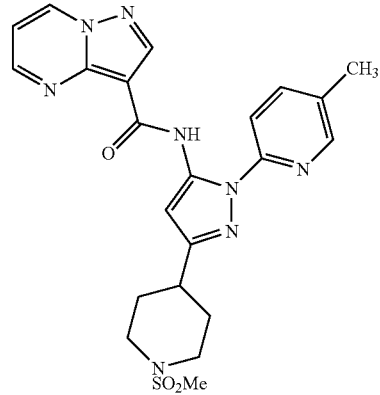

N-(1-(6-methylpyridin-3-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(6-methylpyridin-3-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (400 MHz, CDCl₃) δ 10.33 (br s, 1H), 8.79 (m, 2H), 8.70 (s, 1H), 8.43 (m, 1H), 7.83 (m, 1H), 7.32 (m, 1H), 7.01 (m, 1H), 6.73 (s, 1H), 3.87-3.83 (m, 2H), 2.89-2.81 (m, 3H), 2.80 (s, 3H), 2.66 (s, 3H), 2.17-2.13 (m, 2H), 1.96-1.91 (m, 2H).

Example 169

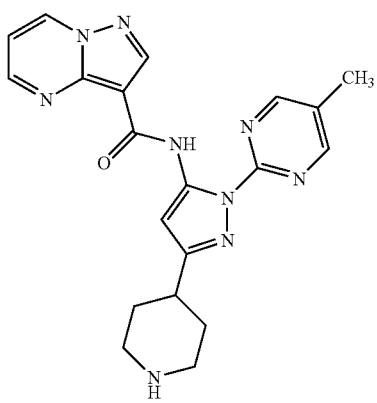

N-(1-(5-methylpyrimidin-2-yl)-3-(piperidin-4-yl)-1H-pyrazol-5-yl)pyrazolo[1,5-a]pyrimidine-3-carboxamide This yridine was prepared according to the general methods outlined for Example 146, using 2-bromo-5-methylpyrimidine in place of 2-bromo-5-cyclopropylpyridine.

Example 170

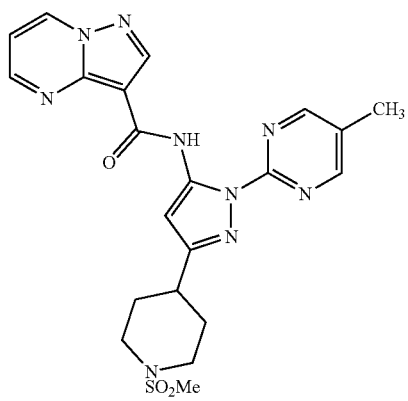

N-(1-(5-methylpyrimidin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-methylpyrimidin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide.

Example 171

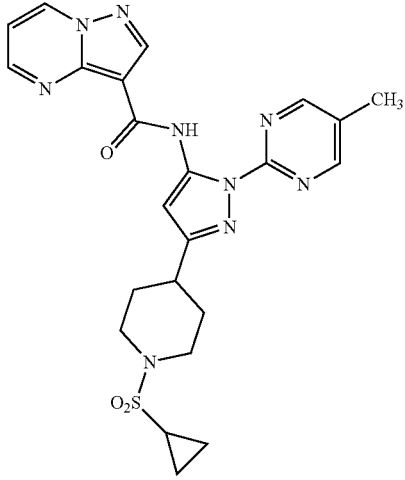

N-(3-(1-(cyclopropylsulfonyl)piperdin-4-yl)-1-(5-methylpyrimidin-2-yl)-1H-pyrazol-5-yl)pyrazolo[1,5-a]pyrimidine-3-carboxamide This compound was prepared according to the general methods outlined for Example 16, using N-(1-(5-methylpyrimidin-2-yl)-3-(piperidin-4-yl)-1H-pyrazol-5-yl)pyrazolo[1,5-a]pyrimidine-3-carboxamide and cyclopropylsulfonyl chloride in place of N-(1-(4-methoxyphenyl)-3-(piperidin-4-yl)-1H-pyrazol-5-yl)pyrazolo[1,5-a]pyrimidine-3-carboxamide and methanseulfonyl chloride, respectively. $^1$H NMR (400 MHz, CDCl$_3$) δ 8.83-8.74 (m, 3H), 8.62 (s, 2H), 7.07 (m, 2H), 3.89 (d, J=12.4 Hz, 2H), 2.98-2.90 (m, 3H), 2.38 (s, 3H), 2.28 (m, 1H), 2.13 (m, 2H), 1.92 (m, 2H), 1.17 (m, 2H), 0.99 (m, 2H).

Example 172

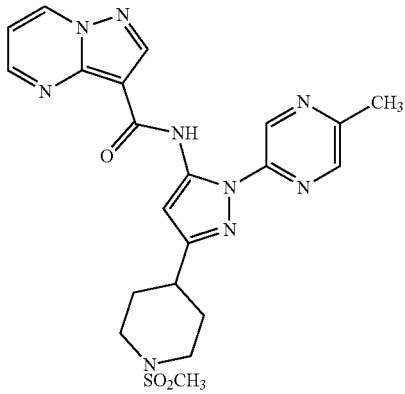

N-(1-(5-methylpyrazin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5-methylpyrazin-2-yl)-3-(piperidin-4-yl)-1H-pyrazol-5-yl)pyrazolo[1,5-a]pyrimidine-3-carboxamide in place of N-(1-(4- methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 9.12 (m, 1H), 8.83 (m, 2H), 8.70 (m, 1H), 8.24 (m, 1H), 7.11 (m, 1H), 6.95 (m, 1H), 3.79 (m, 2H), 2.93-2.77 (m, 6H), 2.58 (s, 3H), 2.12 (m, 2H), 1.90 (m, 2H).

Example 173

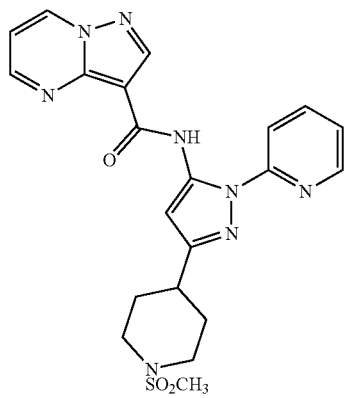

N-3-(1-(methylsulfonyl)piperidin-4-yl)-1-(pyridin-2-yl)1H-pyrazol-5-yl)pyrazolo[1,5-a]pyrimidine-3-carboxamide This compound was prepared according to the general methods outlined for Example 16, using N-(3-(piperidin-4-yl)-1-(pyridin-2-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide.

Example 174

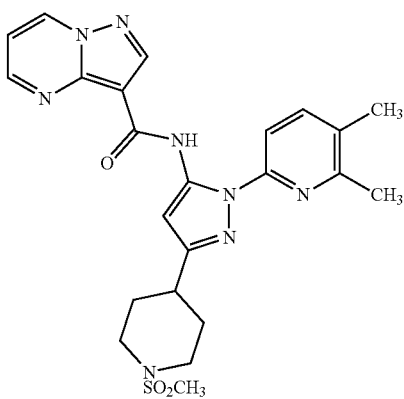

N-(1-(5,6-dimethylpyridin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(5,6-dimethylpyridin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 12.29 (br, s, 1H), 8.90-8.69 (m, 3H), 7.75-7.67 (m, 1H), 7.60-7.51 (m, 1H), 7.09-7.02 (m, 1H), 6.98-6.96 (m, 1H), 3.88-3.76 (m, 2H), 2.96-2.74 (m, 6H), 2.56 (s, 3H), 2.29 (s, 3H), 2.20-2.09 (m, 2H), 2.05-1.89 (m, 2H).

Example 175

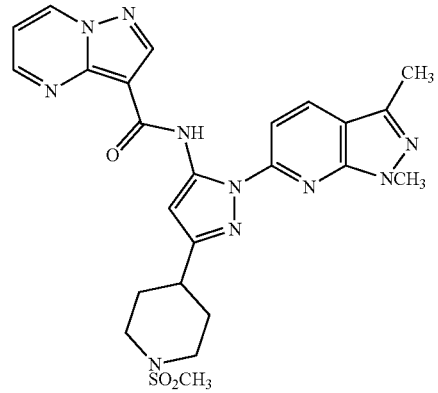

N-(1-(1,3-dimethyl-1H-pyrazolo[3,4-b]pyridin-6-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using N-(1-(1,3-dimethyl-1H-pyrazolo[3,4-b]yridin-6-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 11.95 (br s, 1H), 8.81 (dd, J=7.2, 1.6 Hz, 1H), 8.75 (s, 1H), 8.32 (dd, J=4.0, 1.6 Hz, 1H), 8.09 (m, 1H), 7.73 (m, 1H), 7.00 (m, 2H), 3.82 (m, 2H), 3.76 (s, 3H), 2.87 (m, 3H), 2.79 (s, 3H), 2.56 (s, 3H), 2.15 (m, 2H), 1.94 (m, 2H).

Example 176

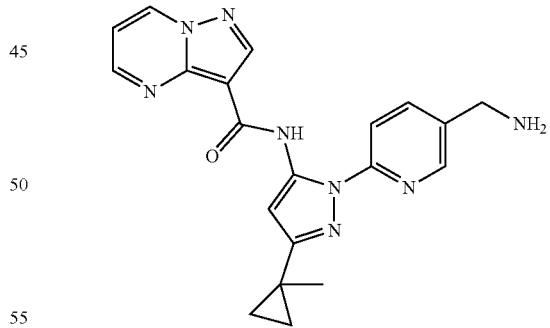

N-(1-(5-(aminomethyl)pyridin-2-yl)-3-(1-methylcyclopropyl)-1H-pyrazol-5-yl)pyrazolo[1,5-a]pyrimidine-3-carboxamide This compound was prepared according to the general methods outlined for Example 157, using 1-(4-(aminomethyl)phenyl)-3-(1-methylcyclopropyl)-1H-pyrazol-5-amine in place of 1-(4-(aminomethyl)phenyl)-3-(1-(methylsulfonyl)piperidin-4-yl)-1H-pyrazol-5-amine. $^1$H NMR (400 MHz, CD$_3$OD) δ 9.14 (m, 1H), 9.07 (m, 1H), 8.72 (m, 1H), 8.69 (s, 1H), 8.03 (m, 2H), 7.29 (m, 1H), 6.85 (s, 1H), 4.28 (br s, 2H), 1.51 (s, 3H), 1.07 (m, 2H), 0.82 (m, 2H).

Example 177

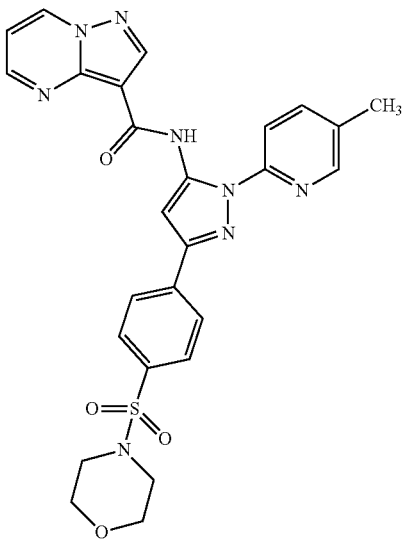

N-(1-(5-methylpyridin-2-yl)-3-(4-(morpholinosulfonyl)phenyl)-1H-pyrazol-5-yl)pyrazolo[1,5-a]pyrimidine-3-carboxamide This compound was prepared according to the general methods outlined for Example 134, using 1-(5-methylpyridin-2-yl)-5-(pyrazolo[1,5-a]pyrimidine-3-carboxamido)-1H-pyrazol-3-yl trifluoromethanesulfonate and 4-((4-(4,4,5,5-tetramethyl-1,3,2-dioxaborolan-2-yl)phenyl)sulfonyl)morpholine and in place of 5-(pyrazolo[1,5a]-pyrimidine-3-carboxamido)-1-(p-tolyl)-1H-pyrazol-3-yl trifluoromethanesulfonate and 4-(methylsulfonyl)phenyl boronic acid, respectively.

Example 178

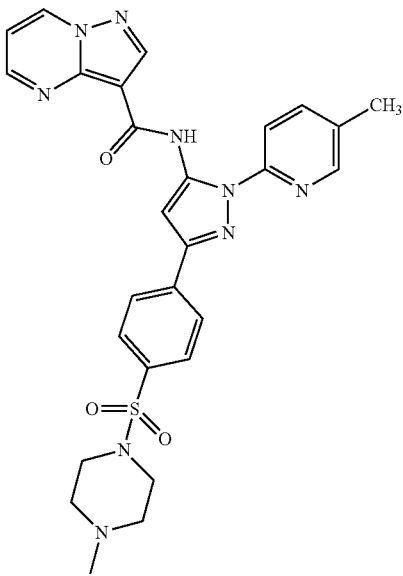

N-(3-(4-((4-methylpiperazin-1-yl)sulfonyl)phenyl)-1-(5-methylpyridin-2-yl)-1H-pyrazol-5-yl)pyrazolo[1,5-a]pyrimidine-3-carboxamide This compound was prepared according to the general methods outlined for Example 134, using 1-(5-methylpyridin-2-yl)-5-(pyrazolo pyrimidine-3-carboxamido)-1H-pyrazol-3-yl trifluoromethanesulfonate and 1-methyl-4-((4-(4,4,5,5-tetramethyl-1,3,2-dioxaborolan-2-yl)phenyl)sulfonyl)piperazine and in place of 5-(pyrazolo[1,5-a]pyrimidine-3-carboxamido)-1-(p-tolyl)-1H-pyrazol-3-yl trifluoromethanesulfonate and 4-(methylsulfonyl)phenyl boronic acid, respectively.

Example 179

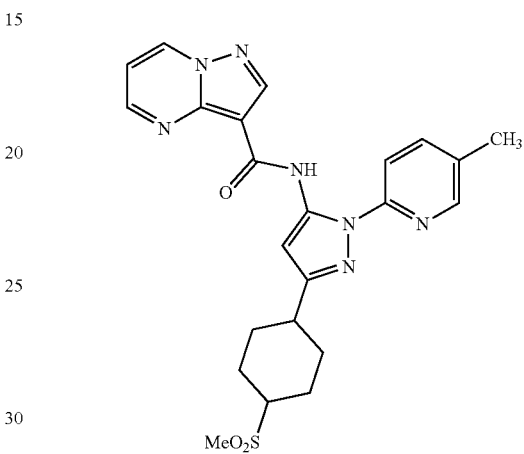

N-(1-(5-methylpyridin-2-yl)-3-(4-(methylsulfonyl)phenyl)-1H-pyrazol-5-yl)pyrazolo[1,5-a]pyrimidine-3-carboxamide This compound was prepared according to the general methods outlined for Example 134, using 1-(5-methylpyridin-2-yl)-5-(pyrazolo[1,5-a]pyrimidine-3-carboxamido)-1H-pyrazol-3-yl trifluoromethanesulfonate in place of 5-(pyrazolo[1,5-a]pyrimidine-3-carboxamido)-1-(p-tolyl)-1H-pyrazol-3-yl trifluoromethanesulfonate. $^1$H NMR (400 MHz, CDCl$_3$) δ 8.86-8.83 (m, 2H), 8.81 (s, 1H), 8.35 (m, 1H), 8.15 (m, 2H), 8.09 (d, J=8.4 Hz, 1H), 7.99 (m, 2H), 7.73 (dd, J=8.4, 2.4 Hz, 1H), 7.59 (s, 1H), 7.10 (dd, J=6.8, 4.0 Hz, 1H), 3.08 (s, 3H), 2.43 (s, 3H).

Example 180

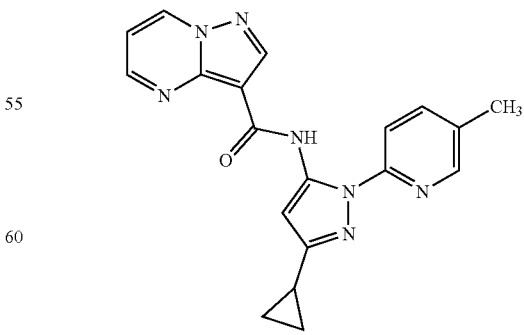

N-(3-cyclopropyl-1-(5-methylpyridin-2-yl)-1H-pyrazol-5-yl)pyrazolo[1,5-a]pyrimidine-3-carboxamide This compound was prepared following the general methods outlined for Example 146, using 3-cyclopropyl-3-oxopropanenitrile in place of tert-butyl 4-(2-cyanoacetyl)piperidine-1-carboxylate. $^1$H NMR (400 MHz, CDCl$_3$) δ 8.77 (m, 2H), 8.72 (s, 1H), 8.21 (m, 1H), 7.85 (m, 1H), 7.60 (m, 1H), 7.03 (m, 1H), 6.77 (s, 1H), 3.22 (s, 3H), 2.02 (m, 1H), 0.97 (m, 2H), 0.87 (m, 2H).

Example 181

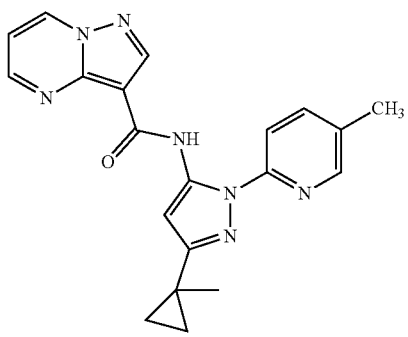

N-(3-(1-methylcyclopropyl)-1-(5-methylpyridin-2-yl)-1H-pyrazol-5-yl)pyrazolo[1,5-a]pyrimidine-3-carboxamide This compound was prepared following the general methods outlined for Example 146, using 3-(1-methylcyclopropyl)-3-oxopropanenitrile in place of tert-butyl 4-(2-cyanoacetyl)piperidine-1-carboxylate. $^1$H NMR (400 MHz, CDCl$_3$) δ 8.70 (m, 2H), 8.65 (s, 1H), 8.13 (m, 1H), 7.78 (m, 1H), 7.52 (m, 1H), 6.97 (m, 1H), 6.85 (s, 1H), 5.28 (s, 1H), 2.32 (s, 3H), 1.51 (s, 3H), 1.08 (m, 2H), 0.77 (m, 2H).

Example 182

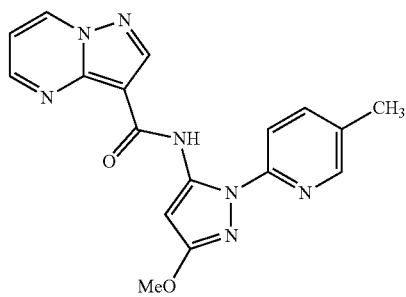

N-(3-methoxy-1-(5-methylpyridin-2-yl)-1H-pyrazol-5-yl)pyrazolo[1,5-a]pyrimidine-3-carboxamide This compound was prepared following the general methods outlined for Example 146, using 4-methoxy-1H-pyrazol-5-amine in place of tert-butyl 4-(2-cyanoacetyl)piperidine-1-carboxylate. $^1$H NMR (400 MHz, CDCl$_3$) δ 8.78 (m, 1H), 8.73 (s, 1H), 8.19 (m, 1H), 7.73 (m, 1H), 7.58 (m, 1H), 7.05 (m, 1H), 6.67 (s, 1H), 3.98 (s, 3H), 2.35 (s, 3H).

Example 183

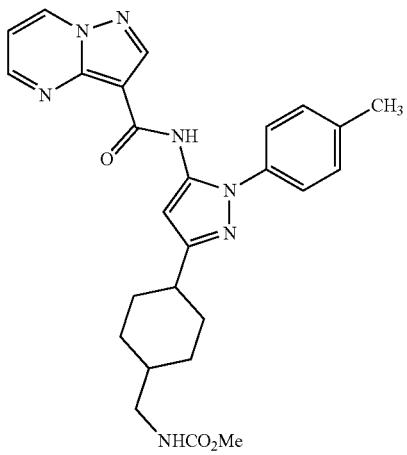

methyl ((4-(5-(pyrazolo[1,5-a]pyrimidine-3-carboxamido)-1-(p-tolyl)-1H-pyrazol-3-yl)cyclohexyl)methyl)carbamate Synthesis of the intermediates is described below.

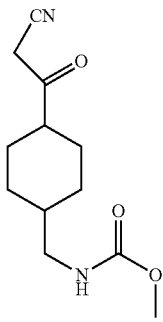

methyl ((4-(2-cyanoacetyl)cyclohexyl)methyl)carbamate

A mixture of 4-(((methoxycarbonyl)amino)methyl)cyclohexanecarboxylic acid (2 g, 7.77 mmol), potassium carbonate (1.61 g, 11.66 mmol) and DMF was stirred at rt for 10 min. Iodomethane (0.968 ml, 15.54 mmol) was added and the mixture was stirred at rt for overnight. Poured into EtOAc (200 mL) and washed with water (3×100 mL). Organic layer dried (Na$_2$SO$_4$), filtered and concentrated. Acetonitrile (1.2 ml, 22.98 mmol), sodium hydride (0.88 g) and THF (40 ml) were added and the mixture was heated at 80° C. for 4 h. Cooled to rt and added 1N HCl slowly. Poured into EtOAC (200 mL), washed with water. Organic layer dried (Na$_2$SO$_4$), filtered and concentrated to give the title compound that was used without further purification.

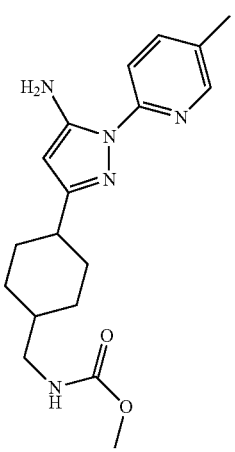

methyl ((4-(5-amino-1-(5-methylpyridin-2-yl)-1H-pyrazol-3-yl)cyclohexyl)methyl)carbamate This compound was prepared following the general methods outlined for Example 7 using methyl 4-(((methoxycarbonyl)amino)methyl)cyclohexanecarboxylate and 2-hydrazinyl-5-methylpyridine in place of 1-tert-butyl 4-ethyl piperidine-1,4-dicarboxylate and -4-methylphenylhydrazine hydrochloride, respectively.

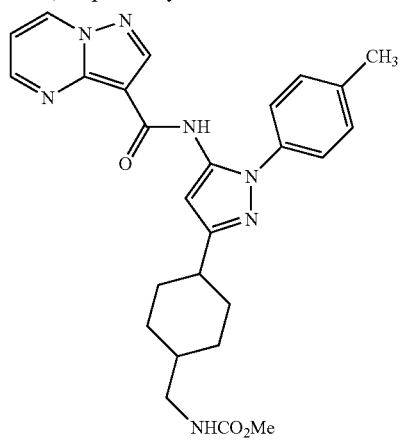

This compound was prepared following the general methods outlined for Example 7, using methyl ((4-(5-amino-1-(5-methylpyridin-2-yl)-1H-pyrazol-3-yl)cyclohexyl)methyl)carbamate in place of tert-butyl 4-(5-amino-1-(p-tolyl)-1H-pyrazol-3-yl)piperidine-1-carboxylate.

Example 184

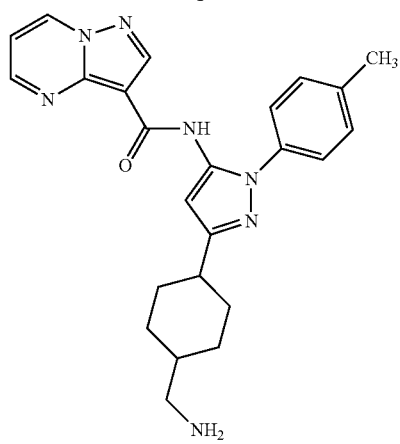

N-(3-(4-(aminomethyl)cyclohexyl)-1-(p-toyl)-1H-pyrazol-5-yl)pyrazolo[1,5-a]pyrimidine-3-carboxamide Synthesis of the intermediates is described below.

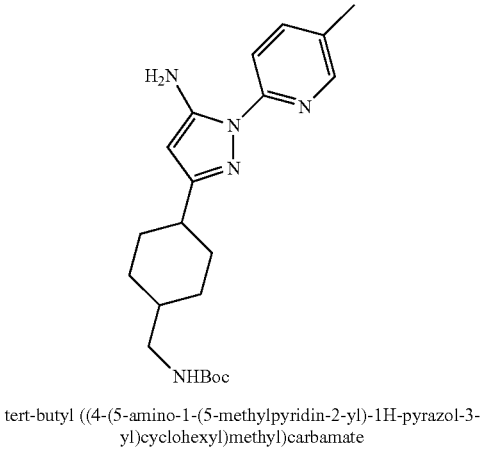 [SMILES: Cc1ccc(-n2nc(C3CCC(CNC(=O)OC(C)(C)C)CC3)cc2N)nc1]

tert-butyl ((4-(5-amino-1-(5-methylpyridin-2-yl)-1H-pyrazol-3-yl)cyclohexyl)methyl)carbamate A mixture of ((4-(5-amino-1-(5-methylpyridin-2-yl)-1H-pyrazol-3-yl)cyclohexyl)methyl)carbamate (0.6 g, 1.747 mmol), aq. 2M sodium hydroxide (4.37 mL) in 1,4-dioxane heated at 80° C. for 72 h. Cooled to rt and di-tert-butylcarbonate (0.4 g) was added and stirred at rt for overnight. Poured into EtOAc (200 mL), washed with sat. NaHCO$_3$ (100 mL) and dried. Purified on silica using 5-100% EtOAc/hexane to give the title compound.

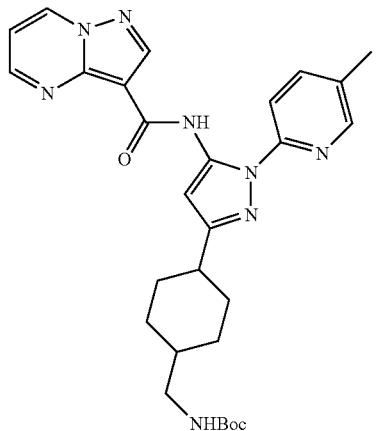

tert-butyl ((4-(1-(5-methylpyridin-2-yl)-5-(pyrazolo[1,5-a]pyrimidine-3-carboxamido)-1H-pyrazol-3-yl)cyclohexyl)methyl)carbamate A mixture of tert-butyl ((4-(5-amino-1-(5-methylpyridin-2-yl)-1H-pyrazol-3-yl)cyclohexyl)methyl)carbamate (300 mg, 0.778 mmol), pyrazolo[1,5-a]pyrimidine-3-carbonyl chloride (141 mg, 0.778 mmol), DIEA (0.14 mL, 0.689 mmol) in DCM (5 mL) was stirred at room temperature for 72 h. Taken up in EtOAc and washed with water. Concentrated, taken up in CH$_2$Cl$_2$ and added ether. Filtered the resulting solid, washed with ether and dried to the title compound.

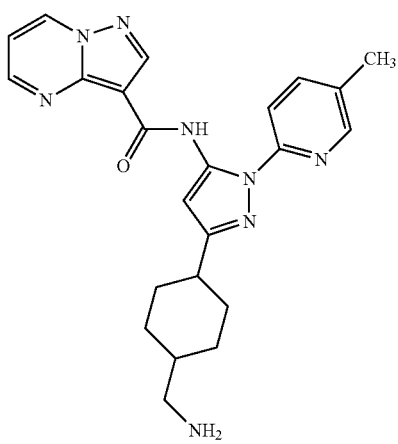 [SMILES: Cc1ccc(-n2nc(C3CCC(CN)CC3)cc2NC(=O)c2cnn3cccnc23)nc1]

A mixture of tert-butyl ((4-(1-(5-methylpyridin-2-yl)-5-(pyrazolo[1,5-a]pyrimidine-3-carboxamido)-1H-pyrazol-3-yl)cyclohexyl)methyl)carbamate (180 mg, 0.467 mmol), 4M HCl in dioxane (1.2 ml) in DCM (10 mL) was stirred at rt for 18 h. Added ether and filtered to give the title compound.

Example 185

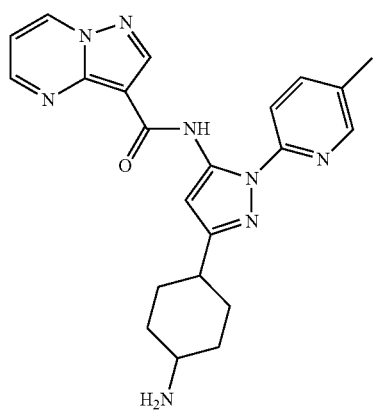

N-(3-(4-aminocyclohexyl)-1-(5-methylpyridin-2-yl)-1H-pyrazol-5-yl)pyrazolo[1,5-a]pyrimidine-3-carboxamide Synthesis of the intermediate is described below.

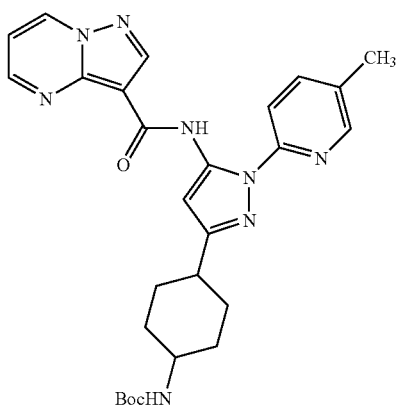 [SMILES: Cc1ccc(-n2nc(C3CCC(NC(=O)OC(C)(C)C)CC3)cc2NC(=O)c2cnn3cccnc23)nc1]

This compound was prepared following the general methods outlined for Example 146 using tert-butyl (4-(2-cyanoacetyl)cyclohexyl)carbamate in place of 4-(2-cyanoacetyl)piperidine-1-carboxylate.

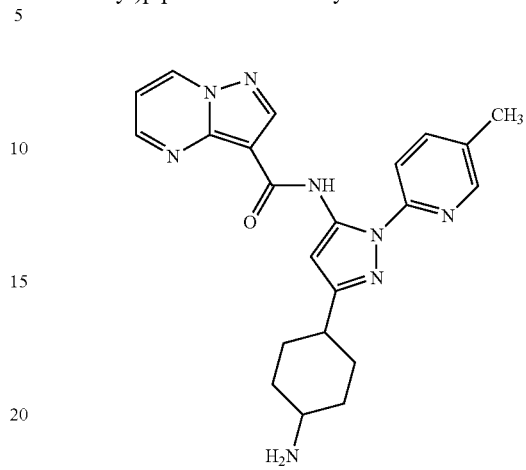

A mixture of tert-butyl (4-(1-(5-methylpyridin-2-yl)-5-(pyrazolo[1,5-a]pyrimidine-3-carboxamido)-1H-pyrazol-3-yl)cyclohexyl)carbamate (300 mg, 0.808 mmol), 4M HCl in dioxane (3 ml) in DCM (10 mL) was stirred at rt for 18 h. Purified on silica using 5-20% MeOH(NH$_3$)/DCM to give the title compound.

Example 186

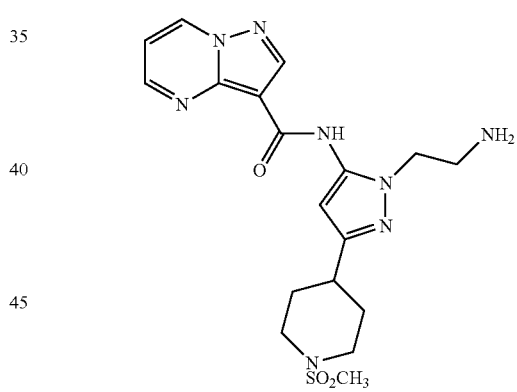

N-(1-(2-aminoethyl)-3-(1-(methylsulfonyl)piperidin-4-yl)-1H-pyrazol-5-yl)pyrazolo[1,5-a]pyrimidine-3-carboxamide Synthesis of the intermediate follows below.

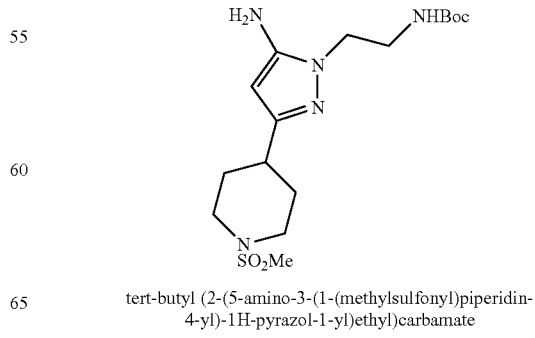

tert-butyl (2-(5-amino-3-(1-(methylsulfonyl)piperidin-4-yl)-1H-pyrazol-1-yl)ethyl)carbamate A mixture of 3-(1-(methylsulfonyl)piperidin-4-yl)-1H-pyrazol-5-amine (300 mg, 1.23 mmol), tert-butyl N-(2-bromoethyl)carbamate (330 mg, 1.47 mmol), Cs₂CO₃ (2.00 g, 6.14 mmol), sodium iodide (46 mg, 0.31 mmol), and DMF (15 mL) was stirred at rt for 16 h, then at 50° C. for 4 h. The mixture was concentrated in vacuo. Water was added and the mixture was extracted with EtOAc. The combined organic extracts were dried (MgSO₄) and concentrated in vacuo. The residue was purified by silica gel chromatography, eluting with a solvent gradient of 0 to 5% MeOH in CH₂Cl₂ to give the title compound.

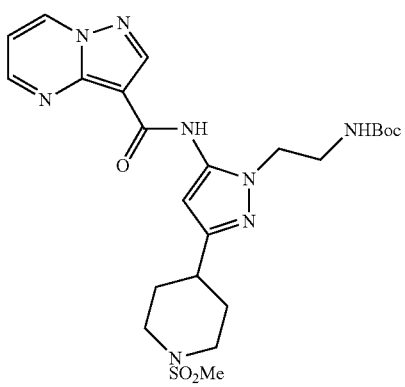

tert-butyl (2-(3-(1-(methylsulfonyl)piperidin-4-yl)-5-(pyrazol[1,5-a]pyrimidine-3-carboxamido)-1H-pyrazol-1-yl)ethyl)carbamate This compound was prepared following the general methods outlined in Example 7, using tert-butyl (2-(5-amino-3-(1-(methylsulfonyl)piperidin-4-yl)-1H-pyrazol-1-yl)ethyl)carbamate in place of tert-butyl 4-(5-amino-1-(p-tolyl)-1H-pyrazol-3-yl)piperidine-1-carboxylate.

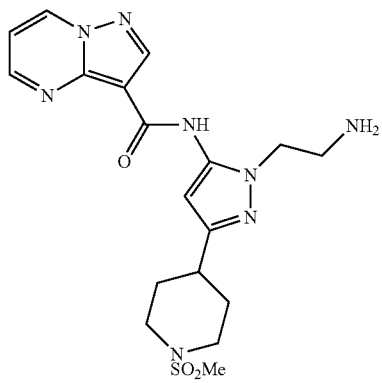

This compound was prepared following the general methods outlined in Example 146, using tert-butyl (2-(3-(1-(methylsulfonyl)piperidin-4-yl)-5-(pyrazolo[1,5-a]pyrimidine-3-carboxamido)-1H-pyrazol-1-yl)ethyl)carbamate in place of tert-Butyl 4-(1-(5-cyclopropyridin-2-yl)-5-(pyrazolo[1,5-a]pyrimidine-3-carboxamido)-1H-pyrazol-3-yl)piperidine-1-carboxylate.

Example 187

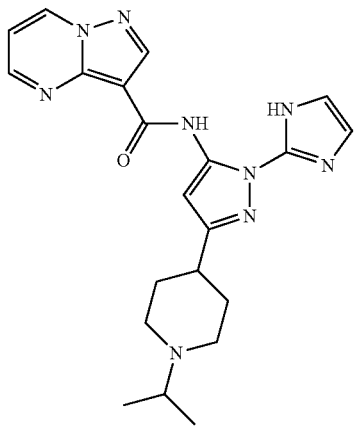

N-(1-(1H-imidazol-2-yl)-3-(1-isopropylpiperidin-4-yl)-1H-pyrazol-5-yl)pyrazolo[1,5-a]pyrimidine-3-carboxamide Synthesis of the intermediate is described below.

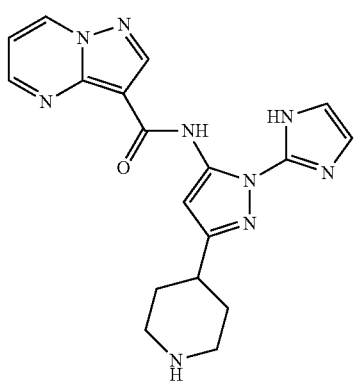

N-(1-(1H-imidazol-2-yl)-3-(piperidin-4-yl)-1H-pyrazol-5-yl)pyrazolo[1,5-a]pyrimidine-3-carboxamide This compound was prepared following the general methods outlined in Example 7, using 2-hydrazinyl-1H-imidazole in place of 4-methylphenyl hydrazine hydrochloride.

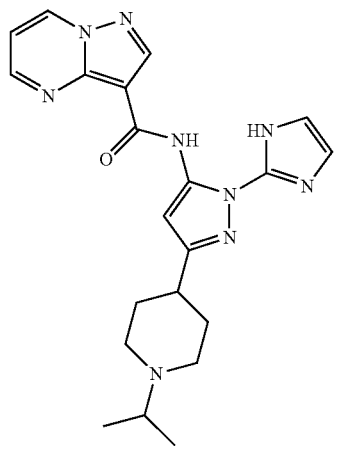

N-(1-(1H-imidazol-2-yl)-3-(1-isopropylpiperidin-4-yl)-1H-pyrazol-5-yl)pyrazolo[1,5-a]pyrimidine-3-carboxamide This compound was prepared according to the general method outlined for Example 36, using acetone and N-(1-(1H-imidazol-2-yl)-3-(piperidin-4-yl)-1H-pyrazol-5-yl)pyrazolo[1,5-a]pyrimidine-3-carboxamide in place of formaldehyde and N-(3-(piperidin-4-yl)-1-(p-tolyl)-1H-pyrazol-5-yl)pyrazolo[1,5-a]pyrimidine-3-carboxamide, respectively. $^1$H NMR (400 MHz, CDCl$_3$) δ 8.79 (m, 2H), 7.05 (m, 1H), 6.96 (s, 2H), 6.87 (m, 1H), 3.13 (m, 2H), 2.99 (m, 1H), 270 (m, 1H), 2.46 (m, 2H), 2.25 (m, 2H), 2.04 (m, 1H), 1.27 (t, J=7.2 Hz, 1H), 1.16 (d, J=6.4 Hz, 6H).

Example 188

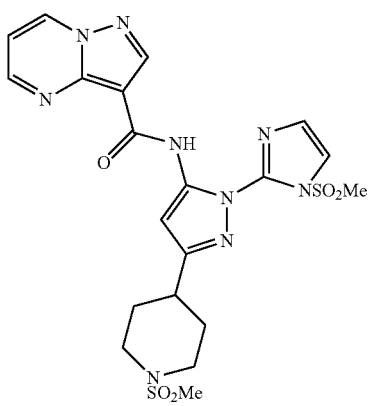

N-(1-(1-(methylsulfonyl)-1H-imidazol-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined in Example 16, using N-(1-(1H-imidazol-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-2-carboxamide. $^1$H NMR (400 MHz, CDCl$_3$) δ 11.12 (br s, 1H), 8.80 (dd, J=7.2, 1.6 Hz, 1H), 8.73 (s, 1H), 8.60 (dd, J=4.0, 1.6 Hz, 1H), 7.49 (m, 1H), 7.15 (m, 1H), 7.04 (m, 1H), 6.88 (s, 1H), 3.88 (s, 3H), 3.81 (m, 2H), 2.90 (m, 2H), 2.81 (s, 3H), 2.19-2.14 (m, 2H), 2.00-1.93 (m, 3H).

Example 189

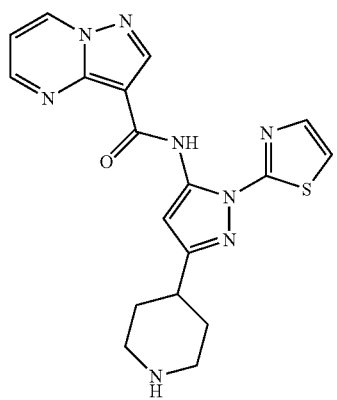

N-(3-(piperidin-4-yl)-1-(thiazol-2-yl)-1H-pyrazol-5-yl)pyrazolo[1,5-a]pyrimidine-3-carboxamide This compound was prepared following the general methods outlined in Example 7, using 2-hydrazinylthiazole in place of 4-methylphenyl hydrazine hydrochloride. $^1$H NMR (400 MHz, CD$_3$OD) δ 9.14 (dd, J=7.2, 1.6 Hz, 1H), 8.97 (dd, J=4.0, 1.6 Hz, 1H), 8.71 (s, 1H), 7.81 (m, 1H), 7.37 (m, 1H), 7.29 (m, 1H), 6.97 (s, 1H), 3.51 (m, 1H), 3.48 (m, 1H), 3.12 (m, 3H), 2.28 (m, 2H), 2.03 (m, 2H).

Example 190

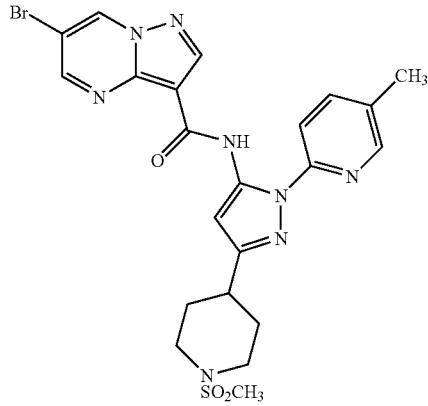

6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide This compound was prepared according to the general methods outlined for Example 16, using 6-bromo-N-(1-(5-methylpyridin-2-yl)-3-(piperidin-4-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. $^1$H NMR (400 MHz, CDCl$_3$) δ 8.98 (d, J=2.0 Hz, 1H), 8.05 (d, J=2.0 Hz, 1H), 8.75 (s, 1H), 8.27 (m, 1H), 7.90 (m, 1H), 7.67 (m, 1H), 7.00 (s, 1H), 3.87-3.82 (m, 2H), 2.94-2.83 (m, 3H), 2.82 (s, 3H), 2.43 (s, 3H), 2.16-2.13 (m, 2H), 2.03-1.92 (m, 2H).

Example 191

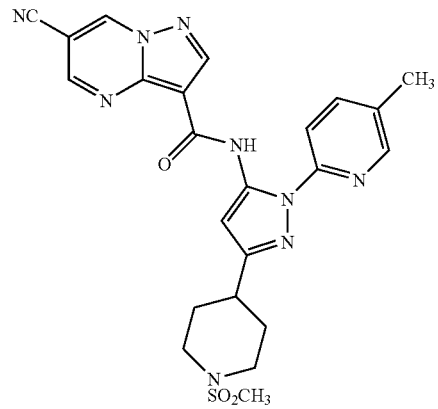

6-cyano-N-(1-(5-methylpyridin-2-yl)-3-(1-(methylsulfonyl)piperidin-4-yl)-1H-pyrazol-5-yl)pyrazolo[1,5-a]pyrimidine-3-carboxamide This compound was prepared according to the general methods outline for Example 121, using 6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide in place of 6-bromo-N-(3-(1-(methylsulfonyl)piperidin-4-yl)-1-(p-tolyl)-1H-pyrazol-5-yl)pyrazolo[1,5-a]pyrimidine-3-carboxamide. $^1$H NMR (400 MHz, CDCl$_3$) δ 9.19 (d, J=2.0 Hz, 1H), 8.93 (s, 1H), 8.90 (d, J=2.0 Hz, 1H), 8.23 (m, 1H), 7.90 (m, 1H), 7.68 (m, 1H), 6.99 (s, 1H), 3.85 (m, 2H), 2.88 (m, 3H), 2.82 (s, 3H), 2.42 (s, 3H), 2.16 (m, 2H), 1.96 (m, 2H).

Example 192

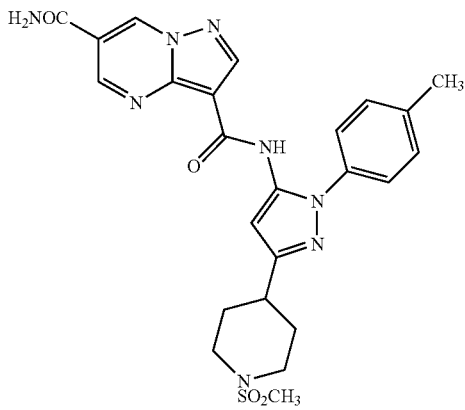

N³-(3-(1-(methylsulfonyl)piperidin-4-yl)-1-(p-tolyl)-1H-pyrazol-5-yl)pyrazolo[1,5-a]pyrimidine-3,6-dicarboxamide This compound was prepared according to the general methods outline for Example 120, using 6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide in place of 6-bromo-N-(3-(1-(methylsulfonyl)piperidin-4-yl)-1-(p-tolyl)-1H-pyrazol-5-yl)pyrazolo[1,5-a]pyrimidine-3-carboxamide. ¹H NMR (400 MHz, CDCl₃) δ 9.94 (s, 1H), 8.66 (s, 1H), 8.57 (s, 1H), 8.23 (m, 1H), 7.75 (m, 1H), 7.61-7.39 (m, 4H), 6.87 (s, 1H), 3.26 (m, 2H), 2.84-2.72 (m, 3H), 2.74 (s, 3H), 2.32 (s, 3H), 2.06 (m, 2H), 1.85 (m, 2H).

Example 193

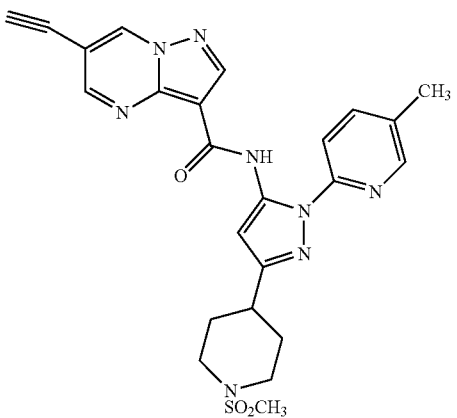

6-ethynyl-N-(1-(5-methylpyridin-2-yl)-3-(1-(methylsulfonyl)piperidin-4-yl)-1H-pyrazol-5-yl)pyrazolo[1,5-a]pyrimidine-3-carboxamide Tributylethynylstannane (76.0 mg, 0.240 mmol) and tetrakis(triphenylphosphine) palladium(0) (24.8 mg, 0.021 mmol) were added to a solution of 6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide (60.0 mg, 0.107 mmol) in anhydrous DMF (3.0 ml) under nitrogen atmosphere. The mixture was stirred at 80° C. for 1 h. After cooling down to room temperature, the reaction mixture was filtered through celite and evaporated under reduced pressure. The crude material was purified on preparative HPLC UV using the low pH shallow gradient method (Mobile phase: 52-66% B; A: H₂O with 0.05% TFA v/v, B: CH₃CN, 11 min run) on XBridge Shield RP18 OBD column, 5 □m, 19×150 mm, to afford the title compound as a yellow solid. ¹H NMR (300 MHz, CDCl₃) δ ppm 1.92-2.04 (m, 2H), 2.23-2.36 (m, 2H), 2.45 (s, 3H), 2.83-3.06 (m, 6H), 3.43 (s, 1H), 3.88 (d, J=12.0 Hz, 2H), 7.08 (s, 1H), 7.73 (d, J=8.1 Hz, 1H), 8.03 (d, J=9.0 Hz, 1H), 8.32 (s, 1H), 8.79-8.85 (m, 2H), 8.96 (s, 1H), 13.23 (s, 1H).

Example 194

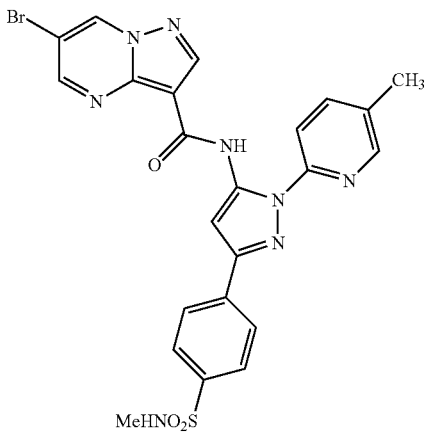

6-bromo-N-(1-(5-methylpyridin-2-yl)-3-(4-(N-methylsulfamoyl)phenyl)-1H-pyrazol-5-yl)pyrazolo[1,5-a]pyrimidine-3-carboxamide This compound was prepared following the general methods outlined for Example 146 using N-(4-(5-amino-1H-pyrazol-3-yl)phenyl)methanesulfonamide, 2-bromo-5-methylpyridine, and 6-bromopyrazolo[1,5-a]pyrimidine-3-carboxylic acid in place of tert-butyl 4-(5-amino-1H-pyrazol-3-yl)piperidine-1-carboxylate and 2-bromo-5-cyclopropylpyridine, and pyrazolo[1,5-a]pyrimidine-3-carboxylic acid, respectively. ¹H NMR (300 MHz, DMSO-d6): δ 2.46-2.498 (m, 6H), 7.47-7.50 (m, 2H), 7.85-8.01 (m, 4H), 8.14 (d, J=8.4 Hz, 2H), 8.63 (s, 1H), 8.74 (s, 1H), 9.29 (d, J=1.8 Hz, 1H), 9.86 (d, J=2.1 Hz, 1H), 13.16 (s, 1H).

Example 195

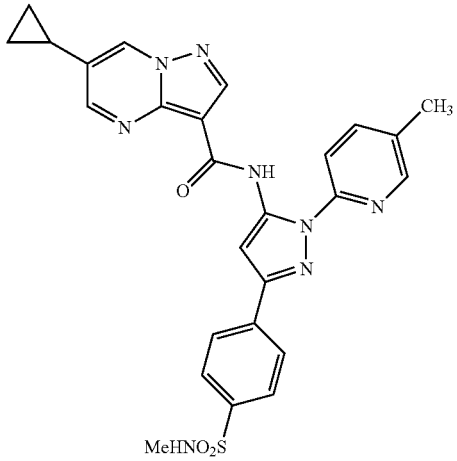

6-cyclopropyl-N-(1-(5-methylpyridin-2-yl)-3-(4-(N-methylsulfamoyl)phenyl)-1H-pyrazol-5-yl)pyrazolo[1,5-a]pyrimidine-3-carboxamide This compound was prepared following the general methods outlined in Example 106, using 6-bromo-N-(1-(5-methylpyridin-2-yl)-3-(4-(N-methylsulfamoyl)phenyl)-1H-pyrazol-5-yl)pyrazolo[1,5-a]pyrimidine-3-carboxamide in place of tert-butyl 4-(5-(6-bromopyrazolo pyrimidine-3-carboxamido)-1-(4-methoxyphenyl)-1H-pyrazol-3-yl)piperidine-1-carboxylate. $^1$H NMR (400 MHz, DMSO-d6) δ 0.85~1.28 (m, 4H), 2.07~2.17 (m, 1H), 2.45-2.55 (m, 6H), 7.52 (s, 2H), 7.69~8.14 (m, 6H), 8.47~8.66 (m, 2H), 8.80~9.10 (m, 2H), 13.13 (s, 1H).

Example 196

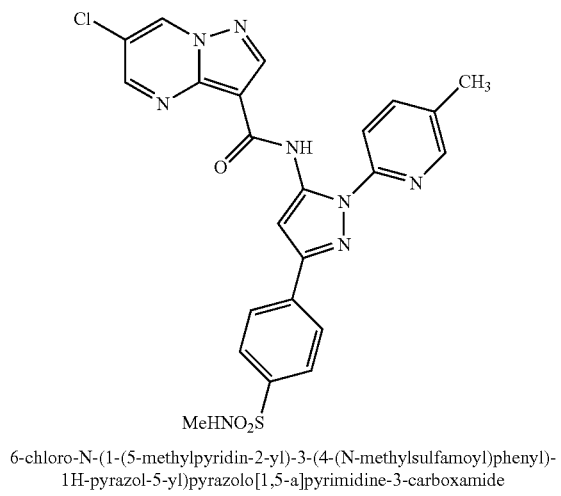

6-chloro-N-(1-(5-methylpyridin-2-yl)-3-(4-(N-methylsulfamoyl)phenyl)-1H-pyrazol-5-yl)pyrazolo[1,5-a]pyrimidine-3-carboxamide This compound was prepared following the general methods outlined for Example 146 using N-(4-(5-amino-1H-pyrazol-3-yl)phenyl)methanesulfonamide, 2-bromo-5-methylpyridine, and 6-bromopyrazolo[1,5-a]pyrimidine-3-carboxylic acid in place of tert-butyl 4-(5-amino-1H-pyrazol-3-yl)piperidine-1-carboxylate, 2-bromo-5-cyclopropylpyridine, and pyrazolo[1,5-a]pyrimidine-3-carboxylic acid, respectively. $^1$H NMR (300 MHz, DMSO-d6) δ 2.26-2.46 (m, 6H), 7.47-7.54 (m, 2H), 7.86-7.93 (m, 3H), 7.99-8.01 (m, 1H), 8.16 (d, J=8.4 Hz, 2H), 8.62 (s, 1H), 8.77 (s, 1H), 9.27 (d, J=2.1 Hz, 1H), 9.82 (d, J=2.1 Hz, 1H), 13.17 (s, 1H).

Scheme 5

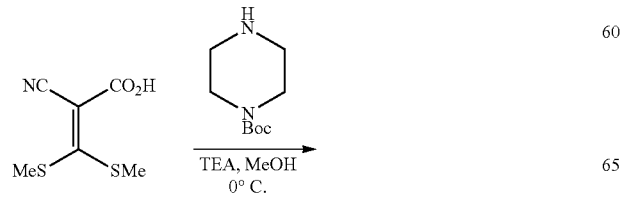

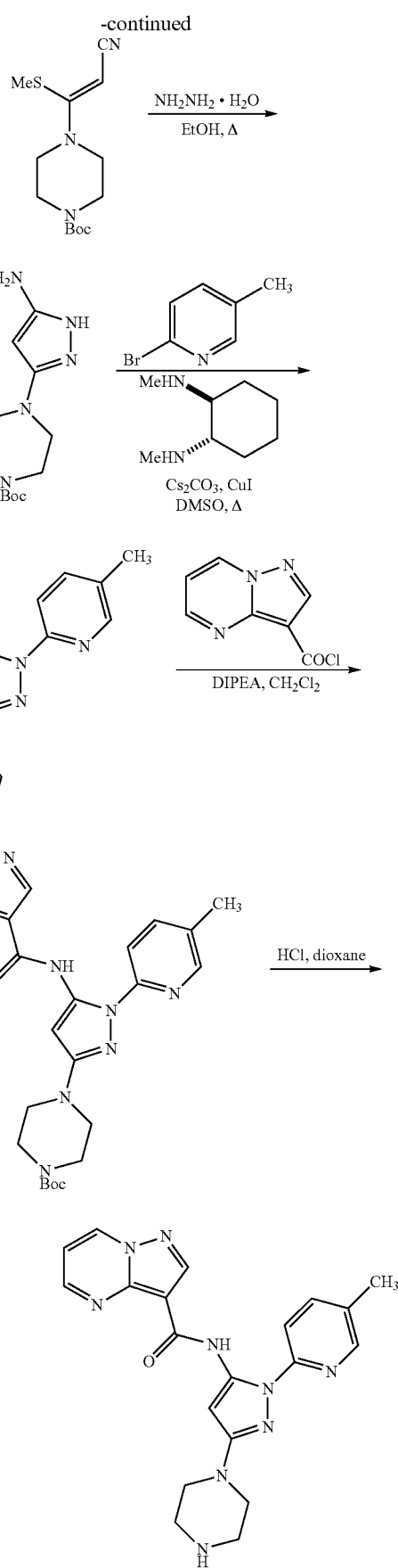

Example 197

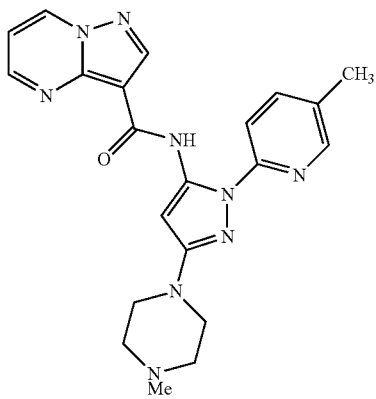

N-(3-(4-(methylpiperazin-1-yl)-1-(5-methylpyridin-2-yl)-1H-pyrazol-5-yl)pyrazolo[1,5-a]pyrimidine-3-carboxamide Synthesis of the intermediates follows below.

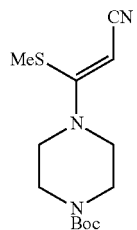

(Z)-tert-butyl 4-(2-cyano-1-(methylthio)vinyl)piperazine-1-carboxylate

Triethylamine (3.78 g, 37.3 mmol) and tert-butyl piperazine-1-carboxylate[2] (13.91 g, 74.7 mmol) were added dropwise to a cold (0° C.) solution of 2-cyano-3,3-bis(methylthio)acrylic acid (7.06 g, 37.3 mmol) in MeOH (60 mL), and the mixture was concentrated on a rotvap (water bath temperature about 20° C.). The crude Z-tert-butyl 4-(2-cyano-1-(methylthio)vinyl)piperazine-1-carboxylate was used without purification.

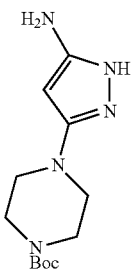

tert-butyl 4-(5-amino-1H-pyrazol-3-yl)piperazine-1-carboxylate

A mixture of (Z)-tert-butyl 4-(2-cyano-1-(methylthio)vinyl)piperazine-1-carboxylate (5.94 g, 20.9 mmol) and hydrazine monohydrate (4.5 mL) in EtOH (50 mL) was heated to reflux for 14 hours. After cooling to room temperature, the reaction mixture was concentrated. The residue was purified by column chromatography, eluting with 0-10% MeOH/CH$_2$Cl$_2$ to give tert-butyl 4-(5-amino-1H-pyrazol-3-yl)piperazine-1-carboxylate.

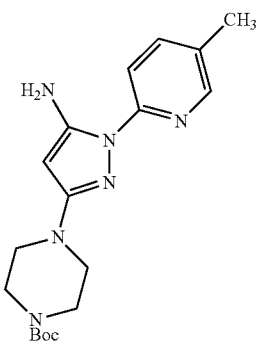

tert-butyl 4-(5-amino-1-(5-methylpyridin-2-yl)-1H-pyrazol-3-yl)piperazine-1-carboxylate This compound was prepared following the general methods outlined for Example 146, using 2-bromo-5-methylpyridine and tert-butyl 4-(5-amino-1H-pyrazol-3-yl)piperazine-1-carboxylate in place of 2-bromo-5-cyclopropylpyridine and tert-butyl 4-(5-amino-1H-pyrazol-3-yl)piperidine-1-carboxylate, respectively.

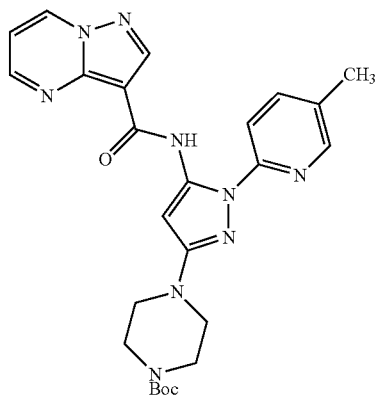

tert-butyl 4-(1-(5-methylpyridin-2-yl)-5-(pyrazolo[1,5-a]pyrimidine-3-carboxamido)-1H-pyrazol-3-yl)piperazine-1-carboxylate This compound was prepared following the general methods outlined in Example 7 using tert-butyl 4-(5-amino-1-(5-methylpyridin-2-yl)-1H-pyrazol-3-yl)piperazine-1-carboxylate in place of tert-butyl 4-(5-amino-1-(5-cyclopropylpyridin-2-yl)-1H-pyrazol-3-yl)piperidine-1-carboxylate.

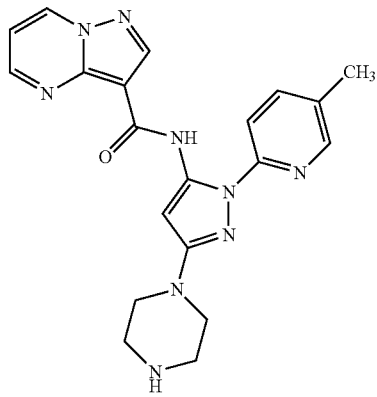

N-(1-(5-methylpyridin-2-yl)-3-(piperazin-1-yl)-1H-pyrazol-5-yl)pyrazolo[1,5-a]pyrimidine-3-carboxamide This compound was prepared according to the general methods outlined in Example 146 using tert-butyl 4-(1-(5-methylpyridin-2-yl)-5-(pyrazolo[1,5-a]pyrimidine-3-carboxamido)-1H-pyrazol-3-yl)piperazine-1-carboxylate in place of tert-butyl 4-(1-(5-cyclopropylpyridin-2-yl)-5-(pyrazolo[1,5-a]pyrimidine-3-carboxamido)-1H-pyrazol-3-yl)piperidine-1-carboxylate.

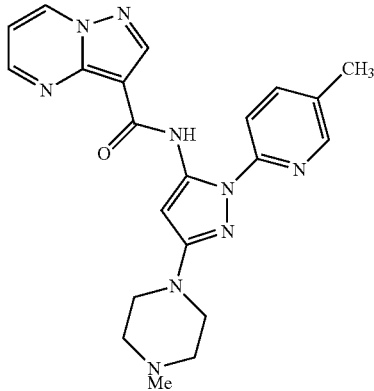 [SMILES: Cc1ccc(-n2nc(N3CCN(C)CC3)cc2NC(=O)c2cnn3cccnc23)nc1]

This compound was prepared according to the general methods outlined in Example 36 using N-(1-(5-methylpyridin-2-yl)-3-(piperazin-1-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. ¹H NMR (400 MHz, CDCl₃) δ 8.76 (m, 3H), 8.16 (d, J=0.8 Hz, 1H), 7.72 (d, J=8.4 Hz, 1H), 7.54 (b, 1H), 7.02 (m, 1H), 6.73 (s, 1H), 3.39 (m, 4H), 2.56 (m, 4H), 2.35 (s, 3H), 2.33 (s, 3H).

Example 198

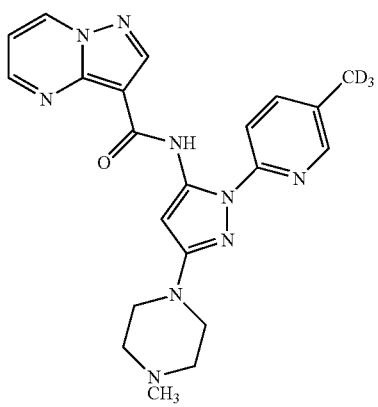

N-(3-(4-methylpiperazin-1-yl)-1-(5-trideuteromethylpyridin-2-yl)-1H-pyrazol-5-yl)pyrazolo[1,5-a]pyrimidine-3-carboxamide This compound was prepared according to the general methods outlined in Example 36 using N-(1-(5-trideuteromethylpyridin-2-yl)-3-(piperazin-1-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. ¹H NMR (400 MHz, CDCl₃) δ 8.58 (m, 1H), 8.52 (m, 1H), 8.47 (m, 1H), 7.90 (s, 1H), 7.45 (m, 1H), 7.34 (m, 1H), 6.84 (m, 1H), 6.53 (s, 1H), 3.28 (m, 4H), 2.48 (m, H), 2.26 (s, 3H).

Example 199

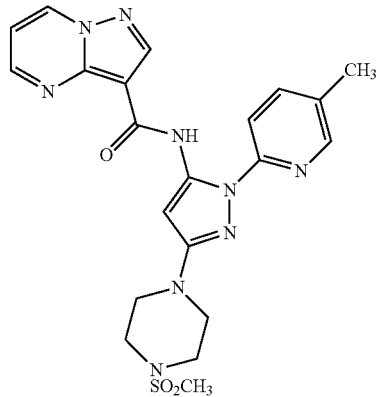

N-(1-(5-methylpyridin-2-yl)-3-(4-(methylsulfonyl)piperazin-1-yl)-1H-pyrazol-5-yl)pyrazolo[1,5-a]pyrimidine-3-carboxamide This compound was prepared according to the general methods outlined in Example 16 using N-(1-(5-methylpyridin-2-yl)-3-(piperazin-1-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (400 MHz, CDCl₃) δ 8.82 (m, 3H), 8.75 (s, 1H), 8.22 (m, 1H), 7.75 (m, 1H), 7.60 (m, 1H), 7.07 (m, 1H), 6.75 (s, 1H), 3.50 (t, J=5.6 Hz, 4H), 3.36 (t, J=5.6 Hz, 4H), 2.81 (s, 3H), 2.36 (s, 3H).

Example 200

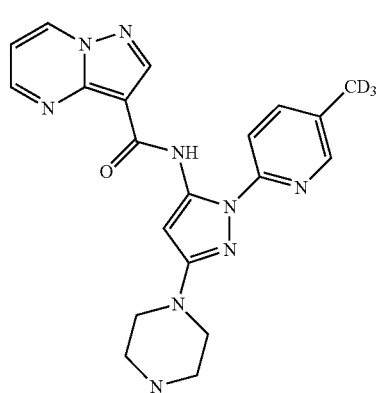

N-(1-(5-trideuteromethylpyridin-2-yl)-3-(4-(methylsulfonyl)piperazin-1-yl)-1H-pyrazol-5-yl)pyrazolo[1,5-a]pyrimidine-3-carboxamide This compound was prepared according to the general methods outlined in Example 16 using N-(1-(5-trideuteromethylpyridin-2-yl)-3-(piperazin-1-yl)-1H-pyrazol-5-yl)pyrazolo[1,5-a]pyrimidine-3-carboxamide in place of N-(1-(4-methoxyphenyl)-3-(piperidin-4-yl)-1H-pyrazol-5-yl)pyrazolo[1,5-a]pyrimidine-3-carboxamide. ¹H NMR (400 MHz, CDCl₃) δ 8.74 (m, 2H), 8.67 (s, 1H), 8.14 (m, 1H), 7.67

(m, 1H), 7.53 (m, 1H), 7.00 (m, 1H), 6.69 (s, 1H), 3.46 (t, J=5.6 Hz, 4H), 3.33 (t, J=5.6 Hz, 4H), 2.79 (s, 3H).

Example 201

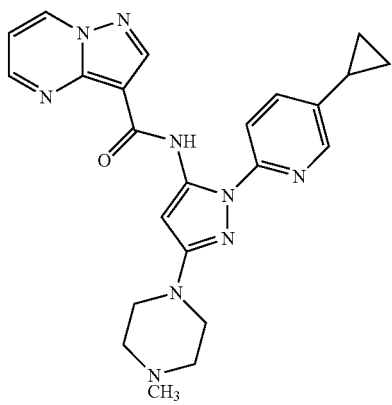

N-(1-(5-cyclopropylpyridin-2-yl)-3-(4-methylpiperazin-1-yl)-1H-pyrazol-5-yl)pyrazolo[1,5-a]pyrimidine-3-carboxamide This compound was prepared according to the general methods outlined in Example 36 using N-(1-(5-cyclopropylpyridin-2-yl)-3-(piperazin-1-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. $^1$H NMR (400 MHz, CDCl$_3$) 8.20 (m, 2H), 8.78 (s, 1H), 8.24 (t, J=1.2 Hz, 1H), 7.7 (d, J=8.4 Hz, 1H), 7.42 (dd, J=8.4, 2.4 Hz, 1H), 7.08 (m, 1H), 6.75 (s, 1H), 3.40 (m, 4H), 2.56 (m, 4H), 2.35 (s, 3H), 1.92 (m, 1H), 1.03 (m, 2H), 0.72 (m, 2H).

Example 202

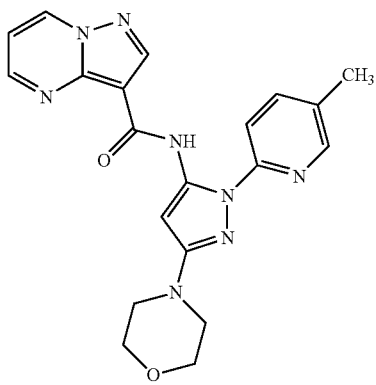

N-(1-(5-methylpyridin-2-yl)-3-morpholino-1H-pyrazol-5-yl)pyrazolo[1,5-a]pyrimidine-3-carboxamide This compound was prepared following the general methods outlined for Example 146, using 2-bromo-5-methylpyridine and 3-(tetrahydro-2H-pyran-4-yl)-1H-pyrazol-5-amine in place of 2-bromo-5-cyclopropylpyridine and tert-butyl 4-(5-amino-1H-pyrazol-3-yl)piperidine-1-carboxylate, respectively. (400 MHz, CDCl$_3$) 8.83 (m, 2H), 8.76 (s, 1H), 8.23 (d, J=0.8 Hz, 1H), 7.77 (d, J=8.4 Hz, 1H), 7.6 (dd, J=8.4, 2 Hz, 1H), 7.08 (m, 1H), 6.75 (s, 1H), 3.85 (m, 4H), 3.35 (m, 4H), 2.36 (s, 3H).

FIG. 1

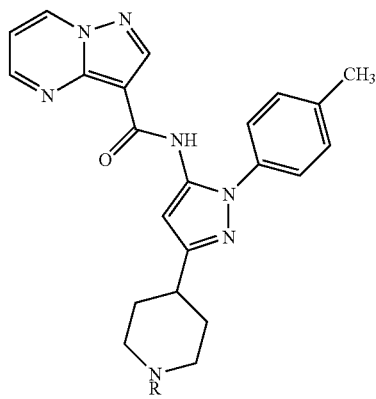

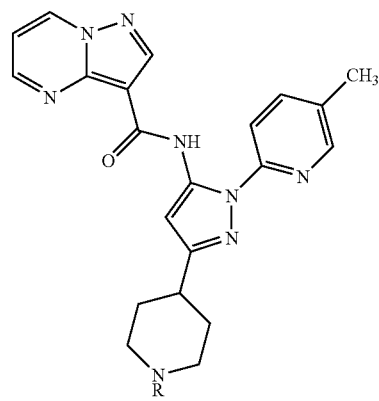

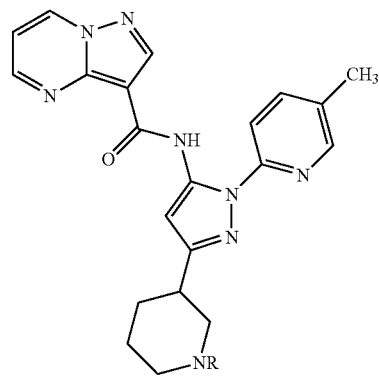

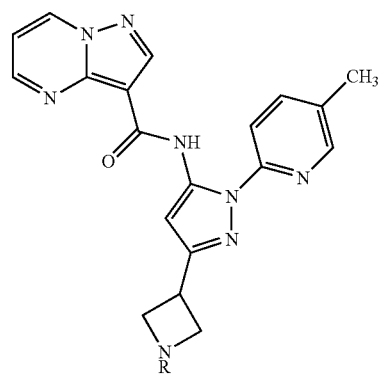

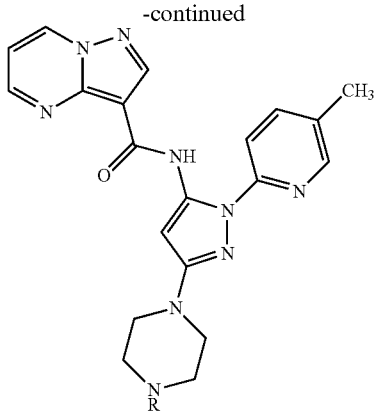

Examples 203-325 were prepared in parallel fashion using the general procedure below.

A mixture of the amine (R=H (TFA or HCl salt), 0.045 mmol), an aldehyde or ketone (0.090 mmol), and MP-cyanoborohydride (2.35 mmol/g, Biotage, 100 mg) in 1 mL of MeOH/HOAc (10:1) was shaken at room temperature. After the amine was consumed, the solid was filtered off. The solutions were concentrated in GeneVac. The residues were purified by HPLC to afford the desired products.

FIG. 2

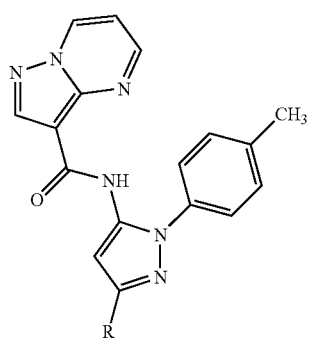

Examples 326-355 were prepared in parallel fashion using the general procedure below.

A mixture of the triflate (R=OTf, 25 mg), a boronic acid or ester (1.5 eq.), and X-Phos pre-catalyst (1.3 mg, 0.03 eq.) in 1 mL of THF was degassed with $N_2$ in 2 dram vials. To the vials were added 322 mL of 0.5 M aqueous $K_3PO_4$. The vials were heated at 70° C. for 20 h. After cooling to room temperature, 1 mL of EtOAc was added. The organic layer was separated and concentrated. The residues were purified by HPLC to afford the desired products.

FIG. 3

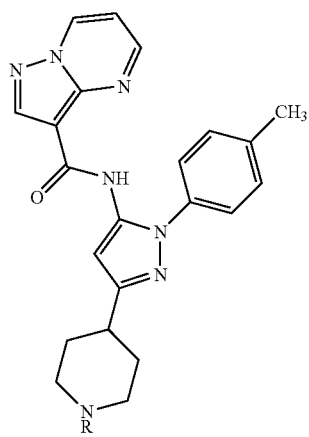

Examples 356-397 were prepared in parallel fashion using the general procedure below.

To a mixture of the piperidine (R=H, TFA salt, 20 mg) and DIPEA (5 eq.) in 1.5 mL of $CH_2Cl_2$ were added sulfonyl chlorides (2.0 eq.) in vials. The vials were shaken at rt overnight. After the reactions were completed, 0.1 mL of water was added to each vial. The solvents were removed in GeneVac. The residues were purified by HPLC.

Example 398

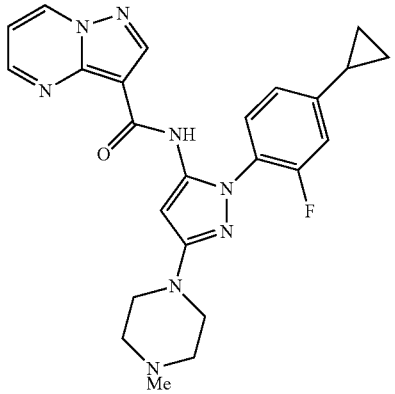

N-(1-(4-cyclopropyl-2-fluorophenyl)-3-(1-methylpiperidin-4-yl)-1H-pyrazol-5-yl)pyrazolo[1,5-a]pyrimidine-3-carboxamide This compound was prepared following the general methods outlined for the synthesis of Example 16, using N-(1-(4-cyclopropyl-2-fluorophenyl)-3-(piperidin-4-yl)-1H-pyrazol-5-yl)pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide, $^1$H NMR (400 MHz, $CDCl_3$) δ 0.80-0.83 (m, 2H), 1.14-1.18 (m, 2H), 2.02-2.06 (m, 1H), 2.25-2.42 (m, 4H), 2.80-3.31 (m, 6H), 3.48-3.50 (m, 1H), 3.80-3.83 (m, 1H), 6.79 (d, J=3.6 Hz, 1H), 6.99-7.28 (m, 3H), 7.41-7.45 (m, 1H), 8.27-8.30 (m, 1H), 8.73 (s, 1H), 8.74-8.84 (m, 1H), 10.17 (s, 0.5H), 10.21 (s, 0.5H), 11.15 (s broad, 0.5H), 11.70 (s broad, 0.5H).

Example 399

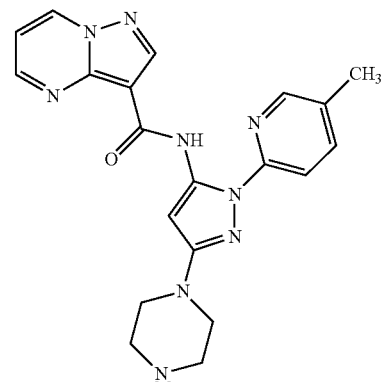

N-(3-(1-methylpiperidin-4-yl)-1-(5-methylpyridin-2-yl)-1H-pyrazol-5-yl)pyrazolo[1,5-a]pyrimidine-3-carboxamide This compound was prepared following the general methods outlined for the synthesis of Example 16, using N-(1-(5-methylpyridin-2-yl)-3-(piperidin-4-yl)-1H-pyrazol-5-yl)

pyrazolo[1,5-a]pyrimidine-3-carboxamide in place of N-(3-(piperidin-4-yl)-1-(p-tolyl)-1H-pyrazol-5-yl)pyrazolo[1,5-a]pyrimidine-3-carboxamide. $^1$H NMR (300 MHz, CDCl3) δ 0.76-0.80 (m, 2H), 1.08-1.14 (m, 2H), 1.95-2.01 (m, 1H), 2.34-2.43 (m, 4H), 2.78-2.89 (m, 6H), 3.30-3.83 (m, 2H), 7.16-7.02 (m, 2H), 7.50-7.53 (m, 1H), 7.85-7.89 (m, 1H), 8.34 (d, J=2.1 Hz, 1H), 8.89-8.83 (m, 3H), 11.80 (s broad, 0.5H), 12.15 (s broad, 0.5H), 13.17 (s, 0.5H), 13.22 (s, 0.5H).
[1]Wu, G., Tormos, W. *J. Org. Chem* 1197, 62, 6412-6414.
[2]Gradl, S.; Rudolph, J.; Ren, L., WO 2011025951.

Pharmaceutical Composition

As a specific embodiment of this invention, 100 mg of N-(3-(4-oxocyclohexyl)-1-p-tolyl-1H-pyrazol-5-yl)pyrazolo[1,5-a]pyrimidine-3-carboxamide, is formulated with sufficient finely divided lactose to provide a total amount of 580 to 590 mg to fill a size 0, hard-gelatin capsule.

Assays

The compounds of the instant invention described in the Examples were tested by the assay described below and were found to have IRAK-4 inhibitory activity.

Other assays are known in the literature and could be readily performed by those of skill in the art.

IRAK-4 Kinase Assay

The kinase activity of IRAK-4 is determined by its ability to catalyze the phosphorylation of a fluorescent polypeptide substrate. The extent of phosphorylation is measured using the IMAP technology (Molecular Devices) where the phosphorylated fluorescent substrate binds to the large M(III)-based nanoparticles which reduces the rotational speed of the substrate and thus increases its fluorescent polarization (FP).

20 μl reaction mixture contains 10 mM TriHCl, pH 7.2, 0.5 nM GST tagged IRAK-4 (SignalChem), 100 nM fluorescent peptide substrate (RP7030, Molecular Devices), 100 μM ATP, 1 mM DTT, 1 mM $MgCl_2$, and 0.01% Tween 20. The reaction is initiated by the addition of ATP. After incubation for 30 minutes at 25° C., 60 μl of Progressive IMAP Reagent (Molecular Devices) is added to stop the reaction. Change in RP7030's FP is determined by a FP reader (Analyst HT, LH, BioSystems).

Compounds of the present invention exhibit IRAK-4 $IC_{50}$ values of <100 nM to >1 μM. The following table shows the activity data for an illustrative list of compounds of the invention.

| Example | Structure | LC-MS (Retention time (min), m/z) | IRAK-4 $IC_{50}$ (nM) |
|---|---|---|---|
| 1 | 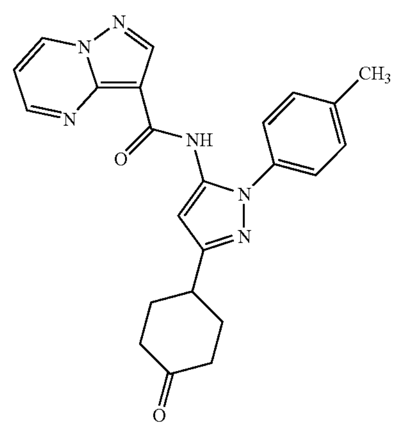 [SMILES: Cc1ccc(-n2nc(C3CCC(=O)CC3)cc2NC(=O)c2cnn3cccnc23)cc1] | 4.03, 415 | <100 nM |
| 2 | 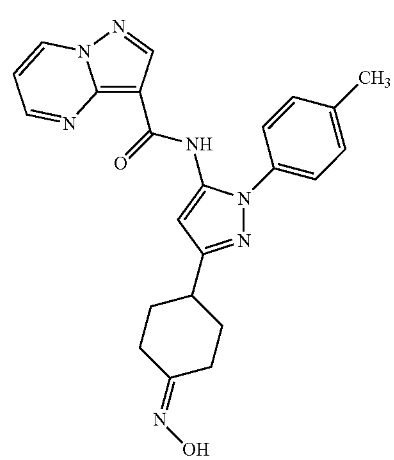 [SMILES: Cc1ccc(-n2nc(C3CCC(=NO)CC3)cc2NC(=O)c2cnn3cccnc23)cc1] | 3.62, 430 | <1 μM |

-continued
| Example | Structure | LC-MS (Retention time (min), m/z) | IRAK-4 IC$_{50}$ (nM) |
|---|---|---|---|
| 3 | 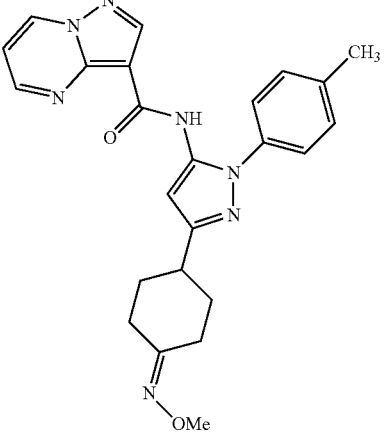 | 4.42, 444 | <1 μM |
| 4 | 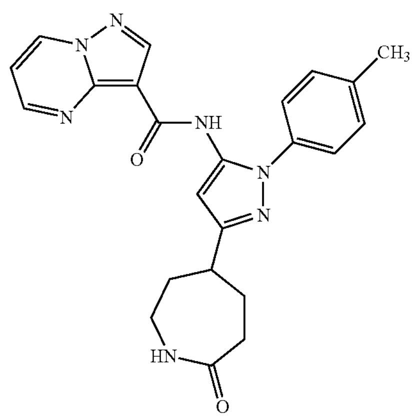 [SMILES: Cc1ccc(-n2nc(C3CCNC(=O)CC3)cc2NC(=O)c2cnn3cccnc23)cc1] | 3.30, 430 | <1 μM |
| 5 | 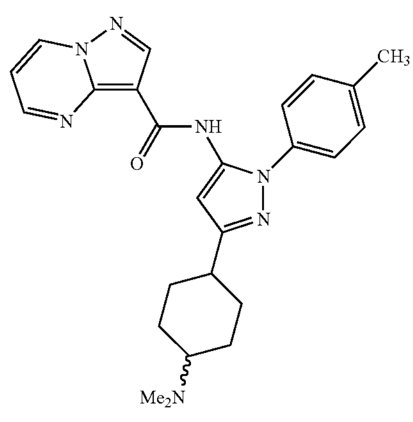 [SMILES: Cc1ccc(-n2nc(C3CCC(N(C)C)CC3)cc2NC(=O)c2cnn3cccnc23)cc1] | 2.94, 444 | <1 μM |

-continued
| Example | Structure | LC-MS (Retention time (min), m/z) | IRAK-4 IC$_{50}$ (nM) |
|---|---|---|---|
| 6 | 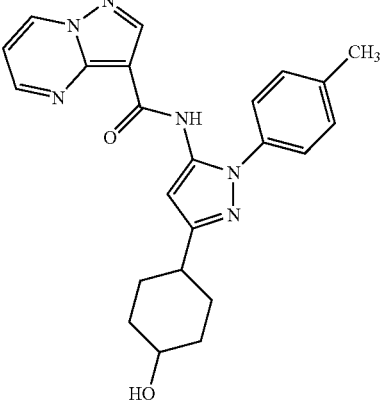 | 3.52, 417 | <1 μM |
| 7 | 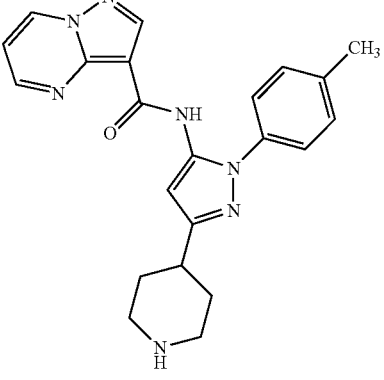 | 3.20, 402 | <100 nM |
| 8 | 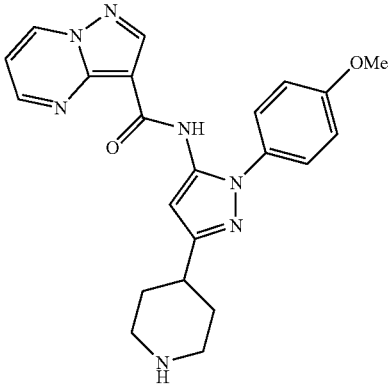 [SMILES: COc1ccc(-n2nc(C3CCNCC3)cc2NC(=O)c2cnn3cccnc23)cc1] | 2.59, 418 | <1 μM |

-continued

| Example | Structure | LC-MS (Retention time (min), m/z) | IRAK-4 IC$_{50}$ (nM) |
| --- | --- | --- | --- |
| 9 | 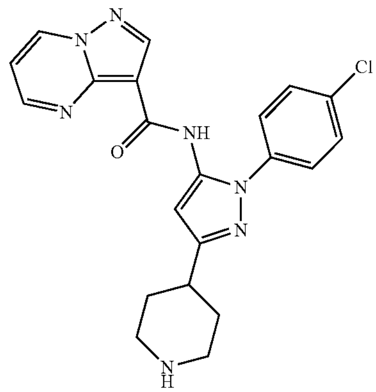 [SMILES: O=C(Nc1cc(C2CCNCC2)nn1-c1ccc(Cl)cc1)c1cnn2cccnc12] | 0.69, 422 | <1 μM |
| 10 | 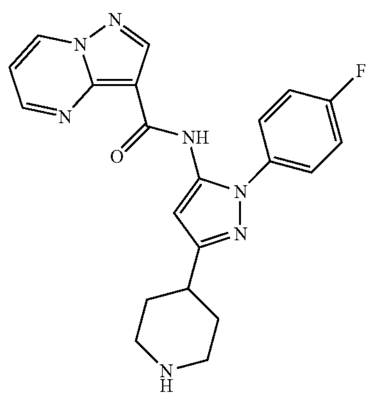 [SMILES: O=C(Nc1cc(C2CCNCC2)nn1-c1ccc(F)cc1)c1cnn2cccnc12] | 2.54, 406 | <1 μM |
| 11 | 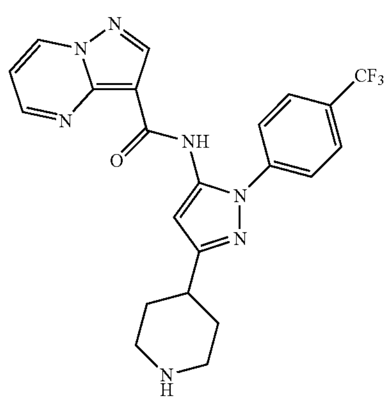 [SMILES: O=C(Nc1cc(C2CCNCC2)nn1-c1ccc(C(F)(F)F)cc1)c1cnn2cccnc12] | 3.07, 456 | <1 μM |
| 12 | 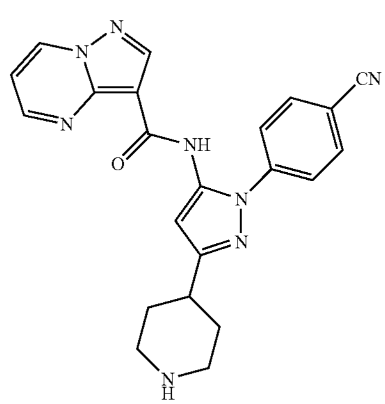 [SMILES: N#Cc1ccc(-n2nc(C3CCNCC3)cc2NC(=O)c2cnn3cccnc23)cc1] | 2.36, 413 | >1 μM |

-continued

| Example | Structure | LC-MS (Retention time (min), m/z) | IRAK-4 IC$_{50}$ (nM) |
|---|---|---|---|
| 13 | 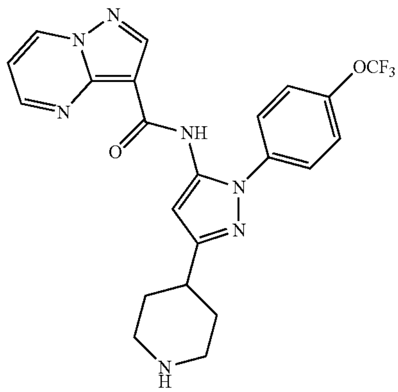 [SMILES: O=C(Nc1cc(C2CCNCC2)nn1-c1ccc(OC(F)(F)F)cc1)c1cnn2cccnc12] | 2.96, 472 | <1 μM |
| 14 | 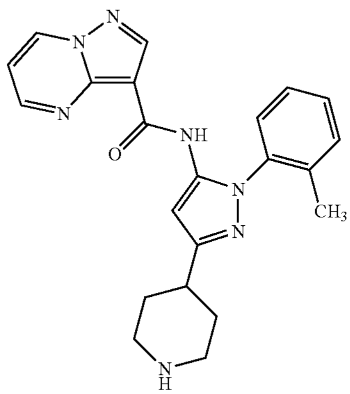 [SMILES: Cc1ccccc1-n1nc(C2CCNCC2)cc1NC(=O)c1cnn2cccnc12] | 1.45, 402 | >1 μM |
| 15 | 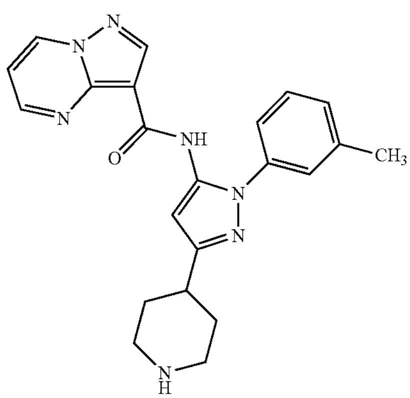 [SMILES: Cc1cccc(-n2nc(C3CCNCC3)cc2NC(=O)c2cnn3cccnc23)c1] | 1.51, 402 | <1 μM |
| 16 | 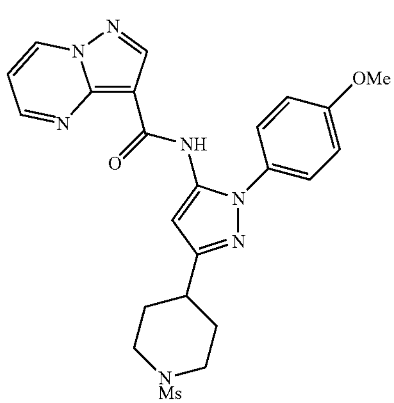 | 3.84, 496 | <100 nM |

-continued

| Example | Structure | LC-MS (Retention time (min), m/z) | IRAK-4 IC$_{50}$ (nM) |
|---|---|---|---|
| 17 | 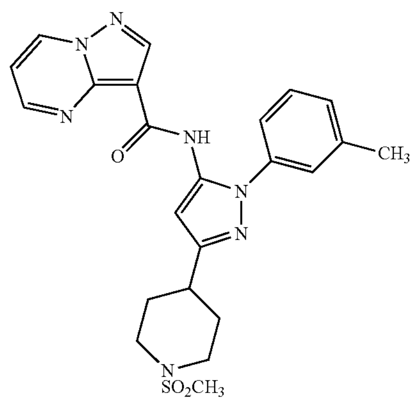 | 0.90, 480 | <1 μM |
| 18 | 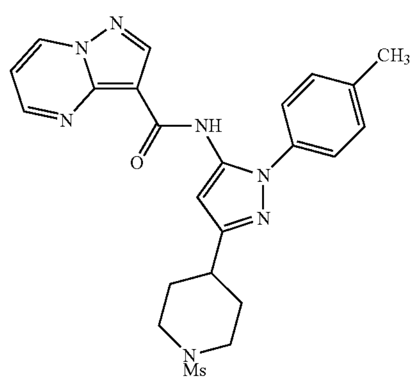 | 4.05, 480 | <100 nM |
| 19 | 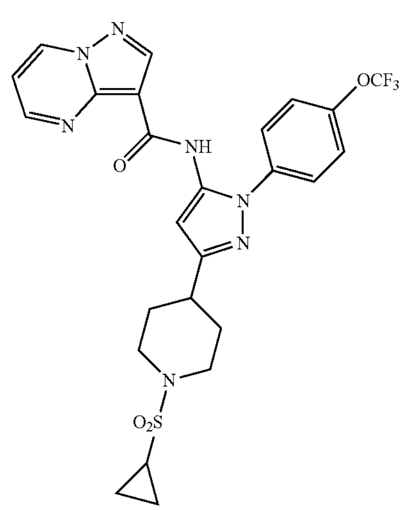 [SMILES: O=C(Nc1cc(C2CCN(S(=O)(=O)C3CC3)CC2)nn1-c1ccc(OC(F)(F)F)cc1)c1cnn2cccnc12] | 4.50, 506 | <1 μM |

-continued

| Example | Structure | LC-MS (Retention time (min), m/z) | IRAK-4 IC$_{50}$ (nM) |
|---|---|---|---|
| 20 | 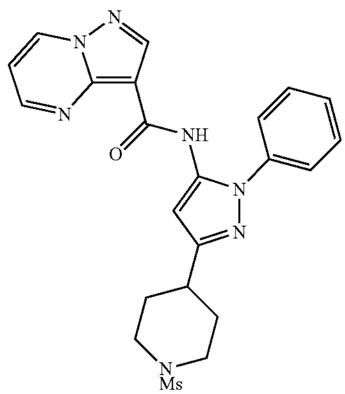 | 1.98, 488 | <1 μM |
| 21 | 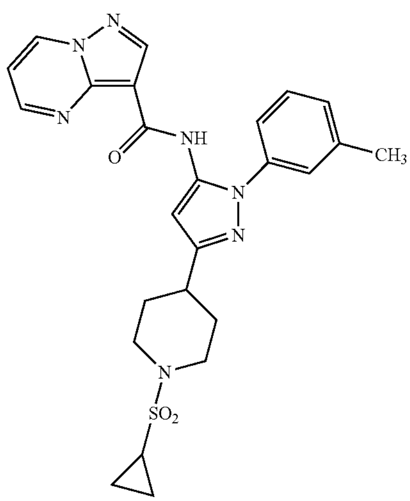 [SMILES: Cc1cccc(-n2nc(C3CCN(S(=O)(=O)C4CC4)CC3)cc2NC(=O)c2cnn3cccnc23)c1] | 0.96, 506 | <1 μM |
| 22 | 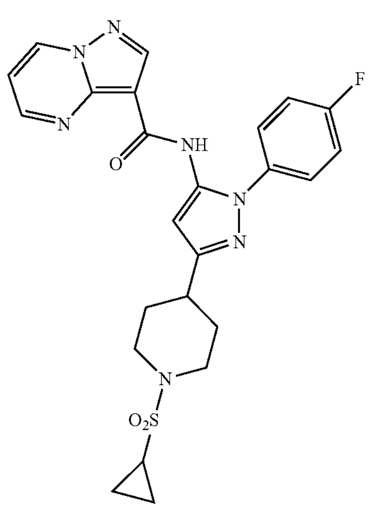 [SMILES: O=C(Nc1cc(C2CCN(S(=O)(=O)C3CC3)CC2)nn1-c1ccc(F)cc1)c1cnn2cccnc12] | 4.23, 510 | <1 μM |

| Example | Structure | LC-MS (Retention time (min), m/z) | IRAK-4 IC$_{50}$ (nM) |
| --- | --- | --- | --- |
| 23 | 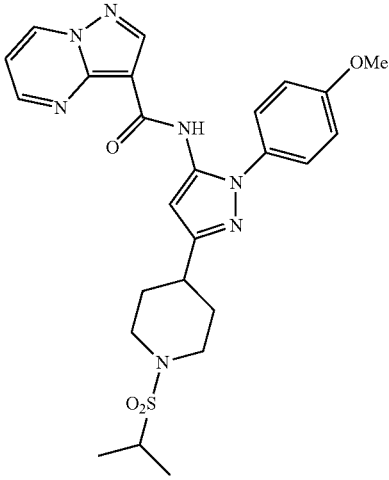 [SMILES: COc1ccc(-n2nc(C3CCN(S(=O)(=O)C(C)C)CC3)cc2NC(=O)c2cnn3cccnc23)cc1] | 4.34, 524 | <100 nM |
| 24 | 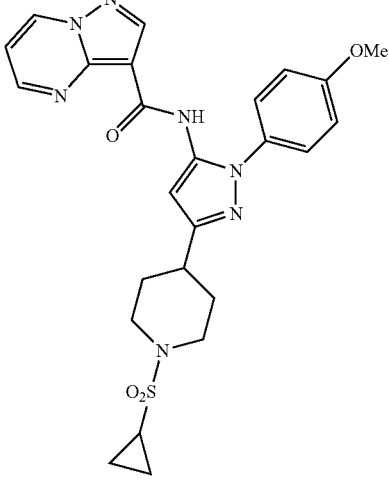 | 4.20, 522 | <100 nM |
| 25 | 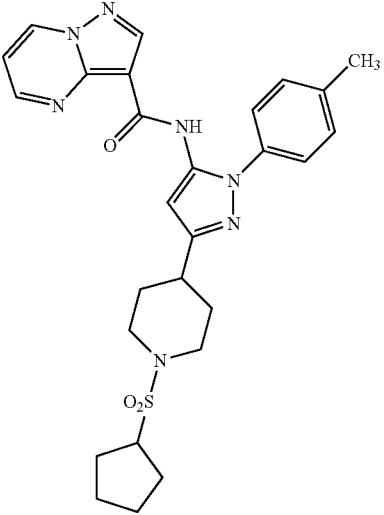 [SMILES: Cc1ccc(-n2nc(C3CCN(S(=O)(=O)C4CCCC4)CC3)cc2NC(=O)c2cnn3cccnc23)cc1] | 5.27, 534 | <1 μM |

-continued

| Example | Structure | LC-MS (Retention time (min), m/z) | IRAK-4 IC$_{50}$ (nM) |
|---|---|---|---|
| 26 | 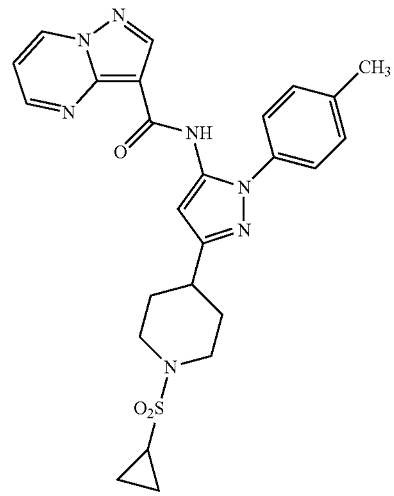 [SMILES: Cc1ccc(-n2nc(C3CCN(S(=O)(=O)C4CC4)CC3)cc2NC(=O)c2cnn3cccnc23)cc1] | 4.50, 506 | <1 μM |
| 27 | 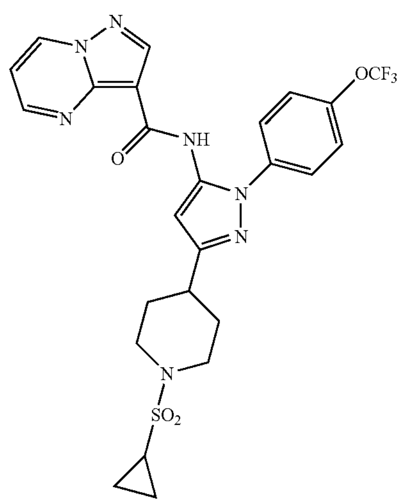 [SMILES: O=C(Nc1cc(C2CCN(S(=O)(=O)C3CC3)CC2)nn1-c1ccc(OC(F)(F)F)cc1)c1cnn2cccnc12] | 4.30, 576 | >1 μM |
| 28 | 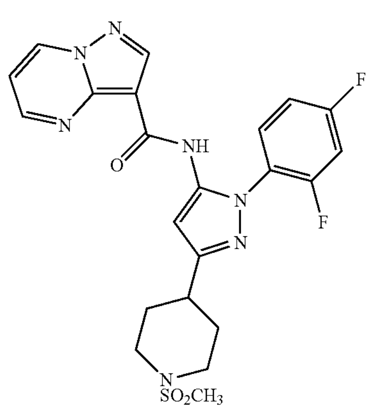 | 1.37, 502 | <1 μM |

-continued
| Example | Structure | LC-MS (Retention time (min), m/z) | IRAK-4 IC$_{50}$ (nM) |
|---|---|---|---|
| 29 | 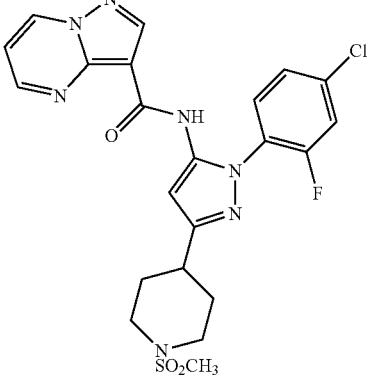 | 1.48, 518 | <1 μM |
| 30 | 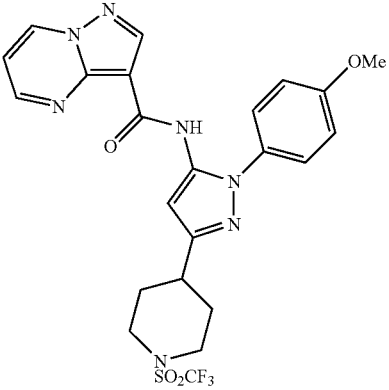 | 5.35, 550 | >1 μM |
| 31 | 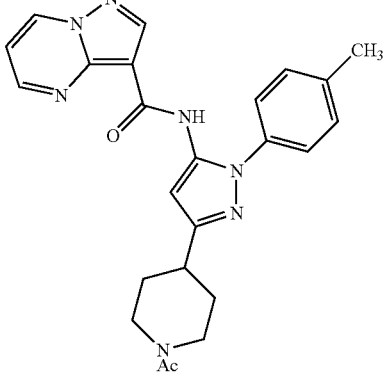 | 3.23, 444 | <1 μM |

-continued
| Example | Structure | LC-MS (Retention time (min), m/z) | IRAK-4 IC$_{50}$ (nM) |
|---------|-----------|-----------------------------------|------------------------|
| 32 | 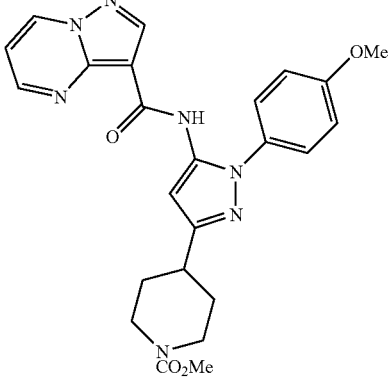 | 3.60, 476 | <1 μM |
| 33 | 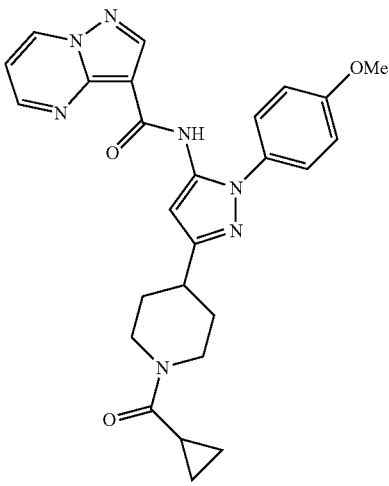 [SMILES: COc1ccc(-n2nc(C3CCN(C(=O)C4CC4)CC3)cc2NC(=O)c2cnn3cccnc23)cc1] | 3.83, 486 | <1 μM |
| 34 | 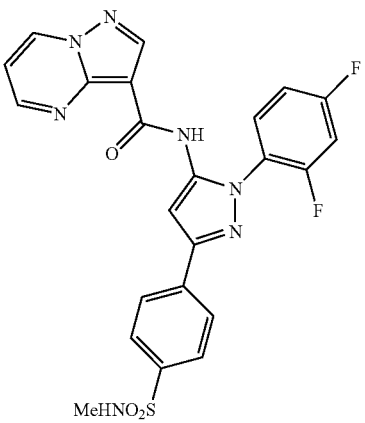 | 1.86, 510 | <100 nM |

-continued
| Example | Structure | LC-MS (Retention time (min), m/z) | IRAK-4 IC$_{50}$ (nM) |
|---|---|---|---|
| 35 | 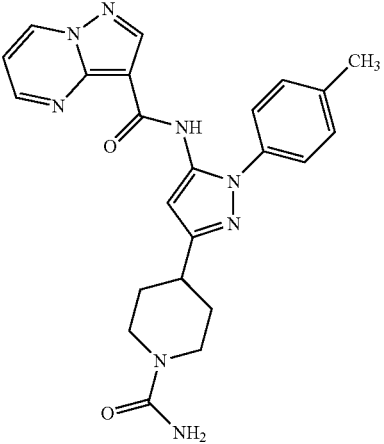 [SMILES: Cc1ccc(-n2nc(C3CCN(C(N)=O)CC3)cc2NC(=O)c2cnn3cccnc23)cc1] | 3.15, 445 | <1 μM |
| 36 | 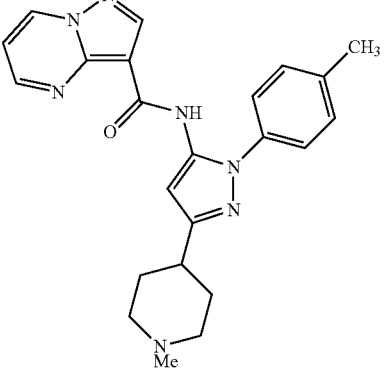 | 2.36, 416 | <1 μM |
| 37 | 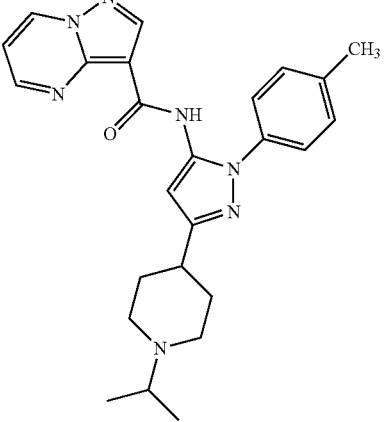 | 2.51, 444 | <100 nM |

| Example | Structure | LC-MS (Retention time (min), m/z) | IRAK-4 IC$_{50}$ (nM) |
|---|---|---|---|
| 38 | 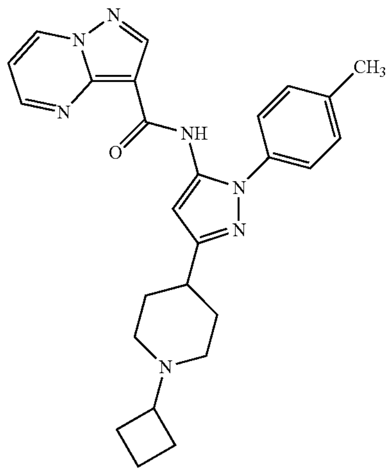 [SMILES: Cc1ccc(-n2nc(C3CCN(C4CCC4)CC3)cc2NC(=O)c2cnn3cccnc23)cc1] | 2.57, 456 | <100 nM |
| 39 | 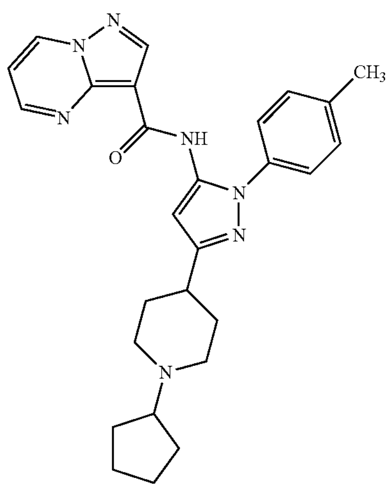 [SMILES: Cc1ccc(-n2nc(C3CCN(C4CCCC4)CC3)cc2NC(=O)c2cnn3cccnc23)cc1] | 2.71, 470 | <100 nM |
| 40 | 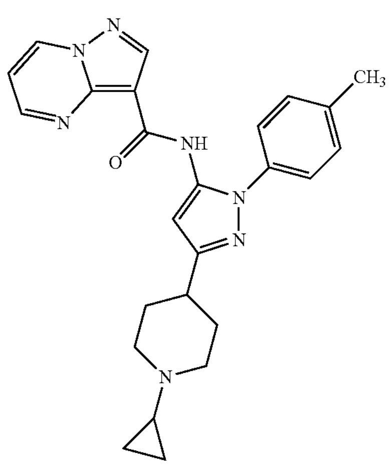 [SMILES: Cc1ccc(-n2nc(C3CCN(C4CC4)CC3)cc2NC(=O)c2cnn3cccnc23)cc1] | 2.58, 442 | <100 nM |

-continued

| Example | Structure | LC-MS (Retention time (min), m/z) | IRAK-4 IC$_{50}$ (nM) |
|---------|-----------|-----------------------------------|------------------------|
| 41 | 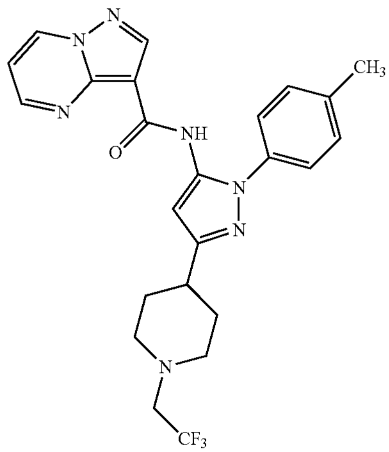 [SMILES: Cc1ccc(-n2nc(C3CCN(CC(F)(F)F)CC3)cc2NC(=O)c2cnn3cccnc23)cc1] | 0.76, 484 | <100 nM |
| 42 | 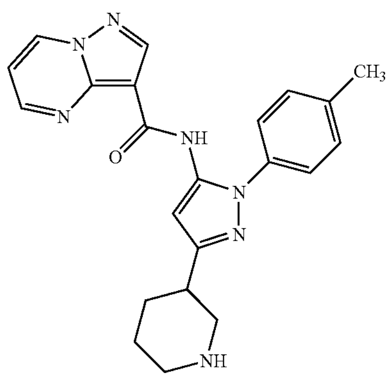 [SMILES: Cc1ccc(-n2nc(C3CCCNC3)cc2NC(=O)c2cnn3cccnc23)cc1] | 1.56, 402 | <1 μM |
| 43 | 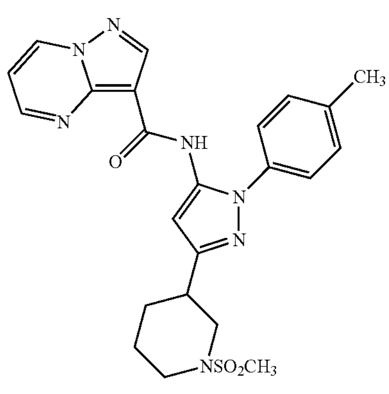 | 1.97, 480 | <1 μM |

-continued

| Example | Structure | LC-MS (Retention time (min), m/z) | IRAK-4 IC$_{50}$ (nM) |
|---------|-----------|-----------------------------------|------------------------|
| 44 | 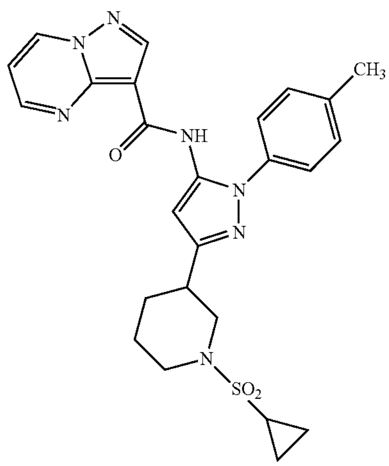 [SMILES: Cc1ccc(-n2nc(C3CCCN(S(=O)(=O)C4CC4)C3)cc2NC(=O)c2cnn3cccnc23)cc1] | 2.09, 506 | <1 μM |
| 45 | 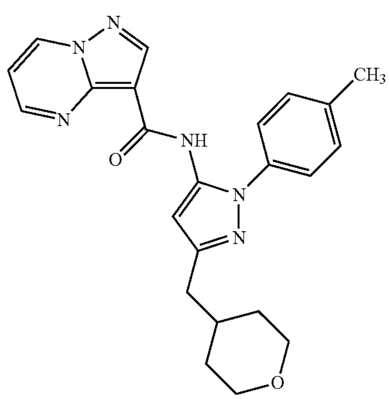 [SMILES: Cc1ccc(-n2nc(CC3CCOCC3)cc2NC(=O)c2cnn3cccnc23)cc1] | 4.10, 417 | <1 μM |
| 46 | 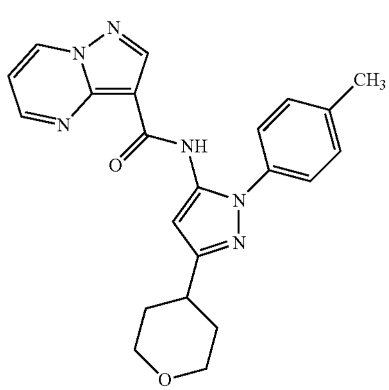 [SMILES: Cc1ccc(-n2nc(C3CCOCC3)cc2NC(=O)c2cnn3cccnc23)cc1] | 3.58, 403 | <1 μM |

-continued

| Example | Structure | LC-MS (Retention time (min), m/z) | IRAK-4 IC$_{50}$ (nM) |
|---|---|---|---|
| 47 | 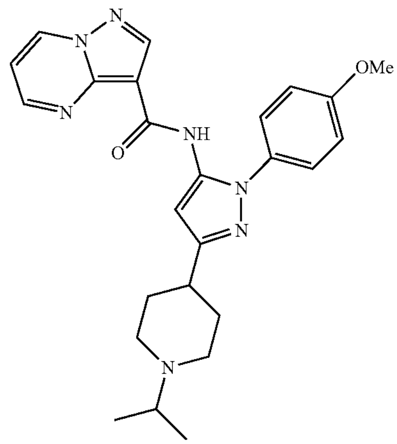 [SMILES: COc1ccc(-n2nc(C3CCN(C(C)C)CC3)cc2NC(=O)c2cnn3cccnc23)cc1] | 2.46, 460 | <100 nM |
| 48 | 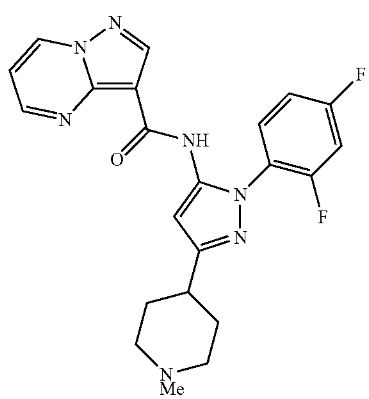 [SMILES: CN1CCC(c2cc(NC(=O)c3cnn4cccnc34)n(-c3ccc(F)cc3F)n2)CC1] | 0.85, 438 | <1 µM |
| 49 | 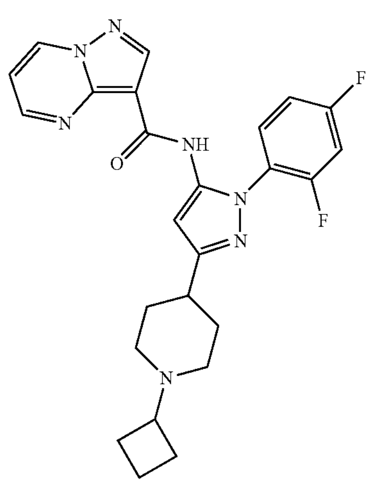 [SMILES: O=C(Nc1cc(C2CCN(C3CCC3)CC2)nn1-c1ccc(F)cc1F)c1cnn2cccnc12] | 0.93, 478 | <100 nM |

-continued
| Example | Structure | LC-MS (Retention time (min), m/z) | IRAK-4 IC$_{50}$ (nM) |
|---|---|---|---|
| 50 | 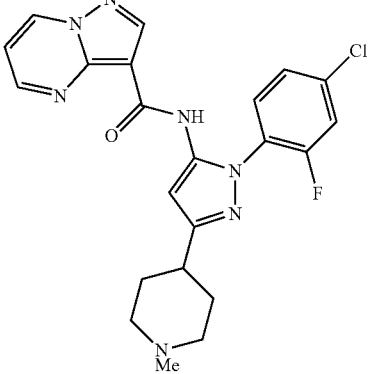 | 0.89, 454 | <1 μM |
| 51 | 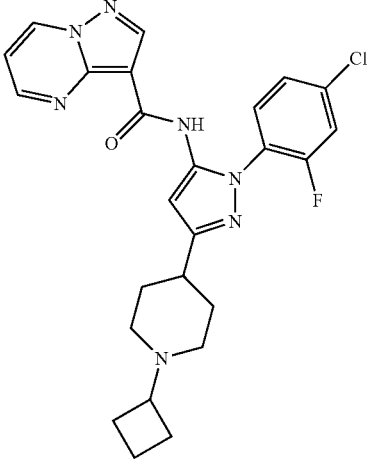 [SMILES: O=C(Nc1cc(C2CCN(C3CCC3)CC2)nn1-c1ccc(Cl)cc1F)c1cnn2cccnc12] | 0.96, 494 | <100 nM |
| 52 | 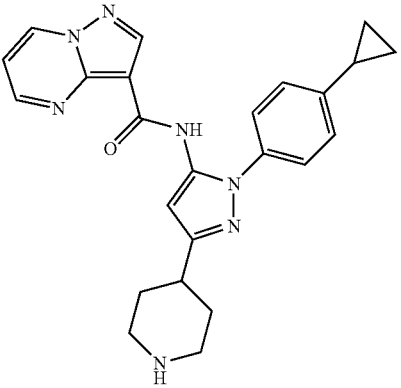 [SMILES: O=C(Nc1cc(C2CCNCC2)nn1-c1ccc(C2CC2)cc1)c1cnn2cccnc12] | 2.98, 428 | <100 nM |

-continued
| Example | Structure | LC-MS (Retention time (min), m/z) | IRAK-4 IC$_{50}$ (nM) |
|---|---|---|---|
| 53 | 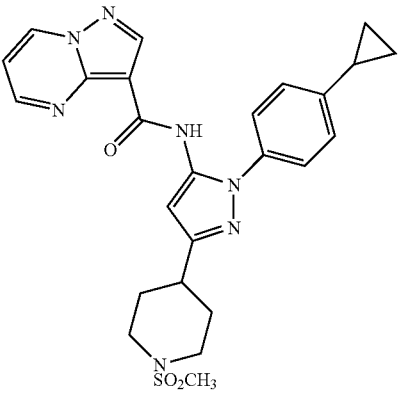 | 4.52, 506 | <100 nM |
| 54 | 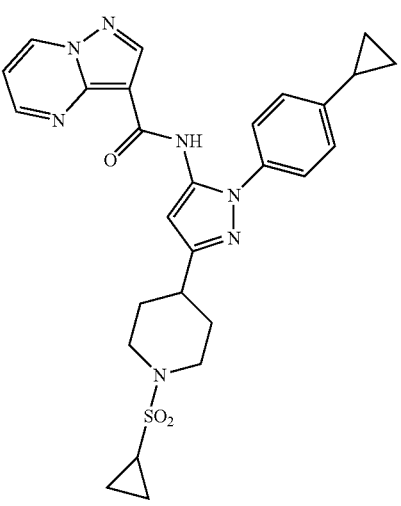 [SMILES: O=C(Nc1cc(C2CCN(S(=O)(=O)C3CC3)CC2)nn1-c1ccc(C2CC2)cc1)c1cnn2cccnc12] | 4.40, 532 | <1 μM |
| 55 | 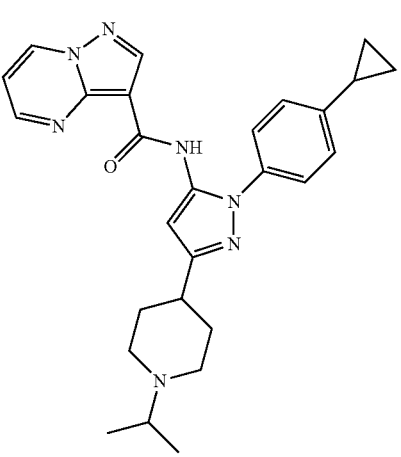 [SMILES: CC(C)N1CCC(c2cc(NC(=O)c3cnn4cccnc34)n(-c3ccc(C4CC4)cc3)n2)CC1] | 2.61, 470 | <100 nM |

-continued

| Example | Structure | LC-MS (Retention time (min), m/z) | IRAK-4 IC$_{50}$ (nM) |
|---|---|---|---|
| 56 | 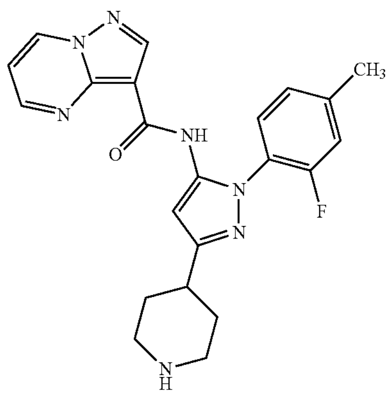 [SMILES: Cc1ccc(-n2nc(C3CCNCC3)cc2NC(=O)c2cnn3cccnc23)c(F)c1] | 3.12, 420 | <100 nM |
| 57 | 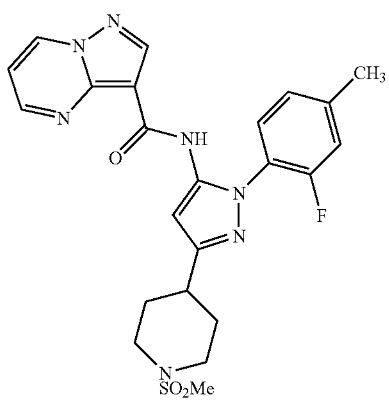 | 4.27, 498 | <100 nM |
| 58 | 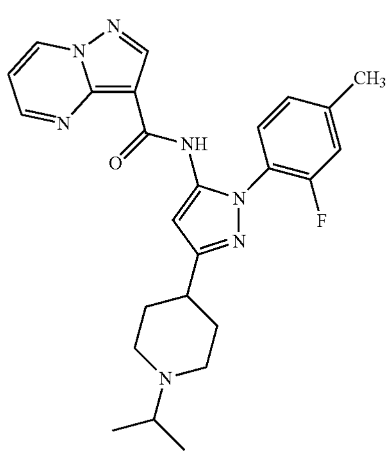 [SMILES: Cc1ccc(-n2nc(C3CCN(C(C)C)CC3)cc2NC(=O)c2cnn3cccnc23)c(F)c1] | 2.39, 462 | <100 nM |

| Example | Structure | LC-MS (Retention time (min), m/z) | IRAK-4 IC$_{50}$ (nM) |
|---|---|---|---|
| 59 | 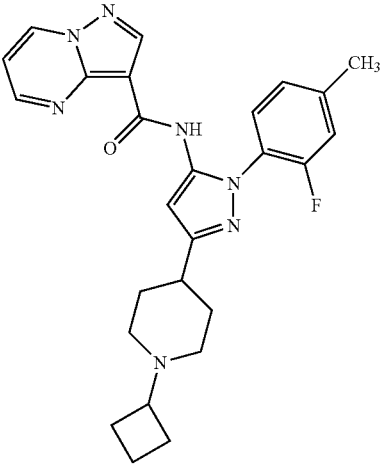 [SMILES: Cc1ccc(-n2nc(C3CCN(C4CCC4)CC3)cc2NC(=O)c2cnn3cccnc23)c(F)c1] | 2.64, 474 | <100 nM |
| 60 | 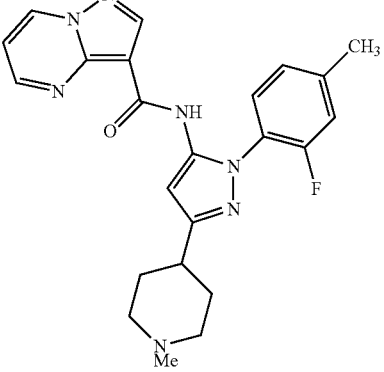 | 0.94, 460 | <1 μM |
| 61 | 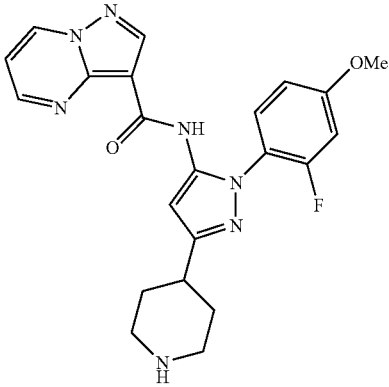 [SMILES: COc1ccc(-n2nc(C3CCNCC3)cc2NC(=O)c2cnn3cccnc23)c(F)c1] | 2.37, 436 | <100 nM |

-continued
| Example | Structure | LC-MS (Retention time (min), m/z) | IRAK-4 IC$_{50}$ (nM) |
| --- | --- | --- | --- |
| 62 | 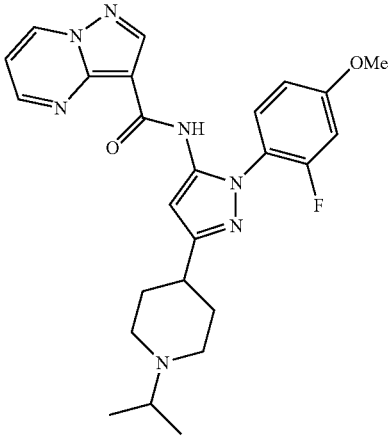 [SMILES: COc1ccc(-n2nc(C3CCN(C(C)C)CC3)cc2NC(=O)c2cnn3cccnc23)c(F)c1] | 2.39, 478 | <100 nM |
| 63 | 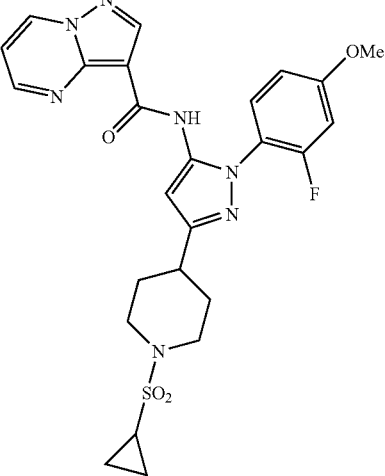 | 3.80, 540 | <100 nM |
| 64 | 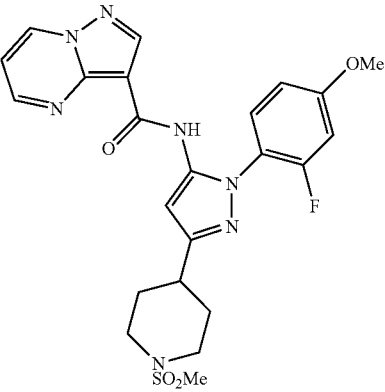 | 3.58, 514 | <100 nM |

-continued
| Example | Structure | LC-MS (Retention time (min), m/z) | IRAK-4 IC$_{50}$ (nM) |
|---|---|---|---|
| 65 | 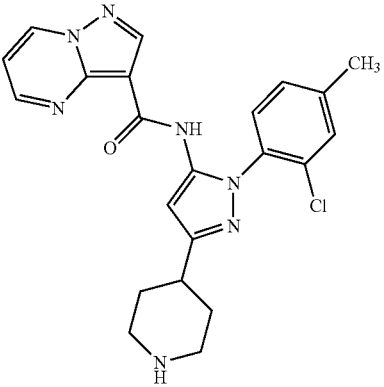 | 0.69, 436 | <1 μM |
| 66 | 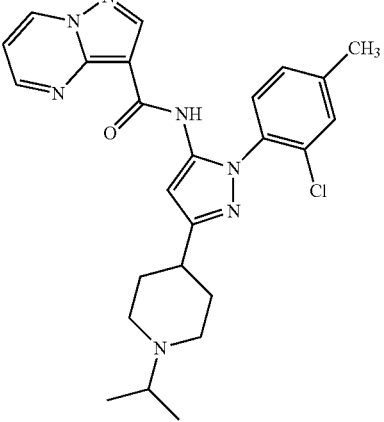 | 0.75, 478 | <1 μM |
| 67 | 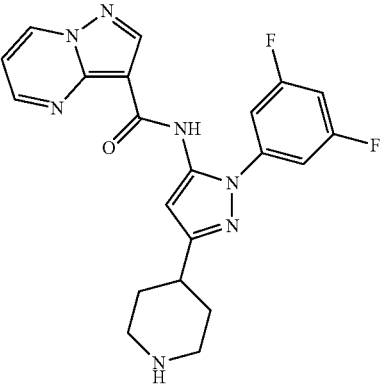 [SMILES: O=C(Nc1cc(C2CCNCC2)nn1-c1cc(F)cc(F)c1)c1cnn2cccnc12] | 2.73, 424 | >1 μM |

-continued
| Example | Structure | LC-MS (Retention time (min), m/z) | IRAK-4 IC$_{50}$ (nM) |
|---|---|---|---|
| 68 | 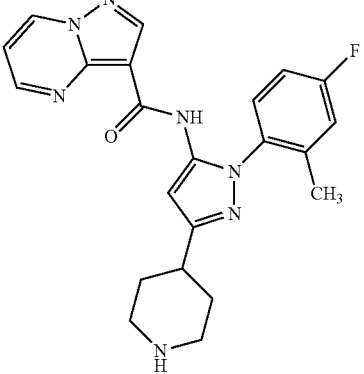 | 2.28, 420 | >1 μM |
| 69 | 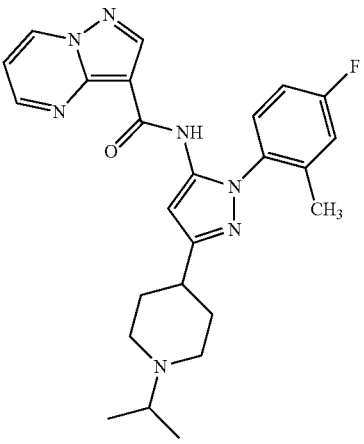 [SMILES: Cc1cc(F)ccc1-n1nc(C2CCN(C(C)C)CC2)cc1NC(=O)c1cnn2cccnc12] | 2.50, 462 | <1 μM |
| 70 | 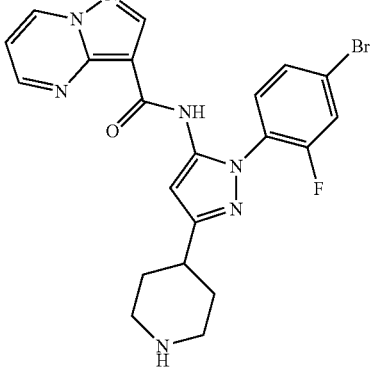 | 3.72, 486 | <1 μM |

-continued

| Example | Structure | LC-MS (Retention time (min), m/z) | IRAK-4 IC$_{50}$ (nM) |
| --- | --- | --- | --- |
| 71 | 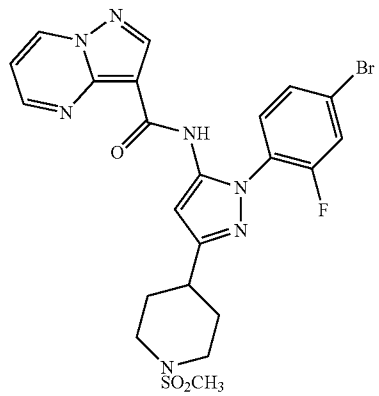 | 3.79, 564 | <1 μM |
| 72 | 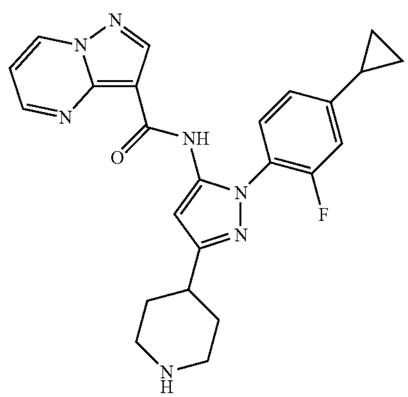 [SMILES: O=C(Nc1cc(C2CCNCC2)nn1-c1ccc(C2CC2)cc1F)c1cnn2cccnc12] | 2.58, 446 | <100 nM |
| 73 | 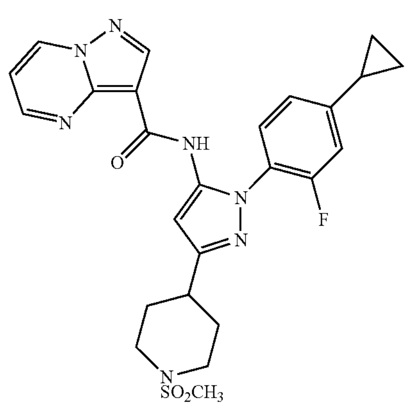 | 3.87, 524 | <100 nM |

| Example | Structure | LC-MS (Retention time (min), m/z) | IRAK-4 IC$_{50}$ (nM) |
|---|---|---|---|
| 74 | 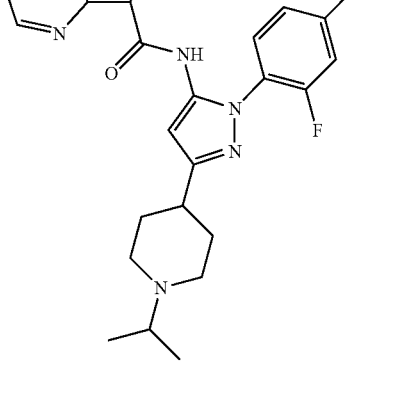 | 2.88, 488 | <100 nM |
| 75 | 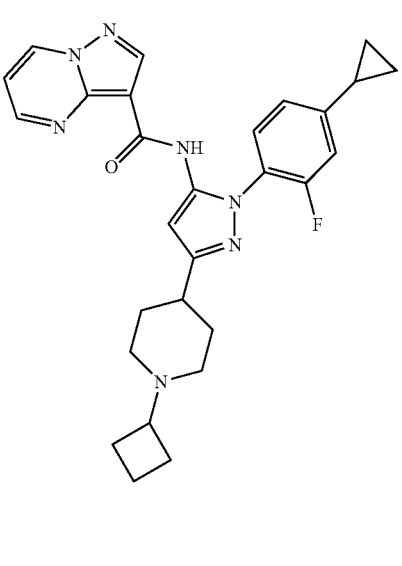 [SMILES: O=C(Nc1cc(C2CCN(C3CCC3)CC2)nn1-c1ccc(C2CC2)cc1F)c1cnn2cccnc12] | 0.82, 500 | <100 nM |
| 76 | 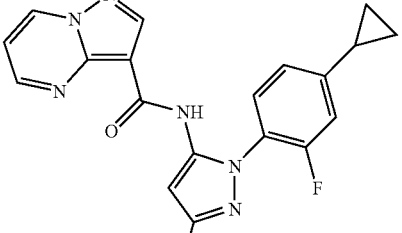 | 0.82, 528 | <1 μM |

| Example | Structure | LC-MS (Retention time (min), m/z) | IRAK-4 IC$_{50}$ (nM) |
|---|---|---|---|
| 77 | 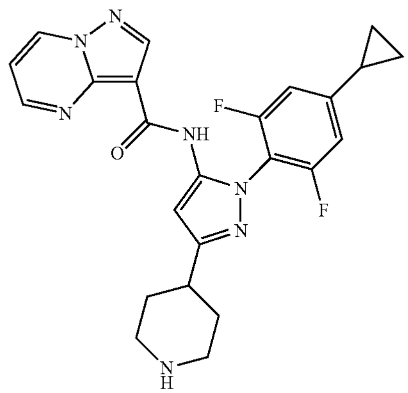 [SMILES: O=C(Nc1cc(C2CCNCC2)nn1-c1c(F)cc(C2CC2)cc1F)c1cnn2cccnc12] | 1.76, 464 | <100 nM |
| 78 | 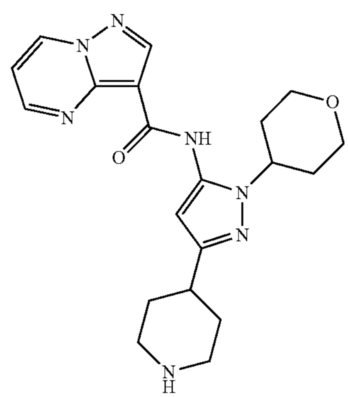 [SMILES: O=C(Nc1cc(C2CCNCC2)nn1C1CCOCC1)c1cnn2cccnc12] | 1.81, 474 | <1 μM |
| 79 | 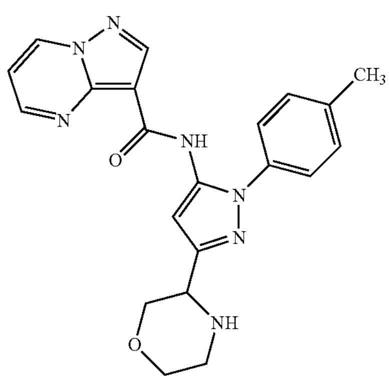 [SMILES: Cc1ccc(-n2nc(C3COCCN3)cc2NC(=O)c2cnn3cccnc23)cc1] | 1.71, 404 | <1 μM |
| 80 | 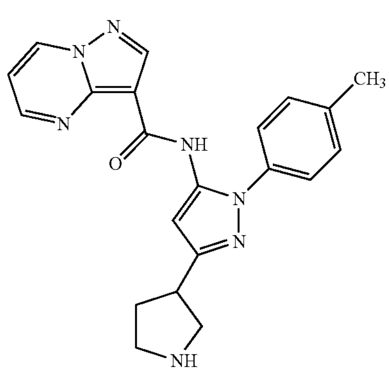 [SMILES: Cc1ccc(-n2nc(C3CCNC3)cc2NC(=O)c2cnn3cccnc23)cc1] | 1.52, 388 | <1 μM |

-continued
| Example | Structure | LC-MS (Retention time (min), m/z) | IRAK-4 IC$_{50}$ (nM) |
|---|---|---|---|
| 81 | 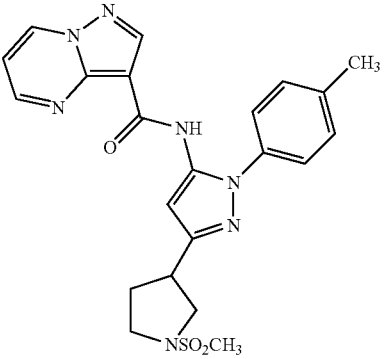 | 0.89, 488 | <1 μM |
| 82 | 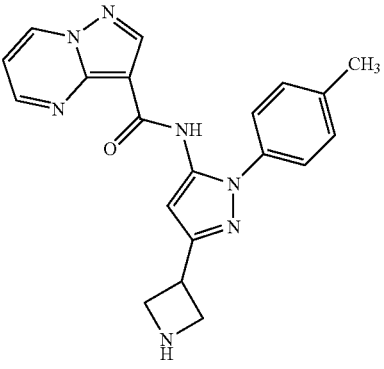 [SMILES: Cc1ccc(-n2nc(C3CNC3)cc2NC(=O)c2cnn3cccnc23)cc1] | 0.73, 374 | >1 μM |
| 83 | 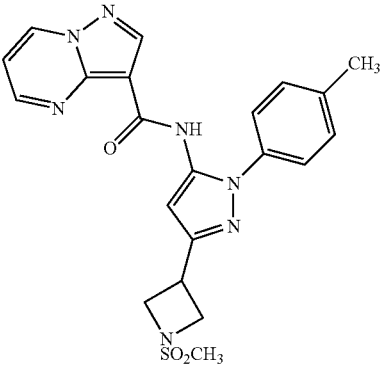 | 0.86, 452 | <1 μM |
| 84 | 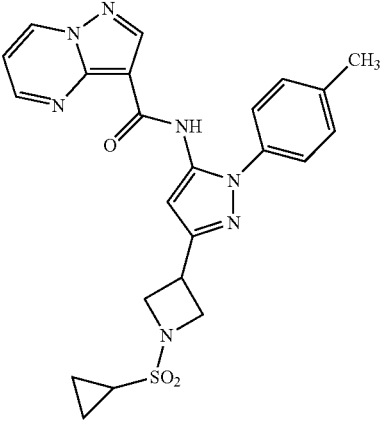 [SMILES: Cc1ccc(-n2nc(C3CN(S(=O)(=O)C4CC4)C3)cc2NC(=O)c2cnn3cccnc23)cc1] | 0.92, 478 | <1 μM |

-continued
| Example | Structure | LC-MS (Retention time (min), m/z) | IRAK-4 IC$_{50}$ (nM) |
| --- | --- | --- | --- |
| 85 | 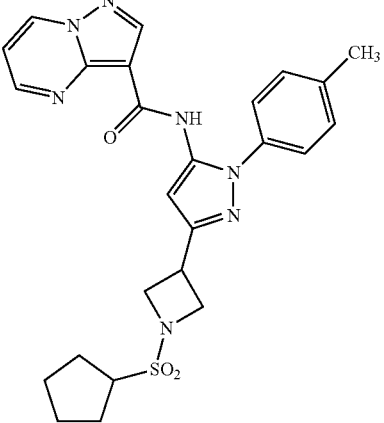 | 2.32, 506 | <1 μM |
| 86 | 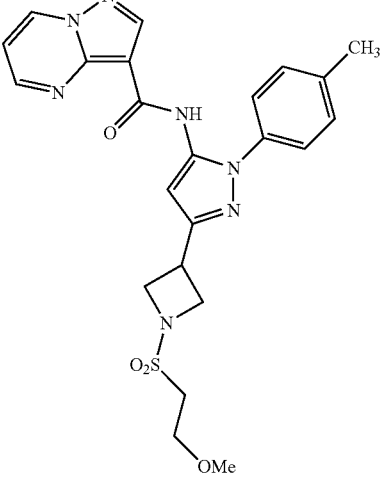 | 2.09, 496 | <1 μM |
| 87 | 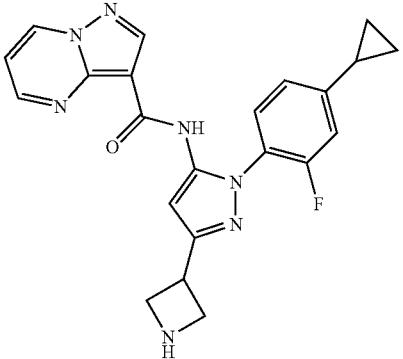 [SMILES: O=C(Nc1cc(C2CNC2)nn1-c1ccc(C2CC2)cc1F)c1cnn2cccnc12] | 0.71, 418 | <100 nM |

-continued

| Example | Structure | LC-MS (Retention time (min), m/z) | IRAK-4 IC$_{50}$ (nM) |
|---|---|---|---|
| 88 | 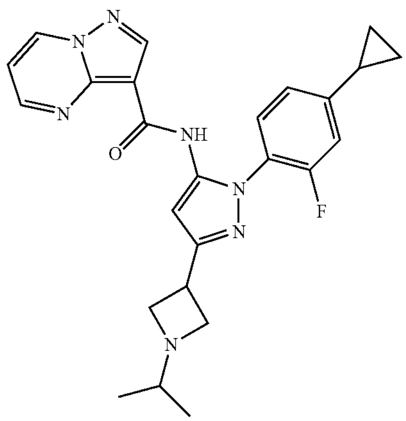 [SMILES: CC(C)N1CC(c2cc(NC(=O)c3cnn4cccnc34)n(-c3ccc(C4CC4)cc3F)n2)C1] | 0.79, 460 | <100 nM |
| 89 | 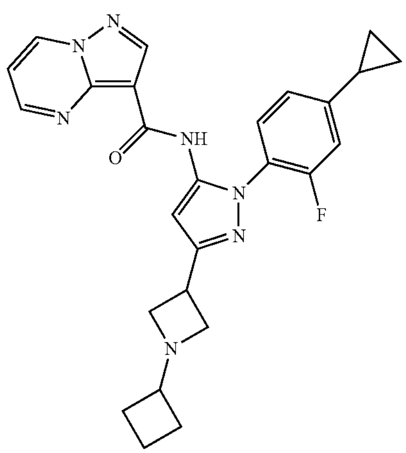 [SMILES: O=C(Nc1cc(C2CN(C3CCC3)C2)nn1-c1ccc(C2CC2)cc1F)c1cnn2cccnc12] | 0.79, 472 | <100 nM |
| 90 | 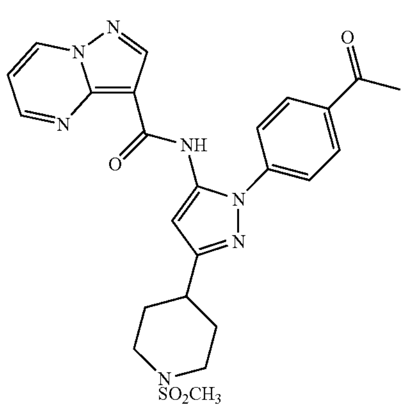 | 0.86, 508 | <1 μM |

| Example | Structure | LC-MS (Retention time (min), m/z) | IRAK-4 IC$_{50}$ (nM) |
|---|---|---|---|
| 91 | 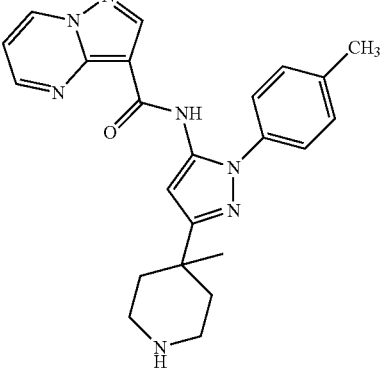 | n/a, 416 | <1 μM |
| 92 | 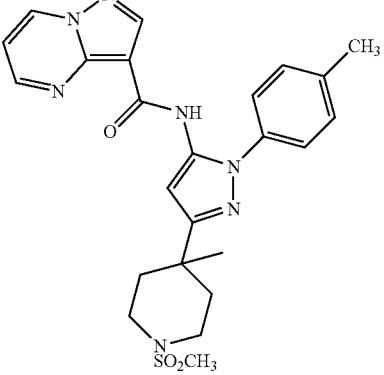 | n/a, 494 | >1 μM |
| 93 | 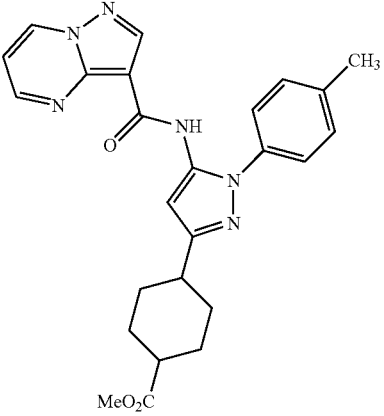 [SMILES: COC(=O)C1CCC(c2cc(NC(=O)c3cnn4cccnc34)n(-c3ccc(C)cc3)n2)CC1] | n/a, 459 | >1 μM |

-continued
| Example | Structure | LC-MS (Retention time (min), m/z) | IRAK-4 IC$_{50}$ (nM) |
|---|---|---|---|
| 94 | 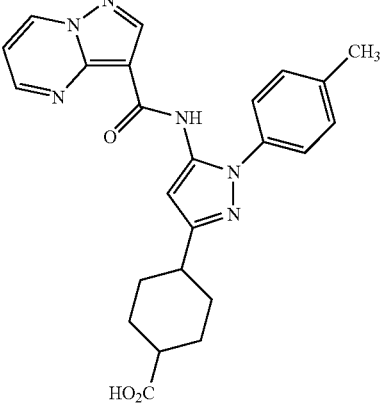 | n/a, 445 | >1 μM |
| 95 | 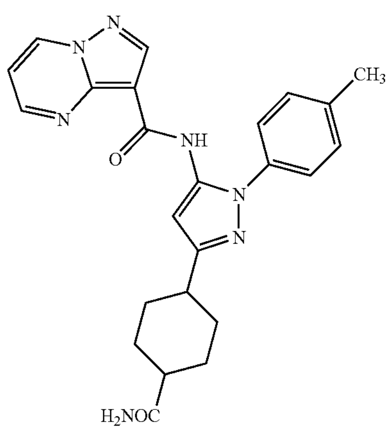 [SMILES: Cc1ccc(-n2nc(C3CCC(C(N)=O)CC3)cc2NC(=O)c2cnn3cccnc23)cc1] | n/a, 444 | <1 μM |
| 96 | 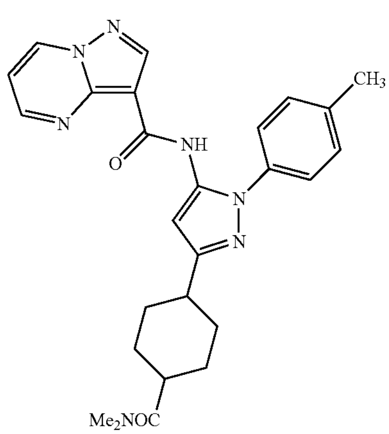 | n/a, 1.72, 472 | <100 nM |

| Example | Structure | LC-MS (Retention time (min), m/z) | IRAK-4 IC$_{50}$ (nM) |
|---|---|---|---|
| 97 | 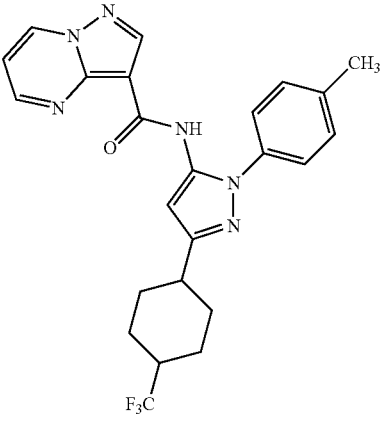 [SMILES: Cc1ccc(-n2nc(C3CCC(C(F)(F)F)CC3)cc2NC(=O)c2cnn3cccnc23)cc1] | n/a, 469 | >1 μM |
| 98 | 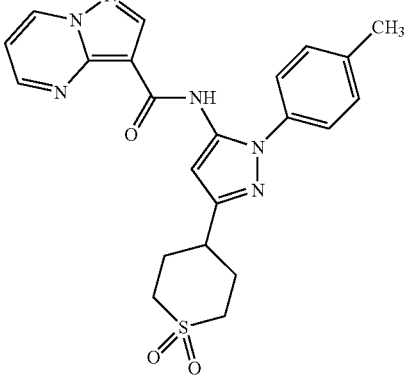 | 1.62, 451 | <1 μM |
| 99 | 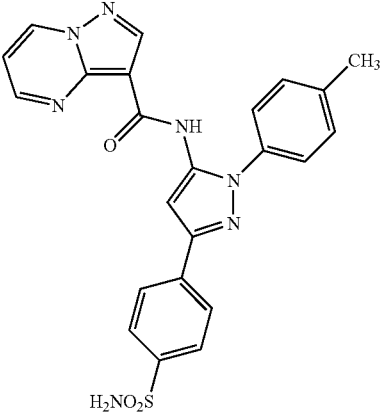 [SMILES: Cc1ccc(-n2nc(-c3ccc(S(N)(=O)=O)cc3)cc2NC(=O)c2cnn3cccnc23)cc1] | 4.47, 474 | <100 nM |

-continued

| Example | Structure | LC-MS (Retention time (min), m/z) | IRAK-4 IC$_{50}$ (nM) |
|---|---|---|---|
| 100 | 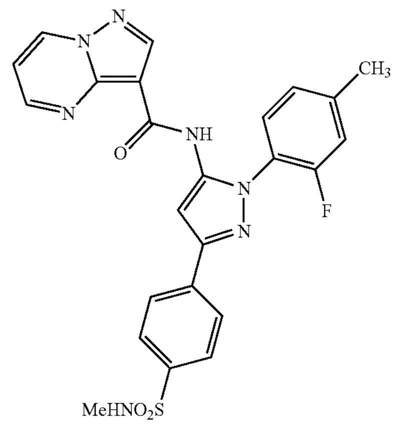 | 1.90, 506 | <100 nM |
| 101 | 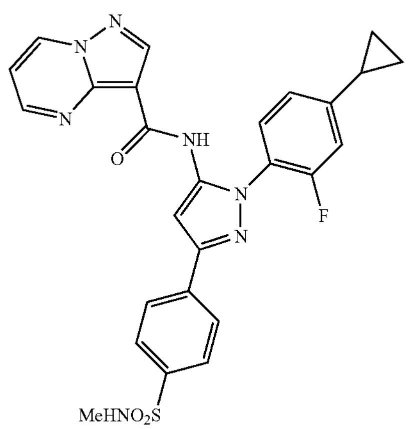 | 1.94, 531 | <100 nM |
| 102 | 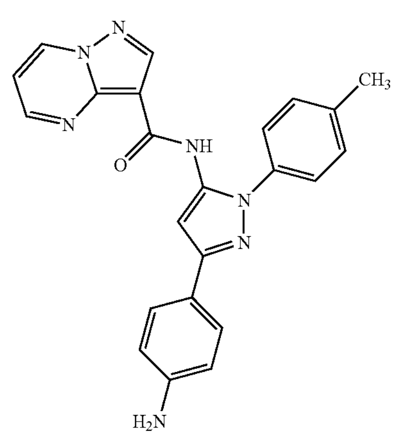 [SMILES: Cc1ccc(-n2nc(-c3ccc(N)cc3)cc2NC(=O)c2cnn3cccnc23)cc1] | 3.03 | <1 μM |

-continued

| Example | Structure | LC-MS (Retention time (min), m/z) | IRAK-4 IC$_{50}$ (nM) |
|---|---|---|---|
| 103 | 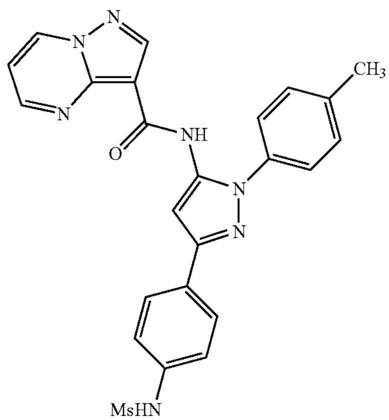 | 4.45, 488 | <100 nM |
| 104 | 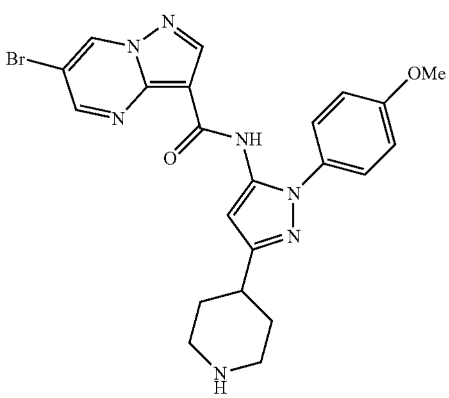 [SMILES: COc1ccc(-n2nc(C3CCNCC3)cc2NC(=O)c2cnn3cc(Br)cnc23)cc1] | 2.94, 498 | <1 μM |
| 105 | 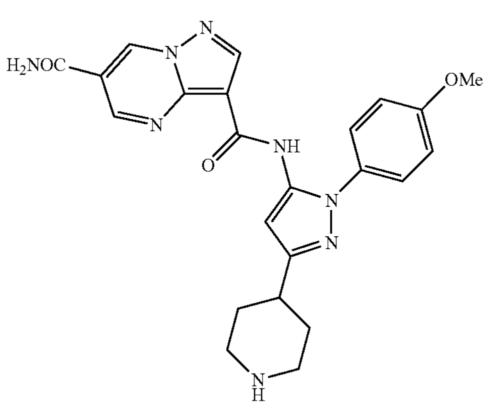 [SMILES: COc1ccc(-n2nc(C3CCNCC3)cc2NC(=O)c2cnn3cc(C(N)=O)cnc23)cc1] | 2.72, 461 | <100 nM |

-continued

| Example | Structure | LC-MS (Retention time (min), m/z) | IRAK-4 IC$_{50}$ (nM) |
|---------|-----------|-----------------------------------|----------------------|
| 106 | 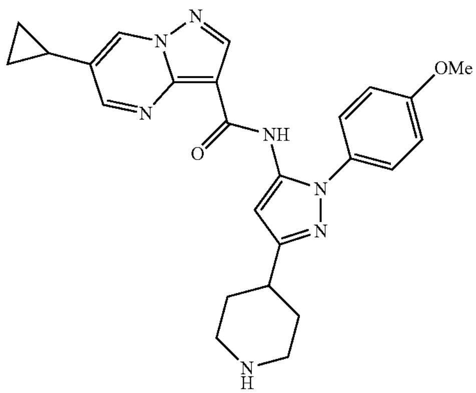 [SMILES: COc1ccc(-n2nc(C3CCNCC3)cc2NC(=O)c2cnn3cc(C4CC4)cnc23)cc1] | 5.72, 510 | <1 μm |
| 107 | 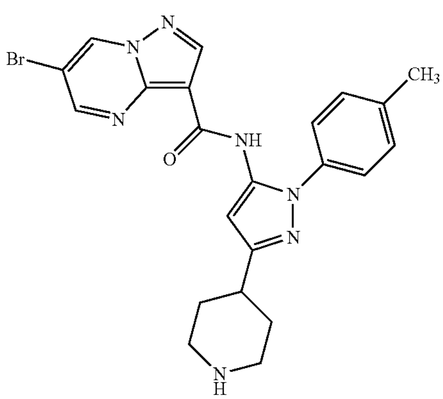 [SMILES: Cc1ccc(-n2nc(C3CCNCC3)cc2NC(=O)c2cnn3cc(Br)cnc23)cc1] | 3.34, 480 | <1 μm |
| 108 | 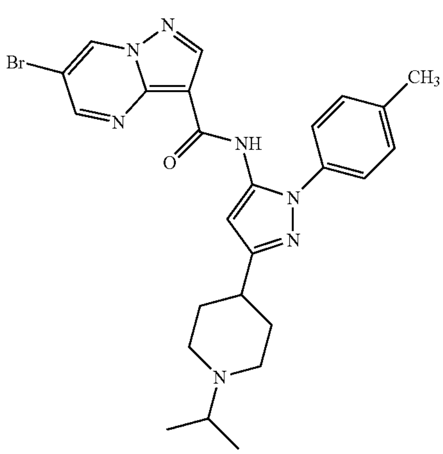 [SMILES: Cc1ccc(-n2nc(C3CCN(C(C)C)CC3)cc2NC(=O)c2cnn3cc(Br)cnc23)cc1] | n/a, 522 | <100 nM |

-continued

| Example | Structure | LC-MS (Retention time (min), m/z) | IRAK-4 IC$_{50}$ (nM) |
|---|---|---|---|
| 109 | 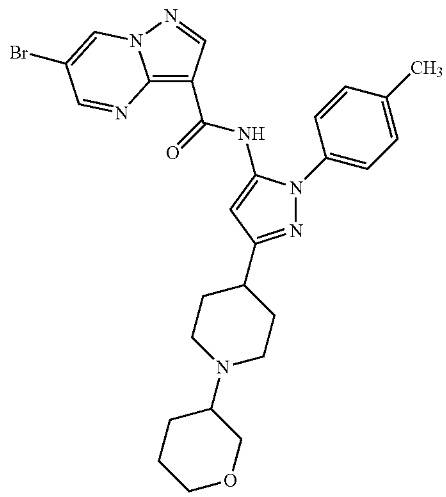 [SMILES: Cc1ccc(-n2nc(C3CCN(C4CCCOC4)CC3)cc2NC(=O)c2cnn3cc(Br)cnc23)cc1] | n/a, 564 | <100 nM |
| 110 | 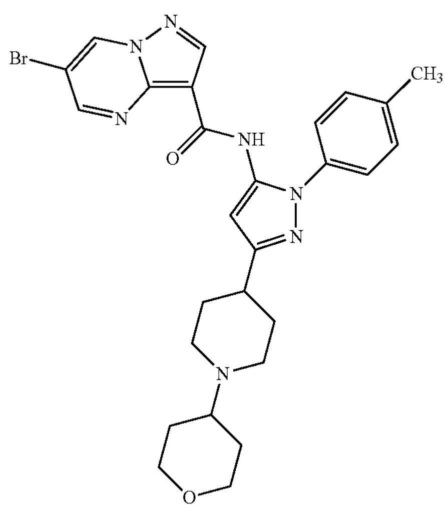 [SMILES: Cc1ccc(-n2nc(C3CCN(C4CCOCC4)CC3)cc2NC(=O)c2cnn3cc(Br)cnc23)cc1] | n/a, 564 | <100 nM |
| 111 | 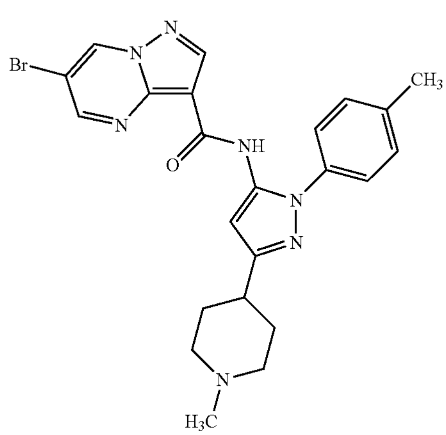 [SMILES: Cc1ccc(-n2nc(C3CCN(C)CC3)cc2NC(=O)c2cnn3cc(Br)cnc23)cc1] | n/a, 494 | <1 μM |

-continued

| Example | Structure | LC-MS (Retention time (min), m/z) | IRAK-4 IC$_{50}$ (nM) |
| --- | --- | --- | --- |
| 112 | 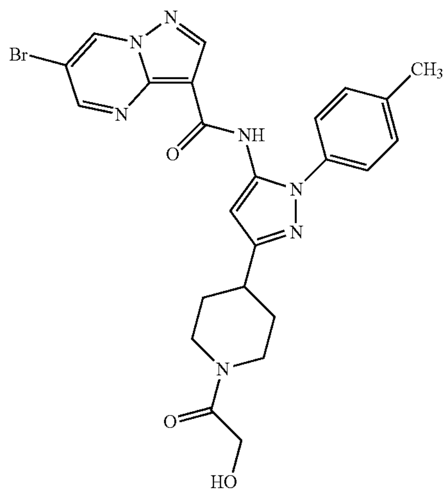 [SMILES: Cc1ccc(-n2nc(C3CCN(C(=O)CO)CC3)cc2NC(=O)c2cnn3cc(Br)cnc23)cc1] | 538 | <1 μM |
| 113 | 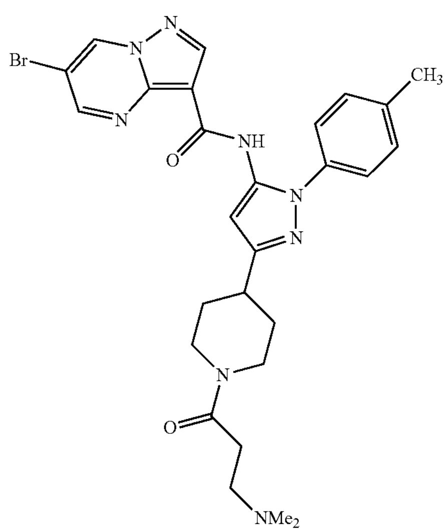 | 2.16, 579 | <100 nM |
| 114 | 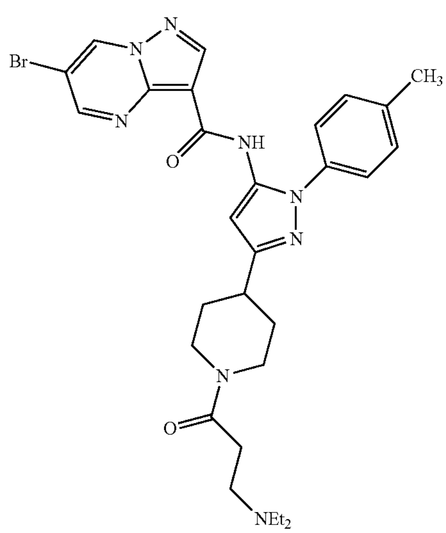 | 2.23, 607 | <100 nM |

| Example | Structure | LC-MS (Retention time (min), m/z) | IRAK-4 IC$_{50}$ (nM) |
|---|---|---|---|
| 115 | 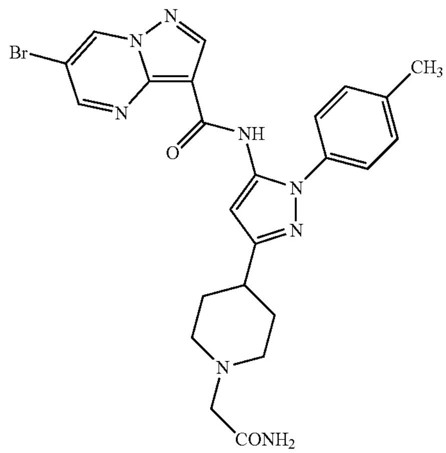 [SMILES: Cc1ccc(-n2nc(C3CCN(CC(N)=O)CC3)cc2NC(=O)c2cnn3cc(Br)cnc23)cc1] | 1.94, 537 | <100 nM |
| 116 | 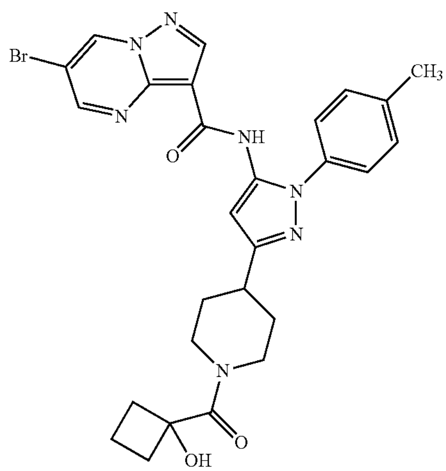 [SMILES: Cc1ccc(-n2nc(C3CCN(C(=O)C4(O)CCC4)CC3)cc2NC(=O)c2cnn3cc(Br)cnc23)cc1] | 2.62, 578 | <100 nM |
| 117 | 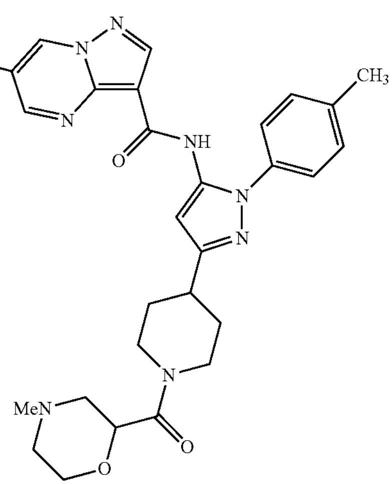 | 2.33, 607 | <1 μM |

-continued

| Example | Structure | LC-MS (Retention time (min), m/z) | IRAK-4 IC$_{50}$ (nM) |
|---------|-----------|-----------------------------------|------------------------|
| 118 | 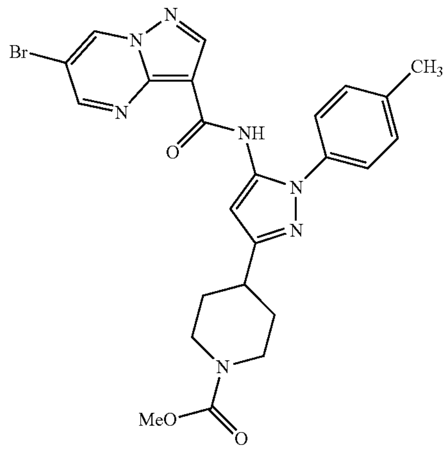 [SMILES: COC(=O)N1CCC(c2cc(NC(=O)c3cnn4cc(Br)cnc34)n(-c3ccc(C)cc3)n2)CC1] | 0.90, 538 | <100 nM |
| 119 | 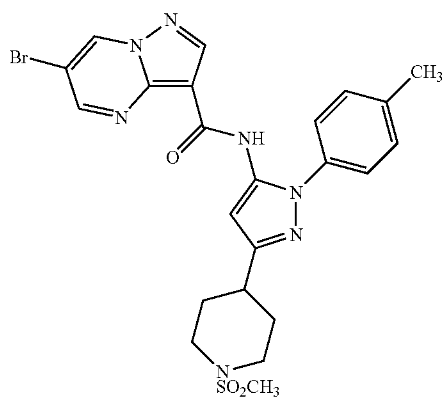 | 5.05, 588 | <1 μM |
| 120 | 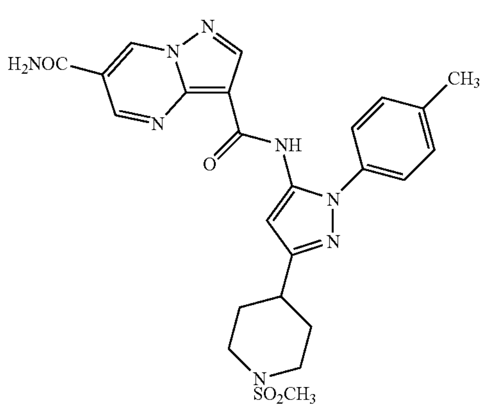 | 4.41, 523 | <100 nM |

| Example | Structure | LC-MS (Retention time (min), m/z) | IRAK-4 IC$_{50}$ (nM) |
|---|---|---|---|
| 121 | 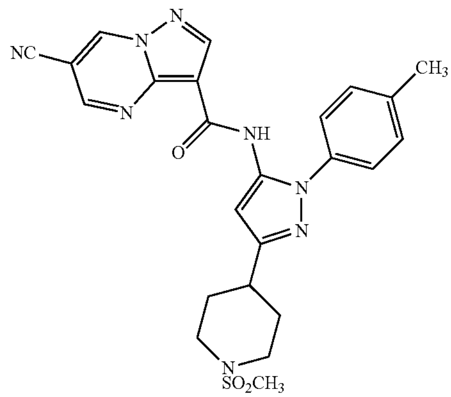 | 4.50, 505 | <1 μM |
| 122 | 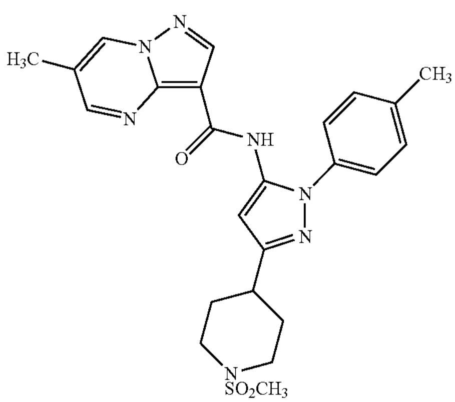 | 2.71, 416 | <1 μM |
| 123 | 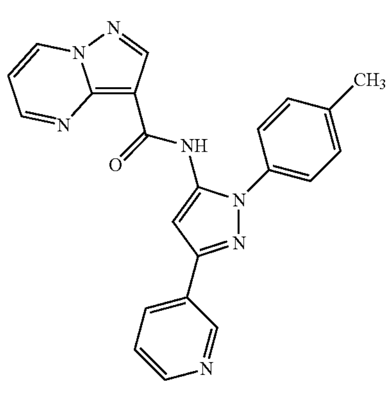 [SMILES: Cc1ccc(-n2nc(-c3cccnc3)cc2NC(=O)c2cnn3cccnc23)cc1] | 2.98, 396 | <100 nM |

| Example | Structure | LC-MS (Retention time (min), m/z) | IRAK-4 IC$_{50}$ (nM) |
|---|---|---|---|
| 124 | 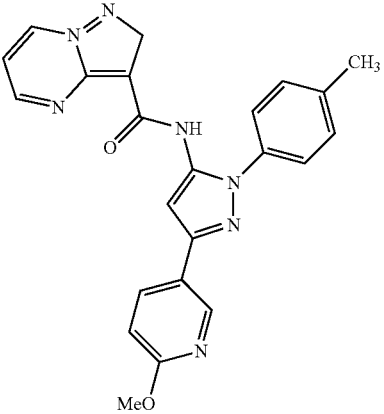 | 4.73, 426 | <1 μM |
| 125 | 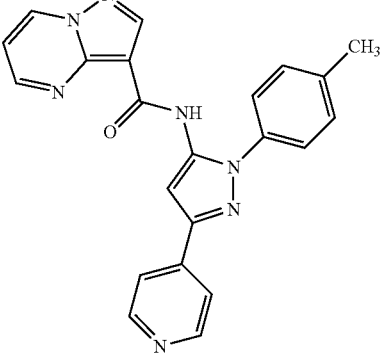 | 3.45, 396 | <100 nM |
| 126 | 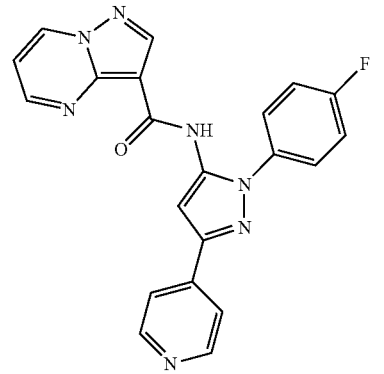 [SMILES: O=C(Nc1cc(-c2ccncc2)nn1-c1ccc(F)cc1)c1cnn2cccnc12] | 2.61, 400 | <1 μM |
| 127 | 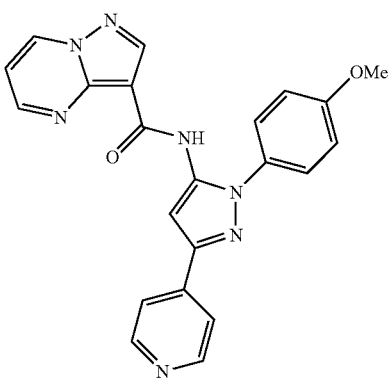 [SMILES: COc1ccc(-n2nc(-c3ccncc3)cc2NC(=O)c2cnn3cccnc23)cc1] | 2.85, 412 | <1 μM |

| Example | Structure | LC-MS (Retention time (min), m/z) | IRAK-4 IC$_{50}$ (nM) |
| --- | --- | --- | --- |
| 128 | 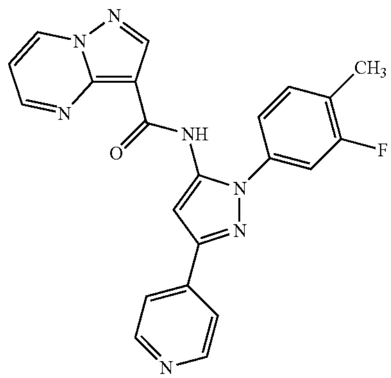 [SMILES: Cc1ccc(-n2nc(-c3ccncc3)cc2NC(=O)c2cnn3cccnc23)cc1F] | 2.79, 414 | <1 μM |
| 129 | 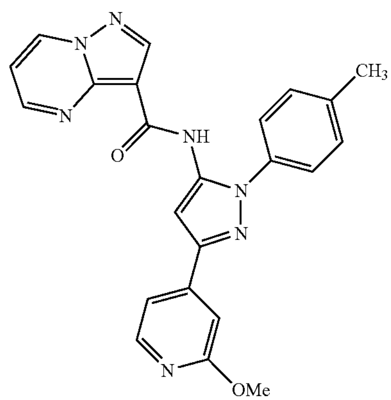 [SMILES: COc1cc(-c2cc(NC(=O)c3cnn4cccnc34)n(-c3ccc(C)cc3)n2)ccn1] | 3.90, 426 | <1 μM |
| 130 | 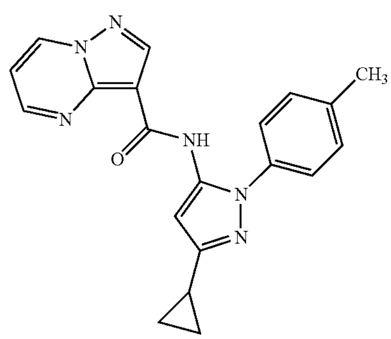 [SMILES: Cc1ccc(-n2nc(C3CC3)cc2NC(=O)c2cnn3cccnc23)cc1] | 3.87, 359 | <1 μM |
| 131 | 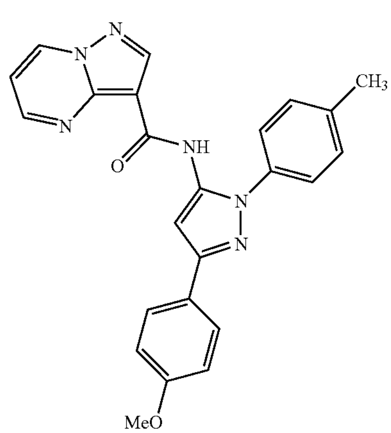 [SMILES: COc1ccc(-c2cc(NC(=O)c3cnn4cccnc34)n(-c3ccc(C)cc3)n2)cc1] | 5.32, 425 | <1 μM |

-continued

| Example | Structure | LC-MS (Retention time (min), m/z) | IRAK-4 IC$_{50}$ (nM) |
|---|---|---|---|
| 132 | pyrazolo[1,5-a]pyrimidine-3-carboxamide, N-[1-(3-fluorophenyl)-3-(4-methoxyphenyl)-1H-pyrazol-5-yl] | 5.28, 429 | <1 µM |
| 133 | pyrazolo[1,5-a]pyrimidine-3-carboxamide, N-[3-(3-methoxy-4-methoxyphenyl)-1-(4-methylphenyl)-1H-pyrazol-5-yl] | 4.03, 455 | <100 nM |
| 134 | pyrazolo[1,5-a]pyrimidine-3-carboxamide, N-[3-(4-methylsulfonylphenyl)-1-(4-methylphenyl)-1H-pyrazol-5-yl] | 4.11, 473 | <100 nM |

| Example | Structure | LC-MS (Retention time (min), m/z) | IRAK-4 IC$_{50}$ (nM) |
|---|---|---|---|
| 135 | 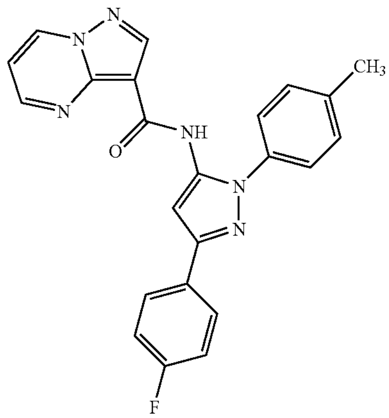 [SMILES: Cc1ccc(-n2nc(-c3ccc(F)cc3)cc2NC(=O)c2cnn3cccnc23)cc1] | 4.71, 413 | >1 μM |
| 136 | 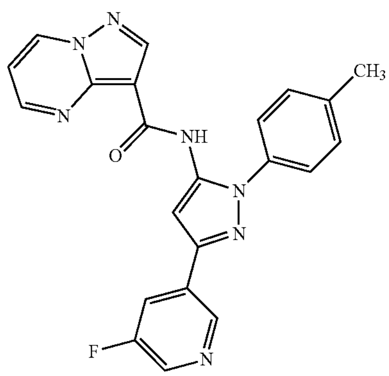 [SMILES: Cc1ccc(-n2nc(-c3cncc(F)c3)cc2NC(=O)c2cnn3cccnc23)cc1] | 3.40, 414 | >1 μM |
| 137 | 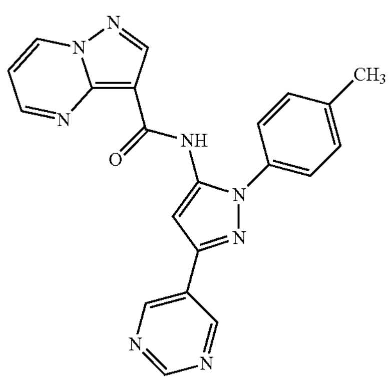 [SMILES: Cc1ccc(-n2nc(-c3cncnc3)cc2NC(=O)c2cnn3cccnc23)cc1] | 3.53, 397 | >1 μM |
| 138 | 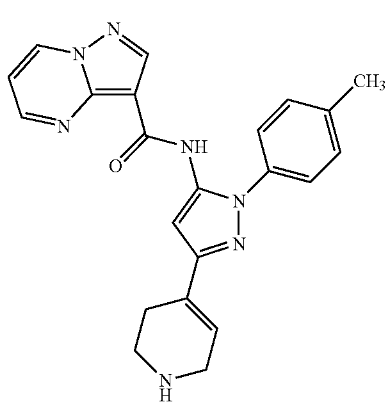 [SMILES: Cc1ccc(-n2nc(C3=CCNCC3)cc2NC(=O)c2cnn3cccnc23)cc1] | 1.78, 400 | <100 nM |

-continued

| Example | Structure | LC-MS (Retention time (min), m/z) | IRAK-4 IC$_{50}$ (nM) |
|---------|-----------|-----------------------------------|----------------------|
| 139 | 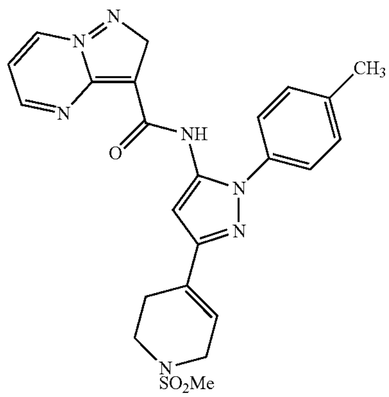 | 2.18, 478 | <100 nM |
| 140 | 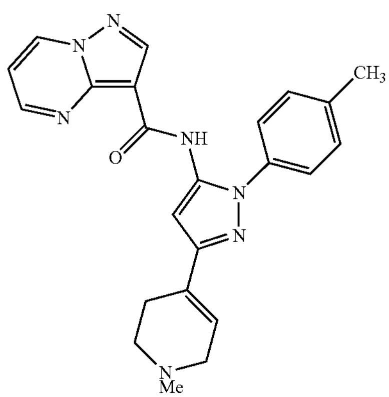 [SMILES: Cc1ccc(-n2nc(C3=CCN(C)CC3)cc2NC(=O)c2cnn3cccnc23)cc1] | 1.70, 414 | <100 nM |
| 141 | 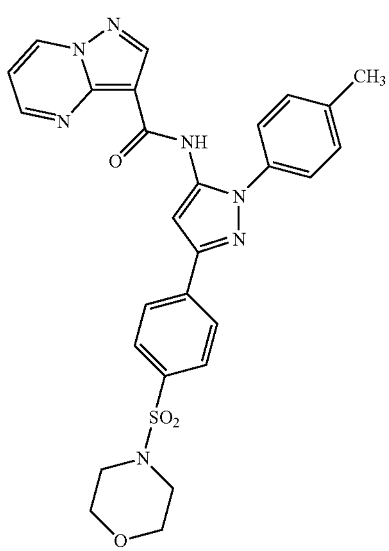 [SMILES: Cc1ccc(-n2nc(-c3ccc(S(=O)(=O)N4CCOCC4)cc3)cc2NC(=O)c2cnn3cccnc23)cc1] | 3.88, 480 | <100 nM |

-continued

| Example | Structure | LC-MS (Retention time (min), m/z) | IRAK-4 IC$_{50}$ (nM) |
|---|---|---|---|
| 142 | 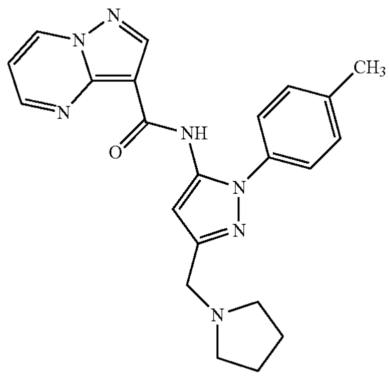 [SMILES: Cc1ccc(-n2nc(CN3CCCC3)cc2NC(=O)c2cnn3cccnc23)cc1] | 2.50, 402 | >1 μM |
| 143 | 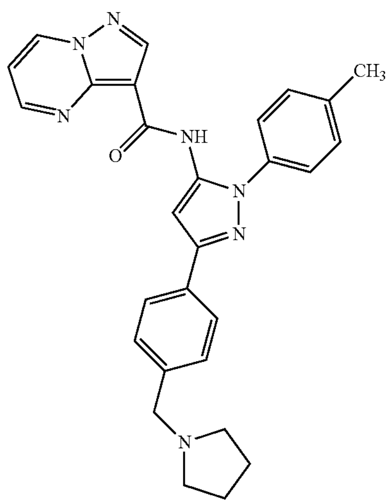 [SMILES: Cc1ccc(-n2nc(-c3ccc(CN4CCCC4)cc3)cc2NC(=O)c2cnn3cccnc23)cc1] | 0.82, 478 | <100 nM |
| 144 | 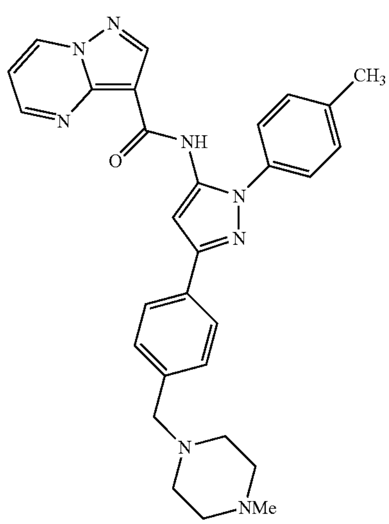 [SMILES: Cc1ccc(-n2nc(-c3ccc(CN4CCN(C)CC4)cc3)cc2NC(=O)c2cnn3cccnc23)cc1] | 0.71, 507 | <100 nM |

| Example | Structure | LC-MS (Retention time (min), m/z) | IRAK-4 IC$_{50}$ (nM) |
|---|---|---|---|
| 145 | 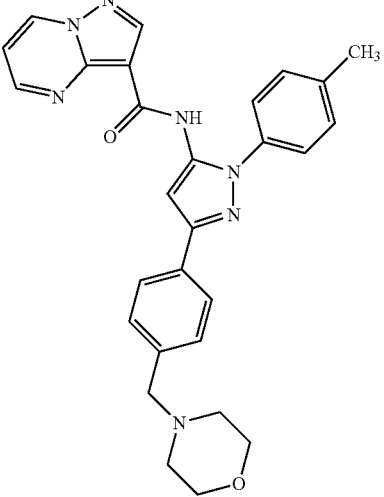 | 0.78, 494 | <100 nM |
| 146 | 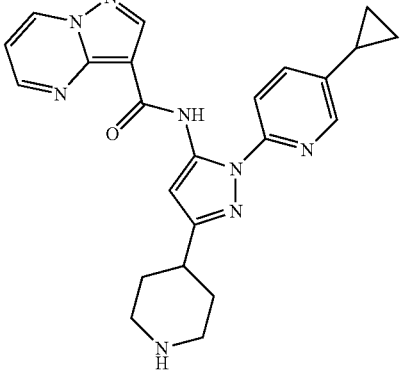 | 0.84, 429 | <100 nM |
| 147 | 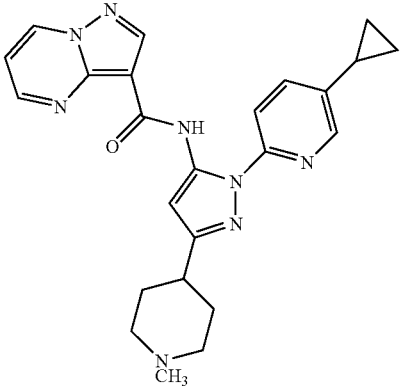 [SMILES: CN1CCC(c2cc(NC(=O)c3cnn4cccnc34)n(-c3ccc(C4CC4)cn3)n2)CC1] | 1.51, 443 | <100 nM |

-continued

| Example | Structure | LC-MS (Retention time (min), m/z) | IRAK-4 IC$_{50}$ (nM) |
|---|---|---|---|
| 148 | (pyrazolo[1,5-a]pyrimidine-3-carboxamide linked to 1-(5-cyclopropylpyridin-2-yl)-3-(1-cyclobutylpiperidin-4-yl)-1H-pyrazol-5-yl) | 0.94, 460 | <100 nM |
| 149 | (pyrazolo[1,5-a]pyrimidine-3-carboxamide linked to 1-(5-cyclopropylpyridin-2-yl)-3-(1-(methylsulfonyl)piperidin-4-yl)-1H-pyrazol-5-yl) | 1.01, 507 | <100 nM |
| 150 | (pyrazolo[1,5-a]pyrimidine-3-carboxamide linked to 1-(5-cyclopropylpyridin-2-yl)-3-(1-(cyclopropylsulfonyl)piperidin-4-yl)-1H-pyrazol-5-yl) | 1.07, 533 | <1 µM |

| Example | Structure | LC-MS (Retention time (min), m/z) | IRAK-4 IC$_{50}$ (nM) |
| --- | --- | --- | --- |
| 151 | 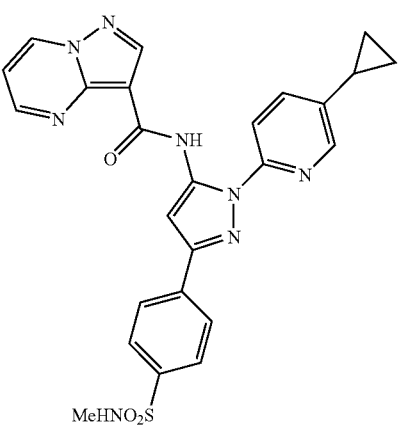 | 2.94, 515 | <100 nM |
| 152 | 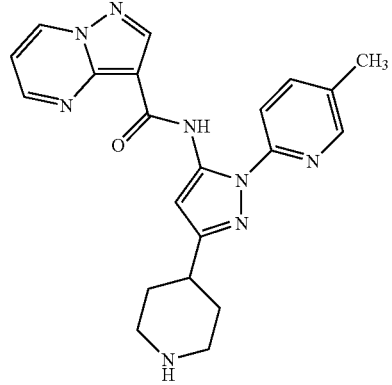 [SMILES: Cc1ccc(-n2nc(C3CCNCC3)cc2NC(=O)c2cnn3cccnc23)nc1] | 0.78, 403 | <100 nM |
| 153 | 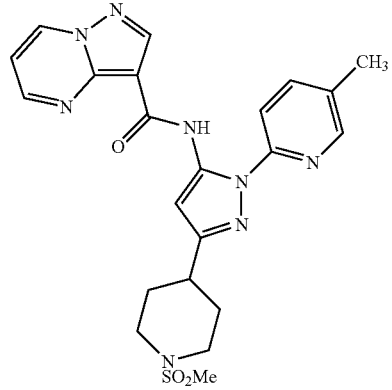 | 1.97, 480 | <100 nM |

-continued
| Example | Structure | LC-MS (Retention time (min), m/z) | IRAK-4 IC$_{50}$ (nM) |
| --- | --- | --- | --- |
| 154 | 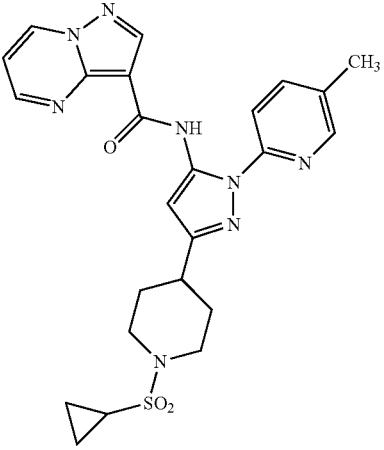 [SMILES: Cc1ccc(-n2nc(C3CCN(S(=O)(=O)C4CC4)CC3)cc2NC(=O)c2cnn3cccnc23)nc1] | 2.18, 529 | <100 nM |
| 155 | 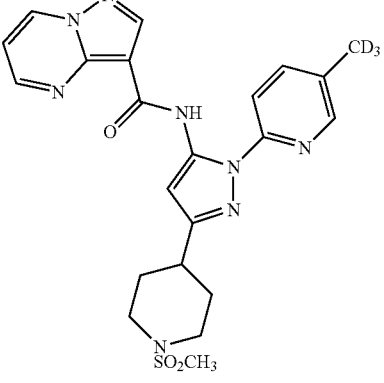 | 2.25, 484 | <100 nM |
| 156 | 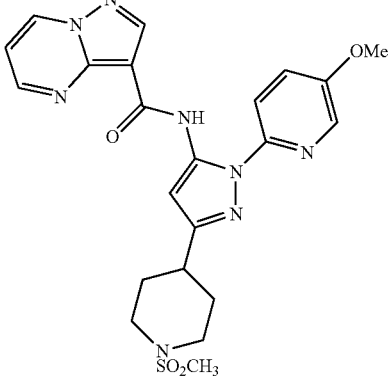 | 2.15, 519 | <1 μM |

| Example | Structure | LC-MS (Retention time (min), m/z) | IRAK-4 IC$_{50}$ (nM) |
| --- | --- | --- | --- |
| 157 | 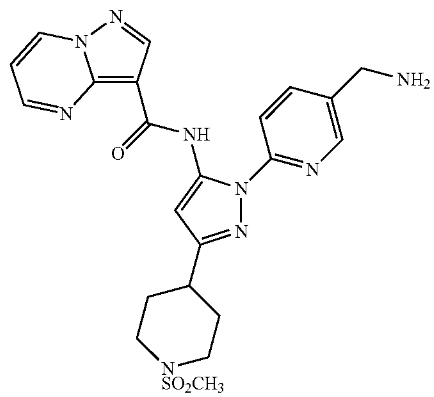 | 0.76, 518 | <100 nM |
| 158 | 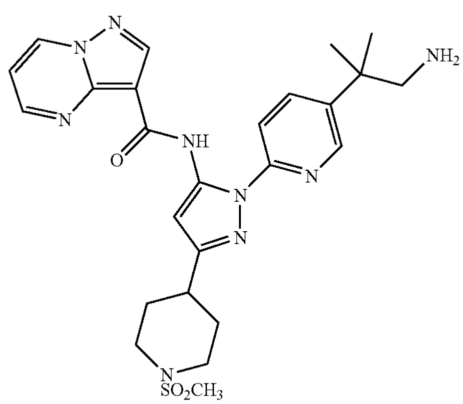 | 1.86, 538 | <100 nM |
| 159 | 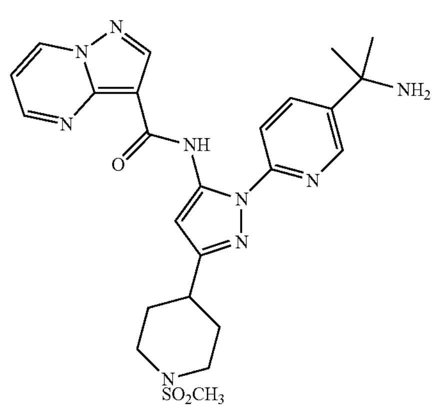 | 1.80, 524 | <100 nM |

-continued
| Example | Structure | LC-MS (Retention time (min), m/z) | IRAK-4 IC$_{50}$ (nM) |
| --- | --- | --- | --- |
| 160 | 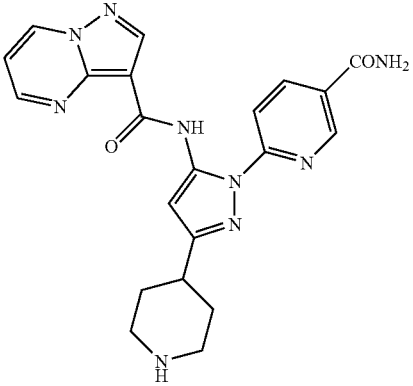 [SMILES: NC(=O)c1ccc(-n2nc(C3CCNCC3)cc2NC(=O)c2cnn3cccnc23)nc1] | 1.67, 432 | <1 μM |
| 161 | 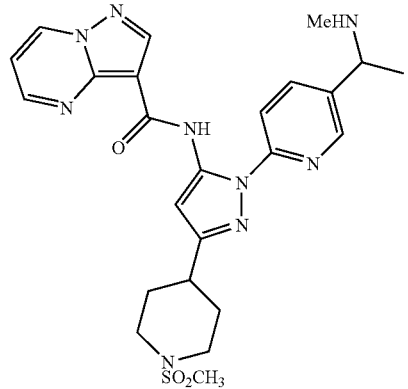 | 1.73, 523 | <1 μM |
| 162 | 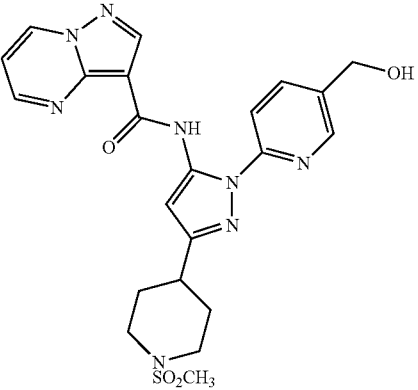 | 1.91, 519 | <100 nM |

| Example | Structure | LC-MS (Retention time (min), m/z) | IRAK-4 IC$_{50}$ (nM) |
|---|---|---|---|
| 163 | 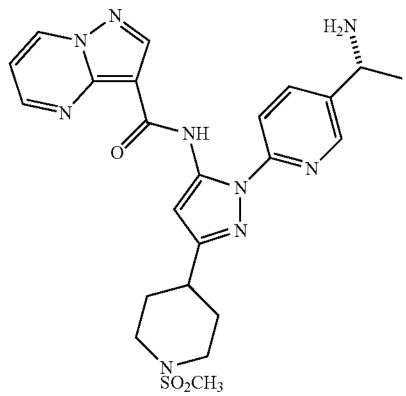 | 1.76, 510 | <100 nM |
| 164 | 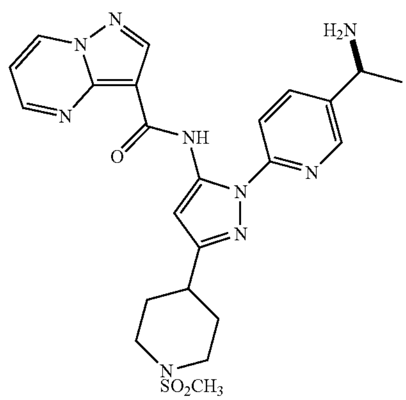 | 1.76, 510 | <100 nM |
| 165 | 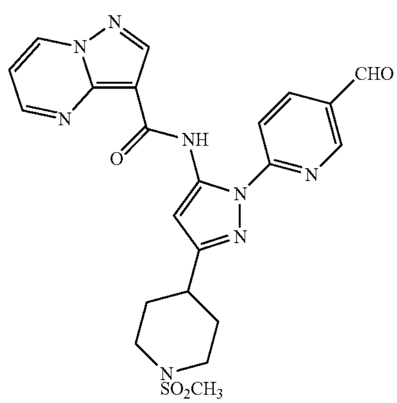 | 2.11, 495 | <100 nM |
| 166 | 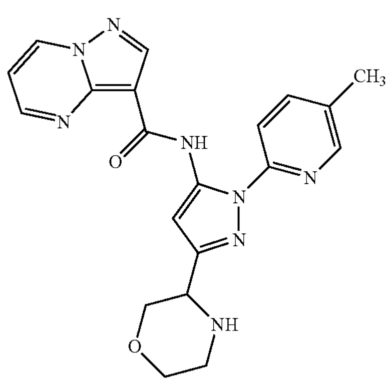 | 1.75, 405 | <1 μM |

-continued
| Example | Structure | LC-MS (Retention time (min), m/z) | IRAK-4 IC$_{50}$ (nM) |
|---|---|---|---|
| 167 | 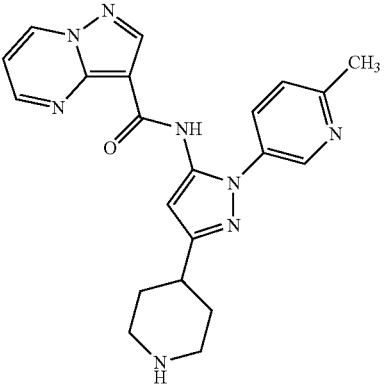 [SMILES: Cc1ccc(-n2nc(C3CCNCC3)cc2NC(=O)c2cnn3cccnc23)cn1] | 1.19, 403 | >1 μM |
| 168 | 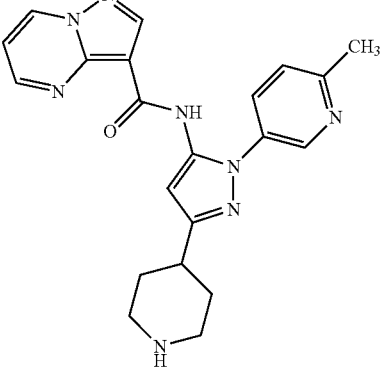 | 1.43, 503 | <1 μM |
| 169 | 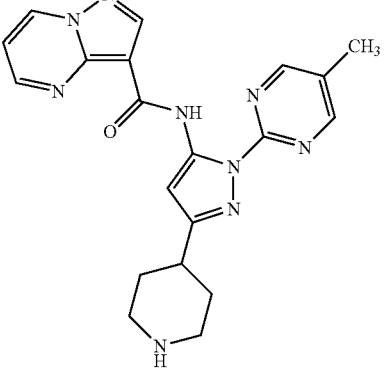 | 1.00, 504 | >1 μM |
| 170 | 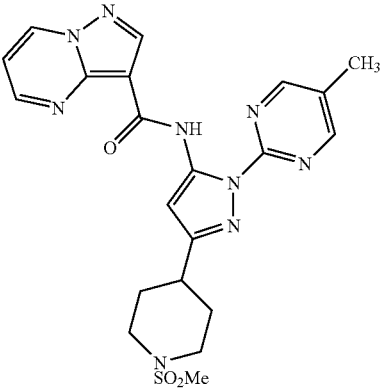 | 0.82, 482 | <100 nM |

| Example | Structure | LC-MS (Retention time (min), m/z) | IRAK-4 IC$_{50}$ (nM) |
|---------|-----------|-----------------------------------|----------------------|
| 171 | 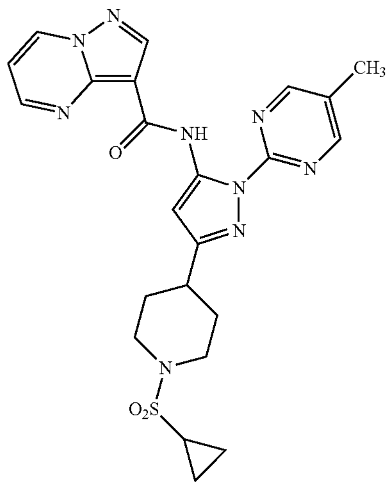 [SMILES: Cc1cnc(-n2nc(C3CCN(S(=O)(=O)C4CC4)CC3)cc2NC(=O)c2cnn3cccnc23)nc1] | 1.83, 508 | <1 μM |
| 172 | 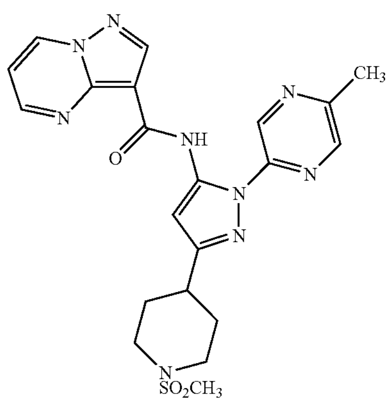 | 2.38, 504 | >1 μM |
| 173 | 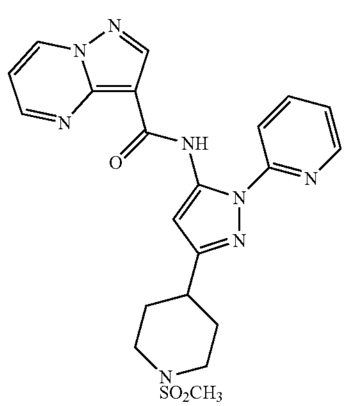 | 2.01, 467 | <1 μM |

-continued

| Example | Structure | LC-MS (Retention time (min), m/z) | IRAK-4 IC$_{50}$ (nM) |
|---|---|---|---|
| 174 | 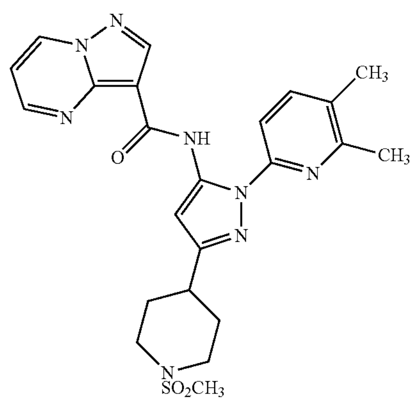 | 2.12, 495 | <1 μM |
| 175 | 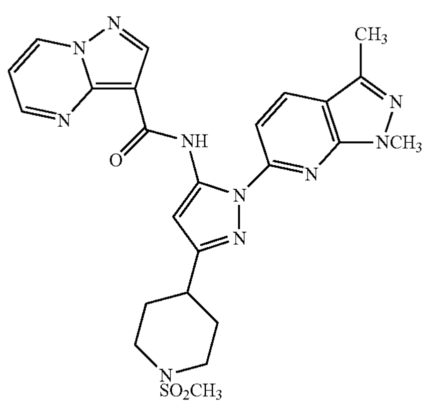 | 2.12, 535 | <1 μM |
| 176 | 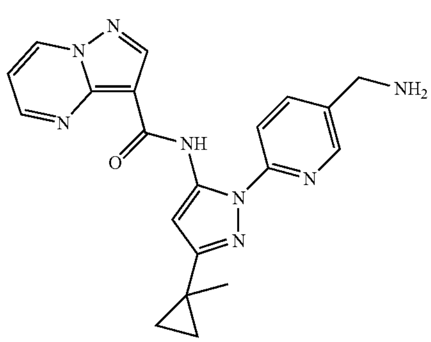 [SMILES: CC1(c2cc(NC(=O)c3cnn4cccnc34)n(-c3ccc(CN)cn3)n2)CC1] | 1.87, 389 | <100 nM |

-continued
| Example | Structure | LC-MS (Retention time (min), m/z) | IRAK-4 IC$_{50}$ (nM) |
|---|---|---|---|
| 177 | 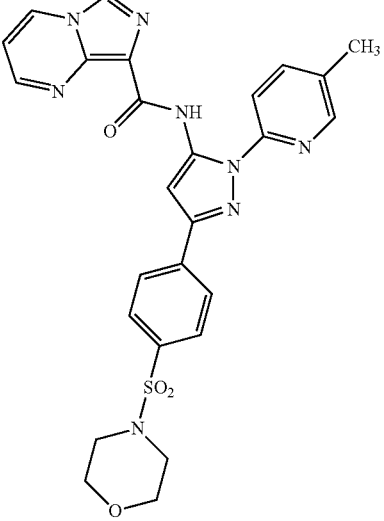 | 2.53, 545 | <100 nM |
| 178 | 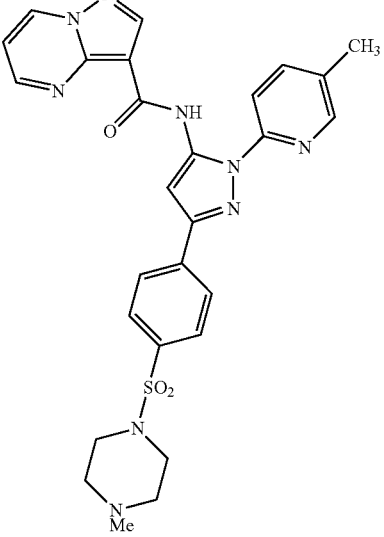 | 2.10, 558 | <100 nM |
| 179 | 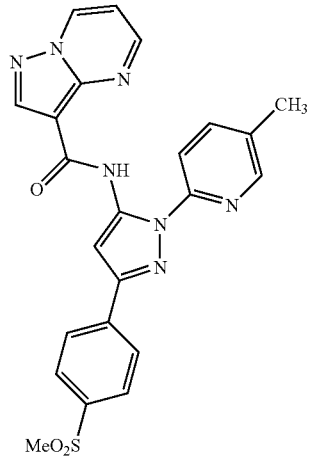 [SMILES: Cc1ccc(-n2nc(-c3ccc(S(C)(=O)=O)cc3)cc2NC(=O)c2cnn3cccnc23)nc1] | 1.05, 474 | <100 nM |

-continued
| Example | Structure | LC-MS (Retention time (min), m/z) | IRAK-4 IC$_{50}$ (nM) |
|---|---|---|---|
| 180 | 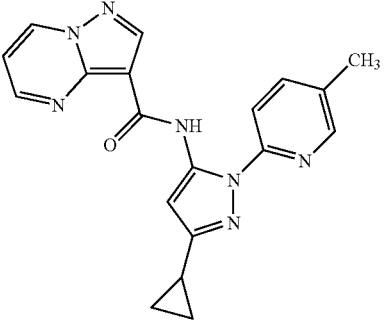 | 1.02, 360 | >1 μM |
| 181 | 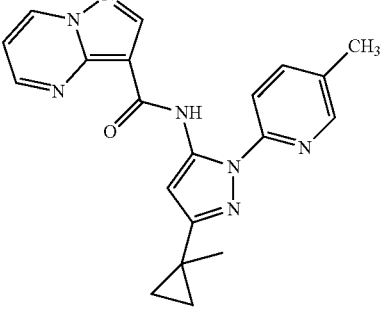 | 2.46, 374 | >1 μM |
| 182 | 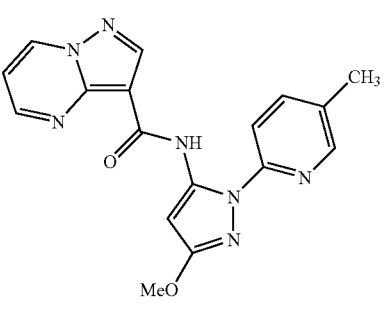 [SMILES: COc1cc(NC(=O)c2cnn3cccnc23)n(-c2ccc(C)cn2)n1] | 2.36, 350 | <1 μM |
| 183 | 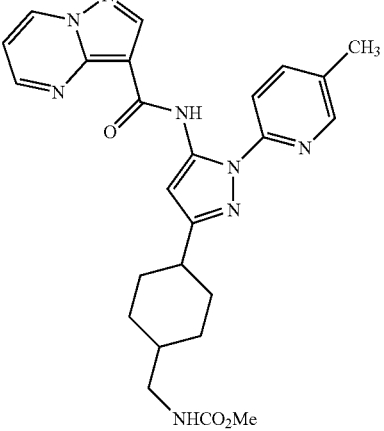 | n/a, 489 | <1 μM |

-continued

| Example | Structure | LC-MS (Retention time (min), m/z) | IRAK-4 IC$_{50}$ (nM) |
|---|---|---|---|
| 184 | 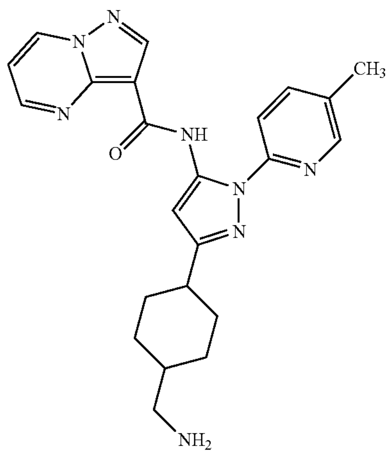 [SMILES: Cc1ccc(-n2nc(C3CCC(CN)CC3)cc2NC(=O)c2cnn3cccnc23)nc1] | 1.49, 431 | <100 nM |
| 185 | 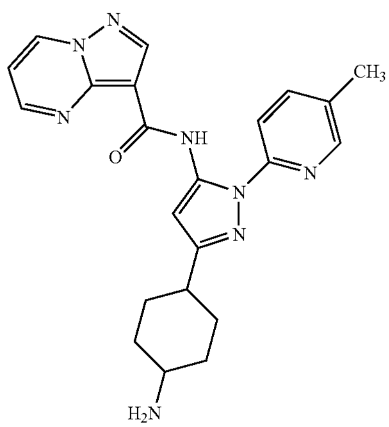 [SMILES: Cc1ccc(-n2nc(C3CCC(N)CC3)cc2NC(=O)c2cnn3cccnc23)nc1] | 1.50, 417 | <100 nM |
| 186 | 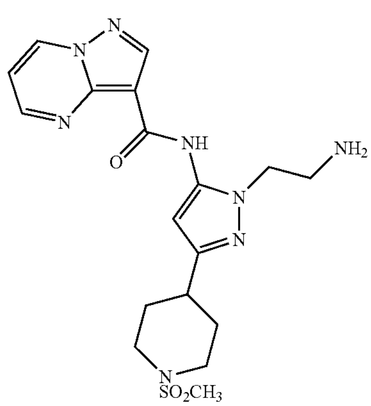 | 1.52, 469 | <1 μM |

| Example | Structure | LC-MS (Retention time (min), m/z) | IRAK-4 IC$_{50}$ (nM) |
|---|---|---|---|
| 187 | 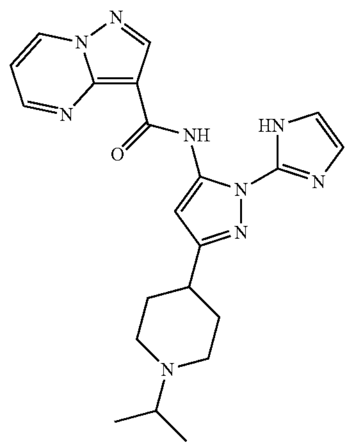 [SMILES: CC(C)N1CCC(c2cc(NC(=O)c3cnn4cccnc34)n(-c3ncc[nH]3)n2)CC1] | 1.66, 420 | <1 μM |
| 188 | 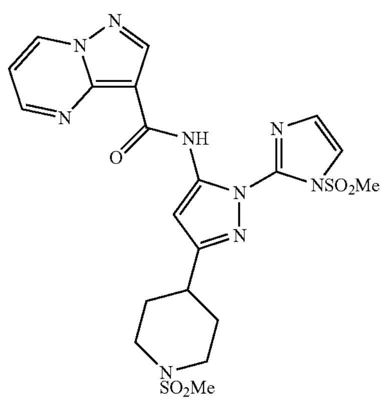 | 1.92, 534 | >1 μM |
| 189 | 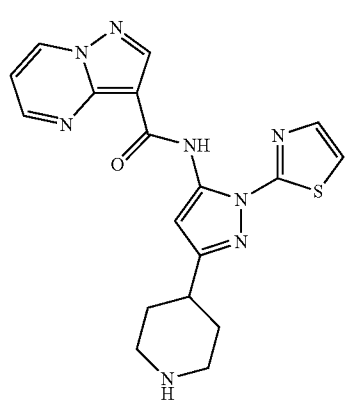 [SMILES: O=C(Nc1cc(C2CCNCC2)nn1-c1nccs1)c1cnn2cccnc12] | 1.78, 395 | <100 nM |

-continued

| Example | Structure | LC-MS (Retention time (min), m/z) | IRAK-4 IC$_{50}$ (nM) |
| --- | --- | --- | --- |
| 190 | 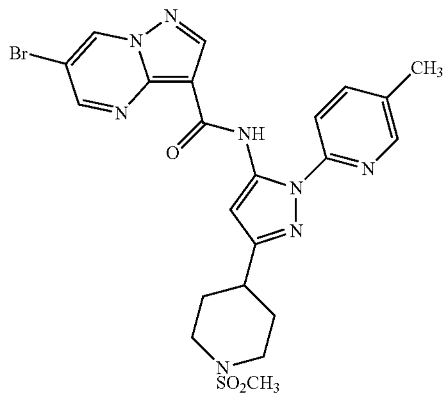 | 2.46, 433 | <100 nM |
| 191 | 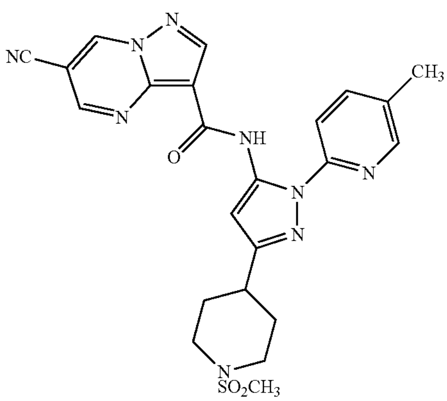 | 2.15, 506 | <100 nM |
| 192 | 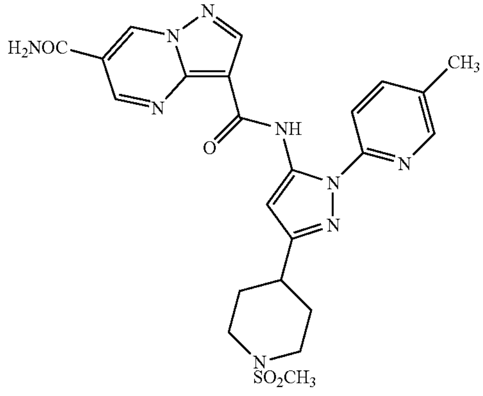 | 2.11, 525 | <100 nM |

-continued
| Example | Structure | LC-MS (Retention time (min), m/z) | IRAK-4 IC$_{50}$ (nM) |
|---|---|---|---|
| 193 | 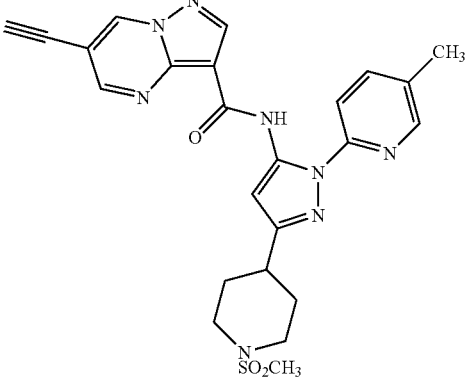 | 2.04, 567 | <100 nM |
| 194 | 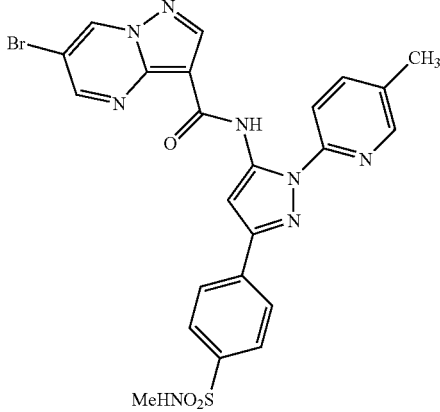 | 2.04, 567 | <100 nM |
| 195 | 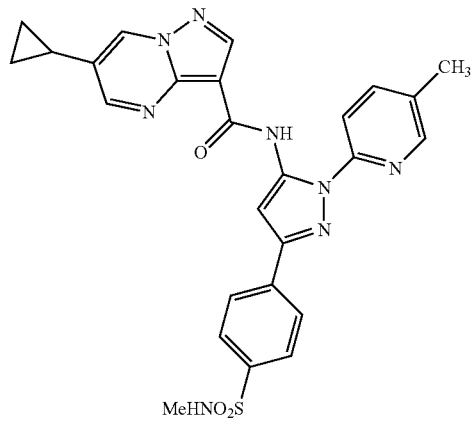 | 3.30, 529 | <1 μM |

-continued

| Example | Structure | LC-MS (Retention time (min), m/z) | IRAK-4 IC$_{50}$ (nM) |
|---|---|---|---|
| 196 | 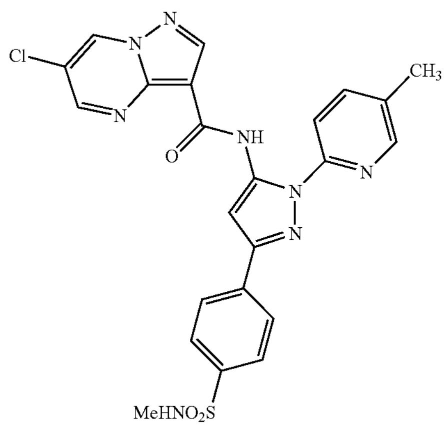 | 2.00, 523 | <100 nM |
| 197 | 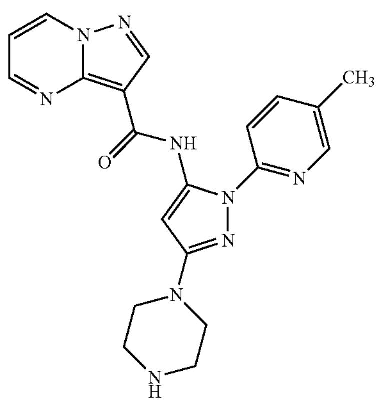 | 1.85, 418 | <100 nM |
| 198 | 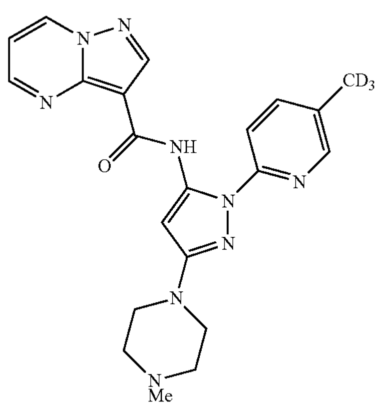 | 1.80, 421 | <100 nM |

-continued

| Example | Structure | LC-MS (Retention time (min), m/z) | IRAK-4 IC$_{50}$ (nM) |
|---|---|---|---|
| 199 | 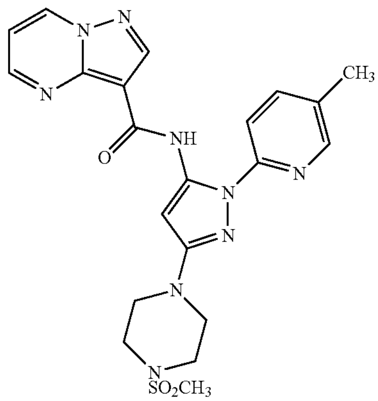 | 2.10, 482 | <100 nM |
| 200 | 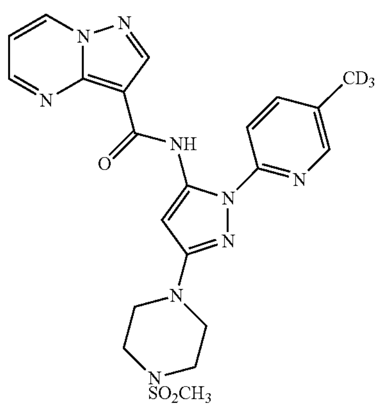 | 2.11, 485 | <100 nM |
| 201 | 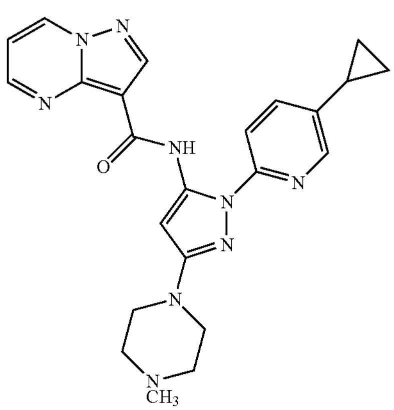 [SMILES: CN1CCN(c2cc(NC(=O)c3cnn4cccnc34)n(-c3ccc(C4CC4)cn3)n2)CC1] | n/a | <100 nM |

-continued

| Example | Structure | LC-MS (Retention time (min), m/z) | IRAK-4 IC$_{50}$ (nM) |
|---|---|---|---|
| 202 | 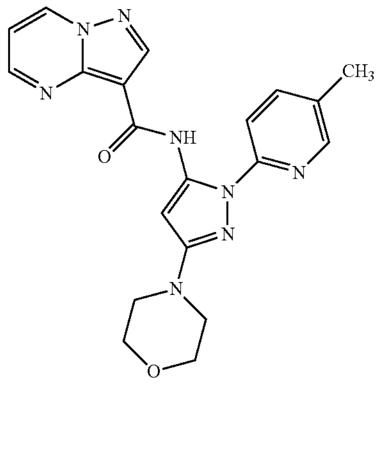 [SMILES: Cc1ccc(-n2nc(N3CCOCC3)cc2NC(=O)c2cnn3cccnc23)nc1] | 2.17, 405 | <100 nM |
| 203 | 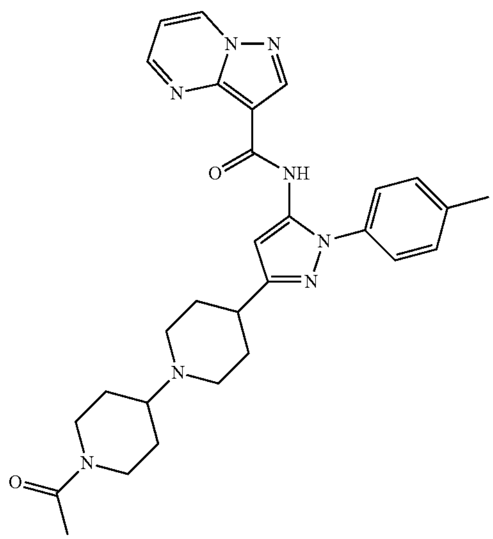 [SMILES: CC(=O)N1CCC(N2CCC(c3cc(NC(=O)c4cnn5cccnc45)n(-c4ccc(C)cc4)n3)CC2)CC1] | 0.81, 528 | <100 nM |
| 204 | 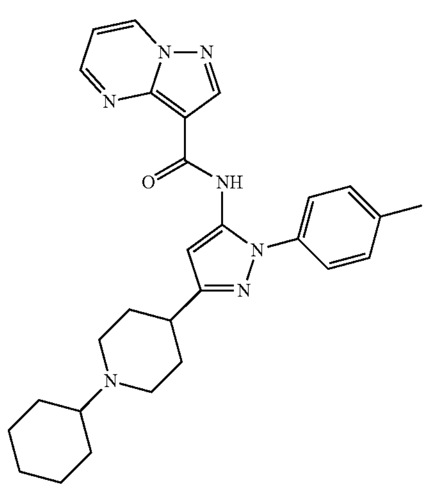 | 1.26, 484 | <100 nM |

| Example | Structure | LC-MS (Retention time (min), m/z) | IRAK-4 IC$_{50}$ (nM) |
|---|---|---|---|
| 205 | 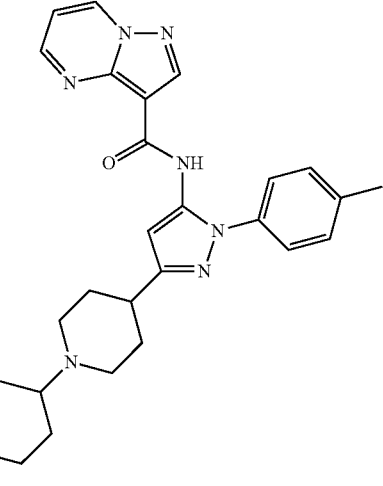 | 0.91, 499 | >1 μM |
| 206 | 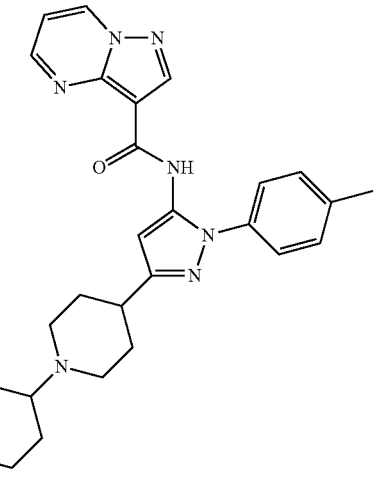 | 0.88, 486 | <100 nM |
| 207 | 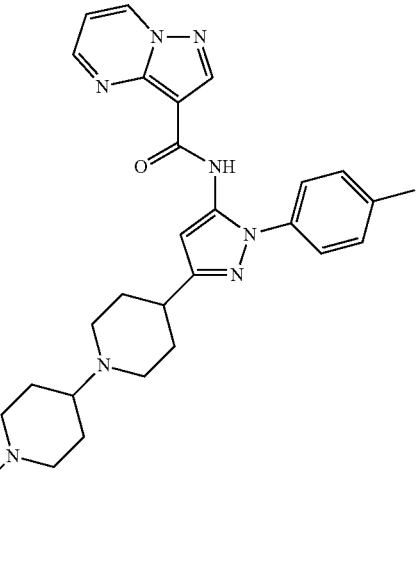 [SMILES: Cc1ccc(-n2nc(C3CCN(C4CCCCC4)CC3)cc2NC(=O)c2cnn3cccnc23)cc1] | 0.99, 558 | <100 nM |

-continued

| Example | Structure | LC-MS (Retention time (min), m/z) | IRAK-4 IC$_{50}$ (nM) |
| --- | --- | --- | --- |
| 208 | 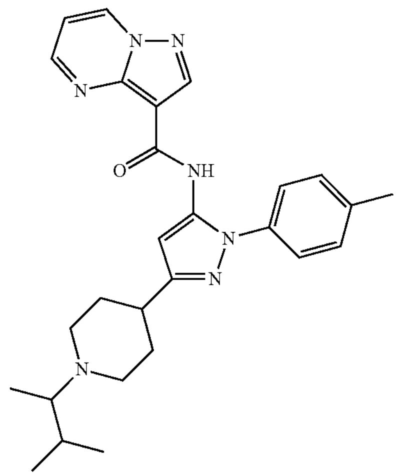 [SMILES: Cc1ccc(-n2nc(C3CCN(C(C)C(C)C)CC3)cc2NC(=O)c2cnn3cccnc23)cc1] | 1.35, 473 | <1 μM |
| 209 | 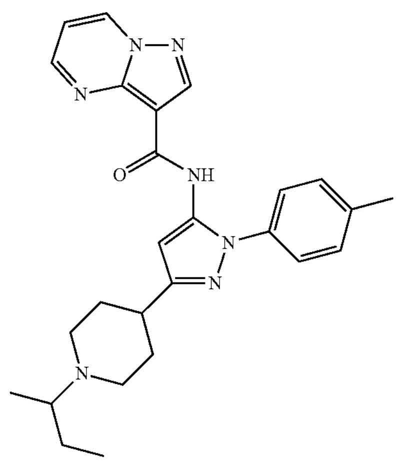 [SMILES: CCC(C)N1CCC(c2cc(NC(=O)c3cnn4cccnc34)n(-c3ccc(C)cc3)n2)CC1] | 1.17, 458 | <100 nM |
| 210 | 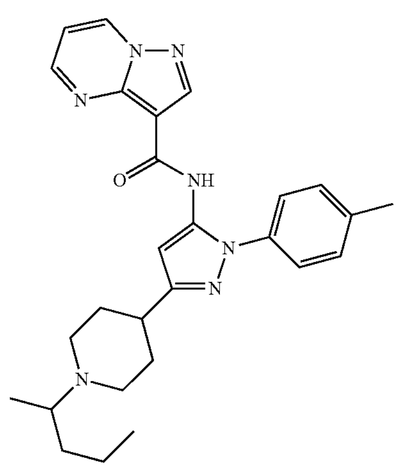 [SMILES: CCCC(C)N1CCC(c2cc(NC(=O)c3cnn4cccnc34)n(-c3ccc(C)cc3)n2)CC1] | 1.27, 472 | <100 nM |

-continued

| Example | Structure | LC-MS (Retention time (min), m/z) | IRAK-4 IC$_{50}$ (nM) |
| --- | --- | --- | --- |
| 211 | 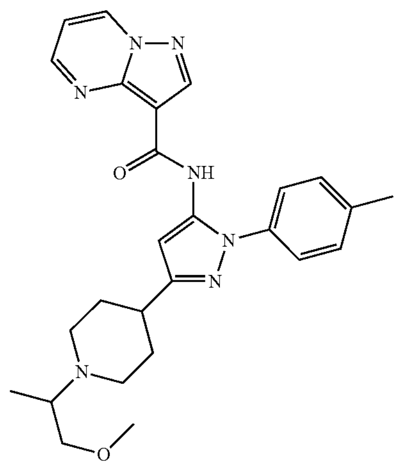 [SMILES: COCC(C)N1CCC(c2cc(NC(=O)c3cnn4cccnc34)n(-c3ccc(C)cc3)n2)CC1] | 0.97, 474 | <100 nM |
| 212 | 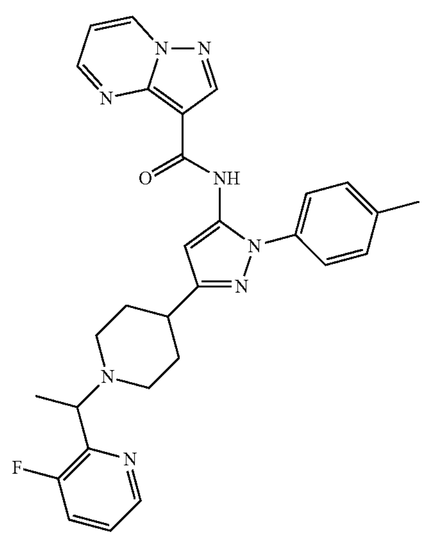 [SMILES: Cc1ccc(-n2nc(C3CCN(C(C)c4ncccc4F)CC3)cc2NC(=O)c2cnn3cccnc23)cc1] | 1.01, 525 | <1 µM |
| 213 | 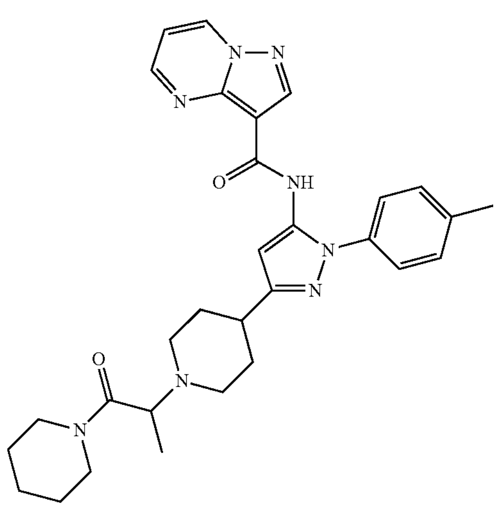 [SMILES: Cc1ccc(-n2nc(C3CCN(C(C)C(=O)N4CCCCC4)CC3)cc2NC(=O)c2cnn3cccnc23)cc1] | 1.01, 542 | <1 µM |

-continued
| Example | Structure | LC-MS (Retention time (min), m/z) | IRAK-4 IC$_{50}$ (nM) |
|---|---|---|---|
| 214 | 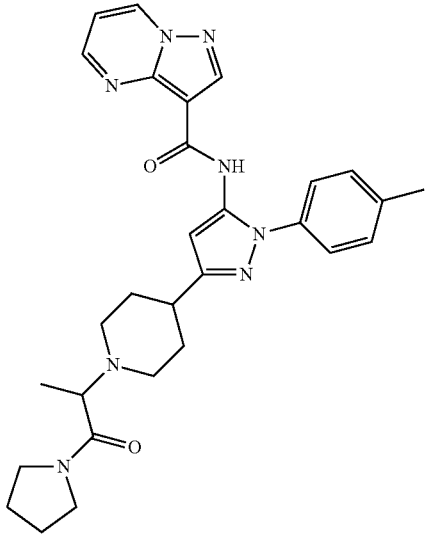 [SMILES: Cc1ccc(-n2nc(C3CCN(C(C)C(=O)N4CCCC4)CC3)cc2NC(=O)c2cnn3cccnc23)cc1] | 0.91, 528 | <100 nM |
| 215 | 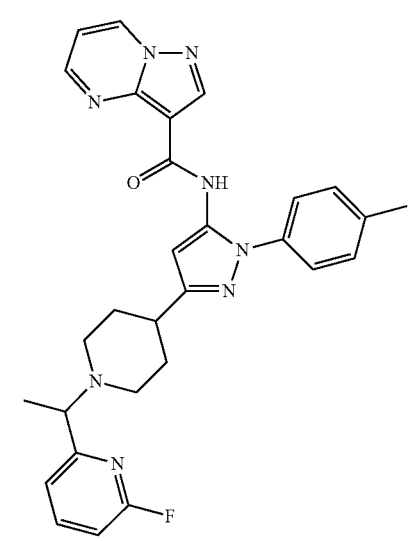 [SMILES: Cc1ccc(-n2nc(C3CCN(C(C)c4cccc(F)n4)CC3)cc2NC(=O)c2cnn3cccnc23)cc1] | 1.06, 526 | <1 μM |

| Example | Structure | LC-MS (Retention time (min), m/z) | IRAK-4 IC$_{50}$ (nM) |
|---------|-----------|-----------------------------------|------------------------|
| 216 | 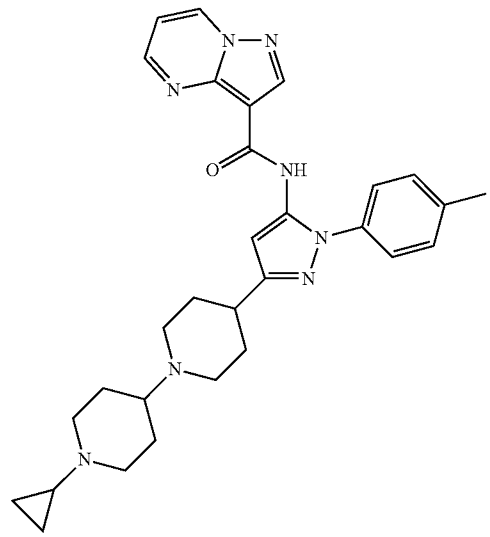 [SMILES: Cc1ccc(-n2nc(C3CCN(C4CCN(C5CC5)CC4)CC3)cc2NC(=O)c2cnn3cccnc23)cc1] | 1.03, 526 | <1 μM |
| 217 | 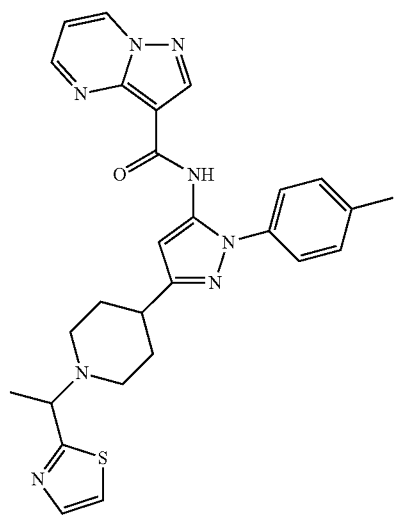 [SMILES: Cc1ccc(-n2nc(C3CCN(C(C)c4nccs4)CC3)cc2NC(=O)c2cnn3cccnc23)cc1] | 1.00, 513 | <1 μM |
| 218 | 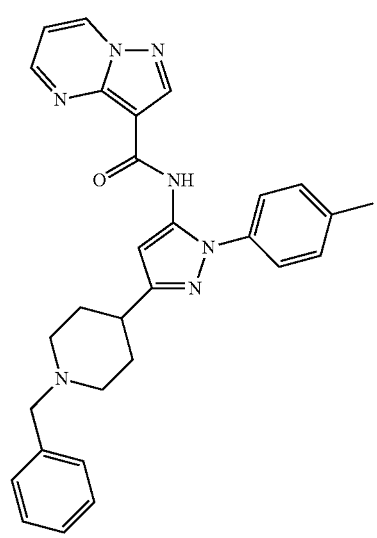 [SMILES: Cc1ccc(-n2nc(C3CCN(Cc4ccccc4)CC3)cc2NC(=O)c2cnn3cccnc23)cc1] | 1.14, 492 | >100 nM |

| Example | Structure | LC-MS (Retention time (min), m/z) | IRAK-4 IC$_{50}$ (nM) |
|---|---|---|---|
| 219 | 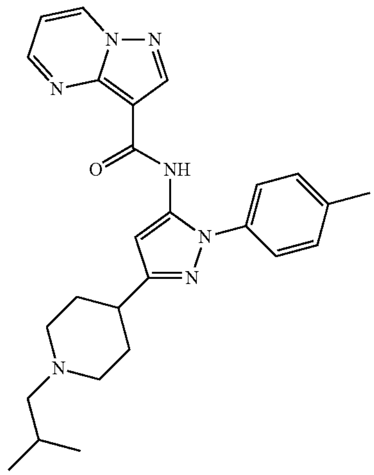 | 1.20, 458 | <100 nM |
| 220 | 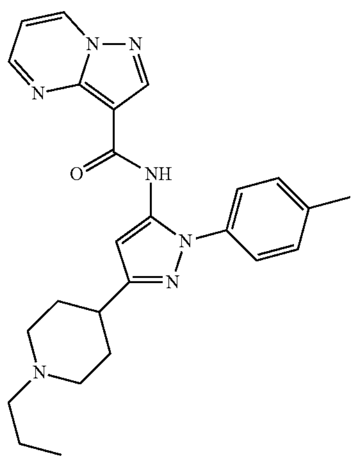 [SMILES: CCCN1CCC(c2cc(NC(=O)c3cnn4cccnc34)n(-c3ccc(C)cc3)n2)CC1] | 1.05, 444 | <100 nM |
| 221 | 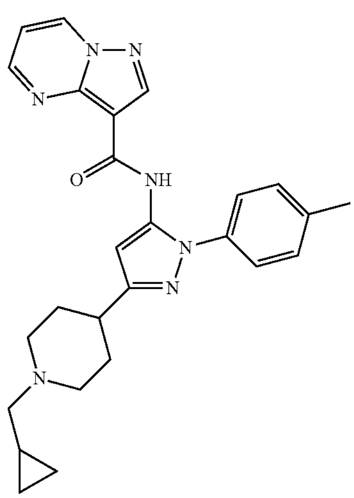 [SMILES: Cc1ccc(-n2nc(C3CCN(CC4CC4)CC3)cc2NC(=O)c2cnn3cccnc23)cc1] | 1.05, 456 | <100 nM |

-continued

| Example | Structure | LC-MS (Retention time (min), m/z) | IRAK-4 IC$_{50}$ (nM) |
|---|---|---|---|
| 222 | 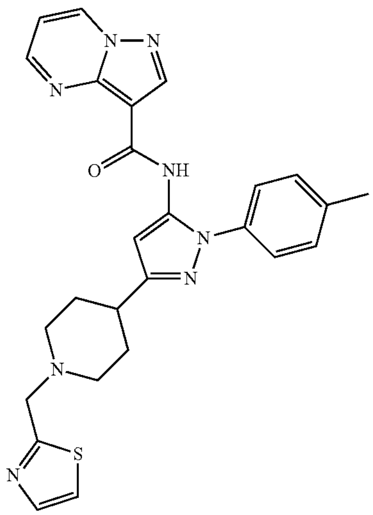 [SMILES: Cc1ccc(-n2nc(C3CCN(Cc4nccs4)CC3)cc2NC(=O)c2cnn3cccnc23)cc1] | 0.93, 499 | <1 µM |
| 223 | 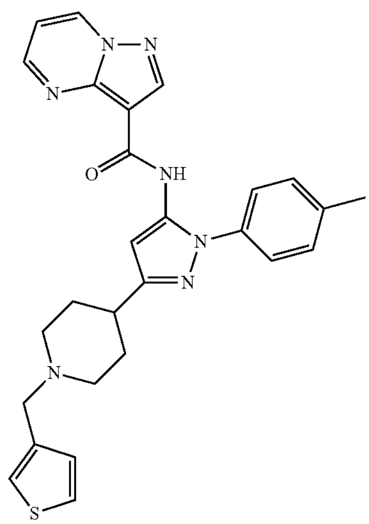 [SMILES: Cc1ccc(-n2nc(C3CCN(Cc4ccsc4)CC3)cc2NC(=O)c2cnn3cccnc23)cc1] | 1.08, 498 | <100 nM |
| 224 | 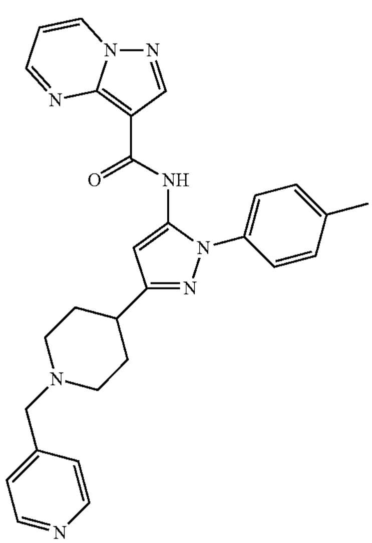 [SMILES: Cc1ccc(-n2nc(C3CCN(Cc4ccncc4)CC3)cc2NC(=O)c2cnn3cccnc23)cc1] | 0.90, 493 | <1 µM |

| Example | Structure | LC-MS (Retention time (min), m/z) | IRAK-4 IC$_{50}$ (nM) |
|---|---|---|---|
| 225 | 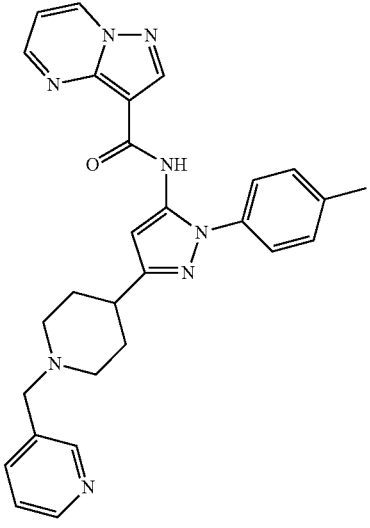 [SMILES: Cc1ccc(-n2nc(C3CCN(Cc4cccnc4)CC3)cc2NC(=O)c2cnn3cccnc23)cc1] | 0.89, 493 | <1 μM |
| 226 | 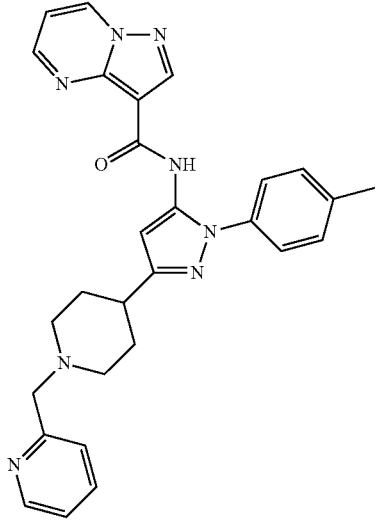 [SMILES: Cc1ccc(-n2nc(C3CCN(Cc4ccccn4)CC3)cc2NC(=O)c2cnn3cccnc23)cc1] | 0.90, 493 | <100 nM |

-continued
| Example | Structure | LC-MS (Retention time (min), m/z) | IRAK-4 IC$_{50}$ (nM) |
|---|---|---|---|
| 227 | 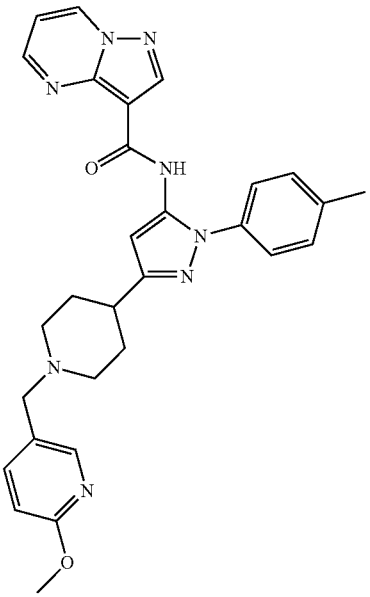 [SMILES: COc1ccc(CN2CCC(c3cc(NC(=O)c4cnn5cccnc45)n(-c4ccc(C)cc4)n3)CC2)cn1] | 1.01, 524 | <1 μM |
| 228 | 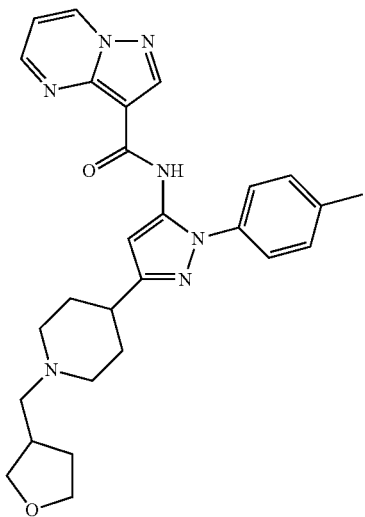 [SMILES: Cc1ccc(-n2nc(C3CCN(CC4CCOC4)CC3)cc2NC(=O)c2cnn3cccnc23)cc1] | 0.92, 486 | <100 nM |

| Example | Structure | LC-MS (Retention time (min), m/z) | IRAK-4 IC$_{50}$ (nM) |
| --- | --- | --- | --- |
| 229 | 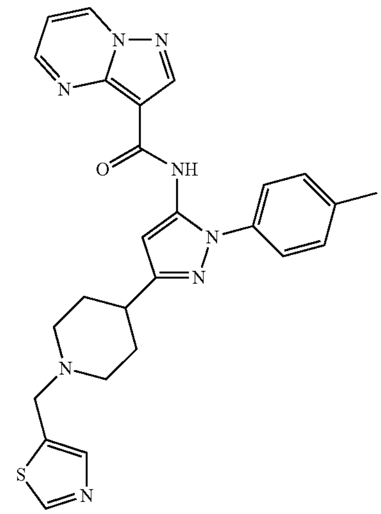 [SMILES: Cc1ccc(-n2nc(C3CCN(Cc4cncs4)CC3)cc2NC(=O)c2cnn3cccnc23)cc1] | 0.89, 499 | <100 nM |
| 230 | 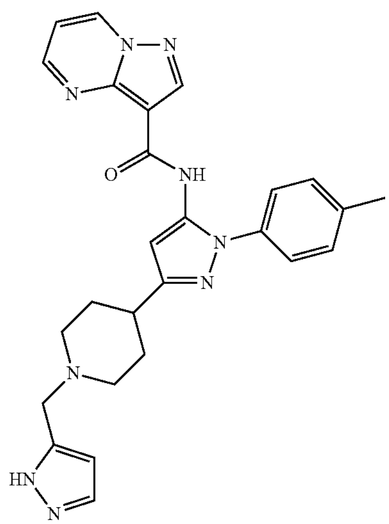 [SMILES: Cc1ccc(-n2nc(C3CCN(Cc4ccn[nH]4)CC3)cc2NC(=O)c2cnn3cccnc23)cc1] | 0.80, 482 | <100 nM |
| 231 | 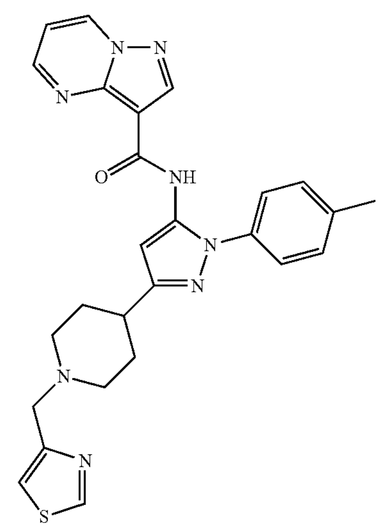 | 0.88, 499 | <100 nM |

-continued

| Example | Structure | LC-MS (Retention time (min), m/z) | IRAK-4 IC$_{50}$ (nM) |
|---|---|---|---|
| 232 | 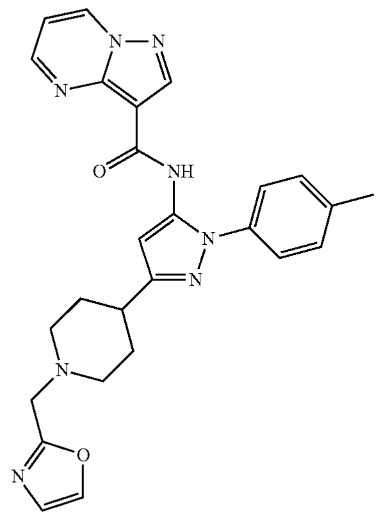 | 0.83, 483 | <1 μM |
| 233 | 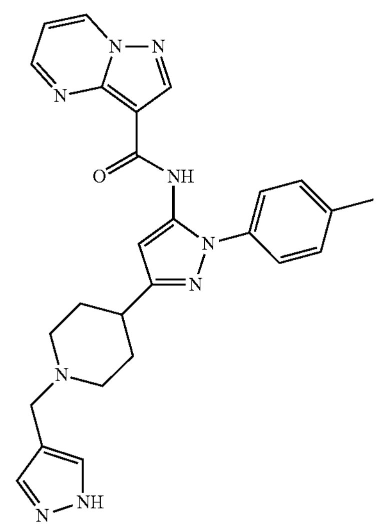 [SMILES: Cc1ccc(-n2nc(C3CCN(Cc4cn[nH]c4)CC3)cc2NC(=O)c2cnn3cccnc23)cc1] | 0.79, 482 | <100 nM |
| 234 | 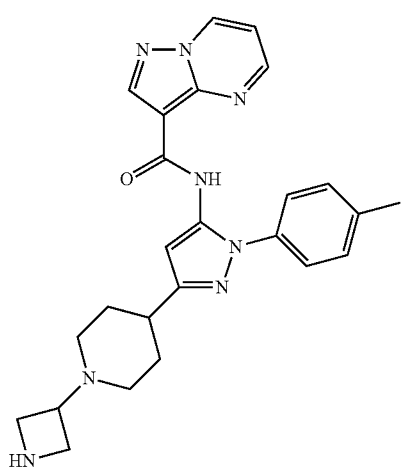 [SMILES: Cc1ccc(-n2nc(C3CCN(C4CNC4)CC3)cc2NC(=O)c2cnn3cccnc23)cc1] | 1.70, 557 | <1 μM |

| Example | Structure | LC-MS (Retention time (min), m/z) | IRAK-4 IC$_{50}$ (nM) |
|---|---|---|---|
| 235 | 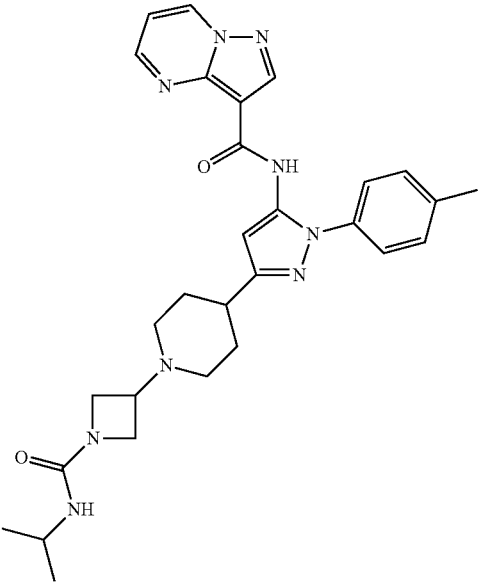 [SMILES: Cc1ccc(-n2nc(C3CCN(C4CN(C(=O)NC(C)C)C4)CC3)cc2NC(=O)c2cnn3cccnc23)cc1] | 0.82, 542 | <1 μM |
| 236 | 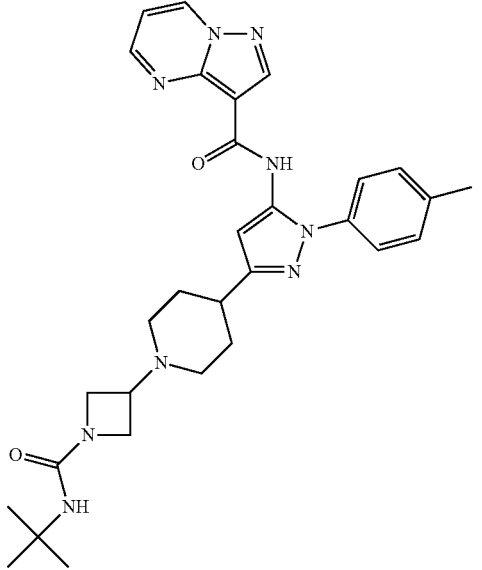 [SMILES: Cc1ccc(-n2nc(C3CCN(C4CN(C(=O)NC(C)(C)C)C4)CC3)cc2NC(=O)c2cnn3cccnc23)cc1] | 0.90, 556 | <1 μM |

| Example | Structure | LC-MS (Retention time (min), m/z) | IRAK-4 IC$_{50}$ (nM) |
| --- | --- | --- | --- |
| 237 | 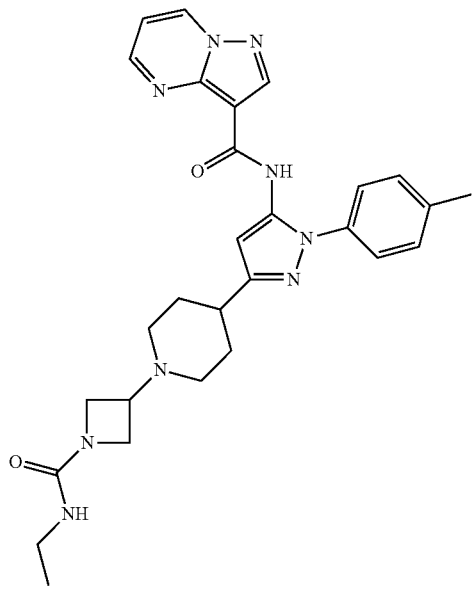 [SMILES: CCNC(=O)N1CC(N2CCC(c3cc(NC(=O)c4cnn5cccnc45)n(-c4ccc(C)cc4)n3)CC2)C1] | 0.78, 528 | <1 μM |
| 238 | 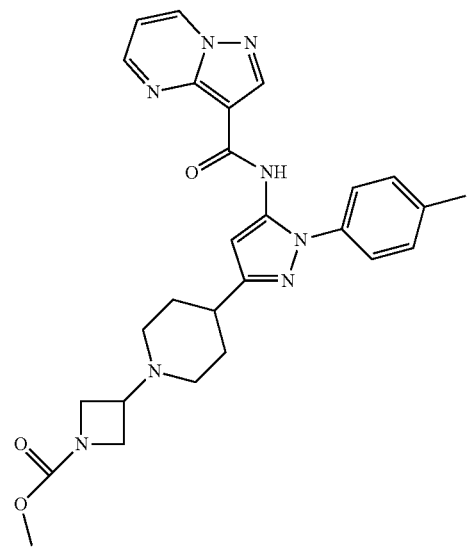 [SMILES: COC(=O)N1CC(N2CCC(c3cc(NC(=O)c4cnn5cccnc45)n(-c4ccc(C)cc4)n3)CC2)C1] | 0.86, 515 | <1 μM |

| Example | Structure | LC-MS (Retention time (min), m/z) | IRAK-4 IC$_{50}$ (nM) |
|---|---|---|---|
| 239 | 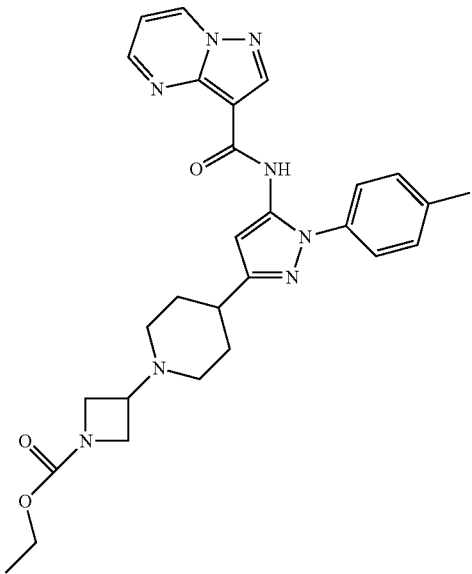 [SMILES: CCOC(=O)N1CC(N2CCC(c3cc(NC(=O)c4cnn5cccnc45)n(-c4ccc(C)cc4)n3)CC2)C1] | 0.92, 529 | <1 μM |
| 240 | 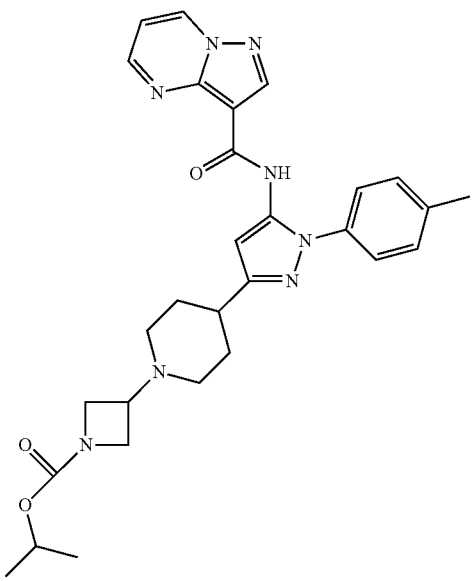 [SMILES: Cc1ccc(-n2nc(C3CCN(C4CN(C(=O)OC(C)C)C4)CC3)cc2NC(=O)c2cnn3cccnc23)cc1] | 0.95, 543 | <1 μM |

| Example | Structure | LC-MS (Retention time (min), m/z) | IRAK-4 IC$_{50}$ (nM) |
|---|---|---|---|
| 241 | 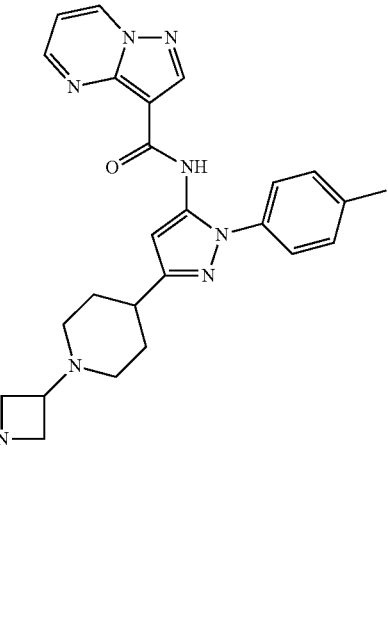 | 0.88, 547 | <1 μM |
| 242 | 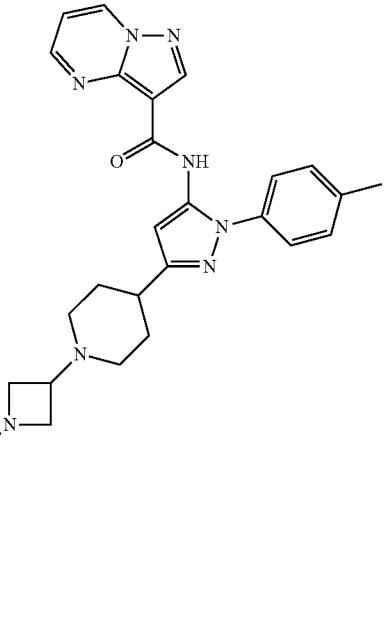 | 0.86, 559 | <1 μM |

| Example | Structure | LC-MS (Retention time (min), m/z) | IRAK-4 IC$_{50}$ (nM) |
|---|---|---|---|
| 243 | 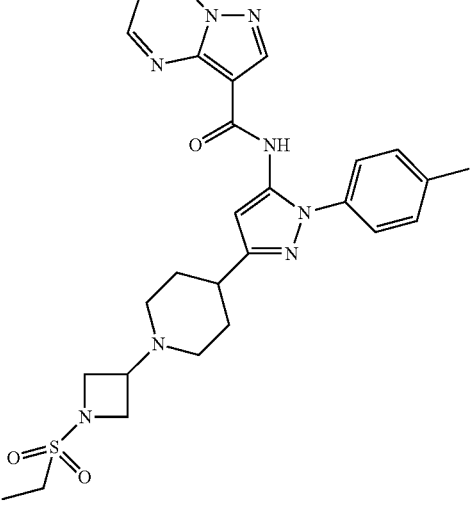 | 0.87, 549 | <1 μM |
| 244 | 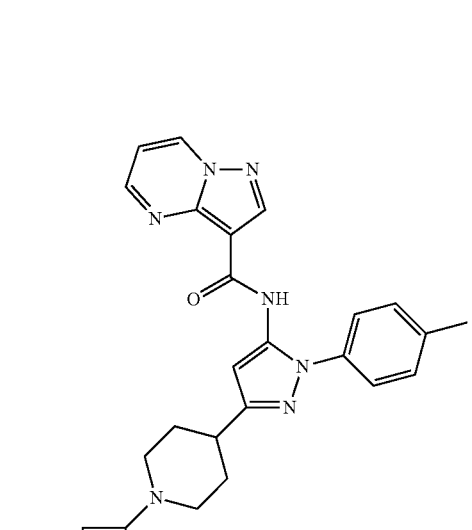 | 0.82, 535 | <1 μM |

| Example | Structure | LC-MS (Retention time (min), m/z) | IRAK-4 IC$_{50}$ (nM) |
|---|---|---|---|
| 245 | 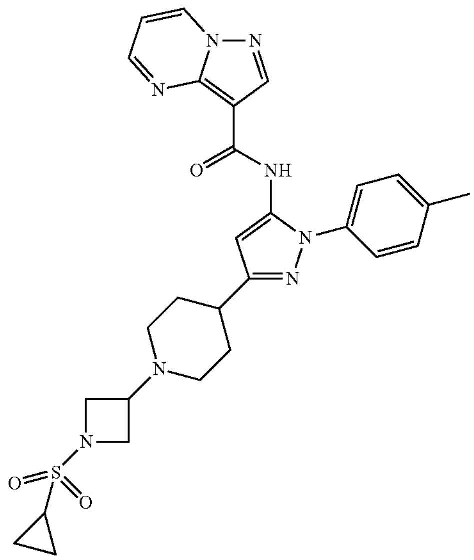 [SMILES: Cc1ccc(-n2nc(C3CCN(C4CN(S(=O)(=O)C5CC5)C4)CC3)cc2NC(=O)c2cnn3cccnc23)cc1] | 0.85, 561 | <1 µM |
| 246 | 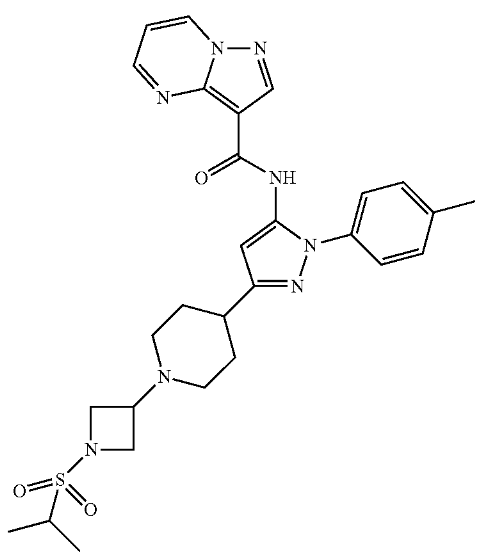 [SMILES: Cc1ccc(-n2nc(C3CCN(C4CN(S(=O)(=O)C(C)C)C4)CC3)cc2NC(=O)c2cnn3cccnc23)cc1] | 0.93, 563 | <1 µM |

| Example | Structure | LC-MS (Retention time (min), m/z) | IRAK-4 IC$_{50}$ (nM) |
| --- | --- | --- | --- |
| 247 | 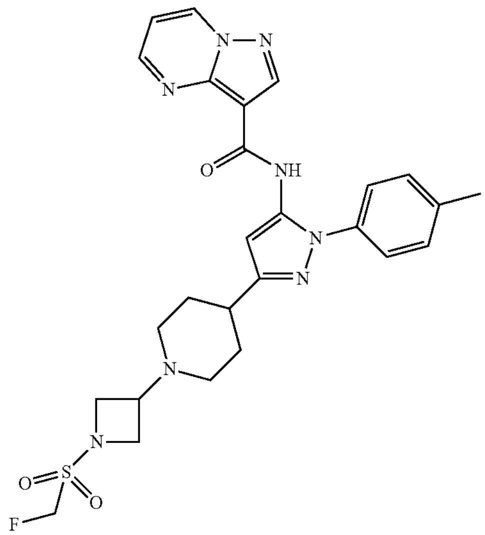 [SMILES: Cc1ccc(-n2nc(C3CCN(C4CN(S(=O)(=O)CF)C4)CC3)cc2NC(=O)c2cnn3cccnc23)cc1] | 0.84, 553 | <1 μM |
| 248 | 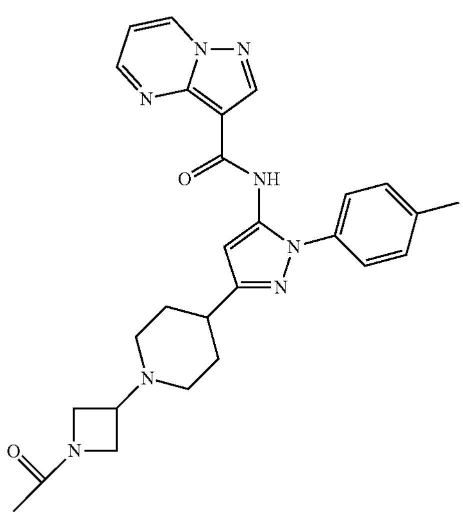 [SMILES: CC(=O)N1CC(N2CCC(c3cc(NC(=O)c4cnn5cccnc45)n(-c4ccc(C)cc4)n3)CC2)C1] | 0.74, 499 | <1 μM |

-continued

| Example | Structure | LC-MS (Retention time (min), m/z) | IRAK-4 IC$_{50}$ (nM) |
|---|---|---|---|
| 249 | 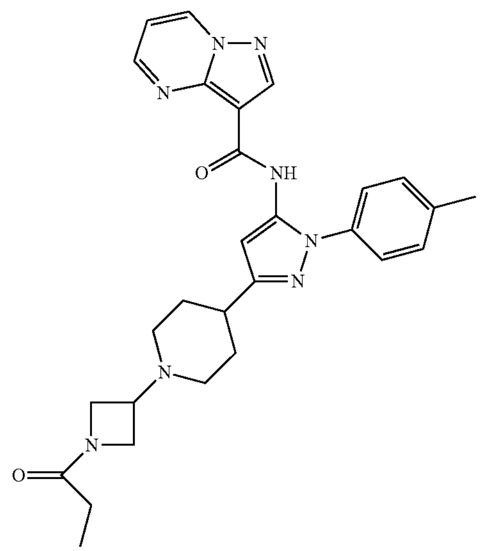 [SMILES: CCC(=O)N1CC(N2CCC(c3cc(NC(=O)c4cnn5cccnc45)n(-c4ccc(C)cc4)n3)CC2)C1] | 0.78, 513 | <1 μM |
| 250 | 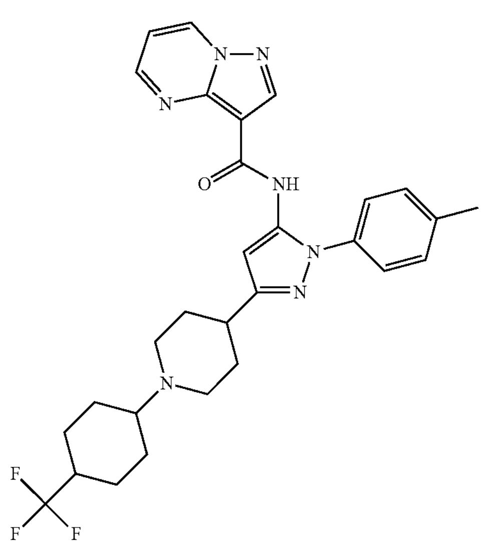 [SMILES: Cc1ccc(-n2nc(C3CCN(C4CCC(C(F)(F)F)CC4)CC3)cc2NC(=O)c2cnn3cccnc23)cc1] | 0.74, 522 | <100 nM |

-continued

| Example | Structure | LC-MS (Retention time (min), m/z) | IRAK-4 IC$_{50}$ (nM) |
|---|---|---|---|
| 251 | 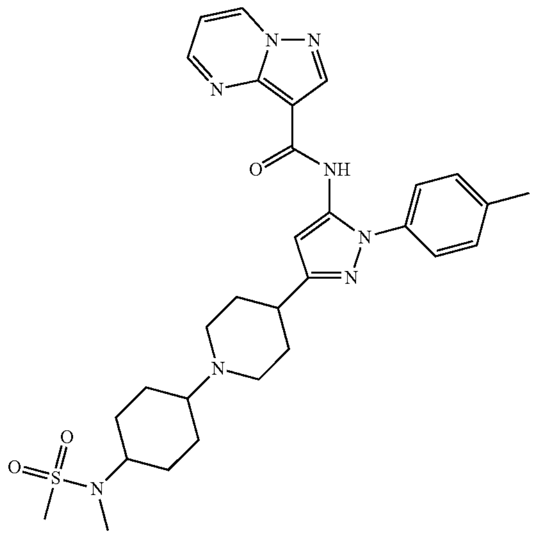 [SMILES: Cc1ccc(-n2nc(C3CCN(C4CCC(N(C)S(C)(=O)=O)CC4)CC3)cc2NC(=O)c2cnn3cccnc23)cc1] | 0.64, 591 | <100 nM |
| 252 | 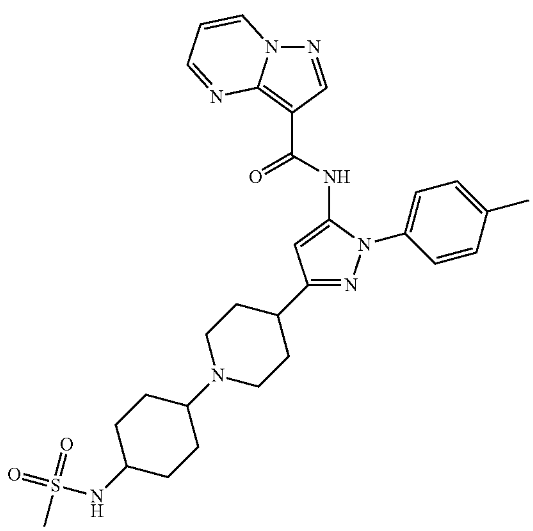 [SMILES: Cc1ccc(-n2nc(C3CCN(C4CCC(NS(C)(=O)=O)CC4)CC3)cc2NC(=O)c2cnn3cccnc23)cc1] | 0.61, 577 | <100 nM |
| 253 | 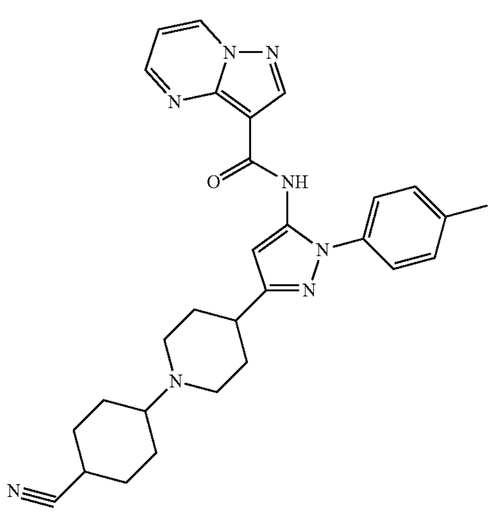 [SMILES: Cc1ccc(-n2nc(C3CCN(C4CCC(C#N)CC4)CC3)cc2NC(=O)c2cnn3cccnc23)cc1] | 0.64, 509 | <100 nM |

| Example | Structure | LC-MS (Retention time (min), m/z) | IRAK-4 IC$_{50}$ (nM) |
|---|---|---|---|
| 254 | 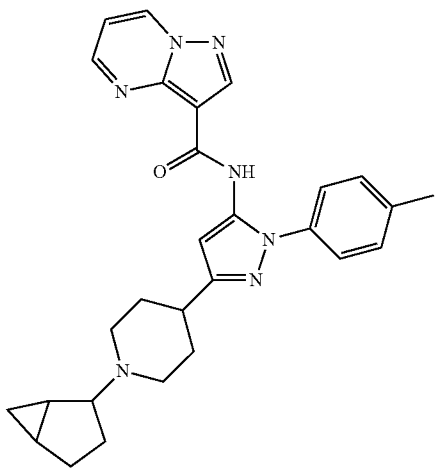 [SMILES: Cc1ccc(-n2nc(C3CCN(C4CCC5CC54)CC3)cc2NC(=O)c2cnn3cccnc23)cc1] | 0.67, 482 | <100 nM |
| 255 | 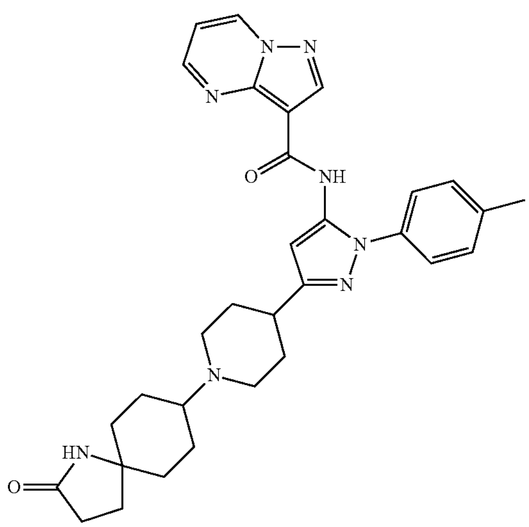 [SMILES: Cc1ccc(-n2nc(C3CCN(C4CCC5(CCC(=O)N5)CC4)CC3)cc2NC(=O)c2cnn3cccnc23)cc1] | 0.61, 553 | <100 nM |
| 256 | 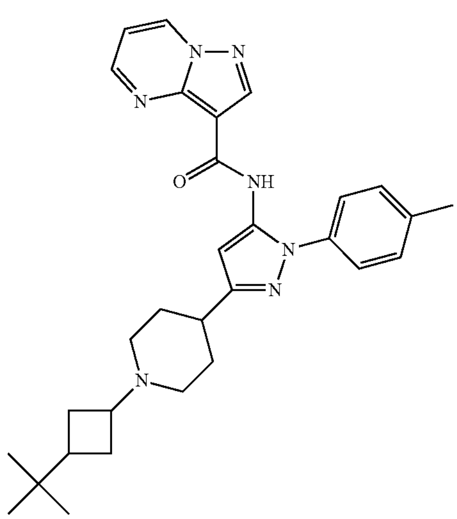 [SMILES: Cc1ccc(-n2nc(C3CCN(C4CC(C(C)(C)C)C4)CC3)cc2NC(=O)c2cnn3cccnc23)cc1] | 0.8, 512 | <100 nM |

-continued

| Example | Structure | LC-MS (Retention time (min), m/z) | IRAK-4 IC$_{50}$ (nM) |
|---|---|---|---|
| 257 | 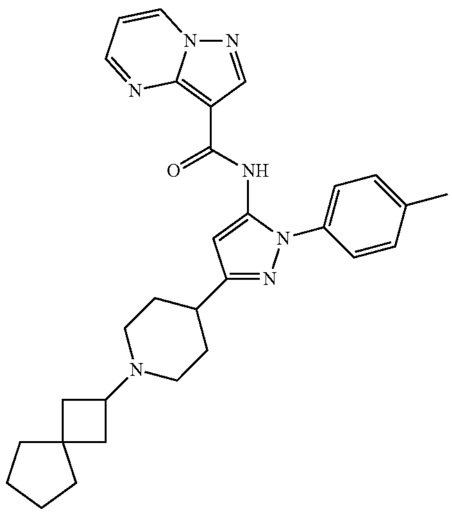 [SMILES: Cc1ccc(-n2nc(C3CCN(C4CC5(CCCC5)C4)CC3)cc2NC(=O)c2cnn3cccnc23)cc1] | 0.78, 510 | <100 nM |
| 258 | 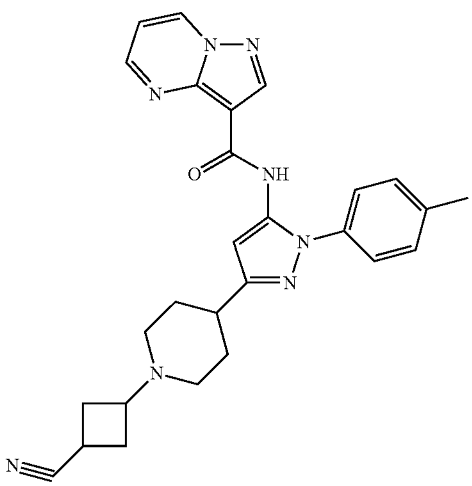 [SMILES: Cc1ccc(-n2nc(C3CCN(C4CC(C#N)C4)CC3)cc2NC(=O)c2cnn3cccnc23)cc1] | 0.60, 481 | <100 nM |
| 259 | 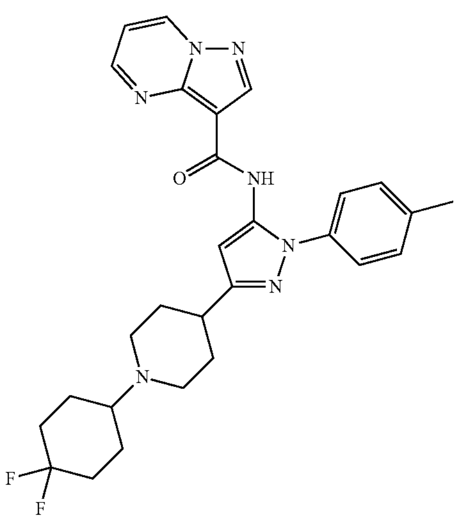 [SMILES: Cc1ccc(-n2nc(C3CCN(C4CCC(F)(F)CC4)CC3)cc2NC(=O)c2cnn3cccnc23)cc1] | 0.70, 520 | <1 μM |

-continued
| Example | Structure | LC-MS (Retention time (min), m/z) | IRAK-4 IC$_{50}$ (nM) |
|---|---|---|---|
| 260 | 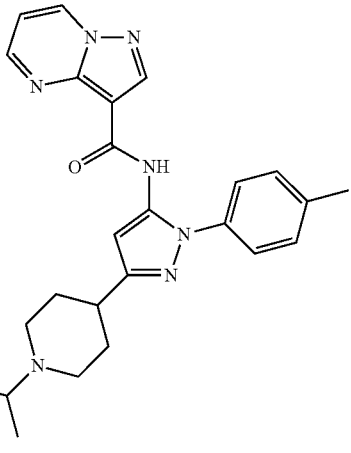 | 0.68, 512 | <1 μM |
| 261 | 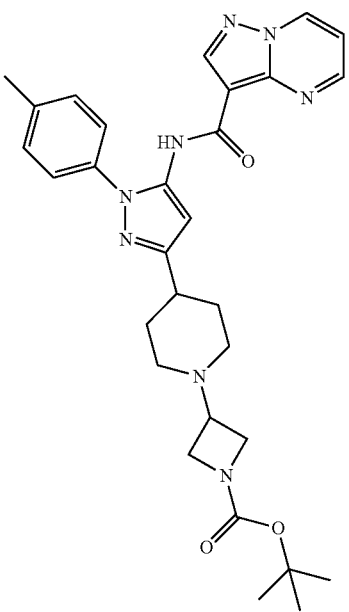 [SMILES: Cc1ccc(-n2nc(C3CCN(C4CN(C(=O)OC(C)(C)C)C4)CC3)cc2NC(=O)c2cnn3cccnc23)cc1] | n/a | <1 μM |

-continued
| Example | Structure | LC-MS (Retention time (min), m/z) | IRAK-4 IC$_{50}$ (nM) |
|---|---|---|---|
| 262 | 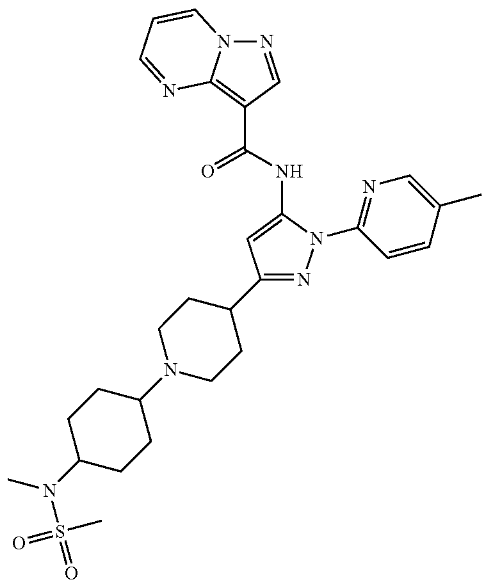 | 1.00, 1.15, 592 | <100 nM |
| 263 | 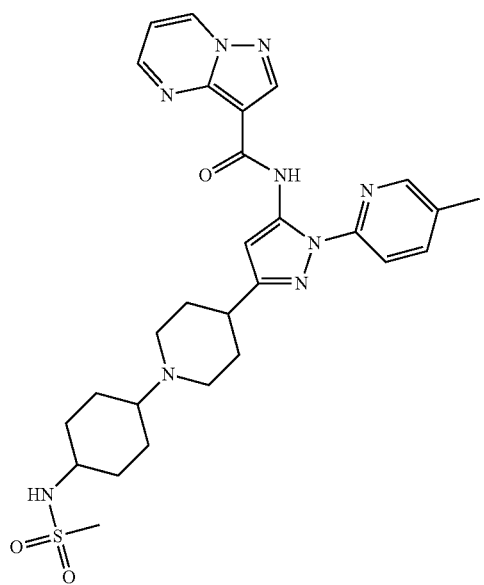 [SMILES: Cc1ccc(-n2nc(C3CCN(C4CCC(NS(C)(=O)=O)CC4)CC3)cc2NC(=O)c2cnn3cccnc23)nc1] | 0.91, 0.96, 578 | <100 nM |

-continued

| Example | Structure | LC-MS (Retention time (min), m/z) | IRAK-4 IC$_{50}$ (nM) |
|---|---|---|---|
| 264 | 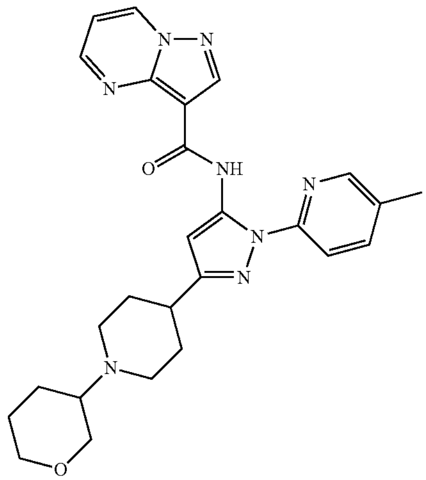 [SMILES: Cc1ccc(-n2nc(C3CCN(C4CCCOC4)CC3)cc2NC(=O)c2cnn3cccnc23)nc1] | 0.99, 487 | <100 nM |
| 265 | 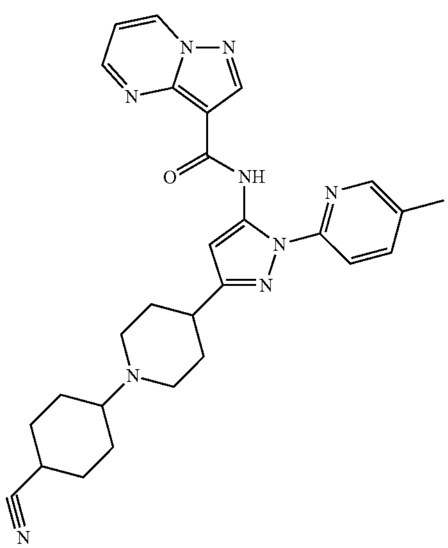 [SMILES: Cc1ccc(-n2nc(C3CCN(C4CCC(C#N)CC4)CC3)cc2NC(=O)c2cnn3cccnc23)nc1] | 1.03, 510 | <100 nM |

-continued

| Example | Structure | LC-MS (Retention time (min), m/z) | IRAK-4 IC$_{50}$ (nM) |
|---|---|---|---|
| 266 | 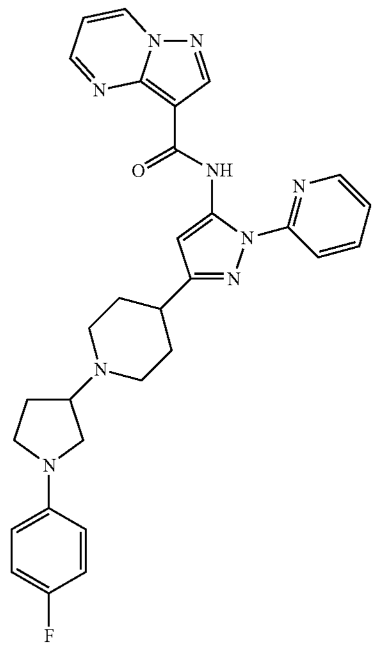 [SMILES: O=C(Nc1cc(C2CCN(C3CCN(c4ccc(F)cc4)C3)CC2)nn1-c1ccccn1)c1cnn2cccnc12] | 1.27, 566 | <100 nM |
| 267 | 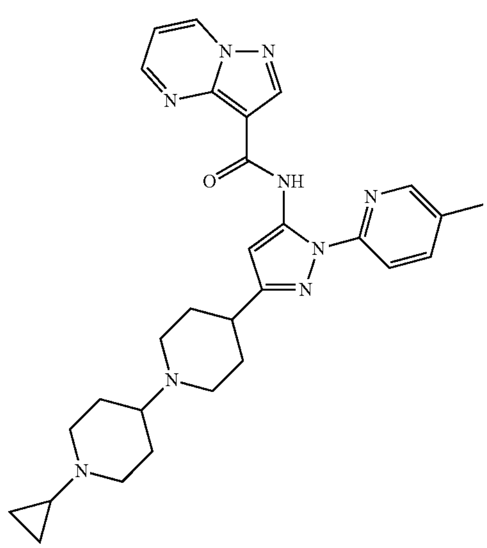 [SMILES: Cc1ccc(-n2nc(C3CCN(C4CCN(C5CC5)CC4)CC3)cc2NC(=O)c2cnn3cccnc23)nc1] | 1.11, 526 | <100 nM |

| Example | Structure | LC-MS (Retention time (min), m/z) | IRAK-4 IC$_{50}$ (nM) |
|---|---|---|---|
| 268 | 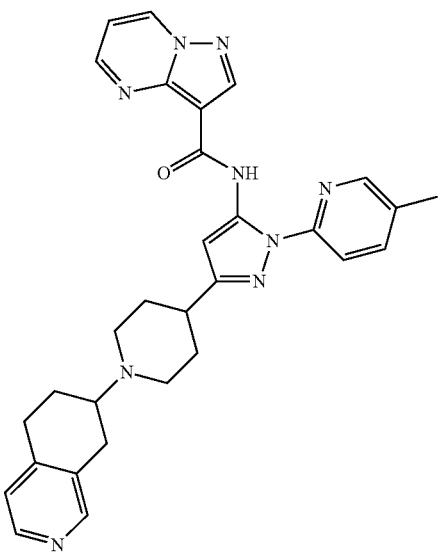 [SMILES: Cc1ccc(-n2nc(C3CCN(C4CCc5ccncc5C4)CC3)cc2NC(=O)c2cnn3cccnc23)nc1] | 1.02, 534 | <100 nM |
| 269 | 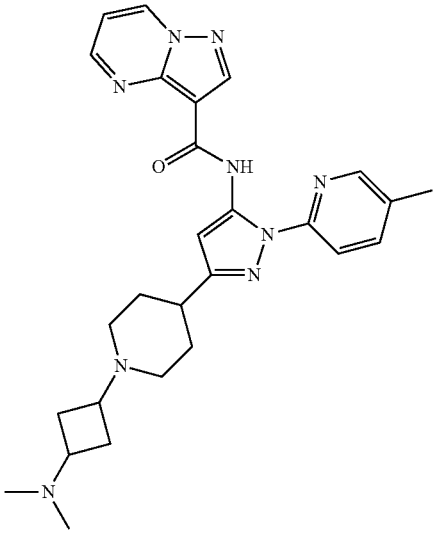 | 1.04, 500 | <100 nM |
| 270 | 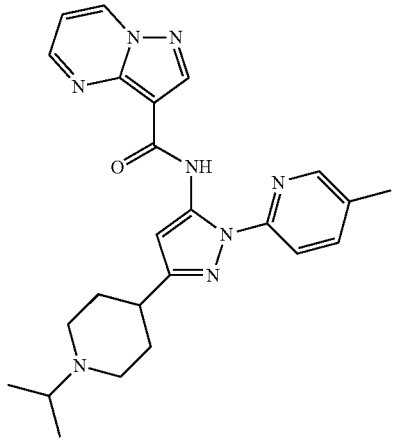 [SMILES: Cc1ccc(-n2nc(C3CCN(C(C)C)CC3)cc2NC(=O)c2cnn3cccnc23)nc1] | 1.10, 445 | <100 nM |

-continued

| Example | Structure | LC-MS (Retention time (min), m/z) | IRAK-4 IC$_{50}$ (nM) |
|---|---|---|---|
| 271 | 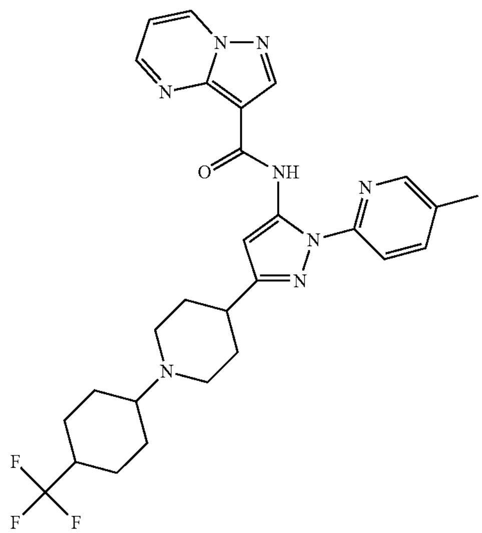 [SMILES: Cc1ccc(-n2nc(C3CCN(C4CCC(C(F)(F)F)CC4)CC3)cc2NC(=O)c2cnn3cccnc23)nc1] | 1.28, 1.36, 553 | <100 nM |
| 272 | 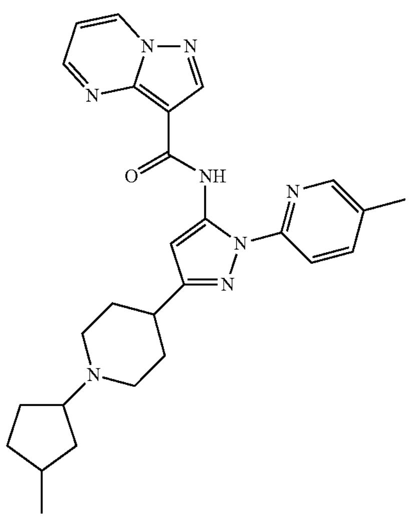 [SMILES: Cc1ccc(-n2nc(C3CCN(C4CCC(C)C4)CC3)cc2NC(=O)c2cnn3cccnc23)nc1] | 1.28, 485 | <100 nM |
| 273 | Chiral | 1.28, 485 | <100 nM |

-continued
| Example | Structure | LC-MS (Retention time (min), m/z) | IRAK-4 IC$_{50}$ (nM) |
|---------|-----------|-----------------------------------|------------------------|
| 274 | 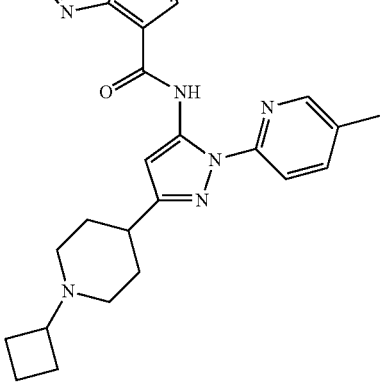 | 1.15, 457 | <100 nM |
| 275 | 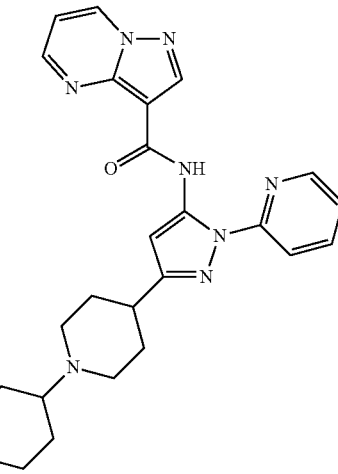 | 0.96, 500 | <100 nM |
| 276 | 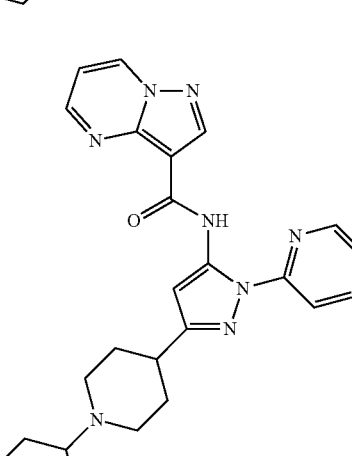 | 1.06, 558 | <100 nM |

-continued

| Example | Structure | LC-MS (Retention time (min), m/z) | IRAK-4 IC$_{50}$ (nM) |
| --- | --- | --- | --- |
| 277 | 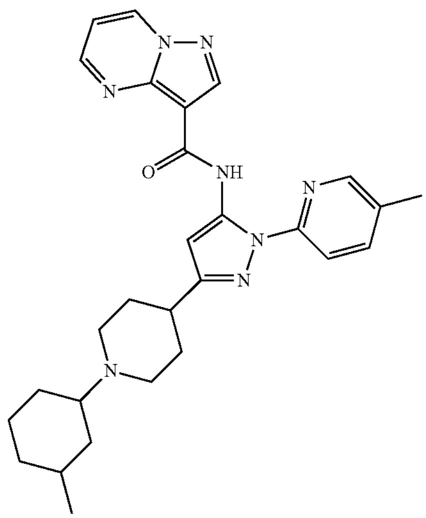 [SMILES: Cc1ccc(-n2nc(C3CCN(C4CCCC(C)C4)CC3)cc2NC(=O)c2cnn3cccnc23)nc1] | 1.39, 1.43, 499 | <100 nM |
| 278 | 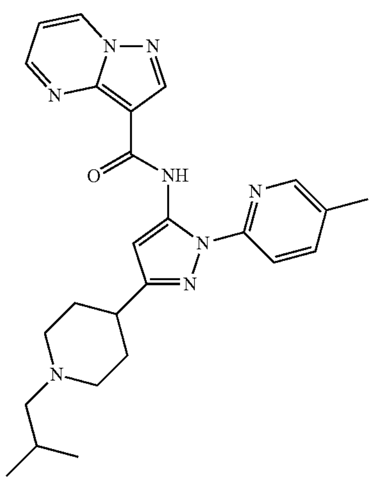 [SMILES: Cc1ccc(-n2nc(C3CCN(CC(C)C)CC3)cc2NC(=O)c2cnn3cccnc23)nc1] | 1.31, 495 | <100 nM |
| 279 | 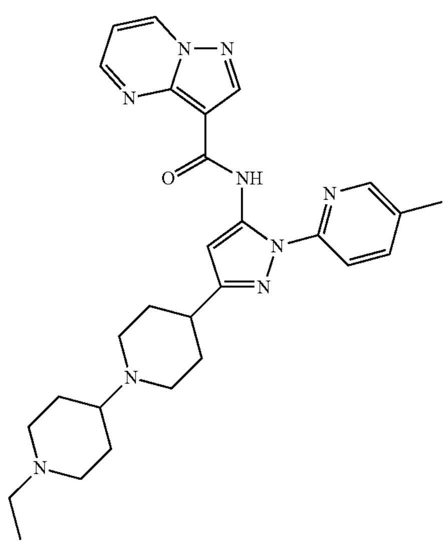 [SMILES: CCN1CCC(N2CCC(c3cc(NC(=O)c4cnn5cccnc45)n(-c4ccc(C)cn4)n3)CC2)CC1] | 1.03, 514 | <100 nM |

-continued
| Example | Structure | LC-MS (Retention time (min), m/z) | IRAK-4 IC$_{50}$ (nM) |
|---|---|---|---|
| 280 | 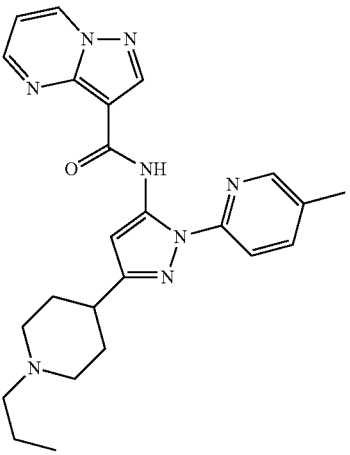 [SMILES: CCCN1CCC(c2cc(NC(=O)c3cnn4cccnc34)n(-c3ccc(C)cn3)n2)CC1] | 1.14, 445 | <100 nM |
| 281 | 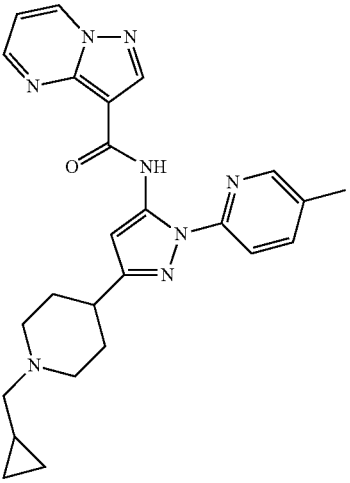 [SMILES: Cc1ccc(-n2nc(C3CCN(CC4CC4)CC3)cc2NC(=O)c2cnn3cccnc23)nc1] | 1.12, 457 | <100 nM |
| 282 | 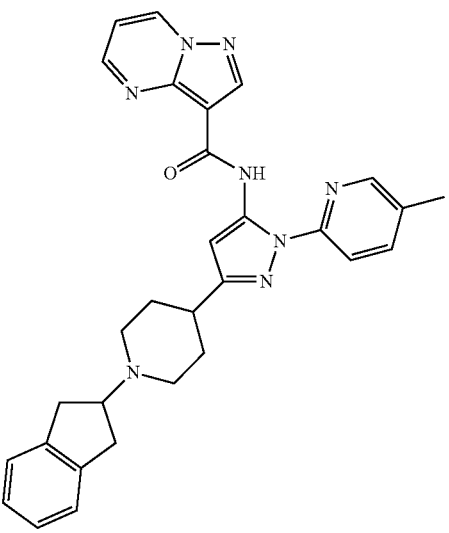 [SMILES: Cc1ccc(-n2nc(C3CCN(C4Cc5ccccc5C4)CC3)cc2NC(=O)c2cnn3cccnc23)nc1] | 1.25, 519 | <100 nM |

-continued

| Example | Structure | LC-MS (Retention time (min), m/z) | IRAK-4 IC$_{50}$ (nM) |
|---|---|---|---|
| 283 | 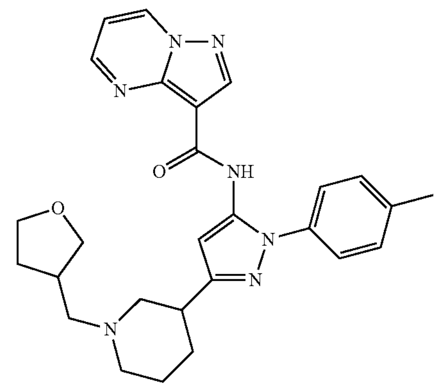 [SMILES: Cc1ccc(-n2nc(C3CCCN(CC4CCOC4)C3)cc2NC(=O)c2cnn3cccnc23)cc1] | 0.94, 487 | <1 μM |
| 284 | 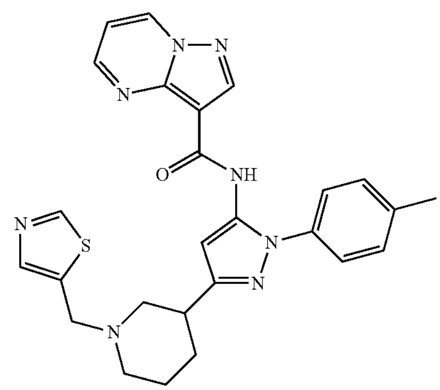 [SMILES: Cc1ccc(-n2nc(C3CCCN(Cc4cncs4)C3)cc2NC(=O)c2cnn3cccnc23)cc1] | 0.91, 499 | <1 μM |
| 285 | 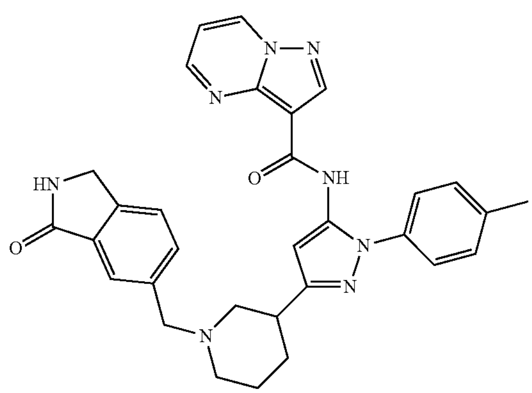 [SMILES: Cc1ccc(-n2nc(C3CCCN(Cc4ccc5c(c4)C(=O)NC5)C3)cc2NC(=O)c2cnn3cccnc23)cc1] | 0.87, 548 | <1 μM |
| 286 | 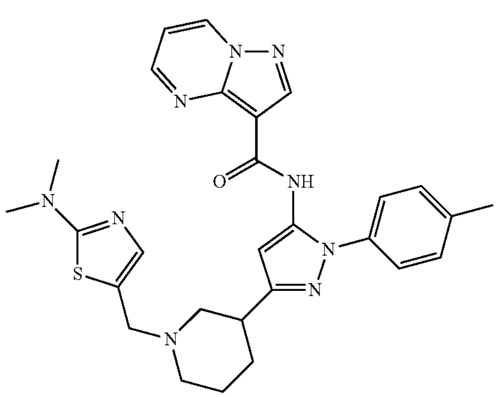 | 0.97, 543 | <1 μM |

-continued

| Example | Structure | LC-MS (Retention time (min), m/z) | IRAK-4 IC$_{50}$ (nM) |
|---|---|---|---|
| 287 | 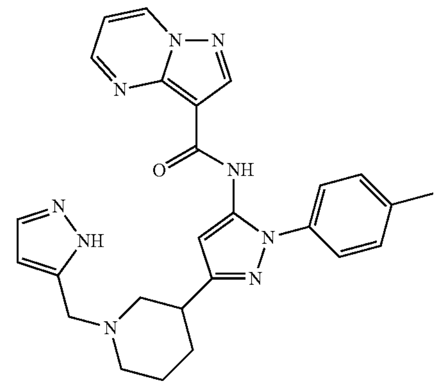 [SMILES: Cc1ccc(-n2nc(C3CCCN(Cc4ccn[nH]4)C3)cc2NC(=O)c2cnn3cccnc23)cc1] | 0.81, 483 | <100 nM |
| 288 | 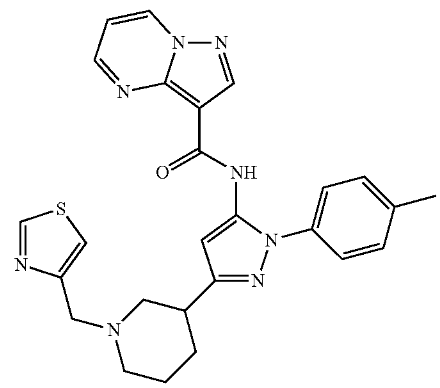 [SMILES: Cc1ccc(-n2nc(C3CCCN(Cc4cscn4)C3)cc2NC(=O)c2cnn3cccnc23)cc1] | 0.91, 499 | <1 μM |
| 289 | 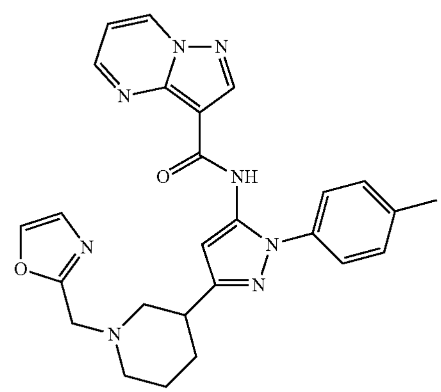 [SMILES: Cc1ccc(-n2nc(C3CCCN(Cc4ncco4)C3)cc2NC(=O)c2cnn3cccnc23)cc1] | 0.85, 482 | <1 μM |
| 290 | 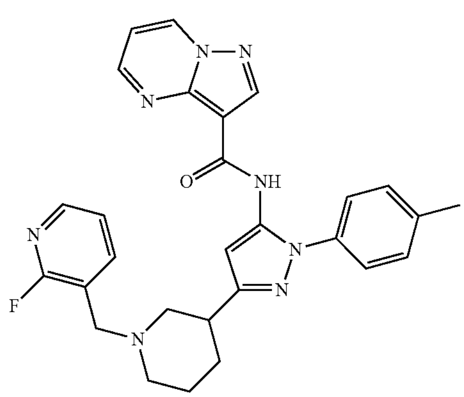 [SMILES: Cc1ccc(-n2nc(C3CCCN(Cc4cccnc4F)C3)cc2NC(=O)c2cnn3cccnc23)cc1] | 1.00, 512 | <1 μM |

-continued

| Example | Structure | LC-MS (Retention time (min), m/z) | IRAK-4 IC$_{50}$ (nM) |
|---|---|---|---|
| 291 | 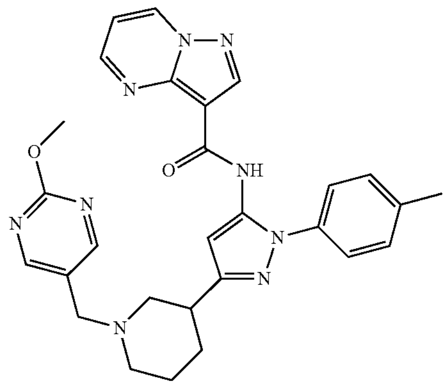 [SMILES: COc1ncc(CN2CCCC(c3cc(NC(=O)c4cnn5cccnc45)n(-c4ccc(C)cc4)n3)C2)cn1] | 0.91, 525 | <1 μM |
| 292 | 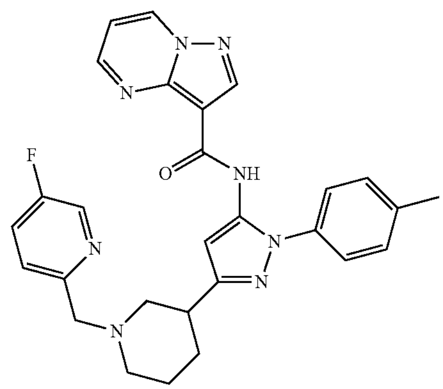 [SMILES: Cc1ccc(-n2nc(C3CCCN(Cc4ccc(F)cn4)C3)cc2NC(=O)c2cnn3cccnc23)cc1] | 0.99, 512 | <1 μM |
| 293 | 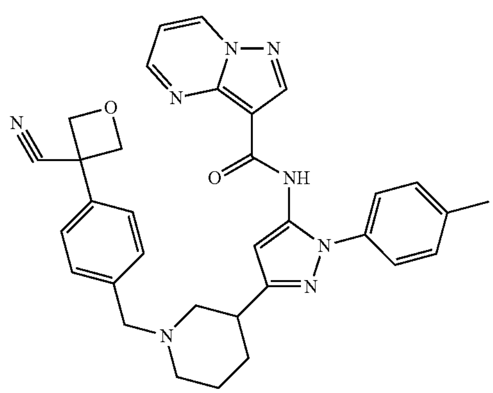 [SMILES: Cc1ccc(-n2nc(C3CCCN(Cc4ccc(C5(C#N)COC5)cc4)C3)cc2NC(=O)c2cnn3cccnc23)cc1] | 1.06, 573 | <1 μM |
| 294 | 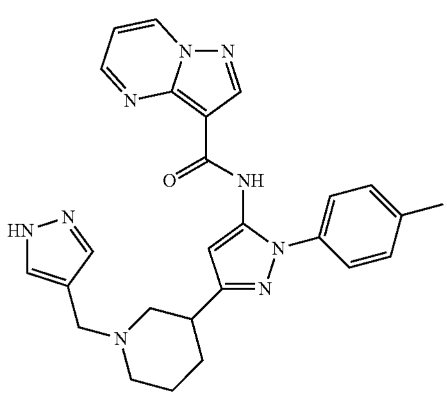 [SMILES: Cc1ccc(-n2nc(C3CCCN(Cc4cn[nH]c4)C3)cc2NC(=O)c2cnn3cccnc23)cc1] | 0.80, 483 | <1 μM |

| Example | Structure | LC-MS (Retention time (min), m/z) | IRAK-4 IC$_{50}$ (nM) |
|---|---|---|---|
| 295 | 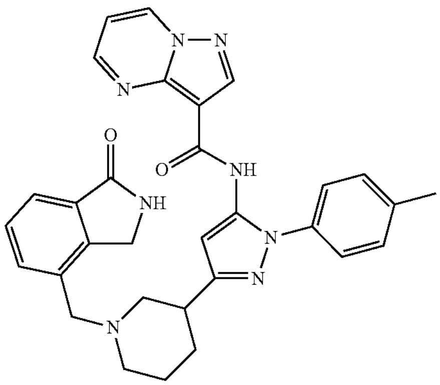 [SMILES: Cc1ccc(-n2nc(C3CCCN(Cc4cccc5c4CNC5=O)C3)cc2NC(=O)c2cnn3cccnc23)cc1] | 0.91, 548 | <100 nM |
| 296 | 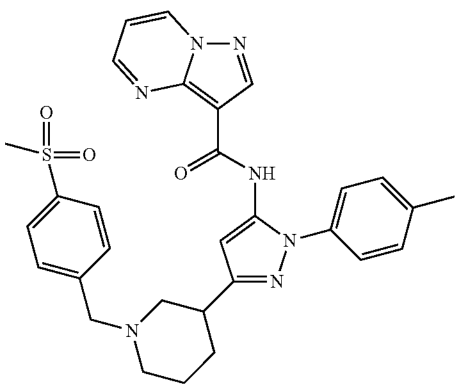 | 0.97, 571 | <100 nM |
| 297 | 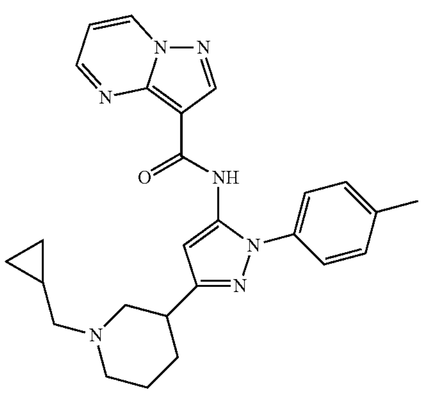 [SMILES: Cc1ccc(-n2nc(C3CCCN(CC4CC4)C3)cc2NC(=O)c2cnn3cccnc23)cc1] | 1.06, 456 | <1 μM |
| 298 | 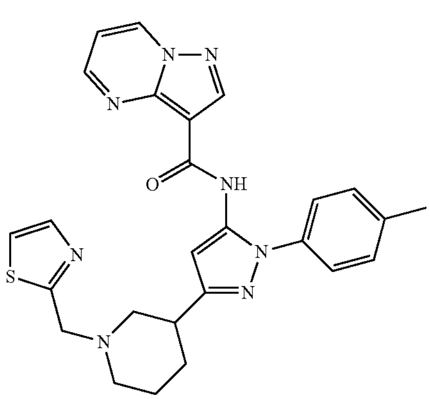 [SMILES: Cc1ccc(-n2nc(C3CCCN(Cc4nccs4)C3)cc2NC(=O)c2cnn3cccnc23)cc1] | 0.96, 499 | <1 μM |

-continued

| Example | Structure | LC-MS (Retention time (min), m/z) | IRAK-4 IC$_{50}$ (nM) |
|---|---|---|---|
| 299 | 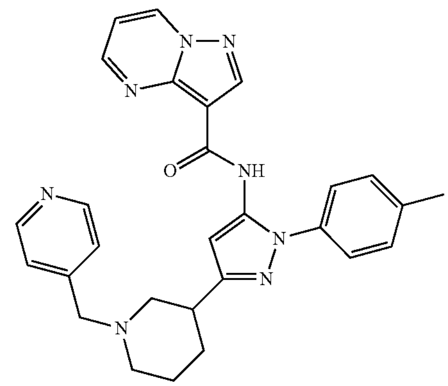 [SMILES: Cc1ccc(-n2nc(C3CCCN(Cc4ccncc4)C3)cc2NC(=O)c2cnn3cccnc23)cc1] | 0.91, 494 | <1 μM |
| 300 | 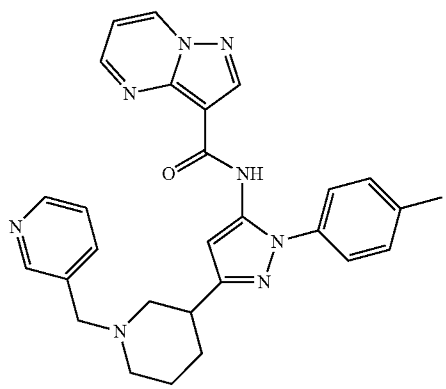 [SMILES: Cc1ccc(-n2nc(C3CCCN(Cc4cccnc4)C3)cc2NC(=O)c2cnn3cccnc23)cc1] | 0.91, 494 | <1 μM |
| 301 | 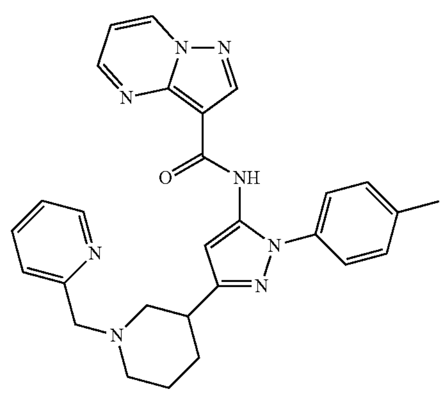 [SMILES: Cc1ccc(-n2nc(C3CCCN(Cc4ccccn4)C3)cc2NC(=O)c2cnn3cccnc23)cc1] | 0.92, 494 | <1 μM |
| 302 | 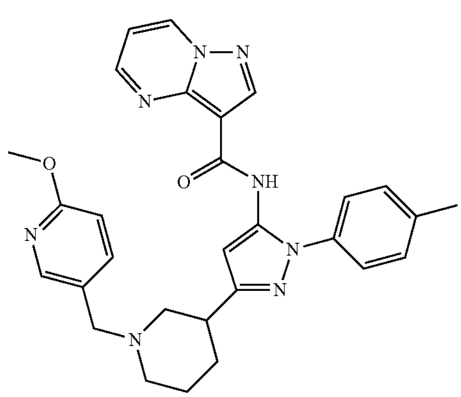 | 1.02, 524 | <1 μM |

-continued
| Example | Structure | LC-MS (Retention time (min), m/z) | IRAK-4 IC$_{50}$ (nM) |
|---|---|---|---|
| 303 | 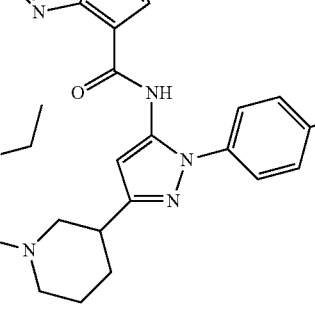 | 1.00, 511 | <1 μM |
| 304 | 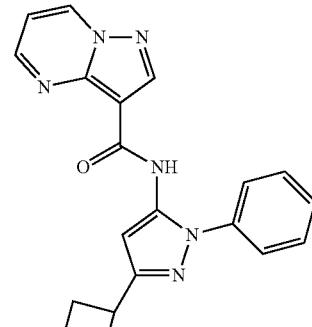 | 0.76, 466 | <1 μM |
| 305 | 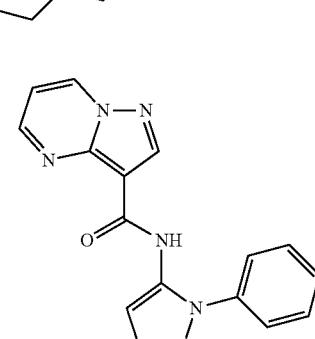 | 0.72, 454 | <100 nM |
| 306 | 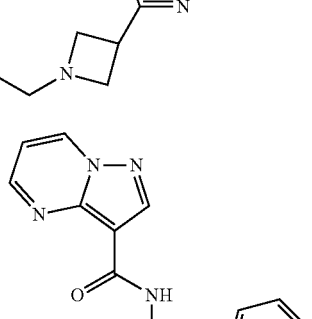 | 1.73, 454 | <1 μM |

-continued

| Example | Structure | LC-MS (Retention time (min), m/z) | IRAK-4 IC$_{50}$ (nM) |
|---|---|---|---|
| 307 | 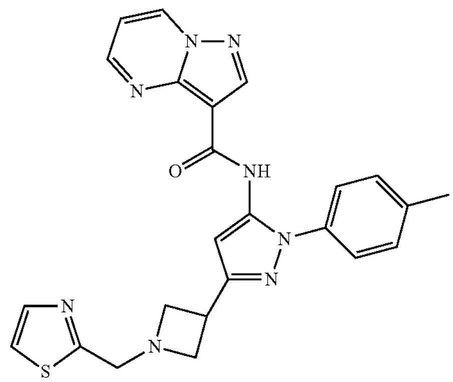 [SMILES: Cc1ccc(-n2nc(C3CN(Cc4nccs4)C3)cc2NC(=O)c2cnn3cccnc23)cc1] | 0.84, 471 | <1 μM |
| 308 | 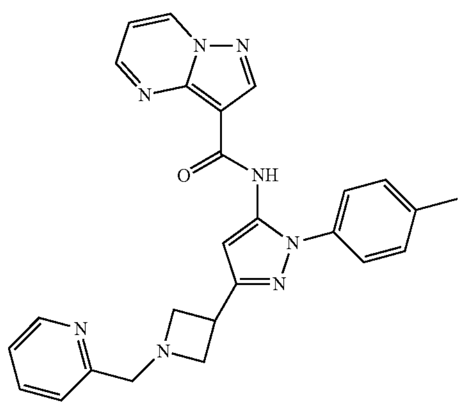 [SMILES: Cc1ccc(-n2nc(C3CN(Cc4ccccn4)C3)cc2NC(=O)c2cnn3cccnc23)cc1] | 0.81, 465 | <1 μM |
| 309 | 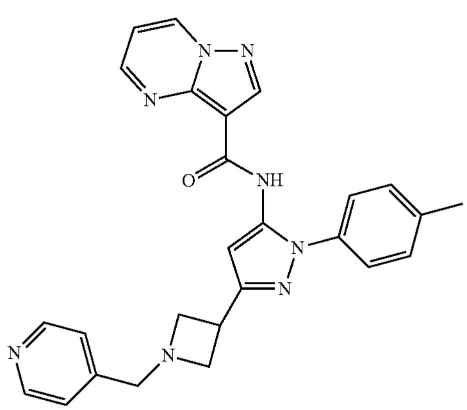 [SMILES: Cc1ccc(-n2nc(C3CN(Cc4ccncc4)C3)cc2NC(=O)c2cnn3cccnc23)cc1] | 0.80, 465 | <1 μM |

-continued

| Example | Structure | LC-MS (Retention time (min), m/z) | IRAK-4 IC$_{50}$ (nM) |
| --- | --- | --- | --- |
| 310 | 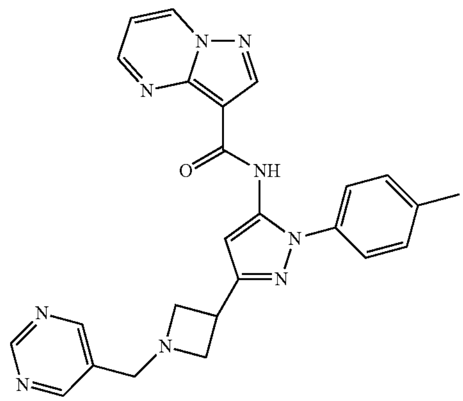 [SMILES: Cc1ccc(-n2nc(C3CN(Cc4cncnc4)C3)cc2NC(=O)c2cnn3cccnc23)cc1] | 0.74, 466 | <1 µM |
| 311 | 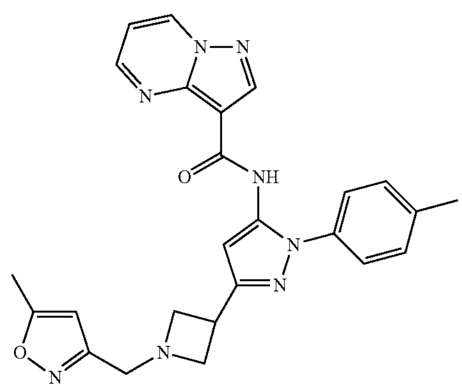 | 0.84, 469 | <1 µM |
| 312 | 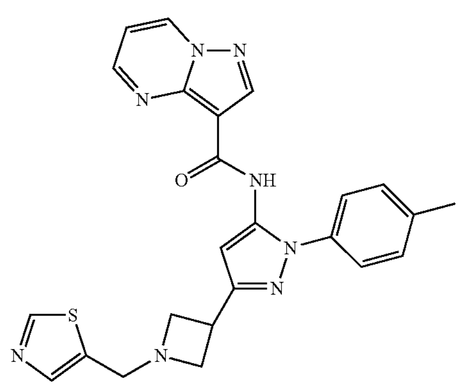 [SMILES: Cc1ccc(-n2nc(C3CN(Cc4cncs4)C3)cc2NC(=O)c2cnn3cccnc23)cc1] | 0.81, 471 | <100 nM |

-continued

| Example | Structure | LC-MS (Retention time (min), m/z) | IRAK-4 IC$_{50}$ (nM) |
|---|---|---|---|
| 313 | 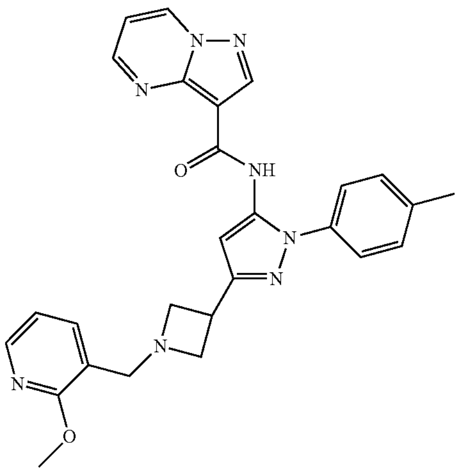 [SMILES: COc1ncccc1CN1CC(c2cc(NC(=O)c3cnn4cccnc34)n(-c3ccc(C)cc3)n2)C1] | 0.92, 495 | <100 nM |
| 314 | 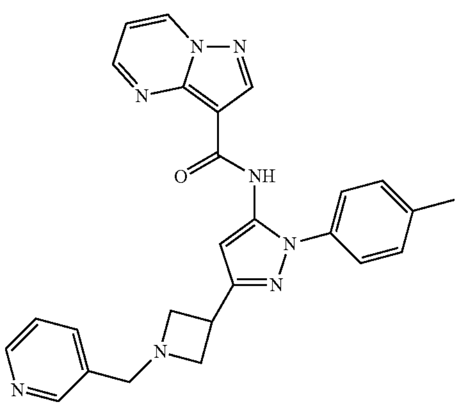 | 0.81, 465 | <100 nM |
| 315 | 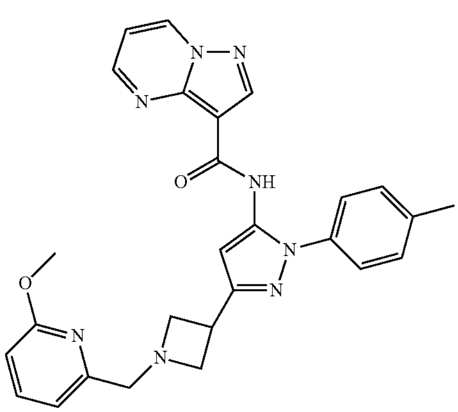 [SMILES: COc1cccc(CN2CC(c3cc(NC(=O)c4cnn5cccnc45)n(-c4ccc(C)cc4)n3)C2)n1] | 0.96, 495 | <100 nM |

| Example | Structure | LC-MS (Retention time (min), m/z) | IRAK-4 IC$_{50}$ (nM) |
| --- | --- | --- | --- |
| 316 | 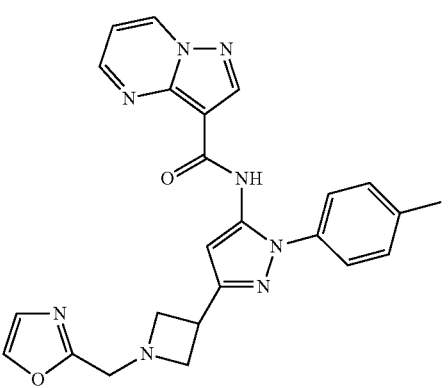 | 0.77, 455 | <1 μM |
| 317 | 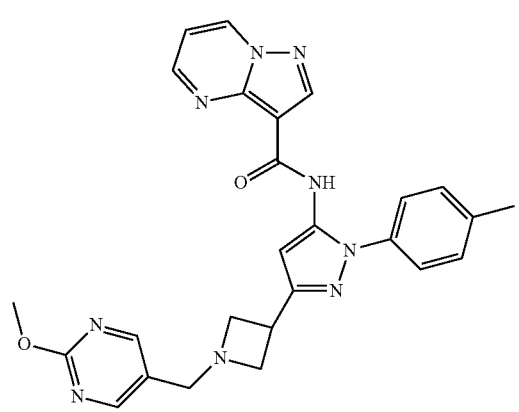 | 0.81, 496 | <1 μM |
| 318 | 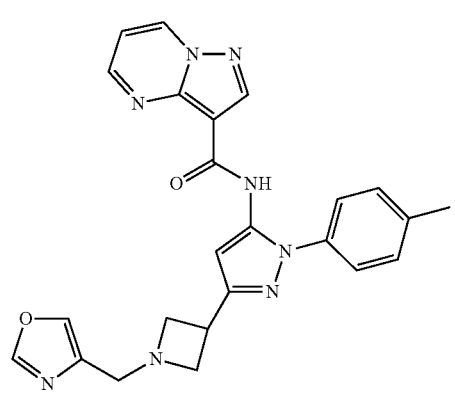 [SMILES: Cc1ccc(-n2nc(C3CN(Cc4cocn4)C3)cc2NC(=O)c2cnn3cccnc23)cc1] | 0.76, 455 | <1 μM |

| Example | Structure | LC-MS (Retention time (min), m/z) | IRAK-4 IC$_{50}$ (nM) |
| --- | --- | --- | --- |
| 319 | 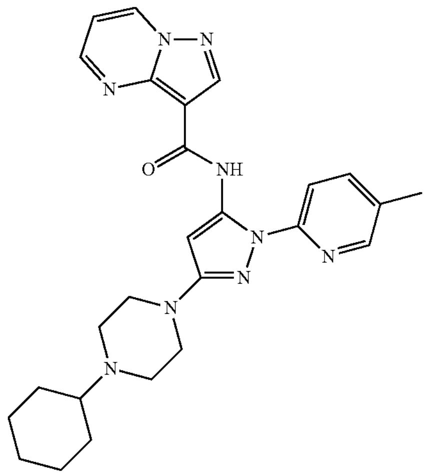 | n/a | <100 nM |
| 320 | 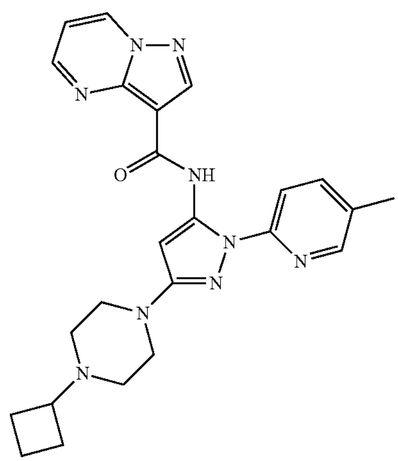 [SMILES: Cc1ccc(-n2nc(N3CCN(C4CCC4)CC3)cc2NC(=O)c2cnn3cccnc23)nc1] | n/a | <100 nM |
| 321 | 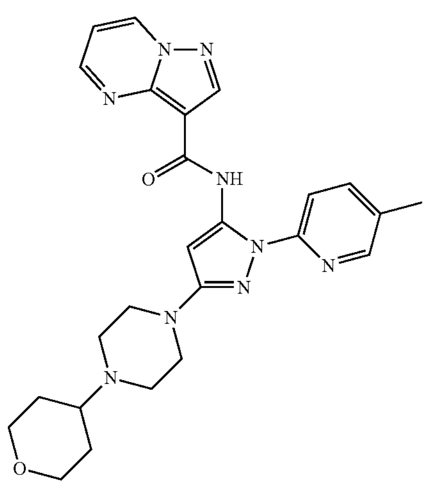 [SMILES: Cc1ccc(-n2nc(N3CCN(C4CCOCC4)CC3)cc2NC(=O)c2cnn3cccnc23)nc1] | n/a | <100 nM |

-continued

| Example | Structure | LC-MS (Retention time (min), m/z) | IRAK-4 IC$_{50}$ (nM) |
| --- | --- | --- | --- |
| 322 | 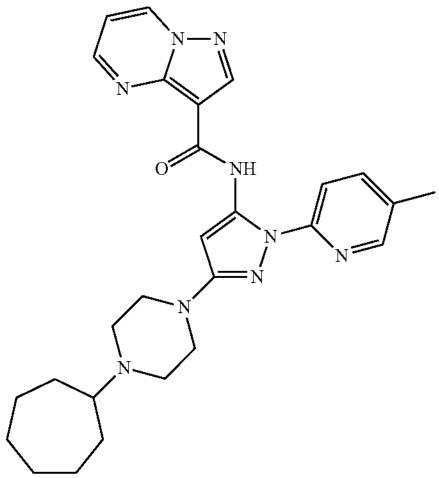 [SMILES: Cc1ccc(-n2nc(N3CCN(C4CCCCCC4)CC3)cc2NC(=O)c2cnn3cccnc23)nc1] | n/a | <100 nM |
| 323 | 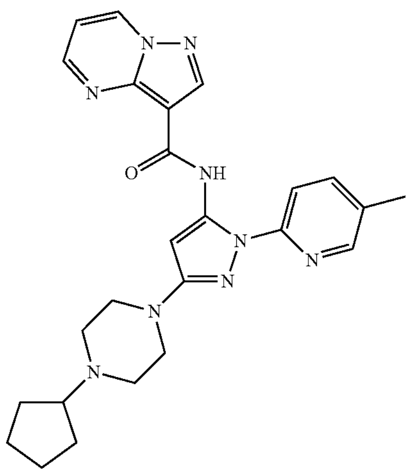 [SMILES: Cc1ccc(-n2nc(N3CCN(C4CCCC4)CC3)cc2NC(=O)c2cnn3cccnc23)nc1] | n/a | <100 nM |
| 324 | 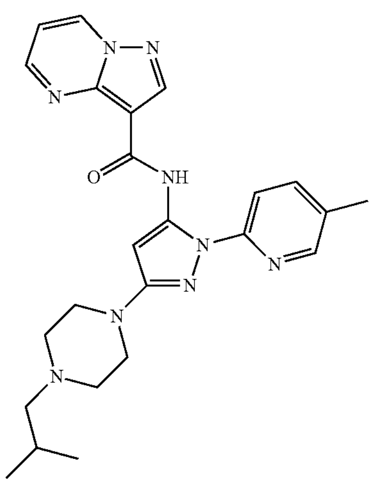 [SMILES: Cc1ccc(-n2nc(N3CCN(CC(C)C)CC3)cc2NC(=O)c2cnn3cccnc23)nc1] | n/a | <100 nM |

-continued

| Example | Structure | LC-MS (Retention time (min), m/z) | IRAK-4 IC$_{50}$ (nM) |
|---|---|---|---|
| 325 | 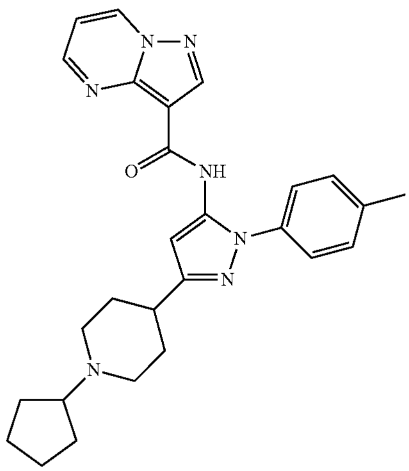 [SMILES: Cc1ccc(-n2nc(C3CCN(C4CCCC4)CC3)cc2NC(=O)c2cnn3cccnc23)cc1] | 1.13, 470 | <100 nM |
| 326 | 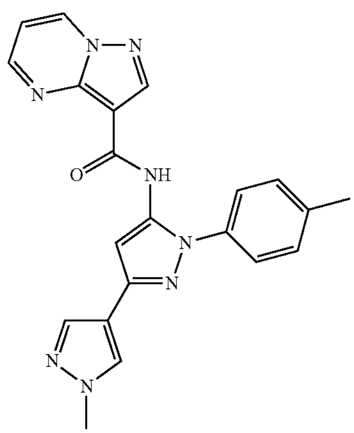 [SMILES: Cc1ccc(-n2nc(-c3cnn(C)c3)cc2NC(=O)c2cnn3cccnc23)cc1] | 0.79, 399 | <1 μM |
| 327 | 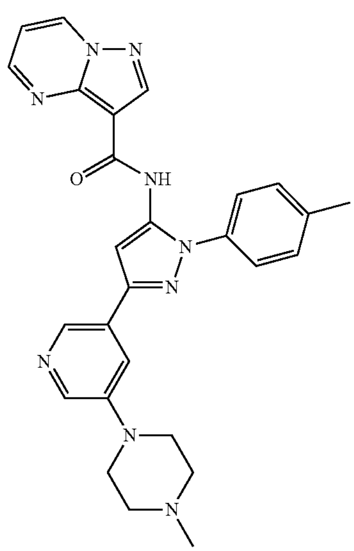 [SMILES: Cc1ccc(-n2nc(-c3cncc(N4CCN(C)CC4)c3)cc2NC(=O)c2cnn3cccnc23)cc1] | 0.87, 495 | <1 μM |

-continued

| Example | Structure | LC-MS (Retention time (min), m/z) | IRAK-4 IC$_{50}$ (nM) |
|---|---|---|---|
| 328 | 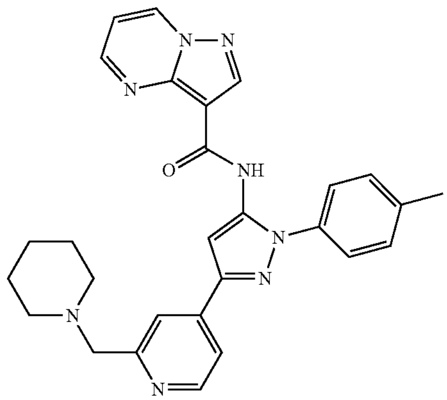 [SMILES: Cc1ccc(-n2nc(-c3ccnc(CN4CCCCC4)c3)cc2NC(=O)c2cnn3cccnc23)cc1] | 1.07, 494 | <100 nM |
| 329 | 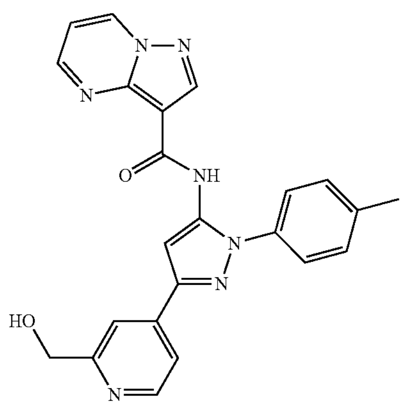 [SMILES: Cc1ccc(-n2nc(-c3ccnc(CO)c3)cc2NC(=O)c2cnn3cccnc23)cc1] | 0.79, 426 | <1 µM |
| 330 | 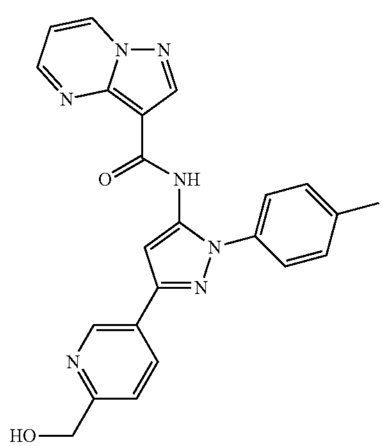 [SMILES: Cc1ccc(-n2nc(-c3ccc(CO)nc3)cc2NC(=O)c2cnn3cccnc23)cc1] | 0.71, 426 | <100 nM |

-continued
| Example | Structure | LC-MS (Retention time (min), m/z) | IRAK-4 IC$_{50}$ (nM) |
|---|---|---|---|
| 331 | 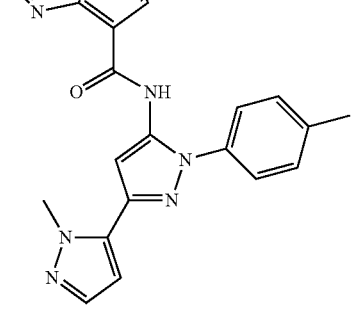 | 0.89, 399 | <1 μM |
| 332 | 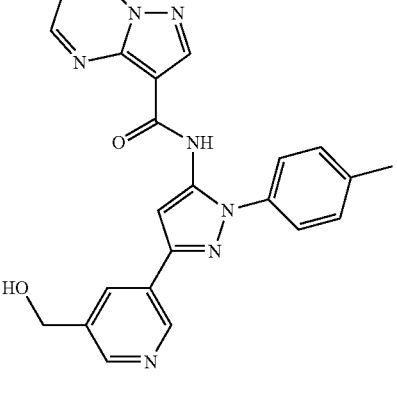 | 0.75, 426 | <1 μM |
| 333 | 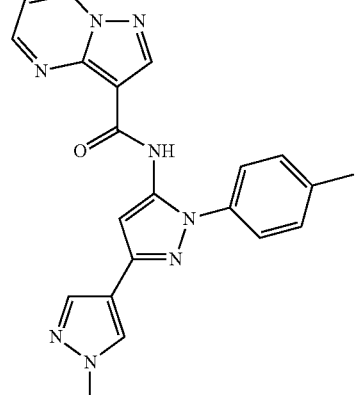 | 0.76, 491 | <1 μM |

| Example | Structure | LC-MS (Retention time (min), m/z) | IRAK-4 IC$_{50}$ (nM) |
|---|---|---|---|
| 334 | 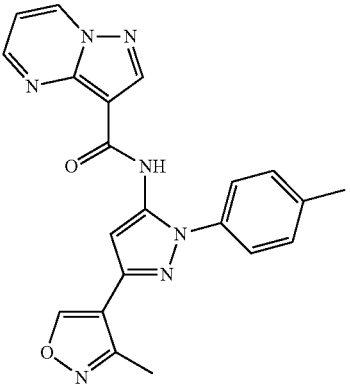 [SMILES: Cc1ccc(-n2nc(-c3conc3C)cc2NC(=O)c2cnn3cccnc23)cc1] | 0.95, 400 | <1 μM |
| 335 | 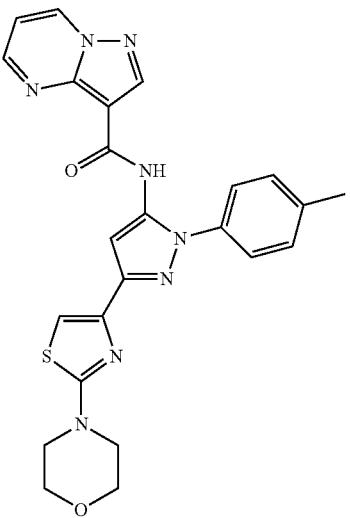 [SMILES: Cc1ccc(-n2nc(-c3csc(N4CCOCC4)n3)cc2NC(=O)c2cnn3cccnc23)cc1] | 0.95, 487 | <1 μM |
| 336 | 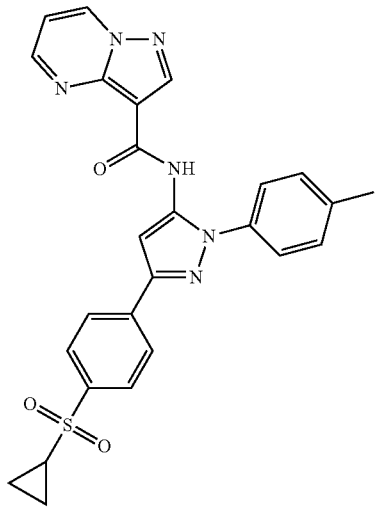 [SMILES: Cc1ccc(-n2nc(-c3ccc(S(=O)(=O)C4CC4)cc3)cc2NC(=O)c2cnn3cccnc23)cc1] | 1.00, 499 | <100 nM |

-continued

| Example | Structure | LC-MS (Retention time (min), m/z) | IRAK-4 IC$_{50}$ (nM) |
|---|---|---|---|
| 337 | 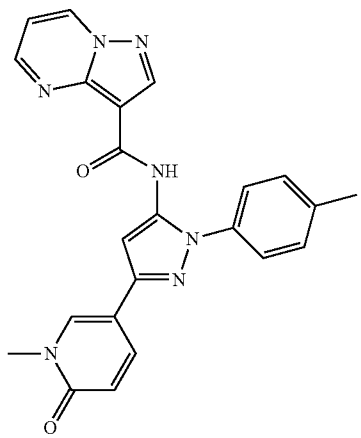 | 0.76, 426 | <1 μM |
| 338 | 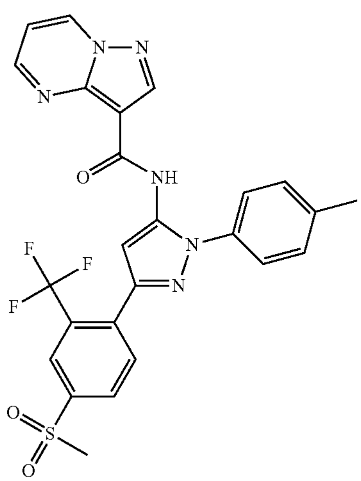 [SMILES: Cc1ccc(-n2nc(-c3ccc(S(C)(=O)=O)cc3C(F)(F)F)cc2NC(=O)c2cnn3cccnc23)cc1] | 0.97, 541 | 100 nM |
| 339 | 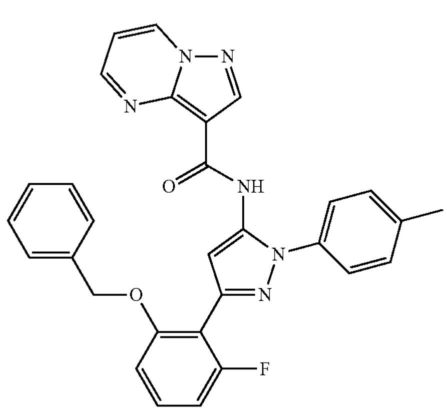 [SMILES: Cc1ccc(-n2nc(-c3c(F)cccc3OCc3ccccc3)cc2NC(=O)c2cnn3cccnc23)cc1] | 1.12, 519 | <1 μM |

-continued

| Example | Structure | LC-MS (Retention time (min), m/z) | IRAK-4 IC$_{50}$ (nM) |
|---|---|---|---|
| 340 | 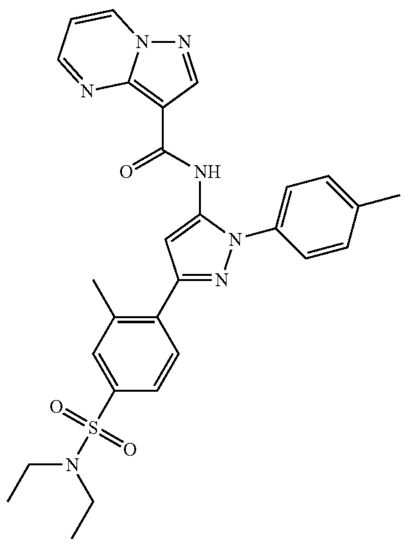 [SMILES: CCN(CC)S(=O)(=O)c1ccc(-c2cc(NC(=O)c3cnn4cccnc34)n(-c3ccc(C)cc3)n2)c(C)c1] | 1.12, 544 | <1 μM |
| 341 | 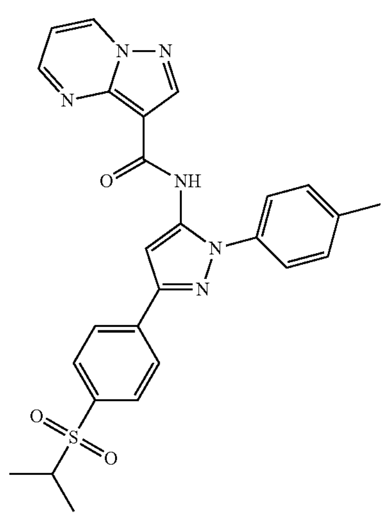 [SMILES: Cc1ccc(-n2nc(-c3ccc(S(=O)(=O)C(C)C)cc3)cc2NC(=O)c2cnn3cccnc23)cc1] | 1.01, 501 | <1 μM |

| Example | Structure | LC-MS (Retention time (min), m/z) | IRAK-4 IC$_{50}$ (nM) |
|---|---|---|---|
| 342 | 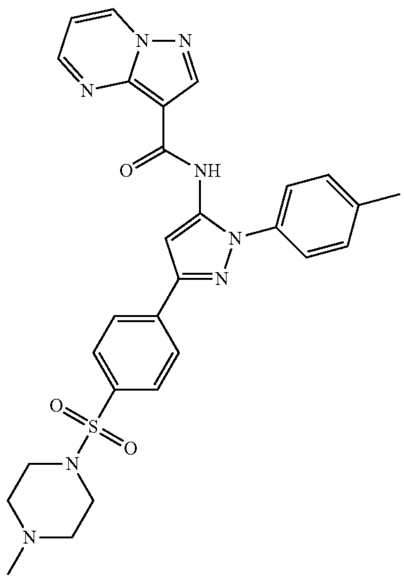 [SMILES: Cc1ccc(-n2nc(-c3ccc(S(=O)(=O)N4CCN(C)CC4)cc3)cc2NC(=O)c2cnn3cccnc23)cc1] | 0.97, 557 | <100 nM |
| 343 | 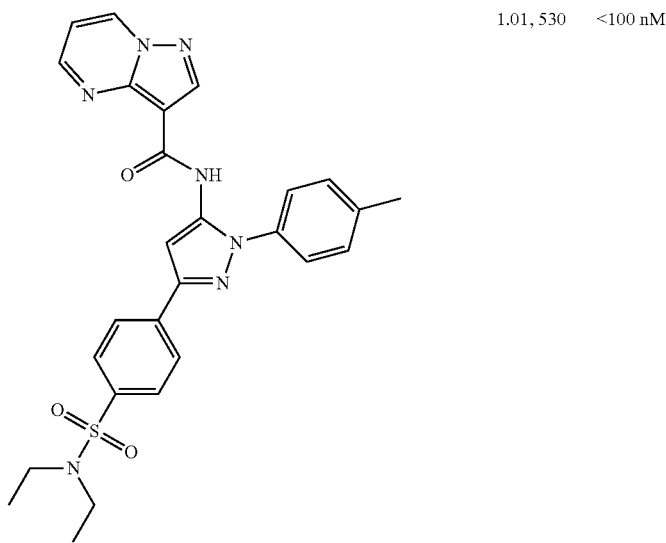 | 1.01, 530 | <100 nM |

| Example | Structure | LC-MS (Retention time (min), m/z) | IRAK-4 IC$_{50}$ (nM) |
|---|---|---|---|
| 344 | 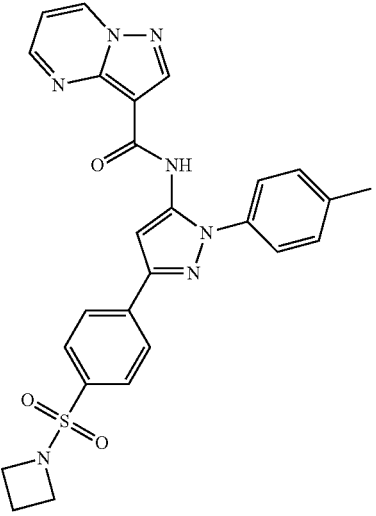 [SMILES: Cc1ccc(-n2nc(-c3ccc(S(=O)(=O)N4CCC4)cc3)cc2NC(=O)c2cnn3cccnc23)cc1] | 1.01, 514 | <100 nM |
| 345 | 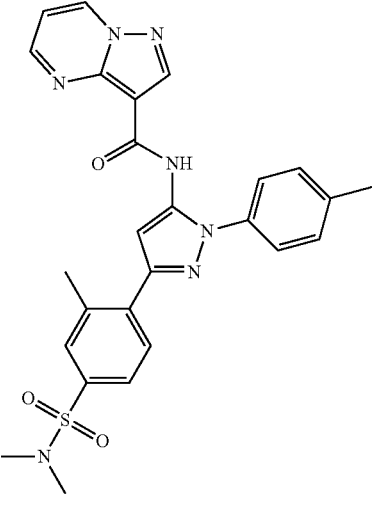 | 1.04, 516 | <100 nM |
| 346 | 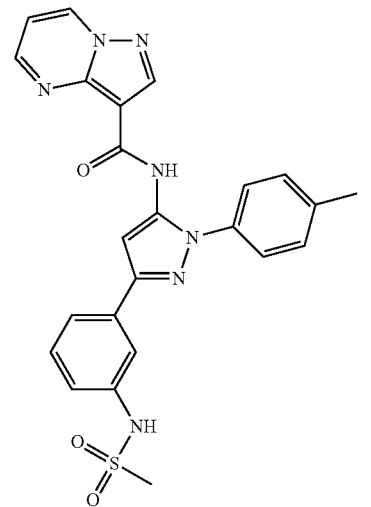 [SMILES: Cc1ccc(-n2nc(-c3cccc(NS(C)(=O)=O)c3)cc2NC(=O)c2cnn3cccnc23)cc1] | 0.76, 488 | <1 μM |

-continued
| Example | Structure | LC-MS (Retention time (min), m/z) | IRAK-4 IC$_{50}$ (nM) |
|---|---|---|---|
| 347 | 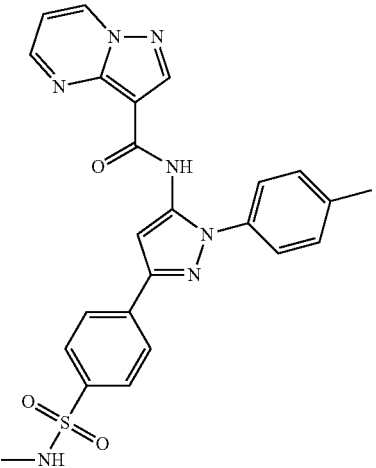 | 0.90, 488 | <100 nM |
| 348 | 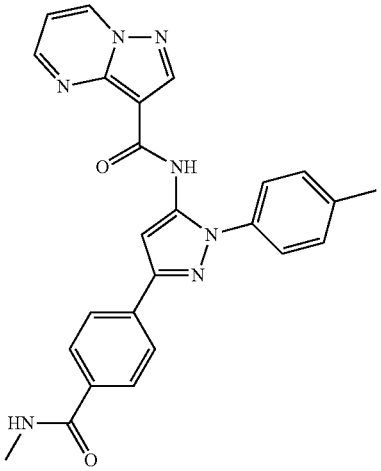 | 0.83, 452 | <100 nM |
| 349 | 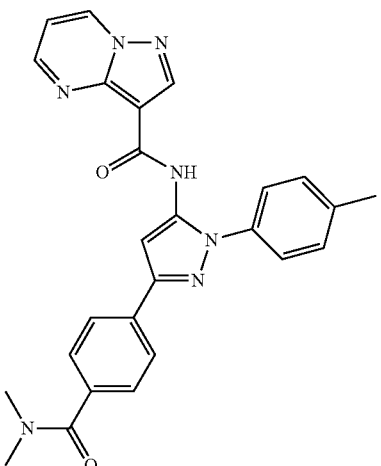 | 0.87, 466 | <100 nM |

-continued
| Example | Structure | LC-MS (Retention time (min), m/z) | IRAK-4 IC$_{50}$ (nM) |
|---|---|---|---|
| 350 | 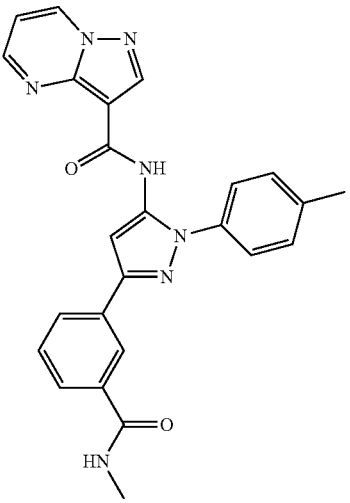 [SMILES: CNC(=O)c1cccc(-c2cc(NC(=O)c3cnn4cccnc34)n(-c3ccc(C)cc3)n2)c1] | 0.85, 452 | <1 μM |
| 351 | 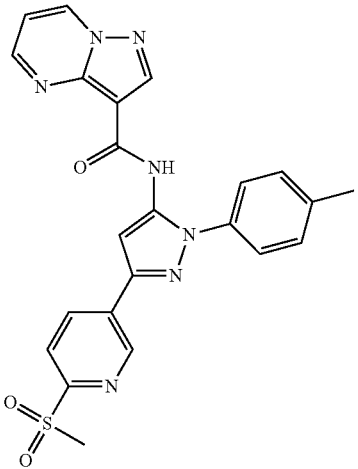 [SMILES: Cc1ccc(-n2nc(-c3ccc(S(C)(=O)=O)nc3)cc2NC(=O)c2cnn3cccnc23)cc1] | 0.86, 474 | <1 μM |
| 352 | 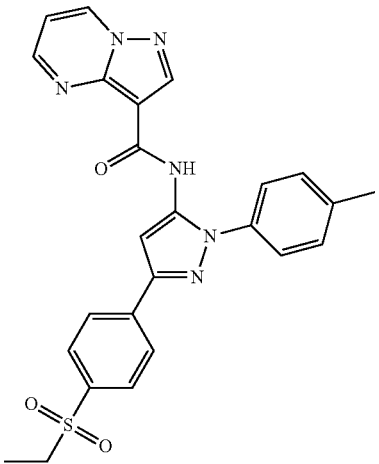 [SMILES: CCS(=O)(=O)c1ccc(-c2cc(NC(=O)c3cnn4cccnc34)n(-c3ccc(C)cc3)n2)cc1] | 0.95, 487 | <100 nM |

-continued

| Example | Structure | LC-MS (Retention time (min), m/z) | IRAK-4 IC$_{50}$ (nM) |
|---|---|---|---|
| 353 | 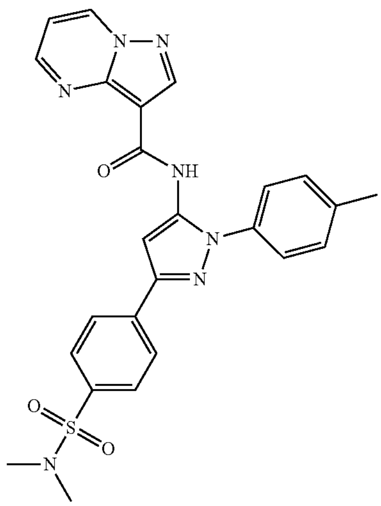 | 1.00, 502 | <100 nM |
| 354 | 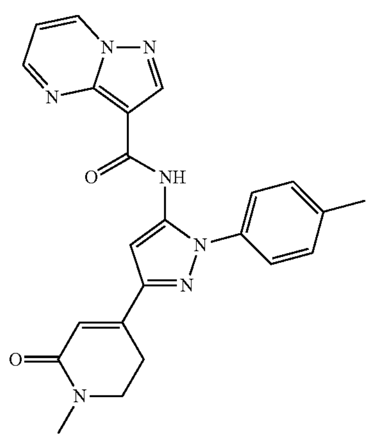 [SMILES: Cc1ccc(-n2nc(C3=CC(=O)N(C)CC3)cc2NC(=O)c2cnn3cccnc23)cc1] | n/a | <1 µM |
| 355 | 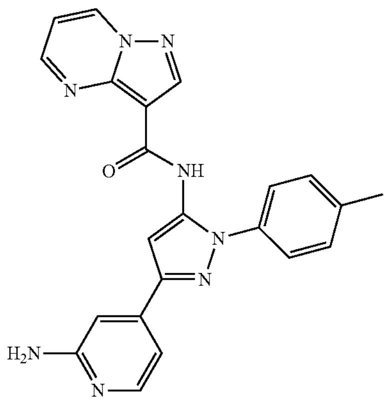 [SMILES: Cc1ccc(-n2nc(-c3ccnc(N)c3)cc2NC(=O)c2cnn3cccnc23)cc1] | n/a | <100 nM |

-continued
| Example | Structure | LC-MS (Retention time (min), m/z) | IRAK-4 IC$_{50}$ (nM) |
|---|---|---|---|
| 356 | 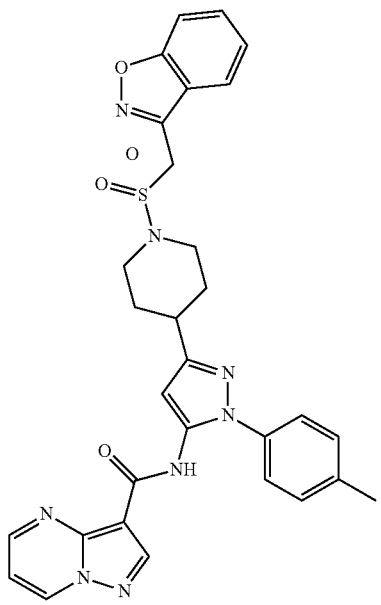 | n/a | <1 μM |
| 357 | 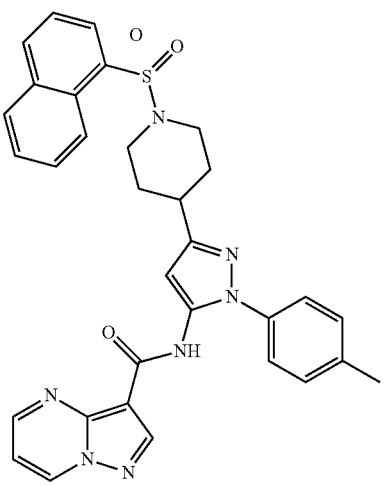 | 1.14, 592 | <1 μM |

-continued
| Example | Structure | LC-MS (Retention time (min), m/z) | IRAK-4 IC$_{50}$ (nM) |
|---|---|---|---|
| 358 | 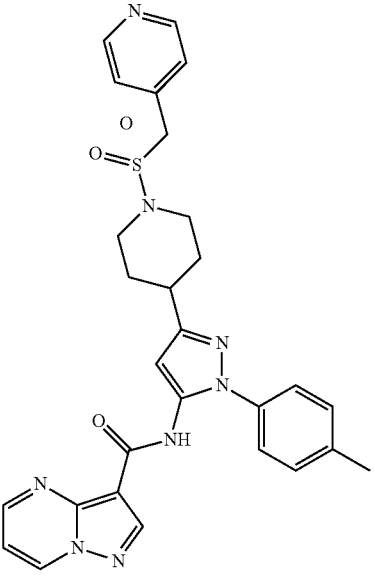 | 0.85, 557 | <1 μM |
| 359 | 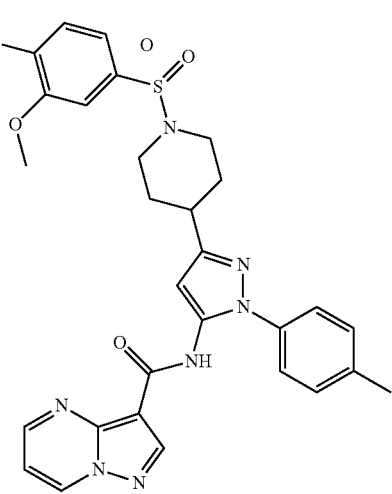 | 1.00, 602 | <1 μM |

-continued
| Example | Structure | LC-MS (Retention time (min), m/z) | IRAK-4 IC$_{50}$ (nM) |
|---|---|---|---|
| 360 | 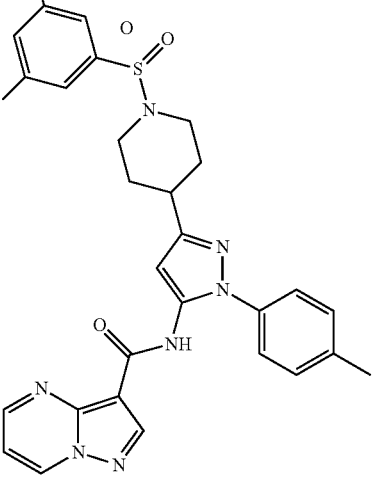 | 1.11, 578 | <1 μM |
| 361 | 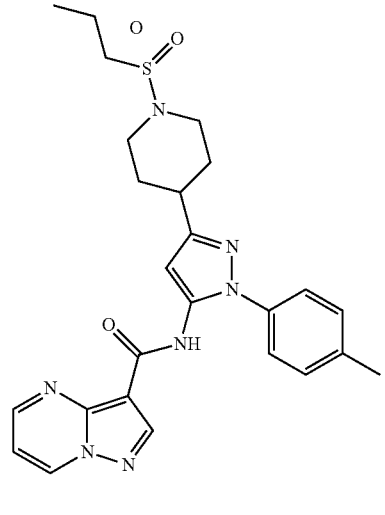 | 0.96, 508 | <1 μM |
| 362 | 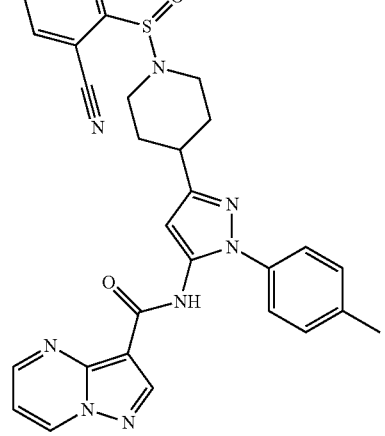 | 1.00, 567 | <1 μM |

-continued

| Example | Structure | LC-MS (Retention time (min), m/z) | IRAK-4 IC$_{50}$ (nM) |
|---------|-----------|-----------------------------------|------------------------|
| 363 | 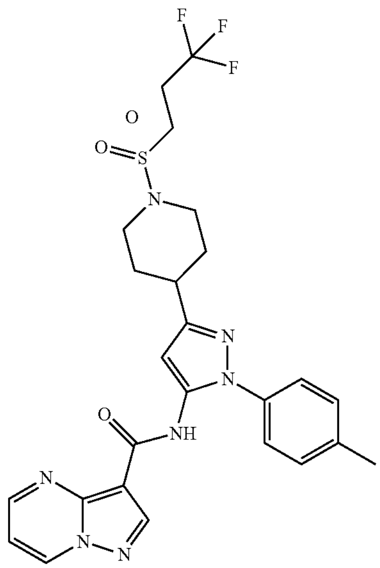 | 1.02, 562 | <1 μM |
| 364 | 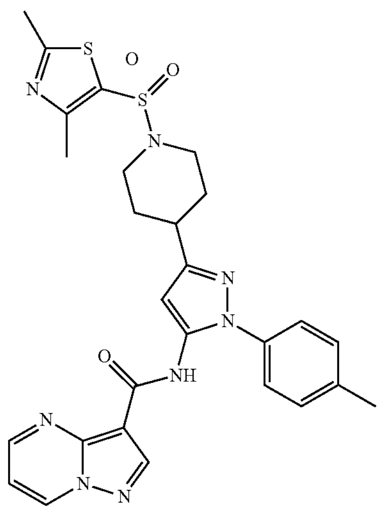 | 1.10, 577 | <100 nM |
| 365 | 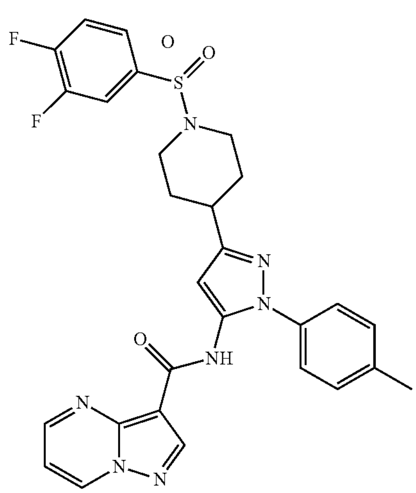 | 1.10, 578 | <1 μM |

-continued
| Example | Structure | LC-MS (Retention time (min), m/z) | IRAK-4 IC$_{50}$ (nM) |
|---|---|---|---|
| 366 | 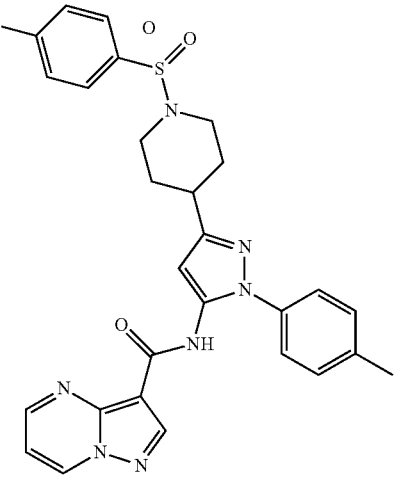 | 1.06, 560 | <1 μM |
| 367 | 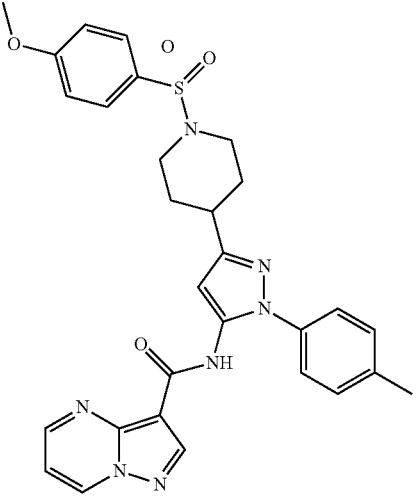 | 1.05, 572 | <1 μM |
| 368 | 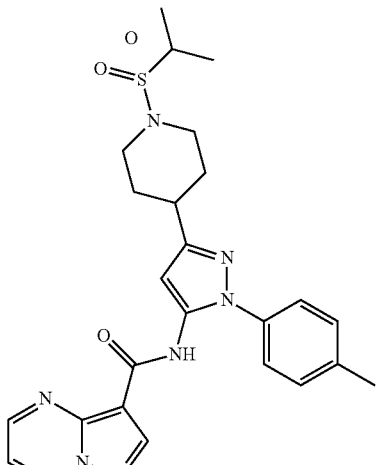 | 0.95, 508 | <100 nM |

-continued
| Example | Structure | LC-MS (Retention time (min), m/z) | IRAK-4 IC$_{50}$ (nM) |
|---|---|---|---|
| 369 | 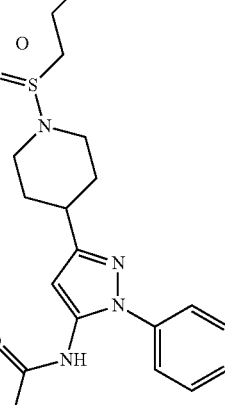 | 1.03, 522 | <1 μM |
| 370 | 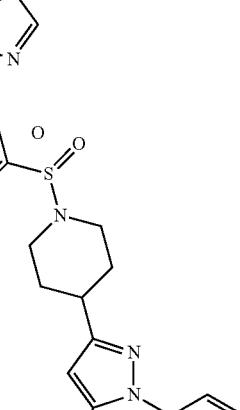 | 1.07, 578 | <1 μM |
| 371 | 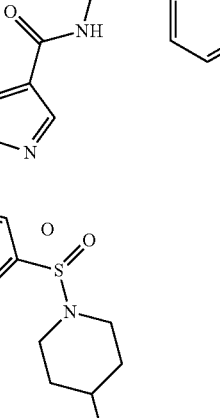 | 1.14, 610 | >1 μM |

| Example | Structure | LC-MS (Retention time (min), m/z) | IRAK-4 IC$_{50}$ (nM) |
| --- | --- | --- | --- |
| 372 | 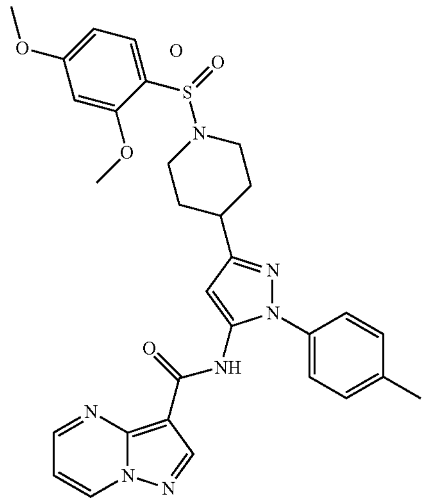 | 1.02, 602 | <1 μM |
| 373 | 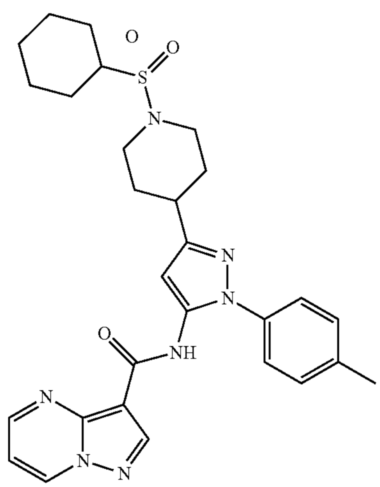 | 1.00, 548 | <1 μM |
| 374 | 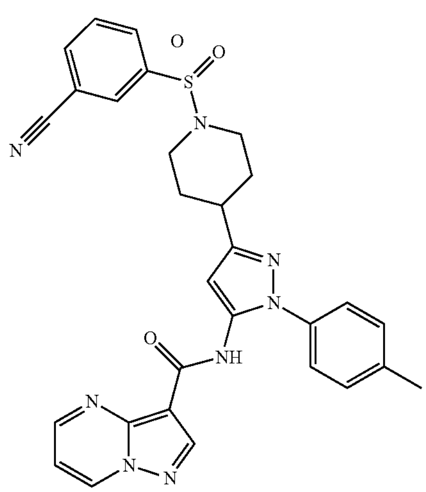 | 1.01, 567 | <1 μM |

-continued
| Example | Structure | LC-MS (Retention time (min), m/z) | IRAK-4 IC$_{50}$ (nM) |
|---|---|---|---|
| 375 | 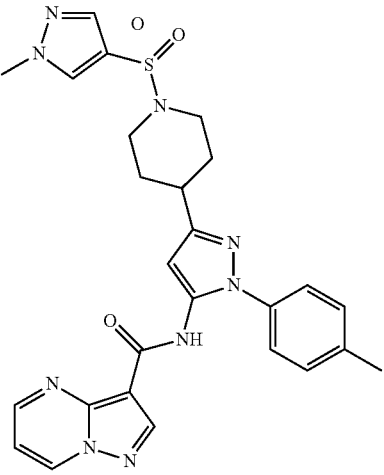 | 0.87, 546 | <1 μM |
| 376 | 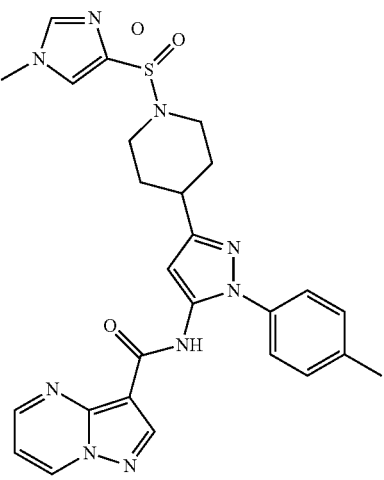 | 0.80, 546 | <1 μM |
| 377 | 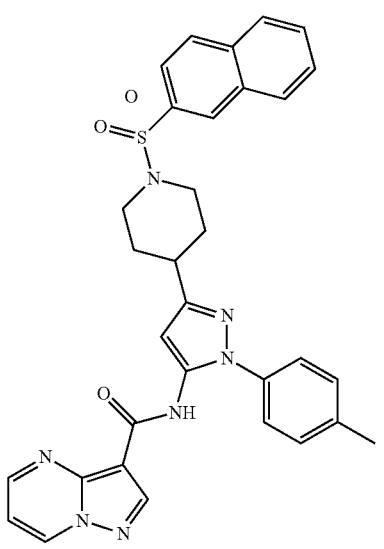 | 1.14, 592 | >1 μM |

| Example | Structure | LC-MS (Retention time (min), m/z) | IRAK-4 IC$_{50}$ (nM) |
|---|---|---|---|
| 378 | 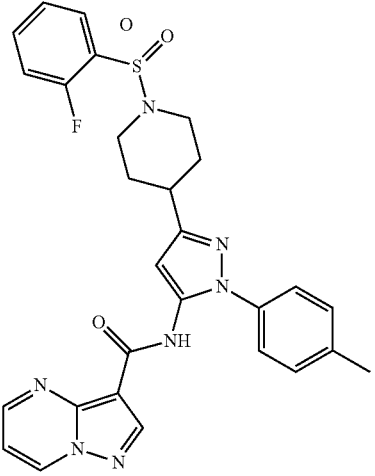 | 1.05, 560 | <1 μM |
| 379 | 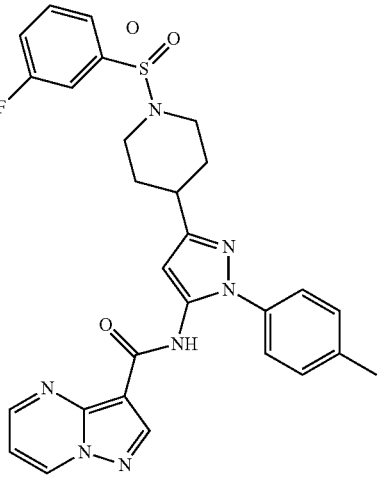 | 1.07, 560 | <1 μM |
| 380 | 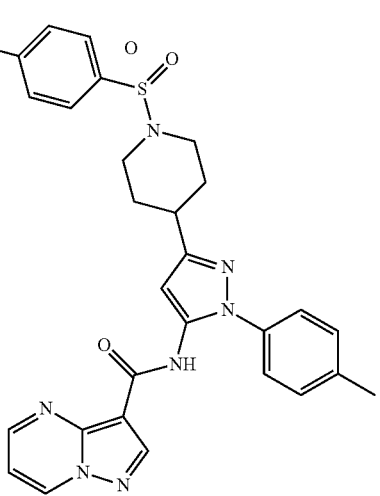 | 1.02, 567 | <1 μM |

-continued

| Example | Structure | LC-MS (Retention time (min), m/z) | IRAK-4 IC$_{50}$ (nM) |
| --- | --- | --- | --- |
| 381 | 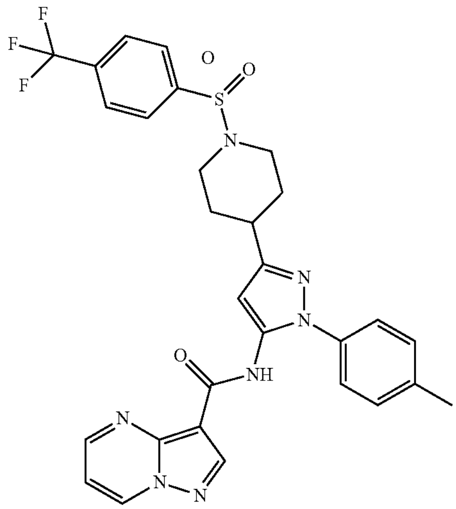 | 1.15, 610 | >1 μM |
| 382 | 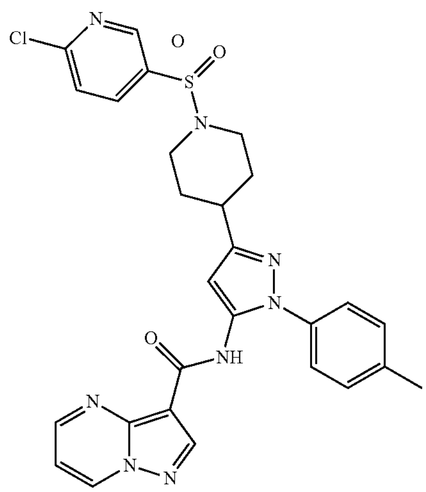 | 1.04, 577 | <1 μM |
| 383 | 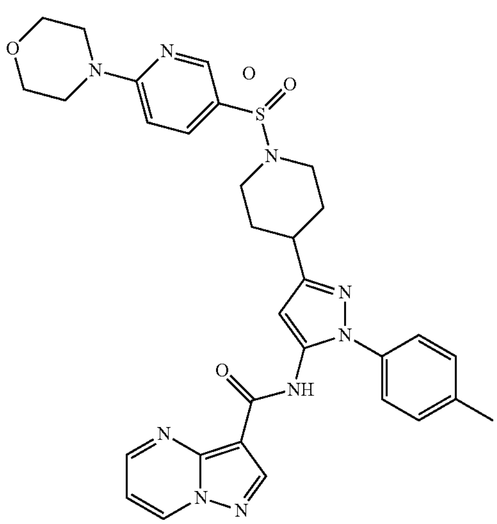 | 0.98, 628 | <1 μM |

| Example | Structure | LC-MS (Retention time (min), m/z) | IRAK-4 IC$_{50}$ (nM) |
|---|---|---|---|
| 384 | 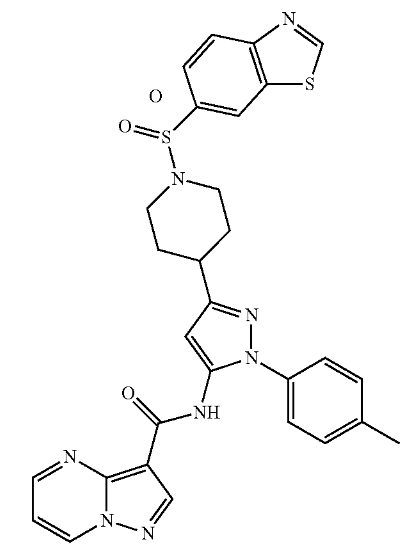 | 1.00, 599 | <1 µM |
| 385 | 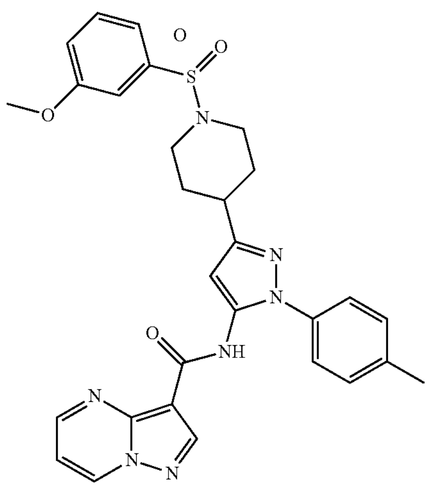 | 1.06, 572 | >1 µM |
| 386 | 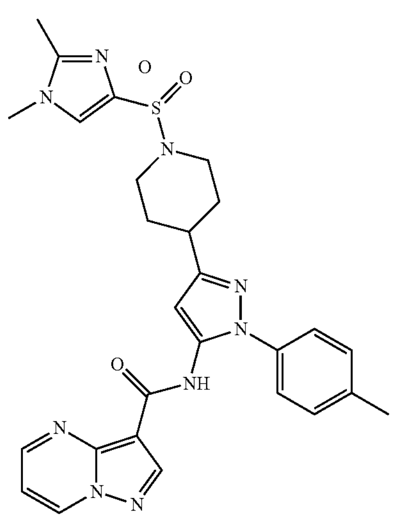 | 0.81, 560 | <1 µM |

-continued
| Example | Structure | LC-MS (Retention time (min), m/z) | IRAK-4 IC$_{50}$ (nM) |
|---|---|---|---|
| 387 | 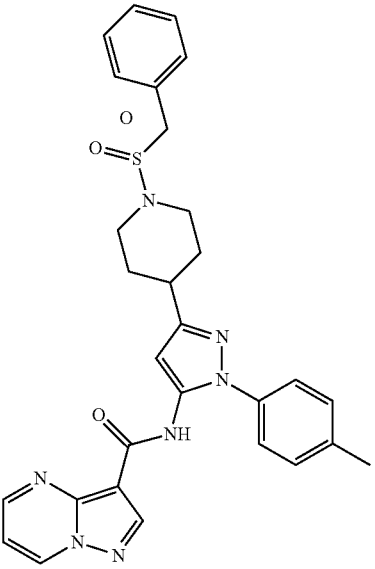 | 1.03, 556 | <1 μM |
| 388 | 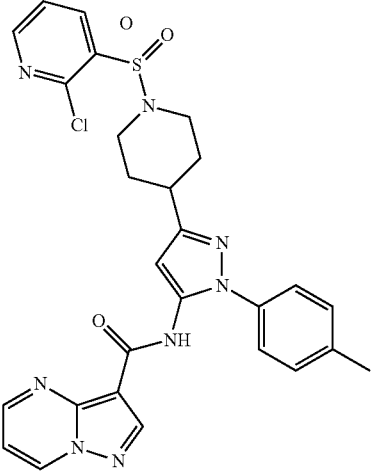 | 1.00, 577 | <1 μM |
| 389 | 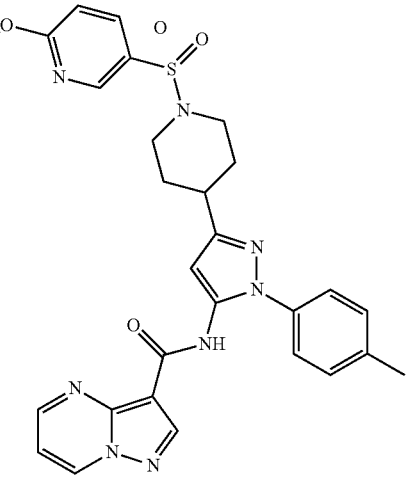 | 1.03, 573 | <1 μM |

| Example | Structure | LC-MS (Retention time (min), m/z) | IRAK-4 IC$_{50}$ (nM) |
|---|---|---|---|
| 390 | 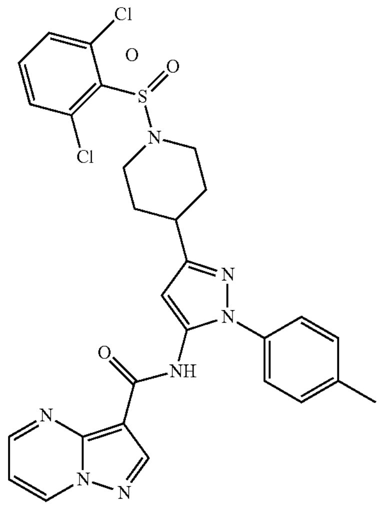 | 1.12, 610 | >1 μM |
| 391 | 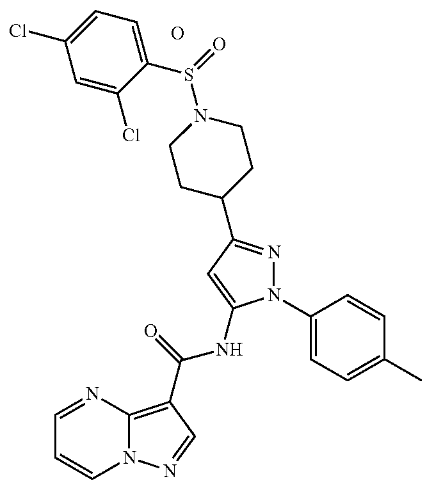 | 1.19, 610 | >1 μM |
| 392 | 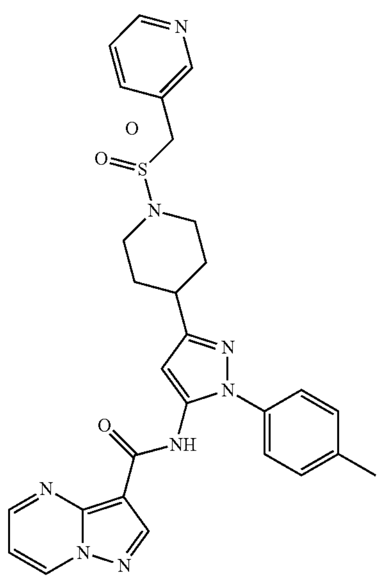 | 0.86, 577 | <100 nM |

-continued

| Example | Structure | LC-MS (Retention time (min), m/z) | IRAK-4 IC$_{50}$ (nM) |
| --- | --- | --- | --- |
| 393 | 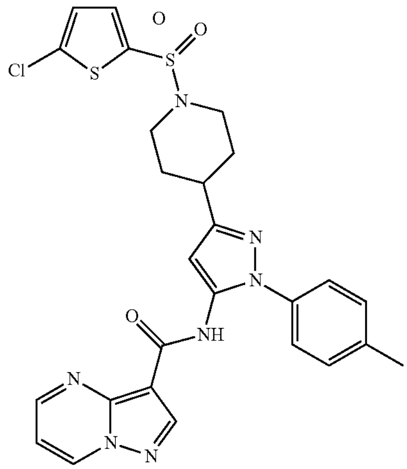 | 1.15, 582 | >1 μM |
| 394 | 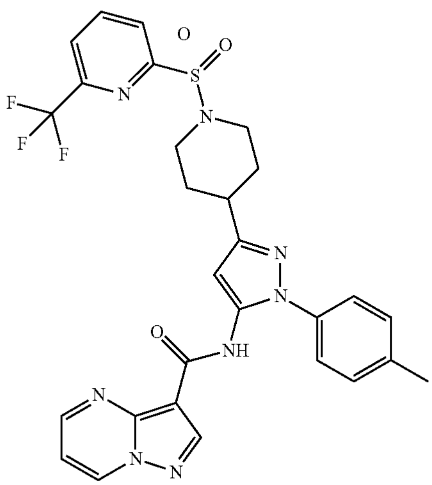 | 1.08, 611 | <1 μM |
| 395 | 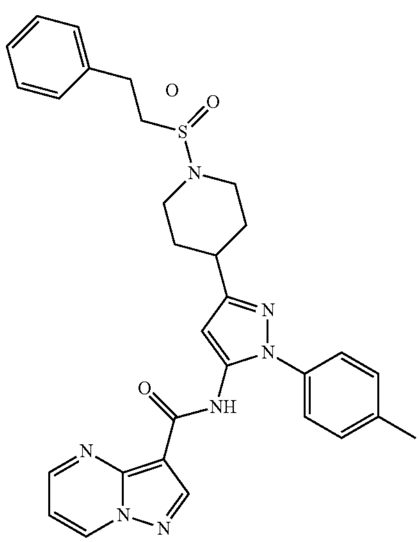 | 1.09, 570 | <1 μM |

-continued
| Example | Structure | LC-MS (Retention time (min), m/z) | IRAK-4 IC₅₀ (nM) |
|---|---|---|---|
| 396 | 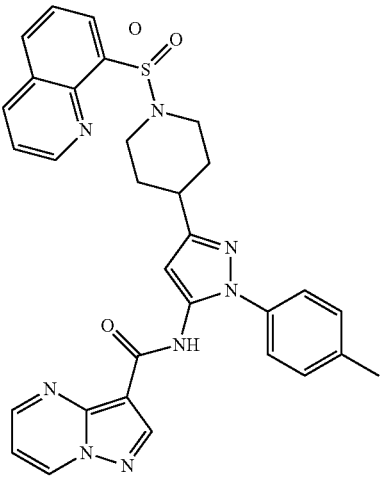 | 1.01, 593 | <1 μM |
| 397 | 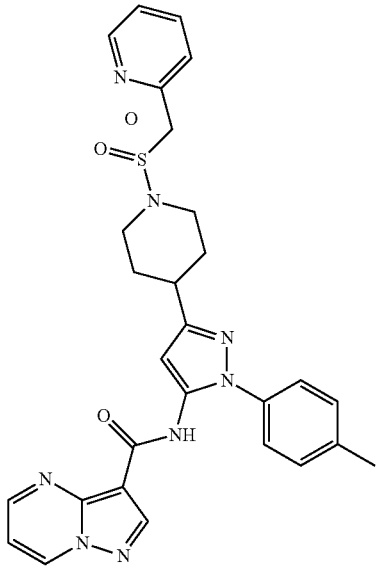 | 0.89, 557 | <100 nM |
| 398 | 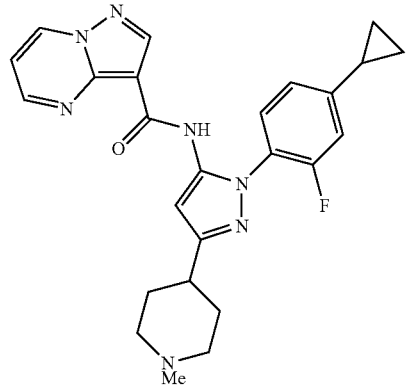 | 0.94, 460 | <100 nM |

| Example | Structure | LC-MS (Retention time (min), m/z) | IRAK-4 IC$_{50}$ (nM) |
|---|---|---|---|
| 399 | 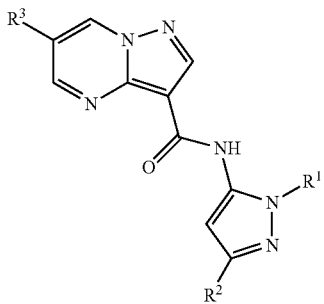 | 1.51, 443 | <100 nM |

What is claimed is:

1. A compound of the following formula:

![structure]

wherein R$^1$ is aryl, heteroaryl, heterocyclyl or (C$_{1-6}$ alkyl) R$^6$, wherein said aryl, heteroaryl, and heterocyclyl groups are optionally substituted with one or two substituents selected from the group consisting of halo, cyano, R$^4$, C$_{3-8}$ cycloalkyl, C$_{1-3}$ aminoalkyl, C$_{1-3}$ hydroxyalkyl, OR$^4$, NR$^4$R$^5$, NR$^4$COR$^6$, NR$^4$SO$_2$R$^6$, SO$_2$NR$^4$R$^5$ and CONR$^4$R$^5$;

R$^2$ is aryl, heteroaryl, C$_{3-8}$ cycloalkyl, heterocyclyl or (C$_{1-6}$ alkyl)R$^6$, wherein said aryl, heteroaryl, cycloalkyl and heterocyclyl groups are optionally substituted with one or two substituents selected from the group consisting of halo, cyano, oxo, hydroxyl, imino, hydroxyimino, R$^4$, OR$^4$, O(C$_{3-8}$ cycloalkyl), (C=O)OR$^4$, SO$_m$R$^6$, SO$_m$R$^4$, NR$^4$R$^5$, SO$_2$NR$^4$R$^5$ and NR$^4$SO$_2$R$^6$;

R$^3$ is halo, cyano, oxo, hydroxyl, imino, hydroxyimino, R$^4$, OR$^4$, C$_{3-8}$ cycloalkyl, SO$_m$R$^6$, SO$_m$R$^4$ NR$^4$R$^5$ or (C=O) NR$^4$R$^5$, NR$^4$(CO)R$^6$, SO$_m$NR$^4$R$^5$ and NR$^4$SO$_2$R$^6$;

R$^4$ is hydrogen or C$_{1-6}$ alkyl, wherein said alkyl is optionally substituted with one to three halo or hydroxyl;

R$^5$ is hydrogen or C$_{1-6}$ alkyl, wherein said alkyl is optionally substituted with halo or hydroxyl;

R$^6$ is aryl, heteroaryl, C$_{3-8}$ cycloalkyl or heterocyclyl;

m is an integer from zero to two;

or a pharmaceutically acceptable salt thereof.

2. The compound of claim 1 wherein R$^1$ is aryl, wherein said aryl group is optionally substituted with one or two substituents selected from the group consisting of halo, cyano, R$^4$, C$_{3-8}$ cycloalkyl, C$_{1-3}$ aminoalkyl, C$_{1-3}$ hydroxyalkyl, OR$^4$, NR$^4$R$^5$, NR$^4$COR$^6$, NR$^4$SO$_2$R$^6$, SO$_2$NR$^4$R$^5$, and CONR$^4$R$^5$, or a pharmaceutically acceptable salt thereof.

3. The compound of claim 2 wherein R$^1$ is aryl, wherein said aryl group is optionally substituted with R$^4$ or OR$^4$, or a pharmaceutically acceptable salt thereof.

4. The compound of claim 3 wherein R$^1$ is phenyl, wherein said phenyl group is optionally substituted with R$^4$ or OR$^4$, or a pharmaceutically acceptable salt thereof.

5. The compound of claim 1 wherein R$^2$ is heteroaryl, wherein said heteroaryl, group is optionally substituted with one or two substituents selected from the group consisting of halo, cyano, oxo, hydroxyl, imino, hydroxyimino, R$^4$, OR$^4$, O(C$_{3-8}$ cycloalkyl), (C=O)OR$^4$, SO$_m$R$^6$, SO$_m$R$^4$, NR$^4$R$^5$, SO$_2$NR$^4$R$^5$ and NR$^4$SO$_2$R$^6$, or a pharmaceutically acceptable salt thereof.

6. The compound of claim 1 selected from

N-(3-(4-oxocyclohexyl)-1-(p-tolyl)-1H-pyrazol-5-yl) pyrazolo[1,5-a]pyrimidine-3-carboxamide;

N-(3-(4-(hydroxyimino)cyclohexyl)-1-(p-tolyl)-1H-pyrazol-5-yl)pyrazolo[1,5-a]pyrimidine-3-carboxamide;

N-(3-(4-(methoxyimino)cyclohexyl)-1-(p-tolyl)-1H-pyrazol-5-yl)pyrazolo[1,5-a]pyrimidine-3-carboxamide;

N-(3-(7-oxoazepan-4-yl)-1-(p-tolyl)-1H-pyrazol-5-yl) pyrazolo[1,5-a]pyrimidine-3-carboxamide;

N-(3-(4-(dimethylamino)cyclohexyl)-1-(p-tolyl)-1H-pyrazol-5-yl)pyrazolo[1,5-a]pyrimidine-3-carboxamide;

N-(3-(4-hydroxycyclohexyl)-1-(p-tolyl)-1H-pyrazol-5-yl)pyrazolo[1,5-a]pyrimidine-3-carboxamide;

N-(3-(piperidin-4-yl)-1-(p-tolyl)-1H-pyrazol-5-yl)pyrazolo[1,5-a]pyrimidine-3-carboxamide;

N-(1-(4-methoxyphenyl)-3-(piperidin-4-yl)-1H-pyrazol-5-yl)pyrazolo[1,5-a]pyrimidine-3-carboxamide;

N-(1-(4-chlorophenyl)-3-(piperidin-4-yl)-1H-pyrazol-5-yl)pyrazolo[1,5-a]pyrimidine-3-carboxamide;

N-(1-(4-fluorophenyl)-3-(piperidin-4-yl)-1H-pyrazol-5-yl)pyrazolo[1,5-a]pyrimidine-3-carboxamide;

N-(3-(piperidin-4-yl)-1-(4-(trifluoromethyl)phenyl)-1H-pyrazol-5-yl)pyrazolo[1,5-a]pyrimidine-3-carboxamide;

N-(1-(4-cyanophenyl)-3-(piperidin-4-yl)-1H-pyrazol-5-yl)pyrazolo[1,5-a]pyrimidine-3-carboxamide;

N-(3-(piperidin-4-yl)-1-(4-(trifluoromethoxy)phenyl)-1H-pyrazol-5-yl)pyrazolo[1,5-a]pyrimidine-3-carboxamide;

N-(3-(piperidin-4-yl)-1-(o-tolyl)-1H-pyrazol-5-yl)pyrazolo[1,5-a]pyrimidine-3-carboxamide;

N-(3-(piperidin-4-yl)-1-(m-tolyl)-1H-pyrazol-5-yl)pyrazolo[1,5-a]pyrimidine-3-carboxamide;

N-(1-(4-methoxyphenyl)-3-(1-(methylsulfonyl)piperidin-4-yl)-1H-pyrazol-5-yl)pyrazolo[1,5-a]pyrimidine-3-carboxamide;

N-(3-(1-(methylsulfonyl)piperidin-4-yl)-1-(m-tolyl)-1H-pyrazol-5-yl)pyrazolo[1,5-a]pyrimidine-3-carboxamide;

N-(3-(1-(methylsulfonyl)piperidin-4-yl)-1-(p-tolyl)-1H-pyrazol-5-yl)pyrazolo[1,5-a]pyrimidine-3-carboxamide;

N-(3-(1-(cyclopropylsulfonyl)piperidin-4-yl)-1-(4-(trifluoromethoxy)phenyl)-1H-pyrazol-5-yl)pyrazolo[1,5-a]pyrimidine-3-carboxamide;

N-(3-(1-(methylsulfonyl)piperidin-4-yl)-1-phenyl-1H-pyrazol-5-yl)pyrazolo[1,5-a]pyrimidine-3-carboxamide;

N-(3-(1-(cyclopropylsulfonyl)piperidin-4-yl)-1-(m-tolyl)-1H-pyrazol-5-yl)pyrazolo[1,5-a]pyrimidine-3-carboxamide;

N-(3-(1-(cyclopropylsulfonyl)piperidin-4-yl)-1-(4-fluorophenyl)-1H-pyrazol-5-yl)pyrazolo[1,5-a]pyrimidine-3-carboxamide;

N-(3-(1-(isopropylsulfonyl)piperidin-4-yl)-1-(4-methoxyphenyl)-1H-pyrazol-5-yl)pyrazolo[1,5-a]pyrimidine-3-carboxamide;

N-(3-(1-(cyclopropylsulfonyl)piperidin-4-yl)-1-(4-methoxyphenyl)-1H-pyrazol-5-yl)pyrazolo[1,5-a]pyrimidine-3-carboxamide;

N-(3-(1-(cyclopentylsulfonyl)piperidin-4-yl)-1-(p-tolyl)-1H-pyrazol-5-yl)pyrazolo[1,5-a]pyrimidine-3-carboxamide;

N-(3-(1-(cyclopropylsulfonyl)piperidin-4-yl)-1-(p-tolyl)-1H-pyrazol-5-yl)pyrazolo[1,5-a]pyrimidine-3-carboxamide;

N-(3-(1-(cyclopropylsulfonyl)piperidin-4-yl)-1-(4-(trifluoromethoxy)phenyl)-1H-pyrazol-5-yl)pyrazolo[1,5-a]pyrimidine-3-carboxamide;

N-(1-(2,4-difluorophenyl)-3-(4-(N-methylsulfamoyl)phenyl)-1H-pyrazol-5-yl)pyrazolo[1,5-a]pyrimidine-3-carboxamide;

N-(1-(4-chloro-2-fluorophenyl)-3-(1-(methylsulfonyl)piperidin-4-yl)-1H-pyrazol-5-yl)pyrazolo[1,5-a]pyrimidine-3-carboxamide;

N-(1-(4-methoxyphenyl)-3-(1-((trifluoromethyl)sulfonyl)piperidin-4-yl)-1H-pyrazol-5-yl)pyrazolo[1,5-a]pyrimidine-3-carboxamide;

N-(3-(1-acetylpiperidin-4-yl)-1-(p-tolyl)-1H-pyrazol-5-yl)pyrazolo[1,5-a]pyrimidine-3-carboxamide;

methyl 4-(1-(4-methoxyphenyl)-5-(pyrazolo[1,5-a]pyrimidine-3-carboxamido)-1H-pyrazol-3-yl)piperidine-1-carboxylate;

N-(3-(1-(cyclopropanecarbonyl)piperidin-4-yl)-1-(4-methoxyphenyl)-1H-pyrazol-5-yl)pyrazolo[1,5-a]pyrimidine-3-carboxamide;

N-(1-(2,4-difluorophenyl)-3-(4-(N-methylsulfamoyl)phenyl)-1H-pyrazol-5-yl)pyrazolo[1,5-a]pyrimidine-3-carboxamide;

N-(3-(1-carbamoylpiperidin-4-yl)-1-(p-tolyl)-1H-pyrazol-5-yl)pyrazolo[1,5-a]pyrimidine-3-carboxamide;

N-(3-(1-methylpiperidin-4-yl)-1-(p-tolyl)-1H-pyrazol-5-yl)pyrazolo[1,5-a]pyrimidine-3-carboxamide;

N-(3-(1-isopropylpiperidin-4-yl)-1-(p-tolyl)-1H-pyrazol-5-yl)pyrazolo[1,5-a]pyrimidine-3-carboxamide;

N-(3-(1-cyclobutylpiperidin-4-yl)-1-(p-tolyl)-1H-pyrazol-5-yl)pyrazolo[1,5-a]pyrimidine-3-carboxamide;

N-(3-(1-cyclopentylpiperidin-4-yl)-1-(p-tolyl)-1H-pyrazol-5-yl)pyrazolo[1,5-a]pyrimidine-3-carboxamide;

N-(3-(1-cyclopropylpiperidin-4-yl)-1-(p-tolyl)-1H-pyrazol-5-yl)pyrazolo[1,5-a]pyrimidine-3-carboxamide;

N-(1-(p-tolyl)-3-(1-(2,2,2-trifluoroethyl)piperidin-4-yl)-1H-pyrazol-5-yl)pyrazolo[1,5-a]pyrimidine-3-carboxamide;

N-(3-(piperidin-3-yl)-1-(p-tolyl)-1H-pyrazol-5-yl)pyrazolo[1,5-a]pyrimidine-3-carboxamide;

N-(3-(1-(methylsulfonyl)piperidin-3-yl)-1-(p-tolyl)-1H-pyrazol-5-yl)pyrazolo[1,5-a]pyrimidine-3-carboxamide;

N-(3-(1-(cyclopropylsulfonyl)piperidin-3-yl)-1-(p-tolyl)-1H-pyrazol-5-yl)pyrazolo[1,5-a]pyrimidine-3-carboxamide;

N-(3-((tetrahydro-2H-pyran-4-yl)methyl)-1-(p-tolyl)-1H-pyrazol-5-yl)pyrazolo[1,5-a]pyrimidine-3-carboxamide;

N-(3-(tetrahydro-2H-pyran-4-yl)-1-(p-tolyl)-1H-pyrazol-5-yl)pyrazolo[1,5-a]pyrimidine-3-carboxamide;

N-(3-(1-isopropylpiperidin-4-yl)-1-(4-methoxyphenyl)-1H-pyrazol-5-yl)pyrazolo[1,5-a]pyrimidine-3-carboxamide;

N-(1-(2,4-difluorophenyl)-3-(1-methylpiperidin-4-yl)-1H-pyrazol-5-yl)pyrazolo[1,5-a]pyrimidine-3-carboxamide;

N-(3-(1-cyclobutylpiperidin-4-yl)-1-(2,4-difluorophenyl)-1H-pyrazol-5-yl)pyrazolo[1,5-a]pyrimidine-3-carboxamide;

N-(1-(4-chloro-2-fluorophenyl)-3-(1-methylpiperidin-4-yl)-1H-pyrazol-5-yl)pyrazolo[1,5-a]pyrimidine-3-carboxamide;

N-(1-(4-chloro-2-fluorophenyl)-3-(1-cyclobutylpiperidin-4-yl)-1H-pyrazol-5-yl)pyrazolo[1,5-a]pyrimidine-3-carboxamide;

N-(1-(4-cyclopropylphenyl)-3-(piperidin-4-yl)-1H-pyrazol-5-yl)pyrazolo[1,5-a]pyrimidine-3-carboxamide;

N-(1-(4-cyclopropylphenyl)-3-(1-(methylsulfonyl)piperidin-4-yl)-1H-pyrazol-5-yl)pyrazolo[1,5-a]pyrimidine-3-carboxamide;

N-(1-(4-cyclopropylphenyl)-3-(1-(cyclopropylsulfonyl)piperidin-4-yl)-1H-pyrazol-5-yl)pyrazolo[1,5-a]pyrimidine-3-carboxamide;

N-(1-(4-cyclopropylphenyl)-3-(1-isopropylpiperidin-4-yl)-1H-pyrazol-5-yl)pyrazolo[1,5-a]pyrimidine-3-carboxamide;

N-(1-(2-fluoro-4-methylphenyl)-3-(piperidin-4-yl)-1H-pyrazol-5-yl)pyrazolo[1,5-a]pyrimidine-3-carboxamide;

N-(1-(2-fluoro-4-methylphenyl)-3-(1-(methylsulfonyl)piperidin-4-yl)-1H-pyrazol-5-yl)pyrazolo[1,5-a]pyrimidine-3-carboxamide;

N-(1-(2-fluoro-4-methylphenyl)-3-(1-isopropylpiperidin-4-yl)-1H-pyrazol-5-yl)pyrazolo[1,5-a]pyrimidine-3-carboxamide;

N-(3-(1-cyclobutylpiperidin-4-yl)-1-(2-fluoro-4-methylphenyl)-1H-pyrazol-5-yl)pyrazolo[1,5-a]pyrimidine-3-carboxamide;

N-(1-(2-fluoro-4-methylphenyl)-3-(1-methylpiperidin-4-yl)-1H-pyrazol-5-yl)pyrazolo[1,5-a]pyrimidine-3-carboxamide;

N-(1-(2-fluoro-4-methoxyphenyl)-3-(piperidin-4-yl)-1H-pyrazol-5-yl)pyrazolo[1,5-a]pyrimidine-3-carboxamide;
N-(1-(2-fluoro-4-methoxyphenyl)-3-(1-isopropylpiperidin-4-yl)-1H-pyrazol-5-yl)pyrazolo[1,5-a]pyrimidine-3-carboxamide;
N-(3-(1-(cyclopropylsulfonyl)piperidin-4-yl)-1-(2-fluoro-4-methoxyphenyl)-1H-pyrazol-5-yl)pyrazolo[1,5-a]pyrimidine-3-carboxamide;
N-(1-(2-fluoro-4-methoxyphenyl)-3-(1-(methylsulfonyl)piperidin-4-yl)-1H-pyrazol-5-yl)pyrazolo[1,5-a]pyrimidine-3-carboxamide;
N-(1-(2-chloro-4-methylphenyl)-3-(piperidin-4-yl)-1H-pyrazol-5-yl)pyrazolo[1,5-a]pyrimidine-3-carboxamide;
N-(1-(2-chloro-4-methylphenyl)-3-(1-isopropylpiperidin-4-yl)-1H-pyrazol-5-yl)pyrazolo[1,5-a]pyrimidine-3-carboxamide;
N-(1-(3,5-difluorophenyl)-3-(piperidin-4-yl)-1H-pyrazol-5-yl)pyrazolo[1,5-a]pyrimidine-3-carboxamide;
N-(1-(4-fluoro-2-methylphenyl)-3-(piperidin-4-yl)-1H-pyrazol-5-yl)pyrazolo[1,5-a]pyrimidine-3-carboxamide;
N-(1-(4-fluoro-2-methylphenyl)-3-(1-isopropylpiperidin-4-yl)-1H-pyrazol-5-yl)pyrazolo[1,5-a]pyrimidine-3-carboxamide;
N-(1-(4-bromo-2-fluorophenyl)-3-(piperidin-4-yl)-1H-pyrazol-5-yl)pyrazolo[1,5-a]pyrimidine-3-carboxamide;
N-(1-(4-bromo-2-fluorophenyl)-3-(1-(methylsulfonyl)piperidin-4-yl)-1H-pyrazol-5-yl)pyrazolo[1,5-a]pyrimidine-3-carboxamide;
N-(1-(4-cyclopropyl-2-fluorophenyl)-3-(piperidin-4-yl)-1H-pyrazol-5-yl)pyrazolo[1,5-a]pyrimidine-3-carboxamide;
N-(1-(4-cyclopropyl-2-fluorophenyl)-3-(1-(methylsulfonyl)piperidin-4-yl)-1H-pyrazol-5-yl)pyrazolo[1,5-a]pyrimidine-3-carboxamide;
N-(1-(4-cyclopropyl-2-fluorophenyl)-3-(1-isopropylpiperidin-4-yl)-1H-pyrazol-5-yl)pyrazolo[1,5-a]pyrimidine-3-carboxamide;
N-(3-(1-cyclobutylpiperidin-4-yl)-1-(4-cyclopropyl-2-fluorophenyl)-1H-pyrazol-5-yl)pyrazolo[1,5-a]pyrimidine-3-carboxamide;
N-(1-(4-cyclopropyl-2-fluorophenyl)-3-(1-(2,2,2-trifluoroethyl)piperidin-4-yl)-1H-pyrazol-5-yl)pyrazolo[1,5-a]pyrimidine-3-carboxamide;
N-(1-(4-cyclopropyl-2,6-difluorophenyl)-3-(piperidin-4-yl)-1H-pyrazol-5-yl)pyrazolo[1,5-a]pyrimidine-3-carboxamide;
N-(3-(piperidin-4-yl)-1-(tetrahydro-2H-pyran-4-yl)-1H-pyrazol-5-yl)pyrazolo[1,5-a]pyrimidine-3-carboxamide;
N-(3-(morpholin-3-yl)-1-(p-tolyl)-1H-pyrazol-5-yl)pyrazolo[1,5-a]pyrimidine-3-carboxamide;
N-(3-(pyrrolidin-3-yl)-1-(p-tolyl)-1H-pyrazol-5-yl)pyrazolo[1,5-a]pyrimidine-3-carboxamide;
N-(3-(1-(methylsulfonyl)pyrrolidin-3-yl)-1-(p-tolyl)-1H-pyrazol-5-yl)pyrazolo[1,5-a]pyrimidine-3-carboxamide;
N-(3-(azetidin-3-yl)-1-(p-tolyl)-1H-pyrazol-5-yl)pyrazolo[1,5-a]pyrimidine-3-carboxamide;
N-(3-(1-(methylsulfonyl)azetidin-3-yl)-1-(p-tolyl)-1H-pyrazol-5-yl)pyrazolo[1,5-a]pyrimidine-3-carboxamide;
N-(3-(1-(cyclopropylsulfonyl)azetidin-3-yl)-1-(p-tolyl)-1H-pyrazol-5-yl)pyrazolo[1,5-a]pyrimidine-3-carboxamide;
N-(3-(1-(cyclopentylsulfonyl)azetidin-3-yl)-1-(p-tolyl)-1H-pyrazol-5-yl)pyrazolo[1,5-a]pyrimidine-3-carboxamide;
N-(3-(1-((2-methoxyethyl)sulfonyl)azetidin-3-yl)-1-(p-tolyl)-1H-pyrazol-5-yl)pyrazolo[1,5-a]pyrimidine-3-carboxamide;
N-(3-(azetidin-3-yl)-1-(4-cyclopropyl-2-fluorophenyl)-1H-pyrazol-5-yl)pyrazolo[1,5-a]pyrimidine-3-carboxamide;
N-(1-(4-cyclopropyl-2-fluorophenyl)-3-(1-isopropylazetidin-3-yl)-1H-pyrazol-5-yl)pyrazolo[1,5-a]pyrimidine-3-carboxamide;
N-(3-(1-cyclobutylazetidin-3-yl)-1-(4-cyclopropyl-2-fluorophenyl)-1H-pyrazol-5-yl)pyrazolo[1,5-a]pyrimidine-3-carboxamide;
N-(1-(4-acetylphenyl)-3-(1-(methylsulfonyl)piperidin-4-yl)-1H-pyrazol-5-yl)pyrazolo[1,5-a]pyrimidine-3-carboxamide;
N-(3-(4-methylpiperidin-4-yl)-1-(p-tolyl)-1H-pyrazol-5-yl)pyrazolo[1,5-a]pyrimidine-3-carboxamide;
N-(3-(4-methyl-1-(methylsulfonyl)piperidin-4-yl)-1-(p-tolyl)-1H-pyrazol-5-yl)pyrazolo[1,5-a]pyrimidine-3-carboxamide;
methyl 4-(5-(pyrazolo[1,5-a]pyrimidine-3-carboxamido)-1-(p-tolyl)-1H-pyrazol-3-yl)cyclohexanecarboxylate;
4-(5-(pyrazolo[1,5-a]pyrimidine-3-carboxamido)-1-(p-tolyl)-1H-pyrazol-3-yl)cyclohexanecarboxylic acid;
N-(3-(4-carbamoylcyclohexyl)-1-(p-tolyl)-1H-pyrazol-5-yl)pyrazolo[1,5-a]pyrimidine-3-carboxamide;
N-(3-(4-(dimethylcarbamoyl)cyclohexyl)-1-(p-tolyl)-1H-pyrazol-5-yl)pyrazolo[1,5-a]pyrimidine-3-carboxamide;
N-(1-(p-tolyl)-3-(4-(trifluoromethyl)cyclohexyl)-1H-pyrazol-5-yl)pyrazolo[1,5-a]pyrimidine-3-carboxamide;
N-(3-(1,1-dioxidotetrahydro-2H-thiopyran-4-yl)-1-(p-tolyl)-1H-pyrazol-5-yl)pyrazolo[1,5-a]pyrimidine-3-carboxamide;
N-(3-(4-sulfamoylphenyl)-1-(p-tolyl)-1H-pyrazol-5-yl)pyrazolo[1,5-a]pyrimidine-3-carboxamide;
N-(1-(2-fluoro-4-methylphenyl)-3-(4-(N-methylsulfamoyl)phenyl)-1H-pyrazol-5-yl)pyrazolo[1,5-a]pyrimidine-3-carboxamide;
N-(1-(4-cyclopropyl-2-fluorophenyl)-3-(4-(N-methylsulfamoyl)phenyl)-1H-pyrazol-5-yl)pyrazolo[1,5-a]pyrimidine-3-carboxamide;
N-(3-(4-aminophenyl)-1-(p-tolyl)-1H-pyrazol-5-yl)pyrazolo[1,5-a]pyrimidine-3-carboxamide;
N-(3-(4-(methylsulfonamido)phenyl)-1-(p-tolyl)-1H-pyrazol-5-yl)pyrazolo[1,5-a]pyrimidine-3-carboxamide;
6-bromo-N-(1-(4-methoxyphenyl)-3-(piperidin-4-yl)-1H-pyrazol-5-yl)pyrazolo[1,5-a]pyrimidine-3-carboxamide;
N3-(1-(4-methoxyphenyl)-3-(piperidin-4-yl)-1H-pyrazol-5-yl)pyrazolo[1,5-a]pyrimidine-3,6-dicarboxamide;
6-cyclopropyl-N-(1-(4-methoxyphenyl)-3-(piperidin-4-yl)-1H-pyrazol-5-yl)pyrazolo[1,5-a]pyrimidine-3-carboxamide;
6-bromo-N-(3-(piperidin-4-yl)-1-(p-tolyl)-1H-pyrazol-5-yl)pyrazolo[1,5-a]pyrimidine-3-carboxamide;

6-bromo-N-(3-(1-isopropylpiperidin-4-yl)-1-(p-tolyl)-1H-pyrazol-5-yl)pyrazolo[1,5-a]pyrimidine-3-carboxamide;
6-bromo-N-(3-(1-(tetrahydro-2H-pyran-3-yl)piperidin-4-yl)-1-(p-tolyl)-1H-pyrazol-5-yl)pyrazolo[1,5-a]pyrimidine-3-carboxamide;
6-bromo-N-(3-(1-(tetrahydro-2H-pyran-4-yl)piperidin-4-yl)-1-(p-tolyl)-1H-pyrazol-5-yl)pyrazolo[1,5-a]pyrimidine-3-carboxamide;
6-bromo-N-(3-(1-methylpiperidin-4-yl)-1-(p-tolyl)-1H-pyrazol-5-yl)pyrazolo[1,5-a]pyrimidine-3-carboxamide;
6-bromo-N-(3-(1-(2-hydroxyacetyl)piperidin-4-yl)-1-(p-tolyl)-1H-pyrazol-5-yl)pyrazolo[1,5-a]pyrimidine-3-carboxamide;
6-bromo-N-(3-(1-(3-(dimethylamino)propanoyl)piperidin-4-yl)-1-(p-tolyl)-1H-pyrazol-5-yl)pyrazolo[1,5-a]pyrimidine-3-carboxamide;
6-bromo-N-(3-(1-(3-(diethylamino)propanoyl)piperidin-4-yl)-1-(p-tolyl)-1H-pyrazol-5-yl)pyrazolo[1,5-a]pyrimidine-3-carboxamide;
N-(3-(1-(2-amino-2-oxoethyl)piperidin-4-yl)-1-(p-tolyl)-1H-pyrazol-5-yl)-6-bromopyrazolo[1,5-a]pyrimidine-3-carboxamide;
6-bromo-N-(3-(1-(1-hydroxycyclobutanecarbonyl)piperidin-4-yl)-1-(p-tolyl)-1H-pyrazol-5-yl)pyrazolo[1,5-a]pyrimidine-3-carboxamide;
6-bromo-N-(3-(1-(4-methylmorpholine-2-carbonyl)piperidin-4-yl)-1-(p-tolyl)-1H-pyrazol-5-yl)pyrazolo[1,5-a]pyrimidine-3-carboxamide;
methyl 4-(5-(6-bromopyrazolo[1,5-a]pyrimidine-3-carboxamido)-1-(p-tolyl)-1H-pyrazol-3-yl)piperidine-1-carboxylate;
6-bromo-N-(3-(1-(methylsulfonyl)piperidin-4-yl)-1-(p-tolyl)-1H-pyrazol-5-yl)pyrazolo[1,5-a]pyrimidine-3-carboxamide;
N3-(3-(1-(methylsulfonyl)piperidin-4-yl)-1-(p-tolyl)-1H-pyrazol-5-yl)pyrazolo[1,5-a]pyrimidine-3,6-dicarboxamide;
6-cyano-N-(3-(1-(methylsulfonyl)piperidin-4-yl)-1-(p-tolyl)-1H-pyrazol-5-yl)pyrazolo[1,5-a]pyrimidine-3-carboxamide;
6-methyl-N-(3-(1-(methylsulfonyl)piperidin-4-yl)-1-(p-tolyl)-1H-pyrazol-5-yl)pyrazolo[1,5-a]pyrimidine-3-carboxamide;
N-(3-(pyridin-3-yl)-1-(p-tolyl)-1H-pyrazol-5-yl)pyrazolo[1,5-a]pyrimidine-3-carboxamide;
N-(3-(6-methoxypyridin-3-yl)-1-(p-tolyl)-1H-pyrazol-5-yl)pyrazolo[1,5-a]pyrimidine-3-carboxamide;
N-(3-(pyridin-4-yl)-1-(p-tolyl)-1H-pyrazol-5-yl)pyrazolo[1,5-a]pyrimidine-3-carboxamide;
N-(1-(4-fluorophenyl)-3-(pyridin-4-yl)-1H-pyrazol-5-yl)pyrazolo[1,5-a]pyrimidine-3-carboxamide;
N-(1-(4-methoxyphenyl)-3-(pyridin-4-yl)-1H-pyrazol-5-yl)pyrazolo[1,5-a]pyrimidine-3-carboxamide;
N-(1-(3-fluoro-4-methylphenyl)-3-(pyridin-4-yl)-1H-pyrazol-5-yl)pyrazolo[1,5-a]pyrimidine-3-carboxamide;
N-(3-(2-methoxypyridin-4-yl)-1-(p-tolyl)-1H-pyrazol-5-yl)pyrazolo[1,5-a]pyrimidine-3-carboxamide;
N-(3-cyclopropyl-1-(p-tolyl)-1H-pyrazol-5-yl)pyrazolo[1,5-a]pyrimidine-3-carboxamide;
N-(3-(4-methoxyphenyl)-1-(p-tolyl)-1H-pyrazol-5-yl)pyrazolo[1,5-a]pyrimidine-3-carboxamide;
N-(1-(3-fluorophenyl)-3-(4-methoxyphenyl)-1H-pyrazol-5-yl)pyrazolo[1,5-a]pyrimidine-3-carboxamide;
N-(3-(3,4-dimethoxyphenyl)-1-(p-tolyl)-1H-pyrazol-5-yl)pyrazolo[1,5-a]pyrimidine-3-carboxamide;
N-(3-(4-(methylsulfonyl)phenyl)-1-(p-tolyl)-1H-pyrazol-5-yl)pyrazolo[1,5-a]pyrimidine-3-carboxamide;
N-(3-(4-fluorophenyl)-1-(p-tolyl)-1H-pyrazol-5-yl)pyrazolo[1,5-a]pyrimidine-3-carboxamide;
N-(3-(5-fluoropyridin-3-yl)-1-(p-tolyl)-1H-pyrazol-5-yl)pyrazolo[1,5-a]pyrimidine-3-carboxamide;
N-(3-(pyrimidin-5-yl)-1-(p-tolyl)-1H-pyrazol-5-yl)pyrazolo[1,5-a]pyrimidine-3-carboxamide;
N-(3-(1,2,3,6-tetrahydropyridin-4-yl)-1-(p-tolyl)-1H-pyrazol-5-yl)pyrazolo[1,5-a]pyrimidine-3-carboxamide;
N-(3-(1-(methylsulfonyl)-1,2,3,6-tetrahydropyridin-4-yl)-1-(p-tolyl)-1H-pyrazol-5-yl)pyrazolo[1,5-a]pyrimidine-3-carboxamide;
N-(3-(1-methyl-1,2,3,6-tetrahydropyridin-4-yl)-1-(p-tolyl)-1H-pyrazol-5-yl)pyrazolo[1,5-a]pyrimidine-3-carboxamide;
N-(3-(4-(morpholinosulfonyl)phenyl)-1-(p-tolyl)-1H-pyrazol-5-yl)pyrazolo[1,5-a]pyrimidine-3-carboxamide;
N-(3-(pyrrolidin-1-ylmethyl)-1-(p-tolyl)-1H-pyrazol-5-yl)pyrazolo[1,5-a]pyrimidine-3-carboxamide;
N-(3-(4-(pyrrolidin-1-ylmethyl)phenyl)-1-(p-tolyl)-1H-pyrazol-5-yl)pyrazolo[1,5-a]pyrimidine-3-carboxamide;
N-(3-(4-((4-methylpiperazin-1-yl)methyl)phenyl)-1-(p-tolyl)-1H-pyrazol-5-yl)pyrazolo[1,5-a]pyrimidine-3-carboxamide;
N-(3-(4-(morpholinomethyl)phenyl)-1-(p-tolyl)-1H-pyrazol-5-yl)pyrazolo[1,5-a]pyrimidine-3-carboxamide;
N-(1-(4-cyclopropylphenyl)-3-(piperidin-4-yl)-1H-pyrazol-5-yl)pyrazolo[1,5-a]pyrimidine-3-carboxamide;
N-(1-(5-cyclopropylpyridin-2-yl)-3-(1-methylpiperidin-4-yl)-1H-pyrazol-5-yl)pyrazolo[1,5-a]pyrimidine-3-carboxamide;
N-(3-(1-cyclobutylpiperidin-4-yl)-1-(5-cyclopropylpyridin-2-yl)-1H-pyrazol-5-yl)pyrazolo[1,5-a]pyrimidine-3-carboxamide;
N-(1-(5-cyclopropylpyridin-2-yl)-3-(1-(methylsulfonyl)piperidin-4-yl)-1H-pyrazol-5-yl)pyrazolo[1,5-a]pyrimidine-3-carboxamide;
N-(1-(5-cyclopropylpyridin-2-yl)-3-(1-(cyclopropylsulfonyl)piperidin-4-yl)-1H-pyrazol-5-yl)pyrazolo[1,5-a]pyrimidine-3-carboxamide;
N-(1-(5-cyclopropylpyridin-2-yl)-3-(4-(N-methylsulfamoyl)phenyl)-1H-pyrazol-5-yl)pyrazolo[1,5-a]pyrimidine-3-carboxamide;
N-(1-(5-methylpyridin-2-yl)-3-(piperidin-4-yl)-1H-pyrazol-5-yl)pyrazolo[1,5-a]pyrimidine-3-carboxamide;
N-(1-(5-methylpyridin-2-yl)-3-(1-(methylsulfonyl)piperidin-4-yl)-1H-pyrazol-5-yl)pyrazolo[1,5-a]pyrimidine-3-carboxamide;
N-(3-(1-(cyclopropylsulfonyl)piperidin-4-yl)-1-(5-methylpyridin-2-yl)-1H-pyrazol-5-yl)pyrazolo[1,5-a]pyrimidine-3-carboxamide;
N-(1-(5-trideuteromethylpyridin-2-yl)-3-(1-(methylsulfonyl)piperidin-4-yl)-1H-pyrazol-5-yl)pyrazolo[1,5-a]pyrimidine-3-carboxamide;
N-(1-(5-methoxypyridin-2-yl)-3-(1-(methylsulfonyl)piperidin-4-yl)-1H-pyrazol-5-yl)pyrazolo[1,5-a]pyrimidine-3-carboxamide;
N-(1-(5-(aminomethyl)pyridin-2-yl)-3-(1-(methylsulfonyl)piperidin-4-yl)-1H-pyrazol-5-yl)pyrazolo[1,5-a]pyrimidine-3-carboxamide;

N-(1-(5-(1-amino-2-methylpropan-2-yl)pyridin-2-yl)-3-(1-(methylsulfonyl)piperidin-4-yl)-1H-pyrazol-5-yl)pyrazolo[1,5-a]pyrimidine-3-carboxamide;

N-(1-(5-(2-aminopropan-2-yl)pyridin-2-yl)-3-(1-(methylsulfonyl)piperidin-4-yl)-1H-pyrazol-5-yl)pyrazolo[1,5-a]pyrimidine-3-carboxamide;

N-(1-(5-carbamoylpyridin-2-yl)-3-(piperidin-4-yl)-1H-pyrazol-5-yl)pyrazolo[1,5-a]pyrimidine-3-carboxamide;

N-(1-(5-(1-(methylamino)ethyl)pyridin-2-yl)-3-(1-(methylsulfonyl)piperidin-4-yl)-1H-pyrazol-5-yl)pyrazolo[1,5-a]pyrimidine-3-carboxamide;

N-(1-(5-(hydroxymethyl)pyridin-2-yl)-3-(1-(methylsulfonyl)piperidin-4-yl)-1H-pyrazol-5-yl)pyrazolo[1,5-a]pyrimidine-3-carboxamide;

(R)—N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide;

(S)—N-(1-(5-(1-aminoethyl)pyridin-2-yl)-3-(1-(methylsulfonyl)piperidin-4-yl)-1H-pyrazol-5-yl)pyrazolo[1,5-a]pyrimidine-3-carboxamide;

N-(1-(5-formylpyridin-2-yl)-3-(1-(methylsulfonyl)piperidin-4-yl)-1H-pyrazol-5-yl)pyrazolo[1,5-a]pyrimidine-3-carboxamide;

N-(1-(5-methylpyridin-2-yl)-3-(morpholin-3-yl)-1H-pyrazol-5-yl)pyrazolo[1,5-a]pyrimidine-3-carboxamide;

N-(1-(6-methylpyridin-3-yl)-3-(piperidin-4-yl)-1H-pyrazol-5-yl)pyrazolo[1,5-a]pyrimidine-3-carboxamide;

N-(1-(6-methylpyridin-3-yl)-3-(1-(methylsulfonyl)piperidin-4-yl)-1H-pyrazol-5-yl)pyrazolo[1,5-a]pyrimidine-3-carboxamide;

N-(1-(5-methylpyrimidin-2-yl)-3-(piperidin-4-yl)-1H-pyrazol-5-yl)pyrazolo[1,5-a]pyrimidine-3-carboxamide;

N-(1-(5-methylpyrimidin-2-yl)-3-(1-(methylsulfonyl)piperidin-4-yl)-1H-pyrazol-5-yl)pyrazolo[1,5-a]pyrimidine-3-carboxamide;

N-(3-(1-(cyclopropylsulfonyl)piperidin-4-yl)-1-(5-methylpyrimidin-2-yl)-1H-pyrazol-5-yl)pyrazolo[1,5-a]pyrimidine-3-carboxamide;

N-(1-(5-methylpyrazin-2-yl)-3-(1-(methylsulfonyl)piperidin-4-yl)-1H-pyrazol-5-yl)pyrazolo[1,5-a]pyrimidine-3-carboxamide;

N-(3-(1-(methylsulfonyl)piperidin-4-yl)-1-(pyridin-2-yl)-1H-pyrazol-5-yl)pyrazolo[1,5-a]pyrimidine-3-carboxamide;

N-(1-(5,6-dimethylpyridin-2-yl)-3-(1-(methylsulfonyl)piperidin-4-yl)-1H-pyrazol-5-yl)pyrazolo[1,5-a]pyrimidine-3-carboxamide;

N-(1-(1,3-dimethyl-1H-pyrazolo[3,4-b]pyridin-6-yl)-3-(1-(methylsulfonyl)piperidin-4-yl)-1H-pyrazol-5-yl)pyrazolo[1,5-a]pyrimidine-3-carboxamide;

N-(1-(5-(aminomethyl)pyridin-2-yl)-3-(1-methylcyclopropyl)-1H-pyrazol-5-yl)pyrazolo[1,5-a]pyrimidine-3-carboxamide;

N-(1-(5-methylpyridin-2-yl)-3-(4-(morpholinosulfonyl)phenyl)-1H-pyrazol-5-yl)pyrazolo[1,5-a]pyrimidine-3-carboxamide;

N-(3-(4-((4-methylpiperazin-1-yl)sulfonyl)phenyl)-1-(5-methylpyridin-2-yl)-1H-pyrazol-5-yl)pyrazolo[1,5-a]pyrimidine-3-carboxamide;

N-(1-(5-methylpyridin-2-yl)-3-(4-(methylsulfonyl)phenyl)-1H-pyrazol-5-yl)pyrazolo[1,5-a]pyrimidine-3-carboxamide;

N-(3-cyclopropyl-1-(5-methylpyridin-2-yl)-1H-pyrazol-5-yl)pyrazolo[1,5-a]pyrimidine-3-carboxamide;

N-(3-(1-methylcyclopropyl)-1-(5-methylpyridin-2-yl)-1H-pyrazol-5-yl)pyrazolo[1,5-a]pyrimidine-3-carboxamide;

N-(3-methoxy-1-(5-methylpyridin-2-yl)-1H-pyrazol-5-yl)pyrazolo[1,5-a]pyrimidine-3-carboxamide;

methyl ((4-(5-(pyrazolo[1,5-a]pyrimidine-3-carboxamido)-1-(p-tolyl)-1H-pyrazol-3-yl)cyclohexyl)methyl)carbamate;

N-(3-(4-(aminomethyl)cyclohexyl)-1-(p-tolyl)-1H-pyrazol-5-yl)pyrazolo[1,5-a]pyrimidine-3-carboxamide;

N-(3-(4-aminocyclohexyl)-1-(5-methylpyridin-2-yl)-1H-pyrazol-5-yl)pyrazolo[1,5-a]pyrimidine-3-carboxamide;

N-(1-(2-aminoethyl)-3-(1-(methylsulfonyl)piperidin-4-yl)-1H-pyrazol-5-yl)pyrazolo[1,5-a]pyrimidine-3-carboxamide;

N-(1-(1H-imidazol-2-yl)-3-(1-isopropylpiperidin-4-yl)-1H-pyrazol-5-yl)pyrazolo[1,5-a]pyrimidine-3-carboxamide;

N-(1-(1-(methylsulfonyl)-1H-imidazol-2-yl)-3-(1-(methylsulfonyl)piperidin-4-yl)-1H-pyrazol-5-yl)pyrazolo[1,5-a]pyrimidine-3-carboxamide;

N-(3-(piperidin-4-yl)-1-(thiazol-2-yl)-1H-pyrazol-5-yl)pyrazolo[1,5-a]pyrimidine-3-carboxamide;

6-bromo-N-(1-(5-methylpyridin-2-yl)-3-(1-(methylsulfonyl)piperidin-4-yl)-1H-pyrazol-5-yl)pyrazolo[1,5-a]pyrimidine-3-carboxamide;

6-cyano-N-(1-(5-methylpyridin-2-yl)-3-(1-(methylsulfonyl)piperidin-4-yl)-1H-pyrazol-5-yl)pyrazolo[1,5-a]pyrimidine-3-carboxamide;

N3-(3-(1-(methylsulfonyl)piperidin-4-yl)-1-(p-tolyl)-1H-pyrazol-5-yl)pyrazolo[1,5-a]pyrimidine-3,6-dicarboxamide;

6-ethynyl-N-(1-(5-methylpyridin-2-yl)-3-(1-(methylsulfonyl)piperidin-4-yl)-1H-pyrazol-5-yl)pyrazolo[1,5-a]pyrimidine-3-carboxamide;

6-bromo-N-(1-(5-methylpyridin-2-yl)-3-(4-(N-methylsulfamoyl)phenyl)-1H-pyrazol-5-yl)pyrazolo[1,5-a]pyrimidine-3-carboxamide;

6-cyclopropyl-N-(1-(5-methylpyridin-2-yl)-3-(4-(N-methylsulfamoyl)phenyl)-1H-pyrazol-5-yl)pyrazolo[1,5-a]pyrimidine-3-carboxamide;

6-chloro-N-(1-(5-methylpyridin-2-yl)-3-(4-(N-methylsulfamoyl)phenyl)-1H-pyrazol-5-yl)pyrazolo[1,5-a]pyrimidine-3-carboxamide;

N-(3-(4-methylpiperazin-1-yl)-1-(5-methylpyridin-2-yl)-1H-pyrazol-5-yl)pyrazolo[1,5-a]pyrimidine-3-carboxamide;

N-(3-(4-methylpiperazin-1-yl)-1-(5-trideuteromethylpyridin-2-yl)-1H-pyrazol-5-yl)pyrazolo[1,5-a]pyrimidine-3-carboxamide;

N-(1-(5-methylpyridin-2-yl)-3-(4-(methylsulfonyl)piperazin-1-yl)-1H-pyrazol-5-yl)pyrazolo[1,5-a]pyrimidine-3-carboxamide;

N-(1-(5-trideuteromethylpyridin-2-yl)-3-(4-(methylsulfonyl)piperazin-1-yl)-1H-pyrazol-5-yl)pyrazolo[1,5-a]pyrimidine-3-carboxamide;

N-(1-(5-cyclopropylpyridin-2-yl)-3-(4-methylpiperazin-1-yl)-1H-pyrazol-5-yl)pyrazolo[1,5-a]pyrimidine-3-carboxamide;

N-(1-(5-methylpyridin-2-yl)-3-morpholino-1H-pyrazol-5-yl)pyrazolo[1,5-a]pyrimidine-3-carboxamide;

N-[3-(1'-acetyl-1,4'-bipiperidin-4-yl)-1-(4-methylphenyl)-1H-pyrazol-5-yl]pyrazolo[1,5-a]pyrimidine-3-carboxamide;

N-[3-(1-cyclohexylpiperidin-4-yl)-1-(4-methylphenyl)-1H-pyrazol-5-yl]pyrazolo[1,5-a]pyrimidine-3-carboxamide;

N-[3-(1-cyclobutylpiperidin-4-yl)-1-(4-methylphenyl)-1H-pyrazol-5-yl]pyrazolo[1,5-a]pyrimidine-3-carboxamide;

N-[3-(1'-methyl-1,4'-bipiperidin-4-yl)-1-(4-methylphenyl)-1H-pyrazol-5-yl]pyrazolo[1,5-a]pyrimidine-3-carboxamide;

N-{1-(4-methylphenyl)-3-[1-(tetrahydro-2H-pyran-4-yl)piperidin-4-yl]-1H-pyrazol-5-yl}pyrazolo[1,5-a]pyrimidine-3-carboxamide;

ethyl 4-{1-(4-methylphenyl)-5-[(pyrazolo[1,5-a]pyrimidin-3-ylcarbonyl)amino]-1H-pyrazol-3-yl}-1,4'-bipiperidine-1'-carboxylate;

N-(3-(1-(3-methylbutan-2-yl)piperidin-4-yl)-1-(p-tolyl)-1H-pyrazol-5-yl)pyrazolo[1,5-a]pyrimidine-3-carboxamide;

N-(3-(1-(sec-butyl)piperidin-4-yl)-1-(p-tolyl)-1H-pyrazol-5-yl)pyrazolo[1,5-a]pyrimidine-3-carboxamide;

N-(3-(1-(1-methoxypropan-2-yl)piperidin-4-yl)-1-(p-tolyl)-1H-pyrazol-5-yl)pyrazolo[1,5-a]pyrimidine-3-carboxamide:

N-(3-(1-(1-(3-fluoropyridin-2-yl)ethyl)piperidin-4-yl)-1-(p-tolyl)-1H-pyrazol-5-yl)pyrazolo[1,5-a]pyrimidine-3-carboxamide;

N-(3-(1-(1-oxo-1-(piperidin-1-yl)propan-2-yl)piperidin-4-yl)-1-(p-tolyl)-1H-pyrazol-5-yl)pyrazolo[1,5-a]pyrimidine-3-carboxamide;

N-(3-(1-(1-oxo-1-(pyrrolidin-1-yl)propan-2-yl)piperidin-4-yl)-1-(p-tolyl)-1H-pyrazol-5-yl)pyrazolo[1,5-a]pyrimidine-3-carboxamide;

N-(3-(1-(1-(6-fluoropyridin-2-yl)ethyl)piperidin-4-yl)-1-(p-tolyl)-1H-pyrazol-5-yl)pyrazolo[1,5-a]pyrimidine-3-carboxamide;

N-[3-(1'-cyclopropyl-1,4'-bipiperidin-4-yl)-1-(4-methylphenyl)-1H-pyrazol-5-yl]pyrazolo[1,5-a]pyrimidine-3-carboxamide;

N-[1-(4-methylphenyl)-3-{1-[1-(1,3-thiazol-2-yl)ethyl]piperidin-4-yl}-1H-pyrazol-5-yl]pyrazolo[1,5-a]pyrimidine-3-carboxamide;

N-[3-(1-benzylpiperidin-4-yl)-1-(4-methylphenyl)-1H-pyrazol-5-yl]pyrazolo[1,5-a]pyrimidine-3-carboxamide;

N-{1-(4-methylphenyl)-3-[1-(2-methylpropyl)piperidin-4-yl]-1H-pyrazol-5-yl}pyrazolo[1,5-a]pyrimidine-3-carboxamide;

N-[1-(4-methylphenyl)-3-(1-propylpiperidin-4-yl)-1H-pyrazol-5-yl]pyrazolo[1,5-a]pyrimidine-3-carboxamide;

N-{3-[1-(cyclopropylmethyl)piperidin-4-yl]-1-(4-methylphenyl)-1H-pyrazol-5-yl}pyrazolo[1,5-a]pyrimidine-3-carboxamide;

N-{1-(4-methylphenyl)-3-[1-(1,3-thiazol-2-ylmethyl)piperidin-4-yl]-1H-pyrazol-5-yl}pyrazolo[1,5-a]pyrimidine-3-carboxamide;

N-{1-(4-methylphenyl)-3-[1-(thiophen-3-ylmethyl)piperidin-4-yl]-1H-pyrazol-5-yl}pyrazolo[1,5-a]pyrimidine-3-carboxamide;

N-(3-(1-(pyridin-4-ylmethyl)piperidin-4-yl)-1-(p-tolyl)-1H-pyrazol-5-yl)pyrazolo[1,5-a]pyrimidine-3-carboxamide;

N-{1-(4-methylphenyl)-3-[1-(pyridin-3-ylmethyl)piperidin-4-yl]-1H-pyrazol-5-yl}pyrazolo[1,5-a]pyrimidine-3-carboxamide;

N-{1-(4-methylphenyl)-3-[1-(pyridin-2-ylmethyl)piperidin-4-yl]-1H-pyrazol-5-yl}pyrazolo[1,5-a]pyrimidine-3-carboxamide;

N-[3-{1-[(6-methoxypyridin-3-yl)methyl]piperidin-4-yl}-1-(4-methylphenyl)-1H-pyrazol-5-yl]pyrazolo[1,5-a]pyrimidine-3-carboxamide;

N-{1-(4-methylphenyl)-3-[1-(tetrahydrofuran-3-ylmethyl)piperidin-4-yl]-1H-pyrazol-5-yl}pyrazolo[1,5-a]pyrimidine-3-carboxamide;

N-{1-(4-methylphenyl)-3-[1-(1,3-thiazol-5-ylmethyl)piperidin-4-yl]-1H-pyrazol-5-yl}pyrazolo[1,5-a]pyrimidine-3-carboxamide;

N-{1-(4-methylphenyl)-3-[1-(1H-pyrazol-5-ylmethyl)piperidin-4-yl]-1H-pyrazol-5-yl}pyrazolo[1,5-a]pyrimidine-3-carboxamide;

N-{1-(4-methylphenyl)-3-[1-(1,3-thiazol-4-ylmethyl)piperidin-4-yl]-1H-pyrazol-5-yl}pyrazolo[1,5-a]pyrimidine-3-carboxamide;

N-{1-(4-methylphenyl)-3-[1-(1,3-oxazol-2-ylmethyl)piperidin-4-yl]-1H-pyrazol-5-yl}pyrazolo[1,5-a]pyrimidine-3-carboxamide;

N-{1-(4-methylphenyl)-3-[1-(1H-pyrazol-4-ylmethyl)piperidin-4-yl]-1H-pyrazol-5-yl}pyrazolo[1,5-a]pyrimidine-3-carboxamide;

N-[3-(1-azetidin-3-ylpiperidin-4-yl)-1-(4-methylphenyl)-1H-pyrazol-5-yl]pyrazolo[1,5-a]pyrimidine-3-carboxamide;

N-[3-(1-{1-[(1-methylethyl)carbamoyl]azetidin-3-yl}piperidin-4-yl)-1-(4-methylphenyl)-1H-pyrazol-5-yl]pyrazolo[1,5-a]pyrimidine-3-carboxamide;

N-[3-{1-[1-(tert-butylcarbamoyl)azetidin-3-yl]piperidin-4-yl}-1-(4-methylphenyl)-1H-pyrazol-5-yl]pyrazolo[1,5-a]pyrimidine-3-carboxamide;

N-[3-{1-[1-(ethylcarbamoyl)azetidin-3-yl]piperidin-4-yl}-1-(4-methylphenyl)-1H-pyrazol-5-yl]pyrazolo[1,5-a]pyrimidine-3-carboxamide;

methyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate;

ethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate;

1-methylethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate;

2-fluoroethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate;

2-methoxyethyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate;

N-[3-{1-[1-(ethylsulfonyl)azetidin-3-yl]piperidin-4-yl}-1-(4-methylphenyl)-1H-pyrazol-5-yl]pyrazolo[1,5-a]pyrimidine-3-carboxamide;

N-[1-(4-methylphenyl)-3-{1-[1-(methylsulfonyl)azetidin-3-yl]piperidin-4-yl}-1H-pyrazol-5-yl]pyrazolo[1,5-a]pyrimidine-3-carboxamide;

N-[3-{1-[1-(cyclopropylsulfonyl)azetidin-3-yl]piperidin-4-yl}-1-(4-methylphenyl)-1H-pyrazol-5-yl]pyrazolo[1,5-a]pyrimidine-3-carboxamide;

N-[3-(1-{1-[(1-methylethyl)sulfonyl]azetidin-3-yl}piperidin-4-yl)-1-(4-methylphenyl)-1H-pyrazol-5-yl]pyrazolo[1,5-a]pyrimidine-3-carboxamide;

N-[3-(1-{1-[(fluoromethyl)sulfonyl]azetidin-3-yl}piperidin-4-yl)-1-(4-methylphenyl)-1H-pyrazol-5-yl]pyrazolo[1,5-a]pyrimidine-3-carboxamide;

N-{3-[1-(1-acetylazetidin-3-yl)piperidin-4-yl]-1-(4-methylphenyl)-1H-pyrazol-5-yl}pyrazolo[1,5-a]pyrimidine-3-carboxamide;

N-{1-(4-methylphenyl)-3-[1-(1-propanoylazetidin-3-yl)piperidin-4-yl]-1H-pyrazol-5-yl}pyrazolo[1,5-a]pyrimidine-3-carboxamide;

N-[1-(4-methylphenyl)-3-{1-[4-(trifluoromethyl)cyclohexyl]piperidin-4-yl}-1H-pyrazol-5-yl]pyrazolo[1,5-a]pyrimidine-3-carboxamide;

N-{3-(1-{4-[methyl(methylsulfonyl)amino]cyclohexyl}piperidin-4-yl)-1-(4-methylphenyl)-1H-pyrazol-5-yl]pyrazolo[1,5-a]pyrimidine-3-carboxamide;

N-{1-(4-methylphenyl)-3-(1-{4-[(methylsulfonyl)amino]cyclohexyl}piperidin-4-yl)-1H-pyrazol-5-yl]pyrazolo[1,5-a]pyrimidine-3-carboxamide;

N-{3-[1-(4-cyanocyclohexyl)piperidin-4-yl]-1-(4-methylphenyl)-1H-pyrazol-5-yl}pyrazolo[1,5-a]pyrimidine-3-carboxamide;

N-{3-(1-bicyclo[3.1.0]hex-2-ylpiperidin-4-yl)-1-(4-methylphenyl)-1H-pyrazol-5-yl]pyrazolo[1,5-a]pyrimidine-3-carboxamide;

N-{1-(4-methylphenyl)-3-[1-(2-oxo-1-azaspiro[4.5]dec-8-yl)piperidin-4-yl]-1H-pyrazol-5-yl}pyrazolo[1,5-a]pyrimidine-3-carboxamide;

N-{3-[1-(3-tert-butylcyclobutyl)piperidin-4-yl]-1-(4-methylphenyl)-1H-pyrazol-5-yl}pyrazolo[1,5-a]pyrimidine-3-carboxamide;

N-[1-(4-methylphenyl)-3-(1-spiro[3.4]oct-2-ylpiperidin-4-yl)-1H-pyrazol-5-yl]pyrazolo[1,5-a]pyrimidine-3-carboxamide;

N-{3-[1-(3-cyanocyclobutyl)piperidin-4-yl]-1-(4-methylphenyl)-1H-pyrazol-5-yl}pyrazolo[1,5-a]pyrimidine-3-carboxamide;

N-{3-[1-(4,4-difluorocyclohexyl)piperidin-4-yl]-1-(4-methylphenyl)-1H-pyrazol-5-yl}pyrazolo[1,5-a]pyrimidine-3-carboxamide;

N-{1-(4-methylphenyl)-3-[1-(3,3,3-trifluoro-1-methylpropyl)piperidin-4-yl]-1H-pyrazol-5-yl}pyrazolo[1,5-a]pyrimidine-3-carboxamide;

tert-butyl 3-(4-{1-(4-methylphenyl)-5-[(pyrazolo[1,5-a]pyrimidin-3-ylcarbonyl)amino]-1H-pyrazol-3-yl}piperidin-1-yl)azetidine-1-carboxylate;

N-{3-(1-{4-[methyl(methylsulfonyl)amino]cyclohexyl}piperidin-4-yl)-1-(5-methylpyridin-2-yl)-1H-pyrazol-5-yl]pyrazolo[1,5-a]pyrimidine-3-carboxamide;

N-[1-(5-methylpyridin-2-yl)-3-(1-{4-[(methylsulfonyl)amino]cyclohexyl}piperidin-4-yl)-1H-pyrazol-5-yl]pyrazolo[1,5-a]pyrimidine-3-carboxamide;

N-{1-(5-methylpyridin-2-yl)-3-[1-(tetrahydro-2H-pyran-3-yl)piperidin-4-yl]-1H-pyrazol-5-yl}pyrazolo[1,5-a]pyrimidine-3-carboxamide;

N-{3-[1-(4-cyanocyclohexyl)piperidin-4-yl]-1-(5-methylpyridin-2-yl)-1H-pyrazol-5-yl}pyrazolo[1,5-a]pyrimidine-3-carboxamide;

N-{3-{1-[1-(4-fluorophenyl)pyrrolidin-3-yl]piperidin-4-yl}-1-(5-methylpyridin-2-yl)-1H-pyrazol-5-yl}pyrazolo[1,5-a]pyrimidine-3-carboxamide;

N-[3-(1'-cyclopropyl-1,4'-bipiperidin-4-yl)-1-(5-methylpyridin-2-yl)-1H-pyrazol-5-yl]pyrazolo[1,5-a]pyrimidine-3-carboxamide;

N-{1-(5-methylpyridin-2-yl)-3-[1-(5,6,7,8-tetrahydroisoquinolin-7-yl)piperidin-4-yl]-1H-pyrazol-5-yl}pyrazolo[1,5-a]pyrimidine-3-carboxamide;

N-[3-{1-[3-(dimethylamino)cyclobutyl]piperidin-4-yl}-1-(5-methylpyridin-2-yl)-1H-pyrazol-5-yl]pyrazolo[1,5-a]pyrimidine-3-carboxamide;

N-{3-[1-(1-methylethyl)piperidin-4-yl]-1-(5-methylpyridin-2-yl)-1H-pyrazol-5-yl}pyrazolo[1,5-a]pyrimidine-3-carboxamide;

N-[1-(5-methylpyridin-2-yl)-3-{1-[4-(trifluoromethyl)cyclohexyl]piperidin-4-yl}-1H-pyrazol-5-yl]pyrazolo[1,5-a]pyrimidine-3-carboxamide;

N-{3-[1-(3-methylcyclopentyl)piperidin-4-yl]-1-(5-methylpyridin-2-yl)-1H-pyrazol-5-yl}pyrazolo[1,5-a]pyrimidine-3-carboxamide;

N-{3-{1-[(3R)-3-methylcyclopentyl]piperidin-4-yl}-1-(5-methylpyridin-2-yl)-1H-pyrazol-5-yl]pyrazolo[1,5-a]pyrimidine-3-carboxamide;

N-{3-(1-cyclobutylpiperidin-4-yl)-1-(5-methylpyridin-2-yl)-1H-pyrazol-5-yl]pyrazolo[1,5-a]pyrimidine-3-carboxamide;

N-[3-(1'-methyl-1,4'-bipiperidin-4-yl)-1-(5-methylpyridin-2-yl)-1H-pyrazol-5-yl]pyrazolo[1,5-a]pyrimidine-3-carboxamide;

ethyl 4-{1-(5-methylpyridin-2-yl)-5-[(pyrazolo[1,5-a]pyrimidin-3-ylcarbonyl)amino]-1H-pyrazol-3-yl}-1,4'-bipiperidine-1'-carboxylate;

N-{3-[1-(3-methylcyclohexyl)piperidin-4-yl]-1-(5-methylpyridin-2-yl)-1H-pyrazol-5-yl}pyrazolo[1,5-a]pyrimidine-3-carboxamide;

N-{3-[1-(2-methylpropyl)piperidin-4-yl]-1-(5-methylpyridin-2-yl)-1H-pyrazol-5-yl}pyrazolo[1,5-a]pyrimidine-3-carboxamide;

N-[3-(1'-ethyl-1,4'-bipiperidin-4-yl)-1-(5-methylpyridin-2-yl)-1H-pyrazol-5-yl]pyrazolo[1,5-a]pyrimidine-3-carboxamide;

N-[1-(5-methylpyridin-2-yl)-3-(1-propylpiperidin-4-yl)-1H-pyrazol-5-yl]pyrazolo[1,5-a]pyrimidine-3-carboxamide;

N-{3-[1-(cyclopropylmethyl)piperidin-4-yl]-1-(5-methylpyridin-2-yl)-1H-pyrazol-5-yl}pyrazolo[1,5-a]pyrimidine-3-carboxamide;

N-{3-[1-(2,3-dihydro-1H-inden-2-yl)piperidin-4-yl]-1-(5-methylpyridin-2-yl)-1H-pyrazol-5-yl}pyrazolo[1,5-a]pyrimidine-3-carboxamide;

N-{1-(4-methylphenyl)-3-[1-(tetrahydrofuran-3-ylmethyl)piperidin-3-yl]-1H-pyrazol-5-yl}pyrazolo[1,5-a]pyrimidine-3-carboxamide;

N-{1-(4-methylphenyl)-3-[1-(1,3-thiazol-5-ylmethyl)piperidin-3-yl]-1H-pyrazol-5-yl}pyrazolo[1,5-a]pyrimidine-3-carboxamide;

N-[1-(4-methylphenyl)-3-{1-[(3-oxo-2,3-dihydro-1H-isoindol-5-yl)methyl]piperidin-3-yl}-1H-pyrazol-5-yl]pyrazolo[1,5-a]pyrimidine-3-carboxamide;

N-{3-(1-{[2-(dimethylamino)-1,3-thiazol-5-yl]methyl}piperidin-3-yl)-1-(4-methylphenyl)-1H-pyrazol-5-yl]pyrazolo[1,5-a]pyrimidine-3-carboxamide;

N-{1-(4-methylphenyl)-3-[1-(1H-pyrazol-5-ylmethyl)piperidin-3-yl]-1H-pyrazol-5-yl}pyrazolo[1,5-a]pyrimidine-3-carboxamide;

N-{1-(4-methylphenyl)-3-[1-(1,3-thiazol-4-ylmethyl)piperidin-3-yl]-1H-pyrazol-5-yl}pyrazolo[1,5-a]pyrimidine-3-carboxamide;

N-{1-(4-methylphenyl)-3-[1-(1,3-oxazol-2-ylmethyl)piperidin-3-yl]-1H-pyrazol-5-yl}pyrazolo[1,5-a]pyrimidine-3-carboxamide;

N-[3-{1-[(2-fluoropyridin-3-yl)methyl]piperidin-3-yl}-1-(4-methylphenyl)-1H-pyrazol-5-yl]pyrazolo[1,5-a]pyrimidine-3-carboxamide;

N-[3-{1-[(2-methoxypyrimidin-5-yl)methyl]piperidin-3-yl}-1-(4-methylphenyl)-1H-pyrazol-5-yl]pyrazolo[1,5-a]pyrimidine-3-carboxamide;
N-[3-{1-[(5-fluoropyridin-2-yl)methyl]piperidin-3-yl}-1-(4-methylphenyl)-1H-pyrazol-5-yl]pyrazolo[1,5-a]pyrimidine-3-carboxamide;
N-[3-{1-[4-(3-cyanooxetan-3-yl)benzyl]piperidin-3-yl}-1-(4-methylphenyl)-1H-pyrazol-5-yl]pyrazolo[1,5-a]pyrimidine-3-carboxamide;
N-{1-(4-methylphenyl)-3-[1-(1H-pyrazol-4-ylmethyl)piperidin-3-yl]-1H-pyrazol-5-yl}pyrazolo[1,5-a]pyrimidine-3-carboxamide;
N-[1-(4-methylphenyl)-3-{1-[(1-oxo-2,3-dihydro-1H-isoindol-4-yl)methyl]piperidin-3-yl}-1H-pyrazol-5-yl]pyrazolo[1,5-a]pyrimidine-3-carboxamide;
N-[1-(4-methylphenyl)-3-{1-[4-(methylsulfonyl)benzyl]piperidin-3-yl}-1H-pyrazol-5-yl]pyrazolo[1,5-a]pyrimidine-3-carboxamide;
N-{3-[1-(cyclopropylmethyl)piperidin-3-yl]-1-(4-methylphenyl)-1H-pyrazol-5-yl}pyrazolo[1,5-a]pyrimidine-3-carboxamide;
N-{1-(4-methylphenyl)-3-[1-(1,3-thiazol-2-ylmethyl)piperidin-3-yl]-1H-pyrazol-5-yl}pyrazolo[1,5-a]pyrimidine-3-carboxamide;
N-{1-(4-methylphenyl)-3-[1-(pyridin-4-ylmethyl)piperidin-3-yl]-1H-pyrazol-5-yl}pyrazolo[1,5-a]pyrimidine-3-carboxamide;
N-{1-(4-methylphenyl)-3-[1-(pyridin-3-ylmethyl)piperidin-3-yl]-1H-pyrazol-5-yl}pyrazolo[1,5-a]pyrimidine-3-carboxamide;
N-{1-(4-methylphenyl)-3-[1-(pyridin-2-ylmethyl)piperidin-3-yl]-1H-pyrazol-5-yl}pyrazolo[1,5-a]pyrimidine-3-carboxamide;
N-[3-{1-[(6-methoxypyridin-3-yl)methyl]piperidin-3-yl}-1-(4-methylphenyl)-1H-pyrazol-5-yl]pyrazolo[1,5-a]pyrimidine-3-carboxamide;
N-[3-{1-[(1-ethyl-1H-pyrazol-5-yl)methyl]piperidin-3-yl}-1-(4-methylphenyl)-1H-pyrazol-5-yl]pyrazolo[1,5-a]pyrimidine-3-carboxamide;
N-{1-(4-methylphenyl)-3-[1-(pyrazin-2-ylmethyl)azetidin-3-yl]-1H-pyrazol-5-yl}pyrazolo[1,5-a]pyrimidine-3-carboxamide;
N-{1-(4-methylphenyl)-3-[1-(1H-pyrazol-4-ylmethyl)azetidin-3-yl]-1H-pyrazol-5-yl}pyrazolo[1,5-a]pyrimidine-3-carboxamide;
N-{1-(4-methylphenyl)-3-[1-(1H-pyrazol-5-ylmethyl)azetidin-3-yl]-1H-pyrazol-5-yl}pyrazolo[1,5-a]pyrimidine-3-carboxamide;
N-{1-(4-methylphenyl)-3-[1-(1,3-thiazol-2-ylmethyl)azetidin-3-yl]-1H-pyrazol-5-yl}pyrazolo[1,5-a]pyrimidine-3-carboxamide;
N-{1-(4-methylphenyl)-3-[1-(pyridin-2-ylmethyl)azetidin-3-yl]-1H-pyrazol-5-yl}pyrazolo[1,5-a]pyrimidine-3-carboxamide;
N-{1-(4-methylphenyl)-3-[1-(pyridin-4-ylmethyl)azetidin-3-yl]-1H-pyrazol-5-yl}pyrazolo[1,5-a]pyrimidine-3-carboxamide;
N-{1-(4-methylphenyl)-3-[1-(pyrimidin-5-ylmethyl)azetidin-3-yl]-1H-pyrazol-5-yl}pyrazolo[1,5-a]pyrimidine-3-carboxamide;
N-[3-{1-[(5-methylisoxazol-3-yl)methyl]azetidin-3-yl}-1-(4-methylphenyl)-1H-pyrazol-5-yl]pyrazolo[1,5-a]pyrimidine-3-carboxamide;
N-{1-(4-methylphenyl)-3-[1-(1,3-thiazol-5-ylmethyl)azetidin-3-yl]-1H-pyrazol-5-yl}pyrazolo[1,5-a]pyrimidine-3-carboxamide;
N-[3-{1-[(2-methoxypyridin-3-yl)methyl]azetidin-3-yl}-1-(4-methylphenyl)-1H-pyrazol-5-yl]pyrazolo[1,5-a]pyrimidine-3-carboxamide;
N-{1-(4-methylphenyl)-3-[1-(pyridin-3-ylmethyl)azetidin-3-yl]-1H-pyrazol-5-yl}pyrazolo[1,5-a]pyrimidine-3-carboxamide;
N-[3-{1-[(6-methoxypyridin-2-yl)methyl]azetidin-3-yl}-1-(4-methylphenyl)-1H-pyrazol-5-yl]pyrazolo[1,5-a]pyrimidine-3-carboxamide;
N-{1-(4-methylphenyl)-3-[1-(1,3-oxazol-2-ylmethyl)azetidin-3-yl]-1H-pyrazol-5-yl}pyrazolo[1,5-a]pyrimidine-3-carboxamide;
N-[3-{1-[(2-methoxypyrimidin-5-yl)methyl]azetidin-3-yl}-1-(4-methylphenyl)-1H-pyrazol-5-yl]pyrazolo[1,5-a]pyrimidine-3-carboxamide;
N-{1-(4-methylphenyl)-3-[1-(1,3-oxazol-4-ylmethyl)azetidin-3-yl]-1H-pyrazol-5-yl}pyrazolo[1,5-a]pyrimidine-3-carboxamide;
N-[3-(4-cyclohexylpiperazin-1-yl)-1-(5-methylpyridin-2-yl)-1H-pyrazol-5-yl]pyrazolo[1,5-a]pyrimidine-3-carboxamide;
N-[3-(4-cyclobutylpiperazin-1-yl)-1-(5-methylpyridin-2-yl)-1H-pyrazol-5-yl]pyrazolo[1,5-a]pyrimidine-3-carboxamide;
N-{1-(5-methylpyridin-2-yl)-3-[4-(tetrahydro-2H-pyran-4-yl)piperazin-1-yl]-1H-pyrazol-5-yl}pyrazolo[1,5-a]pyrimidine-3-carboxamide;
N-[3-(4-cycloheptylpiperazin-1-yl)-1-(5-methylpyridin-2-yl)-1H-pyrazol-5-yl]pyrazolo[1,5-a]pyrimidine-3-carboxamide;
N-[3-(4-cyclopentylpiperazin-1-yl)-1-(5-methylpyridin-2-yl)-1H-pyrazol-5-yl]pyrazolo[1,5-a]pyrimidine-3-carboxamide;
N-{3-[4-(2-methylpropyl)piperazin-1-yl]-1-(5-methylpyridin-2-yl)-1H-pyrazol-5-yl}pyrazolo[1,5-a]pyrimidine-3-carboxamide;
N-(3-(1-cyclopentylpiperidin-4-yl)-1-(p-tolyl)-1H-pyrazol-5-yl)pyrazolo[1,5-a]pyrimidine-3-carboxamide;
N-[1'-methyl-1-(4-methylphenyl)-1H,1'H-3,4'-bipyrazol-5-yl]pyrazolo[1,5-a]pyrimidine-3-carboxamide;
N-{1-(4-methylphenyl)-3-[5-(4-methylpiperazin-1-yl)pyridin-3-yl]-1H-pyrazol-5-yl}pyrazolo[1,5-a]pyrimidine-3-carboxamide;
N-{1-(4-methylphenyl)-3-[2-(piperidin-1-ylmethyl)pyridin-4-yl]-1H-pyrazol-5-yl}pyrazolo[1,5-a]pyrimidine-3-carboxamide;
N-{3-[2-(hydroxymethyl)pyridin-4-yl]-1-(4-methylphenyl)-1H-pyrazol-5-yl}pyrazolo[1,5-a]pyrimidine-3-carboxamide;
N-{3-[6-(hydroxymethyl)pyridin-3-yl]-1-(4-methylphenyl)-1H-pyrazol-5-yl}pyrazolo[1,5-a]pyrimidine-3-carboxamide;
N-[2'-methyl-1-(4-methylphenyl)-1H,2'H-3,3'-bipyrazol-5-yl]pyrazolo[5-a]pyrimidine-3-carboxamide;
N-{3-[5-(hydroxymethyl)pyridin-3-yl]-1-(4-methylphenyl)-1H-pyrazol-5-yl}pyrazolo[1,5-a]pyrimidine-3-carboxamide;
N-{1-(4-methylphenyl)-1'-[2-(methylsulfonyl)ethyl]-1H,1'H-3,4'-bipyrazol-5-yl}pyrazolo[1,5-a]pyrimidine-3-carboxamide;
N-[3-(3-methylisoxazol-4-yl)-1-(4-methylphenyl)-1H-pyrazol-5-yl]pyrazolo[1,5-a]pyrimidine-3-carboxamide;
N-[1-(4-methylphenyl)-3-(2-morpholin-4-yl-1,3-thiazol-4-yl)-1H-pyrazol-5-yl]pyrazolo[1,5-a]pyrimidine-3-carboxamide;

N-{3-[4-(cyclopropylsulfonyl)phenyl]-1-(4-methylphenyl)-1H-pyrazol-5-yl}pyrazolo[1,5-a]pyrimidine-3-carboxamide;

N-[3-(1-methyl-6-oxo-1,6-dihydropyridin-3-yl)-1-(4-methylphenyl)-1H-pyrazol-5-yl]pyrazolo[1,5-a]pyrimidine-3-carboxamide;

N-{1-(4-methylphenyl)-3-[4-(methylsulfonyl)-2-(trifluoromethyl)phenyl]-1H-pyrazol-5-yl}pyrazolo[1,5-a]pyrimidine-3-carboxamide;

N-{3-[2-(benzyloxy)-6-fluorophenyl]-1-(4-methylphenyl)-1H-pyrazol-5-yl}pyrazolo[1,5-a]pyrimidine-3-carboxamide;

N-{3-[4-(diethylsulfamoyl)-2-methylphenyl]-1-(4-methylphenyl)-1H-pyrazol-5-yl}pyrazolo[1,5-a]pyrimidine-3-carboxamide;

N-[3-{4-[(1-methylethyl)sulfonyl]phenyl}-1-(4-methylphenyl)-1H-pyrazol-5-yl]pyrazolo[1,5-a]pyrimidine-3-carboxamide;

N-[1-(4-methylphenyl)-3-{4-[(4-methylpiperazin-1-yl)sulfonyl]phenyl}-1H-pyrazol-5-yl]pyrazolo[1,5-a]pyrimidine-3-carboxamide;

N-{3-[4-(diethylsulfamoyl)phenyl]-1-(4-methylphenyl)-1H-pyrazol-5-yl}pyrazolo[1,5-a]pyrimidine-3-carboxamide;

N-{3-[4-(azetidin-1-ylsulfonyl)phenyl]-1-(4-methylphenyl)-1H-pyrazol-5-yl}pyrazolo[1,5-a]pyrimidine-3-carboxamide;

N-{3-[4-(dimethylsulfamoyl)-2-methylphenyl]-1-(4-methylphenyl)-1H-pyrazol-5-yl}pyrazolo[1,5-a]pyrimidine-3-carboxamide;

N-[1-(4-methylphenyl)-3-{3-[(methylsulfonyl)amino]phenyl}-1H-pyrazol-5-yl]pyrazolo[1,5-a]pyrimidine-3-carboxamide;

N-{1-(4-methylphenyl)-3-[4-(methylsulfamoyl)phenyl]-1H-pyrazol-5-yl}pyrazolo[1,5-a]pyrimidine-3-carboxamide;

N-{3-[4-(methylcarbamoyl)phenyl]-1-(4-methylphenyl)-1H-pyrazol-5-yl}pyrazolo[1,5-a]pyrimidine-3-carboxamide;

N-{3-[4-(dimethylcarbamoyl)phenyl]-1-(4-methylphenyl)-1H-pyrazol-5-yl}pyrazolo[1,5-a]pyrimidine-3-carboxamide;

N-{3-[3-(methylcarbamoyl)phenyl]-1-(4-methylphenyl)-1H-pyrazol-5-yl}pyrazolo[1,5-a]pyrimidine-3-carboxamide;

N-{1-(4-methylphenyl)-3-[6-(methylsulfonyl)pyridin-3-yl]-1H-pyrazol-5-yl}pyrazolo[1,5-a]pyrimidine-3-carboxamide;

N-{3-[4-(ethylsulfonyl)phenyl]-1-(4-methylphenyl)-1H-pyrazol-5-yl}pyrazolo[1,5-a]pyrimidine-3-carboxamide;

N-{3-[4-(dimethylsulfamoyl)phenyl]-1-(4-methylphenyl)-1H-pyrazol-5-yl}pyrazolo[1,5-a]pyrimidine-3-carboxamide;

N-[3-(1-methyl-6-oxo-1,2,3,6-tetrahydropyridin-4-yl)-1-(4-methylphenyl)-1H-pyrazol-5-yl]pyrazolo[1,5-a]pyrimidine-3-carboxamide;

N-[3-(2-aminopyridin-4-yl)-1-(4-methylphenyl)-1H-pyrazol-5-yl]pyrazolo[1,5-a]pyrimidine-3-carboxamide;

N-[3-{1-[(1,2-benzisoxazol-3-ylmethyl)sulfonyl]piperidin-4-yl}-1-(4-methylphenyl)-1H-pyrazol-5-yl]pyrazolo[1,5-a]pyrimidine-3-carboxamide;

N-{1-(4-methylphenyl)-3-[1-(naphthalen-1-ylsulfonyl)piperidin-4-yl]-1H-pyrazol-5-yl}pyrazolo[1,5-a]pyrimidine-3-carboxamide;

N-[1-(4-methylphenyl)-3-{1-[(pyridin-4-ylmethyl)sulfonyl]piperidin-4-yl}-1H-pyrazol-5-yl]pyrazolo[1,5-a]pyrimidine-3-carboxamide;

N-[3-{1-[(3,4-dimethoxyphenyl)sulfonyl]piperidin-4-yl}-1-(4-methylphenyl)-1H-pyrazol-5-yl]pyrazolo[1,5-a]pyrimidine-3-carboxamide;

N-[3-{1-[(3,5-difluorophenyl)sulfonyl]piperidin-4-yl}-1-(4-methylphenyl)-1H-pyrazol-5-yl]pyrazolo[1,5-a]pyrimidine-3-carboxamide;

N-{1-(4-methylphenyl)-3-[1-(propylsulfonyl)piperidin-4-yl]-1H-pyrazol-5-yl}pyrazolo[1,5-a]pyrimidine-3-carboxamide;

N-[3-{1-[(2-cyanophenyl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-{1-[(3,3,3-trifluoropropyl)sulfonyl]piperidin-4-yl}-1H-pyrazol-5-yl]pyrazolo[1,5-a]pyrimidine-3-carboxamide;

N-[3-{1-[(2,4-dimethyl-1,3-thiazol-5-yl)sulfonyl]piperidin-4-yl}-1-(4-methylphenyl)-1H-pyrazol-5-yl]pyrazolo[1,5-a]pyrimidine-3-carboxamide;

N-[3-{1-[(3,4-difluorophenyl)sulfonyl]piperidin-4-yl}-1-(4-methylphenyl)-1H-pyrazol-5-yl]pyrazolo[1,5-a]pyrimidine-3-carboxamide;

N-[3-{1-[(4-fluorophenyl)sulfonyl]piperidin-4-yl}-1-(4-methylphenyl)-1H-pyrazol-5-yl]pyrazolo[1,5-a]pyrimidine-3-carboxamide;

N-[3-{1-[(4-methoxyphenyl)sulfonyl]piperidin-4-yl}-1-(4-methylphenyl)-1H-pyrazol-5-yl]pyrazolo[1,5-a]pyrimidine-3-carboxamide;

N-[3-{1-[(1-methylethyl)sulfonyl]piperidin-4-yl}-1-(4-methylphenyl)-1H-pyrazol-5-yl]pyrazolo[1,5-a]pyrimidine-3-carboxamide;

N-{3-[1-(butylsulfonyl)piperidin-4-yl]-1-(4-methylphenyl)-1H-pyrazol-5-yl}pyrazolo[1,5-a]pyrimidine-3-carboxamide;

N-[3-{1-[(2,4-difluorophenyl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-(1-{[3-(trifluoromethyl)phenyl]sulfonyl}piperidin-4-yl)-1H-pyrazol-5-yl]pyrazolo[1,5-a]pyrimidine-3-carboxamide;

N-[3-{1-[(2,4-dimethoxyphenyl)sulfonyl]piperidin-4-yl}-1-(4-methylphenyl)-1H-pyrazol-5-yl]pyrazolo[1,5-a]pyrimidine-3-carboxamide;

N-{3-[1-(cyclohexylsulfonyl)piperidin-4-yl]-1-(4-methylphenyl)-1H-pyrazol-5-yl}pyrazolo[1,5-a]pyrimidine-3-carboxamide;

N-[3-{1-[(3-cyanophenyl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-{1-[(1-methyl-1H-pyrazol-4-yl)sulfonyl]piperidin-4-yl}-1H-pyrazol-5-yl]pyrazolo[1,5-a]pyrimidine-3-carboxamide;

N-[3-{1-[(1-methyl-1H-imidazol-4-yl)sulfonyl]piperidin-4-yl}-1-(4-methylphenyl)-1H-pyrazol-5-yl]pyrazolo[1,5-a]pyrimidine-3-carboxamide;

N-{1-(4-methylphenyl)-3-[1-(naphthalen-2-ylsulfonyl)piperidin-4-yl]-1H-pyrazol-5-yl}pyrazolo[1,5-a]pyrimidine-3-carboxamide;

N-[3-{1-[(2-fluorophenyl)sulfonyl]piperidin-4-yl}-1-(4-methylphenyl)-1H-pyrazol-5-yl]pyrazolo[1,5-a]pyrimidine-3-carboxamide;

N-[3-{1-[(3-fluorophenyl)sulfonyl]piperidin-4-yl}-1-(4-methylphenyl)-1H-pyrazol-5-yl]pyrazolo[1,5-a]pyrimidine-3-carboxamide;

N-[3-{1-[(4-cyanophenyl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-(1-{[4-(trifluoromethyl)phenyl]sulfonyl}piperidin-4-yl)-1H-pyrazol-5-yl]pyrazolo[1,5-a]pyrimidine-3-carboxamide;

N-[3-{1-[(6-chloropyridin-3-yl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-{1-[(6-morpholin-4-ylpyridin-3-yl)sulfonyl]piperidin-4-yl}-1H-pyrazol-5-yl]pyrazolo[1,5-a]pyrimidine-3-carboxamide;

N-{3-[1-(1,3-benzothiazol-6-ylsulfonyl)piperidin-4-yl]-1-(4-methylphenyl)-1H-pyrazol-5-yl}pyrazolo[1,5-a]pyrimidine-3-carboxamide;

N-[3-{1-[(3-methoxyphenyl)sulfonyl]piperidin-4-yl}-1-(4-methylphenyl)-1H-pyrazol-5-yl]pyrazolo[1,5-a]pyrimidine-3-carboxamide;

N-[3-{1-[(1,2-dimethyl-1H-imidazol-4-yl)sulfonyl]piperidin-4-yl}-1-(4-methylphenyl)-1H-pyrazol-5-yl]pyrazolo[1,5-a]pyrimidine-3-carboxamide;

N-{3-[1-(benzylsulfonyl)piperidin-4-yl]-1-(4-methylphenyl)-1H-pyrazol-5-yl}pyrazolo[1,5-a]pyrimidine-3-carboxamide;

N-[3-{1-[(2-chloropyridin-3-yl)sulfonyl]piperidin-4-yl}-1-(4-methylphenyl)-1H-pyrazol-5-yl]pyrazolo[1,5-a]pyrimidine-3-carboxamide;

N-[3-{1-[(6-methoxypyridin-3-yl)sulfonyl]piperidin-4-yl}-1-(4-methylphenyl)-1H-pyrazol-5-yl]pyrazolo[1,5-a]pyrimidine-3-carboxamide;

N-[3-{1-[(2,6-dichlorophenyl)sulfonyl]piperidin-4-yl}-1-(4-methylphenyl)-1H-pyrazol-5-yl]pyrazolo[1,5-a]pyrimidine-3-carboxamide;

N-[3-{1-[(2,4-dichlorophenyl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-{1-[(pyridin-3-ylmethyl)sulfonyl]piperidin-4-yl}-1H-pyrazol-5-yl]pyrazolo[1,5-a]pyrimidine-3-carboxamide;

N-[3-{1-[(5-chlorothiophen-2-yl)sulfonyl]piperidin-4-yl}-1-(4-methylphenyl)-1H-pyrazol-5-yl]pyrazolo[1,5-a]pyrimidine-3-carboxamide;

N-[1-(4-methylphenyl)-3-(1-{[6-(trifluoromethyl)pyridin-2-yl]sulfonyl}piperidin-4-yl)-1H-pyrazol-5-yl]pyrazolo[1,5-a]pyrimidine-3-carboxamide;

N-[1-(4-methylphenyl)-3-{1-[(2-phenylethyl)sulfonyl]piperidin-4-yl}-1H-pyrazol-5-yl]pyrazolo[1,5-a]pyrimidine-3-carboxamide;

N-{1-(4-methylphenyl)-3-[1-(quinolin-8-ylsulfonyl)piperidin-4-yl]-1H-pyrazol-5-yl}pyrazolo[1,5-a]pyrimidine-3-carboxamide;

N-[1-(4-methylphenyl)-3-{1-[(pyridin-2-ylmethyl)sulfonyl]piperidin-4-yl}-1H-pyrazol-5-yl]pyrazolo[1,5-a]pyrimidine-3-carboxamide;

N-(1-(4-cyclopropyl-2-fluorophenyl)-3-(1-methylpiperidin-4-yl)-1H-pyrazol-5-yl)pyrazolo[1,5-a]pyrimidine-3-carboxamide; and N-(3-(1-methylpiperidin-4-yl)-1-(5-methylpyridin-2-yl)-1H-pyrazol-5-yl)pyrazolo[1,5-a]pyrimidine-3-carboxamide;

or a pharmaceutically acceptable salt or stereoisomer thereof.

7. A pharmaceutical composition comprising a pharmaceutically effective amount of the compound according to claim 1 and a pharmaceutically acceptable carrier.

\* \* \* \* \*